US009969778B2

(12) United States Patent
Meijberg et al.

(10) Patent No.: US 9,969,778 B2
(45) Date of Patent: May 15, 2018

(54) INFLUENZA VIRUS VACCINES AND USES THEREOF

(71) Applicant: Janssen Vaccines & Prevention B.V., Leiden (NL)

(72) Inventors: Jan Willem Meijberg, Leiden (NL); Antonietta Impagliazzo, Leiden (NL); Ronald Vogels, Linschoten (NL); Robert H. E. Friesen, Leiden (NL); Philippe Alard, Merelbeke (BE); Stefan Loverix, Ternat (BE); Katarina Radosevic, Nootdorp (NL)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 0 days. days.

(21) Appl. No.: 15/253,535

(22) Filed: Aug. 31, 2016

(65) Prior Publication Data

US 2016/0362455 A1 Dec. 15, 2016

Related U.S. Application Data

(62) Division of application No. 14/361,281, filed as application No. PCT/EP2012/073706 on Nov. 27, 2012, now Pat. No. 9,452,211.

(60) Provisional application No. 61/564,086, filed on Nov. 28, 2011, provisional application No. 61/564,198, filed on Nov. 28, 2011, provisional application No. 61/720,281, filed on Oct. 30, 2012.

(30) Foreign Application Priority Data

Nov. 28, 2011 (EP) .................................... 11191003
Nov. 28, 2011 (EP) .................................... 11191009
May 1, 2012 (EP) .................................... 12166268

(51) Int. Cl.

| | |
|---|---|
| ***C07K 14/005*** | (2006.01) |
| ***A61K 39/12*** | (2006.01) |
| ***A61K 39/145*** | (2006.01) |
| ***C12N 7/00*** | (2006.01) |
| ***C07K 16/10*** | (2006.01) |
| *A61K 39/00* | (2006.01) |

(52) U.S. Cl.

CPC ............ *C07K 14/005* (2013.01); *A61K 39/12* (2013.01); *A61K 39/145* (2013.01); *C07K 16/1018* (2013.01); *C12N 7/00* (2013.01); *A61K 39/00* (2013.01); *A61K 2039/5258* (2013.01); *A61K 2039/55522* (2013.01); *A61K 2039/575* (2013.01); *C07K 2317/33* (2013.01); *C07K 2317/76* (2013.01); *C07K 2319/21* (2013.01); *C07K 2319/35* (2013.01); *C07K 2319/40* (2013.01); *C07K 2319/50* (2013.01); *C07K 2319/73* (2013.01); *C12N 2760/16122* (2013.01); *C12N 2760/16134* (2013.01); *C12N 2760/16151* (2013.01); *C12N 2760/16171* (2013.01)

(58) Field of Classification Search

CPC ............ C07K 16/1018; C07K 2317/76; C07K 2317/565; A61K 39/145; A61K 2039/505

See application file for complete search history.

(56) References Cited

U.S. PATENT DOCUMENTS

| | | | |
|---|---|---|---|
| 5,057,540 | A | 10/1991 | Kensil et al. |
| 6,413,776 | B1 | 7/2002 | Vogels et al. |
| 6,492,169 | B1 | 12/2002 | Vogels et al. |
| 6,670,188 | B1 | 12/2003 | Vogels et al. |
| 6,803,234 | B2 | 10/2004 | Havenga et al. |
| 6,869,794 | B2 | 3/2005 | Vogels et al. |
| 6,869,936 | B1 | 3/2005 | Vogels et al. |
| 6,878,549 | B1 | 4/2005 | Vogels |
| 6,905,678 | B2 | 6/2005 | Havenga et al. |
| 6,913,922 | B1 | 7/2005 | Bout et al. |
| 6,929,946 | B1 | 8/2005 | Vogels et al. |
| 6,974,695 | B2 | 12/2005 | Vogels et al. |
| 7,037,716 | B2 | 5/2006 | Vogels et al. |
| 7,238,528 | B2 | 7/2007 | Vogels et al. |
| 7,250,293 | B2 | 7/2007 | Vogels et al. |
| 7,270,811 | B2 | 9/2007 | Bout et al. |
| 7,285,265 | B2 | 10/2007 | Vogels et al. |
| 7,344,883 | B2 | 3/2008 | Vogels et al. |
| 7,468,181 | B2 | 12/2008 | Vogels et al. |

(Continued)

FOREIGN PATENT DOCUMENTS

| | | |
|---|---|---|
| EP | 11173953.8 | 7/2011 |
| WO | 9003184 A1 | 4/1990 |

(Continued)

OTHER PUBLICATIONS

Bommakanti et al., PNAS, 2010, 107(31):13701-13706.*
Bommakanti et al., Supporting Information, 2010, 10.1073/PNAS. 1007465107.*
Bommakanti et al., Design of an HA2-based *Escherichia coli* expressed influenza immunogen that protects mice rom pathogenic challenge, Proceedings of the National Academy of Sciences of the United States of America, Aug. 2010, pp. 13701-13706, vol. 107, No. 31.
Bommakanti et al., Supporting Information, Aug. 3, 2010, pp. 1-6, 10.1073/PNAS.1007465107:pdf 1-6.
Steel et al., Influenza Virus Vaccine Based on the Conserved Hemagglutinin Stalk Domain, MBIO, Apr. 2010, vol. 1, No. 1.
Sagawa et al., The immunological activity of a deletion mutant of influenza virus haemagglutinin lacking the globular region, Journal of General Virology, 1996, pp. 1483-1487, vol. 77, No. 7.

(Continued)

*Primary Examiner* — Barry A Chestnut
(74) *Attorney, Agent, or Firm* — TraskBritt, P.C.

(57) ABSTRACT

The present disclosure provides influenza hemagglutinin stem domain polypeptides comprising (a) an influenza hemagglutinin HA1 domain that comprises an HA1 N-terminal stem segment, covalently linked by a linking sequence of 0-50 amino acid residues to an HA1 C-terminal stem segment, and (b) an influenza hemagglutinin HA2 domain, wherein on or more amino acids in the HA2 domain have been mutated. Also provided are nucleic acids encoding the polypeptides, compositions comprising the polypeptides and/or nucleic acid molecules, as well as methods of their use, in particular in the detection, prevention and/or treatment of influenza.

4 Claims, 53 Drawing Sheets

(56) References Cited

U.S. PATENT DOCUMENTS

| | | | |
|---|---|---|---|
| 7,598,078 | B2 | 10/2009 | Havenga et al. |
| 7,604,960 | B2 | 10/2009 | Hateboer et al. |
| 7,749,493 | B2 | 7/2010 | Havenga et al. |
| 7,816,104 | B2 | 10/2010 | Vogels et al. |
| 7,820,440 | B2 | 10/2010 | Vogels et al. |
| 7,906,113 | B2 | 3/2011 | Bout et al. |
| 7,968,087 | B2 | 6/2011 | Vogels et al. |
| 7,968,286 | B2 | 6/2011 | Havenga et al. |
| 8,012,467 | B2 | 9/2011 | Havenga et al. |
| 8,052,967 | B2 | 11/2011 | Vogels et al. |
| 8,076,131 | B2 | 12/2011 | Vogels et al. |
| 8,114,637 | B2 | 2/2012 | Vogels et al. |
| 8,202,723 | B2 | 6/2012 | Havenga et al. |
| 8,221,971 | B2 | 7/2012 | Bout et al. |
| 8,227,243 | B2 | 7/2012 | Vogels et al. |
| 8,470,327 | B2 | 6/2013 | Throsby et al. |
| 8,609,402 | B2 | 12/2013 | Havenga et al. |
| 8,834,881 | B2 | 9/2014 | Vogels et al. |
| 8,852,595 | B2 | 10/2014 | Vogels et al. |
| 8,961,978 | B2 | 2/2015 | Kwaks et al. |
| 9,005,621 | B2 | 4/2015 | Vogels et al. |
| 9,119,813 | B2 | 9/2015 | Radosevic et al. |
| 9,125,870 | B2 | 9/2015 | Radosevic et al. |
| 9,168,292 | B2 | 10/2015 | Rodriguez-Munoz et al. |
| 9,200,064 | B2 | 12/2015 | Vogels et al. |
| 9,228,205 | B2 | 1/2016 | Vogels et al. |
| 2005/0221493 | A1 | 10/2005 | Vogels et al. |
| 2013/0122038 | A1 | 5/2013 | Radosevic et al. |
| 2013/0236494 | A1 | 9/2013 | Radosevic et al. |
| 2014/0357845 | A1 | 12/2014 | Meijberg et al. |
| 2015/0175677 | A9 | 6/2015 | Throsby et al. |
| 2015/0196632 | A1 | 7/2015 | Radosevic et al. |
| 2015/0232537 | A1 | 8/2015 | van den Nieuwenhof et al. |
| 2015/0274811 | A1 | 10/2015 | Kwaks et al. |
| 2015/0320854 | A1 | 11/2015 | Radosevic et al. |
| 2016/0136262 | A1 | 5/2016 | Meijberg et al. |

FOREIGN PATENT DOCUMENTS

| | | | |
|---|---|---|---|
| WO | 9014837 | A1 | 12/1990 |
| WO | 9611711 | A1 | 4/1996 |
| WO | 2004004762 | A1 | 1/2004 |
| WO | 2005002620 | A1 | 1/2005 |
| WO | 2008028946 | A2 | 3/2008 |
| WO | 2008028946 | A3 | 10/2008 |
| WO | 2010/117786 | A1 | 10/2010 |
| WO | 2010117786 | A1 | 10/2010 |
| WO | 2010130636 | A1 | 11/2010 |
| WO | 2011123495 | A1 | 10/2011 |
| WO | 2013007770 | A1 | 1/2013 |
| WO | 2013/079473 | A1 | 6/2013 |
| WO | 2014191435 | A1 | 12/2014 |
| WO | 2016005480 | A1 | 1/2016 |
| WO | 2016005482 | A1 | 1/2016 |

OTHER PUBLICATIONS

Wang et al., Vaccination with a synthetic peptide from the influenza virus hemagglutinin provides protection against distinct viral subtypes, Proceedings of the National Academy of Sciences of the United States of America, Nov. 2, 2010, pp. 18979-18984, vol. 107, No. 44.

Bianchi et al., Universal influenza B vaccine based on the maturational cleavage site of the hemagglutinin precursor, Journal of Virology, The American Society for Microbiology, pp. 7380-7388, vol. 79, No. 12, US.

Kang et al., Novel vaccines against influenza viruses, Virus Research, Oct. 1, 2011, pp. 31-38, vol. 162, No. 1.

Eckert et al., Stalking influenza, Proceedings of the national Academy of Sciences of the United States of America, Aug. 3, 2010, pp. 13563-13564, vol. 107, No. 31.

Wilson et al., Structure of the haemagglutinin membrane glycoprotein of influenza virus at 3 A resolution, Nature: International Weekly Journal of Science, Nature Publishing Group, United Kingdom, Jan. 29, 1981, pp. 366-373, vol. 289, No. 5796.

Steel et al., Live Attenuated Influenza Viruses Containing NS1 Truncations as Vaccine Candidates against H5N1 Highly Pathogenic Avian influenza, Journal of Virology, Feb. 2009, pp. 1742-1753, vol. 83, No. 4.

PCT International Search Report, PCT/EP2012/073706 dated May 3, 2013.

Kodihalli et al., Strategies for inducing protection against avian influenza A virus subtypes with DNA vaccines, 2000, Vaccine, pp. 2592-2599, vol. 18, No. 23.

Zhirnov et al., Cleavage of influenza A virus hemagglutinin in human respiratory epithelium is cell associated and sensitive to exogenous antiproteases, 2002, Journal of Virology, pp. 8682-8689, vol. 76, No. 17.

Ichihashi et al., Cross-protective peptide vaccine against influenza A viruses developed in HLA-A 2402 Human Immunity model, 2011, 6(9):pdf 1-9.

PCT Written Opinion, PCT/EP2012/073706 dated May 3, 2013.

PCT International Preliminary Report on Patentability, PCT/EP2012/073706 dated May 14, 2014.

Chen et al., A soluble domain of the membrane-anchoring chain of influenza virus hemagglutinin (HA2) folds in *Escherichia coli* into the low-pH-induced conformation, PNAS 92, 1995, vol. 92, pp. 12205-12209.

Suzuki et al., An isoleucine zipper peptide forms a native-like triple stranded coiled coil in solution, Prot. Eng., 1998, vol. 11, pp. 1051-1055.

Steven et al., Structure of the Uncleaved Human H1 Hemagglutinin from the Extinct 1918 Influenza Virus, Science, 2004, 303, pp. 1866-1870.

Dopheide et al., The Location of the Bromelain Cleavage Site in a Hong Kong Influenza Virus Haemagglutinin, J. Gen. Viral., 1981, 36x 370.

Wilson et al., Structure of the haemagglutinin membrane glycoprotein of influenza virus at 3 A resolution, Nature, 1981, vol. 289, pp. 366.

Delhaise, et al. Interactive computer animation of macromolecules, J. Mol. Graph., 1984, vol. 2, pp. 10✓ 106.

Devereux et al., A comprehensive set of sequence analysis programs for the VAX, Nucl. Acids Res. 1984, vol. 12, pp. 387-395.

Higgins, Sequence ordinations: a multivariate analysis approach to analyzing large sequence data sets, Comput. Appl. Biosci., (1992), vol. 8, pp. 15-22.

Okuno et al., A Common Neutralizing Epitope Conserved between the Hemagglutinins of Influenza A Virus H1 and H2 Strains, J. Viral. 1993, vol. 67, No. 5, pp. 2552-2558.

Steven et al., Structure and Receptor Specificity of the Hemagglutinin from an H5N1 Influenza Virus, Science, 2006, vol. 312, pp. 404- 410.

Throsby et al., Heterosubtypic Neutralizing Monoclonal Antibodies Cross-Protective against H5N1 and H1N1 Recovered from Human IgM+ Memory B Cells, Plos One, (2008), vol. 12, No. 3, pp. 1-15.

Ekiert et al., Antibody Recognition of a Highly Conserved Influenza Virus Epitope, Science, 2009, vol. 324, pp. 246-251.

Coffman et al., Vaccine Adjuvants: Putting Innate Immunity to Work, Immunity, 2010, vol. 33, pp. 492-503.

Lorieau et al., The complete influenza hemagglutinin fusion domain adopts a tight helical hairpin arrangement at the lipid:water interface, Proc. Natl. Acad. Sci., 2010, USA, vol. 107, pp. 11341-11346.

Steel et al., Influenza Virus Vaccine Based on the Conserved Hemagglutinin Stalk Domain, mBio., 2010, vol. 1, No. 1, pp. 1-9.

Sun et al., Modifications to the Hemagglutinin Cleavage Site Control the Virulence of a Neurotropic H1N1 Influenza Virus, J. Virol., 2010, vol. 84, pp. 8683-8690.

Corti et al., A Neutralizing Antibody Selected from Plasma Cells That Binds to Group 1 and Group 2 Influenza A Hemagglutinins, Science, 2011, vol. 333(6044), pp. 850-856.

Ekiert et al., A Highly Conserved Neutralizing Epitope on Group 2 Influenza A Viruses, Science, 2011, vol. 333, pp. 843-850.

Samanta et al., Quantifying the accessible surface area of protein residues in their local environment, Prot. Eng., 2002, vol. 15, pp. 659-667.

(56) References Cited

OTHER PUBLICATIONS

Ferguson et al., Ecological and immunological determinants of influenza evolution, Nature, 2003, vol. 422, pp. 428-443.
Edgar R.C., Muscle: Multiple sequence alignment with high accuracy and high throughput, Nucleic Acids Res., 2004, vol. 32, No. 5, pp. 1792-1797.
Russel et al., H1 and H7 influenza haemagglutinin structures extend a structural classification of haemagglutinin subtypes, Virology, 2004, vol. 325, pp. 287-296.
Xu & Miranker, A metric model of amino acid substitution, Bioinformatics, 2004, vol. 8, pp. 1214-1221.
Woolfson, The Design of Coiled-Coil Structures and Assemblies, Adv Protein Chem, 2005, vol. 70, pp. 79-112.
Alberini et al., Pseudoparticle neutralization is a reliable assay to measure immunity and cross-reactivity to H5N1 influenza viruses, Vaccine, 2009, pp. 5998-6003, vol. 27.
Atsmon et al., Safety and Immunogenicity of Multimeric-00—A Novel Universal Influenza Vaccine, Journal Clin Immunol., Feb. 9, 2012, pp. 595-603, vol. 32.
Bommakanti et al., Design of *Escherichia coli*-Expressed Stalk Domain Immunogens of H1N1 Hemagglutinin That Protect Mice from Lethal Challenge, Journal of Virology, Dec. 2012, pp. 13434-134444, vol. 86, No. 24.
Cheng et al., Development of a robust reporter-based ADCC assay with frozen, thaw-and-use cells to measure Fc effector function of therapeutic antibodies, Journal of Immunol. Methods, 2014, pp. 69-81, vol. 414.
Degorce et al., HTRF: A Technology Tailored for Drug Discovery a review of Theoretical Aspects and Recent Applications, Curr. Chem. Genomics, Mar. 30, 2009, pp. 22-32, vol. 3.
Dilillo et al., Broadly neutralizing hemagglutinin stalk-specific antibodies required FcgammaR interactions for protection against influenza virus in vivo, Nature Medicine, Feb. 2014, pp. 143-153, vol. 20, No. 2.
Lu et al., Production and stabilization of the trimeric influenza hemagglutinin stem domain for potentially broadly protective influenza vaccines, PNAS, 2013, contains supporting information, 27 pages.
Mallajosyula et al., Influenza hemagglutinin stem-fragment immunogen elicits broadly neutralizing antibodies and confers heterologous protection, PNAS, Jun. 9, 2014, pp. E2514-E2523.
Parekh et al., Development and validation of an antibody-dependent cell-mediated cytotoxicity-reporter gene assay, mAbs, May/Jun. 2012, pp. 310-318.
PCT International Preliminary Report on Patentability, PCT/EP2014/060997, dated Dec. 1, 2015.
PCT International Preliminary Report on Patentability, PCT/EP2015/065663, dated Jan. 10, 2017.
PCT International Search Report, PCT/EP2014/060997, dated Sep. 16, 2014.
PCT International Search Report, PCT/EP2015/065663, dated Sep. 30, 2015.
PCT International Written Opinion, PCT/EP2014/060997, dated Sep. 16, 2014.
PCT International Written Opinion, PCT/EP2015/065663, dated Sep. 30, 2015.
Safronetz et al., Pandemic Swine-Origin H1N1 Influenza A Virus Isolates Show Heterogeneous Virulence in Macaques, Journal of Virology, Feb. 2001, pp. 1214-1223, vol. 85, No. 3.
Sagawa et al., The immunological activity of a deletion mutant of influenza virus haemagglutinin lacking the globular region, Journal of General Virology, 1996, pp. 1483-1487.
Schnueriger et al., Development of a quantitative, cell-line based assay to measure ADCC activity mediated by therapeutic antibodies, Molec. Immun., May 14, 2011, pp. 1512-1517, vol. 48.
Steel et al., Influenza Virus Vaccine Based on the Conserved Hemagglutinin Stalk Domain, mBio, Apr. 2010, pp. 1-9.
Temperton et al., A sensitive retroviral pseudotype assay for influenza H5N1-neutralizing antibodies, Viruses, Jul. 26, 2007, pp. 105-112, vol. 1.

* cited by examiner

A.
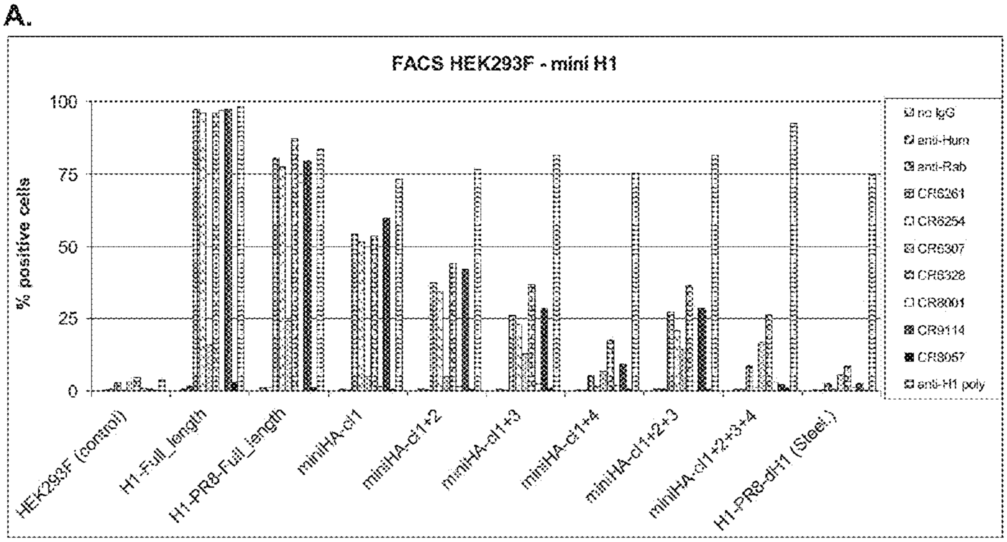
B.
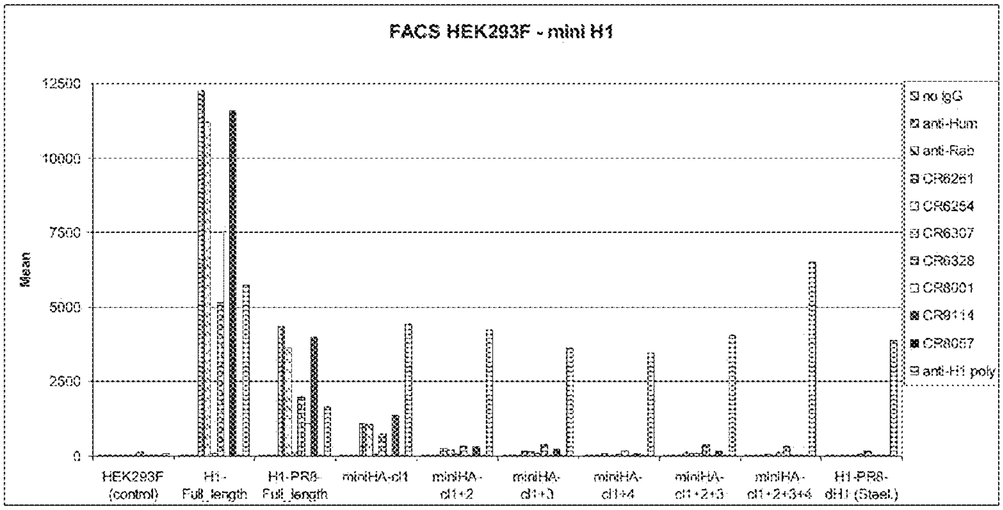
FIG. 2

A.
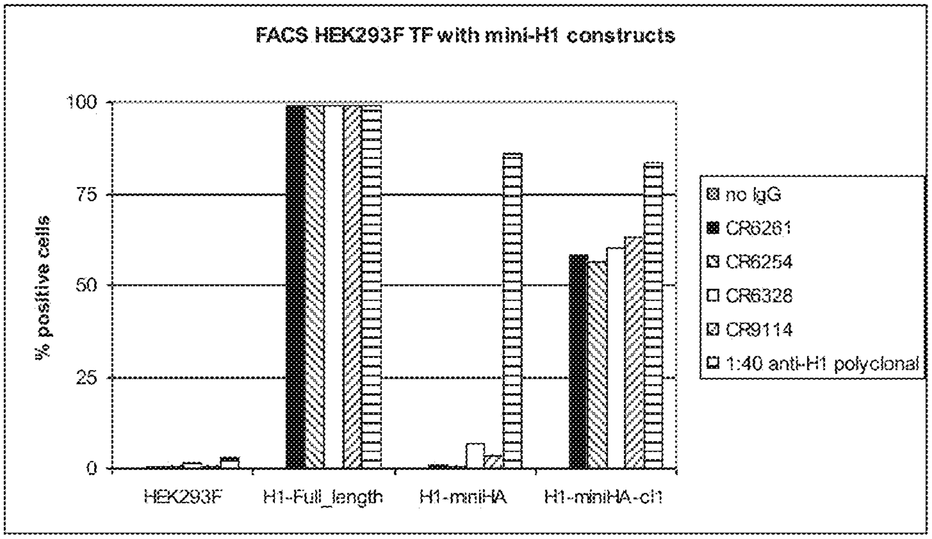
B.
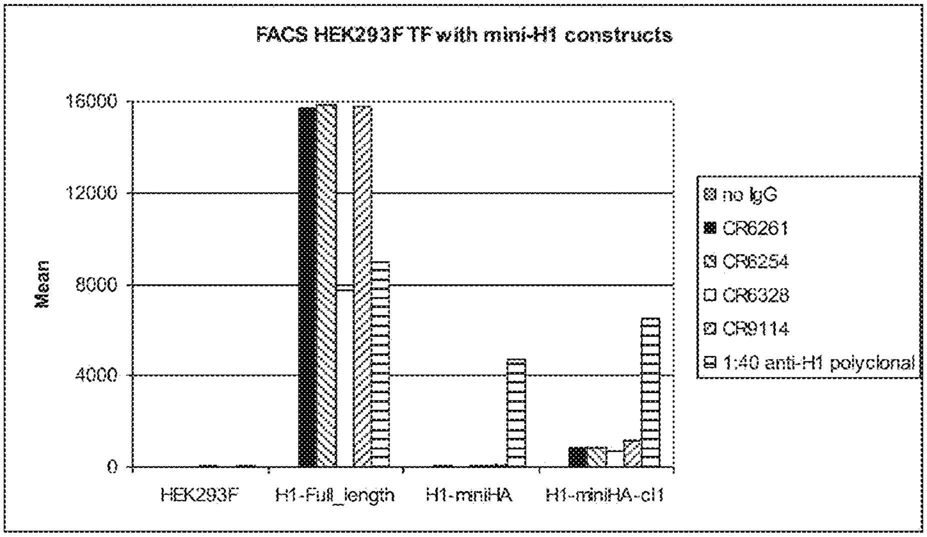
FIG. 3

Figure 25:
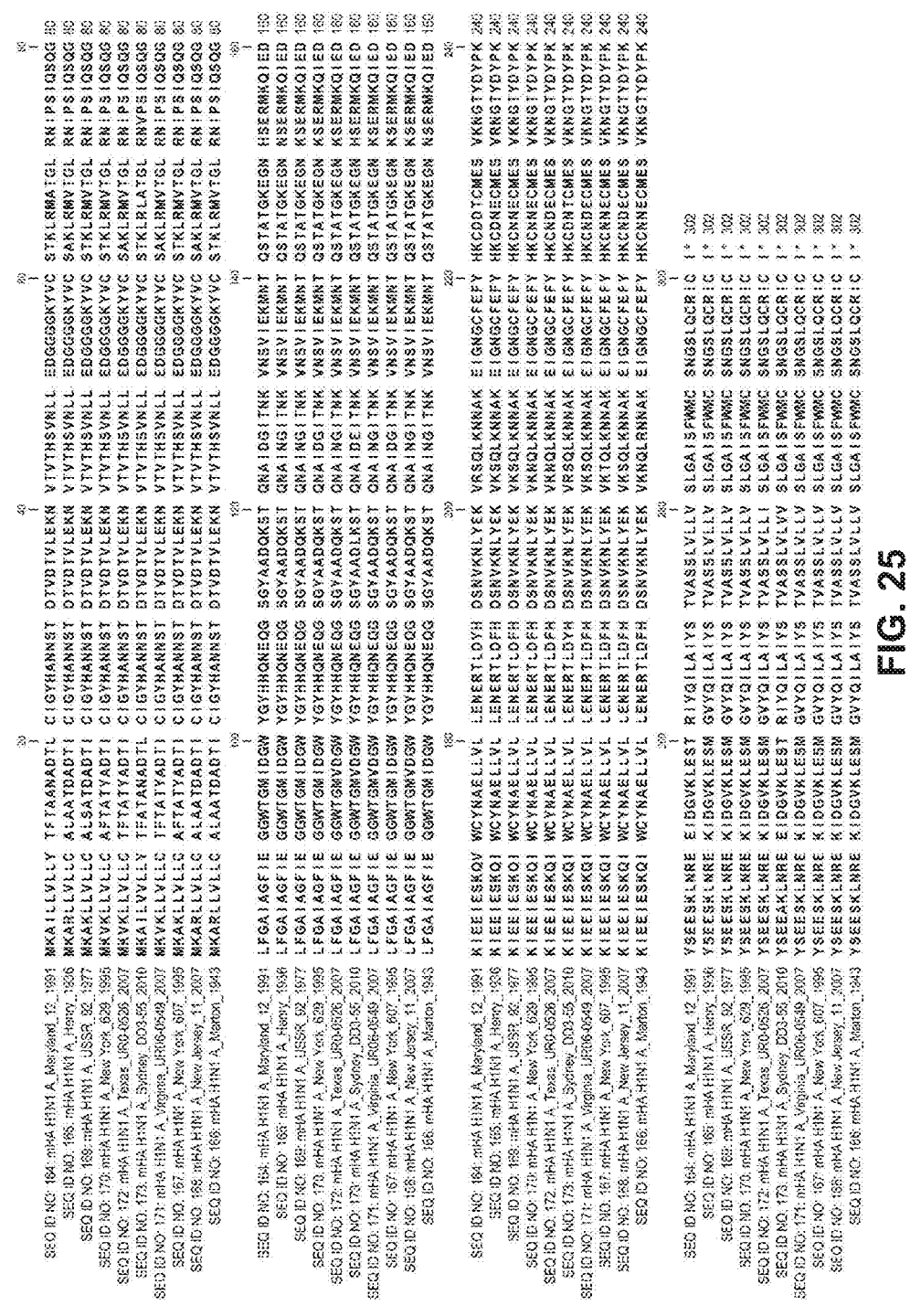

| | | 20 | | 40 | | 60 | | 80 | |
|---|---|---|---|---|---|---|---|---|---|
| SEQ ID NO: 164: mHA H1N1 A_Maryland_12_1991 | MKAILLVLLY | TFTAANADTL | CIGYHANNST | DTVDTVLEKN | VTVTHSVNLL | EDGGGGKYVC | STKLRMATGL | RNIPSIQSQG | 80 |
| SEQ ID NO: 165: mHA H1N1 A_Henry_1936 | MKARLLVLLC | ALAATDADTI | CIGYHANNST | DTVDTVLEKN | VTVTHSVNLL | EDGGGGKYVC | SAKLRMVTGL | RNIPSIQSQG | 80 |
| SEQ ID NO: 169: mHA H1N1 A_USSR_92_1977 | MKAKLLVLLC | ALSATDADTI | CIGYHANNST | DTVDTVLEKN | VTVTHSVNLL | EDGGGGKYVC | STKLRMVTGL | RNIPSIQSQG | 80 |
| SEQ ID NO: 170: mHA H1N1 A_New York_629_1995 | MKVKLLVLLC | AFTATYADTI | CIGYHANNST | DTVDTVLEKN | VTVTHSVNLL | EDGGGGKYVC | STKLRMVTGL | RNIPSIQSQG | 80 |
| SEQ ID NO: 172: mHA H1N1 A_Texas_UR0-0526_2007 | MKVKLLVLLC | TFTATYADTI | CIGYHANNST | DTVDTVLEKN | VTVTHSVNLL | EDGGGGKYVC | SAKLRMVTGL | RNIPSIQSQG | 80 |
| SEQ ID NO: 173: mHA H1N1 A_Sydney_DD3-55_2010 | MKAILVVLLY | TFATANADTL | CIGYHANNST | DTVDTVLEKN | VTVTHSVNLL | EDGGGGKYVC | STKLRLATGL | RNVPSIQSQG | 80 |
| SEQ ID NO: 171: mHA H1N1 A_Virginia_UR06-0549_2007 | MKVKLLVLLC | TFTATYADTI | CIGYHANNST | DTVDTVLEKN | VTVTHSVNLL | EDGGGGKYVC | SAKLRMVTGL | RNIPSIQSQG | 80 |
| SEQ ID NO: 167: mHA H1N1 A_New York_607_1995 | MKAKLLVLLC | AFTATYADTI | CIGYHANNST | DTVDTVLEKN | VTVTHSVNLL | EDGGGGKYVC | STKLRMVTGL | RNIPSIQSQG | 80 |
| SEQ ID NO: 168: mHA H1N1 A_New Jersey_11_2007 | MKARLLVLLC | ALAATDADTI | CIGYHANNST | DTVDTVLEKN | VTVTHSVNLL | EDGGGGKYVC | SAKLRMVTGL | RNIPSIQSQG | 80 |
| SEQ ID NO: 166: mHA H1N1 A_Marton_1943 | MKARLLVLLC | ALAATDADTI | CIGYHANNST | DTVDTVLEKN | VTVTHSVNLL | EDGGGGKYVC | STKLRMVTGL | RNIPSIQSQG | 80 |

| | | 100 | | 120 | | 140 | | 160 | |
|---|---|---|---|---|---|---|---|---|---|
| SEQ ID NO: 164: mHA H1N1 A_Maryland_12_1991 | LFGAIAGFIE | GGWTGMIDGW | YGYHHQNEQG | SGYAADQKST | QNAIDGITNK | VNSVIEKMNT | QSTATGKEGN | HSERMKQIED | 160 |
| SEQ ID NO: 165: mHA H1N1 A_Henry_1936 | LFGAIAGFIE | GGWTGMIDGW | YGYHHQNEQG | SGYAADQKST | QNAINGITNK | VNSVIEKMNT | QSTATGKEGN | NSERMKQIED | 160 |
| SEQ ID NO: 169: mHA H1N1 A_USSR_92_1977 | LFGAIAGFIE | GGWTGMIDGW | YGYHHQNEQG | SGYAADQKST | QNAINGITNK | VNSVIEKMNT | QSTATGKEGN | KSERMKQIED | 160 |
| SEQ ID NO: 170: mHA H1N1 A_New York_629_1995 | LFGAIAGFIE | GGWTGMIDGW | YGYHHQNEQG | SGYAADQKST | QNAIDGITNK | VNSVIEKMNT | QSTATGKEGN | KSERMKQIED | 160 |
| SEQ ID NO: 172: mHA H1N1 A_Texas_UR0-0526_2007 | LFGAIAGFIE | GGWTGMVDGW | YGYHHQNEQG | SGYAADQKST | QNAINGITNK | VNSVIEKMNT | QSTATGKEGN | KSERMKQIED | 160 |
| SEQ ID NO: 173: mHA H1N1 A_Sydney_DD3-55_2010 | LFGAIAGFIE | GGWTGMVDGW | YGYHHQNEQG | SGYAADLKST | QNAIDEITNK | VNSVIEKMNT | QSTATGKEGN | HSERMKQIED | 160 |
| SEQ ID NO: 171: mHA H1N1 A_Virginia_UR06-0549_2007 | LFGAIAGFIE | GGWTGMVDGW | YGYHHQNEQG | SGYAADQKST | QNAINGITNK | VNSVIEKMNT | QSTATGKEGN | KSERMKQIED | 160 |
| SEQ ID NO: 167: mHA H1N1 A_New York_607_1995 | LFGAIAGFIE | GGWTGMIDGW | YGYHHQNEQG | SGYAADQKST | QNAIDGITNK | VNSVIEKMNT | QSTATGKEGN | KSERMKQIED | 160 |
| SEQ ID NO: 168: mHA H1N1 A_New Jersey_11_2007 | LFGAIAGFIE | GGWTGMVDGW | YGYHHQNEQG | SGYAADQKST | QNAINGITNK | VNSVIEKMNT | QSTATGKEGN | KSERMKQIED | 160 |
| SEQ ID NO: 166: mHA H1N1 A_Marton_1943 | LFGAIAGFIE | GGWTGMIDGW | YGYHHQNEQG | SGYAADQKST | QNAINGITNK | VNSVIEKMNT | QSTATGKEGN | NSERMKQIED | 160 |

| | | 180 | | 200 | | 220 | | 240 | |
|---|---|---|---|---|---|---|---|---|---|
| SEQ ID NO: 164: mHA H1N1 A_Maryland_12_1991 | KIEEIESKQV | WCYNAELLVL | LENERTLDYH | DSNVKNLYEK | VRSQLKNNAK | EIGNGCFEFY | HKCDDTCMES | VKNGTYDYPK | 240 |
| SEQ ID NO: 165: mHA H1N1 A_Henry_1936 | KIEEIESKQI | WCYNAELLVL | LENERTLDFH | DSNVKNLYEK | VKSQLKNNAK | EIGNGCFEFY | HKCDNECMES | VRNGTYDYPK | 240 |
| SEQ ID NO: 169: mHA H1N1 A_USSR_92_1977 | KIEEIESKQI | WCYNAELLVL | LENERTLDFH | DSNVKNLYEK | VKSQLKNNAK | EIGNGCFEFY | HKCNNECMES | VKNGTYDYPK | 240 |
| SEQ ID NO: 170: mHA H1N1 A_New York_629_1995 | KIEEIESKQI | WCYNAELLVL | LENERTLDFH | DSNVKNLYEK | VKNQLKNNAK | EIGNGCFEFY | HKCNNECMES | VKNGTYDYPK | 240 |
| SEQ ID NO: 172: mHA H1N1 A_Texas_UR0-0526_2007 | KIEEIESKQI | WCYNAELLVL | LENERTLDFH | DSNVKNLYEK | VKNQLKNNAK | EIGNGCFEFY | HKCNDECMES | VKNGTYDYPK | 240 |
| SEQ ID NO: 173: mHA H1N1 A_Sydney_DD3-55_2010 | KIEEIESKQI | WCYNAELLVL | LENERTLDYH | DSNVKNLYEK | VRSQLKNNAK | EIGNGCFEFY | HKCDNTCMES | VKNGTYDYPK | 240 |
| SEQ ID NO: 171: mHA H1N1 A_Virginia_UR06-0549_2007 | KIEEIESKQI | WCYNAELLVL | LENERTLDFH | DSNVKNLYEK | VKSQLKNNAK | EIGNGCFEFY | HKCNDECMES | VKNGTYDYPK | 240 |
| SEQ ID NO: 167: mHA H1N1 A_New York_607_1995 | KIEEIESKQI | WCYNAELLVL | LENERTLDFH | DSNVKNLYEK | VKTQLKNNAK | EIGNGCFEFY | HKCNNECMES | VKNGTYDYPK | 240 |
| SEQ ID NO: 168: mHA H1N1 A_New Jersey_11_2007 | KIEEIESKQI | WCYNAELLVL | LENERTLDFH | DSNVKNLYEK | VKSQLKNNAK | EIGNGCFEFY | HKCNDECMES | VKNGTYDYPK | 240 |
| SEQ ID NO: 166: mHA H1N1 A_Marton_1943 | KIEEIESKQI | WCYNAELLVL | LENERTLDFH | DSNVKNLYEK | VKNQLRNNAK | EIGNGCFEFY | HKCNNECMES | VKNGTYDYPK | 240 |

| | | 260 | | 280 | | 300 | | |
|---|---|---|---|---|---|---|---|---|
| SEQ ID NO: 164: mHA H1N1 A_Maryland_12_1991 | YSEESKLNRE | EIDGVKLEST | RIYQILAIYS | TVASSLVLLV | SLGAISFWMC | SNGSLQCRIC | I* | 302 |
| SEQ ID NO: 165: mHA H1N1 A_Henry_1936 | YSEESKLNRE | KIDGVKLESM | GVYQILAIYS | TVASSLVLLV | SLGAISFWMC | SNGSLQCRIC | I* | 302 |
| SEQ ID NO: 169: mHA H1N1 A_USSR_92_1977 | YSEESKLNRE | KIDGVKLESM | GVYQILAIYS | TVASSLVLLV | SLGAISFWMC | SNGSLQCRIC | I* | 302 |
| SEQ ID NO: 170: mHA H1N1 A_New York_629_1995 | YSEESKLNRE | KIDGVKLESM | GVYQILAIYS | TVASSLVLLV | SLGAISFWMC | SNGSLQCRIC | I* | 302 |
| SEQ ID NO: 172: mHA H1N1 A_Texas_UR0-0526_2007 | YSEESKLNRE | KIDGVKLESM | GVYQILAIYS | TVASSLVLLI | SLGAISFWMC | SNGSLQCRIC | I* | 302 |
| SEQ ID NO: 173: mHA H1N1 A_Sydney_DD3-55_2010 | YSEEAKLNRE | EIDGVKLEST | RIYQILAIYS | TVASSLVLVV | SLGAISFWMC | SNGSLQCRIC | I* | 302 |
| SEQ ID NO: 171: mHA H1N1 A_Virginia_UR06-0549_2007 | YSEESKLNRE | KIDGVKLESM | GVYQILAIYS | TVASSLVLLV | SLGAISFWMC | SNGSLQCRIC | I* | 302 |
| SEQ ID NO: 167: mHA H1N1 A_New York_607_1995 | YSEESKLNRE | KIDGVKLESM | GVYQILAIYS | TVASSLVLLV | SLGAISFWMC | SNGSLQCRIC | I* | 302 |
| SEQ ID NO: 168: mHA H1N1 A_New Jersey_11_2007 | YSEESKLNRE | KIDGVKLESM | GVYQILAIYS | TVASSLVLLV | SLGAISFWMC | SNGSLQCRIC | I* | 302 |
| SEQ ID NO: 166: mHA H1N1 A_Marton_1943 | YSEESKLNRE | KIDGVKLESM | GVYQILAIYS | TVASSLVLLV | SLGAISFWMC | SNGSLQCRIC | I* | 302 |

FIG. 25 coating: rHA A/HK/1/68

| SEQ ID NO | Name: |
|---|---|
| 121 | pcDNA2004Neo_H3-Hongkong_68 R345Q |
| 130 | pcDNA2004Neo_H3mini2a -linker+cl9+10+11+12-GCN4t |
| 174 | H3 HK mini2a -linker+cl9 +10+11+12+GCN4T -CG7-1 |
| 175 | HK68 H3mini2a -linker+cl9_+10+12+18+GCN4T |
| 176 | HK68 H3mini2a -linker+cl9_+10+12+16+CG7-GCN4T |
| 177 | HK68 H3mini2a -linker+cl9_+10+12+19+GCN4T |
| 178 | HK68 H3mini2a -linker+cl9_+10+12+17+CG7-GCN4T |
| 179 | H3 HK68 mini2a-linker2+cl9_+10+12+GCN4T |
| CM2 | cM2 |

#2766 SEQ ID NO: 105: H3-mini2
#2769 SEQ ID NO: 108: H3-mini2-cl9+10+11
#2773 SEQ ID NO: 112: H3-mini2-cl9+10+12
#2772 SEQ ID NO: 111: H3-mini2-cl9+10+11+12
#2775 SEQ ID NO: 114: H3-mini2-cl9+10+11+12-tri
#2774 SEQ ID NO: 113: H3-mini2-cl9+10+11+12-GCN4
#2780 SEQ ID NO: 119: H3-mini3-cl9+10+11+12+14
#2781 SEQ ID NO: 120: H3-mini4-cl9+10+11+12+14
#1969 SEQ ID NO: 89 H3 Full length A/Wisconsin/67/2005
#1372 cM2

#2766 SEQ ID NO: 105: H3-mini2
#2769 SEQ ID NO: 108: H3-mini2-cl9+10+11
#2773 SEQ ID NO: 112: H3-mini2-cl9+10+12
#2772 SEQ ID NO: 111: H3-mini2-cl9+10+11+12
#2775 SEQ ID NO: 114: H3-mini2-cl9+10+11+12-tri
#2774 SEQ ID NO: 113: H3-mini2-cl9+10+11+12-GCN4
#2780 SEQ ID NO: 119: H3-mini3-cl9+10+11+12+14
#2781 SEQ ID NO: 120: H3-mini4-cl9+10+11+12+14
#1969 SEQ ID NO: 89 H3 Full length A/Wisconsin/67/2005
#1372 cM2

#2766 SEQ ID NO: 105: H3-mini2
#2769 SEQ ID NO: 108: H3-mini2-cl9+10+11
#2773 SEQ ID NO: 112: H3-mini2-cl9+10+12
#2772 SEQ ID NO: 111: H3-mini2-cl9+10+11+12
#2775 SEQ ID NO: 114: H3-mini2-cl9+10+11+12-tri
#2774 SEQ ID NO: 113: H3-mini2-cl9+10+11+12-GCN4
#2780 SEQ ID NO: 119: H3-mini3-cl9+10+11+12+14
#2781 SEQ ID NO: 120: H3-mini4-cl9+10+11+12+14
#1969 SEQ ID NO: 89 H3 Full length A/Wisconsin/67/2005
#1372 cM2

SEQUENCE LISTING

<160> NUMBER OF SEQ ID NOS: 212

<210> SEQ ID NO 1
<211> LENGTH: 565
<212> TYPE: PRT
<213> ORGANISM: Artificial
<220> FEATURE:
<223> OTHER INFORMATION: H1 full length HA (A/Brisbane/59/2007)

<400> SEQUENCE: 1

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

-continued

```
Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460
```

```
Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 2
<211> LENGTH: 338
<212> TYPE: PRT
<213> ORGANISM: Artificial
<220> FEATURE:
<223> OTHER INFORMATION: miniHA (A/Brisbane/59/2007)

<400> SEQUENCE: 2

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Gly Gly Gly Gly Cys
    50                  55                  60

Asp Ala Lys Cys Gln Thr Pro Gln Gly Ala Ile Asn Ser Ser Leu Pro
65                  70                  75                  80

Phe Gln Asn Val His Pro Val Thr Ile Gly Glu Cys Pro Lys Tyr Val
                85                  90                  95

Arg Ser Ala Lys Leu Arg Met Val Thr Gly Leu Arg Asn Ile Pro Ser
            100                 105                 110

Ile Gln Ser Gln Gly Leu Phe Gly Ala Ile Ala Gly Phe Ile Glu Gly
        115                 120                 125

Gly Trp Thr Gly Met Val Asp Gly Trp Tyr Gly Tyr His His Gln Asn
    130                 135                 140

Glu Gln Gly Ser Gly Tyr Ala Ala Asp Gln Lys Ser Thr Gln Asn Ala
145                 150                 155                 160

Ile Asn Gly Ile Thr Asn Lys Val Asn Ser Val Ile Glu Lys Met Asn
                165                 170                 175

Thr Gln Phe Thr Ala Val Gly Lys Glu Phe Asn Lys Leu Glu Arg Arg
            180                 185                 190

Met Glu Asn Leu Asn Lys Lys Val Asp Asp Gly Phe Ile Asp Ile Trp
        195                 200                 205

Thr Tyr Asn Ala Glu Leu Leu Val Leu Leu Glu Asn Glu Arg Thr Leu
    210                 215                 220

Asp Phe His Asp Ser Asn Val Lys Asn Leu Tyr Glu Lys Val Lys Ser
225                 230                 235                 240

Gln Leu Lys Asn Asn Ala Lys Glu Ile Gly Asn Gly Cys Phe Glu Phe
                245                 250                 255
```

-continued

```
Tyr His Lys Cys Asn Asp Glu Cys Met Glu Ser Val Lys Asn Gly Thr
            260                 265                 270

Tyr Asp Tyr Pro Lys Tyr Ser Glu Glu Ser Lys Leu Asn Arg Glu Lys
        275                 280                 285

Ile Asp Gly Val Lys Leu Glu Ser Met Gly Val Tyr Gln Ile Leu Ala
    290                 295                 300

Ile Tyr Ser Thr Val Ala Ser Ser Leu Val Leu Leu Val Ser Leu Gly
305                 310                 315                 320

Ala Ile Ser Phe Trp Met Cys Ser Asn Gly Ser Leu Gln Cys Arg Ile
                325                 330                 335

Cys Ile


<210> SEQ ID NO 3
<211> LENGTH: 338
<212> TYPE: PRT
<213> ORGANISM: Artificial
<220> FEATURE:
<223> OTHER INFORMATION: miniHA cluster1 (A/Brisbane/59/2007)

<400> SEQUENCE: 3

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Thr Cys Gly Gly Gly Gly Cys
    50                  55                  60

Asp Ala Lys Cys Gln Thr Pro Gln Gly Ala Ile Asn Ser Ser Leu Pro
65                  70                  75                  80

Phe Gln Asn Val His Pro Thr Thr Thr Gly Glu Cys Pro Lys Tyr Val
                85                  90                  95

Arg Ser Ala Lys Leu Arg Met Val Thr Gly Leu Arg Asn Ile Pro Ser
            100                 105                 110

Ile Gln Ser Gln Gly Leu Phe Gly Ala Ile Ala Gly Phe Ile Glu Gly
        115                 120                 125

Gly Trp Thr Gly Met Val Asp Gly Trp Tyr Gly Tyr His His Gln Asn
    130                 135                 140

Glu Gln Gly Ser Gly Tyr Ala Ala Asp Gln Lys Ser Thr Gln Asn Ala
145                 150                 155                 160

Ile Asn Gly Ile Thr Asn Lys Val Asn Ser Val Ile Glu Lys Met Asn
                165                 170                 175

Thr Gln Ser Thr Ala Thr Gly Lys Glu Phe Asn Lys Ser Glu Arg Arg
            180                 185                 190

Met Glu Asn Leu Asn Lys Lys Val Asp Asp Gly Phe Ile Asp Ile Trp
        195                 200                 205

Thr Tyr Asn Ala Glu Leu Leu Val Leu Leu Glu Asn Glu Arg Thr Leu
    210                 215                 220

Asp Phe His Asp Ser Asn Val Lys Asn Leu Tyr Glu Lys Val Lys Ser
225                 230                 235                 240

Gln Leu Lys Asn Asn Ala Lys Glu Ile Gly Asn Gly Cys Phe Glu Phe
                245                 250                 255

Tyr His Lys Cys Asn Asp Glu Cys Met Glu Ser Val Lys Asn Gly Thr
            260                 265                 270

Tyr Asp Tyr Pro Lys Tyr Ser Glu Glu Ser Lys Leu Asn Arg Glu Lys
```

-continued

```
        275                 280                 285

Ile Asp Gly Val Lys Leu Glu Ser Met Gly Val Tyr Gln Ile Leu Ala
    290                 295                 300

Ile Tyr Ser Thr Val Ala Ser Ser Leu Val Leu Leu Val Ser Leu Gly
305                 310                 315                 320

Ala Ile Ser Phe Trp Met Cys Ser Asn Gly Ser Leu Gln Cys Arg Ile
                325                 330                 335

Cys Ile


<210> SEQ ID NO 4
<211> LENGTH: 338
<212> TYPE: PRT
<213> ORGANISM: Artificial
<220> FEATURE:
<223> OTHER INFORMATION: miniHA cluster1+2 (A/Brisbane/59/2007)

<400> SEQUENCE: 4

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Thr Cys Gly Gly Gly Gly Cys
    50                  55                  60

Asp Ala Lys Cys Gln Thr Pro Gln Gly Ala Ile Asn Ser Ser Leu Pro
65                  70                  75                  80

Phe Gln Asn Val His Pro Thr Thr Thr Gly Glu Cys Pro Cys Tyr Val
                85                  90                  95

Arg Ser Ala Lys Leu Arg Met Val Thr Gly Leu Arg Asn Ile Pro Ser
            100                 105                 110

Ile Gln Ser Gln Gly Leu Phe Gly Ala Ile Ala Gly Phe Ile Glu Gly
        115                 120                 125

Gly Trp Thr Gly Met Val Asp Gly Trp Tyr Gly Tyr His His Gln Asn
    130                 135                 140

Glu Gln Gly Ser Gly Tyr Ala Ala Asp Gln Lys Ser Thr Gln Asn Ala
145                 150                 155                 160

Ile Asn Gly Ile Thr Asn Lys Val Asn Ser Val Ile Glu Lys Met Asn
                165                 170                 175

Thr Cys Ser Thr Ala Thr Gly Lys Glu Phe Asn Lys Ser Glu Arg Arg
            180                 185                 190

Met Glu Asn Leu Asn Lys Lys Val Asp Asp Gly Phe Ile Asp Ile Trp
        195                 200                 205

Thr Tyr Asn Ala Glu Leu Leu Val Leu Leu Glu Asn Glu Arg Thr Leu
    210                 215                 220

Asp Phe His Asp Ser Asn Val Lys Asn Leu Tyr Glu Lys Val Lys Ser
225                 230                 235                 240

Gln Leu Lys Asn Asn Ala Lys Glu Ile Gly Asn Gly Cys Phe Glu Phe
                245                 250                 255

Tyr His Lys Cys Asn Asp Glu Cys Met Glu Ser Val Lys Asn Gly Thr
            260                 265                 270

Tyr Asp Tyr Pro Lys Tyr Ser Glu Glu Ser Lys Leu Asn Arg Glu Lys
        275                 280                 285

Ile Asp Gly Val Lys Leu Glu Ser Met Gly Val Tyr Gln Ile Leu Ala
    290                 295                 300
```

```
Ile Tyr Ser Thr Val Ala Ser Ser Leu Val Leu Leu Val Ser Leu Gly
305                 310                 315                 320

Ala Ile Ser Phe Trp Met Cys Ser Asn Gly Ser Leu Gln Cys Arg Ile
                325                 330                 335

Cys Ile


<210> SEQ ID NO 5
<211> LENGTH: 338
<212> TYPE: PRT
<213> ORGANISM: Artificial
<220> FEATURE:
<223> OTHER INFORMATION: miniHA clusters1+3 (A/Brisbane/59/2007)

<400> SEQUENCE: 5

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Thr Cys Gly Gly Gly Gly Cys
    50                  55                  60

Asp Ala Lys Cys Gln Thr Pro Gln Gly Ala Ile Asn Ser Ser Leu Pro
65                  70                  75                  80

Phe Gln Asn Val His Pro Thr Thr Thr Gly Glu Cys Pro Lys Tyr Val
                85                  90                  95

Arg Ser Ala Lys Leu Arg Met Val Thr Gly Leu Arg Asn Ile Pro Ser
            100                 105                 110

Ile Gln Ser Gln Gly Leu Phe Gly Ala Ile Ala Gly Phe Ile Glu Gly
        115                 120                 125

Gly Trp Thr Gly Met Val Asp Gly Trp Tyr Gly Tyr His His Gln Asn
    130                 135                 140

Glu Gln Gly Ser Gly Tyr Ala Ala Asp Gln Lys Ser Thr Gln Asn Ala
145                 150                 155                 160

Ile Asn Gly Ile Thr Asn Lys Val Asn Ser Val Ile Glu Lys Met Asn
                165                 170                 175

Thr Gln Ser Thr Ala Thr Gly Lys Glu Cys Asn Lys Ser Glu Arg Arg
            180                 185                 190

Met Cys Asn Leu Asn Lys Lys Val Asp Asp Gly Phe Ile Asp Ile Trp
        195                 200                 205

Thr Tyr Asn Ala Glu Leu Leu Val Leu Leu Glu Asn Glu Arg Thr Leu
    210                 215                 220

Asp Phe His Asp Ser Asn Val Lys Asn Leu Tyr Glu Lys Val Lys Ser
225                 230                 235                 240

Gln Leu Lys Asn Asn Ala Lys Glu Ile Gly Asn Gly Cys Phe Glu Phe
                245                 250                 255

Tyr His Lys Cys Asn Asp Glu Cys Met Glu Ser Val Lys Asn Gly Thr
            260                 265                 270

Tyr Asp Tyr Pro Lys Tyr Ser Glu Glu Ser Lys Leu Asn Arg Glu Lys
        275                 280                 285

Ile Asp Gly Val Lys Leu Glu Ser Met Gly Val Tyr Gln Ile Leu Ala
    290                 295                 300

Ile Tyr Ser Thr Val Ala Ser Ser Leu Val Leu Leu Val Ser Leu Gly
305                 310                 315                 320
```

```
Ala Ile Ser Phe Trp Met Cys Ser Asn Gly Ser Leu Gln Cys Arg Ile
                325                 330                 335

Cys Ile


<210> SEQ ID NO 6
<211> LENGTH: 338
<212> TYPE: PRT
<213> ORGANISM: Artificial
<220> FEATURE:
<223> OTHER INFORMATION: miniHA cluster1+4 (A/Brisbane/59/2007)

<400> SEQUENCE: 6

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Thr Cys Gly Gly Gly Gly Cys
    50                  55                  60

Asp Ala Lys Cys Gln Thr Pro Gln Gly Ala Ile Asn Ser Ser Leu Pro
65                  70                  75                  80

Phe Gln Asn Val His Pro Thr Thr Thr Gly Glu Cys Pro Lys Tyr Val
                85                  90                  95

Arg Ser Ala Lys Leu Arg Met Val Thr Gly Leu Arg Asn Ile Pro Ser
            100                 105                 110

Ile Gln Ser Gln Gly Leu Phe Gly Ala Ile Ala Gly Phe Ile Glu Gly
        115                 120                 125

Gly Trp Thr Gly Met Val Asp Gly Trp Tyr Gly Tyr His His Gln Asn
    130                 135                 140

Glu Gln Gly Ser Gly Tyr Ala Ala Asp Gln Lys Ser Thr Gln Asn Ala
145                 150                 155                 160

Ile Asn Gly Ile Thr Asn Lys Val Asn Ser Val Ile Glu Lys Met Asn
                165                 170                 175

Thr Gln Ser Thr Ala Thr Gly Lys Glu Phe Asn Lys Ser Glu Arg Arg
            180                 185                 190

Met Glu Asn Leu Asn Lys Lys Val Asp Asp Gly Phe Ile Asp Ile Trp
        195                 200                 205

Thr Tyr Asn Ala Glu Leu Leu Val Leu Leu Glu Asn Glu Arg Thr Leu
    210                 215                 220

Asp Phe His Asp Ser Asn Val Lys Asn Leu Tyr Glu Lys Val Lys Ser
225                 230                 235                 240

Gln Leu Lys Asn Asn Ala Lys Glu Ile Gly Asn Gly Cys Phe Glu Phe
                245                 250                 255

Tyr His Lys Cys Asn Asp Glu Cys Met Glu Ser Val Lys Asn Gly Thr
            260                 265                 270

Tyr Asp Tyr Pro Lys Tyr Ser Glu Glu Ser Lys Leu Asn Arg Glu Lys
        275                 280                 285

Ile Asp Gly Val Lys Leu Glu Ser Met Gly Val Tyr Gln Ile Leu Ala
    290                 295                 300

Ile Tyr Ser Thr Val Ala Ser Ser Leu Val Leu Leu Val Ser Leu Gly
305                 310                 315                 320

Ala Ile Ser Phe Trp Met Cys Ser Asn Gly Ser Leu Gln Cys Arg Ile
                325                 330                 335

Cys Ile
```

```
<210> SEQ ID NO 7
<211> LENGTH: 338
<212> TYPE: PRT
<213> ORGANISM: Artificial
<220> FEATURE:
<223> OTHER INFORMATION: miniHA cluster1+2+3 (A/Brisbane/59/2007)

<400> SEQUENCE: 7

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Thr Cys Gly Gly Gly Gly Cys
    50                  55                  60

Asp Ala Lys Cys Gln Thr Pro Gln Gly Ala Ile Asn Ser Ser Leu Pro
65                  70                  75                  80

Phe Gln Asn Val His Pro Thr Thr Thr Gly Glu Cys Pro Cys Tyr Val
                85                  90                  95

Arg Ser Ala Lys Leu Arg Met Val Thr Gly Leu Arg Asn Ile Pro Ser
            100                 105                 110

Ile Gln Ser Gln Gly Leu Phe Gly Ala Ile Ala Gly Phe Ile Glu Gly
        115                 120                 125

Gly Trp Thr Gly Met Val Asp Gly Trp Tyr Gly Tyr His His Gln Asn
    130                 135                 140

Glu Gln Gly Ser Gly Tyr Ala Ala Asp Gln Lys Ser Thr Gln Asn Ala
145                 150                 155                 160

Ile Asn Gly Ile Thr Asn Lys Val Asn Ser Val Ile Glu Lys Met Asn
                165                 170                 175

Thr Cys Ser Thr Ala Thr Gly Lys Glu Cys Asn Lys Ser Glu Arg Arg
            180                 185                 190

Met Cys Asn Leu Asn Lys Lys Val Asp Asp Gly Phe Ile Asp Ile Trp
        195                 200                 205

Thr Tyr Asn Ala Glu Leu Leu Val Leu Leu Glu Asn Glu Arg Thr Leu
    210                 215                 220

Asp Phe His Asp Ser Asn Val Lys Asn Leu Tyr Glu Lys Val Lys Ser
225                 230                 235                 240

Gln Leu Lys Asn Asn Ala Lys Glu Ile Gly Asn Gly Cys Phe Glu Phe
                245                 250                 255

Tyr His Lys Cys Asn Asp Glu Cys Met Glu Ser Val Lys Asn Gly Thr
            260                 265                 270

Tyr Asp Tyr Pro Lys Tyr Ser Glu Glu Ser Lys Leu Asn Arg Glu Lys
        275                 280                 285

Ile Asp Gly Val Lys Leu Glu Ser Met Gly Val Tyr Gln Ile Leu Ala
    290                 295                 300

Ile Tyr Ser Thr Val Ala Ser Ser Leu Val Leu Leu Val Ser Leu Gly
305                 310                 315                 320

Ala Ile Ser Phe Trp Met Cys Ser Asn Gly Ser Leu Gln Cys Arg Ile
                325                 330                 335

Cys Ile


<210> SEQ ID NO 8
<211> LENGTH: 338
```

<212> TYPE: PRT
<213> ORGANISM: Artificial
<220> FEATURE:
<223> OTHER INFORMATION: miniHA cluster1+2+3+4 (A/Brisbane/59/2007)

<400> SEQUENCE: 8

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Thr Cys Gly Gly Gly Gly Cys
    50                  55                  60

Asp Ala Lys Cys Gln Thr Pro Gln Gly Ala Ile Asn Ser Ser Leu Pro
65                  70                  75                  80

Phe Gln Asn Val His Pro Thr Thr Thr Gly Glu Cys Pro Cys Tyr Val
                85                  90                  95

Arg Ser Ala Lys Leu Arg Met Val Thr Gly Leu Arg Asn Ile Pro Ser
            100                 105                 110

Ile Gln Ser Gln Gly Leu Phe Gly Ala Ile Ala Gly Phe Ile Glu Gly
        115                 120                 125

Gly Trp Thr Gly Met Val Asp Gly Trp Tyr Gly Tyr His His Gln Asn
    130                 135                 140

Glu Gln Gly Ser Gly Tyr Ala Ala Asp Gln Lys Ser Thr Gln Asn Ala
145                 150                 155                 160

Ile Asn Gly Ile Thr Asn Lys Val Asn Ser Val Ile Glu Lys Met Asn
                165                 170                 175

Thr Cys Ser Thr Ala Thr Gly Lys Glu Cys Asn Lys Ser Glu Arg Arg
            180                 185                 190

Met Cys Asn Leu Asn Lys Lys Val Asp Asp Gly Phe Ile Asp Ile Trp
        195                 200                 205

Thr Tyr Asn Ala Glu Leu Leu Val Leu Leu Glu Asn Glu Arg Thr Leu
    210                 215                 220

Asp Phe His Asp Ser Asn Val Lys Asn Leu Tyr Glu Lys Val Lys Ser
225                 230                 235                 240

Gln Leu Lys Asn Asn Ala Lys Glu Ile Gly Asn Gly Cys Phe Glu Phe
                245                 250                 255

Tyr His Lys Cys Asn Asp Glu Cys Met Glu Ser Val Lys Asn Gly Thr
            260                 265                 270

Tyr Asp Ser Pro Lys Tyr Ser Glu Glu Ser Lys Leu Asn Arg Glu Lys
        275                 280                 285

Ile Asp Gly Val Lys Leu Glu Ser Met Gly Val Tyr Gln Ile Leu Ala
    290                 295                 300

Ile Tyr Ser Thr Val Ala Ser Ser Leu Val Leu Leu Val Ser Leu Gly
305                 310                 315                 320

Ala Ile Ser Phe Trp Met Cys Ser Asn Gly Ser Leu Gln Cys Arg Ile
                325                 330                 335

Cys Ile
```

<210> SEQ ID NO 9
<211> LENGTH: 338
<212> TYPE: PRT
<213> ORGANISM: Artificial
<220> FEATURE:
<223> OTHER INFORMATION: mini1 cluster11 (A/Brisbane/59/2007)

<400> SEQUENCE: 9

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Ser His Asn Gly Lys Thr Cys Gly Gly Gly Gly Cys
50 55 60

Asp Ala Lys Cys Gln Thr Pro Gln Gly Ala Ile Asn Ser Ser Leu Pro
65 70 75 80

Phe Gln Asn Val His Pro Thr Thr Thr Gly Glu Cys Pro Lys Tyr Val
85 90 95

Arg Ser Ala Lys Leu Arg Met Val Thr Gly Leu Arg Asn Ile Pro Ser
100 105 110

Ile Gln Ser Gln Gly Leu Phe Gly Ala Ile Ala Gly Phe Ile Glu Gly
115 120 125

Gly Trp Thr Gly Met Val Asp Gly Trp Tyr Gly Tyr His His Gln Asn
130 135 140

Glu Gln Gly Ser Gly Tyr Ala Ala Asp Gln Lys Ser Thr Gln Asn Ala
145 150 155 160

Ile Asn Gly Ile Thr Asn Lys Val Asn Ser Val Ile Glu Lys Met Asn
165 170 175

Thr Gln Ser Thr Ala Thr Gly Lys Glu Phe Asn Lys Ser Glu Arg Arg
180 185 190

Ile Glu Asn Leu Asn Lys Lys Ile Asp Asp Gly Phe Ile Asp Ile Trp
195 200 205

Thr Tyr Asn Ala Glu Leu Leu Val Leu Leu Glu Asn Glu Arg Thr Leu
210 215 220

Asp Phe His Asp Ser Asn Val Lys Asn Leu Tyr Glu Lys Val Lys Ser
225 230 235 240

Gln Leu Lys Asn Asn Ala Lys Glu Ile Gly Asn Gly Cys Phe Glu Phe
245 250 255

Tyr His Lys Cys Asn Asp Glu Cys Met Glu Ser Val Lys Asn Gly Thr
260 265 270

Tyr Asp Tyr Pro Lys Tyr Ser Glu Glu Ser Lys Leu Asn Arg Glu Lys
275 280 285

Ile Asp Gly Val Lys Leu Glu Ser Met Gly Val Tyr Gln Ile Leu Ala
290 295 300

Ile Tyr Ser Thr Val Ala Ser Ser Leu Val Leu Leu Val Ser Leu Gly
305 310 315 320

Ala Ile Ser Phe Trp Met Cys Ser Asn Gly Ser Leu Gln Cys Arg Ile
325 330 335

Cys Ile

<210> SEQ ID NO 10
<211> LENGTH: 301
<212> TYPE: PRT
<213> ORGANISM: Artificial
<220> FEATURE:
<223> OTHER INFORMATION: mini2 cluster11 (A/Brisbane/59/2007)

<400> SEQUENCE: 10

Met Lys Val Lys Leu Leu Val Leu Leu Cys Thr Phe Thr Ala Thr Tyr

```
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Arg Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Phe Asn Lys Ser Glu Arg Arg Ile Glu Asn Leu Asn
145                 150                 155                 160

Lys Lys Ile Asp Asp Gly Phe Ile Asp Ile Trp Thr Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 11
<211> LENGTH: 320
<212> TYPE: PRT
<213> ORGANISM: Artificial
<220> FEATURE:
<223> OTHER INFORMATION: mini3 cluster11 (A/Brisbane/59/2007)

<400> SEQUENCE: 11

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser Gly Gly Gly Asn Ser Ser Leu Pro Phe Gln
    50                  55                  60

Asn Val His Pro Thr Thr Thr Gly Glu Cys Pro Lys Tyr Val Arg Ser
```

-continued

```
65                  70                  75                  80

Ala Lys Leu Arg Met Val Thr Gly Leu Arg Asn Ile Pro Ser Ile Gln
                85                  90                  95

Ser Gln Gly Leu Phe Gly Ala Ile Ala Gly Phe Ile Glu Gly Gly Trp
            100                 105                 110

Thr Gly Met Val Asp Gly Trp Tyr Gly Tyr His His Gln Asn Glu Gln
        115                 120                 125

Gly Ser Gly Tyr Ala Ala Asp Gln Lys Ser Thr Gln Asn Ala Ile Asn
    130                 135                 140

Gly Ile Thr Asn Lys Val Asn Ser Val Ile Glu Lys Met Asn Thr Gln
145                 150                 155                 160

Ser Thr Ala Thr Gly Lys Glu Phe Asn Lys Ser Glu Arg Arg Ile Glu
                165                 170                 175

Asn Leu Asn Lys Lys Ile Asp Asp Gly Phe Ile Asp Ile Trp Thr Tyr
            180                 185                 190

Asn Ala Glu Leu Leu Val Leu Leu Glu Asn Glu Arg Thr Leu Asp Phe
        195                 200                 205

His Asp Ser Asn Val Lys Asn Leu Tyr Glu Lys Val Lys Ser Gln Leu
    210                 215                 220

Lys Asn Asn Ala Lys Glu Ile Gly Asn Gly Cys Phe Glu Phe Tyr His
225                 230                 235                 240

Lys Cys Asn Asp Glu Cys Met Glu Ser Val Lys Asn Gly Thr Tyr Asp
                245                 250                 255

Tyr Pro Lys Tyr Ser Glu Glu Ser Lys Leu Asn Arg Glu Lys Ile Asp
            260                 265                 270

Gly Val Lys Leu Glu Ser Met Gly Val Tyr Gln Ile Leu Ala Ile Tyr
        275                 280                 285

Ser Thr Val Ala Ser Ser Leu Val Leu Leu Val Ser Leu Gly Ala Ile
    290                 295                 300

Ser Phe Trp Met Cys Ser Asn Gly Ser Leu Gln Cys Arg Ile Cys Ile
305                 310                 315                 320


<210> SEQ ID NO 12
<211> LENGTH: 307
<212> TYPE: PRT
<213> ORGANISM: Artificial
<220> FEATURE:
<223> OTHER INFORMATION: mini4 cluster11 (A/Brisbane/59/2007)

<400> SEQUENCE: 12

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Gly Gly Gly Glu Cys Pro Lys Tyr
    50                  55                  60

Val Arg Ser Ala Lys Leu Arg Met Val Thr Gly Leu Arg Asn Ile Pro
65                  70                  75                  80

Ser Ile Gln Ser Gln Gly Leu Phe Gly Ala Ile Ala Gly Phe Ile Glu
                85                  90                  95

Gly Gly Trp Thr Gly Met Val Asp Gly Trp Tyr Gly Tyr His His Gln
            100                 105                 110

Asn Glu Gln Gly Ser Gly Tyr Ala Ala Asp Gln Lys Ser Thr Gln Asn
```

```
        115                 120                 125

Ala Ile Asn Gly Ile Thr Asn Lys Val Asn Ser Val Ile Glu Lys Met
    130                 135                 140

Asn Thr Gln Ser Thr Ala Thr Gly Lys Glu Phe Asn Lys Ser Glu Arg
145                 150                 155                 160

Arg Ile Glu Asn Leu Asn Lys Lys Ile Asp Asp Gly Phe Ile Asp Ile
                165                 170                 175

Trp Thr Tyr Asn Ala Glu Leu Leu Val Leu Leu Glu Asn Glu Arg Thr
            180                 185                 190

Leu Asp Phe His Asp Ser Asn Val Lys Asn Leu Tyr Glu Lys Val Lys
        195                 200                 205

Ser Gln Leu Lys Asn Asn Ala Lys Glu Ile Gly Asn Gly Cys Phe Glu
    210                 215                 220

Phe Tyr His Lys Cys Asn Asp Glu Cys Met Glu Ser Val Lys Asn Gly
225                 230                 235                 240

Thr Tyr Asp Tyr Pro Lys Tyr Ser Glu Glu Ser Lys Leu Asn Arg Glu
                245                 250                 255

Lys Ile Asp Gly Val Lys Leu Glu Ser Met Gly Val Tyr Gln Ile Leu
            260                 265                 270

Ala Ile Tyr Ser Thr Val Ala Ser Ser Leu Val Leu Leu Val Ser Leu
        275                 280                 285

Gly Ala Ile Ser Phe Trp Met Cys Ser Asn Gly Ser Leu Gln Cys Arg
    290                 295                 300

Ile Cys Ile
305


<210> SEQ ID NO 13
<211> LENGTH: 338
<212> TYPE: PRT
<213> ORGANISM: Artificial
<220> FEATURE:
<223> OTHER INFORMATION: mini1 cluster11+5 (A/Brisbane/59/2007)

<400> SEQUENCE: 13

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Thr Cys Gly Gly Gly Gly Cys
    50                  55                  60

Asp Ala Lys Cys Gln Thr Pro Gln Gly Ala Ile Asn Ser Ser Leu Pro
65                  70                  75                  80

Phe Gln Asn Val His Pro Thr Thr Thr Gly Glu Cys Pro Lys Tyr Val
                85                  90                  95

Cys Ser Ala Lys Leu Arg Met Val Thr Gly Leu Arg Asn Ile Pro Ser
            100                 105                 110

Ile Gln Ser Gln Gly Leu Phe Gly Ala Ile Ala Gly Phe Ile Glu Gly
        115                 120                 125

Gly Trp Thr Gly Met Val Asp Gly Trp Tyr Gly Tyr His His Gln Asn
    130                 135                 140

Glu Gln Gly Ser Gly Tyr Ala Ala Asp Gln Lys Ser Thr Gln Asn Ala
145                 150                 155                 160

Ile Asn Gly Ile Thr Asn Lys Val Asn Ser Val Ile Glu Lys Met Asn
```

```
                165                 170                 175

Thr Gln Ser Thr Ala Thr Gly Lys Glu Phe Asn Lys Ser Glu Arg Arg
            180                 185                 190

Ile Glu Asn Leu Asn Lys Lys Ile Asp Asp Gly Phe Ile Asp Ile Trp
        195                 200                 205

Cys Tyr Asn Ala Glu Leu Leu Val Leu Leu Glu Asn Glu Arg Thr Leu
    210                 215                 220

Asp Phe His Asp Ser Asn Val Lys Asn Leu Tyr Glu Lys Val Lys Ser
225                 230                 235                 240

Gln Leu Lys Asn Asn Ala Lys Glu Ile Gly Asn Gly Cys Phe Glu Phe
                245                 250                 255

Tyr His Lys Cys Asn Asp Glu Cys Met Glu Ser Val Lys Asn Gly Thr
            260                 265                 270

Tyr Asp Tyr Pro Lys Tyr Ser Glu Glu Ser Lys Leu Asn Arg Glu Lys
        275                 280                 285

Ile Asp Gly Val Lys Leu Glu Ser Met Gly Val Tyr Gln Ile Leu Ala
    290                 295                 300

Ile Tyr Ser Thr Val Ala Ser Ser Leu Val Leu Leu Val Ser Leu Gly
305                 310                 315                 320

Ala Ile Ser Phe Trp Met Cys Ser Asn Gly Ser Leu Gln Cys Arg Ile
                325                 330                 335

Cys Ile
```

<210> SEQ ID NO 14
<211> LENGTH: 301
<212> TYPE: PRT
<213> ORGANISM: Artificial
<220> FEATURE:
<223> OTHER INFORMATION: mini2 cluster11+5 (A/Brisbane/59/2007)

<400> SEQUENCE: 14

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Phe Asn Lys Ser Glu Arg Arg Ile Glu Asn Leu Asn
145                 150                 155                 160

Lys Lys Ile Asp Asp Gly Phe Ile Asp Ile Trp Cys Tyr Asn Ala Glu
                165                 170                 175

Leu Leu Val Leu Leu Glu Asn Glu Arg Thr Leu Asp Phe His Asp Ser
            180                 185                 190
```

```
Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 15
<211> LENGTH: 320
<212> TYPE: PRT
<213> ORGANISM: Artificial
<220> FEATURE:
<223> OTHER INFORMATION: mini3 cluster11+5

<400> SEQUENCE: 15

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser Gly Gly Gly Gly Asn Ser Ser Leu Pro Phe Gln
    50                  55                  60

Asn Val His Pro Thr Thr Thr Gly Glu Cys Pro Lys Tyr Val Cys Ser
65                  70                  75                  80

Ala Lys Leu Arg Met Val Thr Gly Leu Arg Asn Ile Pro Ser Ile Gln
                85                  90                  95

Ser Gln Gly Leu Phe Gly Ala Ile Ala Gly Phe Ile Glu Gly Gly Trp
            100                 105                 110

Thr Gly Met Val Asp Gly Trp Tyr Gly Tyr His His Gln Asn Glu Gln
        115                 120                 125

Gly Ser Gly Tyr Ala Ala Asp Gln Lys Ser Thr Gln Asn Ala Ile Asn
    130                 135                 140

Gly Ile Thr Asn Lys Val Asn Ser Val Ile Glu Lys Met Asn Thr Gln
145                 150                 155                 160

Ser Thr Ala Thr Gly Lys Glu Phe Asn Lys Ser Glu Arg Arg Ile Glu
                165                 170                 175

Asn Leu Asn Lys Lys Ile Asp Asp Gly Phe Ile Asp Ile Trp Cys Tyr
            180                 185                 190

Asn Ala Glu Leu Leu Val Leu Leu Glu Asn Glu Arg Thr Leu Asp Phe
        195                 200                 205

His Asp Ser Asn Val Lys Asn Leu Tyr Glu Lys Val Lys Ser Gln Leu
    210                 215                 220

Lys Asn Asn Ala Lys Glu Ile Gly Asn Gly Cys Phe Glu Phe Tyr His
225                 230                 235                 240

Lys Cys Asn Asp Glu Cys Met Glu Ser Val Lys Asn Gly Thr Tyr Asp
                245                 250                 255
```

```
Tyr Pro Lys Tyr Ser Glu Glu Ser Lys Leu Asn Arg Glu Lys Ile Asp
            260                 265                 270

Gly Val Lys Leu Glu Ser Met Gly Val Tyr Gln Ile Leu Ala Ile Tyr
        275                 280                 285

Ser Thr Val Ala Ser Ser Leu Val Leu Leu Val Ser Leu Gly Ala Ile
    290                 295                 300

Ser Phe Trp Met Cys Ser Asn Gly Ser Leu Gln Cys Arg Ile Cys Ile
305                 310                 315                 320


<210> SEQ ID NO 16
<211> LENGTH: 307
<212> TYPE: PRT
<213> ORGANISM: Artificial
<220> FEATURE:
<223> OTHER INFORMATION: mini4 cluster11+5 (A/Brisbane/59/2007)

<400> SEQUENCE: 16

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Gly Gly Gly Glu Cys Pro Lys Tyr
    50                  55                  60

Val Cys Ser Ala Lys Leu Arg Met Val Thr Gly Leu Arg Asn Ile Pro
65                  70                  75                  80

Ser Ile Gln Ser Gln Gly Leu Phe Gly Ala Ile Ala Gly Phe Ile Glu
                85                  90                  95

Gly Gly Trp Thr Gly Met Val Asp Gly Trp Tyr Gly Tyr His His Gln
            100                 105                 110

Asn Glu Gln Gly Ser Gly Tyr Ala Ala Asp Gln Lys Ser Thr Gln Asn
        115                 120                 125

Ala Ile Asn Gly Ile Thr Asn Lys Val Asn Ser Val Ile Glu Lys Met
    130                 135                 140

Asn Thr Gln Ser Thr Ala Thr Gly Lys Glu Phe Asn Lys Ser Glu Arg
145                 150                 155                 160

Arg Ile Glu Asn Leu Asn Lys Lys Ile Asp Asp Gly Phe Ile Asp Ile
                165                 170                 175

Trp Cys Tyr Asn Ala Glu Leu Leu Val Leu Leu Glu Asn Glu Arg Thr
            180                 185                 190

Leu Asp Phe His Asp Ser Asn Val Lys Asn Leu Tyr Glu Lys Val Lys
        195                 200                 205

Ser Gln Leu Lys Asn Asn Ala Lys Glu Ile Gly Asn Gly Cys Phe Glu
    210                 215                 220

Phe Tyr His Lys Cys Asn Asp Glu Cys Met Glu Ser Val Lys Asn Gly
225                 230                 235                 240

Thr Tyr Asp Tyr Pro Lys Tyr Ser Glu Glu Ser Lys Leu Asn Arg Glu
                245                 250                 255

Lys Ile Asp Gly Val Lys Leu Glu Ser Met Gly Val Tyr Gln Ile Leu
            260                 265                 270

Ala Ile Tyr Ser Thr Val Ala Ser Ser Leu Val Leu Leu Val Ser Leu
        275                 280                 285

Gly Ala Ile Ser Phe Trp Met Cys Ser Asn Gly Ser Leu Gln Cys Arg
    290                 295                 300
```

```
Ile Cys Ile
305


<210> SEQ ID NO 17
<211> LENGTH: 17
<212> TYPE: PRT
<213> ORGANISM: Artificial
<220> FEATURE:
<223> OTHER INFORMATION: H1 consensus sequence residues 402-418
<220> FEATURE:
<221> NAME/KEY: MISC_FEATURE
<222> LOCATION: (14)..(14)
<223> OTHER INFORMATION: H or K
<220> FEATURE:
<221> NAME/KEY: MISC_FEATURE
<222> LOCATION: (17)..(17)
<223> OTHER INFORMATION: K or R

<400> SEQUENCE: 17

Met Asn Thr Gln Phe Thr Ala Val Gly Lys Glu Phe Asn Xaa Leu Glu
1               5                   10                  15

Xaa


<210> SEQ ID NO 18
<211> LENGTH: 121
<212> TYPE: PRT
<213> ORGANISM: Artificial
<220> FEATURE:
<223> OTHER INFORMATION: CR9114 VH region

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
                85                  90                  95

Ala Arg His Gly Asn Tyr Tyr Tyr Tyr Ser Gly Met Asp Val Trp Gly
            100                 105                 110

Gln Gly Thr Thr Val Thr Val Ser Ser
        115                 120


<210> SEQ ID NO 19
<211> LENGTH: 110
<212> TYPE: PRT
<213> ORGANISM: Artificial
<220> FEATURE:
<223> OTHER INFORMATION: CR9114 VL region

<400> SEQUENCE: 19

Ser Tyr Val Leu Thr Gln Pro Pro Ala Val Ser Gly Thr Pro Gly Gln
1               5                   10                  15

Arg Val Thr Ile Ser Cys Ser Gly Ser Asp Ser Asn Ile Gly Arg Arg
            20                  25                  30

Ser Val Asn Trp Tyr Gln Gln Phe Pro Gly Thr Ala Pro Lys Leu Leu
        35                  40                  45
```

-continued

```
Ile Tyr Ser Asn Asp Gln Arg Pro Ser Val Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Ser Leu
                85                  90                  95

Lys Gly Ala Val Phe Gly Gly Gly Thr Gln Leu Thr Val Leu
            100                 105                 110
```

<210> SEQ ID NO 20
<211> LENGTH: 121
<212> TYPE: PRT
<213> ORGANISM: Artificial
<220> FEATURE:
<223> OTHER INFORMATION: CR6261 VH region

<400> SEQUENCE: 20

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120
```

<210> SEQ ID NO 21
<211> LENGTH: 112
<212> TYPE: PRT
<213> ORGANISM: Artificial
<220> FEATURE:
<223> OTHER INFORMATION: CR6261 VL region

<400> SEQUENCE: 21

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asp
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asn Tyr Tyr Cys Ala Thr Trp Asp Arg Arg Pro
                85                  90                  95

Thr Ala Tyr Val Val Phe Gly Gly Gly Thr Lys Leu Thr Val Leu Gly
            100                 105                 110
```

<210> SEQ ID NO 22
<211> LENGTH: 116
<212> TYPE: PRT
<213> ORGANISM: Artificial
<220> FEATURE:
<223> OTHER INFORMATION: CR8057 VH protein

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Asp Ser Val Ile
            20                  25                  30

Phe Met Ser Trp Val Arg Gln Ala Pro Gly Lys Gly Leu Glu Cys Val
        35                  40                  45

Ser Ile Ile Tyr Ile Asp Asp Ser Thr Tyr Tyr Ala Asp Ser Val Lys
    50                  55                  60

Gly Arg Phe Thr Ile Ser Arg His Asn Ser Met Gly Thr Val Phe Leu
65                  70                  75                  80

Glu Met Asn Ser Leu Arg Pro Asp Asp Thr Ala Val Tyr Tyr Cys Ala
                85                  90                  95

Thr Glu Ser Gly Asp Phe Gly Asp Gln Thr Gly Pro Tyr His Tyr Tyr
            100                 105                 110

Ala Met Asp Val
        115
```

<210> SEQ ID NO 23
<211> LENGTH: 100
<212> TYPE: PRT
<213> ORGANISM: Artificial
<220> FEATURE:
<223> OTHER INFORMATION: CR8057 VL protein

<400> SEQUENCE: 23

```
Gln Ser Ala Leu Thr Gln Pro Ala Ser Val Ser Gly Ser Pro Gly Gln
1               5                   10                  15

Ser Ile Thr Ile Ser Cys Thr Gly Ser Ser Gly Asp Ile Gly Gly Tyr
            20                  25                  30

Asn Ala Val Ser Trp Tyr Gln His His Pro Gly Lys Ala Pro Lys Leu
        35                  40                  45

Met Ile Tyr Glu Val Thr Ser Arg Pro Ser Gly Val Ser Asp Arg Phe
    50                  55                  60

Ser Ala Ser Arg Ser Gly Asp Thr Ala Ser Leu Thr Val Ser Gly Leu
65                  70                  75                  80

Gln Ala Glu Asp Glu Ala His Tyr Tyr Cys Cys Ser Phe Ala Asp Ser
                85                  90                  95

Asn Ile Leu Ile
            100
```

<210> SEQ ID NO 24
<211> LENGTH: 338
<212> TYPE: PRT
<213> ORGANISM: Artificial
<220> FEATURE:
<223> OTHER INFORMATION: HA construct according to Steel

<400> SEQUENCE: 24

```
Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30
```

```
Val Asp Thr Val Leu Glu Lys Asn Val Thr Val Thr His Ser Val Asn
        35                  40                  45

Leu Leu Glu Asp Ser His Asn Gly Lys Leu Cys Gly Gly Gly Gly Cys
    50                  55                  60

Asn Thr Lys Cys Gln Thr Pro Leu Gly Ala Ile Asn Ser Ser Leu Pro
65                  70                  75                  80

Tyr Gln Asn Ile His Pro Val Thr Ile Gly Glu Cys Pro Lys Tyr Val
                85                  90                  95

Arg Ser Ala Lys Leu Arg Met Val Thr Gly Leu Arg Asn Ile Pro Ser
            100                 105                 110

Ile Gln Ser Arg Gly Leu Phe Gly Ala Ile Ala Gly Phe Ile Glu Gly
        115                 120                 125

Gly Trp Thr Gly Met Ile Asp Gly Trp Tyr Gly Tyr His His Gln Asn
    130                 135                 140

Glu Gln Gly Ser Gly Tyr Ala Ala Asp Gln Lys Ser Thr Gln Asn Ala
145                 150                 155                 160

Ile Asn Gly Ile Thr Asn Lys Val Asn Ser Val Ile Glu Lys Met Asn
                165                 170                 175

Ile Gln Phe Thr Ala Val Gly Lys Glu Phe Asn Lys Leu Glu Lys Arg
            180                 185                 190

Met Glu Asn Leu Asn Asn Lys Val Asp Asp Gly Phe Leu Asp Ile Trp
        195                 200                 205

Thr Tyr Asn Ala Glu Leu Leu Val Leu Leu Glu Asn Glu Arg Thr Leu
    210                 215                 220

Asp Phe His Asp Ser Asn Val Lys Asn Leu Tyr Glu Lys Val Lys Ser
225                 230                 235                 240

Gln Leu Lys Asn Asn Ala Lys Glu Ile Gly Asn Gly Cys Phe Glu Phe
                245                 250                 255

Tyr His Lys Cys Asp Asn Glu Cys Met Glu Ser Val Arg Asn Gly Thr
            260                 265                 270

Tyr Asp Tyr Pro Lys Tyr Ser Glu Glu Ser Lys Leu Asn Arg Glu Lys
        275                 280                 285

Val Asp Gly Val Lys Leu Glu Ser Met Gly Ile Tyr Gln Ile Leu Ala
    290                 295                 300

Ile Tyr Ser Thr Val Ala Ser Ser Leu Val Leu Leu Val Ser Leu Gly
305                 310                 315                 320

Ala Ile Ser Phe Trp Met Cys Ser Asn Gly Ser Leu Gln Cys Arg Ile
                325                 330                 335

Cys Ile


<210> SEQ ID NO 25
<211> LENGTH: 8
<212> TYPE: PRT
<213> ORGANISM: Artificial
<220> FEATURE:
<223> OTHER INFORMATION: CR9114 HC CDR1

<400> SEQUENCE: 25

Gly Gly Thr Ser Asn Asn Tyr Ala
1               5


<210> SEQ ID NO 26
<211> LENGTH: 8
<212> TYPE: PRT
<213> ORGANISM: Artificial
<220> FEATURE:
```

<223> OTHER INFORMATION: CR9114 HC CDR2

<400> SEQUENCE: 26

Ile Ser Pro Ile Phe Gly Ser Thr
1 5

<210> SEQ ID NO 27
<211> LENGTH: 14
<212> TYPE: PRT
<213> ORGANISM: Artificial
<220> FEATURE:
<223> OTHER INFORMATION: CR9114 HC CDR3

<400> SEQUENCE: 27

Ala Arg His Gly Asn Tyr Tyr Tyr Tyr Ser Gly Met Asp Val
1 5 10

<210> SEQ ID NO 28
<211> LENGTH: 8
<212> TYPE: PRT
<213> ORGANISM: Artificial
<220> FEATURE:
<223> OTHER INFORMATION: CR9114 LC CDR1

<400> SEQUENCE: 28

Asp Ser Asn Ile Gly Arg Arg Ser
1 5

<210> SEQ ID NO 29
<211> LENGTH: 3
<212> TYPE: PRT
<213> ORGANISM: Artificial
<220> FEATURE:
<223> OTHER INFORMATION: LC CDR2

<400> SEQUENCE: 29

Ser Asn Asp
1

<210> SEQ ID NO 30
<211> LENGTH: 11
<212> TYPE: PRT
<213> ORGANISM: Artificial
<220> FEATURE:
<223> OTHER INFORMATION: CR9114 LC CDR3

<400> SEQUENCE: 30

Ala Ala Trp Asp Asp Ser Leu Lys Gly Ala Val
1 5 10

<210> SEQ ID NO 31
<211> LENGTH: 560
<212> TYPE: PRT
<213> ORGANISM: Artificial
<220> FEATURE:
<223> OTHER INFORMATION: H7 full length HA (A/Mallard/Netherlands/2000)

<400> SEQUENCE: 31

Met Asn Thr Gln Ile Leu Val Phe Ala Leu Met Ala Ile Ile Pro Thr
1 5 10 15

Asn Ala Asp Lys Ile Cys Leu Gly His His Ala Val Ser Asn Gly Thr
20 25 30

Lys Val Asn Thr Leu Thr Glu Arg Gly Val Glu Val Val Asn Ala Thr
35 40 45

Glu Thr Val Glu Arg Thr Asn Val Pro Arg Ile Cys Ser Lys Gly Lys

-continued

```
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Thr Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
            180                 185                 190

His Ser Gly Ser Thr Thr Glu Gln Thr Lys Leu Tyr Gly Ser Gly Asn
        195                 200                 205

Lys Leu Ile Thr Val Gly Ser Ser Asn Tyr Gln Gln Ser Phe Val Pro
    210                 215                 220

Ser Pro Gly Ala Arg Pro Gln Val Asn Gly Gln Ser Gly Arg Ile Asp
225                 230                 235                 240

Phe His Trp Leu Ile Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
                405                 410                 415

Gly Asn Val Ile Asn Trp Thr Arg Asp Ser Met Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asn Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480
```

```
His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Ala Met Gly Leu
    530                 535                 540

Val Phe Ile Cys Val Lys Asn Gly Asn Met Arg Cys Thr Ile Cys Ile
545                 550                 555                 560


<210> SEQ ID NO 32
<211> LENGTH: 21
<212> TYPE: PRT
<213> ORGANISM: Artificial
<220> FEATURE:
<223> OTHER INFORMATION: H7 consensus sequence residues 394-414
<220> FEATURE:
<221> NAME/KEY: misc_feature
<222> LOCATION: (3)..(3)
<223> OTHER INFORMATION: E, D or G
<220> FEATURE:
<221> NAME/KEY: misc_feature
<222> LOCATION: (17)..(17)
<223> OTHER INFORMATION: N, T or S
<220> FEATURE:
<221> NAME/KEY: misc_feature
<222> LOCATION: (19)..(19)
<223> OTHER INFORMATION: I or V
<220> FEATURE:
<221> NAME/KEY: misc_feature
<222> LOCATION: (21)..(21)
<223> OTHER INFORMATION: Q or K

<400> SEQUENCE: 32

Leu Ile Xaa Lys Thr Asn Gln Gln Phe Glu Leu Ile Asp Asn Glu Phe
1               5                   10                  15

Xaa Glu Xaa Glu Xaa
            20


<210> SEQ ID NO 33
<211> LENGTH: 301
<212> TYPE: PRT
<213> ORGANISM: Artificial
<220> FEATURE:
<223> OTHER INFORMATION: H7 mini2 (A/Mallard/Netherlands/12/2000)

<400> SEQUENCE: 33

Met Asn Thr Gln Ile Leu Val Phe Ala Leu Met Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Gly Gly Gly Gly Arg Tyr Val Lys Gln Glu Ser Leu
    50                  55                  60

Leu Leu Ala Thr Gly Met Lys Asn Val Pro Glu Ile Pro Lys Gly Gln
65                  70                  75                  80

Gly Leu Phe Gly Ala Ile Ala Gly Phe Ile Glu Asn Gly Trp Glu Gly
                85                  90                  95

Leu Ile Asp Gly Trp Tyr Gly Phe Arg His Gln Asn Ala Gln Gly Glu
            100                 105                 110
```

-continued

```
Gly Thr Ala Ala Asp Tyr Lys Ser Thr Gln Ser Ala Ile Asp Gln Ile
        115                 120                 125

Thr Gly Lys Leu Asn Arg Leu Ile Glu Lys Thr Asn Gln Gln Phe Glu
    130                 135                 140

Leu Ile Asp Asn Glu Phe Thr Glu Val Glu Lys Gln Ile Gly Asn Val
145                 150                 155                 160

Ile Asn Trp Thr Arg Asp Ser Met Thr Glu Val Trp Ser Tyr Asn Ala
                165                 170                 175

Glu Leu Leu Val Ala Met Glu Asn Gln His Thr Ile Asp Leu Ala Asp
            180                 185                 190

Ser Glu Met Asn Lys Leu Tyr Glu Arg Val Lys Arg Gln Leu Arg Glu
        195                 200                 205

Asn Ala Glu Glu Asp Gly Thr Gly Cys Phe Glu Ile Phe His Lys Cys
    210                 215                 220

Asp Asp Asp Cys Met Ala Ser Ile Arg Asn Asn Thr Tyr Asp His Ser
225                 230                 235                 240

Lys Tyr Arg Glu Glu Ala Met Gln Asn Arg Ile Gln Ile Asp Pro Val
                245                 250                 255

Lys Leu Ser Ser Gly Tyr Lys Asp Val Ile Leu Trp Phe Ser Phe Gly
            260                 265                 270

Ala Ser Cys Phe Ile Leu Leu Ala Ile Ala Met Gly Leu Val Phe Ile
        275                 280                 285

Cys Val Lys Asn Gly Asn Met Arg Cys Thr Ile Cys Ile
    290                 295                 300
```

<210> SEQ ID NO 34
<211> LENGTH: 301
<212> TYPE: PRT
<213> ORGANISM: Artificial
<220> FEATURE:
<223> OTHER INFORMATION: H7 mini2 cluster15

<400> SEQUENCE: 34

```
Met Asn Thr Gln Ile Leu Val Phe Ala Leu Met Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Gly Gly Gly Gly Arg Tyr Val Lys Gln Glu Ser Leu
    50                  55                  60

Leu Leu Ala Thr Gly Met Lys Asn Val Pro Glu Ile Pro Lys Gly Gln
65                  70                  75                  80

Gly Leu Phe Gly Ala Ile Ala Gly Phe Ile Glu Asn Gly Trp Glu Gly
                85                  90                  95

Leu Ile Asp Gly Trp Tyr Gly Phe Arg His Gln Asn Ala Gln Gly Glu
            100                 105                 110

Gly Thr Ala Ala Asp Tyr Lys Ser Thr Gln Ser Ala Ile Asp Gln Ile
        115                 120                 125

Thr Gly Lys Leu Asn Arg Leu Ile Glu Lys Thr Asn Gln Gln Ser Glu
    130                 135                 140

Leu Thr Asp Asn Glu Ser Thr Glu Val Glu Lys Gln Ile Gly Asn Val
145                 150                 155                 160

Ile Asn Trp Thr Arg Asp Ser Met Thr Glu Val Trp Ser Tyr Asn Ala
                165                 170                 175
```

-continued

Glu Leu Leu Val Ala Met Glu Asn Gln His Thr Ile Asp Leu Ala Asp
180 185 190

Ser Glu Met Asn Lys Leu Tyr Glu Arg Val Lys Arg Gln Leu Arg Glu
195 200 205

Asn Ala Glu Glu Asp Gly Thr Gly Cys Phe Glu Ile Phe His Lys Cys
210 215 220

Asp Asp Asp Cys Met Ala Ser Ile Arg Asn Asn Thr Tyr Asp His Ser
225 230 235 240

Lys Tyr Arg Glu Glu Ala Met Gln Asn Arg Ile Gln Ile Asp Pro Val
245 250 255

Lys Leu Ser Ser Gly Tyr Lys Asp Val Ile Leu Trp Phe Ser Phe Gly
260 265 270

Ala Ser Cys Phe Ile Leu Leu Ala Ile Ala Met Gly Leu Val Phe Ile
275 280 285

Cys Val Lys Asn Gly Asn Met Arg Cys Thr Ile Cys Ile
290 295 300

<210> SEQ ID NO 35
<211> LENGTH: 301
<212> TYPE: PRT
<213> ORGANISM: Artificial
<220> FEATURE:
<223> OTHER INFORMATION: H7 mini2 cluster15+16

<400> SEQUENCE: 35

Met Asn Thr Gln Ile Leu Val Phe Ala Leu Met Ala Ile Ile Pro Thr
1 5 10 15

Asn Ala Asp Lys Ile Cys Leu Gly His His Ala Val Ser Asn Gly Thr
20 25 30

Lys Val Asn Thr Leu Thr Glu Arg Gly Val Glu Val Val Asn Ala Thr
35 40 45

Glu Thr Val Glu Gly Gly Gly Gly Arg Tyr Val Lys Gln Glu Ser Leu
50 55 60

Leu Leu Ala Thr Gly Met Lys Asn Val Pro Glu Ile Pro Lys Gly Gln
65 70 75 80

Gly Leu Phe Gly Ala Ile Ala Gly Phe Ile Glu Asn Gly Trp Glu Gly
85 90 95

Leu Ile Asp Gly Trp Tyr Gly Phe Arg His Gln Asn Ala Gln Gly Glu
100 105 110

Gly Thr Ala Ala Asp Tyr Lys Ser Thr Gln Ser Ala Ile Asp Gln Ile
115 120 125

Thr Gly Lys Leu Asn Arg Leu Ile Glu Lys Thr Asn Gln Gln Ser Glu
130 135 140

Asn Thr Asp Asn Glu Ser Thr Glu Asn Glu Lys Gln Ile Gly Asn Val
145 150 155 160

Ile Asn Trp Thr Arg Asp Ser Met Thr Glu Val Trp Ser Tyr Asn Ala
165 170 175

Glu Leu Leu Val Ala Met Glu Asn Gln His Thr Ile Asp Leu Ala Asp
180 185 190

Ser Glu Met Asn Lys Leu Tyr Glu Arg Val Lys Arg Gln Leu Arg Glu
195 200 205

Asn Ala Glu Glu Asp Gly Thr Gly Cys Phe Glu Ile Phe His Lys Cys
210 215 220

Asp Asp Asp Cys Met Ala Ser Ile Arg Asn Asn Thr Tyr Asp His Ser
225 230 235 240

```
Lys Tyr Arg Glu Glu Ala Met Gln Asn Arg Ile Gln Ile Asp Pro Val
                245                 250                 255

Lys Leu Ser Ser Gly Tyr Lys Asp Val Ile Leu Trp Phe Ser Phe Gly
            260                 265                 270

Ala Ser Cys Phe Ile Leu Leu Ala Ile Ala Met Gly Leu Val Phe Ile
        275                 280                 285

Cys Val Lys Asn Gly Asn Met Arg Cys Thr Ile Cys Ile
    290                 295                 300


<210> SEQ ID NO 36
<211> LENGTH: 301
<212> TYPE: PRT
<213> ORGANISM: Artificial
<220> FEATURE:
<223> OTHER INFORMATION: H7-mini2 cluster17

<400> SEQUENCE: 36

Met Asn Thr Gln Ile Leu Val Phe Ala Leu Met Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Gly Gly Gly Gly Arg Tyr Val Cys Gln Glu Ser Leu
    50                  55                  60

Leu Leu Ala Thr Gly Met Lys Asn Val Pro Glu Ile Pro Lys Gly Gln
65                  70                  75                  80

Gly Leu Phe Gly Ala Ile Ala Gly Phe Ile Glu Asn Gly Trp Glu Gly
                85                  90                  95

Leu Ile Asp Gly Trp Tyr Gly Phe Arg His Gln Asn Ala Gln Gly Glu
            100                 105                 110

Gly Thr Ala Ala Asp Tyr Lys Ser Thr Gln Ser Ala Ile Asp Gln Ile
        115                 120                 125

Thr Gly Lys Leu Asn Arg Leu Ile Glu Lys Thr Asn Gln Gln Phe Glu
    130                 135                 140

Leu Ile Asp Asn Glu Phe Thr Glu Val Glu Lys Gln Ile Gly Asn Val
145                 150                 155                 160

Ile Asn Trp Thr Arg Asp Ser Met Thr Glu Val Trp Cys Tyr Asn Ala
                165                 170                 175

Glu Leu Leu Val Ala Met Glu Asn Gln His Thr Ile Asp Leu Ala Asp
            180                 185                 190

Ser Glu Met Asn Lys Leu Tyr Glu Arg Val Lys Arg Gln Leu Arg Glu
        195                 200                 205

Asn Ala Glu Glu Asp Gly Thr Gly Cys Phe Glu Ile Phe His Lys Cys
    210                 215                 220

Asp Asp Asp Cys Met Ala Ser Ile Arg Asn Asn Thr Tyr Asp His Ser
225                 230                 235                 240

Lys Tyr Arg Glu Glu Ala Met Gln Asn Arg Ile Gln Ile Asp Pro Val
                245                 250                 255

Lys Leu Ser Ser Gly Tyr Lys Asp Val Ile Leu Trp Phe Ser Phe Gly
            260                 265                 270

Ala Ser Cys Phe Ile Leu Leu Ala Ile Ala Met Gly Leu Val Phe Ile
        275                 280                 285

Cys Val Lys Asn Gly Asn Met Arg Cys Thr Ile Cys Ile
    290                 295                 300
```

<210> SEQ ID NO 37
<211> LENGTH: 301
<212> TYPE: PRT
<213> ORGANISM: Artificial
<220> FEATURE:
<223> OTHER INFORMATION: H7-mini2 cluster15+16+17

<400> SEQUENCE: 37

Met Asn Thr Gln Ile Leu Val Phe Ala Leu Met Ala Ile Ile Pro Thr
1 5 10 15

Asn Ala Asp Lys Ile Cys Leu Gly His His Ala Val Ser Asn Gly Thr
20 25 30

Lys Val Asn Thr Leu Thr Glu Arg Gly Val Glu Val Val Asn Ala Thr
35 40 45

Glu Thr Val Glu Gly Gly Gly Gly Arg Tyr Val Cys Gln Glu Ser Leu
50 55 60

Leu Leu Ala Thr Gly Met Lys Asn Val Pro Glu Ile Pro Lys Gly Gln
65 70 75 80

Gly Leu Phe Gly Ala Ile Ala Gly Phe Ile Glu Asn Gly Trp Glu Gly
85 90 95

Leu Ile Asp Gly Trp Tyr Gly Phe Arg His Gln Asn Ala Gln Gly Glu
100 105 110

Gly Thr Ala Ala Asp Tyr Lys Ser Thr Gln Ser Ala Ile Asp Gln Ile
115 120 125

Thr Gly Lys Leu Asn Arg Leu Ile Glu Lys Thr Asn Gln Gln Ser Glu
130 135 140

Asn Thr Asp Asn Glu Ser Thr Glu Asn Glu Lys Gln Ile Gly Asn Val
145 150 155 160

Ile Asn Trp Thr Arg Asp Ser Met Thr Glu Val Trp Cys Tyr Asn Ala
165 170 175

Glu Leu Leu Val Ala Met Glu Asn Gln His Thr Ile Asp Leu Ala Asp
180 185 190

Ser Glu Met Asn Lys Leu Tyr Glu Arg Val Lys Arg Gln Leu Arg Glu
195 200 205

Asn Ala Glu Glu Asp Gly Thr Gly Cys Phe Glu Ile Phe His Lys Cys
210 215 220

Asp Asp Asp Cys Met Ala Ser Ile Arg Asn Asn Thr Tyr Asp His Ser
225 230 235 240

Lys Tyr Arg Glu Glu Ala Met Gln Asn Arg Ile Gln Ile Asp Pro Val
245 250 255

Lys Leu Ser Ser Gly Tyr Lys Asp Val Ile Leu Trp Phe Ser Phe Gly
260 265 270

Ala Ser Cys Phe Ile Leu Leu Ala Ile Ala Met Gly Leu Val Phe Ile
275 280 285

Cys Val Lys Asn Gly Asn Met Arg Cys Thr Ile Cys Ile
290 295 300

<210> SEQ ID NO 38
<211> LENGTH: 301
<212> TYPE: PRT
<213> ORGANISM: Artificial
<220> FEATURE:
<223> OTHER INFORMATION: H7-mini2 cluster15+16+17

<400> SEQUENCE: 38

Met Asn Thr Gln Ile Leu Val Phe Ala Leu Met Ala Ile Ile Pro Thr
1 5 10 15

Asn Ala Asp Lys Ile Cys Leu Gly His His Ala Val Ser Asn Gly Thr
20 25 30

Lys Val Asn Thr Leu Thr Glu Arg Gly Val Glu Val Val Asn Ala Thr
35 40 45

Glu Thr Val Glu Gly Gly Gly Gly Arg Tyr Val Cys Gln Glu Ser Leu
50 55 60

Leu Leu Ala Thr Gly Met Lys Asn Val Pro Glu Ile Pro Lys Gly Gln
65 70 75 80

Gly Leu Phe Gly Ala Ile Ala Gly Phe Ile Glu Asn Gly Trp Glu Gly
85 90 95

Leu Ile Asp Gly Trp Tyr Gly Phe Arg His Gln Asn Ala Gln Gly Glu
100 105 110

Gly Thr Ala Ala Asp Tyr Lys Ser Thr Gln Ser Ala Ile Asp Gln Ile
115 120 125

Thr Gly Lys Leu Asn Arg Leu Ile Glu Lys Thr Asn Gln Gln Ser Glu
130 135 140

Asn Thr Asp Asn Glu Ser Thr Glu Asn Glu Lys Gln Ile Gly Asn Ile
145 150 155 160

Ile Asn Trp Ile Arg Asp Ile Met Thr Glu Ile Trp Cys Tyr Asn Ala
165 170 175

Glu Leu Leu Val Ala Met Glu Asn Gln His Thr Ile Asp Leu Ala Asp
180 185 190

Ser Glu Met Asn Lys Leu Tyr Glu Arg Val Lys Arg Gln Leu Arg Glu
195 200 205

Asn Ala Glu Glu Asp Gly Thr Gly Cys Phe Glu Ile Phe His Lys Cys
210 215 220

Asp Asp Asp Cys Met Ala Ser Ile Arg Asn Asn Thr Tyr Asp His Ser
225 230 235 240

Lys Tyr Arg Glu Glu Ala Met Gln Asn Arg Ile Gln Ile Asp Pro Val
245 250 255

Lys Leu Ser Ser Gly Tyr Lys Asp Val Ile Leu Trp Phe Ser Phe Gly
260 265 270

Ala Ser Cys Phe Ile Leu Leu Ala Ile Ala Met Gly Leu Val Phe Ile
275 280 285

Cys Val Lys Asn Gly Asn Met Arg Cys Thr Ile Cys Ile
290 295 300

<210> SEQ ID NO 39
<211> LENGTH: 301
<212> TYPE: PRT
<213> ORGANISM: Artificial
<220> FEATURE:
<223> OTHER INFORMATION: H7-mini2-cluster15+16+17+18

<400> SEQUENCE: 39

Met Asn Thr Gln Ile Leu Val Phe Ala Leu Met Ala Ile Ile Pro Thr
1 5 10 15

Asn Ala Asp Lys Ile Cys Leu Gly His His Ala Val Ser Asn Gly Thr
20 25 30

Lys Val Asn Thr Leu Thr Glu Arg Gly Val Glu Val Val Asn Ala Thr
35 40 45

Glu Thr Val Glu Gly Gly Gly Gly Arg Tyr Val Cys Gln Glu Ser Leu
50 55 60

Leu Leu Ala Thr Gly Met Lys Asn Val Pro Glu Ile Pro Lys Gly Gln
65 70 75 80

```
Gly Leu Phe Gly Ala Ile Ala Gly Phe Ile Glu Asn Gly Trp Glu Gly
                85                  90                  95

Leu Ile Asp Gly Trp Tyr Gly Phe Arg His Gln Asn Ala Gln Gly Glu
            100                 105                 110

Gly Thr Ala Ala Asp Tyr Lys Ser Thr Gln Ser Ala Ile Asp Gln Ile
        115                 120                 125

Thr Gly Lys Leu Asn Arg Leu Ile Glu Lys Thr Asn Gln Gln Ser Glu
    130                 135                 140

Asn Thr Asp Asn Glu Ser Thr Glu Asn Glu Lys Gln Ile Glu Ala Ile
145                 150                 155                 160

Glu Lys Lys Ile Glu Ala Ile Met Thr Glu Ile Trp Cys Tyr Asn Ala
                165                 170                 175

Glu Leu Leu Val Ala Met Glu Asn Gln His Thr Ile Asp Leu Ala Asp
            180                 185                 190

Ser Glu Met Asn Lys Leu Tyr Glu Arg Val Lys Arg Gln Leu Arg Glu
        195                 200                 205

Asn Ala Glu Glu Asp Gly Thr Gly Cys Phe Glu Ile Phe His Lys Cys
    210                 215                 220

Asp Asp Asp Cys Met Ala Ser Ile Arg Asn Asn Thr Tyr Asp His Ser
225                 230                 235                 240

Lys Tyr Arg Glu Glu Ala Met Gln Asn Arg Ile Gln Ile Asp Pro Val
                245                 250                 255

Lys Leu Ser Ser Gly Tyr Lys Asp Val Ile Leu Trp Phe Ser Phe Gly
            260                 265                 270

Ala Ser Cys Phe Ile Leu Leu Ala Ile Ala Met Gly Leu Val Phe Ile
        275                 280                 285

Cys Val Lys Asn Gly Asn Met Arg Cys Thr Ile Cys Ile
    290                 295                 300


<210> SEQ ID NO 40
<211> LENGTH: 303
<212> TYPE: PRT
<213> ORGANISM: Artificial
<220> FEATURE:
<223> OTHER INFORMATION: H7-mini5

<400> SEQUENCE: 40

Met Asn Thr Gln Ile Leu Val Phe Ala Leu Met Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Gly Gly Gly Gly Pro Arg Tyr Val Lys Gln Glu
    50                  55                  60

Ser Leu Leu Leu Ala Thr Gly Met Lys Asn Val Pro Glu Ile Pro Lys
65                  70                  75                  80

Gly Gln Gly Leu Phe Gly Ala Ile Ala Gly Phe Ile Glu Asn Gly Trp
                85                  90                  95

Glu Gly Leu Ile Asp Gly Trp Tyr Gly Phe Arg His Gln Asn Ala Gln
            100                 105                 110

Gly Glu Gly Thr Ala Ala Asp Tyr Lys Ser Thr Gln Ser Ala Ile Asp
        115                 120                 125

Gln Ile Thr Gly Lys Leu Asn Arg Leu Ile Glu Lys Thr Asn Gln Gln
    130                 135                 140
```

```
Phe Glu Leu Ile Asp Asn Glu Phe Thr Glu Val Glu Lys Gln Ile Gly
145                 150                 155                 160

Asn Val Ile Asn Trp Thr Arg Asp Ser Met Thr Glu Val Trp Ser Tyr
                165                 170                 175

Asn Ala Glu Leu Leu Val Ala Met Glu Asn Gln His Thr Ile Asp Leu
            180                 185                 190

Ala Asp Ser Glu Met Asn Lys Leu Tyr Glu Arg Val Lys Arg Gln Leu
        195                 200                 205

Arg Glu Asn Ala Glu Glu Asp Gly Thr Gly Cys Phe Glu Ile Phe His
    210                 215                 220

Lys Cys Asp Asp Asp Cys Met Ala Ser Ile Arg Asn Asn Thr Tyr Asp
225                 230                 235                 240

His Ser Lys Tyr Arg Glu Glu Ala Met Gln Asn Arg Ile Gln Ile Asp
                245                 250                 255

Pro Val Lys Leu Ser Ser Gly Tyr Lys Asp Val Ile Leu Trp Phe Ser
            260                 265                 270

Phe Gly Ala Ser Cys Phe Ile Leu Leu Ala Ile Ala Met Gly Leu Val
        275                 280                 285

Phe Ile Cys Val Lys Asn Gly Asn Met Arg Cys Thr Ile Cys Ile
    290                 295                 300
```

<210> SEQ ID NO 41
<211> LENGTH: 303
<212> TYPE: PRT
<213> ORGANISM: Artificial
<220> FEATURE:
<223> OTHER INFORMATION: H7-mini5 cluster15+16

<400> SEQUENCE: 41

```
Met Asn Thr Gln Ile Leu Val Phe Ala Leu Met Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Gly Gly Gly Gly Pro Arg Tyr Val Lys Gln Glu
    50                  55                  60

Ser Leu Leu Leu Ala Thr Gly Met Lys Asn Val Pro Glu Ile Pro Lys
65                  70                  75                  80

Gly Gln Gly Leu Phe Gly Ala Ile Ala Gly Phe Ile Glu Asn Gly Trp
                85                  90                  95

Glu Gly Leu Ile Asp Gly Trp Tyr Gly Phe Arg His Gln Asn Ala Gln
            100                 105                 110

Gly Glu Gly Thr Ala Ala Asp Tyr Lys Ser Thr Gln Ser Ala Ile Asp
        115                 120                 125

Gln Ile Thr Gly Lys Leu Asn Arg Leu Ile Glu Lys Thr Asn Gln Gln
    130                 135                 140

Ser Glu Asn Thr Asp Asn Glu Ser Thr Glu Asn Glu Lys Gln Ile Gly
145                 150                 155                 160

Asn Val Ile Asn Trp Thr Arg Asp Ser Met Thr Glu Val Trp Ser Tyr
                165                 170                 175

Asn Ala Glu Leu Leu Val Ala Met Glu Asn Gln His Thr Ile Asp Leu
            180                 185                 190

Ala Asp Ser Glu Met Asn Lys Leu Tyr Glu Arg Val Lys Arg Gln Leu
        195                 200                 205
```

-continued

```
Arg Glu Asn Ala Glu Glu Asp Gly Thr Gly Cys Phe Glu Ile Phe His
    210                 215                 220

Lys Cys Asp Asp Asp Cys Met Ala Ser Ile Arg Asn Asn Thr Tyr Asp
225                 230                 235                 240

His Ser Lys Tyr Arg Glu Glu Ala Met Gln Asn Arg Ile Gln Ile Asp
                245                 250                 255

Pro Val Lys Leu Ser Ser Gly Tyr Lys Asp Val Ile Leu Trp Phe Ser
            260                 265                 270

Phe Gly Ala Ser Cys Phe Ile Leu Leu Ala Ile Ala Met Gly Leu Val
        275                 280                 285

Phe Ile Cys Val Lys Asn Gly Asn Met Arg Cys Thr Ile Cys Ile
    290                 295                 300


<210> SEQ ID NO 42
<211> LENGTH: 303
<212> TYPE: PRT
<213> ORGANISM: Artificial
<220> FEATURE:
<223> OTHER INFORMATION: H7-mini5 cluster17

<400> SEQUENCE: 42

Met Asn Thr Gln Ile Leu Val Phe Ala Leu Met Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Gly Gly Gly Gly Pro Arg Tyr Cys Lys Gln Glu
    50                  55                  60

Ser Leu Leu Leu Ala Thr Gly Met Lys Asn Val Pro Glu Ile Pro Lys
65                  70                  75                  80

Gly Gln Gly Leu Phe Gly Ala Ile Ala Gly Phe Ile Glu Asn Gly Trp
                85                  90                  95

Glu Gly Leu Ile Asp Gly Trp Tyr Gly Phe Arg His Gln Asn Ala Gln
            100                 105                 110

Gly Glu Gly Thr Ala Ala Asp Tyr Lys Ser Thr Gln Ser Ala Ile Asp
        115                 120                 125

Gln Ile Thr Gly Lys Leu Asn Arg Leu Ile Glu Lys Thr Asn Gln Gln
    130                 135                 140

Phe Glu Leu Ile Asp Asn Glu Phe Thr Glu Val Glu Lys Gln Ile Gly
145                 150                 155                 160

Asn Val Ile Asn Trp Thr Arg Asp Ser Met Thr Glu Val Trp Cys Tyr
                165                 170                 175

Asn Ala Glu Leu Leu Val Ala Met Glu Asn Gln His Thr Ile Asp Leu
            180                 185                 190

Ala Asp Ser Glu Met Asn Lys Leu Tyr Glu Arg Val Lys Arg Gln Leu
        195                 200                 205

Arg Glu Asn Ala Glu Glu Asp Gly Thr Gly Cys Phe Glu Ile Phe His
    210                 215                 220

Lys Cys Asp Asp Asp Cys Met Ala Ser Ile Arg Asn Asn Thr Tyr Asp
225                 230                 235                 240

His Ser Lys Tyr Arg Glu Glu Ala Met Gln Asn Arg Ile Gln Ile Asp
                245                 250                 255

Pro Val Lys Leu Ser Ser Gly Tyr Lys Asp Val Ile Leu Trp Phe Ser
            260                 265                 270
```

```
Phe Gly Ala Ser Cys Phe Ile Leu Leu Ala Ile Ala Met Gly Leu Val
        275                 280                 285

Phe Ile Cys Val Lys Asn Gly Asn Met Arg Cys Thr Ile Cys Ile
    290                 295                 300


<210> SEQ ID NO 43
<211> LENGTH: 303
<212> TYPE: PRT
<213> ORGANISM: Artificial
<220> FEATURE:
<223> OTHER INFORMATION: H7-mini5 cluster15+16+17+18

<400> SEQUENCE: 43

Met Asn Thr Gln Ile Leu Val Phe Ala Leu Met Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Gly Gly Gly Gly Pro Arg Tyr Val Cys Gln Glu
    50                  55                  60

Ser Leu Leu Leu Ala Thr Gly Met Lys Asn Val Pro Glu Ile Pro Lys
65                  70                  75                  80

Gly Gln Gly Leu Phe Gly Ala Ile Ala Gly Phe Ile Glu Asn Gly Trp
                85                  90                  95

Glu Gly Leu Ile Asp Gly Trp Tyr Gly Phe Arg His Gln Asn Ala Gln
            100                 105                 110

Gly Glu Gly Thr Ala Ala Asp Tyr Lys Ser Thr Gln Ser Ala Ile Asp
        115                 120                 125

Gln Ile Thr Gly Lys Leu Asn Arg Leu Ile Glu Lys Thr Asn Gln Gln
    130                 135                 140

Ser Glu Asn Thr Asp Asn Glu Ser Thr Glu Asn Glu Lys Gln Ile Gly
145                 150                 155                 160

Asn Ile Ile Asn Trp Ile Arg Asp Ile Met Thr Glu Ile Trp Cys Tyr
                165                 170                 175

Asn Ala Glu Leu Leu Val Ala Met Glu Asn Gln His Thr Ile Asp Leu
            180                 185                 190

Ala Asp Ser Glu Met Asn Lys Leu Tyr Glu Arg Val Lys Arg Gln Leu
        195                 200                 205

Arg Glu Asn Ala Glu Glu Asp Gly Thr Gly Cys Phe Glu Ile Phe His
    210                 215                 220

Lys Cys Asp Asp Asp Cys Met Ala Ser Ile Arg Asn Asn Thr Tyr Asp
225                 230                 235                 240

His Ser Lys Tyr Arg Glu Glu Ala Met Gln Asn Arg Ile Gln Ile Asp
                245                 250                 255

Pro Val Lys Leu Ser Ser Gly Tyr Lys Asp Val Ile Leu Trp Phe Ser
            260                 265                 270

Phe Gly Ala Ser Cys Phe Ile Leu Leu Ala Ile Ala Met Gly Leu Val
        275                 280                 285

Phe Ile Cys Val Lys Asn Gly Asn Met Arg Cys Thr Ile Cys Ile
    290                 295                 300


<210> SEQ ID NO 44
<211> LENGTH: 301
<212> TYPE: PRT
<213> ORGANISM: Artificial
```

<220> FEATURE:
<223> OTHER INFORMATION: H1 mini2 cluster1+5+6 trim

<400> SEQUENCE: 44

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Ile Glu Ala Ile Glu Lys Lys
145                 150                 155                 160

Ile Glu Ala Ile Glu Lys Lys Ile Glu Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 45
<211> LENGTH: 301
<212> TYPE: PRT
<213> ORGANISM: Artificial
<220> FEATURE:
<223> OTHER INFORMATION: H1 mini2 cluster1+5+6-GCN4

<400> SEQUENCE: 45

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
```

-continued

```
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 46
<211> LENGTH: 301
<212> TYPE: PRT
<213> ORGANISM: Artificial
<220> FEATURE:
<223> OTHER INFORMATION: H1 mini2 cluster1+5+6 (A/Brisbane/59/2007)

<400> SEQUENCE: 46

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
```

```
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Met Glu Asn Leu Asn
145                 150                 155                 160

Lys Lys Val Asp Asp Gly Phe Ile Asp Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 47
<211> LENGTH: 301
<212> TYPE: PRT
<213> ORGANISM: Artificial
<220> FEATURE:
<223> OTHER INFORMATION: H1 mini2 cluster11+5+6 (A/Brisbane/59/2007)

<400> SEQUENCE: 47

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Ile Glu Asn Leu Asn
145                 150                 155                 160

Lys Lys Ile Asp Asp Gly Phe Ile Asp Ile Trp Cys Tyr Asn Ala Glu
```

```
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 48
<211> LENGTH: 301
<212> TYPE: PRT
<213> ORGANISM: Artificial
<220> FEATURE:
<223> OTHER INFORMATION: H1 mini2 cluster1+5 (A/Brisbane/59/2007)

<400> SEQUENCE: 48

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Phe Asn Lys Ser Glu Arg Arg Met Glu Asn Leu Asn
145                 150                 155                 160

Lys Lys Val Asp Asp Gly Phe Ile Asp Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
```

-continued

```
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 49
<211> LENGTH: 301
<212> TYPE: PRT
<213> ORGANISM: Artificial
<220> FEATURE:
<223> OTHER INFORMATION: H1 mini2 cluster1+5+6-trim2

<400> SEQUENCE: 49

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Ile Glu Ala Ile Glu Lys
145                 150                 155                 160

Lys Ile Glu Ala Ile Glu Lys Lys Ile Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
```

-continued 290 295 300

<210> SEQ ID NO 50
<211> LENGTH: 301
<212> TYPE: PRT
<213> ORGANISM: Artificial
<220> FEATURE:
<223> OTHER INFORMATION: H1 mini2 cluster1+5+6-trim3

<400> SEQUENCE: 50

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Ile Glu Ala Ile Glu
145                 150                 155                 160

Lys Lys Ile Glu Ala Ile Glu Lys Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 51
<211> LENGTH: 301
<212> TYPE: PRT
<213> ORGANISM: Artificial
<220> FEATURE:
<223> OTHER INFORMATION: H1 mini2 cluester1+5+6-GCN4t2

<400> SEQUENCE: 51

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 52
<211> LENGTH: 301
<212> TYPE: PRT
<213> ORGANISM: Artificial
<220> FEATURE:
<223> OTHER INFORMATION: H1 mini2-cluster1+5+6-GCN4t3

<400> SEQUENCE: 52

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60
```

```
Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Arg Met Lys Gln Ile Glu Asp Lys
145                 150                 155                 160

Ile Glu Glu Ile Glu Ser Lys Gln Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 53
<211> LENGTH: 301
<212> TYPE: PRT
<213> ORGANISM: Artificial
<220> FEATURE:
<223> OTHER INFORMATION: H1 mini2 cluster1+5+6-IleTri

<400> SEQUENCE: 53

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125
```

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Ile Glu Asn Ile Asn
145                 150                 155                 160

Lys Lys Ile Asp Asp Ile Phe Ile Asp Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 54
<211> LENGTH: 565
<212> TYPE: PRT
<213> ORGANISM: Artificial
<220> FEATURE:
<223> OTHER INFORMATION: A/Solomon Islands/6/2003

<400> SEQUENCE: 54

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Thr Thr Gly Val Ser Ala Ser Cys Ser His Asn Gly Glu Ser Ser Phe
145                 150                 155                 160

Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

```
Trp Gly Val His His Pro Pro Asn Ile Gly Asp Gln Arg Ala Leu Tyr
        195                 200                 205

His Lys Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 55
<211> LENGTH: 565
<212> TYPE: PRT
<213> ORGANISM: Artificial
<220> FEATURE:
<223> OTHER INFORMATION: A/New Caledonia/20/1999

<400> SEQUENCE: 55

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
```

```
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 56
<211> LENGTH: 566
<212> TYPE: PRT
<213> ORGANISM: Artificial
<220> FEATURE:
<223> OTHER INFORMATION: A/California/07/2009

<400> SEQUENCE: 56

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
```

```
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 57
<211> LENGTH: 566
<212> TYPE: PRT
<213> ORGANISM: Artificial
<220> FEATURE:
<223> OTHER INFORMATION: A/Swine/Hubei/S1/2009

<400> SEQUENCE: 57

Met Glu Ala Lys Leu Phe Val Leu Phe Cys Ala Phe Thr Ala Leu Lys
1               5                   10                  15

Ala Asp Thr Phe Cys Val Gly Tyr His Ala Asn Tyr Ser Thr His Thr
            20                  25                  30

Val Asp Thr Ile Leu Glu Lys Asn Val Thr Val Thr His Ser Val Asn
        35                  40                  45

Leu Leu Glu Asn Ser His Asn Gly Lys Leu Cys Ser Leu Asn Gly Lys
    50                  55                  60

Ile Pro Leu Gln Leu Gly Asn Cys Asn Val Ala Gly Trp Ile Leu Gly
65                  70                  75                  80

Asn Pro Lys Cys Asp Leu Leu Leu Thr Ala Asn Ser Ser Ser Tyr Ile
                85                  90                  95

Ile Glu Thr Ser Lys Ser Lys Asn Gly Ala Cys Tyr Pro Gly Glu Phe
            100                 105                 110

Ala Asp Tyr Glu Glu Leu Lys Glu Gln Leu Ser Thr Val Ser Ser Phe
        115                 120                 125

Glu Arg Phe Glu Ile Phe Pro Lys Ala Ile Ser Trp Pro Asp His Asp
    130                 135                 140

Ala Thr Arg Gly Thr Thr Val Ala Cys Ser His Ser Gly Val Asn Ser
145                 150                 155                 160

Phe Tyr Arg Asn Leu Leu Ser Thr Val Lys Lys Gly Asn Ser Tyr Pro
                165                 170                 175

Lys Leu Ser Lys Ser Tyr Thr Asn Asn Lys Gly Lys Glu Val Leu Val
            180                 185                 190

Ile Trp Gly Val His His Pro Pro Thr Asp Ser Val Gln Gln Thr Leu
        195                 200                 205

Tyr Gln Asn Lys His Thr Tyr Val Ser Val Gly Ser Ser Lys Tyr Tyr
    210                 215                 220

Lys Arg Phe Thr Pro Glu Ile Val Ala Arg Pro Lys Val Arg Gly Gln
225                 230                 235                 240

Ala Gly Arg Met Asn Tyr Tyr Trp Thr Leu Phe Asp Gln Gly Asp Thr
                245                 250                 255

Ile Thr Phe Glu Ala Thr Gly Asn Leu Ile Ala Pro Trp His Ala Phe
            260                 265                 270

Ala Leu Lys Lys Gly Ser Ser Ser Gly Ile Met Leu Ser Asp Ala Gln
        275                 280                 285

Val His Asn Cys Thr Thr Lys Cys Gln Thr Pro His Gly Ala Leu Lys
    290                 295                 300

Asn Asn Leu Pro Leu Gln Asn Val His Leu Phe Thr Ile Gly Glu Cys
305                 310                 315                 320

Pro Lys Tyr Val Lys Ser Thr Gln Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Arg Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Ile Ala Ile Asp Gly Ile Asn Asn Lys Ala Asn Ser Val Ile
385                 390                 395                 400

Gly Lys Met Asn Ile Gln Leu Thr Ser Val Gly Lys Glu Phe Asn Ser
                405                 410                 415

```
Leu Glu Lys Arg Lys Glu Asn Leu Asn Lys Thr Val Asp Asp Arg Phe
            420                 425                 430

Leu Asp Val Trp Thr Phe Asn Ala Glu Leu Leu Val Leu Leu Glu Asn
        435                 440                 445

Gln Arg Thr Leu Glu Phe His Asp Leu Asn Ile Lys Ser Leu Tyr Glu
    450                 455                 460

Lys Val Lys Ser His Leu Arg Asn Asn Asp Lys Glu Ile Gly Asn Gly
465                 470                 475                 480

Cys Phe Glu Phe Tyr His Lys Arg Asp Asn Glu Cys Leu Glu Cys Val
                485                 490                 495

Lys Asn Gly Thr Tyr Asn Tyr Pro Lys Tyr Ser Glu Glu Ser Lys Phe
            500                 505                 510

Asn Arg Glu Glu Ile Val Gly Val Lys Leu Glu Ser Met Gly Ile His
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Val Cys Ile
                565


<210> SEQ ID NO 58
<211> LENGTH: 566
<212> TYPE: PRT
<213> ORGANISM: Artificial
<220> FEATURE:
<223> OTHER INFORMATION: A/Swine/Haseluenne/IDT2617/2003

<400> SEQUENCE: 58

Met Glu Ala Lys Leu Phe Val Leu Phe Cys Ala Phe Thr Ala Leu Lys
1               5                   10                  15

Ala Asp Thr Ile Cys Val Gly Tyr His Ala Asn Asn Ser Thr Asp Thr
            20                  25                  30

Val Asp Thr Ile Leu Glu Lys Asn Val Thr Val Thr His Ser Ile Asn
        35                  40                  45

Leu Leu Glu Asn Asn His Asn Gly Lys Leu Cys Ser Leu Asn Gly Lys
    50                  55                  60

Ala Pro Leu Gln Leu Gly Asn Cys Asn Val Ala Gly Trp Ile Leu Gly
65                  70                  75                  80

Asn Pro Glu Cys Asp Leu Leu Leu Thr Val Asp Ser Trp Ser Tyr Ile
                85                  90                  95

Ile Glu Thr Ser Asn Ser Lys Asn Gly Ala Cys Tyr Pro Gly Glu Phe
            100                 105                 110

Ala Asp Tyr Glu Glu Leu Arg Glu Gln Leu Ser Thr Val Ser Ser Phe
        115                 120                 125

Glu Arg Phe Glu Ile Phe Pro Lys Ala Thr Ser Trp Pro Asn His Asp
    130                 135                 140

Thr Thr Arg Gly Thr Thr Ile Ser Cys Ser His Ser Gly Ala Asn Ser
145                 150                 155                 160

Phe Tyr Arg Asn Leu Leu Trp Ile Val Lys Lys Gly Asn Ser Tyr Pro
                165                 170                 175

Lys Leu Ser Lys Ser Tyr Thr Asn Asn Lys Gly Lys Glu Val Leu Val
            180                 185                 190

Ile Trp Gly Val His His Pro Pro Thr Asp Ser Asp Gln Gln Thr Leu
        195                 200                 205
```

Tyr Gln Asn Asn His Thr Tyr Val Ser Val Gly Ser Ser Lys Tyr Tyr
    210                 215                 220

Gln Arg Phe Thr Pro Glu Ile Val Thr Arg Pro Lys Val Arg Gly Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Ile Ala Pro Trp His Ala Phe
            260                 265                 270

Ala Leu Asn Lys Gly Pro Ser Ser Gly Ile Met Ile Ser Asp Ala His
        275                 280                 285

Val His Asn Cys Thr Thr Lys Cys Gln Thr Pro His Gly Ala Leu Lys
    290                 295                 300

Ser Asn Leu Pro Phe Gln Asn Val His Pro Ser Thr Ile Gly Glu Cys
305                 310                 315                 320

Pro Lys Tyr Val Lys Ser Thr Gln Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Ile Ala Ile Asp Gly Ile Asn Asn Lys Val Asn Ser Ile Ile
385                 390                 395                 400

Glu Lys Met Asn Thr Gln Phe Thr Ser Val Gly Lys Glu Phe Asn Asp
                405                 410                 415

Leu Glu Lys Arg Ile Glu Asn Leu Asn Lys Lys Val Asp Asp Gly Phe
            420                 425                 430

Leu Asp Val Trp Thr Tyr Asn Ala Glu Leu Leu Ile Leu Leu Glu Asn
        435                 440                 445

Glu Arg Thr Leu Asp Phe His Asp Phe Asn Val Lys Asn Leu Tyr Glu
    450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Lys Asn Gly Thr Tyr Asn Tyr Pro Lys Tyr Ser Glu Glu Ser Lys Leu
            500                 505                 510

Asn Arg Glu Lys Ile Asp Gly Val Lys Leu Glu Ser Met Gly Val His
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 59
<211> LENGTH: 565
<212> TYPE: PRT
<213> ORGANISM: Artificial
<220> FEATURE:
<223> OTHER INFORMATION: A/New York/8/2006

<400> SEQUENCE: 59

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Phe Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415
```

-continued

```
Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Arg Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 60
<211> LENGTH: 565
<212> TYPE: PRT
<213> ORGANISM: Artificial
<220> FEATURE:
<223> OTHER INFORMATION: A/Solomon Islands/3/2006

<400> SEQUENCE: 60

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Thr Thr Gly Val Ser Ala Ser Cys Ser His Asn Gly Glu Ser Ser Phe
145                 150                 155                 160

Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205
```

-continued

```
His Lys Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 61
<211> LENGTH: 566
<212> TYPE: PRT
<213> ORGANISM: Artificial
<220> FEATURE:
<223> OTHER INFORMATION: A/New York/146/2000

<400> SEQUENCE: 61

-continued

```
Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Thr
    50                  55                  60

Ala Pro Leu Gln Leu Gly Asn Cys Ser Ile Ala Gly Trp Ile Leu Gly
65                  70                  75                  80

Asn Pro Glu Cys Glu Ser Leu Phe Ser Lys Glu Ser Trp Ser Tyr Ile
                85                  90                  95

Ala Glu Thr Pro Asn Pro Lys Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Asp Ser Ser Trp Pro Asn His Thr
    130                 135                 140

Val Thr Lys Gly Val Thr Ala Ser Cys Ser His Asn Gly Lys Ser Ser
145                 150                 155                 160

Phe Tyr Lys Asn Leu Leu Trp Leu Thr Glu Lys Asn Gly Leu Tyr Pro
                165                 170                 175

Asn Leu Ser Lys Ser Tyr Val Asn Lys Lys Gly Lys Glu Val Leu Val
            180                 185                 190

Leu Trp Gly Val His His Pro Ser Asn Met Gly Asp Gln Arg Ala Ile
        195                 200                 205

Tyr His Lys Glu Asn Ala Tyr Val Ser Val Leu Ser Ser His Tyr Ser
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Ile Ser Asn Ala Ser
        275                 280                 285

Met Gly Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Ile Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
```

420 425 430

Leu Asp Ile Trp Thr Tyr Asn Ala Glu Leu Leu Val Leu Leu Glu Asn
435 440 445

Glu Arg Thr Leu Asp Phe His Asp Leu Asn Val Lys Asn Leu Tyr Glu
450 455 460

Lys Val Lys Asn Gln Leu Lys Asn Asn Ala Lys Glu Ile Gly Asn Gly
465 470 475 480

Cys Phe Glu Phe Tyr His Lys Cys Asn Asn Glu Cys Met Glu Ser Val
485 490 495

Lys Asn Gly Thr Tyr Asp Tyr Pro Lys Tyr Ser Lys Glu Ser Lys Leu
500 505 510

Asn Arg Glu Lys Ile Asp Gly Val Lys Leu Glu Ser Met Gly Val Tyr
515 520 525

Gln Ile Leu Ala Ile Tyr Ser Thr Val Ala Ser Ser Leu Val Leu Leu
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 62
<211> LENGTH: 566
<212> TYPE: PRT
<213> ORGANISM: Artificial
<220> FEATURE:
<223> OTHER INFORMATION: A/New York/653/1996

<400> SEQUENCE: 62

Met Lys Ala Lys Leu Leu Val Leu Leu Cys Ala Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Thr
50 55 60

Ala Pro Leu Gln Leu Gly Asn Cys Ser Val Ala Gly Trp Ile Leu Gly
65 70 75 80

Asn Pro Glu Cys Glu Ser Leu Phe Ser Lys Glu Ser Trp Ser Tyr Ile
85 90 95

Ala Glu Thr Pro Asn Pro Glu Asn Gly Thr Cys Tyr Pro Gly Tyr Phe
100 105 110

Ala Asp Tyr Glu Glu Leu Arg Glu Gln Leu Ser Ser Val Ser Ser Phe
115 120 125

Glu Arg Phe Glu Ile Phe Pro Lys Glu Ser Ser Trp Pro Asn His Thr
130 135 140

Val Thr Lys Gly Val Thr Ala Ser Cys Ser His Asn Gly Lys Ser Ser
145 150 155 160

Phe Tyr Lys Asn Leu Leu Trp Leu Thr Glu Lys Asn Gly Leu Tyr Pro
165 170 175

Asn Leu Ser Lys Ser Tyr Val Asn Asn Lys Glu Lys Glu Val Leu Val
180 185 190

Leu Trp Gly Val His His Pro Ser Asn Ile Gly Asp Gln Arg Ala Ile
195 200 205

Tyr His Thr Glu Asn Ala Tyr Val Ser Val Val Ser Ser His Tyr Ser

```
    210                 215                 220

Arg Arg Phe Thr Pro Glu Ile Thr Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Gly Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Thr Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 63
<211> LENGTH: 565
<212> TYPE: PRT
<213> ORGANISM: Artificial
<220> FEATURE:
<223> OTHER INFORMATION: A/Beijing/262/1995

<400> SEQUENCE: 63

```
Met Lys Ala Lys Leu Leu Val Leu Leu Cys Thr Phe Thr Ala Thr Tyr
```

-continued 1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Leu Leu Lys Gly Ile
50 55 60

Ala Pro Leu Gln Leu Gly Asn Cys Ser Val Ala Gly Trp Ile Leu Gly
65 70 75 80

Asn Pro Glu Cys Glu Ser Leu Ile Ser Lys Glu Ser Trp Ser Tyr Ile
85 90 95

Val Glu Thr Pro Asn Pro Glu Asn Gly Thr Cys Tyr Pro Gly Tyr Phe
100 105 110

Ala Asp Tyr Glu Glu Leu Arg Glu Gln Leu Ser Ser Val Ser Ser Phe
115 120 125

Glu Arg Phe Glu Ile Phe Pro Lys Glu Ser Ser Trp Pro Asn His Thr
130 135 140

Val Thr Gly Val Thr Ala Ser Cys Ser His Asn Gly Lys Ser Ser Phe
145 150 155 160

Tyr Arg Asn Leu Leu Trp Leu Thr Glu Lys Asn Gly Leu Tyr Pro Asn
165 170 175

Leu Ser Asn Ser Tyr Val Asn Asn Lys Glu Lys Glu Val Leu Val Leu
180 185 190

Trp Gly Val His His Pro Ser Asn Ile Arg Asp Gln Arg Ala Ile Tyr
195 200 205

His Thr Glu Asn Ala Tyr Val Ser Val Val Ser Ser His Tyr Ser Arg
210 215 220

Arg Phe Thr Pro Glu Ile Ala Lys Arg Pro Lys Val Arg Gly Gln Glu
225 230 235 240

Gly Arg Ile Asn Tyr Tyr Trp Thr Leu Leu Glu Pro Gly Asp Thr Ile
245 250 255

Ile Phe Glu Ala Asn Gly Asn Leu Ile Ala Pro Trp Tyr Ala Phe Ala
260 265 270

Leu Ser Arg Gly Phe Gly Ser Gly Ile Ile Thr Ser Asn Ala Pro Met
275 280 285

Asn Glu Cys Asp Ala Lys Cys Gln Thr Pro Gln Gly Ala Ile Asn Ser
290 295 300

Ser Leu Pro Phe Gln Asn Val His Pro Val Thr Ile Gly Glu Cys Pro
305 310 315 320

Lys Tyr Val Arg Ser Thr Lys Leu Arg Met Val Thr Gly Leu Arg Asn
325 330 335

Ile Pro Ser Ile Gln Ser Arg Gly Leu Phe Gly Ala Ile Ala Gly Phe
340 345 350

Ile Glu Gly Gly Trp Thr Gly Met Met Asp Gly Trp Tyr Gly Tyr His
355 360 365

His Gln Asn Glu Gln Gly Ser Gly Tyr Ala Ala Asp Gln Lys Ser Thr
370 375 380

Gln Asn Ala Ile Asn Gly Ile Thr Asn Lys Val Asn Ser Val Ile Glu
385 390 395 400

Lys Met Asn Thr Gln Phe Thr Ala Val Gly Lys Glu Phe Asn Lys Leu
405 410 415

Glu Arg Arg Met Glu Asn Leu Asn Lys Lys Val Asp Asp Gly Phe Leu
420 425 430

```
Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 64
<211> LENGTH: 626
<212> TYPE: PRT
<213> ORGANISM: Artificial
<220> FEATURE:
<223> OTHER INFORMATION: A/Texas/36/1991

<400> SEQUENCE: 64

Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Val Ala Gly Trp Ile Leu Gly
65                  70                  75                  80

Asn Pro Lys Cys Glu Ser Leu Phe Ser Lys Glu Ser Trp Ser Tyr Ile
                85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Thr Ser Cys Ser His Asn Gly Lys Ser Ser
145                 150                 155                 160

Phe Tyr Arg Asn Leu Leu Trp Leu Thr Lys Lys Asn Gly Leu Tyr Pro
                165                 170                 175

Asn Val Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Ser
    210                 215                 220
```

-continued

```
Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Gly Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Met Glu Asn Leu Asn Lys Lys Val Asp Asp Gly Phe Leu Asp Ile Trp
                485                 490                 495

Thr Tyr Asn Ala Glu Leu Leu Val Leu Leu Glu Asn Glu Arg Thr Leu
            500                 505                 510

Asp Phe His Asp Ser Asn Val Lys Asn Leu Tyr Glu Lys Val Lys Ser
        515                 520                 525

Gln Leu Lys Asn Asn Ala Lys Glu Ile Gly Asn Gly Cys Phe Glu Phe
    530                 535                 540

Tyr His Lys Cys Asn Asn Glu Cys Met Glu Ser Val Lys Asn Gly Thr
545                 550                 555                 560

Tyr Asp Tyr Pro Lys Tyr Ser Glu Glu Ser Lys Leu Asn Arg Gly Lys
                565                 570                 575

Ile Asp Gly Val Lys Leu Glu Ser Met Gly Val Tyr Gln Ile Leu Ala
            580                 585                 590

Ile Tyr Ser Thr Val Ala Ser Ser Leu Val Leu Leu Val Ser Leu Gly
        595                 600                 605

Ala Ile Ser Phe Trp Met Cys Ser Asn Gly Ser Leu Gln Cys Arg Ile
    610                 615                 620

Cys Ile
625
```

<210> SEQ ID NO 65
<211> LENGTH: 566
<212> TYPE: PRT
<213> ORGANISM: Artificial
<220> FEATURE:
<223> OTHER INFORMATION: A/Singapore/6/1986

<400> SEQUENCE: 65

```
Met Lys Ala Lys Leu Leu Val Leu Leu Cys Ala Phe Thr Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ser Cys Ser His Lys Gly Arg Ser Ser
145                 150                 155                 160

Phe Tyr Arg Asn Leu Leu Trp Leu Thr Lys Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Asn
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365
```

```
His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 66
<211> LENGTH: 506
<212> TYPE: PRT
<213> ORGANISM: Artificial
<220> FEATURE:
<223> OTHER INFORMATION: A/Chile/1/1983

<400> SEQUENCE: 66

```
Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Asn His Asn Gly Lys Leu Cys Lys Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Ser Tyr Val Asn Asn Lys Glu Lys
        115                 120                 125

Glu Val Leu Val Leu Trp Gly Val His His Pro Ser Asn Ile Glu Asp
    130                 135                 140

Gln Lys Thr Ile Tyr Arg Lys Glu Asn Ala Tyr Val Ser Val Val Ser
145                 150                 155                 160
```

-continued

```
Ser His Tyr Asn Arg Arg Phe Thr Pro Glu Ile Ala Lys Arg Pro Lys
                165                 170                 175

Val Arg Asn Gln Glu Gly Arg Ile Asn Tyr Tyr Trp Thr Leu Leu Glu
            180                 185                 190

Pro Gly Asp Thr Ile Ile Phe Glu Ala Asn Gly Asn Leu Ile Ala Pro
        195                 200                 205

Trp Tyr Ala Phe Ala Leu Ser Arg Gly Phe Gly Ser Gly Ile Ile Thr
    210                 215                 220

Ser Asn Ala Ser Met Asp Glu Cys Asp Ala Lys Cys Gln Thr Pro Gln
225                 230                 235                 240

Gly Ala Ile Asn Ser Ser Leu Pro Phe Gln Asn Val His Pro Val Thr
                245                 250                 255

Ile Gly Glu Cys Pro Lys Tyr Val Arg Ser Thr Lys Leu Arg Met Val
            260                 265                 270

Thr Gly Leu Arg Asn Ile Pro Ser Ile Gln Ser Arg Gly Leu Phe Gly
        275                 280                 285

Ala Ile Ala Gly Phe Ile Glu Gly Gly Trp Thr Gly Met Ile Asp Gly
    290                 295                 300

Trp Tyr Gly Tyr His His Gln Asn Glu Gln Gly Ser Gly Tyr Ala Ala
305                 310                 315                 320

Asp Gln Lys Ser Thr Gln Asn Ala Ile Asn Gly Ile Thr Asn Lys Val
                325                 330                 335

Asn Ser Ile Ile Glu Lys Met Asn Thr Gln Phe Thr Ala Val Gly Lys
            340                 345                 350

Glu Phe Asn Lys Leu Glu Lys Arg Met Glu Asn Leu Asn Lys Lys Val
        355                 360                 365

Asp Asp Gly Phe Leu Asp Ile Trp Thr Tyr Asn Ala Glu Leu Leu Val
    370                 375                 380

Leu Leu Glu Asn Glu Arg Thr Leu Asp Phe His Asp Ser Asn Val Lys
385                 390                 395                 400

Asn Leu Tyr Glu Lys Val Lys Ser Gln Leu Lys Asn Asn Ala Lys Glu
                405                 410                 415

Ile Gly Asn Gly Cys Phe Glu Phe Tyr His Lys Cys Asn Asn Glu Cys
            420                 425                 430

Met Glu Ser Val Lys Asn Gly Thr Tyr Asp Tyr Pro Lys Tyr Ser Glu
        435                 440                 445

Glu Ser Lys Leu Asn Arg Glu Lys Ile Asp Gly Val Lys Leu Glu Ser
    450                 455                 460

Met Gly Val Tyr Gln Ile Leu Ala Ile Tyr Ser Thr Val Ala Ser Ser
465                 470                 475                 480

Leu Val Leu Leu Val Ser Leu Gly Ala Ile Ser Phe Trp Met Cys Ser
                485                 490                 495

Asn Gly Ser Leu Gln Cys Arg Ile Cys Ile
            500                 505
```

<210> SEQ ID NO 67
<211> LENGTH: 566
<212> TYPE: PRT
<213> ORGANISM: Artificial
<220> FEATURE:
<223> OTHER INFORMATION: A/Baylor/11515/1982

<400> SEQUENCE: 67

```
Met Lys Ala Lys Leu Leu Val Leu Leu Cys Ala Leu Ser Ala Thr Asp
1               5                   10                  15
```

-continued

```
Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Ser
    130                 135                 140

Val Thr Arg Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asp Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser His Tyr Asn
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Val Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
```

```
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 68
<211> LENGTH: 506
<212> TYPE: PRT
<213> ORGANISM: Artificial
<220> FEATURE:
<223> OTHER INFORMATION: A/Brazil/11/1978

<400> SEQUENCE: 68

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Lys His Asn
    130                 135                 140

Ile Thr Arg Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Lys Arg Pro Lys Val Arg Gly Gln
```

-continued

```
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Leu Val Leu Leu Val Ser Leu Gly Ala Ile Ser Phe Trp Met Cys Ser
                485                 490                 495

Asn Gly Ser Leu Gln Cys Arg Ile Cys Ile
            500                 505


<210> SEQ ID NO 69
<211> LENGTH: 566
<212> TYPE: PRT
<213> ORGANISM: Artificial
<220> FEATURE:
<223> OTHER INFORMATION: A/USSR/90/1977

<400> SEQUENCE: 69

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Phe Ser Lys Lys Ser Trp Ser Tyr Ile
```

-continued

```
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Lys His Asn
    130                 135                 140

Val Thr Arg Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp His Ala Phe
            260                 265                 270

Ala Leu Asn Arg Gly Phe Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510
```

```
Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 70
<211> LENGTH: 566
<212> TYPE: PRT
<213> ORGANISM: Artificial
<220> FEATURE:
<223> OTHER INFORMATION: A/NewJersey/8/1976

<400> SEQUENCE: 70

Met Lys Ala Lys Leu Leu Val Leu Leu Cys Ala Phe Thr Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ser Cys Ser His Lys Gly Arg Ser Ser
145                 150                 155                 160

Phe Tyr Arg Asn Leu Leu Trp Leu Thr Lys Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Asn
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300
```

Ser Ser Leu Pro Phe Gln Asn Val His Pro Val Thr Ile Gly Glu Cys
305 310 315 320

Pro Lys Tyr Val Arg Ser Thr Lys Leu Arg Met Val Thr Gly Leu Arg
325 330 335

Asn Ile Pro Ser Ile Gln Ser Arg Gly Leu Phe Gly Ala Ile Ala Gly
340 345 350

Phe Ile Glu Gly Gly Trp Thr Gly Met Ile Asp Gly Trp Tyr Gly Tyr
355 360 365

His His Gln Asn Glu Gln Gly Ser Gly Tyr Ala Ala Asp Gln Lys Ser
370 375 380

Thr Gln Asn Ala Ile Asn Gly Ile Thr Asn Lys Val Asn Ser Val Ile
385 390 395 400

Glu Lys Met Asn Thr Gln Phe Thr Ala Val Gly Lys Glu Phe Asn Lys
405 410 415

Leu Glu Arg Arg Met Glu Asn Leu Asn Lys Lys Val Asp Asp Gly Phe
420 425 430

Leu Asp Ile Trp Thr Tyr Asn Ala Glu Leu Leu Val Leu Leu Glu Asn
435 440 445

Glu Arg Thr Leu Asp Phe His Asp Ser Asn Val Lys Asn Leu Tyr Glu
450 455 460

Lys Val Lys Ser Gln Leu Lys Asn Asn Ala Lys Glu Ile Gly Asn Gly
465 470 475 480

Cys Phe Glu Phe Tyr His Lys Cys Asn Asn Glu Cys Met Glu Ser Val
485 490 495

Lys Asn Gly Thr Tyr Asp Tyr Pro Lys Tyr Ser Glu Glu Ser Lys Leu
500 505 510

Asn Arg Glu Lys Ile Asp Gly Val Lys Leu Glu Ser Met Gly Val Tyr
515 520 525

Gln Ile Leu Ala Ile Tyr Ser Thr Val Ala Ser Ser Leu Val Leu Leu
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 71
<211> LENGTH: 565
<212> TYPE: PRT
<213> ORGANISM: Artificial
<220> FEATURE:
<223> OTHER INFORMATION: A/Denver/1957

<400> SEQUENCE: 71

Met Lys Ala Lys Leu Leu Ile Leu Leu Cys Ala Leu Ser Ala Thr Asp
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Lys
50 55 60

Ala Pro Leu Gln Leu Gly Asn Cys Asn Ile Ala Gly Trp Val Leu Gly
65 70 75 80

Asn Pro Glu Cys Glu Ser Leu Leu Ser Asn Arg Ser Trp Ser Tyr Ile
85 90 95

-continued

```
Ala Glu Thr Pro Asn Ser Glu Asn Gly Thr Cys Tyr Pro Gly Asp Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Asn His Thr
    130                 135                 140

Thr Arg Gly Val Thr Ala Ala Cys Pro His Ala Arg Lys Ser Ser Phe
145                 150                 155                 160

Tyr Lys Asn Leu Val Trp Leu Thr Glu Ala Asn Gly Ser Tyr Pro Asn
                165                 170                 175

Leu Ser Arg Ser Tyr Val Asn Asn Gln Glu Lys Glu Val Leu Val Leu
            180                 185                 190

Trp Gly Val His His Pro Ser Asn Ile Glu Glu Gln Arg Ala Leu Tyr
        195                 200                 205

Arg Lys Asp Asn Ala Tyr Val Ser Val Val Ser Ser Asn Tyr Asn Arg
    210                 215                 220

Arg Phe Thr Pro Glu Ile Ala Lys Arg Pro Lys Val Arg Asp Gln Ser
225                 230                 235                 240

Gly Arg Met Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Pro Gly Ser Gly Ile Ile Thr Ser Asn Ala Pro Leu
        275                 280                 285

Asp Glu Cys Asp Thr Lys Cys Gln Thr Pro Gln Gly Ala Ile Asn Ser
    290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Val Gln Ser Arg Gly Leu Phe Gly Ala Ile Ala Gly Phe
            340                 345                 350

Ile Glu Gly Gly Trp Thr Gly Met Met Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Lys Arg Met Glu Asn Leu Asn Lys Lys Val Asp Asp Gly Phe Met
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Asn Gln Leu Arg Asn Asn Ala Lys Glu Leu Gly Asn Gly Cys
465                 470                 475                 480

Phe Glu Phe Tyr His Lys Cys Asp Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510
```

```
Arg Glu Lys Ile Asp Gly Val Lys Leu Glu Ser Met Gly Val Tyr Arg
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 72
<211> LENGTH: 566
<212> TYPE: PRT
<213> ORGANISM: Artificial
<220> FEATURE:
<223> OTHER INFORMATION: A/Albany/4835/1948

<400> SEQUENCE: 72

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Lys His Asn
    130                 135                 140

Ile Thr Arg Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Asn Lys Ser Tyr Val Asn Asn Lys Glu Lys Glu Val Leu Val
            180                 185                 190

Leu Trp Gly Val His His Pro Ser Asn Ile Glu Asp Gln Lys Thr Leu
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp His Ala Phe
            260                 265                 270

Ala Leu Ser Arg Gly Phe Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300
```

-continued

```
Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 73
<211> LENGTH: 566
<212> TYPE: PRT
<213> ORGANISM: Artificial
<220> FEATURE:
<223> OTHER INFORMATION: A/FortMonmouth/1/1947

<400> SEQUENCE: 73

```
Met Lys Ala Lys Leu Leu Ile Leu Leu Cys Ala Leu Thr Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Lys Arg Ser Trp Ser Tyr Ile
                85                  90                  95
```

-continued

```
Ala Glu Thr Pro Asn Ser Glu Asn Gly Ala Cys Tyr Pro Gly Asp Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Lys His Asn
    130                 135                 140

Ile Thr Arg Gly Val Thr Ala Ala Cys Ser His Ala Gly Lys Ser Ser
145                 150                 155                 160

Phe Tyr Lys Asn Leu Leu Trp Leu Thr Glu Thr Asp Gly Ser Tyr Pro
                165                 170                 175

Lys Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Leu
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Asp Phe Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Lys Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Trp Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Asn Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
```

```
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 74
<211> LENGTH: 566
<212> TYPE: PRT
<213> ORGANISM: Artificial
<220> FEATURE:
<223> OTHER INFORMATION: A/Cameron/1946

<400> SEQUENCE: 74

Met Lys Ala Lys Leu Leu Ile Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Lys Arg Ser Trp Ser Tyr Ile
                85                  90                  95

Ala Glu Thr Pro Asn Ser Glu Asn Gly Ala Cys Tyr Pro Gly Asp Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Gly Arg Ser Trp Pro Glu His Asn
    130                 135                 140

Ile Asp Ile Gly Val Thr Ala Ala Cys Ser His Ala Gly Lys Ser Ser
145                 150                 155                 160

Phe Tyr Lys Asn Leu Leu Trp Leu Thr Glu Lys Asp Gly Ser Tyr Pro
                165                 170                 175

Asn Leu Asn Lys Ser Tyr Val Asn Lys Lys Glu Lys Glu Val Leu Ile
            180                 185                 190

Leu Trp Gly Val His His Pro Pro Asn Ile Glu Asn Gln Lys Thr Leu
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Asn Arg Gly Ile Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Ile His Pro Phe Thr Ile Gly Glu Cys
```

```
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Asp Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Asn Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Phe Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 75
<211> LENGTH: 566
<212> TYPE: PRT
<213> ORGANISM: Artificial
<220> FEATURE:
<223> OTHER INFORMATION: A/Weiss/1943

<400> SEQUENCE: 75

Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Glu Arg Ser Trp Ser Tyr Ile
                85                  90                  95

Val Glu Ile Pro Asn Ser Glu Asn Gly Thr Cys Tyr Pro Gly Asp Phe
```

-continued

```
            100                 105                 110

Thr Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Asn
    130                 135                 140

Thr Ala Arg Gly Val Thr Ala Ala Cys Ser His Ala Gly Lys Ser Ser
145                 150                 155                 160

Phe Tyr Arg Asn Leu Leu Trp Leu Thr Glu Lys Asp Gly Ser Tyr Pro
                165                 170                 175

Asn Leu Lys Asn Ser Tyr Val Asn Lys Lys Gly Lys Glu Val Leu Val
            180                 185                 190

Leu Trp Gly Val His His Pro Ser Ser Ile Lys Glu Gln Gln Thr Leu
        195                 200                 205

Tyr Gln Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met His Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Ile Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525
```

```
Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 76
<211> LENGTH: 565
<212> TYPE: PRT
<213> ORGANISM: Artificial
<220> FEATURE:
<223> OTHER INFORMATION: A/Iowa/1943

<400> SEQUENCE: 76

Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Glu Arg Ser Trp Ser Tyr Ile
                85                  90                  95

Val Glu Thr Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Ser Lys Glu Ser Ser Trp Pro Lys His Thr
    130                 135                 140

Thr Gly Gly Val Thr Ala Ala Cys Ser His Ala Gly Lys Ser Ser Phe
145                 150                 155                 160

Tyr Arg Asn Leu Leu Trp Leu Thr Glu Lys Asp Gly Ser Tyr Pro Asn
                165                 170                 175

Leu Asn Asn Ser Tyr Val Asn Lys Lys Gly Lys Glu Val Leu Val Leu
            180                 185                 190

Trp Gly Val His His Pro Ser Asn Ile Lys Asp Gln Gln Thr Leu Tyr
        195                 200                 205

Gln Lys Glu Asn Ala Tyr Val Ser Val Val Ser Ser Asn Tyr Asn Arg
    210                 215                 220

Arg Phe Thr Pro Glu Ile Ala Glu Arg Pro Lys Val Arg Gly Gln Ala
225                 230                 235                 240

Gly Arg Ile Asn Tyr Tyr Trp Thr Leu Leu Lys Pro Gly Asp Thr Ile
                245                 250                 255

Met Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Ser Met
        275                 280                 285

His Glu Cys Asp Thr Lys Cys Gln Thr Pro Gln Gly Ala Ile Asn Ser
    290                 295                 300

Ser Leu Pro Phe Gln Asn Ile His Pro Val Thr Ile Gly Glu Cys Pro
305                 310                 315                 320
```

```
Lys Tyr Val Arg Ser Thr Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Asn Gln Leu Arg Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Ala Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 77
<211> LENGTH: 446
<212> TYPE: PRT
<213> ORGANISM: Artificial
<220> FEATURE:
<223> OTHER INFORMATION: A/Bellamy/1942

<400> SEQUENCE: 77

Met Lys Ala Arg Leu Leu Val Leu Leu Cys Ala Ile Ala Ala Thr Asp
1               5                   10                  15

Ala Asp Thr Ile Cys Ile Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Glu Arg Ser Trp Ser Tyr Ile
                85                  90                  95

Val Glu Thr Pro Asn Ser Glu Asn Gly Thr Cys Tyr Pro Gly Asp Phe
            100                 105                 110
```

```
Ile Asp Tyr Glu Glu Leu Arg Glu Gln Leu Ser Ser Val Thr Ser Phe
        115                 120                 125

Glu Arg Phe Glu Ile Phe Pro Lys Glu Thr Ser Trp Pro Lys His Asn
    130                 135                 140

Thr Thr Lys Gly Val Thr Ala Ala Cys Ser His Ala Gly Lys Cys Ser
145                 150                 155                 160

Phe Tyr Arg Asn Leu Leu Trp Leu Thr Glu Lys Asp Gly Ser Tyr Pro
                165                 170                 175

Asn Leu Asn Asn Ser Tyr Val Asn Lys Lys Gly Lys Glu Val Leu Val
            180                 185                 190

Leu Trp Gly Val His His Pro Ser Asn Ile Lys Asp Gln Gln Thr Leu
        195                 200                 205

Tyr Gln Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met His Glu Cys Asn Thr Lys Cys Gln Thr Pro Gln Met Ile Asp Gly
    290                 295                 300

Trp Tyr Gly Tyr His His Gln Asn Glu Gln Gly Ser Gly Tyr Ala Ala
305                 310                 315                 320

Asp Gln Lys Ser Thr Gln Asn Ala Ile Asn Gly Ile Thr Asn Lys Val
                325                 330                 335

Asn Ser Val Ile Glu Lys Met Asn Thr Gln Phe Thr Ala Val Gly Lys
            340                 345                 350

Glu Phe Asn Asn Leu Glu Lys Arg Met Glu Asn Leu Asn Lys Lys Val
        355                 360                 365

Asp Asp Gly Phe Leu Asp Ile Trp Thr Tyr Asn Ala Glu Leu Leu Val
    370                 375                 380

Leu Leu Glu Asn Glu Arg Thr Leu Asp Phe His Asp Ser Asn Val Lys
385                 390                 395                 400

Asn Leu Tyr Glu Lys Val Lys Ser Gln Leu Arg Asn Asn Ala Lys Glu
                405                 410                 415

Ile Gly Asn Gly Leu Val Leu Leu Val Ser Leu Gly Ala Ile Ser Phe
            420                 425                 430

Trp Met Cys Ser Asn Gly Ser Leu Gln Cys Arg Ile Cys Ile
        435                 440                 445


<210> SEQ ID NO 78
<211> LENGTH: 565
<212> TYPE: PRT
<213> ORGANISM: Artificial
<220> FEATURE:
<223> OTHER INFORMATION: A/PuertoRico/8/1934

<400> SEQUENCE: 78

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30
```

-continued

```
Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Arg Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Asn Lys Val Asp Asp Gly Phe Leu
            420                 425                 430

Asp Ile Trp Thr Tyr Asn Ala Glu Leu Leu Val Leu Leu Glu Asn Glu
        435                 440                 445
```

```
Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 79
<211> LENGTH: 565
<212> TYPE: PRT
<213> ORGANISM: Artificial
<220> FEATURE:
<223> OTHER INFORMATION: A/WSN/1933

<400> SEQUENCE: 79

Met Lys Ala Lys Leu Leu Val Leu Leu Tyr Ala Phe Val Ala Thr Asp
1               5                   10                  15

Ala Asp Thr Ile Cys Ile Gly Tyr His Ala Asn Asn Ser Thr Asp Thr
            20                  25                  30

Val Asp Thr Ile Phe Glu Lys Asn Val Ala Val Thr His Ser Val Asn
        35                  40                  45

Leu Leu Glu Asp Arg His Asn Gly Lys Leu Cys Lys Leu Lys Gly Ile
    50                  55                  60

Ala Pro Leu Gln Leu Gly Lys Cys Asn Ile Thr Gly Trp Leu Leu Gly
65                  70                  75                  80

Asn Pro Glu Cys Asp Ser Leu Leu Pro Ala Arg Ser Trp Ser Tyr Ile
                85                  90                  95

Val Glu Thr Pro Asn Ser Glu Asn Gly Ala Cys Tyr Pro Gly Asp Phe
            100                 105                 110

Ile Asp Tyr Glu Glu Leu Arg Glu Gln Leu Ser Ser Val Ser Ser Leu
        115                 120                 125

Glu Arg Phe Glu Ile Phe Pro Lys Glu Ser Ser Trp Pro Asn His Thr
    130                 135                 140

Phe Asn Gly Val Thr Val Ser Cys Ser His Arg Gly Lys Ser Ser Phe
145                 150                 155                 160

Tyr Arg Asn Leu Leu Trp Leu Thr Lys Lys Gly Asp Ser Tyr Pro Lys
                165                 170                 175

Leu Thr Asn Ser Tyr Val Asn Asn Lys Gly Lys Glu Val Leu Val Leu
            180                 185                 190

Trp Gly Val His His Pro Ser Ser Ser Asp Glu Gln Gln Ser Leu Tyr
        195                 200                 205

Ser Asn Gly Asn Ala Tyr Val Ser Val Ala Ser Ser Asn Tyr Asn Arg
    210                 215                 220

Arg Phe Thr Pro Glu Ile Ala Ala Arg Pro Lys Val Lys Asp Gln His
225                 230                 235                 240
```

```
Gly Arg Met Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Phe Glu Ser Gly Ile Ile Thr Ser Asn Ala Ser Met
        275                 280                 285

His Glu Cys Asn Thr Lys Cys Gln Thr Pro Gln Gly Ser Ile Asn Ser
    290                 295                 300

Asn Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Tyr Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Leu Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 80
<211> LENGTH: 566
<212> TYPE: PRT
<213> ORGANISM: Artificial
<220> FEATURE:
<223> OTHER INFORMATION: A/SouthCarolina/1/1918

<400> SEQUENCE: 80

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30
```

```
Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Pro Thr Gly Thr Asp Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
        275                 280                 285

Val His Asp Cys Asn Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
```

```
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 81
<211> LENGTH: 10
<212> TYPE: PRT
<213> ORGANISM: Artificial
<220> FEATURE:
<223> OTHER INFORMATION: artificial sequence

<400> SEQUENCE: 81

Ala Gly Arg His His His His His His His
1               5                   10


<210> SEQ ID NO 82
<211> LENGTH: 48
<212> TYPE: PRT
<213> ORGANISM: Artificial
<220> FEATURE:
<223> OTHER INFORMATION: artificial sequence

<400> SEQUENCE: 82

Ser Gly Arg Ser Leu Val Pro Arg Gly Ser Pro Gly Ser Gly Tyr Ile
1               5                   10                  15

Pro Glu Ala Pro Arg Asp Gly Gln Ala Tyr Val Arg Lys Asp Gly Glu
            20                  25                  30

Trp Val Leu Leu Ser Thr Phe Leu Gly His His His His His His His
        35                  40                  45


<210> SEQ ID NO 83
<211> LENGTH: 16
<212> TYPE: PRT
<213> ORGANISM: Artificial
<220> FEATURE:
<223> OTHER INFORMATION: artificial sequence

<400> SEQUENCE: 83

Ile Glu Ala Ile Glu Lys Lys Ile Glu Ala Ile Glu Lys Lys Ile Glu
1               5                   10                  15


<210> SEQ ID NO 84
<211> LENGTH: 15
<212> TYPE: PRT
<213> ORGANISM: Artificial
<220> FEATURE:
<223> OTHER INFORMATION: artificial sequence

<400> SEQUENCE: 84

Met Lys Gln Ile Glu Asp Lys Ile Glu Glu Ile Glu Ser Lys Gln
```

1 5 10 15

<210> SEQ ID NO 85
<211> LENGTH: 15
<212> TYPE: PRT
<213> ORGANISM: Artificial
<220> FEATURE:
<223> OTHER INFORMATION: artificial sequence

<400> SEQUENCE: 85

Ile Glu Ala Ile Glu Lys Lys Ile Glu Ala Ile Glu Lys Lys Ile
1 5 10 15

<210> SEQ ID NO 86
<211> LENGTH: 14
<212> TYPE: PRT
<213> ORGANISM: Artificial
<220> FEATURE:
<223> OTHER INFORMATION: artificial sequence

<400> SEQUENCE: 86

Ile Glu Ala Ile Glu Lys Lys Ile Glu Ala Ile Glu Lys Lys
1 5 10

<210> SEQ ID NO 87
<211> LENGTH: 14
<212> TYPE: PRT
<213> ORGANISM: Artificial
<220> FEATURE:
<223> OTHER INFORMATION: artificial sequence

<400> SEQUENCE: 87

Met Lys Gln Ile Glu Asp Lys Ile Glu Glu Ile Glu Ser Lys
1 5 10

<210> SEQ ID NO 88
<211> LENGTH: 17
<212> TYPE: PRT
<213> ORGANISM: Artificial
<220> FEATURE:
<223> OTHER INFORMATION: artificial sequence

<400> SEQUENCE: 88

Arg Met Lys Gln Ile Glu Asp Lys Ile Glu Glu Ile Glu Ser Lys Gln
1 5 10 15

Lys

<210> SEQ ID NO 89
<211> LENGTH: 566
<212> TYPE: PRT
<213> ORGANISM: Artificial Sequence
<220> FEATURE:
<223> OTHER INFORMATION: H3 Full length A/Wisconsin/67/2005

<400> SEQUENCE: 89

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Gln Ile Glu Val Thr Asn Ala Thr Glu Leu Val Gln Ser Ser Ser Thr
50 55 60

Gly Gly Ile Cys Asp Ser Pro His Gln Ile Leu Asp Gly Glu Asn Cys

```
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495
```

```
Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565


<210> SEQ ID NO 90
<211> LENGTH: 346
<212> TYPE: PRT
<213> ORGANISM: Artificial Sequence
<220> FEATURE:
<223> OTHER INFORMATION: mini-H3

<400> SEQUENCE: 90

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Gly Gly Gly Gly Cys Asn Ser Glu Cys Ile Thr Pro
65                  70                  75                  80

Asn Gly Ser Ile Pro Asn Asp Lys Pro Phe Gln Asn Val Asn Arg Ile
                85                  90                  95

Thr Tyr Gly Ala Cys Pro Arg Tyr Val Lys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Leu Asn Arg Leu Ile Gly Lys Thr Asn Glu Lys Phe His Gln Ile Glu
            180                 185                 190

Lys Glu Phe Ser Glu Val Glu Gly Arg Ile Gln Asp Leu Glu Lys Tyr
        195                 200                 205

Val Glu Asp Thr Lys Ile Asp Leu Trp Ser Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Gly Ser Ile Arg Asn Gly Thr Tyr Asp His Asp Val Tyr Arg
        275                 280                 285
```

```
Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345


<210> SEQ ID NO 91
<211> LENGTH: 346
<212> TYPE: PRT
<213> ORGANISM: Artificial Sequence
<220> FEATURE:
<223> OTHER INFORMATION: mini-H3 cluster 1

<400> SEQUENCE: 91

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Ala Cys Pro Arg Tyr Val Lys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Leu Asn Arg Leu Ile Gly Lys Thr Asn Glu Lys Thr Ser Gln Ile Glu
            180                 185                 190

Lys Glu Phe Ser Glu Ser Glu Gly Arg Ile Gln Asp Leu Glu Lys Tyr
        195                 200                 205

Val Glu Asp Thr Lys Ile Asp Leu Trp Ser Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Gly Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300
```

```
Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345


<210> SEQ ID NO 92
<211> LENGTH: 346
<212> TYPE: PRT
<213> ORGANISM: Artificial Sequence
<220> FEATURE:
<223> OTHER INFORMATION: mini-H3 cluster1+2

<400> SEQUENCE: 92

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Cys Cys Pro Arg Tyr Val Lys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Leu Asn Arg Leu Ile Gly Lys Thr Asn Cys Lys Thr Ser Gln Ile Glu
            180                 185                 190

Lys Glu Phe Ser Glu Ser Glu Gly Arg Ile Gln Asp Leu Glu Lys Tyr
        195                 200                 205

Val Glu Asp Thr Lys Ile Asp Leu Trp Ser Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Gly Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320
```

```
Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345


<210> SEQ ID NO 93
<211> LENGTH: 346
<212> TYPE: PRT
<213> ORGANISM: Artificial Sequence
<220> FEATURE:
<223> OTHER INFORMATION: mini-H3 cluster1+3

<400> SEQUENCE: 93

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Ala Cys Pro Arg Tyr Val Cys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Leu Asn Arg Leu Ile Gly Lys Thr Asn Glu Lys Thr Ser Gln Ile Glu
            180                 185                 190

Lys Glu Phe Ser Glu Ser Glu Gly Arg Ile Gln Asp Leu Glu Lys Tyr
        195                 200                 205

Val Glu Asp Thr Lys Ile Ala Leu Trp Cys Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Gly Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335
```

```
Lys Gly Asn Ile Arg Cys Asn Ile Cys Ile
            340                 345


<210> SEQ ID NO 94
<211> LENGTH: 346
<212> TYPE: PRT
<213> ORGANISM: Artificial Sequence
<220> FEATURE:
<223> OTHER INFORMATION: mini-H3 cluster1+4

<400> SEQUENCE: 94

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Ala Cys Pro Arg Tyr Val Lys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Lys Asn Arg Leu Thr Gly Lys Thr Asn Glu Lys Thr Ser Gln Ile Glu
            180                 185                 190

Lys Glu Phe Ser Glu Ser Glu Gly Arg Ile Gln Asp Leu Glu Lys Tyr
        195                 200                 205

Val Glu Asp Thr Lys Ile Asp Leu Trp Ser Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Gly Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345
```

<210> SEQ ID NO 95
<211> LENGTH: 346
<212> TYPE: PRT
<213> ORGANISM: Artificial Sequence
<220> FEATURE:
<223> OTHER INFORMATION: mini-H3 cluster1+5 N60A

<400> SEQUENCE: 95

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Ala Cys Pro Arg Tyr Val Lys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Leu Asn Arg Leu Ile Gly Lys Thr Ala Glu Lys Thr Ser Gln Ile Glu
            180                 185                 190

Lys Glu Phe Ser Glu Ser Glu Gly Arg Ile Gln Asp Leu Glu Lys Tyr
        195                 200                 205

Val Glu Asp Thr Lys Ile Asp Leu Trp Ser Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Gly Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345
```

<210> SEQ ID NO 96

<211> LENGTH: 346
<212> TYPE: PRT
<213> ORGANISM: Artificial Sequence
<220> FEATURE:
<223> OTHER INFORMATION: mini-H3 cluster1+5 N60D

<400> SEQUENCE: 96

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Ala Cys Pro Arg Tyr Val Lys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Leu Asn Arg Leu Ile Gly Lys Thr Asp Glu Lys Thr Ser Gln Ile Glu
            180                 185                 190

Lys Glu Phe Ser Glu Ser Glu Gly Arg Ile Gln Asp Leu Glu Lys Tyr
        195                 200                 205

Val Glu Asp Thr Lys Ile Asp Leu Trp Ser Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Gly Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345
```

<210> SEQ ID NO 97
<211> LENGTH: 346
<212> TYPE: PRT
<213> ORGANISM: Artificial Sequence
<220> FEATURE:
<223> OTHER INFORMATION: mini-H3 cluster1+5 N60E

<400> SEQUENCE: 97

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Ala Cys Pro Arg Tyr Val Lys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Leu Asn Arg Leu Ile Gly Lys Thr Glu Glu Lys Thr Ser Gln Ile Glu
            180                 185                 190

Lys Glu Phe Ser Glu Ser Glu Gly Arg Ile Gln Asp Leu Glu Lys Tyr
        195                 200                 205

Val Glu Asp Thr Lys Ile Asp Leu Trp Ser Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Gly Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345
```

<210> SEQ ID NO 98
<211> LENGTH: 346
<212> TYPE: PRT
<213> ORGANISM: Artificial Sequence
<220> FEATURE:
<223> OTHER INFORMATION: mini-H3 cluster1+6

<400> SEQUENCE: 98

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Ala Cys Pro Arg Tyr Val Lys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Leu Asn Arg Leu Ile Gly Lys Thr Asn Glu Lys Thr Ser Gln Ile Glu
            180                 185                 190

Lys Glu Cys Ser Glu Ser Glu Gly Arg Ile Cys Asp Leu Glu Lys Tyr
        195                 200                 205

Val Glu Asp Thr Lys Ile Asp Leu Trp Ser Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Gly Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345
```

<210> SEQ ID NO 99
<211> LENGTH: 346
<212> TYPE: PRT
<213> ORGANISM: Artificial Sequence
<220> FEATURE:
<223> OTHER INFORMATION: mini-H3 cluster1+7

<400> SEQUENCE: 99

```
Met Lys Thr Ile Ile Ala Leu Ser Tyr Ile Leu Cys Leu Val Phe Ala
```

-continued

```
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Ala Cys Pro Arg Tyr Val Lys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Leu Asn Arg Leu Ile Gly Lys Thr Asn Glu Lys Thr Ser Gln Ile Glu
            180                 185                 190

Lys Glu Phe Ser Glu Ser Glu Gly Arg Ile Gln Asp Leu Glu Lys Tyr
        195                 200                 205

Val Glu Asp Thr Lys Ile Asp Leu Trp Ser Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Glu Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345
```

<210> SEQ ID NO 100
<211> LENGTH: 346
<212> TYPE: PRT
<213> ORGANISM: Artificial Sequence
<220> FEATURE:
<223> OTHER INFORMATION: mini-H3 cluster1+2+3+4+5+6+7-N405E

<400> SEQUENCE: 100

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
```

```
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Cys Cys Pro Arg Tyr Val Cys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Lys Asn Arg Leu Thr Gly Lys Thr Glu Cys Lys Thr Ser Gln Ile Glu
            180                 185                 190

Lys Glu Cys Ser Glu Ser Glu Gly Arg Ile Cys Asp Leu Glu Lys Tyr
        195                 200                 205

Val Glu Asp Thr Lys Ile Ala Leu Trp Cys Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Glu Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345


<210> SEQ ID NO 101
<211> LENGTH: 346
<212> TYPE: PRT
<213> ORGANISM: Artificial Sequence
<220> FEATURE:
<223> OTHER INFORMATION: mini-H3 cluster1+2+3+4+5+6+7-N405A

<400> SEQUENCE: 101

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
```

```
        35                  40                  45

Gln Ile Glu Val Thr Asn Ala Thr Glu Leu Val Gln Ser Ser Thr
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Cys Cys Pro Arg Tyr Val Cys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Lys Asn Arg Leu Thr Gly Lys Thr Ala Cys Lys Thr Ser Gln Ile Glu
            180                 185                 190

Lys Glu Cys Ser Glu Ser Glu Gly Arg Ile Cys Asp Leu Glu Lys Tyr
        195                 200                 205

Val Glu Asp Thr Lys Ile Ala Leu Trp Cys Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Glu Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345


<210> SEQ ID NO 102
<211> LENGTH: 346
<212> TYPE: PRT
<213> ORGANISM: Artificial Sequence
<220> FEATURE:
<223> OTHER INFORMATION: mini-H3 cluster1+2+3+4+5+6+7-N405D

<400> SEQUENCE: 102

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Thr
```

```
    50                  55                  60

Gly Gly Thr Cys Gly Gly Gly Gly Cys Asn Ser Glu Cys Thr Thr Pro
65                  70                  75                  80

Asn Gly Ser Ile Pro Asn Asp Lys Pro Phe Gln Asn Val Asn Arg Gln
                85                  90                  95

Thr Tyr Gly Cys Cys Pro Arg Tyr Val Cys Gln Asn Thr Leu Lys Leu
            100                 105                 110

Ala Thr Gly Met Arg Asn Val Pro Glu Lys Gln Thr Gln Gly Ile Phe
        115                 120                 125

Gly Ala Ile Ala Gly Phe Ile Glu Asn Gly Trp Glu Gly Met Val Asp
    130                 135                 140

Gly Trp Tyr Gly Phe Arg His Gln Asn Ser Glu Gly Ile Gly Gln Ala
145                 150                 155                 160

Ala Asp Leu Lys Ser Thr Gln Ala Ala Ile Asn Gln Ile Asn Gly Lys
                165                 170                 175

Lys Asn Arg Leu Thr Gly Lys Thr Asp Cys Lys Thr Ser Gln Ile Glu
            180                 185                 190

Lys Glu Cys Ser Glu Ser Glu Gly Arg Ile Cys Asp Leu Glu Lys Tyr
        195                 200                 205

Val Glu Asp Thr Lys Ile Ala Leu Trp Cys Tyr Asn Ala Glu Leu Leu
    210                 215                 220

Val Ala Leu Glu Asn Gln His Thr Ile Asp Leu Thr Asp Ser Glu Met
225                 230                 235                 240

Asn Lys Leu Phe Glu Arg Thr Lys Lys Gln Leu Arg Glu Asn Ala Glu
                245                 250                 255

Asp Met Gly Asn Gly Cys Phe Lys Ile Tyr His Lys Cys Asp Asn Ala
            260                 265                 270

Cys Ile Glu Ser Ile Arg Asn Gly Thr Tyr Asp His Asp Val Tyr Arg
        275                 280                 285

Asp Glu Ala Leu Asn Asn Arg Phe Gln Ile Lys Gly Val Glu Leu Lys
    290                 295                 300

Ser Gly Tyr Lys Asp Trp Ile Leu Trp Ile Ser Phe Ala Ile Ser Cys
305                 310                 315                 320

Phe Leu Leu Cys Val Val Leu Leu Gly Phe Ile Met Trp Ala Cys Gln
                325                 330                 335

Lys Gly Asn Ile Arg Cys Asn Ile Cys Ile
            340                 345


<210> SEQ ID NO 103
<211> LENGTH: 346
<212> TYPE: PRT
<213> ORGANISM: Artificial Sequence
<220> FEATURE:
<223> OTHER INFORMATION: mini-H3 cluster1+8

<400> SEQUENCE: 103

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Thr Cys Gly Gly Gly Gly Cys Asn Ser Glu Cys Thr Thr Pro
```

65 70 75 80

Asn Gly Ser Ile Pro Asn Asp Lys Pro Phe Gln Asn Val Asn Arg Gln
85 90 95

Thr Tyr Gly Ala Cys Pro Arg Tyr Val Lys Gln Asn Thr Leu Lys Leu
100 105 110

Ala Thr Gly Met Arg Asn Val Pro Glu Lys Gln Thr Gln Gly Ile Cys
115 120 125

Gly Ala Ile Ala Gly Phe Ile Glu Asn Gly Trp Glu Gly Met Val Asp
130 135 140

Gly Trp Tyr Gly Phe Arg His Gln Asn Ser Glu Gly Ile Gly Gln Ala
145 150 155 160

Ala Asp Leu Lys Cys Thr Gln Ala Ala Ile Asn Gln Ile Asn Gly Lys
165 170 175

Leu Asn Arg Leu Ile Gly Lys Thr Asn Glu Lys Thr Ser Gln Ile Glu
180 185 190

Lys Glu Phe Ser Glu Ser Glu Gly Arg Ile Gln Asp Leu Glu Lys Tyr
195 200 205

Val Glu Asp Thr Lys Ile Asp Leu Trp Ser Tyr Asn Ala Glu Leu Leu
210 215 220

Val Ala Leu Glu Asn Gln His Thr Ile Asp Leu Thr Asp Ser Glu Met
225 230 235 240

Cys Lys Cys Phe Glu Arg Thr Lys Lys Gln Leu Arg Glu Asn Ala Glu
245 250 255

Asp Met Gly Asn Gly Cys Phe Lys Ile Tyr His Lys Cys Asp Asn Ala
260 265 270

Cys Ile Gly Ser Ile Arg Asn Gly Thr Tyr Asp His Asp Val Tyr Arg
275 280 285

Asp Glu Ala Leu Asn Asn Arg Phe Gln Ile Lys Gly Val Glu Leu Lys
290 295 300

Ser Gly Tyr Lys Asp Trp Ile Leu Trp Ile Ser Phe Ala Ile Ser Cys
305 310 315 320

Phe Leu Leu Cys Val Val Leu Leu Gly Phe Ile Met Trp Ala Cys Gln
325 330 335

Lys Gly Asn Ile Arg Cys Asn Ile Cys Ile
340 345

<210> SEQ ID NO 104
<211> LENGTH: 21
<212> TYPE: PRT
<213> ORGANISM: Artificial Sequence
<220> FEATURE:
<223> OTHER INFORMATION: H3 consensus sequence residue 401-421
<220> FEATURE:
<221> NAME/KEY: misc_feature
<222> LOCATION: (2)..(2)
<223> OTHER INFORMATION: Xaa can be any naturally occurring amino acid

<400> SEQUENCE: 104

Ile Xaa Lys Thr Asn Glu Lys Phe His Gln Ile Glu Lys Glu Phe Ser
1 5 10 15

Glu Val Glu Gly Arg
20

<210> SEQ ID NO 105
<211> LENGTH: 309
<212> TYPE: PRT
<213> ORGANISM: Artificial Sequence
<220> FEATURE:

<223> OTHER INFORMATION: H3-mini2

<400> SEQUENCE: 105

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Gly Gly Gly
    50                  55                  60

Gly Arg Tyr Val Lys Gln Asn Thr Leu Lys Leu Ala Thr Gly Met Arg
65                  70                  75                  80

Asn Val Pro Glu Lys Gln Thr Gln Gly Ile Phe Gly Ala Ile Ala Gly
                85                  90                  95

Phe Ile Glu Asn Gly Trp Glu Gly Met Val Asp Gly Trp Tyr Gly Phe
            100                 105                 110

Arg His Gln Asn Ser Glu Gly Ile Gly Gln Ala Ala Asp Leu Lys Ser
        115                 120                 125

Thr Gln Ala Ala Ile Asn Gln Ile Asn Gly Lys Leu Asn Arg Leu Ile
    130                 135                 140

Gly Lys Thr Asn Glu Lys Phe His Gln Ile Glu Lys Glu Phe Ser Glu
145                 150                 155                 160

Val Glu Gly Arg Ile Gln Asp Leu Glu Lys Tyr Val Glu Asp Thr Lys
                165                 170                 175

Ile Asp Leu Trp Ser Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Arg Thr Lys Lys Gln Leu Arg Glu Asn Ala Glu Asp Met Gly Asn Gly
    210                 215                 220

Cys Phe Lys Ile Tyr His Lys Cys Asp Asn Ala Cys Ile Gly Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Lys Gly Asn Ile Arg
    290                 295                 300

Cys Asn Ile Cys Ile
305

<210> SEQ ID NO 106
<211> LENGTH: 309
<212> TYPE: PRT
<213> ORGANISM: Artificial Sequence
<220> FEATURE:
<223> OTHER INFORMATION: H3-mini2-cl9+10

<400> SEQUENCE: 106

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
35 40 45

Gln Ile Glu Val Thr Asn Ala Thr Glu Leu Val Gln Ser Gly Gly Gly
50 55 60

Gly Arg Tyr Val Lys Gln Asn Thr Leu Lys Leu Ala Thr Gly Met Arg
65 70 75 80

Asn Val Pro Glu Lys Gln Thr Gln Gly Ile Phe Gly Ala Ile Ala Gly
85 90 95

Phe Ile Glu Asn Gly Trp Glu Gly Met Val Asp Gly Trp Tyr Gly Phe
100 105 110

Arg His Gln Asn Ser Glu Gly Ile Gly Gln Ala Ala Asp Leu Lys Ser
115 120 125

Thr Gln Ala Ala Ile Asn Gln Ile Asn Gly Lys Leu Asn Arg Leu Ile
130 135 140

Gly Lys Thr Asn Glu Lys Ser His Gln Thr Glu Lys Glu Ser Ser Glu
145 150 155 160

Gly Glu Gly Arg Ile Gln Asp Leu Glu Lys Tyr Val Glu Asp Thr Lys
165 170 175

Ile Asp Leu Trp Ser Tyr Asn Ala Glu Leu Leu Val Ala Leu Glu Asn
180 185 190

Gln His Thr Ile Asp Leu Thr Asp Ser Glu Met Asn Lys Leu Phe Glu
195 200 205

Arg Thr Lys Lys Gln Leu Arg Glu Asn Ala Glu Asp Met Gly Asn Gly
210 215 220

Cys Phe Lys Ile Tyr His Lys Cys Asp Asn Ala Cys Ile Gly Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Leu Trp Ile Ser Phe Ala Ile Ser Cys Phe Leu Leu Cys Val
275 280 285

Val Leu Leu Gly Phe Ile Met Trp Ala Cys Gln Lys Gly Asn Ile Arg
290 295 300

Cys Asn Ile Cys Ile
305

<210> SEQ ID NO 107
<211> LENGTH: 309
<212> TYPE: PRT
<213> ORGANISM: Artificial Sequence
<220> FEATURE:
<223> OTHER INFORMATION: H3-mini2-cl9+11

<400> SEQUENCE: 107

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Gln Ile Glu Val Thr Asn Ala Thr Glu Leu Val Gln Ser Gly Gly Gly
50 55 60

Gly Arg Tyr Val Lys Gln Asn Thr Leu Lys Leu Ala Thr Gly Met Arg
65 70 75 80

Asn Val Pro Glu Lys Gln Thr Gln Gly Ile Phe Gly Ala Ile Ala Gly
                85                  90                  95

Phe Ile Glu Asn Gly Trp Glu Gly Met Val Asp Gly Trp Tyr Gly Phe
            100                 105                 110

Arg His Gln Asn Ser Glu Gly Ile Gly Gln Ala Ala Asp Leu Lys Ser
        115                 120                 125

Thr Gln Ala Ala Ile Asn Gln Ile Asn Gly Lys Leu Asn Arg Leu Arg
    130                 135                 140

Gly Lys Thr Asn Glu Lys Ser His Gln Thr Glu Lys Glu Ser Ser Glu
145                 150                 155                 160

Val Glu Gly Arg Ile Gln Asp Leu Glu Lys Tyr Val Glu Asp Thr Lys
                165                 170                 175

Ile Asp Leu Trp Ser Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Arg Thr Lys Lys Gln Leu Arg Glu Asn Ala Glu Asp Met Gly Asn Gly
    210                 215                 220

Cys Phe Lys Ile Tyr His Lys Cys Asp Asn Ala Cys Ile Gly Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Lys Gly Asn Ile Arg
    290                 295                 300

Cys Asn Ile Cys Ile
305

<210> SEQ ID NO 108
<211> LENGTH: 309
<212> TYPE: PRT
<213> ORGANISM: Artificial Sequence
<220> FEATURE:
<223> OTHER INFORMATION: H3-mini2-cl9+10+11

<400> SEQUENCE: 108

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Gly Gly Gly
    50                  55                  60

Gly Arg Tyr Val Lys Gln Asn Thr Leu Lys Leu Ala Thr Gly Met Arg
65                  70                  75                  80

Asn Val Pro Glu Lys Gln Thr Gln Gly Ile Phe Gly Ala Ile Ala Gly
                85                  90                  95

Phe Ile Glu Asn Gly Trp Glu Gly Met Val Asp Gly Trp Tyr Gly Phe
            100                 105                 110

Arg His Gln Asn Ser Glu Gly Ile Gly Gln Ala Ala Asp Leu Lys Ser
        115                 120                 125

```
Thr Gln Ala Ala Ile Asn Gln Ile Asn Gly Lys Leu Asn Arg Leu Arg
    130                 135                 140

Gly Lys Thr Asn Glu Lys Ser His Gln Thr Glu Lys Glu Ser Ser Glu
145                 150                 155                 160

Gly Glu Gly Arg Ile Gln Asp Leu Glu Lys Tyr Val Glu Asp Thr Lys
                165                 170                 175

Ile Asp Leu Trp Ser Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Arg Thr Lys Lys Gln Leu Arg Glu Asn Ala Glu Asp Met Gly Asn Gly
    210                 215                 220

Cys Phe Lys Ile Tyr His Lys Cys Asp Asn Ala Cys Ile Gly Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Lys Gly Asn Ile Arg
    290                 295                 300

Cys Asn Ile Cys Ile
305
```

<210> SEQ ID NO 109
<211> LENGTH: 309
<212> TYPE: PRT
<213> ORGANISM: Artificial Sequence
<220> FEATURE:
<223> OTHER INFORMATION: H3-mini2-cl9+10+11-tri

<400> SEQUENCE: 109

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Gly Gly Gly
    50                  55                  60

Gly Arg Tyr Val Lys Gln Asn Thr Leu Lys Leu Ala Thr Gly Met Arg
65                  70                  75                  80

Asn Val Pro Glu Lys Gln Thr Gln Gly Ile Phe Gly Ala Ile Ala Gly
                85                  90                  95

Phe Ile Glu Asn Gly Trp Glu Gly Met Val Asp Gly Trp Tyr Gly Phe
            100                 105                 110

Arg His Gln Asn Ser Glu Gly Ile Gly Gln Ala Ala Asp Leu Lys Ser
        115                 120                 125

Thr Gln Ala Ala Ile Asn Gln Ile Asn Gly Lys Leu Asn Arg Leu Arg
    130                 135                 140

Gly Lys Thr Asn Glu Lys Ser His Gln Thr Glu Lys Glu Ser Ser Glu
145                 150                 155                 160

Gly Glu Gly Ile Glu Ala Ile Glu Lys Lys Ile Glu Ala Ile Glu Lys
                165                 170                 175
```

Lys Ile Glu Ala Ile Glu Lys Lys Glu Leu Leu Val Ala Leu Glu Asn
180 185 190

Gln His Thr Ile Asp Leu Thr Asp Ser Glu Met Asn Lys Leu Phe Glu
195 200 205

Arg Thr Lys Lys Gln Leu Arg Glu Asn Ala Glu Asp Met Gly Asn Gly
210 215 220

Cys Phe Lys Ile Tyr His Lys Cys Asp Asn Ala Cys Ile Gly Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Leu Trp Ile Ser Phe Ala Ile Ser Cys Phe Leu Leu Cys Val
275 280 285

Val Leu Leu Gly Phe Ile Met Trp Ala Cys Gln Lys Gly Asn Ile Arg
290 295 300

Cys Asn Ile Cys Ile
305

<210> SEQ ID NO 110
<211> LENGTH: 309
<212> TYPE: PRT
<213> ORGANISM: Artificial Sequence
<220> FEATURE:
<223> OTHER INFORMATION: H3-mini2-cl9+10+11-GCN4

<400> SEQUENCE: 110

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Gln Ile Glu Val Thr Asn Ala Thr Glu Leu Val Gln Ser Gly Gly Gly
50 55 60

Gly Arg Tyr Val Lys Gln Asn Thr Leu Lys Leu Ala Thr Gly Met Arg
65 70 75 80

Asn Val Pro Glu Lys Gln Thr Gln Gly Ile Phe Gly Ala Ile Ala Gly
85 90 95

Phe Ile Glu Asn Gly Trp Glu Gly Met Val Asp Gly Trp Tyr Gly Phe
100 105 110

Arg His Gln Asn Ser Glu Gly Ile Gly Gln Ala Ala Asp Leu Lys Ser
115 120 125

Thr Gln Ala Ala Ile Asn Gln Ile Asn Gly Lys Leu Asn Arg Leu Arg
130 135 140

Gly Lys Thr Asn Glu Lys Ser His Gln Thr Glu Lys Glu Ser Ser Glu
145 150 155 160

Gly Glu Gly Arg Met Lys Gln Ile Glu Asp Lys Ile Glu Glu Ile Glu
165 170 175

Ser Lys Gln Lys Lys Ile Glu Asn Glu Leu Leu Val Ala Leu Glu Asn
180 185 190

Gln His Thr Ile Asp Leu Thr Asp Ser Glu Met Asn Lys Leu Phe Glu
195 200 205

Arg Thr Lys Lys Gln Leu Arg Glu Asn Ala Glu Asp Met Gly Asn Gly
210 215 220

Cys Phe Lys Ile Tyr His Lys Cys Asp Asn Ala Cys Ile Gly Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Leu Trp Ile Ser Phe Ala Ile Ser Cys Phe Leu Leu Cys Val
275 280 285

Val Leu Leu Gly Phe Ile Met Trp Ala Cys Gln Lys Gly Asn Ile Arg
290 295 300

Cys Asn Ile Cys Ile
305

<210> SEQ ID NO 111
<211> LENGTH: 309
<212> TYPE: PRT
<213> ORGANISM: Artificial Sequence
<220> FEATURE:
<223> OTHER INFORMATION: H3-mini2-cl9+10+11+12

<400> SEQUENCE: 111

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Gln Ile Glu Val Thr Asn Ala Thr Glu Leu Val Gln Ser Gly Gly Gly
50 55 60

Gly Arg Tyr Val Cys Gln Asn Thr Leu Lys Leu Ala Thr Gly Met Arg
65 70 75 80

Asn Val Pro Glu Lys Gln Thr Gln Gly Ile Phe Gly Ala Ile Ala Gly
85 90 95

Phe Ile Glu Asn Gly Trp Glu Gly Met Val Asp Gly Trp Tyr Gly Phe
100 105 110

Arg His Gln Asn Ser Glu Gly Ile Gly Gln Ala Ala Asp Leu Lys Ser
115 120 125

Thr Gln Ala Ala Ile Asn Gln Ile Asn Gly Lys Leu Asn Arg Leu Arg
130 135 140

Gly Lys Thr Asn Glu Lys Ser His Gln Thr Glu Lys Glu Ser Ser Glu
145 150 155 160

Gly Glu Gly Arg Ile Gln Asp Leu Glu Lys Tyr Val Glu Asp Thr Lys
165 170 175

Ile Asp Leu Trp Cys Tyr Asn Ala Glu Leu Leu Val Ala Leu Glu Asn
180 185 190

Gln His Thr Ile Asp Leu Thr Asp Ser Glu Met Asn Lys Leu Phe Glu
195 200 205

Arg Thr Lys Lys Gln Leu Arg Glu Asn Ala Glu Asp Met Gly Asn Gly
210 215 220

Cys Phe Lys Ile Tyr His Lys Cys Asp Asn Ala Cys Ile Gly Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

```
Trp Ile Leu Trp Ile Ser Phe Ala Ile Ser Cys Phe Leu Leu Cys Val
        275                 280                 285

Val Leu Leu Gly Phe Ile Met Trp Ala Cys Gln Lys Gly Asn Ile Arg
    290                 295                 300

Cys Asn Ile Cys Ile
305


<210> SEQ ID NO 112
<211> LENGTH: 309
<212> TYPE: PRT
<213> ORGANISM: Artificial Sequence
<220> FEATURE:
<223> OTHER INFORMATION: H3-mini2-cl9+10+12

<400> SEQUENCE: 112

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Gly Gly Gly
    50                  55                  60

Gly Arg Tyr Val Cys Gln Asn Thr Leu Lys Leu Ala Thr Gly Met Arg
65                  70                  75                  80

Asn Val Pro Glu Lys Gln Thr Gln Gly Ile Phe Gly Ala Ile Ala Gly
                85                  90                  95

Phe Ile Glu Asn Gly Trp Glu Gly Met Val Asp Gly Trp Tyr Gly Phe
            100                 105                 110

Arg His Gln Asn Ser Glu Gly Ile Gly Gln Ala Ala Asp Leu Lys Ser
        115                 120                 125

Thr Gln Ala Ala Ile Asn Gln Ile Asn Gly Lys Leu Asn Arg Leu Ile
    130                 135                 140

Gly Lys Thr Asn Glu Lys Ser His Gln Thr Glu Lys Glu Ser Ser Glu
145                 150                 155                 160

Gly Glu Gly Arg Ile Gln Asp Leu Glu Lys Tyr Val Glu Asp Thr Lys
                165                 170                 175

Ile Asp Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Arg Thr Lys Lys Gln Leu Arg Glu Asn Ala Glu Asp Met Gly Asn Gly
    210                 215                 220

Cys Phe Lys Ile Tyr His Lys Cys Asp Asn Ala Cys Ile Gly Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Lys Gly Asn Ile Arg
    290                 295                 300

Cys Asn Ile Cys Ile
305
```

<210> SEQ ID NO 113
<211> LENGTH: 309
<212> TYPE: PRT
<213> ORGANISM: Artificial Sequence
<220> FEATURE:
<223> OTHER INFORMATION: H3-mini2-cl9+10+11+12-GCN4

<400> SEQUENCE: 113

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Gly Gly Gly
    50                  55                  60

Gly Arg Tyr Val Cys Gln Asn Thr Leu Lys Leu Ala Thr Gly Met Arg
65                  70                  75                  80

Asn Val Pro Glu Lys Gln Thr Gln Gly Ile Phe Gly Ala Ile Ala Gly
                85                  90                  95

Phe Ile Glu Asn Gly Trp Glu Gly Met Val Asp Gly Trp Tyr Gly Phe
            100                 105                 110

Arg His Gln Asn Ser Glu Gly Ile Gly Gln Ala Ala Asp Leu Lys Ser
        115                 120                 125

Thr Gln Ala Ala Ile Asn Gln Ile Asn Gly Lys Leu Asn Arg Leu Arg
    130                 135                 140

Gly Lys Thr Asn Glu Lys Ser His Gln Thr Glu Lys Glu Ser Ser Glu
145                 150                 155                 160

Gly Glu Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Arg Thr Lys Lys Gln Leu Arg Glu Asn Ala Glu Asp Met Gly Asn Gly
    210                 215                 220

Cys Phe Lys Ile Tyr His Lys Cys Asp Asn Ala Cys Ile Gly Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Lys Gly Asn Ile Arg
    290                 295                 300

Cys Asn Ile Cys Ile
305
```

<210> SEQ ID NO 114
<211> LENGTH: 309
<212> TYPE: PRT
<213> ORGANISM: Artificial Sequence
<220> FEATURE:
<223> OTHER INFORMATION: H3-mini2-cl9+10+11+12-tri

<400> SEQUENCE: 114

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Gln Ile Glu Val Thr Asn Ala Thr Glu Leu Val Gln Ser Gly Gly Gly
50 55 60

Gly Arg Tyr Val Cys Gln Asn Thr Leu Lys Leu Ala Thr Gly Met Arg
65 70 75 80

Asn Val Pro Glu Lys Gln Thr Gln Gly Ile Phe Gly Ala Ile Ala Gly
85 90 95

Phe Ile Glu Asn Gly Trp Glu Gly Met Val Asp Gly Trp Tyr Gly Phe
100 105 110

Arg His Gln Asn Ser Glu Gly Ile Gly Gln Ala Ala Asp Leu Lys Ser
115 120 125

Thr Gln Ala Ala Ile Asn Gln Ile Asn Gly Lys Leu Asn Arg Leu Arg
130 135 140

Gly Lys Thr Asn Glu Lys Ser His Gln Thr Glu Lys Glu Ser Ser Glu
145 150 155 160

Gly Glu Gly Ile Glu Ala Ile Glu Lys Lys Ile Glu Ala Ile Glu Lys
165 170 175

Lys Ile Leu Trp Cys Tyr Asn Ala Glu Leu Leu Val Ala Leu Glu Asn
180 185 190

Gln His Thr Ile Asp Leu Thr Asp Ser Glu Met Asn Lys Leu Phe Glu
195 200 205

Arg Thr Lys Lys Gln Leu Arg Glu Asn Ala Glu Asp Met Gly Asn Gly
210 215 220

Cys Phe Lys Ile Tyr His Lys Cys Asp Asn Ala Cys Ile Gly Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Leu Trp Ile Ser Phe Ala Ile Ser Cys Phe Leu Leu Cys Val
275 280 285

Val Leu Leu Gly Phe Ile Met Trp Ala Cys Gln Lys Gly Asn Ile Arg
290 295 300

Cys Asn Ile Cys Ile
305

<210> SEQ ID NO 115
<211> LENGTH: 309
<212> TYPE: PRT
<213> ORGANISM: Artificial Sequence
<220> FEATURE:
<223> OTHER INFORMATION: H3-mini2-cl9+13

<400> SEQUENCE: 115

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Ile Val Lys Thr Ile Thr Asn Asp

```
        35                  40                  45

Gln Ile Glu Val Thr Asn Ala Thr Glu Leu Val Gln Ser Gly Gly Gly
    50                  55                  60

Gly Arg Tyr Val Lys Gln Asn Thr Leu Lys Leu Ala Cys Gly Met Arg
65                  70                  75                  80

Asn Val Pro Glu Lys Gln Thr Gln Gly Ile Phe Gly Ala Ile Ala Gly
                85                  90                  95

Phe Ile Glu Asn Gly Trp Glu Gly Met Val Asp Gly Trp Tyr Gly Phe
            100                 105                 110

Arg His Gln Asn Ser Glu Gly Ile Gly Gln Ala Ala Asp Leu Lys Ser
        115                 120                 125

Thr Gln Ala Ala Ile Asn Gln Cys Asn Gly Lys Leu Asn Arg Leu Ile
    130                 135                 140

Gly Lys Thr Asn Glu Lys Ser His Gln Thr Glu Lys Glu Ser Ser Glu
145                 150                 155                 160

Val Glu Gly Arg Ile Gln Asp Leu Glu Lys Tyr Val Glu Asp Thr Lys
                165                 170                 175

Ile Asp Leu Trp Ser Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Arg Thr Lys Lys Gln Leu Arg Glu Asn Ala Glu Asp Met Gly Asn Gly
    210                 215                 220

Cys Phe Lys Ile Tyr His Lys Cys Asp Asn Ala Cys Ile Gly Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Lys Gly Asn Ile Arg
    290                 295                 300

Cys Asn Ile Cys Ile
305


<210> SEQ ID NO 116
<211> LENGTH: 309
<212> TYPE: PRT
<213> ORGANISM: Artificial Sequence
<220> FEATURE:
<223> OTHER INFORMATION: H3-mini2-cl9+10+11+13

<400> SEQUENCE: 116

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Gly Gly Gly
    50                  55                  60

Gly Arg Tyr Val Lys Gln Asn Thr Leu Lys Leu Ala Cys Gly Met Arg
65                  70                  75                  80

Asn Val Pro Glu Lys Gln Thr Gln Gly Ile Phe Gly Ala Ile Ala Gly
```

85 90 95

Phe Ile Glu Asn Gly Trp Glu Gly Met Val Asp Gly Trp Tyr Gly Phe
100 105 110

Arg His Gln Asn Ser Glu Gly Ile Gly Gln Ala Ala Asp Leu Lys Ser
115 120 125

Thr Gln Ala Ala Ile Asn Gln Cys Asn Gly Lys Leu Asn Arg Leu Arg
130 135 140

Gly Lys Thr Asn Glu Lys Ser His Gln Thr Glu Lys Glu Ser Ser Glu
145 150 155 160

Gly Glu Gly Arg Ile Gln Asp Leu Glu Lys Tyr Val Glu Asp Thr Lys
165 170 175

Ile Asp Leu Trp Ser Tyr Asn Ala Glu Leu Leu Val Ala Leu Glu Asn
180 185 190

Gln His Thr Ile Asp Leu Thr Asp Ser Glu Met Asn Lys Leu Phe Glu
195 200 205

Arg Thr Lys Lys Gln Leu Arg Glu Asn Ala Glu Asp Met Gly Asn Gly
210 215 220

Cys Phe Lys Ile Tyr His Lys Cys Asp Asn Ala Cys Ile Gly Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Leu Trp Ile Ser Phe Ala Ile Ser Cys Phe Leu Leu Cys Val
275 280 285

Val Leu Leu Gly Phe Ile Met Trp Ala Cys Gln Lys Gly Asn Ile Arg
290 295 300

Cys Asn Ile Cys Ile
305

<210> SEQ ID NO 117
<211> LENGTH: 309
<212> TYPE: PRT
<213> ORGANISM: Artificial Sequence
<220> FEATURE:
<223> OTHER INFORMATION: H3-mini2-cl9+10+11+13-GCN4

<400> SEQUENCE: 117

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Gln Ile Glu Val Thr Asn Ala Thr Glu Leu Val Gln Ser Gly Gly Gly
50 55 60

Gly Arg Tyr Val Lys Gln Asn Thr Leu Lys Leu Ala Cys Gly Met Arg
65 70 75 80

Asn Val Pro Glu Lys Gln Thr Gln Gly Ile Phe Gly Ala Ile Ala Gly
85 90 95

Phe Ile Glu Asn Gly Trp Glu Gly Met Val Asp Gly Trp Tyr Gly Phe
100 105 110

Arg His Gln Asn Ser Glu Gly Ile Gly Gln Ala Ala Asp Leu Lys Ser
115 120 125

Thr Gln Ala Ala Ile Asn Gln Cys Asn Gly Lys Leu Asn Arg Leu Arg

```
    130                 135                 140

Gly Lys Thr Asn Glu Lys Ser His Gln Thr Glu Lys Glu Ser Ser Glu
145                 150                 155                 160

Gly Glu Gly Arg Met Lys Gln Ile Glu Asp Lys Ile Glu Glu Ile Glu
                165                 170                 175

Ser Lys Gln Lys Lys Ile Glu Asn Glu Leu Leu Val Ala Leu Glu Asn
            180                 185                 190

Gln His Thr Ile Asp Leu Thr Asp Ser Glu Met Asn Lys Leu Phe Glu
        195                 200                 205

Arg Thr Lys Lys Gln Leu Arg Glu Asn Ala Glu Asp Met Gly Asn Gly
    210                 215                 220

Cys Phe Lys Ile Tyr His Lys Cys Asp Asn Ala Cys Ile Gly Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Lys Gly Asn Ile Arg
    290                 295                 300

Cys Asn Ile Cys Ile
305
```

<210> SEQ ID NO 118
<211> LENGTH: 309
<212> TYPE: PRT
<213> ORGANISM: Artificial Sequence
<220> FEATURE:
<223> OTHER INFORMATION: H3-mini2-cl9+10+11+13-tri

<400> SEQUENCE: 118

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Gly Gly Gly
    50                  55                  60

Gly Arg Tyr Val Lys Gln Asn Thr Leu Lys Leu Ala Cys Gly Met Arg
65                  70                  75                  80

Asn Val Pro Glu Lys Gln Thr Gln Gly Ile Phe Gly Ala Ile Ala Gly
                85                  90                  95

Phe Ile Glu Asn Gly Trp Glu Gly Met Val Asp Gly Trp Tyr Gly Phe
            100                 105                 110

Arg His Gln Asn Ser Glu Gly Ile Gly Gln Ala Ala Asp Leu Lys Ser
        115                 120                 125

Thr Gln Ala Ala Ile Asn Gln Cys Asn Gly Lys Leu Asn Arg Leu Arg
    130                 135                 140

Gly Lys Thr Asn Glu Lys Ser His Gln Thr Glu Lys Glu Ser Ser Glu
145                 150                 155                 160

Gly Glu Gly Ile Glu Ala Ile Glu Lys Lys Ile Glu Ala Ile Glu Lys
                165                 170                 175

Lys Ile Glu Ala Ile Glu Lys Lys Glu Leu Leu Val Ala Leu Glu Asn
```

```
            180                 185                 190

Gln His Thr Ile Asp Leu Thr Asp Ser Glu Met Asn Lys Leu Phe Glu
        195                 200                 205

Arg Thr Lys Lys Gln Leu Arg Glu Asn Ala Glu Asp Met Gly Asn Gly
    210                 215                 220

Cys Phe Lys Ile Tyr His Lys Cys Asp Asn Ala Cys Ile Gly Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Lys Gly Asn Ile Arg
    290                 295                 300

Cys Asn Ile Cys Ile
305


<210> SEQ ID NO 119
<211> LENGTH: 327
<212> TYPE: PRT
<213> ORGANISM: Artificial Sequence
<220> FEATURE:
<223> OTHER INFORMATION: H3-mini3-cl9+10+11+12+14

<400> SEQUENCE: 119

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Gly Gly
    50                  55                  60

Gly Gly Asn Asp Lys Pro Phe Gln Asn Val Asn Arg Ile Thr Tyr Gly
65                  70                  75                  80

Ala Gly Pro Arg Tyr Val Cys Gln Asn Thr Leu Lys Leu Ala Thr Gly
                85                  90                  95

Met Arg Asn Val Pro Glu Lys Gln Thr Gln Gly Ile Phe Gly Ala Ile
            100                 105                 110

Ala Gly Phe Ile Glu Asn Gly Trp Glu Gly Met Val Asp Gly Trp Tyr
        115                 120                 125

Gly Phe Arg His Gln Asn Ser Glu Gly Ile Gly Gln Ala Ala Asp Leu
    130                 135                 140

Lys Ser Thr Gln Ala Ala Ile Asn Gln Ile Asn Gly Lys Leu Asn Arg
145                 150                 155                 160

Leu Arg Gly Lys Thr Asn Glu Lys Ser His Gln Thr Glu Lys Glu Ser
                165                 170                 175

Ser Glu Gly Glu Gly Arg Ile Gln Asp Leu Glu Lys Tyr Val Glu Asp
            180                 185                 190

Thr Lys Ile Asp Leu Trp Cys Tyr Asn Ala Glu Leu Leu Val Ala Leu
        195                 200                 205

Glu Asn Gln His Thr Ile Asp Leu Thr Asp Ser Glu Met Asn Lys Leu
    210                 215                 220

Phe Glu Arg Thr Lys Lys Gln Leu Arg Glu Asn Ala Glu Asp Met Gly
```

```
225                 230                 235                 240

Asn Gly Cys Phe Lys Ile Tyr His Lys Cys Asp Asn Ala Cys Ile Gly
                245                 250                 255

Ser Ile Arg Asn Gly Thr Tyr Asp His Asp Val Tyr Arg Asp Glu Ala
            260                 265                 270

Leu Asn Asn Arg Phe Gln Ile Lys Gly Val Glu Leu Lys Ser Gly Tyr
        275                 280                 285

Lys Asp Trp Ile Leu Trp Ile Ser Phe Ala Ile Ser Cys Phe Leu Leu
    290                 295                 300

Cys Val Val Leu Leu Gly Phe Ile Met Trp Ala Cys Gln Lys Gly Asn
305                 310                 315                 320

Ile Arg Cys Asn Ile Cys Ile
                325


<210> SEQ ID NO 120
<211> LENGTH: 317
<212> TYPE: PRT
<213> ORGANISM: Artificial Sequence
<220> FEATURE:
<223> OTHER INFORMATION: H3-mini4-cl9+10+11+12+14

<400> SEQUENCE: 120

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Gly Gly Tyr Gly Ala Gly Pro Arg Tyr Val Cys Gln Asn Thr
65                  70                  75                  80

Leu Lys Leu Ala Thr Gly Met Arg Asn Val Pro Glu Lys Gln Thr Gln
                85                  90                  95

Gly Ile Phe Gly Ala Ile Ala Gly Phe Ile Glu Asn Gly Trp Glu Gly
            100                 105                 110

Met Val Asp Gly Trp Tyr Gly Phe Arg His Gln Asn Ser Glu Gly Ile
        115                 120                 125

Gly Gln Ala Ala Asp Leu Lys Ser Thr Gln Ala Ala Ile Asn Gln Ile
    130                 135                 140

Asn Gly Lys Leu Asn Arg Leu Arg Gly Lys Thr Asn Glu Lys Ser His
145                 150                 155                 160

Gln Thr Glu Lys Glu Ser Ser Glu Gly Glu Gly Arg Ile Gln Asp Leu
                165                 170                 175

Glu Lys Tyr Val Glu Asp Thr Lys Ile Asp Leu Trp Cys Tyr Asn Ala
            180                 185                 190

Glu Leu Leu Val Ala Leu Glu Asn Gln His Thr Ile Asp Leu Thr Asp
        195                 200                 205

Ser Glu Met Asn Lys Leu Phe Glu Arg Thr Lys Lys Gln Leu Arg Glu
    210                 215                 220

Asn Ala Glu Asp Met Gly Asn Gly Cys Phe Lys Ile Tyr His Lys Cys
225                 230                 235                 240

Asp Asn Ala Cys Ile Gly Ser Ile Arg Asn Gly Thr Tyr Asp His Asp
                245                 250                 255

Val Tyr Arg Asp Glu Ala Leu Asn Asn Arg Phe Gln Ile Lys Gly Val
```

```
            260                 265                 270

Glu Leu Lys Ser Gly Tyr Lys Asp Trp Ile Leu Trp Ile Ser Phe Ala
        275                 280                 285

Ile Ser Cys Phe Leu Leu Cys Val Val Leu Leu Gly Phe Ile Met Trp
    290                 295                 300

Ala Cys Gln Lys Gly Asn Ile Arg Cys Asn Ile Cys Ile
305                 310                 315


<210> SEQ ID NO 121
<211> LENGTH: 566
<212> TYPE: PRT
<213> ORGANISM: Artificial Sequence
<220> FEATURE:
<223> OTHER INFORMATION: H3 Full length A/Hong Kong/1/1968

<400> SEQUENCE: 121

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
```

```
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565


<210> SEQ ID NO 122
<211> LENGTH: 309
<212> TYPE: PRT
<213> ORGANISM: Artificial Sequence
<220> FEATURE:
<223> OTHER INFORMATION: HK68 H3m2-cl9

<400> SEQUENCE: 122

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Lys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
```

```
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Ile
    130                 135                 140

Glu Lys Thr Asn Glu Lys Ser His Gln Thr Glu Lys Glu Ser Ser Glu
145                 150                 155                 160

Val Glu Gly Arg Ile Gln Asp Leu Glu Lys Tyr Val Glu Asp Thr Lys
                165                 170                 175

Ile Asp Leu Trp Ser Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
    290                 295                 300

Cys Asn Ile Cys Ile
305


<210> SEQ ID NO 123
<211> LENGTH: 309
<212> TYPE: PRT
<213> ORGANISM: Artificial Sequence
<220> FEATURE:
<223> OTHER INFORMATION: HK68 H3m2-cl9+10

<400> SEQUENCE: 123

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Lys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Ile
    130                 135                 140

Glu Lys Thr Asn Glu Lys Ser His Gln Thr Glu Lys Glu Ser Ser Glu
```

```
145                 150                 155                 160

Gly Glu Gly Arg Ile Gln Asp Leu Glu Lys Tyr Val Glu Asp Thr Lys
                165                 170                 175

Ile Asp Leu Trp Ser Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
    290                 295                 300

Cys Asn Ile Cys Ile
305


<210> SEQ ID NO 124
<211> LENGTH: 309
<212> TYPE: PRT
<213> ORGANISM: Artificial Sequence
<220> FEATURE:
<223> OTHER INFORMATION: HK68 H3m2-cl9+10+11

<400> SEQUENCE: 124

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Lys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Arg
    130                 135                 140

Glu Lys Thr Asn Glu Lys Ser His Gln Thr Glu Lys Glu Ser Ser Glu
145                 150                 155                 160

Gly Glu Gly Arg Ile Gln Asp Leu Glu Lys Tyr Val Glu Asp Thr Lys
                165                 170                 175

Ile Asp Leu Trp Ser Tyr Asn Ala Glu Leu Leu Val Ala Leu Glu Asn
            180                 185                 190

Gln His Thr Ile Asp Leu Thr Asp Ser Glu Met Asn Lys Leu Phe Glu
```

```
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
    290                 295                 300

Cys Asn Ile Cys Ile
305


<210> SEQ ID NO 125
<211> LENGTH: 309
<212> TYPE: PRT
<213> ORGANISM: Artificial Sequence
<220> FEATURE:
<223> OTHER INFORMATION: HK68 H3m2-cl9+10+12

<400> SEQUENCE: 125

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Ile
    130                 135                 140

Glu Lys Thr Asn Glu Lys Ser His Gln Thr Glu Lys Glu Ser Ser Glu
145                 150                 155                 160

Gly Glu Gly Arg Ile Gln Asp Leu Glu Lys Tyr Val Glu Asp Thr Lys
                165                 170                 175

Ile Asp Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
```

```
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
    290                 295                 300

Cys Asn Ile Cys Ile
305


<210> SEQ ID NO 126
<211> LENGTH: 309
<212> TYPE: PRT
<213> ORGANISM: Artificial Sequence
<220> FEATURE:
<223> OTHER INFORMATION: HK68 H3m2-cl9+10+11+12

<400> SEQUENCE: 126

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Arg
    130                 135                 140

Glu Lys Thr Asn Glu Lys Ser His Gln Thr Glu Lys Glu Ser Ser Glu
145                 150                 155                 160

Gly Glu Gly Arg Ile Gln Asp Leu Glu Lys Tyr Val Glu Asp Thr Lys
                165                 170                 175

Ile Asp Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
```

290 295 300

Cys Asn Ile Cys Ile
305

<210> SEQ ID NO 127
<211> LENGTH: 309
<212> TYPE: PRT
<213> ORGANISM: Artificial Sequence
<220> FEATURE:
<223> OTHER INFORMATION: HK68 H3m2-cl9+10+11+13

<400> SEQUENCE: 127

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Gly Gly Gly
50 55 60

Gly Lys Tyr Val Lys Gln Asn Thr Leu Lys Leu Ala Cys Gly Met Arg
65 70 75 80

Asn Val Pro Glu Lys Gln Thr Gln Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Cys Asn Gly Lys Leu Asn Arg Val Arg
130 135 140

Glu Lys Thr Asn Glu Lys Ser His Gln Thr Glu Lys Glu Ser Ser Glu
145 150 155 160

Gly Glu Gly Arg Ile Gln Asp Leu Glu Lys Tyr Val Glu Asp Thr Lys
165 170 175

Ile Asp Leu Trp Ser Tyr Asn Ala Glu Leu Leu Val Ala Leu Glu Asn
180 185 190

Gln His Thr Ile Asp Leu Thr Asp Ser Glu Met Asn Lys Leu Phe Glu
195 200 205

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Leu Trp Ile Ser Phe Ala Ile Ser Cys Phe Leu Leu Cys Val
275 280 285

Val Leu Leu Gly Phe Ile Met Trp Ala Cys Gln Arg Gly Asn Ile Arg
290 295 300

Cys Asn Ile Cys Ile
305

<210> SEQ ID NO 128
<211> LENGTH: 309
<212> TYPE: PRT

<213> ORGANISM: Artificial Sequence
<220> FEATURE:
<223> OTHER INFORMATION: HK68 H3m2-cl9+10+11+12-tri

<400> SEQUENCE: 128

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Arg
    130                 135                 140

Glu Lys Thr Asn Glu Lys Ser His Gln Thr Glu Lys Glu Ser Ser Glu
145                 150                 155                 160

Gly Glu Gly Ile Glu Ala Ile Glu Lys Lys Ile Glu Ala Ile Glu Lys
                165                 170                 175

Lys Ile Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
    290                 295                 300

Cys Asn Ile Cys Ile
305
```

<210> SEQ ID NO 129
<211> LENGTH: 309
<212> TYPE: PRT
<213> ORGANISM: Artificial Sequence
<220> FEATURE:
<223> OTHER INFORMATION: HK68 H3m2-cl9+10+11+13-tri

<400> SEQUENCE: 129

```
Met Lys Thr Ile Ile Ala Leu Ser Tyr Ile Phe Cys Leu Ala Leu Gly
1               5                   10                  15
```

-continued

```
Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Lys Gln Asn Thr Leu Lys Leu Ala Cys Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Cys Asn Gly Lys Leu Asn Arg Val Arg
    130                 135                 140

Glu Lys Thr Asn Glu Lys Ser His Gln Thr Glu Lys Glu Ser Ser Glu
145                 150                 155                 160

Gly Glu Gly Ile Glu Ala Ile Glu Lys Lys Ile Glu Ala Ile Glu Lys
                165                 170                 175

Lys Ile Leu Trp Ser Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
    290                 295                 300

Cys Asn Ile Cys Ile
305
```

<210> SEQ ID NO 130
<211> LENGTH: 309
<212> TYPE: PRT
<213> ORGANISM: Artificial Sequence
<220> FEATURE:
<223> OTHER INFORMATION: HK68 H3m2-cl9+10+11+12-GCN4

<400> SEQUENCE: 130

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60
```

```
Gly Lys Tyr Val Cys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Arg
    130                 135                 140

Glu Lys Thr Asn Glu Lys Ser His Gln Thr Glu Lys Glu Ser Ser Glu
145                 150                 155                 160

Gly Glu Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
    290                 295                 300

Cys Asn Ile Cys Ile
305
```

<210> SEQ ID NO 131
<211> LENGTH: 309
<212> TYPE: PRT
<213> ORGANISM: Artificial Sequence
<220> FEATURE:
<223> OTHER INFORMATION: HK68 H3m2-cl9+10+11+13-GCN4

<400> SEQUENCE: 131

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Lys Gln Asn Thr Leu Lys Leu Ala Cys Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110
```

```
Arg His Gln Asn Ser Glu Gly Thr Gly Gln Ala Ala Asp Leu Lys Ser
        115                 120                 125

Thr Gln Ala Ala Ile Asp Gln Cys Asn Gly Lys Leu Asn Arg Val Arg
    130                 135                 140

Glu Lys Thr Asn Glu Lys Ser His Gln Thr Glu Lys Glu Ser Ser Glu
145                 150                 155                 160

Gly Glu Gly Arg Met Lys Gln Ile Glu Asp Lys Ile Glu Glu Ile Glu
                165                 170                 175

Ser Lys Leu Trp Ser Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
    290                 295                 300

Cys Asn Ile Cys Ile
305


<210> SEQ ID NO 132
<211> LENGTH: 584
<212> TYPE: PRT
<213> ORGANISM: Artificial Sequence
<220> FEATURE:
<223> OTHER INFORMATION: B/Florida/4/2006 Full length HA

<400> SEQUENCE: 132

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160
```

```
Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asp Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
```

580

<210> SEQ ID NO 133
<211> LENGTH: 302
<212> TYPE: PRT
<213> ORGANISM: Artificial Sequence
<220> FEATURE:
<223> OTHER INFORMATION: FL4-06 B-m2

<400> SEQUENCE: 133

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Gly Gly Gly Gly Ile Trp Val Lys Thr Pro Leu Lys Leu Ala
    50                  55                  60

Asn Gly Thr Lys Tyr Arg Pro Pro Ala Lys Leu Leu Lys Glu Gln Gly
65                  70                  75                  80

Phe Phe Gly Ala Ile Ala Gly Phe Leu Glu Gly Gly Trp Glu Gly Met
                85                  90                  95

Ile Ala Gly Trp His Gly Tyr Thr Ser His Gly Ala His Gly Val Ala
            100                 105                 110

Val Ala Ala Asp Leu Lys Ser Thr Gln Glu Ala Ile Asn Lys Ile Thr
        115                 120                 125

Lys Asn Leu Asn Ser Leu Ser Glu Leu Glu Val Lys Asn Leu Gln Arg
    130                 135                 140

Leu Ser Gly Ala Met Asp Glu Leu His Asn Glu Ile Leu Glu Leu Asp
145                 150                 155                 160

Glu Lys Val Asp Asp Leu Arg Ala Asp Thr Ile Ser Ser Gln Ile Glu
                165                 170                 175

Leu Ala Val Leu Leu Ser Asn Glu Gly Ile Ile Asn Ser Glu Asp Glu
            180                 185                 190

His Leu Leu Ala Leu Glu Arg Lys Leu Lys Lys Met Leu Gly Pro Ser
        195                 200                 205

Ala Val Glu Ile Gly Asn Gly Cys Phe Glu Thr Lys His Lys Cys Asn
    210                 215                 220

Gln Thr Cys Leu Asp Arg Ile Ala Ala Gly Thr Phe Asn Ala Gly Glu
225                 230                 235                 240

Phe Ser Leu Pro Thr Phe Asp Ser Leu Asn Ile Thr Ala Ala Ser Leu
                245                 250                 255

Asn Asp Asp Gly Leu Asp Asn His Thr Ile Leu Leu Tyr Tyr Ser Thr
            260                 265                 270

Ala Ala Ser Ser Leu Ala Val Thr Leu Met Leu Ala Ile Phe Ile Val
        275                 280                 285

Tyr Met Val Ser Arg Asp Asn Val Ser Cys Ser Ile Cys Leu
    290                 295                 300

<210> SEQ ID NO 134
<211> LENGTH: 302
<212> TYPE: PRT
<213> ORGANISM: Artificial Sequence
<220> FEATURE:
<223> OTHER INFORMATION: FL4-06 B-m2-CL1+5

<400> SEQUENCE: 134

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Gly Gly Gly Gly Ile Trp Val Cys Thr Pro Leu Lys Leu Ala
    50                  55                  60

Asn Gly Thr Lys Tyr Arg Pro Pro Ala Lys Leu Leu Lys Glu Gln Gly
65                  70                  75                  80

Phe Phe Gly Ala Ile Ala Gly Phe Leu Glu Gly Gly Trp Glu Gly Met
                85                  90                  95

Ile Ala Gly Trp His Gly Tyr Thr Ser His Gly Ala His Gly Val Ala
            100                 105                 110

Val Ala Ala Asp Leu Lys Ser Thr Gln Glu Ala Ile Asn Lys Ile Thr
        115                 120                 125

Lys Asn Leu Asn Ser Leu Ser Glu Leu Glu Thr Lys Asn Ser Gln Arg
    130                 135                 140

Thr Ser Gly Ala Met Asp Glu Gly His Asn Glu Ile Leu Glu Leu Asp
145                 150                 155                 160

Glu Lys Val Asp Asp Leu Arg Ala Asp Thr Ile Cys Ser Gln Ile Glu
                165                 170                 175

Leu Ala Val Leu Leu Ser Asn Glu Gly Ile Ile Asn Ser Glu Asp Glu
            180                 185                 190

His Leu Leu Ala Leu Glu Arg Lys Leu Lys Lys Met Leu Gly Pro Ser
        195                 200                 205

Ala Val Glu Ile Gly Asn Gly Cys Phe Glu Thr Lys His Lys Cys Asn
    210                 215                 220

Gln Thr Cys Leu Asp Arg Ile Ala Ala Gly Thr Phe Asn Ala Gly Glu
225                 230                 235                 240

Phe Ser Leu Pro Thr Phe Asp Ser Leu Asn Ile Thr Ala Ala Ser Leu
                245                 250                 255

Asn Asp Asp Gly Leu Asp Asn His Thr Ile Leu Leu Tyr Tyr Ser Thr
            260                 265                 270

Ala Ala Ser Ser Leu Ala Val Thr Leu Met Leu Ala Ile Phe Ile Val
        275                 280                 285

Tyr Met Val Ser Arg Asp Asn Val Ser Cys Ser Ile Cys Leu
    290                 295                 300
```

<210> SEQ ID NO 135
<211> LENGTH: 302
<212> TYPE: PRT
<213> ORGANISM: Artificial Sequence
<220> FEATURE:
<223> OTHER INFORMATION: FL4-06 B-m2-CL1+5-GCN4a

<400> SEQUENCE: 135

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Gly Gly Gly Gly Ile Trp Val Cys Thr Pro Leu Lys Leu Ala
    50                  55                  60
```

```
Asn Gly Thr Lys Tyr Arg Pro Pro Ala Lys Leu Leu Lys Glu Gln Gly
65                  70                  75                  80

Phe Phe Gly Ala Ile Ala Gly Phe Leu Glu Gly Gly Trp Glu Gly Met
                85                  90                  95

Ile Ala Gly Trp His Gly Tyr Thr Ser His Gly Ala His Gly Val Ala
            100                 105                 110

Val Ala Ala Asp Leu Lys Ser Thr Gln Glu Ala Ile Asn Lys Ile Thr
        115                 120                 125

Lys Asn Leu Asn Ser Leu Ser Glu Leu Glu Thr Lys Asn Ser Gln Arg
    130                 135                 140

Thr Ser Gly Ala Met Asp Glu Gly His Arg Arg Met Lys Gln Ile Glu
145                 150                 155                 160

Asp Lys Ile Glu Glu Ile Leu Ser Lys Ile Ile Cys Ser Gln Ile Glu
                165                 170                 175

Leu Ala Val Leu Leu Ser Asn Glu Gly Ile Ile Asn Ser Glu Asp Glu
            180                 185                 190

His Leu Leu Ala Leu Glu Arg Lys Leu Lys Lys Met Leu Gly Pro Ser
        195                 200                 205

Ala Val Glu Ile Gly Asn Gly Cys Phe Glu Thr Lys His Lys Cys Asn
    210                 215                 220

Gln Thr Cys Leu Asp Arg Ile Ala Ala Gly Thr Phe Asn Ala Gly Glu
225                 230                 235                 240

Phe Ser Leu Pro Thr Phe Asp Ser Leu Asn Ile Thr Ala Ala Ser Leu
                245                 250                 255

Asn Asp Asp Gly Leu Asp Asn His Thr Ile Leu Leu Tyr Tyr Ser Thr
            260                 265                 270

Ala Ala Ser Ser Leu Ala Val Thr Leu Met Leu Ala Ile Phe Ile Val
        275                 280                 285

Tyr Met Val Ser Arg Asp Asn Val Ser Cys Ser Ile Cys Leu
    290                 295                 300


<210> SEQ ID NO 136
<211> LENGTH: 302
<212> TYPE: PRT
<213> ORGANISM: Artificial Sequence
<220> FEATURE:
<223> OTHER INFORMATION: FL4-06 B-m2-CL1+5-GCN4b

<400> SEQUENCE: 136

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Gly Gly Gly Gly Ile Trp Val Cys Thr Pro Leu Lys Leu Ala
    50                  55                  60

Asn Gly Thr Lys Tyr Arg Pro Pro Ala Lys Leu Leu Lys Glu Gln Gly
65                  70                  75                  80

Phe Phe Gly Ala Ile Ala Gly Phe Leu Glu Gly Gly Trp Glu Gly Met
                85                  90                  95

Ile Ala Gly Trp His Gly Tyr Thr Ser His Gly Ala His Gly Val Ala
            100                 105                 110

Val Ala Ala Asp Leu Lys Ser Thr Gln Glu Ala Ile Asn Lys Ile Thr
        115                 120                 125
```

```
Lys Asn Leu Asn Ser Leu Ser Glu Leu Glu Thr Lys Asn Ser Gln Arg
    130                 135                 140

Thr Ser Gly Ala Met Asp Glu Gly His Arg Met Lys Gln Ile Glu Asp
145                 150                 155                 160

Lys Ile Glu Glu Ile Leu Ser Lys Ile Thr Ile Cys Ser Gln Ile Glu
                165                 170                 175

Leu Ala Val Leu Leu Ser Asn Glu Gly Ile Ile Asn Ser Glu Asp Glu
            180                 185                 190

His Leu Leu Ala Leu Glu Arg Lys Leu Lys Lys Met Leu Gly Pro Ser
        195                 200                 205

Ala Val Glu Ile Gly Asn Gly Cys Phe Glu Thr Lys His Lys Cys Asn
    210                 215                 220

Gln Thr Cys Leu Asp Arg Ile Ala Ala Gly Thr Phe Asn Ala Gly Glu
225                 230                 235                 240

Phe Ser Leu Pro Thr Phe Asp Ser Leu Asn Ile Thr Ala Ala Ser Leu
                245                 250                 255

Asn Asp Asp Gly Leu Asp Asn His Thr Ile Leu Leu Tyr Tyr Ser Thr
            260                 265                 270

Ala Ala Ser Ser Leu Ala Val Thr Leu Met Leu Ala Ile Phe Ile Val
        275                 280                 285

Tyr Met Val Ser Arg Asp Asn Val Ser Cys Ser Ile Cys Leu
    290                 295                 300


<210> SEQ ID NO 137
<211> LENGTH: 585
<212> TYPE: PRT
<213> ORGANISM: Artificial Sequence
<220> FEATURE:
<223> OTHER INFORMATION: B/Malaysia/2506/2004 Full length HA

<400> SEQUENCE: 137

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190
```

-continued

```
Pro Tyr Ile Cys Thr Glu Gly Glu Asp Gln Ile Thr Val Trp Gly Phe
        195                 200                 205

His Ser Asp Asn Glu Ala Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585
```

<210> SEQ ID NO 138
<211> LENGTH: 302
<212> TYPE: PRT

<213> ORGANISM: Artificial Sequence
<220> FEATURE:
<223> OTHER INFORMATION: Mal2506-04 B-m2

<400> SEQUENCE: 138

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Gly Gly Gly Gly Ile Trp Val Lys Thr Pro Leu Lys Leu Ala
    50                  55                  60

Asn Gly Thr Lys Tyr Arg Pro Pro Ala Lys Leu Leu Lys Glu Gln Gly
65                  70                  75                  80

Phe Phe Gly Ala Ile Ala Gly Phe Leu Glu Gly Gly Trp Glu Gly Met
                85                  90                  95

Ile Ala Gly Trp His Gly Tyr Thr Ser His Gly Ala His Gly Val Ala
            100                 105                 110

Val Ala Ala Asp Leu Lys Ser Thr Gln Glu Ala Ile Asn Lys Ile Thr
        115                 120                 125

Lys Asn Leu Asn Ser Leu Ser Glu Leu Glu Val Lys Asn Leu Gln Arg
    130                 135                 140

Leu Ser Gly Ala Met Asp Glu Leu His Asn Glu Ile Leu Glu Leu Asp
145                 150                 155                 160

Glu Lys Val Asp Asp Leu Arg Ala Asp Thr Ile Ser Ser Gln Ile Glu
                165                 170                 175

Leu Ala Val Leu Leu Ser Asn Glu Gly Ile Ile Asn Ser Glu Asp Glu
            180                 185                 190

His Leu Leu Ala Leu Glu Arg Lys Leu Lys Lys Met Leu Gly Pro Ser
        195                 200                 205

Ala Val Glu Ile Gly Asn Gly Cys Phe Glu Thr Lys His Lys Cys Asn
    210                 215                 220

Gln Thr Cys Leu Asp Arg Ile Ala Ala Gly Thr Phe Asp Ala Gly Glu
225                 230                 235                 240

Phe Ser Leu Pro Thr Phe Asp Ser Leu Asn Ile Thr Ala Ala Ser Leu
                245                 250                 255

Asn Asp Asp Gly Leu Asp Asn His Thr Ile Leu Leu Tyr Tyr Ser Thr
            260                 265                 270

Ala Ala Ser Ser Leu Ala Val Thr Leu Met Ile Ala Ile Phe Val Val
        275                 280                 285

Tyr Met Val Ser Arg Asp Asn Val Ser Cys Ser Ile Cys Leu
    290                 295                 300
```

<210> SEQ ID NO 139
<211> LENGTH: 302
<212> TYPE: PRT
<213> ORGANISM: Artificial Sequence
<220> FEATURE:
<223> OTHER INFORMATION: Mal2506-04 B-m2-CL1+5

<400> SEQUENCE: 139

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30
```

```
Thr Ala Thr Gln Gly Glu Val Asn Val Thr Gly Val Ile Pro Leu Thr
        35                  40                  45

Thr Thr Gly Gly Gly Gly Ile Trp Val Cys Thr Pro Leu Lys Leu Ala
    50                  55                  60

Asn Gly Thr Lys Tyr Arg Pro Pro Ala Lys Leu Leu Lys Glu Gln Gly
65                  70                  75                  80

Phe Phe Gly Ala Ile Ala Gly Phe Leu Glu Gly Gly Trp Glu Gly Met
                85                  90                  95

Ile Ala Gly Trp His Gly Tyr Thr Ser His Gly Ala His Gly Val Ala
            100                 105                 110

Val Ala Ala Asp Leu Lys Ser Thr Gln Glu Ala Ile Asn Lys Ile Thr
        115                 120                 125

Lys Asn Leu Asn Ser Leu Ser Glu Leu Glu Thr Lys Asn Ser Gln Arg
    130                 135                 140

Thr Ser Gly Ala Met Asp Glu Gly His Asn Glu Ile Leu Glu Leu Asp
145                 150                 155                 160

Glu Lys Val Asp Asp Leu Arg Ala Asp Thr Ile Cys Ser Gln Ile Glu
                165                 170                 175

Leu Ala Val Leu Leu Ser Asn Glu Gly Ile Ile Asn Ser Glu Asp Glu
            180                 185                 190

His Leu Leu Ala Leu Glu Arg Lys Leu Lys Lys Met Leu Gly Pro Ser
        195                 200                 205

Ala Val Glu Ile Gly Asn Gly Cys Phe Glu Thr Lys His Lys Cys Asn
    210                 215                 220

Gln Thr Cys Leu Asp Arg Ile Ala Ala Gly Thr Phe Asp Ala Gly Glu
225                 230                 235                 240

Phe Ser Leu Pro Thr Phe Asp Ser Leu Asn Ile Thr Ala Ala Ser Leu
                245                 250                 255

Asn Asp Asp Gly Leu Asp Asn His Thr Ile Leu Leu Tyr Tyr Ser Thr
            260                 265                 270

Ala Ala Ser Ser Leu Ala Val Thr Leu Met Ile Ala Ile Phe Val Val
        275                 280                 285

Tyr Met Val Ser Arg Asp Asn Val Ser Cys Ser Ile Cys Leu
    290                 295                 300


<210> SEQ ID NO 140
<211> LENGTH: 302
<212> TYPE: PRT
<213> ORGANISM: Artificial Sequence
<220> FEATURE:
<223> OTHER INFORMATION: Mal2506-04 B-m2-CL1+5-GCN4a

<400> SEQUENCE: 140

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Gly Gly Gly Gly Ile Trp Val Cys Thr Pro Leu Lys Leu Ala
    50                  55                  60

Asn Gly Thr Lys Tyr Arg Pro Pro Ala Lys Leu Leu Lys Glu Gln Gly
65                  70                  75                  80

Phe Phe Gly Ala Ile Ala Gly Phe Leu Glu Gly Gly Trp Glu Gly Met
                85                  90                  95
```

```
Ile Ala Gly Trp His Gly Tyr Thr Ser His Gly Ala His Gly Val Ala
            100                 105                 110

Val Ala Ala Asp Leu Lys Ser Thr Gln Glu Ala Ile Asn Lys Ile Thr
        115                 120                 125

Lys Asn Leu Asn Ser Leu Ser Glu Leu Glu Thr Lys Asn Ser Gln Arg
    130                 135                 140

Thr Ser Gly Ala Met Asp Glu Gly His Arg Arg Met Lys Gln Ile Glu
145                 150                 155                 160

Asp Lys Ile Glu Glu Ile Leu Ser Lys Ile Ile Cys Ser Gln Ile Glu
                165                 170                 175

Leu Ala Val Leu Leu Ser Asn Glu Gly Ile Ile Asn Ser Glu Asp Glu
            180                 185                 190

His Leu Leu Ala Leu Glu Arg Lys Leu Lys Lys Met Leu Gly Pro Ser
        195                 200                 205

Ala Val Glu Ile Gly Asn Gly Cys Phe Glu Thr Lys His Lys Cys Asn
    210                 215                 220

Gln Thr Cys Leu Asp Arg Ile Ala Ala Gly Thr Phe Asp Ala Gly Glu
225                 230                 235                 240

Phe Ser Leu Pro Thr Phe Asp Ser Leu Asn Ile Thr Ala Ala Ser Leu
                245                 250                 255

Asn Asp Asp Gly Leu Asp Asn His Thr Ile Leu Leu Tyr Tyr Ser Thr
            260                 265                 270

Ala Ala Ser Ser Leu Ala Val Thr Leu Met Ile Ala Ile Phe Val Val
        275                 280                 285

Tyr Met Val Ser Arg Asp Asn Val Ser Cys Ser Ile Cys Leu
    290                 295                 300


<210> SEQ ID NO 141
<211> LENGTH: 302
<212> TYPE: PRT
<213> ORGANISM: Artificial Sequence
<220> FEATURE:
<223> OTHER INFORMATION: Mal2506-04 B-m2-CL1+5-GCN4b

<400> SEQUENCE: 141

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Gly Gly Gly Gly Ile Trp Val Cys Thr Pro Leu Lys Leu Ala
    50                  55                  60

Asn Gly Thr Lys Tyr Arg Pro Pro Ala Lys Leu Leu Lys Glu Gln Gly
65                  70                  75                  80

Phe Phe Gly Ala Ile Ala Gly Phe Leu Glu Gly Gly Trp Glu Gly Met
                85                  90                  95

Ile Ala Gly Trp His Gly Tyr Thr Ser His Gly Ala His Gly Val Ala
            100                 105                 110

Val Ala Ala Asp Leu Lys Ser Thr Gln Glu Ala Ile Asn Lys Ile Thr
        115                 120                 125

Lys Asn Leu Asn Ser Leu Ser Glu Leu Glu Thr Lys Asn Ser Gln Arg
    130                 135                 140

Thr Ser Gly Ala Met Asp Glu Gly His Arg Met Lys Gln Ile Glu Asp
145                 150                 155                 160
```

```
Lys Ile Glu Glu Ile Leu Ser Lys Ile Thr Ile Cys Ser Gln Ile Glu
                165                 170                 175

Leu Ala Val Leu Leu Ser Asn Glu Gly Ile Ile Asn Ser Glu Asp Glu
            180                 185                 190

His Leu Leu Ala Leu Glu Arg Lys Leu Lys Lys Met Leu Gly Pro Ser
        195                 200                 205

Ala Val Glu Ile Gly Asn Gly Cys Phe Glu Thr Lys His Lys Cys Asn
    210                 215                 220

Gln Thr Cys Leu Asp Arg Ile Ala Ala Gly Thr Phe Asp Ala Gly Glu
225                 230                 235                 240

Phe Ser Leu Pro Thr Phe Asp Ser Leu Asn Ile Thr Ala Ala Ser Leu
                245                 250                 255

Asn Asp Asp Gly Leu Asp Asn His Thr Ile Leu Leu Tyr Tyr Ser Thr
            260                 265                 270

Ala Ala Ser Ser Leu Ala Val Thr Leu Met Ile Ala Ile Phe Val Val
        275                 280                 285

Tyr Met Val Ser Arg Asp Asn Val Ser Cys Ser Ile Cys Leu
    290                 295                 300


<210> SEQ ID NO 142
<211> LENGTH: 21
<212> TYPE: PRT
<213> ORGANISM: Artificial Sequence
<220> FEATURE:
<223> OTHER INFORMATION: Influenza B HA consensus sequence residue 416-
      436

<400> SEQUENCE: 142

Leu Ser Glu Leu Glu Val Lys Asn Leu Gln Arg Leu Ser Gly Ala Met
1               5                   10                  15

Asp Glu Leu His Asn
            20


<210> SEQ ID NO 143
<211> LENGTH: 12
<212> TYPE: PRT
<213> ORGANISM: Artificial Sequence
<220> FEATURE:
<223> OTHER INFORMATION: foldon sequence

<400> SEQUENCE: 143

Ala Tyr Val Arg Lys Asp Gly Glu Trp Val Leu Leu
1               5                   10


<210> SEQ ID NO 144
<211> LENGTH: 275
<212> TYPE: PRT
<213> ORGANISM: Artificial Sequence
<220> FEATURE:
<223> OTHER INFORMATION: s-H1-mini2-cluster1+5+6-trim
      (A/Brisbane/59/2007)

<400> SEQUENCE: 144

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60
```

```
Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Ile Glu Ala Ile Glu Lys Lys
145                 150                 155                 160

Ile Glu Ala Ile Glu Lys Lys Ile Glu Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Glu Gly Arg His His His His
            260                 265                 270

His His His
        275


<210> SEQ ID NO 145
<211> LENGTH: 275
<212> TYPE: PRT
<213> ORGANISM: Artificial Sequence
<220> FEATURE:
<223> OTHER INFORMATION: s-H1-mini2-cluster1+5+6-GCN4
      (A/Brisbane/59/2007)

<400> SEQUENCE: 145

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
```

130 135 140

Thr Gly Lys Glu Gly Asn Lys Ser Glu Arg Met Lys Gln Ile Glu Asp
145 150 155 160

Lys Ile Glu Glu Ile Glu Ser Lys Gln Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Glu Gly Arg His His His His
260 265 270

His His His
275

<210> SEQ ID NO 146
<211> LENGTH: 275
<212> TYPE: PRT
<213> ORGANISM: Artificial Sequence
<220> FEATURE:
<223> OTHER INFORMATION: s-H1-mini2-cluster1+5+6 (A/Brisbane/59/2007)

<400> SEQUENCE: 146

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Ile Pro Ser Ile Gln Ser Gln Gly
65 70 75 80

Leu Phe Gly Ala Ile Ala Gly Phe Ile Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Ser Thr Ala
130 135 140

Thr Gly Lys Glu Gly Asn Lys Ser Glu Arg Arg Met Glu Asn Leu Asn
145 150 155 160

Lys Lys Val Asp Asp Gly Phe Ile Asp Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn

```
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Glu Gly Arg His His His His
            260                 265                 270

His His His
        275


<210> SEQ ID NO 147
<211> LENGTH: 275
<212> TYPE: PRT
<213> ORGANISM: Artificial Sequence
<220> FEATURE:
<223> OTHER INFORMATION: s-H1-mini2-cluster11+5+6 (A/Brisbane/59/2007)

<400> SEQUENCE: 147

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Ile Glu Asn Leu Asn
145                 150                 155                 160

Lys Lys Ile Asp Asp Gly Phe Ile Asp Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Glu Gly Arg His His His His
            260                 265                 270

His His His
        275
```

-continued

<210> SEQ ID NO 148
<211> LENGTH: 275
<212> TYPE: PRT
<213> ORGANISM: Artificial Sequence
<220> FEATURE:
<223> OTHER INFORMATION: s-H1-mini2-cluster1+5 (A/Brisbane/59/2007)

<400> SEQUENCE: 148

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Ile Pro Ser Ile Gln Ser Gln Gly
65 70 75 80

Leu Phe Gly Ala Ile Ala Gly Phe Ile Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Ser Thr Ala
130 135 140

Thr Gly Lys Glu Phe Asn Lys Ser Glu Arg Arg Met Glu Asn Leu Asn
145 150 155 160

Lys Lys Val Asp Asp Gly Phe Ile Asp Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Glu Gly Arg His His His His
260 265 270

His His His
275

<210> SEQ ID NO 149
<211> LENGTH: 539
<212> TYPE: PRT
<213> ORGANISM: Artificial Sequence
<220> FEATURE:
<223> OTHER INFORMATION: s-H1 Full length R343Q (A/Brisbane/59/2007)

<400> SEQUENCE: 149

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

```
Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Gln Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
```

```
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Glu Gly Arg His His His His His His His
    530                 535


<210> SEQ ID NO 150
<211> LENGTH: 275
<212> TYPE: PRT
<213> ORGANISM: Artificial Sequence
<220> FEATURE:
<223> OTHER INFORMATION: s-H1-mini2-cluster1+5+6-nl (A/Brisbane/59/2007

<400> SEQUENCE: 150

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn His Asn Gly Lys Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Met Glu Asn Leu Asn
145                 150                 155                 160

Lys Lys Val Asp Asp Gly Phe Ile Asp Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Glu Gly Arg His His His His
            260                 265                 270

His His His
```

275

<210> SEQ ID NO 151
<211> LENGTH: 274
<212> TYPE: PRT
<213> ORGANISM: Artificial Sequence
<220> FEATURE:
<223> OTHER INFORMATION: s-H1-mini2-cluster1+5+6-nl2
(A/Brisbane/59/2007)

<400> SEQUENCE: 151

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn His Asn Gly Lys Tyr Val Cys Ser Ala Lys Leu Arg
50 55 60

Met Val Thr Gly Leu Arg Asn Ile Pro Ser Ile Gln Ser Gln Gly Leu
65 70 75 80

Phe Gly Ala Ile Ala Gly Phe Ile Glu Gly Gly Trp Thr Gly Met Val
85 90 95

Asp Gly Trp Tyr Gly Tyr His His Gln Asn Glu Gln Gly Ser Gly Tyr
100 105 110

Ala Ala Asp Gln Lys Ser Thr Gln Asn Ala Ile Asn Gly Ile Thr Asn
115 120 125

Lys Val Asn Ser Val Ile Glu Lys Met Asn Thr Gln Ser Thr Ala Thr
130 135 140

Gly Lys Glu Gly Asn Lys Ser Glu Arg Arg Met Glu Asn Leu Asn Lys
145 150 155 160

Lys Val Asp Asp Gly Phe Ile Asp Ile Trp Cys Tyr Asn Ala Glu Leu
165 170 175

Leu Val Leu Leu Glu Asn Glu Arg Thr Leu Asp Phe His Asp Ser Asn
180 185 190

Val Lys Asn Leu Tyr Glu Lys Val Lys Ser Gln Leu Lys Asn Asn Ala
195 200 205

Lys Glu Ile Gly Asn Gly Cys Phe Glu Phe Tyr His Lys Cys Asn Asp
210 215 220

Glu Cys Met Glu Ser Val Lys Asn Gly Thr Tyr Asp Tyr Pro Lys Tyr
225 230 235 240

Ser Glu Glu Ser Lys Leu Asn Arg Glu Lys Ile Asp Gly Val Lys Leu
245 250 255

Glu Ser Met Gly Val Tyr Gln Ile Glu Gly Arg His His His His His
260 265 270

His His

<210> SEQ ID NO 152
<211> LENGTH: 301
<212> TYPE: PRT
<213> ORGANISM: Artificial Sequence
<220> FEATURE:
<223> OTHER INFORMATION: H1mini2a-cl1+5+6_no_linker(HNGK)

<400> SEQUENCE: 152

Met Lys Val Lys Leu Leu Val Leu Leu Cys Thr Phe Thr Ala Thr Tyr
1 5 10 15

-continued

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn His Asn Gly Lys Lys Tyr Val Cys Ser Ala Lys Leu
50 55 60

Arg Met Val Thr Gly Leu Arg Asn Ile Pro Ser Ile Gln Ser Gln Gly
65 70 75 80

Leu Phe Gly Ala Ile Ala Gly Phe Ile Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Ser Thr Ala
130 135 140

Thr Gly Lys Glu Gly Asn Lys Ser Glu Arg Arg Met Glu Asn Leu Asn
145 150 155 160

Lys Lys Val Asp Asp Gly Phe Ile Asp Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val
260 265 270

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 153
<211> LENGTH: 300
<212> TYPE: PRT
<213> ORGANISM: Artificial Sequence
<220> FEATURE:
<223> OTHER INFORMATION: H1mini2a-cl1+5+6_no_linker2s

<400> SEQUENCE: 153

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn His Asn Gly Lys Tyr Val Cys Ser Ala Lys Leu Arg
50 55 60

Met Val Thr Gly Leu Arg Asn Ile Pro Ser Ile Gln Ser Gln Gly Leu
65 70 75 80

```
Phe Gly Ala Ile Ala Gly Phe Ile Glu Gly Gly Trp Thr Gly Met Val
                85                  90                  95

Asp Gly Trp Tyr Gly Tyr His His Gln Asn Glu Gln Gly Ser Gly Tyr
            100                 105                 110

Ala Ala Asp Gln Lys Ser Thr Gln Asn Ala Ile Asn Gly Ile Thr Asn
        115                 120                 125

Lys Val Asn Ser Val Ile Glu Lys Met Asn Thr Gln Ser Thr Ala Thr
    130                 135                 140

Gly Lys Glu Gly Asn Lys Ser Glu Arg Arg Met Glu Asn Leu Asn Lys
145                 150                 155                 160

Lys Val Asp Asp Gly Phe Ile Asp Ile Trp Cys Tyr Asn Ala Glu Leu
                165                 170                 175

Leu Val Leu Leu Glu Asn Glu Arg Thr Leu Asp Phe His Asp Ser Asn
            180                 185                 190

Val Lys Asn Leu Tyr Glu Lys Val Lys Ser Gln Leu Lys Asn Asn Ala
        195                 200                 205

Lys Glu Ile Gly Asn Gly Cys Phe Glu Phe Tyr His Lys Cys Asn Asp
    210                 215                 220

Glu Cys Met Glu Ser Val Lys Asn Gly Thr Tyr Asp Tyr Pro Lys Tyr
225                 230                 235                 240

Ser Glu Glu Ser Lys Leu Asn Arg Glu Lys Ile Asp Gly Val Lys Leu
                245                 250                 255

Glu Ser Met Gly Val Tyr Gln Ile Leu Ala Ile Tyr Ser Thr Val Ala
            260                 265                 270

Ser Ser Leu Val Leu Leu Val Ser Leu Gly Ala Ile Ser Phe Trp Met
        275                 280                 285

Cys Ser Asn Gly Ser Leu Gln Cys Arg Ile Cys Ile
    290                 295                 300


<210> SEQ ID NO 154
<211> LENGTH: 301
<212> TYPE: PRT
<213> ORGANISM: Artificial Sequence
<220> FEATURE:
<223> OTHER INFORMATION: H1-mini2-cl1+5+6-no_linker2s-GCN4

<400> SEQUENCE: 154

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140
```

```
Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 155
<211> LENGTH: 301
<212> TYPE: PRT
<213> ORGANISM: Artificial Sequence
<220> FEATURE:
<223> OTHER INFORMATION: H1mini2a-cl1+5+6_no_linker2s-trim3

<400> SEQUENCE: 155

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Ile Glu Ala Ile Glu
145                 150                 155                 160

Lys Lys Ile Glu Ala Ile Glu Lys Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205
```

```
Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 156
<211> LENGTH: 301
<212> TYPE: PRT
<213> ORGANISM: Artificial Sequence
<220> FEATURE:
<223> OTHER INFORMATION: H1mini2a-cl1+5+6-12

<400> SEQUENCE: 156

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Asn Pro Ser Asn Gln Ser Gln Gly
65                  70                  75                  80

Leu Phe Gly Ala Ile Ala Gly Tyr Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Met Glu Asn Leu Asn
145                 150                 155                 160

Lys Lys Val Asp Asp Gly Phe Ile Asp Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270
```

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 157
<211> LENGTH: 301
<212> TYPE: PRT
<213> ORGANISM: Artificial Sequence
<220> FEATURE:
<223> OTHER INFORMATION: H1mini2a-cl1+5+6-12+13

<400> SEQUENCE: 157

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Asn Pro Ser Asn Gln Ser Gln Gly
65 70 75 80

Leu Phe Gly Ala Ile Ala Gly Tyr Asn Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Ser Thr Ala
130 135 140

Thr Gly Lys Glu Gly Asn Lys Ser Glu Arg Arg Met Glu Asn Leu Asn
145 150 155 160

Lys Lys Val Asp Asp Gly Phe Ile Asp Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val
260 265 270

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 158
<211> LENGTH: 568
<212> TYPE: PRT
<213> ORGANISM: Artificial Sequence
<220> FEATURE:

<223> OTHER INFORMATION: H5 FL HA A/Vietnam/1203/2004

<400> SEQUENCE: 158

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400
```

Ile Ile Asp Lys Met Asn Thr Gln Phe Glu Ala Val Gly Arg Glu Phe
405 410 415

Asn Asn Leu Glu Arg Arg Ile Glu Asn Leu Asn Lys Lys Met Glu Asp
420 425 430

Gly Phe Leu Asp Val Trp Thr Tyr Asn Ala Glu Leu Leu Val Leu Met
435 440 445

Glu Asn Glu Arg Thr Leu Asp Phe His Asp Ser Asn Val Lys Asn Leu
450 455 460

Tyr Asp Lys Val Arg Leu Gln Leu Arg Asp Asn Ala Lys Glu Leu Gly
465 470 475 480

Asn Gly Cys Phe Glu Phe Tyr His Lys Cys Asp Asn Glu Cys Met Glu
485 490 495

Ser Val Arg Asn Gly Thr Tyr Asp Tyr Pro Gln Tyr Ser Glu Glu Ala
500 505 510

Arg Leu Lys Arg Glu Glu Ile Ser Gly Val Lys Leu Glu Ser Ile Gly
515 520 525

Ile Tyr Gln Ile Leu Ser Ile Tyr Ser Thr Val Ala Ser Ser Leu Ala
530 535 540

Leu Ala Ile Met Val Ala Gly Leu Ser Leu Trp Met Cys Ser Asn Gly
545 550 555 560

Ser Leu Gln Cys Arg Ile Cys Ile
565

<210> SEQ ID NO 159
<211> LENGTH: 566
<212> TYPE: PRT
<213> ORGANISM: Artificial Sequence
<220> FEATURE:
<223> OTHER INFORMATION: H1 FL HA A/California/04/2009 R343Q

<400> SEQUENCE: 159

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Ser Ser Trp Ser Tyr Ile
85 90 95

Val Glu Thr Pro Ser Ser Asp Asn Gly Thr Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Thr Ser Ser Trp Pro Asn His Asp
130 135 140

Ser Asn Lys Gly Val Thr Ala Ala Cys Pro His Ala Gly Ala Lys Ser
145 150 155 160

Phe Tyr Lys Asn Leu Ile Trp Leu Val Lys Lys Gly Asn Ser Tyr Pro
165 170 175

Lys Leu Ser Lys Ser Tyr Ile Asn Asp Lys Gly Lys Glu Val Leu Val
180 185 190

```
Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 160
<211> LENGTH: 301
<212> TYPE: PRT
<213> ORGANISM: Artificial Sequence
<220> FEATURE:
<223> OTHER INFORMATION: H1mini-HAA/California/07/2009

<400> SEQUENCE: 160

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Leu Ala Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Leu Lys Ser Thr Gln Asn Ala Ile Asp Glu Ile Thr
        115                 120                 125

Asn Lys Val Asn Ser Val Ile Glu Lys Met Asn Thr Gln Ser Thr Ala
    130                 135                 140

Thr Gly Lys Glu Gly Asn His Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Tyr His Asp Ser
            180                 185                 190

Asn Val Lys Asn Leu Tyr Glu Lys Val Arg Ser Gln Leu Lys Asn Asn
        195                 200                 205

Ala Lys Glu Ile Gly Asn Gly Cys Phe Glu Phe Tyr His Lys Cys Asp
    210                 215                 220

Asn Thr Cys Met Glu Ser Val Lys Asn Gly Thr Tyr Asp Tyr Pro Lys
225                 230                 235                 240

Tyr Ser Glu Glu Ala Lys Leu Asn Arg Glu Glu Ile Asp Gly Val Lys
                245                 250                 255

Leu Glu Ser Thr Arg Ile Tyr Gln Ile Leu Ala Ile Tyr Ser Thr Val
            260                 265                 270

Ala Ser Ser Leu Val Leu Val Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 161
<211> LENGTH: 301
<212> TYPE: PRT
<213> ORGANISM: Artificial Sequence
<220> FEATURE:
<223> OTHER INFORMATION: H1mini-HAA/PuertoRico/8/1934

<400> SEQUENCE: 161

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

```
Leu Leu Glu Asp Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Ile Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Thr Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asp
    210                 215                 220

Asn Glu Cys Met Glu Ser Val Arg Asn Gly Thr Tyr Asp Tyr Pro Lys
225                 230                 235                 240

Tyr Ser Glu Glu Ser Lys Leu Asn Arg Glu Lys Val Asp Gly Val Lys
                245                 250                 255

Leu Glu Ser Met Gly Ile Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 162
<211> LENGTH: 301
<212> TYPE: PRT
<213> ORGANISM: Artificial Sequence
<220> FEATURE:
<223> OTHER INFORMATION: H1mini-HAA/Texas/36/1991

<400> SEQUENCE: 162

Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Ile Asp Gly Trp Tyr Gly Tyr His His Gln Asn Glu Gln Gly Ser Gly
            100                 105                 110
```

```
Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Gly Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asn Glu Cys Met Glu Ser Val Lys Asn Gly Thr Tyr Asp Tyr Pro Lys
225                 230                 235                 240

Tyr Ser Glu Glu Ser Lys Leu Asn Arg Gly Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 163
<211> LENGTH: 300
<212> TYPE: PRT
<213> ORGANISM: Artificial Sequence
<220> FEATURE:
<223> OTHER INFORMATION: H5mini-HAA/Vietnam/1203/2004

<400> SEQUENCE: 163

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Gly Gly Gly Gly Lys Tyr Val Cys Ser Asn Arg Leu Val
    50                  55                  60

Leu Ala Thr Gly Leu Arg Asn Ser Pro Gln Arg Glu Ser Gln Gly Leu
65                  70                  75                  80

Phe Gly Ala Ile Ala Gly Phe Ile Glu Gly Gly Trp Gln Gly Met Val
                85                  90                  95

Asp Gly Trp Tyr Gly Tyr His His Ser Asn Glu Gln Gly Ser Gly Tyr
            100                 105                 110

Ala Ala Asp Lys Glu Ser Thr Gln Lys Ala Ile Asp Gly Val Thr Asn
        115                 120                 125

Lys Val Asn Ser Ile Ile Asp Lys Met Asn Thr Gln Ser Glu Ala Thr
    130                 135                 140

Gly Arg Glu Gly Asn Asn Ser Glu Arg Met Lys Gln Ile Glu Asp Lys
145                 150                 155                 160

Ile Glu Glu Ile Glu Ser Lys Gln Ile Trp Cys Tyr Asn Ala Glu Leu
                165                 170                 175
```

```
Leu Val Leu Met Glu Asn Glu Arg Thr Leu Asp Phe His Asp Ser Asn
            180                 185                 190

Val Lys Asn Leu Tyr Asp Lys Val Arg Leu Gln Leu Arg Asp Asn Ala
        195                 200                 205

Lys Glu Leu Gly Asn Gly Cys Phe Glu Phe Tyr His Lys Cys Asp Asn
    210                 215                 220

Glu Cys Met Glu Ser Val Arg Asn Gly Thr Tyr Asp Tyr Pro Gln Tyr
225                 230                 235                 240

Ser Glu Glu Ala Arg Leu Lys Arg Glu Glu Ile Ser Gly Val Lys Leu
                245                 250                 255

Glu Ser Ile Gly Ile Tyr Gln Ile Leu Ser Ile Tyr Ser Thr Val Ala
            260                 265                 270

Ser Ser Leu Ala Leu Ala Ile Met Val Ala Gly Leu Ser Leu Trp Met
        275                 280                 285

Cys Ser Asn Gly Ser Leu Gln Cys Arg Ile Cys Ile
    290                 295                 300


<210> SEQ ID NO 164
<211> LENGTH: 301
<212> TYPE: PRT
<213> ORGANISM: Artificial Sequence
<220> FEATURE:
<223> OTHER INFORMATION: mHA_H1N1_A_Maryland_12_1991

<400> SEQUENCE: 164

Met Lys Ala Ile Leu Leu Val Leu Leu Tyr Thr Phe Thr Ala Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Met Ala Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Ile Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asp Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn His Ser Glu Arg Met Lys Gln Ile Glu Asp
145                 150                 155                 160

Lys Ile Glu Glu Ile Glu Ser Lys Gln Val Trp Cys Tyr Asn Ala Glu
                165                 170                 175

Leu Leu Val Leu Leu Glu Asn Glu Arg Thr Leu Asp Tyr His Asp Ser
            180                 185                 190

Asn Val Lys Asn Leu Tyr Glu Lys Val Arg Ser Gln Leu Lys Asn Asn
        195                 200                 205

Ala Lys Glu Ile Gly Asn Gly Cys Phe Glu Phe Tyr His Lys Cys Asp
    210                 215                 220

Asp Thr Cys Met Glu Ser Val Lys Asn Gly Thr Tyr Asp Tyr Pro Lys
225                 230                 235                 240
```

```
Tyr Ser Glu Glu Ser Lys Leu Asn Arg Glu Glu Ile Asp Gly Val Lys
                245                 250                 255

Leu Glu Ser Thr Arg Ile Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 165
<211> LENGTH: 301
<212> TYPE: PRT
<213> ORGANISM: Artificial Sequence
<220> FEATURE:
<223> OTHER INFORMATION: mHA_H1N1_A_Henry_1936

<400> SEQUENCE: 165

```
Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Ile Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Asn Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asp
    210                 215                 220

Asn Glu Cys Met Glu Ser Val Arg Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 166
<211> LENGTH: 301
<212> TYPE: PRT
<213> ORGANISM: Artificial Sequence
<220> FEATURE:
<223> OTHER INFORMATION: mHA_H1N1 A/AA/Marton/1943

<400> SEQUENCE: 166

Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Ile Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Asn Ser Glu Arg Met Lys Gln Ile Glu Asp
145                 150                 155                 160

Lys Ile Glu Glu Ile Glu Ser Lys Asp Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Asn Gln Leu Arg Asn Asn
        195                 200                 205

Ala Lys Glu Ile Gly Asn Gly Cys Phe Glu Phe Tyr His Lys Cys Asn
    210                 215                 220

Asn Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 167
<211> LENGTH: 301
<212> TYPE: PRT
<213> ORGANISM: Artificial Sequence
<220> FEATURE:
<223> OTHER INFORMATION: mHA_H1N1_A_New_York_607_1995

<400> SEQUENCE: 167

Met Lys Ala Lys Leu Leu Val Leu Leu Cys Ala Phe Thr Ala Thr Tyr
1               5                   10                  15

```
Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Ile Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asp Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Thr Gln Leu Lys Asn Asn
        195                 200                 205

Ala Lys Glu Ile Gly Asn Gly Cys Phe Glu Phe Tyr His Lys Cys Asn
    210                 215                 220

Asn Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 168
<211> LENGTH: 301
<212> TYPE: PRT
<213> ORGANISM: Artificial Sequence
<220> FEATURE:
<223> OTHER INFORMATION: mHA_H1N1_A_New_Jersey_11_2007

<400> SEQUENCE: 168

```
Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80
```

```
Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 169
<211> LENGTH: 301
<212> TYPE: PRT
<213> ORGANISM: Artificial Sequence
<220> FEATURE:
<223> OTHER INFORMATION: mHA_H1N1_A_USSR_92_1977

<400> SEQUENCE: 169

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Ile Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140
```

Thr Gly Lys Glu Gly Asn Lys Ser Glu Arg Met Lys Gln Ile Glu Asp
145 150 155 160

Lys Ile Glu Glu Ile Glu Ser Lys Gln Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asn Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val
260 265 270

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 170
<211> LENGTH: 301
<212> TYPE: PRT
<213> ORGANISM: Artificial Sequence
<220> FEATURE:
<223> OTHER INFORMATION: mHA_H1N1_A_New_York_629_1995

<400> SEQUENCE: 170

Met Lys Val Lys Leu Leu Val Leu Leu Cys Ala Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Gly Gly Gly Gly Lys Tyr Val Cys Ser Thr Lys Leu
50 55 60

Arg Met Val Thr Gly Leu Arg Asn Ile Pro Ser Ile Gln Ser Gln Gly
65 70 75 80

Leu Phe Gly Ala Ile Ala Gly Phe Ile Glu Gly Gly Trp Thr Gly Met
85 90 95

Ile Asp Gly Trp Tyr Gly Tyr His His Gln Asn Glu Gln Gly Ser Gly
100 105 110

Tyr Ala Ala Asp Gln Lys Ser Thr Gln Asn Ala Ile Asp Gly Ile Thr
115 120 125

Asn Lys Val Asn Ser Val Ile Glu Lys Met Asn Thr Gln Ser Thr Ala
130 135 140

Thr Gly Lys Glu Gly Asn Lys Ser Glu Arg Met Lys Gln Ile Glu Asp
145 150 155 160

Lys Ile Glu Glu Ile Glu Ser Lys Gln Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Asn Gln Leu Lys Asn Asn
195 200 205

```
Ala Lys Glu Ile Gly Asn Gly Cys Phe Glu Phe Tyr His Lys Cys Asn
    210                 215                 220

Asn Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 171
<211> LENGTH: 301
<212> TYPE: PRT
<213> ORGANISM: Artificial Sequence
<220> FEATURE:
<223> OTHER INFORMATION: mHA_H1N1_A_Virginia_UR06-0549_2007

<400> SEQUENCE: 171

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270
```

```
Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 172
<211> LENGTH: 301
<212> TYPE: PRT
<213> ORGANISM: Artificial Sequence
<220> FEATURE:
<223> OTHER INFORMATION: mHA_H1N1_A_Texas_UR0-0526_2007

<400> SEQUENCE: 172

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Asn Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Ile Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 173
<211> LENGTH: 301
<212> TYPE: PRT
<213> ORGANISM: Artificial Sequence
```

<220> FEATURE:
<223> OTHER INFORMATION: mHA_H1N1_A_Sydney_DD3-55_2010

<400> SEQUENCE: 173

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Gly Gly Gly Gly Lys Tyr Val Cys Ser Thr Lys Leu
50 55 60

Arg Leu Ala Thr Gly Leu Arg Asn Val Pro Ser Ile Gln Ser Gln Gly
65 70 75 80

Leu Phe Gly Ala Ile Ala Gly Phe Ile Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Leu Lys Ser Thr Gln Asn Ala Ile Asp Glu Ile Thr
115 120 125

Asn Lys Val Asn Ser Val Ile Glu Lys Met Asn Thr Gln Ser Thr Ala
130 135 140

Thr Gly Lys Glu Gly Asn His Ser Glu Arg Met Lys Gln Ile Glu Asp
145 150 155 160

Lys Ile Glu Glu Ile Glu Ser Lys Gln Ile Trp Cys Tyr Asn Ala Glu
165 170 175

Leu Leu Val Leu Leu Glu Asn Glu Arg Thr Leu Asp Tyr His Asp Ser
180 185 190

Asn Val Lys Asn Leu Tyr Glu Lys Val Arg Ser Gln Leu Lys Asn Asn
195 200 205

Ala Lys Glu Ile Gly Asn Gly Cys Phe Glu Phe Tyr His Lys Cys Asp
210 215 220

Asn Thr Cys Met Glu Ser Val Lys Asn Gly Thr Tyr Asp Tyr Pro Lys
225 230 235 240

Tyr Ser Glu Glu Ala Lys Leu Asn Arg Glu Glu Ile Asp Gly Val Lys
245 250 255

Leu Glu Ser Thr Arg Ile Tyr Gln Ile Leu Ala Ile Tyr Ser Thr Val
260 265 270

Ala Ser Ser Leu Val Leu Val Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 174
<211> LENGTH: 309
<212> TYPE: PRT
<213> ORGANISM: Artificial Sequence
<220> FEATURE:
<223> OTHER INFORMATION: H3mini2a-linker+cl9_+10+11+12+GCN4T_CG7-1
(A/HongKong/1/1968(H3N2))

<400> SEQUENCE: 174

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

```
His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Arg
    130                 135                 140

Glu Lys Thr Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
    290                 295                 300

Cys Asn Ile Cys Ile
305
```

<210> SEQ ID NO 175
<211> LENGTH: 318
<212> TYPE: PRT
<213> ORGANISM: Artificial Sequence
<220> FEATURE:
<223> OTHER INFORMATION: H3mini2a-linker+cl9_+10+12+18+GCN4T
(A/HongKong/1/1968(H3N2))

<400> SEQUENCE: 175

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Cys Gln Asn Thr Leu Lys Leu Ala Thr Gly Met Arg
65                  70                  75                  80
```

Asn Val Pro Glu Lys Gln Thr Gln Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser
115 120 125

Thr Gln Ala Ala Ile Asp Gln Ile Asn Gly Lys Leu Asn Arg Val Ile
130 135 140

Glu Lys Thr Asn Glu Lys Ser His Gln Thr Glu Lys Glu Ser Ser Glu
145 150 155 160

Gly Glu Gly Asn Ala Thr Gly Gly Cys Cys Gly Gly Arg Met Lys Gln
165 170 175

Ile Glu Asp Lys Ile Glu Glu Ile Glu Ser Lys Leu Trp Cys Tyr Asn
180 185 190

Ala Glu Leu Leu Val Ala Leu Glu Asn Gln His Thr Ile Asp Leu Thr
195 200 205

Asp Ser Glu Met Asn Lys Leu Phe Glu Lys Thr Arg Arg Gln Leu Arg
210 215 220

Glu Asn Ala Glu Asp Met Gly Asn Gly Cys Phe Lys Ile Tyr His Lys
225 230 235 240

Cys Asp Asn Ala Cys Ile Glu Ser Ile Arg Asn Gly Thr Tyr Asp His
245 250 255

Asp Val Tyr Arg Asp Glu Ala Leu Asn Asn Arg Phe Gln Ile Lys Gly
260 265 270

Val Glu Leu Lys Ser Gly Tyr Lys Asp Trp Ile Leu Trp Ile Ser Phe
275 280 285

Ala Ile Ser Cys Phe Leu Leu Cys Val Val Leu Leu Gly Phe Ile Met
290 295 300

Trp Ala Cys Gln Arg Gly Asn Ile Arg Cys Asn Ile Cys Ile
305 310 315

<210> SEQ ID NO 176
<211> LENGTH: 309
<212> TYPE: PRT
<213> ORGANISM: Artificial Sequence
<220> FEATURE:
<223> OTHER INFORMATION: H3mini2a-linker+cl9_+10+12+16+CG7-GCN4T
(A/HongKong/1/1968(H3N2))

<400> SEQUENCE: 176

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Cys Asn Ala Thr Glu Leu Val Gln Ser Gly Gly Gly
50 55 60

Gly Lys Tyr Val Cys Gln Asn Thr Leu Lys Leu Ala Thr Cys Met Arg
65 70 75 80

Asn Val Pro Glu Lys Gln Thr Gln Gly Leu Phe Gly Ala Ile Ala Gly
85 90 95

Phe Ile Glu Asn Gly Trp Glu Gly Met Ile Asp Gly Trp Tyr Gly Phe
100 105 110

Arg His Gln Asn Ser Glu Gly Thr Gly Gln Ala Ala Asp Leu Lys Ser

```
        115                 120                 125

Thr Gln Ala Ala Ile Asp Gln Ile Asn Gly Lys Leu Asn Arg Val Ile
    130                 135                 140

Glu Lys Thr Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys Phe Leu Leu Cys Val
        275                 280                 285

Val Leu Leu Gly Phe Ile Met Trp Ala Cys Gln Arg Gly Asn Ile Arg
    290                 295                 300

Cys Asn Ile Cys Ile
305


<210> SEQ ID NO 177
<211> LENGTH: 318
<212> TYPE: PRT
<213> ORGANISM: Artificial Sequence
<220> FEATURE:
<223> OTHER INFORMATION: 177H3mini2a-linker+cl9_+10+12+19+GCN4T
      (A/HongKong/1/1968(H3N2))

<400> SEQUENCE: 177

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Ile
    130                 135                 140

Glu Lys Thr Asn Glu Lys Ser His Gln Thr Glu Lys Glu Ser Ser Glu
145                 150                 155                 160
```

```
Gly Glu Gly Ser Gly Ser Gly Gly Cys Cys Gly Gly Arg Met Lys Gln
                165                 170                 175

Ile Glu Asp Lys Ile Glu Glu Ile Glu Ser Lys Leu Trp Cys Tyr Asn
            180                 185                 190

Ala Glu Leu Leu Val Ala Leu Glu Asn Gln His Thr Ile Asp Leu Thr
        195                 200                 205

Asp Ser Glu Met Asn Lys Leu Phe Glu Lys Thr Arg Arg Gln Leu Arg
    210                 215                 220

Glu Asn Ala Glu Asp Met Gly Asn Gly Cys Phe Lys Ile Tyr His Lys
225                 230                 235                 240

Cys Asp Asn Ala Cys Ile Glu Ser Ile Arg Asn Gly Thr Tyr Asp His
                245                 250                 255

Asp Val Tyr Arg Asp Glu Ala Leu Asn Asn Arg Phe Gln Ile Lys Gly
            260                 265                 270

Val Glu Leu Lys Ser Gly Tyr Lys Asp Trp Ile Leu Trp Ile Ser Phe
        275                 280                 285

Ala Ile Ser Cys Phe Leu Leu Cys Val Val Leu Leu Gly Phe Ile Met
    290                 295                 300

Trp Ala Cys Gln Arg Gly Asn Ile Arg Cys Asn Ile Cys Ile
305                 310                 315


<210> SEQ ID NO 178
<211> LENGTH: 309
<212> TYPE: PRT
<213> ORGANISM: Artificial Sequence
<220> FEATURE:
<223> OTHER INFORMATION: 178H3mini2a-linker+cl9_+10+12+17+CG7-GCN4T
      (A/HongKong/1/1968(H3N2))

<400> SEQUENCE: 178

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Cys Thr Leu Val Lys Thr Ile Thr Asp Asp
        35                  40                  45

Gln Ile Cys Val Thr Asn Ala Thr Glu Leu Val Gln Ser Gly Gly Gly
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Ile
    130                 135                 140

Glu Lys Thr Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205
```

Lys Thr Arg Arg Gln Leu Arg Glu Asn Ala Glu Asp Met Gly Asn Gly
210 215 220

Cys Phe Lys Ile Tyr His Lys Cys Asp Asn Ala Cys Ile Glu Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Leu Trp Ile Ser Phe Ala Ile Ser Cys Phe Leu Leu Cys Val
275 280 285

Val Leu Leu Gly Phe Ile Met Trp Ala Cys Gln Arg Gly Asn Ile Arg
290 295 300

Cys Asn Ile Cys Ile
305

<210> SEQ ID NO 179
<211> LENGTH: 314
<212> TYPE: PRT
<213> ORGANISM: Artificial Sequence
<220> FEATURE:
<223> OTHER INFORMATION: H3_HK68_mini2a-linker2+cl9_+10+12+GCN4T

<400> SEQUENCE: 179

Leu Ala Thr Met Lys Thr Ile Ile Ala Leu Ser Tyr Ile Phe Cys Leu
1 5 10 15

Ala Leu Gly Gln Asp Leu Pro Gly Asn Asp Asn Ser Thr Ala Thr Leu
20 25 30

Cys Leu Gly His His Ala Val Pro Asn Gly Thr Leu Val Lys Thr Ile
35 40 45

Thr Asp Asp Gln Ile Glu Val Thr Asn Ala Thr Glu Leu Val Gln Ser
50 55 60

Gly Ser Gly Ser Gly Gly Lys Tyr Val Cys Gln Asn Thr Leu Lys Leu
65 70 75 80

Ala Thr Gly Met Arg Asn Val Pro Glu Lys Gln Thr Gln Gly Leu Phe
85 90 95

Gly Ala Ile Ala Gly Phe Ile Glu Asn Gly Trp Glu Gly Met Ile Asp
100 105 110

Gly Trp Tyr Gly Phe Arg His Gln Asn Ser Glu Gly Thr Gly Gln Ala
115 120 125

Ala Asp Leu Lys Ser Thr Gln Ala Ala Ile Asp Gln Ile Asn Gly Lys
130 135 140

Leu Asn Arg Val Ile Glu Lys Thr Asn Glu Lys Ser His Gln Thr Glu
145 150 155 160

Lys Glu Ser Ser Glu Gly Glu Gly Arg Met Lys Gln Ile Glu Asp Lys
165 170 175

Ile Glu Glu Ile Glu Ser Lys Leu Trp Cys Tyr Asn Ala Glu Leu Leu
180 185 190

Val Ala Leu Glu Asn Gln His Thr Ile Asp Leu Thr Asp Ser Glu Met
195 200 205

Asn Lys Leu Phe Glu Lys Thr Arg Arg Gln Leu Arg Glu Asn Ala Glu
210 215 220

Asp Met Gly Asn Gly Cys Phe Lys Ile Tyr His Lys Cys Asp Asn Ala
225 230 235 240

Cys Ile Glu Ser Ile Arg Asn Gly Thr Tyr Asp His Asp Val Tyr Arg
245 250 255

Asp Glu Ala Leu Asn Asn Arg Phe Gln Ile Lys Gly Val Glu Leu Lys
260 265 270

Ser Gly Tyr Lys Asp Trp Ile Leu Trp Ile Ser Phe Ala Ile Ser Cys
275 280 285

Phe Leu Leu Cys Val Val Leu Leu Gly Phe Ile Met Trp Ala Cys Gln
290 295 300

Arg Gly Asn Ile Arg Cys Asn Ile Cys Ile
305 310

<210> SEQ ID NO 180
<211> LENGTH: 301
<212> TYPE: PRT
<213> ORGANISM: Artificial Sequence
<220> FEATURE:
<223> OTHER INFORMATION: H1-mini2-cluster1+5+6+GCN4-T49N

<400> SEQUENCE: 180

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Ile Pro Ser Ile Gln Ser Gln Gly
65 70 75 80

Leu Phe Gly Ala Ile Ala Gly Phe Ile Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Asn
115 120 125

Asn Lys Val Asn Ser Val Ile Glu Lys Met Asn Thr Gln Ser Thr Ala
130 135 140

Thr Gly Lys Glu Gly Asn Lys Ser Glu Arg Met Lys Gln Ile Glu Asp
145 150 155 160

Lys Ile Glu Glu Ile Glu Ser Lys Gln Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val
260 265 270

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 181
<211> LENGTH: 270
<212> TYPE: PRT
<213> ORGANISM: Artificial Sequence
<220> FEATURE:
<223> OTHER INFORMATION: sH1-mini2-cl1+5+6-GCN4-Bromelain

<400> SEQUENCE: 181

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Arg Ser
                245                 250                 255

Leu Val Pro Arg Gly Ser Pro Gly His His His His His His
            260                 265                 270
```

<210> SEQ ID NO 182
<211> LENGTH: 270
<212> TYPE: PRT
<213> ORGANISM: Artificial Sequence
<220> FEATURE:
<223> OTHER INFORMATION: sH1-mini2-cl1+5+6-GCN4-Bromelain-Foldon

<400> SEQUENCE: 182

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
```

```
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Arg Ser
                245                 250                 255

Leu Val Pro Arg Gly Ser Pro Gly His His His His His His
            260                 265                 270


<210> SEQ ID NO 183
<211> LENGTH: 275
<212> TYPE: PRT
<213> ORGANISM: Artificial Sequence
<220> FEATURE:
<223> OTHER INFORMATION: sH1-mini2-cl1+5+6-GCN4t2

<400> SEQUENCE: 183

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
```

130 135 140

Thr Gly Lys Glu Gly Asn Lys Ser Glu Arg Arg Met Lys Gln Ile Glu
145 150 155 160

Asp Lys Ile Glu Glu Ile Glu Ser Lys Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Glu Gly Arg His His His His
260 265 270

His His His
275

<210> SEQ ID NO 184
<211> LENGTH: 270
<212> TYPE: PRT
<213> ORGANISM: Artificial Sequence
<220> FEATURE:
<223> OTHER INFORMATION: sH1-mini2-cl1+5+6-GCN4t2-Bromelain

<400> SEQUENCE: 184

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Ile Pro Ser Ile Gln Ser Gln Gly
65 70 75 80

Leu Phe Gly Ala Ile Ala Gly Phe Ile Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Ser Thr Ala
130 135 140

Thr Gly Lys Glu Gly Asn Lys Ser Glu Arg Arg Met Lys Gln Ile Glu
145 150 155 160

Asp Lys Ile Glu Glu Ile Glu Ser Lys Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn

```
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Arg Ser
                245                 250                 255

Leu Val Pro Arg Gly Ser Pro Gly His His His His His His
            260                 265                 270


<210> SEQ ID NO 185
<211> LENGTH: 299
<212> TYPE: PRT
<213> ORGANISM: Artificial Sequence
<220> FEATURE:
<223> OTHER INFORMATION: sH1-mini2-cl1+5+6-GCN4t2-Bromelain-Foldon

<400> SEQUENCE: 185

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Arg Ser
                245                 250                 255

Leu Val Pro Arg Gly Ser Pro Gly Ser Gly Tyr Ile Pro Glu Ala Pro
            260                 265                 270

Arg Asp Gly Gln Ala Tyr Val Arg Lys Asp Gly Glu Trp Val Leu Leu
        275                 280                 285

Ser Thr Phe Leu Gly His His His His His His
    290                 295
```

<210> SEQ ID NO 186
<211> LENGTH: 279
<212> TYPE: PRT
<213> ORGANISM: Artificial Sequence
<220> FEATURE:
<223> OTHER INFORMATION: sH3 HK mini2a-linker+cl9 +10+11+12+GCN4T-CG7-His

<400> SEQUENCE: 186

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Arg
    130                 135                 140

Glu Lys Thr Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Arg Ser Leu Val Pro Arg Gly Ser Pro
            260                 265                 270

Gly His His His His His His
        275
```

<210> SEQ ID NO 187
<211> LENGTH: 308
<212> TYPE: PRT
<213> ORGANISM: Artificial Sequence
<220> FEATURE:
<223> OTHER INFORMATION: sH3 HK mini2a-linker+cl9 +10+11+12+GCN4T-CG7-Foldon-His

<400> SEQUENCE: 187

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
```

```
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Gly Gly Gly
    50                  55                  60

Gly Lys Tyr Val Cys Gln Asn Thr Leu Lys Leu Ala Thr Gly Met Arg
65                  70                  75                  80

Asn Val Pro Glu Lys Gln Thr Gln Gly Leu Phe Gly Ala Ile Ala Gly
                85                  90                  95

Phe Ile Glu Asn Gly Trp Glu Gly Met Ile Asp Gly Trp Tyr Gly Phe
            100                 105                 110

Arg His Gln Asn Ser Glu Gly Thr Gly Gln Ala Ala Asp Leu Lys Ser
        115                 120                 125

Thr Gln Ala Ala Ile Asp Gln Ile Asn Gly Lys Leu Asn Arg Val Arg
    130                 135                 140

Glu Lys Thr Asn Glu Lys Ser His Gln Thr Glu Lys Glu Ser Ser Asn
145                 150                 155                 160

Ala Thr Gly Arg Met Lys Gln Ile Glu Asp Lys Ile Glu Glu Ile Glu
                165                 170                 175

Ser Lys Leu Trp Cys Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Lys Thr Arg Arg Gln Leu Arg Glu Asn Ala Glu Asp Met Gly Asn Gly
    210                 215                 220

Cys Phe Lys Ile Tyr His Lys Cys Asp Asn Ala Cys Ile Glu Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Arg Ser Leu Val Pro Arg Gly Ser Pro
            260                 265                 270

Gly Ser Gly Tyr Ile Pro Glu Ala Pro Arg Asp Gly Gln Ala Tyr Val
        275                 280                 285

Arg Lys Asp Gly Glu Trp Val Leu Leu Ser Thr Phe Leu Gly His His
    290                 295                 300

His His His His
305


<210> SEQ ID NO 188
<211> LENGTH: 7
<212> TYPE: PRT
<213> ORGANISM: Artificial
<220> FEATURE:
<223> OTHER INFORMATION: 7-amino acid linker

<400> SEQUENCE: 188

Gly Ser Ala Gly Ser Ala Gly
1               5


<210> SEQ ID NO 189
<211> LENGTH: 6
<212> TYPE: PRT
<213> ORGANISM: Artificial
<220> FEATURE:
<223> OTHER INFORMATION: 6-amino acid linker

<400> SEQUENCE: 189
```

Gly Ser Ala Gly Ser Ala
1 5

<210> SEQ ID NO 190
<211> LENGTH: 17
<212> TYPE: PRT
<213> ORGANISM: Artificial
<220> FEATURE:
<223> OTHER INFORMATION: Linking sequence
<220> FEATURE:
<221> NAME/KEY: MISC_FEATURE
<222> LOCATION: (5)..(5)
<223> OTHER INFORMATION: X = any amino acids
<220> FEATURE:
<221> NAME/KEY: MISC_FEATURE
<222> LOCATION: (8)..(8)
<223> OTHER INFORMATION: X = any amino acids
<220> FEATURE:
<221> NAME/KEY: MISC_FEATURE
<222> LOCATION: (12)..(12)
<223> OTHER INFORMATION: X = any amino acids
<220> FEATURE:
<221> NAME/KEY: MISC_FEATURE
<222> LOCATION: (14)..(14)
<223> OTHER INFORMATION: X = H or K
<220> FEATURE:
<221> NAME/KEY: MISC_FEATURE
<222> LOCATION: (15)..(15)
<223> OTHER INFORMATION: X = any amino acid
<220> FEATURE:
<221> NAME/KEY: MISC_FEATURE
<222> LOCATION: (17)..(17)
<223> OTHER INFORMATION: X = K or R

<400> SEQUENCE: 190

Met Asn Thr Gln Xaa Thr Ala Xaa Gly Lys Glu Xaa Asn Xaa Xaa Glu
1 5 10 15

Xaa

<210> SEQ ID NO 191
<211> LENGTH: 7
<212> TYPE: PRT
<213> ORGANISM: Artificial
<220> FEATURE:
<223> OTHER INFORMATION: His tag

<400> SEQUENCE: 191

His His His His His His His
1 5

<210> SEQ ID NO 192
<211> LENGTH: 4
<212> TYPE: PRT
<213> ORGANISM: Artificial
<220> FEATURE:
<223> OTHER INFORMATION: Linking sequence

<400> SEQUENCE: 192

Gly Ser Gly Ser
1

<210> SEQ ID NO 193
<211> LENGTH: 4
<212> TYPE: PRT
<213> ORGANISM: Artificial
<220> FEATURE:
<223> OTHER INFORMATION: Linking sequence

<400> SEQUENCE: 193

Gly Ser Ala Gly

1

<210> SEQ ID NO 194
<211> LENGTH: 4
<212> TYPE: PRT
<213> ORGANISM: Artificial
<220> FEATURE:
<223> OTHER INFORMATION: Linking sequence

<400> SEQUENCE: 194

Gly Gly Gly Gly
1

<210> SEQ ID NO 195
<211> LENGTH: 5
<212> TYPE: PRT
<213> ORGANISM: Artificial
<220> FEATURE:
<223> OTHER INFORMATION: Linking sequence

<400> SEQUENCE: 195

Gly Ser Ala Gly Ser
1 5

<210> SEQ ID NO 196
<211> LENGTH: 5
<212> TYPE: PRT
<213> ORGANISM: Artificial
<220> FEATURE:
<223> OTHER INFORMATION: Linking sequence

<400> SEQUENCE: 196

Gly Ser Gly Ser Gly
1 5

<210> SEQ ID NO 197
<211> LENGTH: 7
<212> TYPE: PRT
<213> ORGANISM: Artificial
<220> FEATURE:
<223> OTHER INFORMATION: Linking sequence

<400> SEQUENCE: 197

Gly Ser Gly Ser Gly Ser Gly
1 5

<210> SEQ ID NO 198
<211> LENGTH: 21
<212> TYPE: PRT
<213> ORGANISM: Artificial
<220> FEATURE:
<223> OTHER INFORMATION: trimeric coiled coil

<400> SEQUENCE: 198

Ile Glu Ala Ile Glu Lys Lys Ile Glu Ala Ile Glu Lys Lys Ile Glu
1 5 10 15

Ala Ile Glu Lys Lys
20

<210> SEQ ID NO 199
<211> LENGTH: 15
<212> TYPE: PRT
<213> ORGANISM: Artificial
<220> FEATURE:
<223> OTHER INFORMATION: trimeric coiled coil

<400> SEQUENCE: 199

Ile Glu Ala Ile Glu Lys Lys Ile Glu Ala Ile Glu Lys Lys Ile
1 5 10 15

<210> SEQ ID NO 200
<211> LENGTH: 21
<212> TYPE: PRT
<213> ORGANISM: Artificial
<220> FEATURE:
<223> OTHER INFORMATION: trimeric coiled coil

<400> SEQUENCE: 200

Arg Met Lys Gln Ile Glu Asp Lys Ile Glu Glu Ile Glu Ser Lys Gln
1 5 10 15

Lys Lys Ile Glu Asn
20

<210> SEQ ID NO 201
<211> LENGTH: 15
<212> TYPE: PRT
<213> ORGANISM: Artificial
<220> FEATURE:
<223> OTHER INFORMATION: trimeric coiled coil

<400> SEQUENCE: 201

Arg Met Lys Gln Ile Glu Asp Lys Ile Glu Glu Ile Glu Ser Lys
1 5 10 15

<210> SEQ ID NO 202
<211> LENGTH: 29
<212> TYPE: PRT
<213> ORGANISM: Artificial
<220> FEATURE:
<223> OTHER INFORMATION: Linking sequence

<400> SEQUENCE: 202

Gly Ser Gly Tyr Ile Pro Glu Ala Pro Arg Asp Gly Gln Ala Tyr Val
1 5 10 15

Arg Lys Asp Gly Glu Trp Val Leu Leu Ser Thr Phe Leu
20 25

<210> SEQ ID NO 203
<211> LENGTH: 21
<212> TYPE: PRT
<213> ORGANISM: Artificial
<220> FEATURE:
<223> OTHER INFORMATION: B hemagglutinin consensus sequence

<400> SEQUENCE: 203

Leu Ser Glu Leu Glu Val Lys Asn Leu Gln Arg Leu Ser Gly Ala Met
1 5 10 15

Asp Glu Leu His Asn
20

<210> SEQ ID NO 204
<211> LENGTH: 16
<212> TYPE: PRT
<213> ORGANISM: Artificial
<220> FEATURE:
<223> OTHER INFORMATION: Stabilizing element

<400> SEQUENCE: 204

Arg Met Lys Gln Ile Glu Asp Lys Ile Glu Glu Ile Glu Ser Lys Gln
1 5 10 15

<210> SEQ ID NO 205
<211> LENGTH: 17
<212> TYPE: PRT
<213> ORGANISM: Artificial
<220> FEATURE:
<223> OTHER INFORMATION: Stabilizing element

<400> SEQUENCE: 205

Arg Met Lys Gln Ile Glu Asp Lys Ile Glu Glu Ile Glu Ser Lys Gln
1 5 10 15

Ile

<210> SEQ ID NO 206
<211> LENGTH: 9
<212> TYPE: PRT
<213> ORGANISM: Artificial
<220> FEATURE:
<223> OTHER INFORMATION: Insertion sequence

<400> SEQUENCE: 206

Asn Ala Thr Gly Gly Cys Cys Gly Gly
1 5

<210> SEQ ID NO 207
<211> LENGTH: 8
<212> TYPE: PRT
<213> ORGANISM: Artificial
<220> FEATURE:
<223> OTHER INFORMATION: Insertion sequence

<400> SEQUENCE: 207

Gly Ser Gly Lys Cys Cys Gly Gly
1 5

<210> SEQ ID NO 208
<211> LENGTH: 6
<212> TYPE: PRT
<213> ORGANISM: Artificial
<220> FEATURE:
<223> OTHER INFORMATION: His tag

<400> SEQUENCE: 208

His His His His His His
1 5

<210> SEQ ID NO 209
<211> LENGTH: 10
<212> TYPE: PRT
<213> ORGANISM: Artificial
<220> FEATURE:
<223> OTHER INFORMATION: trimeric coiled coil

<400> SEQUENCE: 209

Glu Ala Ile Glu Lys Lys Ile Glu Ala Ile
1 5 10

<210> SEQ ID NO 210
<211> LENGTH: 4
<212> TYPE: PRT
<213> ORGANISM: Artificial
<220> FEATURE:
<223> OTHER INFORMATION: Replacement amino acid sequence

<400> SEQUENCE: 210

His Asn Gly Lys
1

-continued

```
<210> SEQ ID NO 211
<211> LENGTH: 10
<212> TYPE: PRT
<213> ORGANISM: Artificial
<220> FEATURE:
<223> OTHER INFORMATION: H1N1 A/Brisbane/59/2007 linear sequence

<400> SEQUENCE: 211

Glu Arg Arg Met Glu Asn Leu Asn Lys Lys
1               5                   10


<210> SEQ ID NO 212
<211> LENGTH: 10
<212> TYPE: PRT
<213> ORGANISM: Artificial
<220> FEATURE:
<223> OTHER INFORMATION: H1N1 A/California/07/2009 linear sequence

<400> SEQUENCE: 212

Glu Lys Arg Ile Glu Asn Leu Asn Lys Lys
1               5                   10
```

INFLUENZA VIRUS VACCINES AND USES THEREOF

CROSS-REFERENCE TO RELATED APPLICATIONS

This application is a divisional of U.S. patent application Ser. No. 14/361,281, filed May 28, 2014, now U.S. Pat. No. 9,452,211, and published as US 2014/0357845 A1 on Dec. 4, 2014, the contents of which are incorporated by reference herein, which is a national phase entry under 35 U.S.C. §371 of International Patent Application PCT/EP2012/073706, filed Nov. 27, 2012, designating the United States of America and published in English as International Patent Publication WO 2013/079473 A1 on Jun. 6, 2013, which claims the benefit under Article 8 of the Patent Cooperation Treaty and under 35 U.S.C. §119(e) to U.S. Provisional Patent Application Ser. No. 61/720,281, filed Oct. 30, 2012, to European Patent Application Serial No. 12166268.8, filed May 1, 2012, to U.S. Provisional Patent Application Ser. No. 61/564,198, filed Nov. 28, 2011, to European Patent Application Serial No. 11191009.7, filed Nov. 28, 2011, to U.S. Provisional Patent Application Ser. No. 61/564,086, filed Nov. 28, 2011, and to European Patent Application Serial No. 11191003.0, filed Nov. 28, 2011, the contents of all of which are incorporated herein by reference.

STATEMENT ACCORDING TO 37 C.F.R. §1.821(c) or (e)-SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

This application relates to the field of medicine. Provided herein are influenza hemagglutinin stem domain polypeptides, methods for providing hemagglutinin stem domain polypeptides, compositions comprising the same, vaccines comprising the same and methods of their use, in particular in the detection, prevention and/or treatment of influenza.

BACKGROUND

Influenza viruses are major human pathogens, causing a respiratory disease (commonly referred to as "influenza" or "the flu") that ranges in severity from sub-clinical infection to primary viral pneumonia which can result in death. The clinical effects of infection vary with the virulence of the influenza strain and the exposure, history, age, and immune status of the host. Every year it is estimated that approximately 1 billion people worldwide undergo infection with influenza virus, leading to severe illness in 3-5 million cases and an estimated 300,000 to 500,000 of influenza related deaths. The bulk of these infections can be attributed to influenza A viruses carrying H1 or H3 hemagglutinin subtypes, with a smaller contribution from Influenza B viruses and, therefore, representatives of all three are included in the seasonal vaccine. The current immunization practice relies on early identification of circulating influenza viruses to allow for timely production of an effective seasonal influenza vaccine. Apart from the inherent difficulties in predicting the strains that will be dominant during the next season, antiviral resistance and immune escape also play a role in failure of current vaccines to prevent morbidity and mortality. In addition to this, the possibility of a pandemic caused by a highly virulent viral strain originating from animal reservoirs and reassorted to increase human to human spread, poses a significant and realistic threat to global health.

Influenza A viruses are widely distributed in nature and can infect a variety of birds and mammals. Influenza viruses are enveloped RNA viruses that belong to the family of Orthomyxoviridae. Their genomes consist of eight single-stranded RNA segments that code for 11 different proteins, one nucleoprotein (NP), three polymerase proteins (PA, PB1, and PB2), two matrix proteins (M1 and M2), three non-structural proteins (NS1, NS2, and PB1-F2), and two external glycoproteins: hemagglutinin (HA) and neuraminidase (NA). The viruses are classified on the basis of differences in antigenic structure of the HA and NA proteins, with their different combinations representing unique virus subtypes that are further classified into specific influenza virus strains. Although all known subtypes can be found in birds, currently circulating human influenza A subtypes are H1N1 and H3N2. Phylogenetic analysis has demonstrated a subdivision of hemagglutinins into two main groups: inter alia the H1, H2, H5 and H9 subtypes in phylogenetic group 1 and inter alia the H3, H4 and H7 subtypes in phylogenetic group 2.

The influenza type B virus strains are strictly human. The antigenic variation in HA within the influenza type B virus strains is smaller than those observed within the type A strains. Two genetically and antigenically distinct lineages of influenza B virus are circulating in humans, as represented by the B/Yamagata/16/88 (also referred to as B/Yamagata) and B/Victoria/2/87 (B/Victoria) lineages (Ferguson et al., 2003). Although the spectrum of disease caused by influenza B viruses is generally milder than that caused by influenza A viruses, severe illness requiring hospitalization is still frequently observed with influenza B infection.

It is known that antibodies that neutralize the influenza virus are primarily directed against hemagglutinin (HA). Hemagglutinin or HA is a trimeric glycoprotein that is anchored to the viral coat and has a dual function: it is responsible for binding to the cell surface receptor sialic acid and, after uptake, it mediates the fusion of the viral and endosomal membrane leading to release of the viral RNA in the cytosol of the cell. HA comprises a large head domain and a smaller stem domain. Attachment to the viral membrane is mediated by a C-terminal anchoring sequence connected to the stem domain. The protein is post-translationally cleaved in a designated loop to yield two polypeptides, HA1 and HA2 (the full sequence is referred to as HA0). The membrane distal head region is mainly derived from HA1 and the membrane proximal stem region primarily from HA2 (FIG. 1).

The reason that the seasonal influenza vaccine must be updated every year is the large variability of the virus. In the hemagglutinin molecule this variation is particularly manifested in the head domain where antigenic drift and shift have resulted in a large number of different variants. Since this is also the area that is immunodominant, most neutralizing antibodies are directed against this domain and act by interfering with receptor binding. The combination of immunodominance and large variation of the head domain also explains why infection with a particular strain does not lead to immunity to other strains: the antibodies elicited by the first infection only recognize a limited number of strains closely related to the virus of the primary infection.

Recently, influenza hemagglutinin stem domain polypeptides, lacking all or substantially all of the influenza hemagglutinin globular head domain, have been described and used to generate an immune response to one or more conserved epitopes of the stem domain polypeptide. It is believed that epitopes of the stem domain polypeptide are less immunogenic than the highly immunogenic regions of a globular head domain, thus the absence of a globular head domain in the stem domain polypeptide might allow an immune response against one or more epitopes of the stem domain polypeptide to develop (Steel et al., 2010). Steel et al. thus have created a new molecule by deleting amino acid residue 53 to 276 of HA1 of the A/Puerto Rico/8/1934 (H1N1) and A/Hong Kong/1968 (H3N2) strains from the HA primary sequence, and replacing this by a short flexible linking sequence GGGG (SEQ ID NO: 194). Vaccination of mice with the H3 HK68 construct did not elicit antisera that were cross-reactive with group 1 HAs. In addition, as shown in the Examples below, the stem domain polypeptides were highly unstable and did not adopt the correct conformation as proven by the lack of binding of antibodies that were shown to bind to conserved epitopes in the stem region.

In addition, Bommakanti et al. (2010) described an HA2 based polypeptide comprising amino acid residues 1-172 of HA2, a 7-amino acid linker (GSAGSAG (SEQ ID NO: 188)), amino acid residues 7-46 of HA1, a 6-amino acid linker GSAGSA (SEQ ID NO: 189), followed by residues 290-321 of HA1, with the mutations V297T, I300E, Y302T and C305T in HA1. The design was based on the sequence of H3 HA (A/Hong Kong/1968). The polypeptide did only provide cross-protection against another influenza virus strain within the H3 subtype (A/Phil/2/82 but not against an H1 subtype (A/PR/8/34).

There thus still exists a need for a safe and effective universal vaccine that stimulates the production of a robust, broadly neutralizing antibody response and that offers protection against a broad set of current and future influenza virus strains (both seasonal and pandemic), in particular providing protection against one or more influenza A virus subtypes within phylogenetic group 1 and/or group 2, for effective prevention and therapy of influenza.

DISCLOSURE

Provided herein are influenza hemagglutinin stem domain polypeptides, methods for providing stem domain polypeptides, compositions comprising the same, vaccines comprising the same and methods of their use.

In a first aspect, provided are immunogenic polypeptides comprising an influenza hemagglutinin stem domain and lacking the globular head, referred to as influenza hemagglutinin (HA) stem domain polypeptides. The polypeptides are capable of inducing an immune response when administered to a subject, in particular a human subject. The polypeptides present conserved epitopes of the membrane proximal stem domain HA molecule to the immune system in the absence of dominant epitopes that are present in the membrane distal head domain. To this end, part of the primary sequence of the HA0 protein making up the head domain is removed and the remaining amino acid sequence is reconnected, either directly or, in some embodiments, by introducing a short flexible linking sequence ("linker") to restore the continuity of the amino acid chain. The resulting sequence is further modified by introducing specific mutations that stabilize the native 3-dimensional structure of the remaining part of the HA0 molecule. The immunogenic polypeptides do not comprise the full-length HA1 and/or HA2 of an influenza virus.

The influenza hemagglutinin stem domain polypeptides are based on HA of influenza virus strains that are generally used for human influenza vaccine production. In particular, the polypeptides are based on HA of influenza A viruses of the H1, H5 and/or H3 subtype.

In certain embodiments, provided are influenza hemagglutinin stem domain polypeptides comprising (a) an influenza hemagglutinin HA1 domain that comprises an HA1 N-terminal stem segment, covalently linked by a linking sequence of 0-50 amino acid residues to an HA1 C-terminal stem segment, and (b) an influenza hemagglutinin HA2 domain, wherein the hemagglutinin stem domain polypeptides are resistant to protease cleavage at the junction between HA1 and HA2, and wherein one or more amino acids in the amino acid sequence connecting the A helix and the helix CD of HA2 have been mutated as compared to a wild-type influenza HA2 domain. Preferably, the HA1 and HA2 domain are derived from an influenza A virus selected from the group consisting of the H1, H5, and H3 subtype.

The polypeptides hereof comprise one or more mutations in the HA2 amino acid sequence connecting the C-terminal residue of helix A to the N-terminal residue of helix CD, as indicated in FIG. 1. In certain embodiments, one or more hydrophobic amino acids in the HA2 amino acid sequence have been substituted by hydrophilic amino acids, such as polar and/or charged amino acids, or the flexible amino acid glycine (G).

In certain embodiments, the HA1 N-terminal stem segment comprises the amino acids 1-x of HA1, and the HA1 C-terminal stem segment comprises the amino acids y-end (i.e., C-terminal amino acid of HA1) of HA1. Thus, in certain embodiments, the deletion in the HA1 segment comprises the amino acid sequence from the amino acid at position x+1 up to and including the amino acid at position y. In certain embodiments, the polypeptides do not comprise the signal sequence. Thus, in certain embodiments, the HA1 N-terminal segment comprises the amino acid p-x of HA1, wherein p is the first amino acid of the mature HA molecule (e.g., p=18 in case of SEQ ID NO: 1). The skilled person will be able to prepare the polypeptides described herein without the signal peptides (e.g., amino acids 1-17 of SEQ ID NO: 1). In certain embodiments, the polypeptides hereof contain the intracellular sequences of HA and the transmembrane domain. In other embodiments, the polypeptides hereof do not comprise the intracellular sequences of HA and the transmembrane domain. In certain embodiments, the intracellular and transmembrane sequence, e.g., the amino acid sequence from position (or the equivalent of) 523, 524, 525, 526, 527, 526, 528, 529, or 530 of the HA2 domain to the C-terminus of the HA2 domain has been removed.

The polypeptides do not comprise the full-length HA1.

In certain embodiments, the polypeptides are glycosylated.

In certain embodiments, the immunogenic polypeptides are substantially smaller than HA0, preferably lacking all or substantially all of the globular head of HA. Preferably, the immunogenic polypeptides are no more than 360, preferably no more than 350, 340, 330, 320, 310, 305, 300, 295, 290, 285, 280, 275, or 270 amino acids in length. In certain embodiments, the immunogenic polypeptides are from about 250 to about 350, preferably from about 260 to about 340, preferably from about 270 to about 330, preferably from about 270 to about 330 amino acids in length.

In certain embodiments, the polypeptides further comprise one or more additional mutations in the HA1 and/or HA2 domain, as compared to the amino acid sequence of the HA on which the HA1 and HA2 domains are based.

Also provided are methods for providing influenza hemagglutinin stem polypeptides, comprising the general steps of:

(a) Providing an influenza HA0 amino acid sequence;

(b) Removing the cleavage site between HA1 and HA2;

(c) Removing the amino acid sequence of the globular head domain from the HA0 sequence, in particular the amino acid sequence starting from position x+1 to y−1;

(d) Introducing one or more mutations in the amino acid sequence connecting the C-terminal residue of helix A to the N-terminal residue of helix CD; and (e) Introducing one or more disulfide bridges in the HA stem domain polypeptide.

Polypeptides obtainable by such methods are also part hereof.

In certain embodiments, the polypeptides comprise the conserved stem domain epitopes of the group 1 cross-neutralizing antibody CR6261 (as disclosed in WO2008/028946) and/or of the antibody CR9114 (as described below and in the co-pending application EP 11173953.8), an antibody capable of binding to and neutralizing both group 1 and group 2 influenza A viruses, as well as influenza B viruses. It is thus another aspect of the disclosure to provide HA stem domain polypeptides, wherein the polypeptides bind to the antibody CR6261 and/or the antibody CR9114. In an embodiment, the polypeptides do not bind to CR8057 (described in WO 2010/130636), a monoclonal antibody that binds to H3 influenza viruses only. In certain embodiments, the polypeptides bind to the antibody CR8020, CR8043 and/or CR9114. The influenza hemagglutinin stem domain polypeptides provided herein are suitable for use in immunogenic compositions (e.g., vaccines) capable of generating immune responses against a plurality of influenza virus A and/or B strains. In an embodiment, the influenza hemagglutinin stem domain polypeptides are capable of generating immune responses against influenza A virus strains of phylogenetic group 1 and/or group 2, in particular against influenza virus strains of both phylogenetic group 1 and group 2. In an embodiment, the polypeptides are capable of generating an immune response against homologous influenza virus strains. In an embodiment, the polypeptides are capable of generating an immune response against heterologous influenza virus strains of the same and/or different subtypes. In a further embodiment, the polypeptides are capable of generating an immune response to influenza virus strains of both phylogenetic group 1 and group 2 and influenza B virus strains.

The polypeptides may be used, e.g., in stand-alone therapy and/or prophylaxis and/or diagnosis of a disease or condition caused by an influenza virus, in particular a phylogenetic group 1 or 2 influenza A virus and/or an influenza B virus, or in combination with other prophylactic and/or therapeutic treatments, such as (existing or future) vaccines, antiviral agents and/or monoclonal antibodies.

In a further aspect, provided are nucleic acid molecules encoding the influenza HA stem domain polypeptides. In yet another aspect, provided are vectors comprising the nucleic acids encoding the immunogenic polypeptides.

In a further aspect, provided are methods for inducing an immune response in a subject, such a method comprising administering to the subject a polypeptide and/or nucleic acid molecule according to the disclosure.

In another aspect, provided are immunogenic compositions comprising a polypeptide and/or a nucleic acid molecule hereof. The immunogenic compositions provided herein can be in any form that allows for the compositions to be administered to a subject, e.g., mice, ferrets or humans. In a specific embodiment, the immunogenic compositions are suitable for human administration. The polypeptides, nucleic acid molecules and compositions may be used in methods of preventing and/or treating an influenza virus disease and/or for diagnostic purposes. The compositions may further comprise a pharmaceutically acceptable carrier or excipient. In certain embodiments, the compositions described herein comprise, or are administered in combination with, an adjuvant.

In another aspect, provided are polypeptides, nucleic acids and/or immunogenic compositions for use as a vaccine. The disclosure in particular relates to immunogenic polypeptides, nucleic acids, and/or immunogenic compositions for use as a vaccine in the prevention and/or treatment of a disease or condition caused by an influenza virus A subtype of phylogenetic group 1 and/or 2 and/or influenza B virus.

The various embodiments and uses of the polypeptides hereof will become clear from the following detailed description.

BRIEF DESCRIPTION OF THE FIGURES

FIG. 2: Binding of monoclonal antibodies to full-length HA and HA stem domain polypeptides according to the disclosure as analyzed by FACS. Panel A: Percentage of cells positive after staining. Panel B: mean fluorescence intensity. H1-Full-Length (SEQ ID NO: 1), miniHA-cl1 (SEQ ID NO: 3), miniHA-cl1+2 (SEQ ID NO: 4), miniHA-cl1+3 (SEQ ID NO: 5), miniHA-cl1+4 (SEQ ID NO: 6) miniHA-cl1+2+3 (SEQ ID NO: 7), miniHA-cl1+2+3+4 (SEQ ID NO: 8).

FIG. 3: Binding of monoclonal antibodies to full-length HA and HA stem domain polypeptides as analyzed by FACS. Panel A: Percentage of cells positive after staining. Panel B: mean fluorescence intensity. H1-Full-Length (SEQ ID NO: 1), miniHA (SEQ ID NO: 2), miniHA-cl1 (SEQ ID NO: 3).

FIG. 4A: mean fluorescence intensity. FIG. 4B: Percentage of cells positive after staining. H1-FL (SEQ ID NO: 1), CL1 (SEQ ID NO: 3), CL1+2 (SEQ ID NO: 4) and CL1+4 (SEQ ID NO: 6). cM2 is a negative control.

FIG. 6A: 28 days after first immunization. FIG. 6B: after 49 days of immunization.

FIG. 8A: Percentage of cells positive after staining. FIG. 8B: mean fluorescence intensity.

FIG. 9A: Percentage of cells positive after staining. FIG. 9B: mean fluorescence intensity.

FIG. 15A: Western Blot analysis of the supernatant of cells expressing SEQ ID NO: 145. For the Western Blot an antibody directed against the his-tag was used for detection. FIG. 15B: Binding of monoclonal antibody CR9114 (squares), CR6261 (circles), CR8020 (up triangles) and FI6v3 (down triangles) to SEQ ID NO: 145 as detected by ELISA.

FIG. 25: Alignment of H1N1 sequences selected according to Example 22.

DETAILED DESCRIPTION

Definitions

Figure 1:
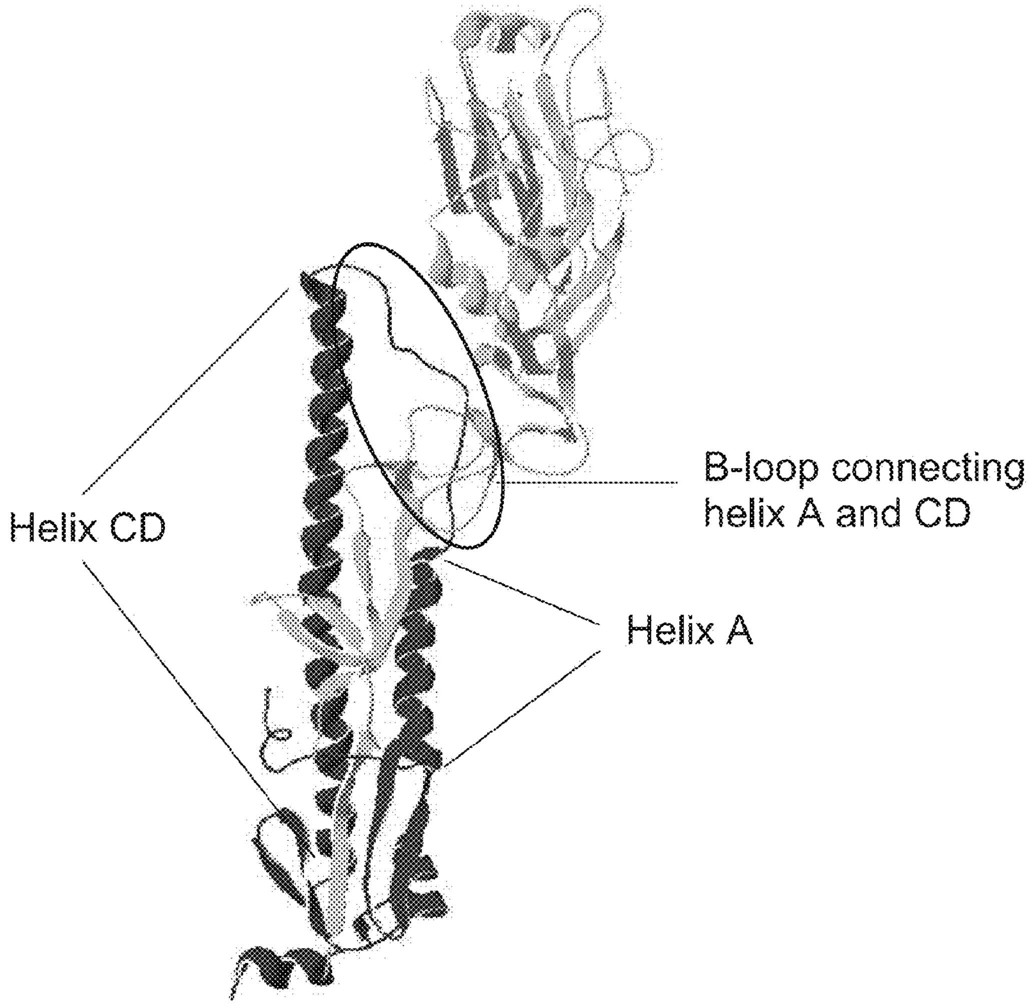
FIG. 1 shows a model of the HA monomer in the pre-fusion state as present in the native trimer. HA1 is shown in light grey, HA2 is shown in dark grey. Helix A (an important part of the epitope of CR6261) and helix CD (part of the trimer interface) are indicated, as is the loop connecting these secondary structure elements.

Definitions of terms as used herein are given below.

An amino acid hereof can be any of the twenty naturally occurring (or "standard" amino acids) or variants thereof, such as, e.g., D-proline (the D-enantiomer of proline), or any variants that are not naturally found in proteins, such as, e.g., norleucine. The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that forms a cycle to the polypeptide backbone, and glycine that is more flexible than other amino acids. Table 5 shows the abbreviations and properties of the standard amino acids.

The term "amino acid sequence identity" refers to the degree of identity or similarity between a pair of aligned amino acid sequences, usually expressed as a percentage. Percent identity is the percentage of amino acid residues in a candidate sequence that are identical (i.e., the amino acid residues at a given position in the alignment are the same residue) or similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, are determined using sequence alignment techniques well-known in the art, such as by visual inspection and mathematical calculation, or more preferably, the comparison is done by comparing sequence information using a computer program. An exemplary, preferred computer program is the Genetics Computer Group (GCG; Madison, Wis.) Wisconsin package version 10.0 program, "GAP" (Devereux et al. (1984)).

"Conservative substitution" refers to replacement of an amino acid of one class is with another amino acid of the same class. In particular embodiments, a conservative substitution does not alter the structure or function, or both, of a polypeptide. Classes of amino acids for the purposes of conservative substitution include hydrophobic (e.g., Met, Ala, Val, Leu), neutral hydrophilic (e.g., Cys, Ser, Thr), acidic (e.g., Asp, Glu), basic (e.g., Asn, Gln, His, Lys, Arg), conformation disrupters (e.g., Gly, Pro) and aromatic (e.g., Trp, Tyr, Phe).

As used herein, the terms "disease" and "disorder" are used interchangeably to refer to a condition in a subject. In some embodiments, the condition is a viral infection, in particular an influenza virus infection. In specific embodiments, a term "disease" refers to the pathological state resulting from the presence of the virus in a cell or a subject, or by the invasion of a cell or subject by the virus. In certain embodiments, the condition is a disease in a subject, the severity of which is decreased by inducing an immune response in the subject through the administration of an immunogenic composition.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve a reduction or amelioration of the severity of an influenza virus infection, disease or symptom associated therewith, such as, but not limited to a reduction in the duration of an influenza virus infection, disease or symptom associated therewith, the prevention of the progression of an influenza virus infection, disease or symptom associated therewith, the prevention of the development or onset or recurrence of an influenza virus infection, disease or symptom associated therewith, the prevention or reduction of the spread of an influenza virus from one subject to another subject, the reduction of hospitalization of a subject and/or hospitalization length, an increase of the survival of a subject with an influenza virus infection or disease associated therewith, elimination of an influenza virus infection or disease associated therewith, inhibition or reduction of influenza virus replication, reduction of influenza virus titer; and/or enhancement and/or improvement of the prophylactic or therapeutic effect(s) of another therapy. In certain embodiments, the effective amount does not result in complete protection from an influenza virus disease, but results in a lower titer or reduced number of influenza viruses compared to an untreated subject. Benefits of a reduction in the titer, number or total burden of influenza virus include, but are not limited to, less severe symptoms of the infection, fewer symptoms of the infection and a reduction in the length of the disease associated with the infection.

The term "host," as used herein, is intended to refer to an organism or a cell into which a vector such as a cloning vector or an expression vector has been introduced. The organism or cell can be prokaryotic or eukaryotic. Preferably, the host comprises isolated host cells, e.g., host cells in culture. The term "host cells" merely signifies that the cells are modified for the (over)-expression of the polypeptides hereof. It should be understood that the term host is intended to refer not only to the particular subject organism or cell but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

The term "included" or "including" as used herein is deemed to be followed by the words "without limitation."

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

Influenza viruses are classified into influenza virus types: genus A, B and C. The term "influenza virus subtype" as used herein refers to influenza A virus variants that are characterized by combinations of the hemagglutinin (H) and neuramidase (N) viral surface proteins. According to the disclosure, influenza virus subtypes may be referred to by their H number, such as, for example, "influenza virus comprising HA of the H3 subtype," "influenza virus of the H3 subtype" or "H3 influenza," or by a combination of a H number and an N number, such as, for example, "influenza virus subtype H3N2" or "H3N2." The term "subtype" specifically includes all individual "strains," within each subtype, which usually result from mutations and show different pathogenic profiles, including natural isolates as well as man-made mutants or reassortants and the like. Such strains may also be referred to as various "isolates" of a viral subtype. Accordingly, as used herein, the terms "strains" and "isolates" may be used interchangeably. The current nomenclature for human influenza virus strains or isolates includes the type (genus) of virus, i.e., A, B or C, the geographical location of the first isolation, strain number and year of isolation, usually with the antigenic description of HA and NA given in brackets, e.g., A/Moscow/10/00 (H3N2). Non-human strains also include the host of origin in the nomenclature. The influenza A virus subtypes can further be classified by reference to their phylogenetic group. Phylogenetic analysis has demonstrated a subdivision of hemagglutinins into two main groups: inter alia the H1, H2, H5 and H9 subtypes in phylogenetic group 1 ("group 1" influenza viruses) and inter alia the H3, H4, H7 and H10 subtypes in phylogenetic group 2 ("group 2" influenza viruses).

As used herein, the term "influenza virus disease" refers to the pathological state resulting from the presence of an influenza virus, e.g., an influenza A or B virus in a cell or subject or the invasion of a cell or subject by an influenza virus. In specific embodiments, the term refers to a respiratory illness caused by an influenza virus.

As used herein, the term "nucleic acid" (or polynucleotide) is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

As used herein, in certain embodiments, the numbering of the amino acids in HA is based on the numbering of amino acids in HA0 of a wild-type influenza virus, e.g., the numbering of the amino acids of the H1N1 influenza strain A/Brisbane/59/2007 (SEQ ID NO: 1). As used in the disclosure, the wording "the amino acid at position "x" in HA" thus means the amino acid corresponding to the amino acid at position x in HA0 of the particular wild-type influenza virus, e.g., A/Brisbane/59/2007 (SEQ ID NO: 1; wherein the amino acids of the HA2 domain have been indicated in italics). It will be understood by the skilled person that equivalent amino acids in other influenza virus strains and/or subtypes can be determined by multiple sequence alignment (see, e.g., Table 8). Note that, in the numbering system used throughout this application 1 refers to the N-terminal amino acid of an immature HA0 protein (SEQ ID NO: 1). The mature sequence starts, e.g., on position 18 of SEQ ID NO: 1. In certain embodiments, the numbering of the equivalent amino acids is based on the numbering of amino acids in H3 HA0, in particular the numbering of the amino acids of the H3N2 influenza strain A/Wisconsin/67/2005 (SEQ ID NO: 89). The equivalent amino acids in other H3 HA sequences can be determined by alignment. It will be understood by the skilled person that the leader sequence (or signal sequence) that directs transport of a protein during production (e.g., corresponding to amino acids 1-17 of SEQ ID NO: 89), generally is not present in the final polypeptide, that is, e.g., used in a vaccine. In certain embodiments, the polypeptides according to the disclosure thus comprise an amino acid sequence without the leader sequence, i.e., the amino acid sequence is based on the amino acid sequence of HA0 without the signal sequence.

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example, by post-translational processing such as signal peptide cleavage, disulfide bond formation, glycosylation (e.g., N-linked glycosylation), protease cleavage and lipid modification (e.g., S-palmitoylation).

"Stem domain polypeptide" refers to a polypeptide that comprises one or more polypeptide chains that make up a stem domain of a naturally-occurring (or wild-type) hemagglutinin (HA). Typically, a stem domain polypeptide is a single polypeptide chain (i.e., corresponding to the stem domain of a hemagglutinin HA0 polypeptide) or two polypeptide chains (i.e., corresponding to the stem domain of a hemagglutinin HA1 polypeptide in association with a hemagglutinin HA2 polypeptide). According to the disclosure, a stem domain polypeptide comprises one or more mutations as compared to the wild-type HA molecule, in particular one or more amino acid residues of the wild-type HA may have been substituted by other amino acids, not naturally occurring on the corresponding position in a particular wild-type HA. Stem domain polypeptides according to the disclosure can furthermore comprise one or more linking sequences, as described below.

The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome. As used herein, the term "wild-type" in the context of a virus refers to influenza viruses that are prevalent, circulating naturally and producing typical outbreaks of disease.

Influenza viruses have a significant impact on global public health, causing millions of cases of severe illness each year, thousands of deaths, and considerable economic losses. Current trivalent influenza vaccines elicit a potent neutralizing antibody response to the vaccine strains and closely related isolates, but rarely extend to more diverged strains within a subtype or to other subtypes. In addition, selection of the appropriate vaccine strains presents many challenges and frequently results in sub-optimal protection. Furthermore, predicting the subtype of the next pandemic virus, including when and where it will arise, is currently impossible.

Hemagglutinin (HA) is the major envelope glycoprotein from influenza A viruses which is the major target of neutralizing antibodies. Hemagglutinin has two main functions during the entry process. First, hemagglutinin mediates attachment of the virus to the surface of target cells through interactions with sialic acid receptors. Second, after endocytosis of the virus, hemagglutinin subsequently triggers the fusion of the viral and endosomal membranes to release its genome into the cytoplasm of the target cell. HA comprises a large ectodomain of ~500 amino acids that is cleaved by host-derived enzymes to generate 2 polypeptides that remain linked by a disulfide bond. The majority of the N-terminal fragment (HA1, 320-330 amino acids) forms a membrane-distal globular domain that contains the receptor-binding site and most determinants recognized by virus-neutralizing antibodies. The smaller C-terminal portion (HA2, ~180 amino acids) forms a stem-like structure that anchors the globular domain to the cellular or viral membrane. The degree of sequence homology between subtypes is smaller in the HA1 polypeptides (34%-59% homology between subtypes) than in the HA2 polypeptide (51%-80% homology). The most conserved region is the sequence around the cleavage site, particularly the HA2 N-terminal 23 amino acids, which is conserved among all influenza A virus subtypes (Lorieau et al., 2010). Part of this region is exposed as a surface loop in the HA precursor molecule (HA0), but becomes inaccessible when HA0 is cleaved into HA1 and HA2.

Most neutralizing antibodies bind to the loops that surround the receptor binding site and interfere with receptor binding and attachment. Since these loops are highly variable, most antibodies targeting these regions are strain-specific, explaining why current vaccines elicit such limited, strain-specific immunity. Recently, however, fully human monoclonal antibodies against influenza virus hemagglutinin with broad cross-neutralizing potency were generated. Functional and structural analysis have revealed that these antibodies interfere with the membrane fusion process and are directed against highly conserved epitopes in the stem domain of the influenza HA protein (Throsby et al., 2008; Ekiert et al., 2009, WO 2008/028946, WO 2010/130636).

New HA stem domain polypeptides have been designed containing these epitopes in order to create a universal epitope-based vaccine inducing protection against a broad range of influenza strains. Essentially, the highly variable and immunodominant part, i.e., the head domain, is first removed from the full-length HA molecule to create a stem domain polypeptide, also called mini-HA. In this way the immune response will be redirected towards the stem domain where the epitopes for the broadly neutralizing antibodies are located. The broadly neutralizing antibodies mentioned above were used to probe the correct folding of the newly created molecules, and to confirm the presence of the neutralizing epitopes.

The stem domain polypeptides hereof are capable of presenting the conserved epitopes of the membrane proximal stem domain HA molecule to the immune system in the absence of dominant epitopes that are present in the membrane distal head domain. To this end, part of the primary sequence of the HA0 protein making up the head domain is removed and reconnected, either directly or, in some embodiments, by introducing a short flexible linking sequence ("linker") to restore the continuity of the polypeptide chain. The resulting polypeptide sequence is further modified by introducing specific mutations that stabilize the native 3-dimensional structure of the remaining part of the HA0 molecule.

Thus provided are polypeptides comprising (a) an influenza hemagglutinin HA1 domain that comprises an HA1 N-terminal stem segment, covalently linked by a linking sequence of 0-50 amino acid residues to an HA1 C-terminal stem segment, and (b) an influenza hemagglutinin HA2 domain, wherein on or more amino acids in the HA2 domain have been mutated. In the polypeptides hereof, the HA2 domain thus comprises one or more mutations as compared to the HA2 domain of a wild-type influenza hemagglutinin on which the HA stem domain polypeptide is based.

The influenza hemagglutinin stem domain polypeptides are based on HA of influenza A virus subtypes that are generally used in human influenza virus vaccines. In preferred embodiments, the stem domain polypeptides are based on HA of an influenza virus comprising HA of the H1, H5 and/or H3 subtype.

In particular, provided are influenza hemagglutinin stem domain polypeptides comprising (a) an influenza hemagglutinin HA1 domain that comprises an HA1 N-terminal stem segment, covalently linked by a linking sequence of 0-50 amino acid residues to an HA1 C-terminal stem segment, and (b) an influenza hemagglutinin HA2 domain, wherein the hemagglutinin stem domain polypeptide is resistant to protease cleavage at the junction between HA1 and HA2, and wherein one or more amino acids in the amino acid sequence connecting the A helix and the helix CD of HA2 have been mutated as compared to a wild-type influenza HA2 domain. Preferably, the HA1 and HA2 domain are derived from an influenza A virus subtype selected from the group consisting of H1, H5 and H3.

The polypeptides hereof thus comprise one or more mutations in the HA2 amino acid sequence connecting the C-terminal residue of helix A to the N-terminal residue of helix CD, as indicated in FIG. 1. In certain embodiments, one or more hydrophobic amino acids in the HA2 amino acid sequence have been substituted by hydrophilic amino acids, such as polar and/or charged amino acids, or the flexible amino acid glycine (G).

The polypeptides hereof do not comprise the full-length HA1.

In certain embodiments, the immunogenic polypeptides are substantially smaller than HA0, preferably lacking all or substantially all of the globular head of HA. Preferably, the immunogenic polypeptides are no more than 360, preferably no more than 350, 340, 330, 320, 310, 305, 300, 295, 290, 285, 280, 275, or 270 amino acids in length. In certain embodiments, the immunogenic polypeptides are from about 250 to about 350, preferably from about 260 to about 340, preferably from about 270 to about 330, preferably from about 270 to about 330 amino acids in length.

In certain embodiments, the polypeptides further comprise one or more additional mutations in the HA1 and/or HA2 domain, as compared to the amino acid sequence of the HA of which the HA1 and HA2 domains are derived. Thus, the stability of the stem polypeptides is further increased.

As used herein, the "HA1 N-terminal segment" refers to a polypeptide segment that corresponds to the amino-terminal portion of the HA1 domain of an influenza hemagglutinin (HA) molecule. In certain embodiments, the HA1 N-terminal polypeptide segment comprises the amino acids from position 1 to position x of the HA1 domain, wherein amino acid on position x is an amino acid residue within HA1. The term "HA1 C-terminal segment" refers to a polypeptide segment that corresponds to the carboxy-terminal portion of an influenza hemagglutinin HA1 domain. In certain embodiments, the HA1 C-terminal polypeptide segment comprises the amino acids from position y to and including the C-terminal amino acid of the HA1 domain, wherein the amino acid on position y is an amino acid residue within HA1. According to the disclosure, y is greater than x, thus a segment of the HA1 domain between the HA1 N-terminal segment and the HA1 C-terminal segment, i.e., between the amino acid on position x and the amino acid on position y of HA1, has been deleted, and in some embodiments, replaced by a linking sequence.

In certain embodiments, the HA1 N-terminal stem segment comprises the amino acids 1-x of HA1, and the HA1 C-terminal stem segment comprises the amino acids y-end of HA1. Thus, in certain embodiments, the deletion in the HA1 segment comprises the amino acid sequence from the amino acid at position x+1 up to and including the amino acid at position y−1.

In certain embodiments, the polypeptides do not comprise the signal sequence. Thus, in certain embodiments, the HA1 N-terminal segment comprises the amino acid p-x of HA1, wherein p is the first amino acid of the mature HA molecule (e.g., p=18 in case of SEQ ID NO: 1). The skilled person will be able to prepare the polypeptides described herein without the signal peptides (e.g., amino acids 1-17 of SEQ ID NO: 1). In certain embodiments, the polypeptides hereof contain the intracellular sequences of HA and the transmembrane domain. In other embodiments, the polypeptides hereof do not comprise the intracellular sequences of HA and the transmembrane domain. In certain embodiments, the intracellular and transmembrane sequence, e.g., the amino acid sequence from position (or the equivalent of) 523, 524, 525, 526, 527, 526, 528, 529, or 530 of the HA2 domain to the C-terminus of the HA2 domain has been removed.

The hemagglutinin stem domain polypeptides are resistant to protease cleavage at the junction between HA1 and HA2. It is known to those of skill in the art that the Arg (R)-Gly (G) sequence spanning HA1 and HA2 is a recognition site for trypsin and trypsin-like proteases and is typically cleaved for hemagglutinin activation. Since the HA stem domain polypeptides described herein should not be activated, the influenza hemagglutinin stem domain polypeptides of the disclosure are resistant to protease cleavage. According to the disclosure, thus the protease cleavage site is removed or the protease site spanning HA1 and HA2 is mutated to a sequence that is resistant to protease cleavage.

In certain embodiments, the C-terminal amino acid residue of the HA1 C-terminal stem segment is any amino acid other than arginine (R) or lysine (K). In certain embodiments, the HA1 C-terminal amino acid is glutamine (Q), serine (S), threonine (T), asparagine (N), aspartic acid (D) or glutamic acid (E). In certain embodiments, the C-terminal amino acid residue of the HA1 C-terminal stem segment is glutamine (Q).

In certain embodiments, the polypeptides are glycosylated.

The influenza hemagglutinin stem domain polypeptides may be based on HA of any naturally occurring influenza A hemagglutinin virus of a subtype that is used in human influenza vaccines. Influenza A virus subtypes that are generally used in influenza vaccines are influenza A viruses of the H1, H3 or H5 subtypes. With "based on" it is meant that the N-terminal segments, and/or C-terminal segments of the HA1 domain and/or the HA2 domains have at least 70%, 75%, 80%, 85%, 90%, 95%, 96%, 97%, 98%, or 99% amino acid sequence identity with the corresponding N-terminal and/or C-terminal segments of HA1 and/or the HA2 domains of any naturally occurring influenza hemagglutinin of a H1, H3 and/or H5 subtype known to those of skill in the art or later discovered. In certain embodiments, the influenza hemagglutinin stem domain polypeptides are based on an influenza hemagglutinin of a group 1 influenza A virus. In certain embodiments, the influenza hemagglutinin stem domain polypeptides are based on an influenza hemagglutinin of a group 2 influenza A virus. In some embodiments, the influenza hemagglutinin stem domain polypeptide is a hybrid or chimeric polypeptide that comprises or consists of segments and/or domains from a plurality of influenza strains or subtypes. For example, an influenza hemagglutinin stem domain polypeptide may comprise HA1 N-terminal and HA1 C-terminal stem segments and/or HA2 domains from different influenza A virus HA subtypes.

In certain embodiments, the polypeptides are based on H1 HA. In a particular embodiment, the polypeptides comprise hemagglutinin stem domains from or based on HA of an influenza A virus comprising HA of the H1 subtype, such as from the influenza virus A/Brisbane/59/2007 (H1N1) (SEQ ID NO: 1), as described below. It will be understood by the skilled person that also other influenza A viruses comprising HA of the H1 subtype may be used according to the disclosure. In certain embodiments, the polypeptides comprise hemagglutinin stem domains based on HA of an influenza A H1 virus selected from Table 7.

In certain embodiments, the polypeptides comprise a HA1 N-terminal polypeptide segment comprising the amino acids from position 1 to position x of the H1 HA1 domain, wherein x is any amino acid between the amino acid on position 46 and the amino acid on position 60, such as the amino acid on position 47, 48, 49, 50, 51, 52, 53, 54, 55, 56, 57, 58, or 59, preferably wherein x is 52, 53, 55 or 59.

Preferably, the polypeptides comprise a HA1 N-terminal segment without the signal sequence, i.e., a HA1 N-terminal segment comprising the amino acids from position 18 (e.g., for H1 HA, such as SEQ ID NO: 1), or an equivalent position in other H1 influenza virus strains, to position x of the HA1 domain. In certain embodiments, the HA1 N-terminal segment thus comprises the amino acids from position p (wherein p=18 for H1 HA in SEQ ID NO: 1 or an equivalent position on other H1 HAs), to position x of the HA1 domain.

In certain embodiments, the HA1 C-terminal polypeptide segment comprises the amino acids from position y to and including the C-terminal amino acid of the H1 HA1 domain, wherein y is any amino acid between the amino acid on positions 290 and the amino acid on position 325 of H1 HAL preferably wherein y is 291, 303, 318, or 321. The HA2 domain comprises one or more mutations in the HA2 amino acid sequence connecting the C-terminal residue of helix A to the N-terminal residue of helix CD (FIG. 1). In certain embodiments, one or more hydrophobic amino acids in the HA2 amino acid sequence have been substituted by hydrophilic amino acids, such as polar and/or charged amino acids. In certain embodiments (e.g., for H1 HA, such as SEQ ID NO: 1), the HA2 amino acid sequence connecting the C-terminal residue of helix A and the N-terminal residue of helix CD comprises the amino acid sequence between residues 402-418 of influenza HA2. In certain embodiments, the HA2 amino acid sequence connecting the C-terminal residue of helix A and the N-terminal residue of helix CD comprises the amino acid sequence MNTQFTAVGKEFN (H/K)LE(K/R) (SEQ ID NO: 17).

In certain embodiments, x is 59 and y is 291.

In certain embodiments, x is 52 and y is 321.

In certain embodiments, x is 53 and y is 303.

In certain embodiments, x is 55 and y is 318.

In an embodiment, the amino acid sequence connecting the C-terminal residue of helix A to the N-terminal residue of helix CD corresponds to the amino acid sequence between the amino acid on position 402 and the amino acid on position 418 of HA2 of SEQ ID NO: 1, wherein the polypeptides comprise one or more mutations in the amino acid sequence spanning from amino acid 402 to 418 of SEQ ID NO: 1. The amino acid sequence between residue 402-418 of influenza HA of serotype H1 comprises the amino acid sequence MNTQFTAVGKEFN(H/K)LE(K/R) (SEQ ID NO: 17). In certain embodiments, the amino acid sequence between residue 402-418 of influenza HA of serotype H1 comprises the amino acid sequence MNTQ$X_1$TA$X_2$GKE$X_3$N(H/K)$X_4$E(K/R) (SEQ ID NO: 190).

In certain embodiments, the polypeptides thus comprise one or more of the mutations in the H1 HA2 domain as indicated in Table 6. In certain embodiments, one or more of the amino acids on position 406, 409, 413 and 416, i.e., one or more of the amino acids $X_1$, $X_2$, $X_3$ and $X_4$ have been mutated (numbering refers to SEQ ID NO: 1). In certain embodiments, the amino acid on position 406, i.e., $X_1$ has been changed into an amino acid selected from the group consisting of S, T, N, Q, R, H, K, D, E, and G, preferably S. In certain embodiments, the amino acid on position 409, i.e., $X_2$ has been changed into an amino acid selected from the group consisting of S, T, N, Q, R, H, K, D, E, and G, preferably T, Q or G. In certain embodiments, the amino acid on position 413, i.e., $X_3$ has been changed into an amino acid selected from the group consisting of S, T, N, Q, R, H, K, D, E, G, preferably S. In certain embodiments, the amino acid on position 416, i.e., $X_4$ has been changed into an amino acid selected from the group consisting of S, T, N, Q, R, H, K, D, E, G, preferably S. Combinations of these mutations are also possible.

In certain embodiments, the HA1 N-terminal stem segment comprises the amino acid residues 1-59 of HA1, and the HA1 C-terminal stem segment comprises the amino acid residues 291-343 of HA1 wherein the amino acid on position 343, i.e., R343, has been mutated and is an amino acid other than R, preferably glutamine (Q). In certain embodiments, the HA1 N-terminal segment consists of the amino acid residues 1-59 of HA1 and the HA1 C-terminal segment consists of the amino acid residues 291-343 of HA1. It is noted that the numbering of the amino acids is based on the numbering of amino acids in H1 HA0, in particular the numbering of the amino acids of the H1N1 influenza strain A/Brisbane/59/2007 (SEQ ID NO: 1). It is noted that since HA sequences of different influenza subtypes/strains may have insertions or deletions in the head region compared to each other, the numbering is not always the same. The skilled person will be able to determine the equivalent amino acid positions in HA sequences of different influenza virus strains and/or subtypes by sequence alignment.

In certain embodiments, the HA1 N-terminal polypeptide segment does not comprise the signal sequence. In preferred embodiments, the HA1 N-terminal segment comprises the amino acids from position 18 to position 59 of the HA1 domain. In certain embodiments, the HA1 N-terminal segment consists of the amino acids 18-59 of the HA1 domain.

In some embodiments, the polypeptides hereof, comprise one or more further mutations, i.e., amino acid substitutions, in the HA1 domain and/or the HA2 domain. In certain embodiments, the HA1 domain thus further comprises one or more of the following mutations: L58T, V314T and I316T. It is again noted that the numbering of the amino acids is based on the numbering of amino acids in H1 HA0, in particular the numbering of the amino acids of the H1N1 influenza strain A/Brisbane/59/2007 (SEQ ID NO: 1). The skilled person will be able to determine the equivalent amino acids in HA of other influenza H1 viruses and, thus, will be able to determine equivalent mutations.

In a specific embodiment, the HA1 domain comprises the mutations L58T, V314T, and I316T, and the HA2 domain comprises one or more of the following mutations: F406S, V409T, and L416S.

In certain embodiments, the HA1 domain further comprises the mutation K321C and/or the HA2 domain further comprises one or more of the following mutations: Q405C, F413C, E421C, and Y502S.

In a specific embodiment, the HA1 domain comprises the mutations L58T, V314T, I316T, and K321C and the HA2 domain comprises the mutations: Q405C, F406S, V409T, and L416S.

In a specific embodiment, the HA1 domain comprises the mutations L58T, V314T, and I316T, and the HA2 domain comprises the mutations: F406S, V409T, F413C, L416S and E421C.

In a specific embodiment, the HA1 domain comprises the mutations L58T, V314T, and I316T, and the HA2 domain comprises the mutations: F406S, V409T, L416S, and Y502S.

In a specific embodiment, the HA1 domain comprises the mutations L58T, V314T, I316T, and K321C and the HA2 domain comprises the mutations: Q405C, F406S, V409T, F413C, L416S and E421C.

In a specific embodiment, the HA1 domain comprises the mutations L58T, V314T, I316T, and K321C and the HA2 domain comprises the mutations: Q405C, F406S, V409T, F413C, L416S, E421C and Y502S.

In other embodiments, the HA2 domain further comprises one or more of the mutations M420I and V421I, or equivalent mutations.

In a specific embodiment, the HA1 domain comprises the mutations L58T, V314T, and I316T, and the HA2 domain comprises one or more of the following mutations: F406S, V409T, L416S, M420I and V421I.

In certain embodiments, the HA1 N-terminal stem segment comprises the amino acid residues 1-52 of HA1, preferably the amino acid residues 18-52 of HA1, and the HA1 C-terminal stem segment comprises the amino acid residues 321-343 of HA1, wherein the amino acid on position 343, i.e., R343, has been mutated and is an amino acid other than R, preferably glutamine (Q), wherein the HA2 domain comprises the mutations F406S, V409T, L416S, M420I and V421I. In certain embodiments, the HA1 N-terminal stem segment consists of the amino acid residues 1-52 of HA1, preferably the amino acid residues 18-52 of HA1, and the HA1 C-terminal stem segment consists of the amino acid residues 321-343 of HA1.

In certain embodiments, the HA1 N-terminal stem segment comprises the amino acid residues 1-53 of HA1, preferably the amino acid residues 18-53 of HA1, and the HA1 C-terminal stem segment comprises the amino acid residues 303-343 of HA1, wherein the amino acid on position 343, i.e., R343, has been mutated and is an amino acid other than R, preferably glutamine (Q). In certain embodiments, the HA1 N-terminal stem segment consists of the amino acid residues 1-53 of HA1, preferably the amino acid residues 18-53 of HA1, and the HA1 C-terminal stem segment consists of the amino acid residues 303-343 of HA1, In a specific embodiment, the HA1 domain comprises the mutations V314T and I316T, and the HA2 domain comprises one or more of the following mutations: F406S, V409T, L416S, M420I and V421I. In a preferred embodiment, the polypeptide comprises the amino acid sequence of SEQ ID NO: 11.

In certain embodiments, the HA1 N-terminal stem segment comprises the amino acid residues 1-55 of HA1, preferably the amino acid residues 18-55 of HA1, and the HA1 C-terminal stem segment comprises the amino acid residues 318-343 of HA1, wherein the amino acid on position 343, i.e., R343, has been mutated and is an amino acid other than R, preferably glutamine (Q). In certain embodiments, the HA1 N-terminal stem segment consists of the amino acid residues 1-55 of HA1, preferably the amino acid residues 18-55 of HA1, and the HA1 C-terminal stem segment consists of the amino acid residues 318-343 of HA1. In an embodiment, the HA2 domain comprises the mutations F406S, V409T, L416S, M420I and V421I.

In certain embodiments, the polypeptides further comprise the mutation R324C in the HA1 domain and T436C in the HA2 domain.

In a specific embodiment, the HA1 domain comprises the mutations L58T, V314T, I316T, and R324C and the HA2 domain comprises one or more of the following mutations: F406S, V409T, L416S, M420I, V421I and T436C.

In an embodiment, the HA1 domain comprises the mutation R324C, and the HA2 domain comprises the mutations F406S, V409T, L416S, M420I, V421I and T436C.

In another embodiment, the HA1 domain comprises the mutations V314T, I316T and R324C, and the HA2 domain comprises one or more of the following mutations: F406S, V409T, L416S, M420I, V421I and T436C.

In an embodiment, the HA1 domain comprises the mutation R324C, and the HA2 domain comprises the mutations F406S, V409T, L416S, M420I, V421I and T436C.

In certain embodiments, the polypeptides contain the intracellular sequences of HA and the transmembrane domain. In other embodiments, the intracellular and transmembrane sequences, e.g., the amino acid sequence from position (or the equivalent of) 523, 524, 525, 526, 527, 526, 528, 529, or 530 of the HA2 domain to the C-terminus of the HA2 domain (numbering according to SEQ ID NO: 1) has been removed. In certain embodiments, the polypeptides are further stabilized by introducing a sequence known to form trimeric structures, e.g., AYVRKDGEWVLL (SEQ ID NO: 143) ("foldon" sequence), optionally connected through a linker. The linker may optionally contain a cleavage site for processing afterwards according to protocols well known to those skilled in the art. To facilitate purification of the soluble form a tag sequence may be added, e.g., a his-tag (HHHHHHH (SEQ ID NO: 191)) connected via a short linker, e.g., EGR. In some embodiments the linker and his-tag sequence are added without the foldon sequence being present.

In certain embodiments, the amino acid sequence from position (or the equivalent of) 530 of the HA2 domain to the C-terminus of the HA2 domain (numbering according to SEQ ID NO: 1) has been removed. In certain embodiments, the intracellular and transmembrane sequence have been replaced by the amino acid sequence AGRHHHHHHH (SEQ ID NO: 81) or SGRSLVPRGSPGSGYIPEAPRDGQAYVRKDGEWVLLSTFLGHHHHHHH (SEQ ID NO: 82).

In certain embodiments, the polypeptides selectively bind to the antibodies CR6261 and/or CR9114. In an embodiment, the polypeptide does not bind to the antibody CR8057. In an embodiment, CR6261 comprises a heavy chain variable region comprising the amino acid sequence of SEQ ID NO: 20 and a light chain variable region comprising the amino acid sequence of SEQ ID NO: 21; CR9114 comprises a heavy chain variable region comprising the amino acid sequence of SEQ ID NO: 18 and a light chain variable region comprising the amino acid sequence of SEQ ID NO: 19. In an embodiment, CR8057 comprises a heavy chain variable region comprising the amino acid sequence of SEQ ID NO: 22 and a light chain variable region comprising the amino acid sequence of SEQ ID NO: 23.

As described above, the polypeptides comprise an influenza hemagglutinin HA1 domain that comprises an HA1 N-terminal stem segment that is covalently linked by a linking sequence of 0-50 amino acid residues to the HA1 C-terminal stem segment. The linking sequence does not occur in naturally occurring, or wild-type, HA. In certain embodiments, the linker is a peptide that comprises one amino acid residue, two or less amino acid residues, three or less amino acid residues, four or less amino acid residues, five or less amino acid residues, ten or less amino acid residues, 15 or less amino acid residues, or 20 or less amino acid residues or 30 or less amino acid residues or 40 or less amino acid residues or 50 or less amino acid residues. In a specific embodiment, the linking sequence is a sequence selected from the group consisting of G, GS, GGG, GSG, GSA, GSGS (SEQ ID NO: 192), GSAG (SEQ ID NO: 193), GGGG (SEQ ID NO: 194), GSAGS (SEQ ID NO: 195), GSGSG (SEQ ID NO: 196), GSAGSA (SEQ ID NO: 189), GSAGSAG (SEQ ID NO: 188), and GSGSGSG (SEQ ID NO: 197).

Also provided are methods to provide the polypeptides, in particular, to provide the H1 HA stem domain polypeptide according to the disclosure, as well as the polypeptides obtainable or obtained by these methods. In certain embodiments, the methods comprise the steps of:

(a) Providing an influenza HA0 amino acid sequence, in particular an influenza HA0 amino acid sequence of serotype H1;

(b) Removing the cleavage site between HA1 and HA2, preferably by mutating the C-terminal amino acid of HA1 into an amino acid other that arginine (R) or lysine (K);

(c) Removing the amino acid sequence of the globular head domain from the HA0 sequence; This is done by deleting a segment of the HA1 domain between amino acid on position x and an amino acid on position y, and reconnecting the N-terminal segment (spanning from amino acid on position 1 to and including amino acid on position x of HA1) and the C-terminal segment of HA1 (spanning from amino acid y to the C-terminal amino acid of HA1), thus obtained, optionally through a linking sequence of 0-50 amino acids. In certain embodiments, x is an amino acid on any position between positions 46 and 60, preferably the amino acid on position 52, 53, 55 or 59 of HA1 and wherein y is an amino acid on any position between positions 290 and 325, preferably an amino acid on position 291, 303, 318, or 321 of HA1. Again, the numbering used refers to SEQ ID NO: 1. It will be understood by the skilled person that the leader sequence (or signal sequence) that directs transport of a protein during production (e.g., corresponding to amino acids 1-17 of SEQ ID NO: 1), generally will not be present in the final polypeptide, that is, e.g., used in a vaccine. In certain embodiments, the polypeptides according to the disclosure thus comprise a HA1 N-terminal segment without the leader sequence.

(d) Increasing the stability of the pre-fusion conformation and destabilizing the post-fusion conformation of the modified HA, preferably by introducing one or more mutations in the amino acid sequence connecting the C-terminal residue of helix A to the N-terminal residue of helix CD, preferably in the amino acid sequence spanning from amino acid 402-418 of SEQ ID NO: 1 in particular comprising the amino acid sequence of MNTQFTAVGKEFN(H/K)LE(K/R) (SEQ ID NO: 17). The mutations preferably comprise the substitution of hydrophobic amino acid residues into hydrophilic amino acid residues.

(e) Introducing one or more disulfide bridges in the HA stem domain polypeptide.

Removal of the cleavage site between HA1 and HA2 can be achieved by mutation of R (in a small number of cases K) to Q at the P1 position (see, e.g., Sun et al., 2010, for an explanation of the nomenclature of the cleavage site (position 343 in SEQ ID NO: 1). A mutation to Q is preferred but S, T, N, D or E are alternatives.

Removal of the head domain can be achieved, e.g., by deleting amino acids 53 to 320 from SEQ ID NO; 1, or at equivalent positions in HA from other influenza viruses. Equivalent positions can be easily determined by those skilled in the art by aligning the sequences using a suitable algorithm such as, e.g., Clustal or Muscle. The remaining parts of the sequence can be joined directly, or alternatively a flexible linker can be introduced. Linker sequences can be 1 to 50 amino acids in length. Preferred are flexible linkers of limited length (smaller or equal to 10 amino acids), e.g., GGG, GGGG (SEQ ID NO: 194), GSA, GSAG (SEQ ID NO: 193), GSAGSA (SEQ ID NO: 189), GSAGSAG (SEQ ID NO: 188) or similar. The length of the deletion can also be varied, e.g., by starting the deletion at (the equivalent of) position (x), e.g., at position 54, 55, 56, 57 or 58, or to increase the length of the deletion, by cutting at position 47, 48, 49, 50, 51, or 52. Similarly, the last amino acid to be deleted can be at (the equivalent of) position (y), such as 315, 316, 317, 318 or 319, or to increase the length of the deletion at (the equivalent of) position 321, 322, 323, 324, or 325. It is important to realize that changes in the length of the deletion can be in part compensated for by matching the length of the linker sequence, i.e., a larger deletion can be matched with a longer linker and vice versa. These polypeptides are also encompassed by the disclosure.

The solubility of the loop between the A-helix and the CD helix is increased. This loop is formed by (the equivalent of) residues 402 to 418 in H1 A/Brisbane/59/2007 (SEQ ID NO: 1). Thus, the stability of the pre-fusion conformation is increased and the post-fusion conformation of the modified HA is destabilized. This loop is highly conserved in H1 sequences, as can be seen in Table 6 below. This can, for example, be achieved by replacing the amino acids I, L, F or V in the loop with hydrophilic counterparts. Equivalent position can be easily determined by those skilled in the art by aligning the sequences using a suitable algorithm such as, e.g., Clustal or Muscle. Mutations to glycine destabilize the post-fusion conformation since the high flexibility of this amino acid leads to a decrease in stability of the post-fusion helix to be formed by this part of the HA sequence. The consensus sequence describing the loop between residue 402-418 of influenza HA of serotype H1 is (SEQ ID NO: 17) MNTQFTAVGKEFN(H/K)LE(K/R). In polypeptides of the disclosure, the amino acid at positions 406, 409, 413 and/or 416 (or their equivalent, as determined from a sequence alignment) is a polar (S, T, N, Q), charged (R, H, K, D, E) or flexible (G) amino acid. Combinations of mutations at these sites are also possible, for example, F406S, V409T, L416S. In some cases, a mutation to restore the consensus amino acid is preferred, e.g., where V or M is at position 404 (to T), V at 408 (to A) or 410 (to G) or I at 414 (to N); the incidence of sequences with these particular amino acids is very low. An overview of the mutations described above that characterize polypeptides of the disclosure is given in Table 6.

One or more disulfide bridges are introduced in the stem domain polypeptides, preferably between amino acids of (or the equivalent of) position 324 and 436 in H1 A/Brisbane/59/2007. Equivalent positions can be easily determined by those skilled in the art by aligning the sequences using a suitable algorithm such as Clustal, Muscle etc. Engineered disulfide bridges are created by mutating at least one (if the other is already a cysteine), but usually two residues that are spatially close into cysteine, that will spontaneously or by active oxidation form a covalent bond between the sulfur atoms of these residues.

The native HA exists as a trimer on the cell surface. Most of the interactions between the individual monomers that keep the trimer together are located in the head domain. After removal of the head the tertiary structure is thus destabilized and, therefore, reinforcing the interactions between the monomers in the truncated molecule will increase the stability. In the stem domain trimerization is mediated by the formation of a trimeric coiled coil motif. By strengthening this motif a more stable trimer can be created. According to the disclosure, a consensus sequence for the formation of a trimeric coiled coil, e.g., IEAIEKKIEAIEKKIE (SEQ ID NO: 83), may be introduced in a polypeptide of the disclosure at (the equivalent of) position 418 to 433. In certain embodiments, the sequence MKQIEDKIEEIESKQ (SEQ ID NO: 84), derived from GCN4 and also known to trimerize is introduced at (the equivalent of)

position 419-433. In certain embodiments, the trimer interface is stabilized by modifying M420, L423, V427, G430 into isoleucine.

In certain embodiments, the polypeptides hereof contain the intracellular sequences of H1 HA and the transmembrane domain. In other embodiments, the intracellular and transmembrane sequences, e.g., the amino acid sequence from position (or the equivalent of) 523, 524, 525, 526, 527, 526, 528, 529, or 530 of the HA2 domain to the C-terminus of the HA2 domain (numbering according to SEQ ID NO: 1) has been removed to produce a soluble polypeptide following expression in cells. In certain embodiments, the polypeptides are further stabilized by introducing a sequence known to form trimeric structures, i.e., AYVRKDGEWVLL (SEQ ID NO: 80), optionally connected through a linker. The linker may optionally contain a cleavage site for processing afterwards according to protocols well known to those skilled in the art. To facilitate purification of the soluble form a tag sequence may be added, e.g., a his-tag (HHHHHHHH (SEQ ID NO: 191)) connected via a short linker, e.g., EGR. In some embodiments, the linker and his-tag sequence are added without the foldon sequence being present. In certain embodiments, the intracellular and transmembrane sequence have been replaced by the amino acid sequence AGRHH-HHHHH (SEQ ID NO: 97) or SGRSLVPRGSPGSGYI-PEAPRDGQAYVRKDGEWVLLSTFLGHHHHHHH (SEQ ID NO: 82).

Applicants have previously identified broadly neutralizing antibodies isolated from primary human B-cells from vaccinated individuals some of which were specific for group 1 (e.g., CR6261, as described in WO 2008/028946) and some of which were specific for group 2 influenza viruses (e.g., CR8020 as described in WO 2010/130636). Detailed analysis of the epitopes of these monoclonal antibodies has revealed the reason for the lack of cross-reactivity of these specific antibodies. In both cases the presence of glycans in group 1 or group 2 HA molecules on different positions at least partly explained the fact that the antibodies are group-specific. With the identification of CR9114-like antibodies that cross-react with many group 1 and 2 HA molecules, as described below, it has become clear that it is possible for the human immune system to elicit very broad neutralizing antibodies against influenza viruses. However, given the need for a yearly vaccination scheme these antibodies are apparently not, or only to a very low extent elicited following infection or vaccination with (seasonal) influenza viruses of subtypes H1 and/or H3. In certain embodiments, the disclosure thus provides polypeptides that present the stem region of HA in a conformational correct manner so that the epitopes that elicit the broadly neutralizing antibodies are presented to the immune system in the absence of immune dominant variable regions. Since it is known that the pattern of glycans differs between H1 and H3 HA, and that this difference may lead to more group restricted antibody response, in different embodiments, the polypeptides hereof are based on group 2 HA molecules (e.g., HA of the H3). As shown in Example 3, below, the in vitro neutralizing capacity of CR9114 is higher on H1 subtypes compared to H3 subtypes. Therefore, it is hypothesized that the epitope of CR9114 is more accessible on H1 compared to H3 HA molecules which could be due to a glycan on N38 in HA1 common to many group 2 HA subtypes. Without wishing to be bound to this theory, it may be reasoned that if a polypeptide of the disclosure is based on H1, the resulting antibodies are more likely to be hindered by the glycan on N38 on group 2 HA molecules and thus be somewhat less active on group 2 influenza viruses.

Therefore, to enable elicitation of broadly neutralizing antibodies that act on both group 1 and group 2 influenza viruses with good activity, in certain embodiments, the stem domain polypeptides hereof are based on H3 HA subtypes.

Humans are frequently infected with seasonal influenza viruses comprising HA of the H1 or H3 subtype. Apparently despite the exposure to these influenza viruses, broadly neutralizing antibodies are not often raised in the natural situation. One of the reasons for this, besides the presence of the variable head region in HA, might be that the exposure to a new subtype that is closely related to the one seen previously somehow makes the response less broad. It thus may be preferred to expose the individual to a more unrelated subtype sequence. Therefore, in yet another embodiment, the stem domain polypeptides hereof are based on HA of a group 2 subtype that does contain an asparagine (N) on position 38 in HA1 (N38), and that is not an H3 subtype.

In certain embodiments, the polypeptides are based on an influenza A virus subtype. In certain embodiments, the polypeptides are not based on H7 HA.

As described above, polypeptides of the disclosure are not only designed based on parental HA sequences from influenza vaccine virus subtypes of group 1 (such as, e.g., H1 and H5), but can also be based on HA sequences of influenza subtypes from group 2, in particular influenza virus subtypes of group 2 that are used for influenza vaccines, such as H3. According to the disclosure, polypeptides were constructed that conserve the epitope of CR8020 and CR8043 because these antibodies are capable of neutralizing a wide range of group 2 strains (WO 2010/130636). In these polypeptides, the beta-sheet at the bottom of the stem region and its surroundings should be as conserved as possible since this is the region where CR8020 and CR8043 bind to H3 HA.

In certain embodiments, the HA domains are of a H3 subtype, preferably of A/Wisconsin/67/2005 (SEQ ID NO: 89), or A/Hong Kong/1/1968 (SEQ ID NO: 121). It will be understood by the skilled person that also other influenza A viruses comprising HA of the H3 subtype may be used according to the disclosure.

In certain embodiments, the polypeptides comprise, or consist of, a HA1 N-terminal polypeptide segment comprising the amino acids from position 1 to position x of the H3 HA1 domain, preferably the amino acids from position p to position x of the HA1 domain, wherein x is any amino acid between the positions 56 and 69, such as 57, 58, 59, 60, 61, 62, 63, 64, 65, 66, 67 or 68, of H3 HAL preferably wherein x is 61, 62, 63 or 68. In certain embodiments, the HA1 C-terminal polypeptide segment comprises the amino acids from position y to and including the C-terminal amino acid of the H3 HA1 domain, wherein y is any amino acid between and including the positions 292 and 325, of H3 HAL preferably wherein y is 293, 306, 318 or 323.

In certain embodiments, the HA domains are of a H3 subtype, preferably A/Wisconsin/67/2005 (SEQ ID NO: 89), or A/Hong Kong/1/1968 (SEQ ID NO: 121).

The head domain may be removed by deleting a large part of the HA1 sequence and reconnecting the N- and C-terminal sequences through a short linker. The deletion can vary in length, but it is preferred that the last residue of the N-terminal sequence of HA1 and the first residue of the C-terminal sequence are spatially close together to avoid introducing strain through the linking sequence. In H3 sequence deletions can be introduced at (the equivalent positions of) S62-P322, S63-P305 and T64-T317. Equivalent positions can be easily determined by those skilled in the art by aligning the sequences using a suitable algorithm such as, e.g., Clustal or Muscle. The remaining parts of the sequence can be joined directly or alternatively a flexible linker can be introduced. Linker sequences can be 1 to 50, amino acids in length. Preferred are flexible linkers of limited length (smaller or equal to 10 amino acids), e.g., GGG, GGGG (SEQ ID NO: 194), GSA, GSAG (SEQ ID NO: 193), GSAGSA (SEQ ID NO: 189), GSAGSAG (SEQ ID NO: 188) or similar. The length of the deletion can also be varied, e.g., by decreasing the number of residues in the deletion by starting at (the equivalent of) position 63, 64, 65, 66, 67, or to increase the length of the deletion, by cutting at position 57, 58, 59, 60 or 61. Similarly, the last amino acid to be deleted can be at (the equivalent of) position 317, 318, 319, 320 or 321, or to increase the length of the deletion at (the equivalent of) position 323, 324, 325, 326, or 327. It is important to realize that changes in the length of the deletion can be in part compensated for by matching the length of the linker sequence, i.e., a larger deletion can be matched with a longer linker and vice versa. These polypeptides are also included in the disclosure.

In certain embodiments, x is 61 and y is 323.

In certain embodiments, x is 62 and y is 306.

In certain embodiments, x is 63 and y is 318.

In certain embodiments, x is (the equivalent of) position 62, 63, 64, 65, 66, or position 56, 57, 58, 59 or 60.

In certain embodiments, y is (the equivalent of) position 306, 318, 319, 320, 321 or 322, or (the equivalent of) position 324, 325, 326, 327, or 328.

In an embodiment, the amino acid sequence connecting the C-terminal residue of helix A to the N-terminal residue of helix CD corresponds to the amino acid sequence between the amino acid on position 400 and the amino acid on position 420 of HA2 of SEQ ID NO: 89, or the amino acid residues on equivalent positions in other H3 virus strains, wherein the polypeptides comprise one or more mutations in the amino acid sequence connecting the C-terminal residue of helix A to the N-terminal residue of helix CD, i.e., the amino acid sequence spanning from amino acid 400-420 of SEQ ID NO: 89, or equivalent amino acid residues in other H3 influenza virus strains.

In certain embodiments, the amino acid sequence connecting the C-terminal residue of helix A to the N-terminal residue of helix CD of influenza HA of serotype H3 comprises the amino acid sequence of SEQ ID NO: 104.

The polypeptides comprise one or more mutations in the amino acid sequence connecting the C-terminal residue of helix A to the N-terminal residue of helix CD. In certain embodiments, the polypeptides comprise one or more mutations of Table 8, or equivalent mutations in other influenza virus strains of the H3 subtype.

The cleavage site between HA1 and HA2 has been removed. In certain embodiments, the removal of the cleavage site at position 345 (numbering refers to SEQ ID NO: 89) has been mutated (R345Q) to prevent the formation of HA1 and HA2 from HA0. Optionally, residue 347 to 351 (IFGAI, part of the fusion peptide) can additionally be deleted to minimize the exposure of hydrophobic residues to the aqueous solvent. The positive charge at the cleavage is 100% conserved in H3 and this mutation can, therefore, be applied in all sequences.

The deletion of the head domain leaves the B-loop between residues 400 to 420 now exposed to the aqueous solvent. In H3 HAs this loop is highly conserved (see Table 9). The consensus sequence is: 401 I(E/G)KTNEKFHQ-IEKEFSEVEGR 421 (SEQ ID NO: 104; numbering refers to SEQ ID NO: 89). To increase the solubility of this loop for the polypeptides hereof in the pre-fusion conformation and destabilize the post-fusion conformation, some hydrophobic residues have to be modified into polar (S, T, N, Q), charged amino acids (R, H, K, D, E), or flexibility has to be increased by mutation to G. Specifically mutations at positions 401, 408, 411, 415, 418, (numbering refers to SEQ ID NO: 89) will contribute to the stability of a polypeptide of the disclosure.

To stabilize the pre-fusion conformation of polypeptides of the disclosure, a covalent bond between two parts distant in the primary sequences but close in the folded pre-fusion conformation is introduced. To this end, a disulfide bridge may be engineered in the polypeptides hereof, preferably between (the equivalent of) position 326 and 438 in H3 A/Wisconsin/67/2005 (SEQ ID NO: 89). Equivalent positions can be easily determined by those skilled in the art by aligning the sequences using a suitable algorithm such as Clustal, Muscle etc. Engineered disulfide bridges are created by mutating at least one (if the other is already a cysteine), but usually two residues that are spatially close into cysteine, that will spontaneously or by active oxidation form a covalent bond between the sulfur atoms of these residues. An alternative cysteine bridge can be created between (the equivalent of) position 334 and 393 in H3 A/Wisconsin/67/2005 (SEQ ID NO: 89) by mutation of these residues into cysteine. In some cases the cysteine at (the equivalent of) position 321 is modified into a glycine to avoid formation of unwanted disulfide bridges.

In certain embodiments, the polypeptides comprise one or more of the following mutations: F408S, I411T, F415S, V418G, I401R, K326C, S438C, T334C, I393C, C321G.

The native HA exists as a trimer on the cell surface. Most of the interactions between the individual monomers that keep the trimer together are located in the head domain. After removal of the head the tertiary structure is thus destabilized and, therefore, reinforcing the interactions between the monomers in the truncated molecule will increase the stability. In the stem domain trimerization is mediated by the formation of a trimeric coiled coil motif. By strengthening this motif a more stable trimer can be created. A consensus sequence for the formation of a trimeric coiled coil, IEAIEKKIEAIEKKIEAIEKK (SEQ ID NO: 198), is introduced at (the equivalent of) position 421 to 441. To avoid interference with the formation of the disulfide bridge between positions 326 and 438 an alternative shorter sequence IEAIEKKIEAIEKKI (SEQ ID NO: 199) at (the equivalent of) positions 421 to 435 was also used. An alternative is to introduce the sequence RMKQIEDKIEE-IESKQKKIEN (SEQ ID NO: 200), derived from GCN4 and known to trimerize, at position 421-441 or the shorter sequence RMKQIEDKIEEIESK (SEQ ID NO: 201) at position 421 to 435.

The polypeptides hereof may contain the intracellular sequences of HA and the transmembrane domain so that the resulting polypeptides are presented on the cell surface when expressed in cells. In other embodiments, the cytoplasmic sequence and the transmembrane sequence from (the equivalent of) position 522 to the C-terminus is removed so that a secreted (soluble) polypeptide is produced following expression in cells. Optionally, some additional residues can be included in the soluble protein by deleting the sequence from (the equivalent of) 523, 524, 525, 526, 527, 528 or 529. The soluble polypeptide can be further stabilized by introducing a sequence known to form trimeric structures, i.e., AYVRKDGEWVLL (SEQ ID NO: 143) ("foldon" sequence), optionally connected through a linker. The linker may optionally contain a cleavage site for processing afterwards according to protocols well known to those skilled in the art. To facilitate purification of the soluble form a tag sequence may be added, e.g., a his-tag (HHHHHHH (SEQ ID NO: 191)) connected via a short linker, e.g., EGR. In some embodiments, the linker and his-tag sequence are added without the foldon sequence being present.

According to the disclosure, the amino acid sequence from position 530 (numbering according to SEQ ID NO: 1) to the C-terminal amino acid of the HA2 domain may be removed and replaced by the following sequences: EGRHHHHHHH (SEQ ID NO: 81), or SGRSLVPRGSPGSGYIPEAPRDGQAYVRKDGEWVLLSTFLGHHHHHHH (SEQ ID NO: 82).

In certain embodiments, the HA1 N-terminal stem segment does not comprise the signal sequence. It will be understood by the skilled person that the leader sequence (or signal sequence) that directs transport of a protein during production (e.g., corresponding to amino acids 1-17 of SEQ ID NO: 89), generally will not be present in the final polypeptide, that is, e.g., used in a vaccine. In certain embodiments, the polypeptides according to the disclosure thus comprise an amino acid sequence without the leader sequence.

According to the disclosure, the polypeptides are not based on HA molecules of Influenza B. The influenza type B virus strains are strictly human. The antigenic variation in HA within the influenza type B virus strains is smaller than those observed within the type A strains. Two genetically and antigenically distinct lineages of influenza B virus are circulating in humans, as represented by the B/Yamagata/16/88 (also referred to as B/Yamagata) and B/Victoria/2/87 (B/Victoria) lineages (Ferguson et al., 2003). Although the spectrum of disease caused by influenza B viruses is generally milder than that caused by influenza A viruses, severe illness requiring hospitalization is still frequently observed with influenza B infection.

Polypeptides are provided herein that mimic the specific epitopes of CR6261 and CR9114, and that can be used as immunogenic polypeptides, e.g., to elicit cross-neutralizing antibodies when administered in vivo, either alone, or in combination with other prophylactic and/or therapeutic treatments. With "cross-neutralizing antibodies," antibodies are meant that are capable of neutralizing at least two, preferably at least three, four, or five different subtypes of influenza A viruses of phylogenetic group 1, and/or at least two, preferably at least three, four, or five different subtypes of influenza A viruses of phylogenetic group 2, and/or at least two, different subtypes of influenza B viruses, in particular at least all virus strains that are neutralized by CR6261 and CR9114.

The polypeptides hereof do not comprise the full-length HA1. In certain embodiments, the immunogenic polypeptides are substantially smaller than HA0, preferably lacking all or substantially all of the globular head of HA. Preferably, the immunogenic polypeptides are no more than 360, preferably no more than 350, 340, 330, 320, 310, 305, 300, 295, 290, 285, 280, 275, or 270 amino acids in length. In an embodiment, the immunogenic polypeptide is from about 250 to about 350, preferably from about 260 to about 340, preferably from about 270 to about 330, preferably from about 270 to about 330 amino acids in length.

In certain embodiments, the polypeptides selectively bind to the antibodies CR6261 and/or CR9114. In an embodiment, the polypeptide does not bind to the antibody CR8057. In an embodiment, CR6261 comprises a heavy chain variable region comprising the amino acid sequence of SEQ ID NO: 20 and a light chain variable region comprising the amino acid sequence of SEQ ID NO: 21; CR9114 comprises a heavy chain variable region comprising the amino acid sequence of SEQ ID NO: 18 and a light chain variable region comprising the amino acid sequence of SEQ ID NO: 19. In an embodiment, CR8057 comprises a heavy chain variable region comprising the amino acid sequence of SEQ ID NO: 22 and a light chain variable region comprising the amino acid sequence of SEQ ID NO: 23.

As described above, the polypeptides comprise an influenza hemagglutinin HA1 domain that comprises an HA1 N-terminal stem segment that is covalently linked by a linking sequence of 0-50 amino acid residues to the HA1 C-terminal stem segment. The linking sequence does not occur in naturally occurring, or wild-type, HA. In certain embodiments, the linker is a peptide that comprises one amino acid residue, two or less amino acid residues, three or less amino acid residues, four or less amino acid residues, five or less amino acid residues, ten or less amino acid residues, 15 or less amino acid residues, or 20 or less amino acid residues or 30 or less amino acid residues or 40 or less amino acid residues or 50 or less amino acid residues. In a specific embodiment, the linking sequence is a sequence selected from the group consisting of G, GS, GGG, GSG, GSA, GSGS (SEQ ID NO: 192), GSAG (SEQ ID NO: 193), GGGG (SEQ ID NO: 194), GSAGS (SEQ ID NO: 195), GSGSG (SEQ ID NO: 196), GSAGSA (SEQ ID NO: 189), GSAGSAG (SEQ ID NO: 188), and GSGSGSG (SEQ ID NO: 197).

Also provided are methods to provide the polypeptides, in particular, to provide the amino acid sequence of the HA stem domain polypeptide according to the disclosure, as well as the polypeptides obtainable or obtained by these methods. In certain embodiments, the methods comprise the steps of:

- Providing an influenza HA0 amino acid sequence, e.g., an influenza HA0 sequence of serotype H1, H5 or H3;
- Removing the cleavage site between HA1 and HA2, preferably by mutating the C-terminal amino acid of HA1 into an amino acid other that arginine (R) or lysine (K);
- Removing the amino acid sequence of the globular head domain from the HA0 sequence; This is done by deleting a segment of the HA1 domain between amino acid on position x and an amino acid on position y, and reconnecting the N-terminal segment (spanning from amino acid on position 1 to and including amino acid on position x of HA1) and the C-terminal segment of HA1 (spanning from amino acid y to the C-terminal amino acid of HA1), thus obtained, optionally through a linking sequence of 0-50 amino acids.
- Increasing the stability of the pre-fusion conformation and destabilizing the post-fusion conformation of the modified HA, preferably by introducing one or more mutations in the amino acid sequence connecting the C-terminal residue of helix A to the N-terminal residue of helix CD, preferably in the amino acid sequence spanning from amino acid 402-418 of H1 HA, in particular comprising the amino acid sequence of MNTQFTAVGKEFN(H/K)LE(K/R) (SEQ ID NO: 17) or I(E/G)KTNEKFHQIEKEFSEVEGR 421 (SEQ ID NO: 104) for H3 HA. The mutations preferably comprise the substitution of hydrophobic amino acid residues into hydrophilic amino acid residues.
- Introducing one or more disulfide bridges in the HA stem domain polypeptide.

Removal of the cleavage site between HA1 and HA2 can be achieved by mutation of R (in a small number of cases K) to Q at the P1 position (see, e.g., Sun et al., 2010, for an explanation of the nomenclature of the cleavage site (position 343 in SEQ ID NO: 1). A mutation to Q is preferred but S, T, N, D or E are alternatives.

Removal of the head domain can be achieved, e.g., by deleting amino acids 53 to 320 from SEQ ID NO: 1. Equivalent positions can be easily determined by those skilled in the art by aligning the sequences using a suitable algorithm such as, e.g., Clustal or Muscle. The remaining parts of the sequence can be joined directly, or alternatively a flexible linker can be introduced. Linker sequences can be 1 to 50 amino acids in length. Preferred are flexible linkers of limited length (smaller or equal to 10 amino acids), e.g., GGG, GGGG (SEQ ID NO: 194), GSA, GSAG (SEQ ID NO: 193), GSAGSA (SEQ ID NO: 189), GSAGSAG (SEQ ID NO: 188) or similar. The length of the deletion can also be varied, e.g., by starting the deletion at (the equivalent of) position (x), e.g., at position 54, 55, 56, 57 or 58, or to increase the length of the deletion, by cutting at position 47, 48, 49, 50, 51, or 52. Similarly, the last amino acid to be deleted can be at (the equivalent of) position (y), such as 315, 316, 317, 318 or 319, or to increase the length of the deletion at (the equivalent of) position 321, 322, 323, 324, or 325. It is important to realize that changes in the length of the deletion can be in part compensated for by matching the length of the linker sequence, i.e., a larger deletion can be matched with a longer linker and vice versa. These polypeptides are also encompassed by the disclosure.

According to the disclosure, the solubility of the loop between the A-helix and the CD helix is increased. This loop is formed by (the equivalent of) residues 402 to 418 in H1 A/Brisbane/59/2007 (SEQ ID NO: 1). Thus, the stability of the pre-fusion conformation is increased and the post-fusion conformation of the modified HA is destabilized. This loop is highly conserved in H1 sequences, as can be seen in Table 6 below. This can, for example, be achieved by replacing the amino acids I, L, F or V in the loop with hydrophilic counterparts. Equivalent position can be easily determined by those skilled in the art by aligning the sequences using a suitable algorithm such as, e.g., Clustal or Muscle. Mutations to glycine destabilize the post-fusion conformation since the high flexibility of this amino acid leads to a decrease in stability of the post-fusion helix to be formed by this part of the HA sequence. The consensus sequence describing the loop between residue 402-418 of influenza HA of serotype H1 is (SEQ ID NO: 17) MNTQFTAVG-KEFN(H/K)LE(K/R). In certain polypeptides of the disclosure, the amino acid at positions 406, 409, 413 and/or 416 (or their equivalent, as determined from a sequence alignment) is a polar (S, T, N, Q), charged (R, H, K, D, E) or flexible (G) amino acid. Combinations of mutations at these sites are also possible, for example, F406S, V409T, L416S as in SEQ ID NO: 10 and SEQ ID NO: 14. In some cases a mutation to restore the consensus amino acid is preferred, e.g., where V or M is at position 404 (to T), V at 408 (to A) or 410 (to G) or I at 414 (to N); the incidence of sequences with these particular amino acids is very low. An overview of the mutations described above that characterize polypeptides of the disclosure is given in Table 6.

According to the disclosure, one or more disulfide bridges are introduced in the stem domain polypeptides, preferably between amino acids of (or the equivalent of) position 324 and 436 in H1 A/Brisbane/59/2007: SEQ ID NOs: 13-16. Equivalent positions can be easily determined by those skilled in the art by aligning the sequences using a suitable algorithm such as Clustal, Muscle, etc. Engineered disulfide bridges are created by mutating at least one (if the other is already a cysteine), but usually two residues that are spatially close into cysteine, that will spontaneously or by active oxidation form a covalent bond between the sulfur atoms of these residues.

Polypeptides obtainable by the method are also part of the disclosure.

The native HA exists as a trimer on the cell surface. Most of the interactions between the individual monomers that keep the trimer together are located in the head domain. After removal of the head the tertiary structure is thus destabilized and, therefore, reinforcing the interactions between the monomers in the truncated molecule will increase the stability. In the stem domain trimerization is mediated by the formation of a trimeric coiled coil motif. By strengthening this motif a more stable trimer can be created. According to the disclosure, a consensus sequence for the formation of a trimeric coiled coil, IEAIEKKIEAIEKKIE (SEQ ID NO: 83), may be introduced in a polypeptide of the disclosure at (the equivalent of) position 418 to 433. In certain embodiments, the sequence MKQIEDKIEEIESKQ (SEQ ID NO: 84), derived from GCN4 and known to trimerize is introduced at (the equivalent of) position 419-43. In certain embodiments, the trimer interface is stabilized by modifying M420, L423, V427, G430 into Isoleucine.

In certain embodiments, the polypeptides comprise an amino acid sequence selected from the group consisting of SEQ ID NO: 3-16, SEQ ID NO: 44-53, SEQ ID NO: 111-114, SEQ ID NO: 119-120, SEQ ID NO: 125, 126, 130, SEQ ID NO: 144-175 and SEQ ID NO: 177-187.

In certain embodiments, the polypeptides are selected from the group consisting of SEQ ID NO: 45, SEQ ID NO: 113 and SEQ ID NO: 130.

It will be understood by the skilled person that the leader sequence (or signal sequence) that directs transport of a protein during production (e.g., corresponding to amino acids 1-17 of SEQ ID NO: 1), is not present in the final polypeptide, that is, e.g., used in a vaccine. In certain embodiments, the polypeptides according to the disclosure thus comprise an amino acid sequence without the leader sequence.

The influenza hemagglutinin stem domain polypeptides can be prepared according to any technique deemed suitable to one of skill, including techniques described below.

Thus, the immunogenic polypeptides of the disclosure may be synthesized as DNA sequences by standard methods known in the art and cloned and subsequently expressed, in vitro or in vivo, using suitable restriction enzymes and methods known in the art. The disclosure thus also relates to nucleic acid molecules encoding the above described polypeptides. The disclosure further relates to vectors comprising the nucleic acids encoding the polypeptides hereof. In certain embodiments, a nucleic acid molecule according to the disclosure is part of a vector, e.g., a plasmid. Such vectors can easily be manipulated by methods well known to the person skilled in the art, and can, for instance, be designed for being capable of replication in prokaryotic and/or eukaryotic cells. In addition, many vectors can directly or in the form of an isolated desired fragment there from be used for transformation of eukaryotic cells and will integrate in whole or in part into the genome of such cells, resulting in stable host cells comprising the desired nucleic acid in their genome. The vector used can be any vector that is suitable for cloning DNA and that can be used for transcription of a nucleic acid of interest. When host cells are used it is preferred that the vector is an integrating vector. Alternatively, the vector may be an episomally replicating vector.

The person skilled in the art is capable of choosing suitable expression vectors, and inserting the nucleic acid sequences of the disclosure in a functional manner. To obtain expression of nucleic acid sequences encoding polypeptides, it is well known to those skilled in the art that sequences capable of driving expression can be functionally linked to the nucleic acid sequences encoding the polypeptide, resulting in recombinant nucleic acid molecules encoding a protein or polypeptide in expressible format. In general, the promoter sequence is placed upstream of the sequences that should be expressed. Many expression vectors are available in the art, e.g., the pcDNA and pEF vector series of Invitrogen, pMSCV and pTK-Hyg from BD Sciences, pCMV-Script from Stratagene, etc., which can be used to obtain suitable promoters and/or transcription terminator sequences, polyA sequences, and the like. Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. The person skilled in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000). Some well-known and much used promoters for expression in eukaryotic cells comprise promoters derived from viruses, such as adenovirus, e.g., the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (Das et al., 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001), actin promoter, an immunoglobulin promoter, heat shock promoters, and the like. Testing for promoter function and strength of a promoter is a matter of routine for a person skilled in the art, and in general may for instance encompass cloning a test gene such as lacZ, luciferase, GFP, etc., behind the promoter sequence, and test for expression of the test gene. Of course, promoters may be altered by deletion, addition, mutation of sequences therein, and tested for functionality, to find new, attenuated, or improved promoter sequences. According to the disclosure, strong promoters that give high transcription levels in the eukaryotic cells of choice are preferred.

The constructs may be transfected into eukaryotic cells (e.g., plant, fungal, yeast or animal cells) or suitable prokaryotic expression systems like *E. coli* using methods that are well known to persons skilled in the art. In some cases, a suitable "tag" sequence (such as, for example, but not limited to, a his-, myc-, strep-, or flag-tag) or complete protein (such as, for example, but not limited to, maltose binding protein or glutathione S transferase) may be added to the sequences of the disclosure to allow for purification and/or identification of the polypeptides from the cells or supernatant. Optionally, a sequence containing a specific proteolytic site can be included to afterwards remove the tag by proteolytic digestion.

Purified polypeptides can be analyzed by spectroscopic methods known in the art (e.g., circular dichroism spectroscopy, Fourier Transform Infrared spectroscopy and NMR spectroscopy or X-ray crystallography) to investigate the presence of desired structures like helices and beta sheets. ELISA, Octet and FACS and the like can be used to investigate binding of the polypeptides hereof to the broadly neutralizing antibodies described before (CR6261, CR9114, CR8057). Thus, polypeptides according to the disclosure having the correct conformation can be selected.

The disclosure further relates to immunogenic compositions comprising a therapeutically effective amount of at least one of the polypeptides and/or nucleic acids of the disclosure. In certain embodiments, the compositions comprise polypeptides comprising hemagglutinin stem domains from (or based on) HA of one influenza subtype, e.g., based on HA of an influenza virus comprising HA of, e.g., a H1 or H7 subtype. In certain embodiments, the compositions comprise polypeptides comprising hemagglutinin stem domains based on HA of two or more different influenza subtypes, e.g., compositions comprising both polypeptides comprising hemagglutinin stem domains based on HA of the H1 subtype and polypeptides comprising hemagglutinin stem domains based on HA of the H7 subtype.

The immunogenic compositions preferably further comprise a pharmaceutically acceptable carrier. In the present context, the term "pharmaceutically acceptable" means that the carrier, at the dosages and concentrations employed, will not cause unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)). The term "carrier" refers to a diluent, adjuvant, excipient, or vehicle with which the composition is administered. Saline solutions and aqueous dextrose and glycerol solutions can, e.g., be employed as liquid carriers, particularly for injectable solutions. The exact formulation should suit the mode of administration. The polypeptides and/or nucleic acid molecules preferably are formulated and administered as a sterile solution. Sterile solutions are prepared by sterile filtration or by other methods known per se in the art. The solutions can then be lyophilized or filled into pharmaceutical dosage containers. The pH of the solution generally is in the range of pH 3.0 to 9.5, e.g., pH 5.0 to 7.5.

The disclosure also relates to methods for inducing an immune response in a subject, the method comprising administering to a subject, a polypeptide, nucleic acid molecule and/or immunogenic composition as described above. A subject according to the disclosure preferably is a mammal that is capable of being infected with an infectious disease-causing agent, in particular an influenza virus, or otherwise can benefit from the induction of an immune response, such subject for instance being a rodent, e.g., a mouse, a ferret, or a domestic or farm animal, or a non-human-primate, or a human. Preferably, the subject is a human subject. The disclosure thus provides methods for inducing an immune response to an influenza virus hemagglutinin (HA), in particular of a group 1 and/or group 2 influenza A virus, such as an influenza virus comprising HA of the H1, H2, H3, H4, H5, H7 and/or H10 subtype, and/or of an influenza B virus, in a subject utilizing the polypeptides, nucleic acids and/or immunogenic compositions described herein. In some embodiments, the immune response induced is effective to prevent and/or treat an influenza virus infection caused group 1 and/or group 2 influenza A virus subtypes and/or influenza B viruses. In some embodiments, the immune response induced by the polypeptides, nucleic acids and/or immunogenic compositions described herein is effective to prevent and/or treat an influenza A and/or B virus infection caused by two, three, four, five or six subtypes of influenza A and/or B viruses.

Since it is well known that small proteins and/or nucleic acid molecules do not always efficiently induce a potent immune response it may be necessary to increase the immunogenicity of the polypeptides and/or nucleic acid molecules by adding an adjuvant. In certain embodiments, the immunogenic compositions described herein comprise, or are administered in combination with, an adjuvant. The adjuvant for administration in combination with a composition described herein may be administered before, concomitantly with, or after administration of the composition. Examples of suitable adjuvants include aluminium salts such as aluminium hydroxide and/or aluminium phosphate; oil-emulsion compositions (or oil-in-water compositions), including squalene-water emulsions, such as MF59 (see, e.g., WO 90/14837); saponin formulations, such as, for example, QS21 and Immunostimulating Complexes (ISCOMS) (see, e.g., U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, pertussis toxin PT, or tetanus toxoid TT, Matrix M (Isconova). In addition, known immunopotentiating technologies may be used, such as fusing the polypeptides hereof to proteins known in the art to enhance immune response (e.g., tetanus toxoid, CRM197, rCTB, bacterial flagellins or others) or including the polypeptides in virosomes, or combinations thereof. Other non-limiting examples that can be used are, e.g., disclosed by Coffman et al. (2010).

In one embodiment, the influenza hemagglutinin stem domain polypeptides of the disclosure are incorporated into viral-like particle (VLP) vectors. VLPs generally comprise a viral polypeptide(s) typically derived from a structural protein(s) of a virus. Preferably, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art.

In a specific embodiment, the polypeptide is incorporated into a virosome. A virosome containing a polypeptide according to the disclosure may be produced using techniques known to those skilled in the art. For example, a virosome may be produced by disrupting a purified virus, extracting the genome, and reassembling particles with the viral proteins (e.g., an influenza hemagglutinin stem domain polypeptide) and lipids to form lipid particles containing viral proteins.

The disclosure also relates to the above-described polypeptides, nucleic acids and/or immunogenic compositions for inducing an immune response in a subject against influenza HA, in particular for use as a vaccine. The influenza hemagglutinin stem domain polypeptides, nucleic acids encoding such polypeptides, or vectors comprising such nucleic acids or polypeptides described herein thus may be used to elicit neutralizing antibodies against influenza viruses, for example, against the stem region of influenza virus hemagglutinin. The disclosure in particular relates to polypeptides, nucleic acids, and/or immunogenic compositions as described above for use as a vaccine in the prevention and/or treatment of a disease or condition caused by an influenza A virus of phylogenetic group 1 and/or phylogenetic group 2 and/or an influenza B virus. In an embodiment, the vaccine may be used in the prevention and/or treatment of diseases caused by two, three, four, five, six or more different subtypes of phylogenetic group 1 and/or 2 and/or influenza B viruses. The polypeptides hereof may be used after synthesis in vitro or in a suitable cellular expression system, including bacterial and eukaryotic cells, or alternatively, may be expressed in vivo in a subject in need thereof, by expressing a nucleic acid coding for the immunogenic polypeptide. Such nucleic acid vaccines may take any form, including naked DNA, plasmids, or viral vectors including adenoviral vectors.

Administration of the polypeptides, nucleic acid molecules, and/or immunogenic compositions according to the disclosure can be performed using standard routes of administration. Non-limiting examples include parenteral administration, such as intravenous, intradermal, transdermal, intramuscular, subcutaneous, etc., or mucosal administration, e.g., intranasal, oral, and the like. The skilled person will be capable to determine the various possibilities to administer the polypeptides, nucleic acid molecules, and/or immunogenic compositions according to the disclosure, in order to induce an immune response. In certain embodiments, the polypeptide, nucleic acid molecule, and/or immunogenic composition (or vaccine) is administered more than one time, i.e., in a so-called homologous prime-boost regimen. In certain embodiments where the polypeptide, nucleic acid molecule, and/or immunogenic composition is administered more than once, the administration of the second dose can be performed after a time interval of, for example, one week or more after the administration of the first dose, two weeks or more after the administration of the first dose, three weeks or more after the administration of the first dose, one month or more after the administration of the first dose, six weeks or more after the administration of the first dose, two months or more after the administration of the first dose, 3 months or more after the administration of the first dose, 4 months or more after the administration of the first dose, etc., up to several years after the administration of the first dose of the polypeptide, nucleic acid molecule, and/or immunogenic composition. It is also possible to administer the vaccine more than twice, e.g., three times, four times, etc., so that the first priming administration is followed by more than one boosting administration. In other embodiments, the polypeptide, nucleic acid molecule, and/or immunogenic composition according to the disclosure is administered only once.

The polypeptides, nucleic acid molecules, and/or immunogenic compositions may also be administered, either as prime, or as boost, in a heterologous prime-boost regimen.

Further provided are methods for preventing and/or treating an influenza virus disease in a subject utilizing the polypeptides, nucleic acids and/or compositions described herein. In a specific embodiment, a method for preventing and/or treating an influenza virus disease in a subject comprises administering to a subject in need thereof an effective amount of a polypeptide, nucleic acid and/or immunogenic composition, as described above. A therapeutically effective amount refers to an amount of the polypeptide, nucleic acid, and/or composition as defined herein, that is effective for preventing, ameliorating and/or treating a disease or condition resulting from infection by a group 1 or 2 influenza A virus, and/or an influenza B virus. Prevention encompasses inhibiting or reducing the spread of influenza virus or inhibiting or reducing the onset, development or progression of one or more of the symptoms associated with infection by an influenza virus. "Amelioration" as used in herein may refer to the reduction of visible or perceptible disease symptoms, viremia, or any other measurable manifestation of influenza infection.

Those in need of treatment include those already inflicted with a condition resulting from infection with a group 1 or a group 2 influenza A virus, or an influenza B virus, as well as those in which infection with influenza virus is to be prevented. The polypeptides, nucleic acids and/or compositions of the disclosure thus may be administered to a naive subject, i.e., a subject that does not have a disease caused by influenza virus infection or has not been and is not currently infected with an influenza virus infection, or to subjects that already are and/or have been infected with an influenza virus.

In an embodiment, prevention and/or treatment may be targeted at patient groups that are susceptible to influenza virus infection. Such patient groups include, but are not limited to e.g., the elderly (e.g., ≥50 years old, ≥60 years old, and preferably ≥65 years old), the young (e.g., ≤5 years old, ≤1 year old), hospitalized patients and patients who have been treated with an antiviral compound but have shown an inadequate antiviral response.

In another embodiment, the polypeptides, nucleic acids and/or immunogenic compositions may be administered to a subject in combination with one or more other active agents, such as existing, or future influenza vaccines, monoclonal antibodies and/or antiviral agents, and/or antibacterial, and/or immunomodulatory agents. The one or more other active agents may be beneficial in the treatment and/or prevention of an influenza virus disease or may ameliorate a symptom or condition associated with an influenza virus disease. In some embodiments, the one or more other active agents are pain relievers, anti-fever medications, or therapies that alleviate or assist with breathing.

Dosage regimens of the polypeptides and/or nucleic acid molecules of the disclosure can be adjusted to provide the optimum desired response (e.g., a therapeutic response). A suitable dosage range may for instance be 0.1-100 mg/kg body weight, preferably 1-50 mg/kg body weight, preferably 0.5-15 mg/kg body weight. The precise dosage of the polypeptides and/or nucleic acid molecules to be employed will, e.g., depend on the route of administration, and the seriousness of the infection or disease caused by it, and should be decided according to the judgment of the practitioner and each subject's circumstances. For example, effective doses vary depending target site, physiological state of the patient (including age, body weight, health), and whether treatment is prophylactic or therapeutic. Usually, the patient is a human but non-human mammals including transgenic mammals can also be treated. Treatment dosages are optimally titrated to optimize safety and efficacy.

The polypeptides hereof may also be used to verify binding of monoclonal antibodies identified as potential therapeutic candidates. In addition, the polypeptides hereof may be used as diagnostic tool, for example, to test the immune status of an individual by establishing whether there are antibodies in the serum of such individual capable of binding to the polypeptide of the disclosure. The disclosure thus also relates to an in vitro diagnostic method for detecting the presence of an influenza infection in a patient, the method comprising the steps of a) contacting a biological sample obtained from the patient with a polypeptide according to the disclosure; and b) detecting the presence of antibody-antigen complexes.

The polypeptides hereof may also be used to identify new binding molecules or improve existing binding molecules, such as monoclonal antibodies and antiviral agents.

The disclosure is further illustrated in the following Examples and Figures. The Examples are not intended to limit the scope of the disclosure in any way.

EXAMPLES

Example 1: Identification of a Novel Group 1 and Group 2 Cross-Neutralizing Antibody: CR9114

Peripheral blood was collected from normal healthy donors by venapuncture in EDTA anti-coagulation sample tubes. scFv phage display libraries were obtained essentially as described in WO 2008/028946, which is incorporated by reference herein. Selection was performed against recombinant hemagglutinin (HA) of influenza A subtype H1 (A/New Caledonia/20/99), H3 (A/Wisconsin/67/2005), H4 (A/Duck/Hong Kong/24/1976), H5 (A/Chicken/Vietnam/28/2003), H7 (A/Netherlands/219/2003) and H9 (A/Hong Kong/1073/99). Two consecutive rounds of selections were performed before isolation of individual single-chain phage antibodies. After the second round of selection, individual *E. coli* colonies were used to prepare monoclonal phage antibodies. Selected supernatants containing single-chain phage antibodies that were obtained in the screenings described above were validated in ELISA for specificity, i.e., binding to different HA antigens. For this purpose, baculovirus expressed recombinant H1 (A/New Caledonia/20/99), H3 (A/Wisconsin/67/2005), H5 (A/Vietnam/1203/04) H7 (A/Netherlands/219/2003), and B (B/Ohio/01/2005) HAs (Protein Sciences, CT, USA) were coated to MAXISORP™ ELISA plates. Of the single-chain phage antibodies that were obtained, single-chain phage antibody SC09-114 was shown to specifically bind recombinant influenza A H1, H3, H5, H7 and influenza B HA. Binding and specificity of SC09-114 was validated by FACS analysis. For this purpose, full-length recombinant influenza A subtypes H1 (A/New Caledonia/20/1999), H3 (A/Wisconsin/67/2005) and H7 (A/Netherlands/219/2003) HAs were expressed on the surface of PER.C6® cells. SC09-114 was shown to specifically bind to influenza A subtypes H1, H3 and H7 HA. Heavy and light chain variable regions of the scFv were cloned as described before (WO 2008/028946). The resulting expression constructs encoding the human IgG1 heavy and light chains were transiently expressed in combination in 293T cells and supernatants containing the human IgG1 antibody CR9114 were obtained and produced using standard purification procedures. The amino acid sequence of the CDRs of the heavy and light chains of CR9114 are given in Table 1. The nucleotide and amino acid sequences and of the heavy and light chain variable regions are given below.

Example 2: Cross-Binding Reactivity of CR9114

CR9114 was validated in ELISA for binding specificity, i.e., binding to different HA antigens. For this purpose, baculovirus expressed recombinant H1 (A/New Caledonia/

20/1999), H3 (A/Wisconsin/67/2005), H5 (A/Vietnam/1203/04, H7 (A/Netherlands/219/2003) and H9 (A/Hong Kong/1073/99) HAs (Protein Sciences, CT, USA) were coated to MAXISORP™ ELISA plates. As a control, an unrelated IgG CR4098 was used. CR114 was shown to have heterosubtypic cross-binding activity to all the recombinant HAs tested. See Table 2.

Additionally, the antibody was tested for heterosubtypic binding by FACS analysis. For this purpose, full-length recombinant influenza A subtypes H1 (A/New Caledonia/20/1999), H3 (A/Wisconsin/67/2005) and H7 (A/Netherlands/219/2003) HAs were expressed on the surface of PER.C6® cells. The cells were incubated with CR9114 for 1 hour followed by three wash steps with PBS+0.1% BSA. Bound antibody was detected using PE conjugated anti-human antibody. As a control, untransfected PER.C6® cells were used. CR9114 showed cross-binding activity to influenza A subtypes H1, H3 and H7 HA but not wild-type PER.C6® cells. See Table 2.

Example 3: Cross-Neutralizing Activity of CR9114

In order to determine whether CR9114 was capable of blocking multiple influenza A strains, additional in vitro virus neutralization assays (VNA) were performed. The VNA were performed on MDCK cells (ATCC CCL-34). MDCK cells were cultured in MDCK cell culture medium (MEM medium supplemented with antibiotics, 20 mM Hepes and 0.15% (w/v) sodium bicarbonate (complete MEM medium), supplemented with 10% (v/v) fetal bovine serum). The H1 (A/WSN/33, A/New Caledonia/20/1999, A/Solomon Islands/IVR-145 (high-growth reassortant of A/Solomon Islands/3/2006), A/Brisbane/59/2007, A/NYMC/X-181 (high-growth reassortant of A/California/07/2009), H2 (A/Env/MPU3156/05), H3 (A/Hong Kong/1/68, A/Johannesburg/33/94, A/Panama/2000/1999, A/Hiroshima/52/2005, A/Wisconsin/67/2005 and A/Brisbane/10/2007), H4 (A/WF/HK/MPA892/06), H5 (PR8-H5N1-HK97 (6:2 reassortant of A/Hong Kong/156/97 and A/PR/8/34) and A/Eurasian Wigeon/MPF461/07), H6 (A/Eurasian Wigeon/MPD411/07), H7 (NIBRG-60 (6:2 reassortant of A/Mallard/Netherlands/12/2000) and PR8-H7N7-NY (7:1 reassortant of A/New York/107/2003 (H7N7) and A/PR/8/34)), H8 (A/Eurasian Wigeon/MPH571/08) H9 (A/Hong Kong/1073/99 and A/Chick/HK/SSP176/09), H10 (A/Chick/Germany/N/49) and H14 (PR8-H14N5 (6:2 reassortant of A/mallard/Astrakhan/263/1982 (H14N5) and A/PR/8/34)) strains which were used in the assay were all diluted to a titer of $5.7\times10^3$ TCID50/ml (50% tissue culture infective dose per ml), with the titer calculated according to the method of Spearman and Karber. The IgG preparations (200 μg/ml) were serially 2-fold diluted (1:2-1:512) in complete MEM medium in quadruplicate wells. 25 μl of the respective IgG dilution was mixed with 25 μl of virus suspension (100 TCID50/25 μl) and incubated for one hour at 37° C. The suspension was then transferred in quadruplicate onto 96-well plates containing confluent MDCK cultures in 50 μl complete MEM medium. Prior to use, MDCK cells were seeded at $3\times10^4$ cells per well in MDCK cell culture medium, grown until cells had reached confluence, washed with 300-350 μl PBS, pH 7.4 and finally 50 μl complete MEM medium was added to each well. The inoculated cells were cultured for 3-4 days at 37° C. and observed daily for the development of cytopathogenic effect (CPE). CPE was compared to the positive control.

CR9114 was shown to have heterosubtypic cross-neutralizing activity to representative strains of all tested influenza A subtypes H1, H2, H3, H4, H5, H6, H7, H8, H9 and H10 viruses. See Table 3.

Example 4: Design of a Stem Domain Polypeptide Comprising the Conserved Stem Domain Epitopes of CR6261 and CR9114 Based on H1 HA Fully human monoclonal antibodies against influenza virus hemagglutinin with broad cross-neutralizing potency were identified previously. CR6261 (as described in WO 2008/028946) was shown to have broadly cross-neutralizing activity against influenza A viruses of phylogenetic group 1. In addition, CR9114, described above, has been shown to be able to bind to and neutralize influenza A viruses of both phylogenetic group 1 and 2, as well as influenza B viruses. Functional and structural analysis have revealed that these antibodies interfere with the membrane fusion process and are directed against highly conserved epitopes in the stem domain of the influenza HA protein (Throsby et al. (2008); Ekiert et al. (2009) WO2008/028946, and co-pending application no. EP11173953.8).

In the research that led to the disclosure, new molecules comprising the stem domains of HA containing these epitopes were designed in order to create universal epitope-based immunogenic polypeptides that can be used, e.g., as a vaccine inducing protection against a broad range of influenza strains. Essentially, the highly variable and immunodominant part, i.e., the head domain is first removed from the full-length HA molecule to create a HA stem-domain polypeptide, also referred to as "mini-HA." In this way the immune response will be redirected towards the stem domain where the epitopes for the broadly neutralizing antibodies are located. The antibodies CR6261 and CR9114 are used to probe the correct folding of the newly created molecules, and to confirm the presence of the neutralizing epitopes.

The polypeptides hereof thus present the conserved epitopes of the membrane proximal stem domain HA molecule to the immune system in the absence of dominant epitopes that are present in the membrane distal head domain. To this end, part of the primary sequence of the HA0 protein making up the head domain is removed and reconnected, either directly or by introducing a short flexible linking sequence ("linker") to restore the continuity of the chain. The resulting sequence is further modified by introducing specific mutations that stabilize the native 3-dimensional structure of the remaining part of the HA0 molecule.

The function of the HA molecule in the virus is binding to the cell surface receptor sialic acid and, after uptake in endosomes, mediating the fusion of viral and endosomal membranes leading to release of the viral RNA into the cell. An essential step in the fusion process is a large conformational change of the HA molecule that rearranges the secondary structure elements of the molecule so that the fusion peptide becomes exposed. Consequently, two conformations (pre- and post-fusion) of the HA molecule exist that are very different in terms in their tertiary structure. Since the viral HA protein is primarily exposed to the immune system in the pre-fusion state, it is important to make sure that the polypeptide of the disclosure adopts this conformation. This requirement can be met by stabilizing the pre-fusion conformation and at the same time destabilizing the post-fusion conformation. This stabilization/destabilization is a necessity since the pre-fusion conformation is metastable and adopting the post-fusion conformation results in a stable conformation, i.e., a low energy minimum (Chen et al., 1995).

In this example, HA from H1N1 A/Brisbane/59/2007 (SEQ ID NO: 1) is taken as the primary (or wild-type) sequence to create the polypeptides hereof.

In a first step, polypeptides hereof are constructed by removing HA1 sequences between positions 59 and 291 (the numbering refers to the position in the HA0 sequence, as shown in SEQ ID NO: 1. In certain embodiments, the HA1 part comprises the amino acids 18-343 and the HA2 part the amino acid residues 344-565; since SEQ ID NO: 1 comprises the signal peptide, and the HA1 part starts at position 18). This results in the removal of residues 60 to 290 of HA0. These residues were replaced by a GGGG (SEQ ID NO: 194) linking sequence. Next, the accessible surface area of each residue in both the pre- and post-fusion conformation was calculated with the aid of Brugel (Delhaise et al., 1984). The degree of exposure and burial of each residue was determined as described in Samantha et al. (2002), wherein was focused on residues that are exposed in the pre-fusion conformation and get buried in the post-fusion conformation. Further analysis of these residues indicated that some of these amino acid residues can be mutated in such a way that the mutation does not have an effect on the pre-fusion conformation but destabilizes the post-fusion conformation. These residues have in general a hydrophobic side chain and are involved in the formation of the coiled coil in the post-fusion conformation. Mutating these amino acid residues to a hydrophilic amino acid will disturb the coiled coil properties—the contacts between the helices in a coiled coil are in general hydrophobic—and hence destabilize the post-fusion conformation.

Following this reasoning, in the HA2 part of the sequence some mutations were introduced: Phe 406 to Ser (F406S), Val 409 to Thr (V409T), Leu 416 to Ser (L416S) and Tyr 502 to Ser (Y502S). These are mutations that remove a hydrophobic residue from the surface of HA. It should be noted that mutation of L416 to either S or T also introduces a consensus N-glycosylation site (consensus sequence is NX(S/T). Glycosylation at this position will further increase solubility of this region. In addition, Leu 58 was mutated to Thr (L58T), Val 314 to Thr (V314T) and Ile 316 to Thr (I316T); these mutations are all in the HA1 domain, i.e., the part of the sequence corresponding to HA1 after cleavage of the native HA0 chain. The latter two mutations maintain the beta-branch of the side chain but remove a hydrophobic residue from the surface. As will be shown below some of these mutations were introduced in all variants, others were tested in separate polypeptides to investigate whether the mutations influence each other in an undesirable manner.

To increase the stability of the polypeptides, two disulfide bridges were investigated to lock HA in the pre-fusion conformation. The disulfide bridges are formed between residues which are spatially at an appropriate distance from each other (in the full-length HA molecule) and which have their C-beta atom already at the correct position to form a disulfide bridge. The first disulfide bridge proposed is between position 321 (HA1 domain) and position 405 (HA2 domain). Within the HA2 domain, a disulfide bridge was created between positions 413 and 421.

Since cleavage of HA at position R343 is an essential step for the conformational change to be able to take place, in the polypeptides hereof the cleavage site was removed by introducing a mutation of Arg (R) to a Gln (Q). Another solution according to the disclosure is to change Arg into a Gln and to delete residues 345 to 350, a small part of the fusion peptide of HA2. Removal of these (hydrophobic) sequence will further stabilize the polypeptide.

In certain embodiments, the polypeptides hereof contain the intracellular sequences of HA and the transmembrane domain. In other embodiments, the cytoplasmic sequence and the transmembrane sequence from position (or the equivalent thereof) 523, 524, 525, 526, 527, 528, 529, or 530 of HA2 to the C-terminus of HA2 (numbering according to SEQ ID NO: 1) were removed so that a secreted (soluble) polypeptide was produced following expression in cells, which can be used, e.g., in a vaccine. The soluble polypeptide was further stabilized by introducing a sequence known to form trimeric structures, i.e., AYVRKDGEWVLL (SEQ ID NO: 143), optionally connected through a linker. The linker may optionally contain a cleavage site for processing afterwards according to protocols well known to those skilled in the art. To facilitate purification of the soluble form a tag sequence may be added, e.g., a his-tag (HHHHHHH (SEQ ID NO: 191)) connected via a short linker, e.g., EGR. In some embodiments, the linker and his-tag sequence are added without the foldon sequence being present. According to the disclosure, the amino acid sequence from position 530 (numbering according to SEQ ID NO: 1) to the C-terminal amino acid of the HA2 domain was removed and replaced by the following sequences:

EGRHHHHHHH (SEQ ID NO: 81), comprising a short linker and his-tag, or SGRSLVPRGSPGSGYIPEAPRDGQAYVRKDGEWVLLSTFLGHHHHHHH (SEQ ID NO: 82), comprising a thrombin cleavage site, trimerization domain, and his-tag.

The mutations described above were grouped into clusters according to their function and location in the 3-dimensional structure of the HA stem polypeptides. All polypeptides contain H1 HA sequence 1-59 and 291-565 and the R343Q mutation, with the following additional mutations: L58T, V314T, I316T, F406S, V409T, L416S (SEQ ID NO: 3; named cluster 1). In addition variants were made that have additional mutations:

Cluster 2: K321C, Q405C (SEQ ID NO: 4)

Cluster 3: F413C, E421C (SEQ ID NO: 5)

Cluster 4: HA2 Y502S (SEQ ID NO: 6)

Furthermore two variants were made that contained the cluster 1 sequence and in addition the mutations of cluster 2 and 3 (SEQ ID NO: 7) or cluster 2, 3 and 4 (SEQ ID NO: 8).

The genes encoding the above protein sequences were synthesized and cloned into expression vector pcDNA2004 using methods generally known to those skilled in the art. For reasons of comparison the full-length sequence (SEQ ID NO: 1) was included in the experiment as well as the sequence described by Steel et al. (2010) (H1-PR8-dH1; SEQ ID NO: 24), which is based on the H1N1 A/Puerto Rico/8/1934 sequence.

HEK293F (Invitrogen) suspension cells ($10^6$ cells/ml, 30 ml) were transfected with the expression vectors (1 μg/ml) using 40 μl 293transfectin as the transfection agent and allowed to further propagate for 2 days. Cells were harvested, aliquotted (0.3 ml, approximately $3*10^5$ cells) and aliquots were treated with either polyclonal serum raised against H1 HA to probe expression or a HA-specific monoclonal antibody (5 microgram/ml) and a secondary antibody used for staining. The cells were then analyzed by fluorescence associated cell sorting (FACS) for expression of the membrane attached HA stem domain polypeptides of the disclosure using polyclonal serum raised against H1 HA to probe expression. A panel of monoclonal antibodies of known specificity that bind the full-length protein (e.g., CR6261 and CR9114) were used to probe for the presence of conserved epitopes and, by inference, correct folding of the full-length HA and the mini-HA polypeptides of the disclosure. Results are expressed as percentage positive cells and mean fluorescence intensity and are shown in FIG. 2.

The results show that all constructs are expressed on the cell surface since the reaction with the polyclonal serum (anti-H1 poly) results in 75% or higher of all cells analyzed being positive compared to ca 4% for non-transfected cells. This is confirmed by the values of the mean fluorescence intensity (MFI), which is similar for all constructs after treatment with polyclonal serum. Control experiments in the absence of IgG, using only the labeled anti-Human IgG or an irrelevant mAb are all negative. Both the A/Brisbane/59/2007 and A/Puerto Rico/8/1934 full-length HA proteins are recognized by monoclonal antibodies CR6261, CR6254, CR6328 (all known to bind and neutralize H1 HA; Throsby et al. (2008), WO 2008/028946), CR9114 (described above), CR8001 (binds to H1 HA, but does not neutralize H1; described in WO 2010/130636), but not CR8057 (binds only to some H3 strains, also described in WO 2010/130636) and CR6307 (Throsby et al. (2008), WO 2008/028946).

Considering the discontinuous and conformational character of the CR6261 epitope (Ekiert et al. 2009) it is concluded that both full-length proteins are present in their native 3-dimensional conformation. For the newly designed polypeptides of the disclosure that are tested in this experiment the same pattern of recognition by the panel of monoclonal antibodies was observed: binding by CR6261, CR6254, CR6328, CR9114 and CR8001 but not CR6307 and CR8057. This is most evident in the data on the percentage positive cells, but is also observed in the mean fluorescence intensity data. Best results are obtained with miniHA-cluster1 both with respect to % cells positive as well as mean fluorescence intensity.

Adding further modifications, such as the above described disulfide bridges (cluster 2 and 3) and the Y502S mutation of cluster 4 (or combinations of these, resulted in decreased percentages of positive cells and lower mean intensities. The construct described by Steel et al. (2010) (SEQ ID NO: 24) which contains the deletion of the head domain, but lacks further modifications is not recognized above background level by any of the antibodies used in this experiment. Therefore, it is concluded that after DNA transfection this protein is not displayed in the native 3-dimensional conformation that it has in HA.

The results described above point towards the importance of cluster 1 mutations increasing the hydrophilic character of the loop formed by residues 402 to 418 connecting the A-helix and the long backbone helix (CD) of the HA-molecule and the surrounding area. To further establish the beneficial effect the mutations of cluster1 on the stability and folding of the polypeptides hereof miniHA (SEQ ID NO: 2; polypeptide according to Steel, but based on A/Brisbane) and miniHA_cluster1 (polypeptide according to the disclosure; SEQ ID NO: 3) were compared in a separate experiment (FIG. 3).

Whereas about 60% of cells transfected with miniHA-cluster1 is positive after binding of CR6261, CR6254, CR6328 and CR9114, transfection with miniHA (polypeptide according to Steel, but based on A/Brisbane; SEQ ID NO: 2) leads to values very close to background level (1-3%). We conclude that the mutations of cluster1 contribute favorably to proper folding and stability of the polypeptides according to the disclosure, as compared to unmodified miniHA protein (SEQ ID NO: 2) that lacks these mutations.

Steel et al. created a new molecule by deleting amino acid residue 53 to 276 of HA1 of the H1 A/Puerto Rico/8/1934 and H3 HK68 strain from the primary sequence, and replacing this by a short flexible linker. As shown in this example, this results in a highly unstable molecule that does not adjust the correct conformation, as proven by the lack of binding of antibodies that were previously shown to bind to conserved epitopes in the stem region. The incorrect folding is caused by solvent exposure of a large area that is normally shielded by the globular head in the full-length HA molecule. Since this area is hydrophobic in nature the molecule is no longer stable and, therefore, adaptations are necessary.

Exchange of hydrophobic residues for hydrophilic residues as has been done in the polypeptides hereof counteracts this effect and stabilizes the HA stem domain polypeptides. Further stabilization of the native 3-dimensional fold of the stem domain is achieved by introducing disulfide bridges at appropriate locations to closely connect residues that are spatially close in the native tertiary structure but separated in the primary structure.

Example 5: Immunogenicity of HA Stem Domain Polypeptides of Example 4

In order to assess the immunogenicity of the stem domain polypeptides mice were immunized with the expression vectors encoding full-length H1 from A/Brisbane/59/2007 (SEQ ID NO: 1), miniHA-cluster1 (SEQ ID NO: 3), miniHA-cluster1+2 (SEQ ID NO: 4) and miniHA-cluster1+4 (SEQ ID NO: 6). For reasons of comparison the miniHA design by Steel et al. (2010) (mini-PR8; SEQ ID NO: 24) and the corresponding full-length protein HA from A/Puerto Rico/8/1934 were also included in the experiment. An expression vector encoding for cM2 was also included as a negative control.

Figure 4A:
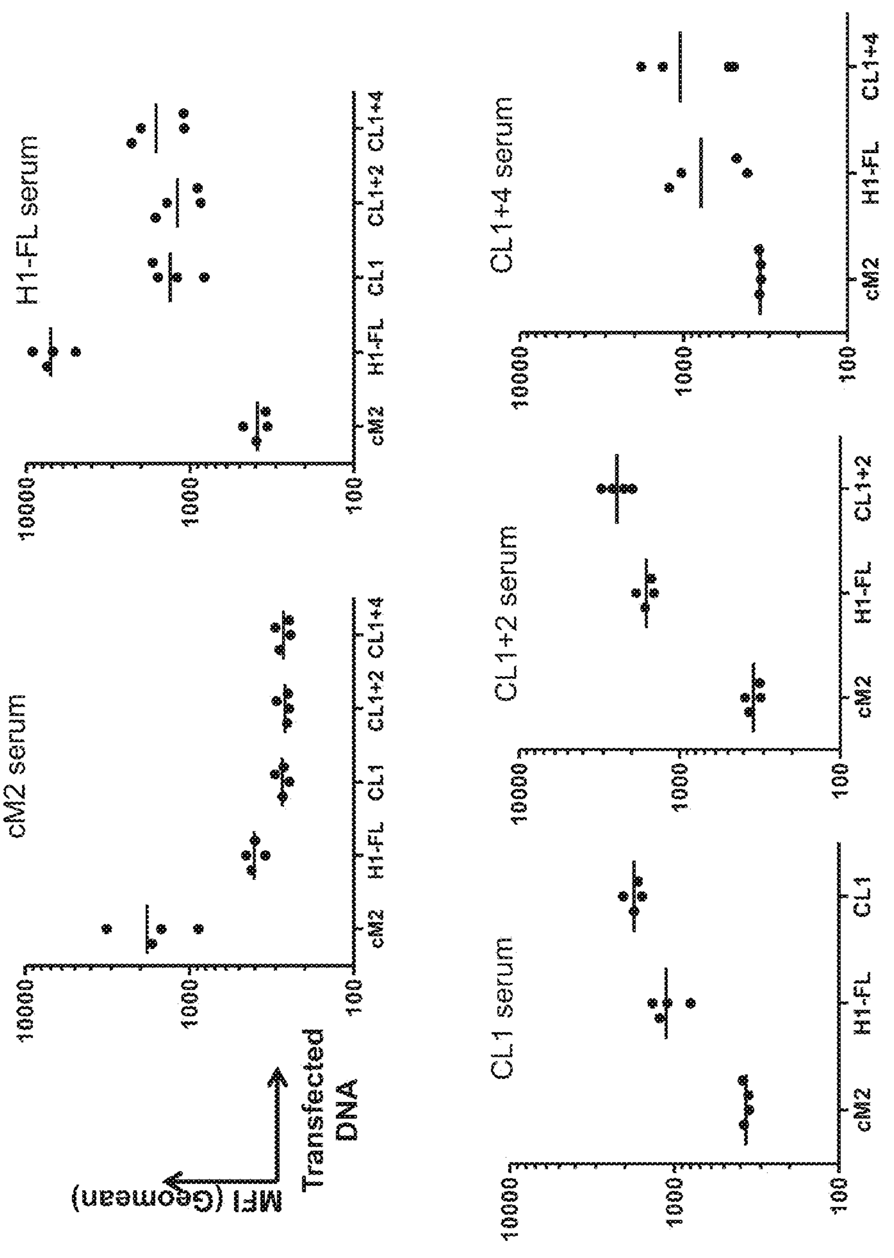
FIGS. 4A and 4B: Binding of serum antibodies to HEK293F expressed full-length HA and polypeptides of the disclosure.
Figure 4B:
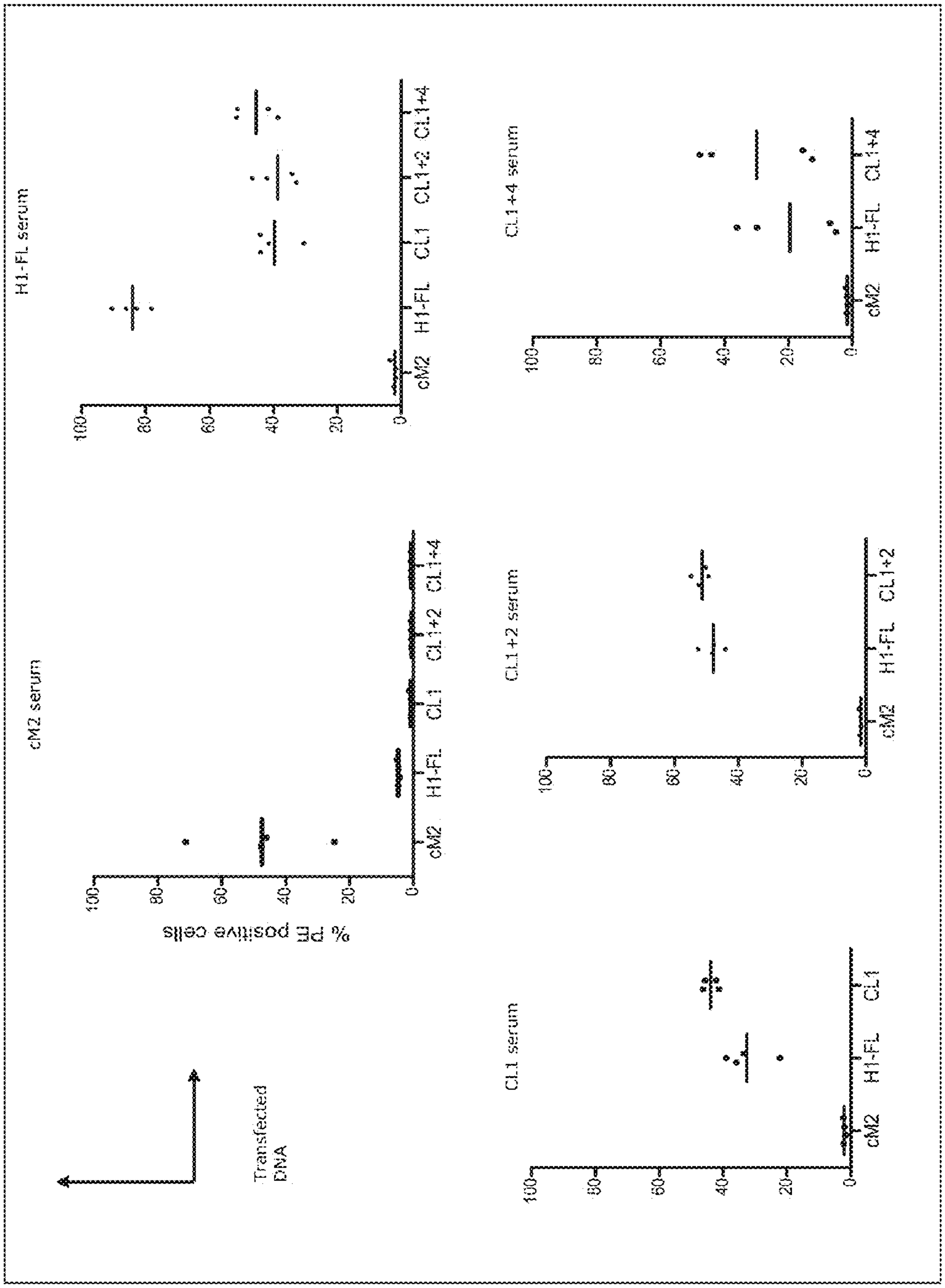

Groups of 4 mice (BALB\c) were immunized with 50 μg construct+50 μg adjuvant (pUMCV1-GM-CSF) i.m. on day 1, 21 and 42. On day 49 a final bleed was performed and serum collected. The sera were analyzed by FACS assay. HEK293F (Invitrogen) suspension cells ($10^6$ cell/ml, 30 ml) were transfected with the expression vectors (1 microgram/ml) using 40 microliter 293transfectin as the transfection agent and allowed to further propagate for 2 days. Cells were harvested, aliquotted (0.3 ml, approximately $3*10^5$ cells) and aliquots were treated with the construct-specific sera, stained with secondary antibodies and analyzed by fluorescence associated cell sorting. The results are shown in FIGS. 4A and 4B.

As expected, the cM2-specific serum (negative control) recognizes cM2, but none of the full-length HA or stem domain polypeptides as evidenced by the % positive cells and MFI. In contrast, the full-length HA-specific serum stains cells expressing the corresponding full-length HA (SEQ ID NO: 1), but also miniHA-cluster1 (SEQ ID NO: 3), miniHA-cluster1+2 (SEQ ID NO: 4) and miniHA-cluster1+4 (SEQ ID NO: 6), albeit at a lower level (ca 40% positive cells versus ca 80% for full-length MFI ca 1000 versus ca 7000 for full length). The reverse is also true: sera specific for miniHA-cluster1 (SEQ ID NO: 3), miniHA-cluster1+2 (SEQ ID NO: 4) and miniHA-cluster1+4 (SEQ ID NO: 6) recognize cells expressing the corresponding construct as well as the full-length HA (SEQ ID NO: 1). The results are summarized in Table 4, below.

In contrast to the result above for miniHA-cluster1 (SEQ ID NO: 3), miniHA-cluster1+2 (SEQ ID NO: 4) and miniHA-cluster1+4 (SEQ ID NO: 6), the serum obtained from mice immunized with the full-length PR8 did not bind very well to cells transfected with H1-PR8-dH1 (SEQ ID NO: 24). Percentage cells positive was around 20%, compared to 40-50% for the miniHA-cluster1 (SEQ ID NO: 3) and miniHA-cluster 1+2 (SEQ ID NO: 4). The results are also reflected in the observed in the mean fluorescent intensity which is barely above background level.

In conclusion, the data show that polypeptides of the disclosure are capable of inducing an immune response directed towards full-length HA. In particular modifications in the region between residue 402 and 418 (numbering according to SEQ ID NO: 1) is important to create a stable molecule.

Example 6: Preparation of Second Generation of Stem Domain Polypeptides

The mean fluorescence intensities for the stem domain polypeptides described in Example 4 are in all cases lower than observed for the corresponding full-length proteins; in fact the best design, miniHA-cluster 1 (SEQ ID NO: 3), has an intensity that is in the order of 10% of the mean intensity of the full-length construct after binding with monoclonal antibodies. This indicates that the expression and/or folding of the stem domain polypeptides on the cells surface is lower than observed for the full-length proteins and that the designs can be further improved. The results obtained from the first generation show that improvement of the first generation constructs is possible and, therefore, a second round of design was initiated.

The polypeptides described in Example 4 were based on the same deletion of the HA0 chain, i.e., residues L60 to K290 (mini1; numbering refers to position in the full-length HA0 from H1N1 A/Brisbane/59/2007; SEQ ID NO: 1). This approach creates a long unstructured loop that is now no longer attached to the head domain. It was reasoned that this loop is not contributing to the overall protein stability and can be shortened considerably without affecting folding of the other parts of the polypeptide. Three additional deletions were designed and replaced with a GGGG (SEQ ID NO: 194) linker sequence as before and combined with the mutations of cluster1 described above. The deletions are S53 to P320 (mini2), H54 to I302 (mini3), G56 to G317 (mini4). Additional modifications were introduced identical to cluster 1 above (L58T, V314T, I316T, F406S, V409T, L416S). Some of the residues belonging to this cluster are part of the deleted sequences and can, therefore, no longer be modified (see below). Furthermore, two additional mutations were created in the long helix C that forms a trimeric coiled-coil in the pre-fusion state. It is well known in the art that trimeric coiled coils are stabilized by Ile at positions 420 a and d of the heptad repeat sequence that is the hallmark of this structural motif (Suzuki et al. (2005); Woolfson et al. (2005)). This knowledge was applied by introducing Ile at positions 420 (M420I) and 427 (V427I). The combination of these two mutations and the mutations of cluster 1 were designated cluster11; for clarification the combinations are listed below:

| Mini1: | deletion L60 to K290 | cluster11: | M420I, V427I, L58T, V314T, I316T, F406S, V409T, L416S |
| Mini2: | deletion S53 to P320 | cluster11: | M420I, V427I, F406S, V409T, L416S |
| Mini3: | deletion H54 to I302 | cluster11: | M420I, V427I, V314T, I316T, F406S, V409T, L416S |
| Mini4: | deletion G56 to G317 | cluster11: | M420I, V427I, F406S, V409T, L416S |

To further stabilize the pre-fusion state of the stem domain polypeptides an additional disulfide bridge was introduced between positions 324 and 436 (cluster 5: R324C, T436C) and combined with the different deletion mutants. The following combinations were synthesized and tested for binding in the FACS assay as described above:

Mini1-cluster11 (SEQ ID NO: 9)
Mini2-cluster11 (SEQ ID NO: 10)
Mini3-cluster11 (SEQ ID NO: 11)
Mini4-cluster11 (SEQ ID NO: 12)
Mini1-cluster11+5 (SEQ ID NO: 13)
Mini2-cluster11+5 (SEQ ID NO: 14)
Mini3-cluster11+5 (SEQ ID NO: 15)
Mini4-cluster11+5 (SEQ ID NO: 16)

Figure 5:
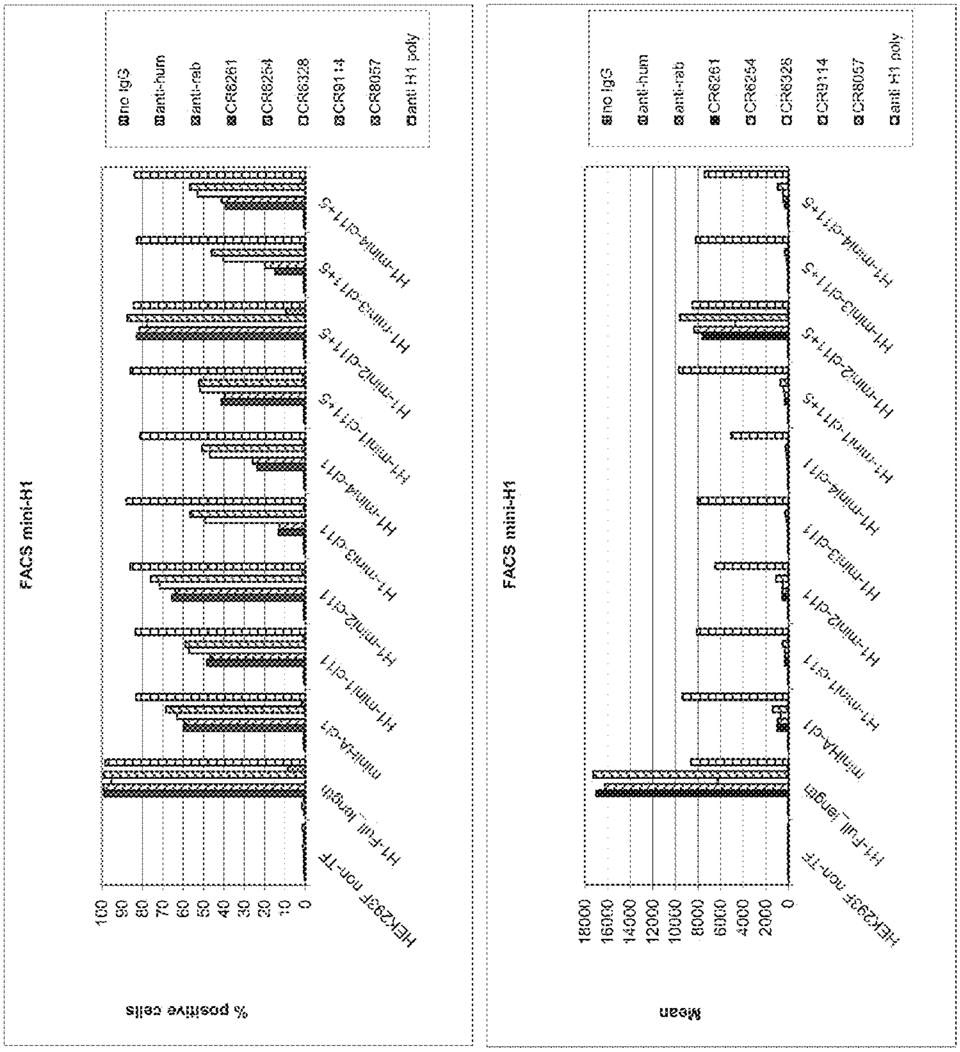
FIG. 5: Binding of monoclonal antibodies to full-length HA and HA stem domain polypeptides as analyzed by FACS. Top: Percentage of cells positive after staining. Bottom: mean fluorescence intensity. H1-Full-Length (SEQ ID NO: 1), miniHA-cl1 (SEQ ID NO: 3), H1-mini1-cl11 (SEQ ID NO: 9), H1-mini2-cl11 (SEQ ID NO: 10), H1-mini3-cl11 (SEQ ID NO: 11), H1-mini4-cl11 (SEQ ID NO: 12), H1-mini1-cl11+5 (SEQ ID NO: 13), H1-mini2-cl11+5 (SEQ ID NO: 14), H1 mini3-cl11+5 (SEQ ID NO: 15), and H1-mini4-cl11+5 (SEQ ID NO: 16).

For reasons of comparison, miniHA-cluster1 (SEQ ID NO: 3) was also included in the experiment. The results are shown in FIG. 5.

In all cases, the stem domain polypeptides were present on the cell surface after transfection of expression vectors into HEK293F cells, as evidenced by the percentage of positive cells (90% or larger) after treatment with polyclonal anti-H1 serum.

All HA stem domain polypeptides in this experiment were recognized by CR6261, CR6254, CR6328 and CR9114, but not CR8057; the latter is expected since this mAb is specific for H3 HA. There are, however, clear differences in the percentages of cells positive and MFI for the different antibodies. The best characterized antibody is CR6261, of which the epitope is known in detail. The epitope is discontinuous and conformational, and binding of this antibody can, therefore, be regarded as a stringent test of correct folding of the HA stem domain polypeptides. CR9114 is broadly neutralizing, covering strains from both group 1 and 2 (Table 3). Of the epitopes of CR6328 and CR6254 less details are known, but based on the higher values that are found for % positive cells and MFI, as well as a smaller spread in the data, binding of these antibodies seems to be a less sensitive probe of correct folding than CR6261.

Comparing the percentage positive cells (taking into account the data for all antibodies) Mini1 to 4 constructs can be ranked (highest to lowest %).

Mini2>Mini1>Mini4>Mini3 for combinations with cluster11 and

Mini2>Mini1=Mini4>Mini3 for combinations with cluster11+5

This ranking is also reflected in the data on the MFI, and leads to the conclusion that the deletion of the Mini2 construct, S53 to P320, leads to the highest level of proteins displayed on the cell surface in the correct conformation from this set.

Comparing MiniHA-cluster1 (SEQ ID NO: 3) with mini1-cluster11 (SEQ ID NO: 9), the additional mutations M420I, V427I do not seem to lead to additional stabilization of the construct; if anything, they lead to lower percentages of positive cells and MFI values, but the differences are small.

The introduction of disulfide bridge R324C, T436C (cluster 5) leads to an increase of correctly folded protein on the cell surface for mini2-cluster11 (SEQ ID NO: 10) and mini4-cluster11 (SEQ ID NO: 12), but minimal or no improvement for mini1-cluster11 (SEQ ID NO: 9) and mini3-cluster11 (SEQ ID NO: 11). The best results overall are obtained with mini2-cluster11+5 (SEQ ID NO: 14). This is in particular evident from the MFI values which for this construct are ca 50% of the value for the full-length construct.

In certain embodiments, the polypeptides hereof contain the intracellular sequences of HA and the transmembrane domain. In other embodiments, the cytoplasmic sequence and the transmembrane sequence from position (or the equivalent thereof) 523, 524, 525, 526, 527, 528, 529, or 530 of HA2 to the C-terminus of HA2 (numbering according to SEQ ID NO: 1) is removed, and optionally replaced by introducing a sequence known to form trimeric structures, i.e., AYVRKDGEWVLL (SEQ ID NO: 143), optionally connected through a linker. The linker may optionally contain a cleavage site for processing afterwards according to protocols well known to those skilled in the art. To facilitate purification of the soluble form a tag sequence may be added, e.g., a his-tag HHHHHHH (SEQ ID NO: 191) connected via a short linker, e.g., EGR. According to the disclosure, the amino acid sequence from position 530 (numbering according to SEQ ID NO: 1) to the C-terminal amino acid of the HA2 domain was removed and replaced by SEQ ID NO: 81 or SEQ ID NO: 82.

Example 7: Immunogenicity of Second Generation HA Stem Domain Polypeptides

In order to assess the immunogenicity of the stem domain polypeptides of Example 6, mice were immunized with the expression vectors encoding full-length H1 from A/Brisbane/59/2007 (SEQ ID NO: 1), miniHA-cluster1 (SEQ ID NO: 3), Mini2-cluster11 (SEQ ID NO: 10), Mini1-cluster11+5 (SEQ ID NO: 13), Mini2-cluster11+5 (SEQ ID NO: 14). An expression vector encoding for cM2 was also included as a negative control.

Groups of 4 mice (BALB\c) were immunized with 50 μg construct+50 μg adjuvant (pUMCV1-GM-CSF) i.m. on day 1, 21 and 42. On day 49 a final bleed was performed and serum collected. Full-length HA0 (SEQ ID NO: 1), negative control cM2 and Mini2-cluster11+5 (SEQ ID NO: 14) were also administered to separate groups of mice by gene gun, using ca 10 μg construct+ca. 2 μg adjuvant (pUMCV1-GM-CSF) and the same immunization scheme. The sera were analyzed by ELISA using the recombinant ectodomain of the full-length HA from A/Brisbane/59/2007 strain (obtained from Protein Sciences Corporation, Meriden, Conn., USA) as the antigen. In short, 96-well plates were coated with 50 ng HA overnight at 4° C., followed by incubation with block buffer (100 μl PBS, pH 7.4+2% skim milk) for 1 hour at room temperature. Plates were washed with PBS+0.05% TWEEN®-20, and 100 μl of a 2-fold dilution series in block buffer, starting from a 20-fold dilution of the serum is added. Bound antibody is detected using HRP-conjugated goat-anti-mouse IgG, using standard protocols well-established in the art. Titers are compared to a standard curve using mAb 3AH1 InA134 (Hytest, Turku, Finland) to derive ELISA units/ml (EU/ml).

Figure 6A:
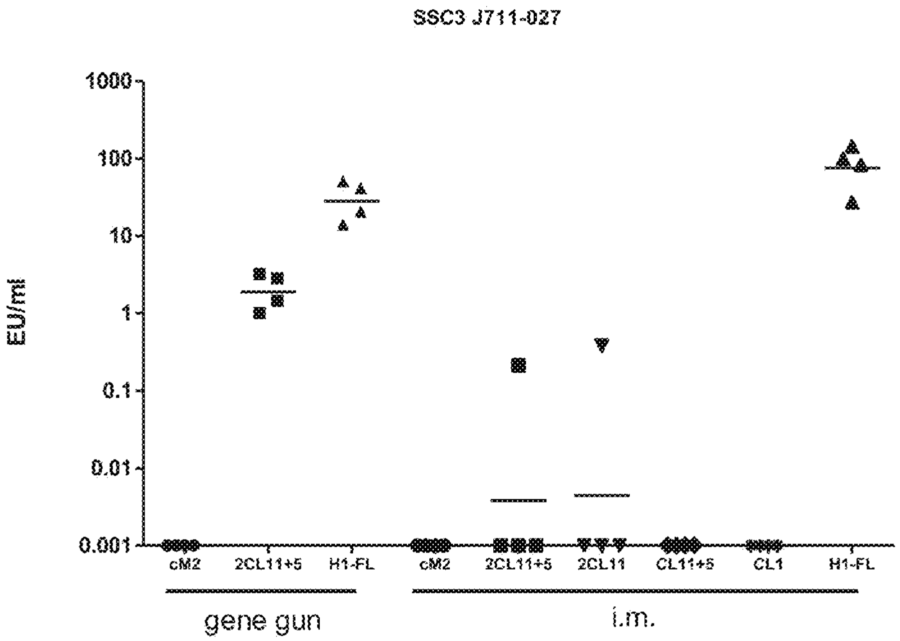
FIGS. 6A and 6B: Binding of serum antibodies to the ectodomain of full-length HA from A/Brisbane 59/2007 after i.m. immunization with DNA encoding HA A/Brisbane/59/2007 (SEQ ID NO: 1), miniHA-cluster1 (SEQ ID NO: 3), Mini2-cluster11 (SEQ ID NO: 10), Mini1-cluster11+5 (SEQ ID NO: 13), Mini2-cluster11+5 (SEQ ID NO: 14) and cM2 (consensus M2 sequence) or gene gun immunization of DNA encoding HA A/Brisbane/59/2007 (SEQ ID NO: 1), Mini2-cluster11+5 (SEQ ID NO: 14) and cM2 (consensus M2 sequence).
Figure 6B:
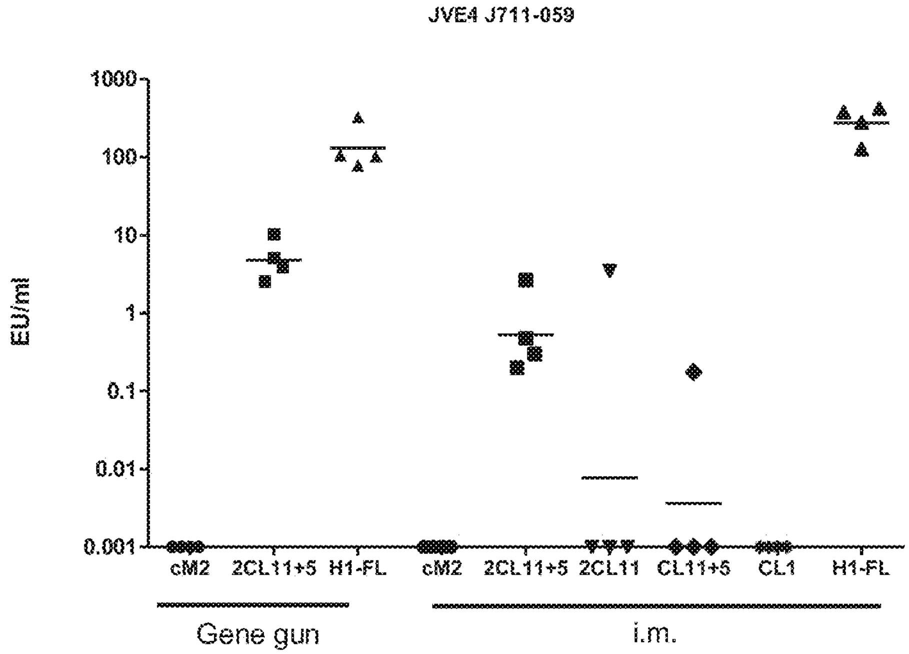

Results of the ELISA after 28 and 49 days are shown in FIGS. 6A and 6B, respectively. Serum obtained from mice immunized with DNA encoding Mini2-cluster11+5 (SEQ ID NO: 14) exhibit clear binding to the ectodomain full-length HA after 28 and 49 days after immunization using the gene gun and also after 49 days when immunized IM. For Mini2-cluster11 (SEQ ID NO: 10) and Mini1-cluster11+5 (SEQ ID NO: 13) a response was detected for 1 out of 4 mice, whereas for miniHA-cluster1 (SEQ ID NO: 3) no binding was detected.

In conclusion, the data show that polypeptides of the disclosure are capable of inducing an immune response directed toward full-length HA. In particular modifications in the region between residue 402 and 418 (numbering according to SEQ ID NO: 1), deletion S53 to P320 in combination with disulfide bridge R324C, T436C are important to create a stable molecule.

Example 8: Preparation of Third Generation Stem Domain Polypeptides

To further improve the design of the stem domain polypeptides a third round of design was implemented. An additional mutation to increase hydrophilicity of surfaces buried in the full-length HA, but not the stem domain polypeptides was introduced at position 413, F413G (numbering according to SEQ ID NO: 1), and named cluster 6. This cluster was combined with the deletion of mini-2 (S53 to P320), the disulfide bridge of cluster 5 (R324C, T436C) and the mutations of either cluster 1 (i.e., F406S, V409T, L416S; SEQ ID NO: 46) or cluster 11 (M420I, V427I, F406S, V409T, L416S; SEQ ID NO: 47). The combination of the mini-2 deletion (S53 to P320) with cluster 1 (F406S, V409T, L416S) and cluster 5 (R324C, T436C) is also included in this experiment for reference (SEQ ID NO: 48).

The native HA exists as a trimer on the cell surface. Most of the interactions between the individual monomers that keep the trimer together are located in the head domain. After removal of the head the tertiary structure is thus destabilized and, therefore, reinforcing the interactions between the monomers in the truncated molecule will increase the stability. In the stem domain trimerization is mediated by the formation of a trimeric coiled coil motif. By strengthening this motif a more stable trimer can be created. According to the disclosure, a consensus sequence for the formation of a trimeric coiled coil, IEAIEKKIEAIEKKIE (SEQ ID NO: 83), is introduced in a polypeptide of the disclosure at (the equivalent of) position 418 to 433 (SEQ ID NO: 44) in H1 A/Brisbane/59/2007 (numbering according to SEQ ID NO: 1). An alternative is to introduce the sequence MKQIEDKIEEIESKQ (SEQ ID NO: 84), derived from GCN4 and known to trimerize, at position 419-433 (SEQ ID NO: 45).

Figure 7:
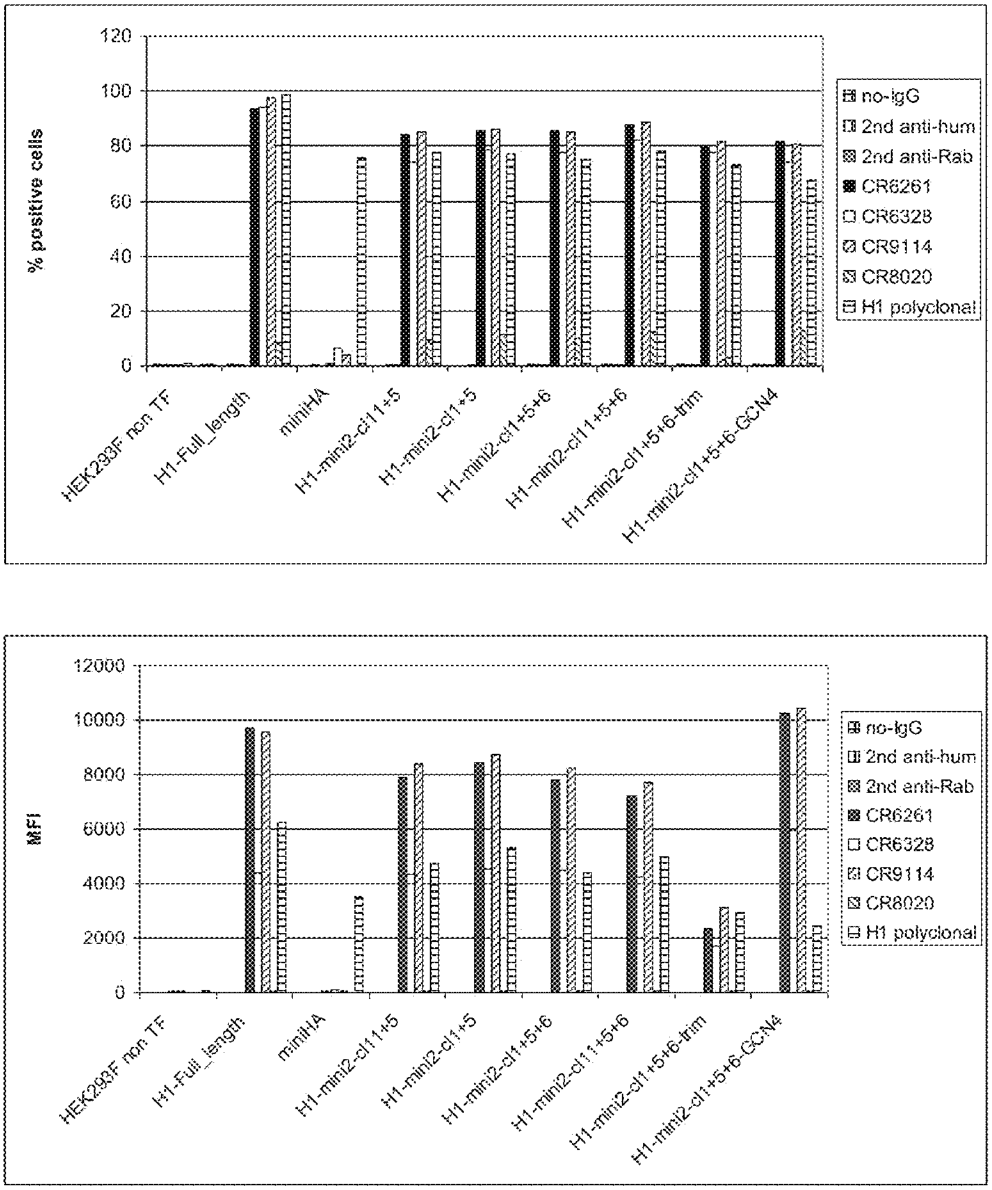
FIG. 7: Binding of monoclonal antibodies to full-length HA and HA stem domain polypeptides as analyzed by FACS. Top panel: Percentage of cells positive after staining. Bottom panel: mean fluorescence intensity. H1-Full-Length (SEQ ID NO: 1), miniHA (SEQ ID NO: 2), H1-mini2-cl1+5 (SEQ ID NO: 14), H1-mini2-cl1+5 (SEQ ID NO: 48), H1-mini2-cl1+5+6 (SEQ ID NO: 46), H1-mini2-cl11+5+6 (SEQ ID NO: 47), H1-mini2-cl1+5+6-trim (SEQ ID NO: 44), H1-mini2-cl1+5+6-GCN4 (SEQ ID NO: 45).

In the case of the stem domain polypeptides described by SEQ ID NO: 44 to SEQ ID NO: 48 all proteins were present on the cell surface after transfection of expression vectors into HEK293F cells, as evidenced by the percentage of positive cells (90% or larger) after treatment with polyclonal anti-H1 serum. The results are shown in FIG. 7.

All HA stem domain polypeptides in this experiment, with the exception of miniHA (SEQ ID NO: 2), were recognized by CR6261, CR6328 and CR9114, but not CR8020; the latter is expected since this mAb is specific for H3 HA. The percentage positive cells is around 80% for the stem domain polypeptides using CR6261, CR6328 and CR9114 for staining, with the exception of miniHA, which is only recognized by the polyclonal anti-H1 serum. Again, this is indicative of a lack of proper folding of this particular construct. There are, however, clear differences in the MFI for the different antibodies. The best characterized antibody is CR6261, of which the epitope is known in detail. The epitope is discontinuous and conformational, and binding of this antibody can, therefore, be regarded as a stringent test of correct folding of the HA stem domain polypeptides.

CR9114 is broadly neutralizing, covering strains from both group 1 and 2 (Table 3). Less details of the epitope of CR6328 are known, but in binding experiments on full-length HA, competition with CR6261 is observed.

The MFI for H1-mini2-cl11+5 (SEQ ID NO: 14), H1-mini2-cl1+5 (SEQ ID NO: 48), H1-mini2-cl1+5+6 (SEQ ID NO: 46) and H1-mini2-cl11+5+6 (SEQ ID NO: 47) are very similar, irrespective of the monoclonal antibody that is used in the experiment. The inclusion of the consensus trimerization domain (SEQ ID NO: 44) reduces the MFI by a factor 3 to 4 compared to the equivalent sequence without the trimerization domain (i.e., H1-mini2-cluster1+5+6; SEQ ID NO: 46), but the result is still clearly better than in the absence of modifications to the stem polypeptide after deletion of the head domain (cf miniHA results). The addition of the GCN4 trimerization sequence (SEQ ID NO: 45) increases the MFI to levels comparable to the full-length protein.

Example 9: Design of Further Stem Domain Polypeptides Comprising the Conserved Stem Domain Epitopes of CR6261 and CR9114

Polypeptides of the disclosure designed following the procedure described above can be further modified to increase the stability. Such modifications can be introduced to enhance the formation of trimeric forms of the polypeptides hereof over monomeric and/or dimeric species. As described above, the native HA exists as a trimer on the cell surface. Most of the interactions between the individual monomers that keep the trimer together are located in the head domain. After removal of the head the tertiary structure is thus destabilized and, therefore, reinforcing the interactions between the monomers in the truncated molecule will increase the stability. In the stem domain trimerization is mediated by the formation of a trimeric coiled coil motif. By strengthening this motif a more stable trimer can be created.

According to the disclosure, a consensus sequence for the formation of a trimeric coiled coil, IEAIEKKIEAIEKKIE (SEQ ID NO; 83), was introduced in a polypeptide of the disclosure, at (the equivalent of) position 418 to 433 (SEQ ID NO: 44) in H1 A/Brisbane/59/2007 (numbering according to SEQ ID NO: 1). Alternatively IEAIEKKIEAIEKKI (SEQ ID NO: 85) can be introduced at 419-433 (SEQ ID NO: 49) or IEAIEKKIEAIEKK (SEQ ID NO: 86) at 420-433 (SEQ ID NO: 50). An alternative is to introduce the sequence MKQIEDKIEEIESKQ (SEQ ID NO: 84) derived from GCN4 and known to trimerize, at position 419-433 (SEQ ID NO: 45). Alternatively, MKQIEDKIEEIESK (SEQ ID NO: 87) can be introduced at position 420-433 (SEQ ID NO: 51) or RMKQIEDKIEEIESKQK (SEQ ID NO: 88) at position 417-433 (SEQ ID NO: 52). Similarly, the trimer interface is strengthened by modifying M420, L423, V427, G430 into Isoleucine. (SEQ ID NO: 53).

All peptides were shown to bind CR9114 and CR6261.

In certain embodiments, the polypeptides hereof do not contain the signal sequence and/or the intracellular sequences and the transmembrane domain of HA, as described earlier.

Example 10: Design of a Stem Domain Polypeptide Comprising the Conserved Stem Domain Epitopes of CR6261 and CR9114 Based on H7 HA The procedure described above to design polypeptides of the disclosure was also be applied to H7. In this example, the design of a polypeptide of the disclosure on the basis of serotype H7 is described. HA of the H7 influenza virus A/Mallard/Netherlands/12/2000 (SEQ ID NO: 31) was used as the parental sequence, but those skilled in the art will understand that the use of other H7 sequences would have been equally possible because the sequences are well conserved, in particular in the stem region.

The first modification in the sequence is the removal of the cleavage site at position 339 (numbering refers to SEQ ID NO: 31 by mutating R to Q (R339Q) to prevent the formation of HA1 and HA2 from HA0. Optionally, residue 341 to 345 (LFGAI, part of the fusion peptide) can additionally be deleted to minimize the exposure of hydrophobic residues to the aqueous solvent. The positive charge at the cleavage is 100% conserved in H7 and this mutation can, therefore, be applied in all sequences.

The second modification is the removal of the head domain by deleting a large part of the HA1 sequence and reconnecting the N- and C-terminal sequences through a short linker. The deletion can vary in length, but it is preferred that the last residue of the N-terminal sequence of HA1 and the first residue of the C-terminal sequence are spatially close together to avoid introducing strain through the linking sequence. In H7 sequences deletions can be introduced at (the equivalent positions of) R53-P315 (mini2; SEQ ID NO: 33) in H7 A/Mallard/Netherlands/12/2000 (SEQ ID NO: 31). Equivalent positions can be easily determined by those skilled in the art by aligning the sequences using a suitable algorithm such as, e.g., Clustal or Muscle. The remaining parts of the sequence can be joined directly or alternatively a flexible linker can be introduced. Linker sequences can be 1 to 50 amino acids in length. Preferred are flexible linkers of limited length (smaller or equal to 10 amino acids), e.g., GGG, GGGG (SEQ ID NO: 194), GSA, GSAG (SEQ ID NO: 193), GSAGSA (SEQ ID NO: 189), GSAGSAG (SEQ ID NO: 188) or similar.

SEQ ID NO: 40 describes such a polypeptide containing deletion T54-C314 (mini5; SEQ ID NO: 40). The deletions described above ensure that the unstructured regions formed by residues 280-310 are also removed; this is beneficial to the overall stability of the polypeptides hereof. A similar effect was observed for polypeptides of the disclosure derived from a H1 sequence (see above).

The deletion of the head domain leaves the loop between residues 394 to 414 now exposed to the aqueous solvent. In H7 HAs, this loop is highly conserved (see Table 7). The consensus sequence is: LI (E/D/G) KTNQQFELIDNEF (N/T/S) E (I/V) E (Q/K) (SEQ ID NO: 32).

To increase the solubility of this loop in the pre-fusion conformation and destabilize the post-fusion conformation some hydrophobic residues were modified into polar (S, T, N, Q), charged amino acids (R, H, K, D, E), or flexibility was increased by mutation to G. Specifically mutations at positions 402, 404, 405, 409, 412 (numbering refers to SEQ ID NO: 31) will contribute to the stability of a polypeptide of the disclosure.

For positions F402 and F409 mutation to S is preferred but other polar (T, N, Q), charged (R, H, K, D, E) and highly flexible amino acids (G) will have the same effect. For position 404 (96% L), mutation to N or S is preferred; the latter amino acid also occurs naturally, albeit at low frequency, and mutation of this position is in those cases unnecessary. Other polar (T, Q), charged (R, H, K, D, E) and highly flexible amino acids (G) will have the same effect. For position 405 (99% I) mutation to T or D is preferred. D also occurs naturally and mutation of this position is then unnecessary. Other polar (S, N, Q), charged (R, H, K), and highly flexible amino acids (G) will have the same effect.

For position 412 (I or V) mutation to N is preferred but other polar (S, T, Q), charged (R, H, K, D, E) or flexible (G) residues are also possible. So polypeptides contain at least one of the mutations described above. Combinations of more than one mutation have also been applied, as shown, for example, in SEQ ID NOs: 34-39 and 41-43.

To stabilize the pre-fusion conformation of polypeptides of the disclosure a covalent bond between two parts distant in the primary sequences but close in the folded pre-fusion conformation was introduced. To this end, a disulfide bridge was engineered in the polypeptides hereof, preferably between (the equivalent of) position 319 and 432 in H7 A/Mallard/Netherlands/12/2000 (SEQ ID NOS: 36-39, 42, 43). Equivalent positions can be easily determined by those skilled in the art by aligning the sequences using a suitable algorithm such as Clustal, Muscle, etc. Engineered disulfide bridges are created by mutating at least one (if the other is already a cysteine), but usually two residues that are spatially close into cysteine, that will spontaneously or by active oxidation form a covalent bond between the sulfur atoms of these residues.

As described above, the native HA exists as a trimer on the cell surface. Most of the interactions between the individual monomers that keep the trimer together are located in the head domain. After removal of the head the tertiary structure is thus destabilized and, therefore, reinforcing the interactions between the monomers in the truncated molecule will increase the stability. In the stem domain trimerization is mediated by the formation of a trimeric coiled coil motif. By strengthening this motif a more stable trimer can be created. It is well known in the art that trimeric coiled coils are stabilized by Ile at positions a and d of the heptad repeat sequence that is the hallmark of this structural motif. Here this knowledge was applied by introducing Ile at (the equivalent of) positions 419, 423, 426 and 430 (SEQ ID NO: 38, 43). Alternatively a consensus sequence for the formation of a trimeric coiled coil, EAIEKKIEAI (SEQ ID NO: 209), is introduced at (the equivalent of) position 417 to 426 (SEQ ID NO: 39).

These sequences (SEQ ID NOS: 33-43) were subjected to the Fluorescence Associated Cell Sorting assay described above. However, no binding of monoclonal antibodies CR8020, CR8043, CR9114 or CR8957 could be detected. It was concluded that these sequences do not present the epitopes of these antibodies and consequently the proteins as present on the cell-membrane are not folded into their native 3-dimensional structure.

Example 11: Design of Stem Domain Polypeptides Comprising the Conserved Stem Domain Epitopes of CR8020, CR8043 and CR9114 Based on H3 HA In a first step, a sequence representing a polypeptide of the disclosure was constructed analogously as described by Steel and coworkers (Steel et al., 2010) using HA from H3 A/Wisconsin/67/2005 as the parental sequence (SEQ ID NO: 89). The head of HA is removed by deletion of a part of HA1 from amino acid D69 to amino acid K292.

These residues can be replaced by 3 or 4 Gly. The 4 Gly linker was tested by Steel and coworkers and gave good results of expression and was adopted here to create mini-H3 (SEQ ID NO: 90). To prevent cleavage of the polypeptide chain, a normal post-translational processing step for the full-length HA protein, the cleavage site at position 345 (arginine) was mutated into a glutamine (R345Q).

Next, the accessible surface area of each residue in both the constructed mini-HA and the post-fusion conformation was calculated with the aid of Brugel. The degree of exposure and burial of each residue was determined as described in Samantha and coworkers (Samantha et al., 2002). It was focused on residues which are exposed in the pre-fusion conformation and get buried in the post-fusion conformation. Further analysis of these residues indicates that some of them can be modified in such a way that the mutation does not have an effect on the pre-fusion but destabilizes the post-fusion conformation. In general these residues have a hydrophobic side chain and are involved in the formation of the coiled coil in the post-fusion conformation. Mutation of these residues to include a hydrophilic side-chain will disturb the coiled coil properties—the contacts between the helices in a coiled coil are in general hydrophobic—and hence destabilize the post-fusion conformation. Residues that go from exposed in pre-fusion to buried in the post-fusion conformation and that are expected to have a destabilizing effect on the latter conformation after mutation are L397, I401 and L425 (numbering according to SEQ ID NO: 89). Here L397K and I401T are included.

The loop (B-loop, residues 401 to 420) that connects helix A (residue 383 to 400) with the central helix CD (residues 421 to 470) changes conformation upon adopting the post-fusion state; it becomes helical and is part of an extended trimeric coiled coil. To stabilize the pre-fusion loop conformation of this linker and/or to destabilize its post-fusion conformation it was reasoned that it should be sufficient to mutate all residues that are involved in formation of the core of the coiled coil. For position N405 several mutations are designed, in particular residues carrying a negative charge (Asp and Glu, N405D, N405E) since this extra charge will reinforce the ionic network observed in the prefusion conformation. A mutation to the neutral Ala (N405A) is also included in this study. We also mutated Phe 408 to Thr, His 409 to Ser and Val 418 to Ser (numbering according to SEQ ID NO: 89; F408T, H409S, V418S) to further increase the solubility of the newly exposed surface after removal of the head domain.

Five disulfide bridges were designed to lock HA in the pre-fusion conformation. These bridges are formed between residues which are spatially at an appropriate distance from each other and which have their Cβ atoms already at the correct position to form a disulfide bridge. They are introduced between positions 320 and 406 (A320C, E406C; numbering according to SEQ ID NO: 89), 326 and 438 (K326C, S438C) and between 415 and 423 (F415C, Q423C). The first two are cross-links between HA1 and HA2 parts of the chain, whereas the last covalently connects the top of the B-loop together. The K326C, S438C disulfide bridge is accompanied by mutation of Asp 435 to Ala (D435A). Disulfide bridges F347C/N461C and S385C/L463C were taken from the paper by Bommakanti et al. (2010), and also used in this study.

To remove newly exposed hydrophobic residues form the solvent several additional mutations are designed. The Ile at position 67 (numbering according to SEQ ID NO: 89) is mutated to a Thr (I67T). This mutation maintains the beta-branch of the side chain but removes a hydrophobic residue from the surface. The same can be said for the mutation of Ile 298 to Thr (I298T). Another mutation is introduced at position 316, isoleucine in the native sequence. Intuitively, one would propose to mutate this residue to a Thr to maintain the beta-branch but remove the hydrophobicity from the surface. However, this mutation would result in the introduction of an extra N-glycosylation site (position 314 is an Asn) and, therefore, a mutation to Gln is introduced (I316Q).

Gly 495 was also mutated to Glu (G495E). This mutation is designed to introduce an ionic bridge since there is a positive charge in the surrounding Nature already provided some H3 strains with a Glu at this position.

An important residue of HA is position 345 (Arg) since this is the position where the protease cleavage occurs to render the protein fusion competent. Mutation of this Arg to a Gln (R345Q) prevents cleavage from occurring thereby locking the protein in the pre-fusion state.

The mutations described above were clustered as described below:

Cluster 1: I67T, I98T, I316Q, F408T, H409S, V418S
Cluster 2: A320C, E406C
Cluster 3: K326C, D435A, S438C
Cluster 4: L397K, I401T
Cluster 5: N405D or N405E or N405A
Cluster 6: F415C, Q423C
Cluster 7: G495E
Cluster 8: F347C, S385C, N461C, L463C To arrive at the polypeptides hereof, the clusters were combined with the deletion D69 to K292 and the R345Q mutation according to the scheme described below:

H3 Mini-HA cluster 1 (SEQ ID NO: 91)
H3 Mini-HA cluster 1+2 (SEQ ID NO: 92)
H3 Mini-HA cluster 1+3 (SEQ ID NO: 93)
H3 Mini-HA cluster 1+4 (SEQ ID NO: 94)
H3 Mini-HA cluster 1+5 N405A (SEQ ID NO: 95)
H3 Mini-HA cluster 1+5 N405D (SEQ ID NO: 96)
H3 Mini-HA cluster 1+5 N405E (SEQ ID NO: 97)
H3 Mini-HA cluster 1+6 (SEQ ID NO: 98)
H3 Mini-HA cluster 1+7 (SEQ ID NO: 99)
H3 Mini-HA cluster 1+2+3+4+5+6+7-N405E (SEQ ID NO: 100)
H3 Mini-HA cluster 1+2+3+4+5+6+7-N405A (SEQ ID NO: 101)
H3 Mini-HA cluster 1+2+3+4+5+6+7-N405D (SEQ ID NO: 102)
H3 Mini-HA cluster 1+8 (SEQ ID NO: 103).

The genes encoding the above protein sequences were synthesized and cloned into expression vector pcDNA2004 using methods generally known to those skilled in the art. For reasons of comparison the full-length HA sequence of H3 A/Wisconsin/67/2005 was included in the experiment, as well as the full-length HA sequence of H1 A/Brisbane/59/2007 containing the cleavage site mutation R343Q.

HEK293F (Invitrogen) suspension cells ($10^6$ cells/ml, 30 ml) were transfected with the expression vectors (1 μg/ml) using 40 μl 293 transfectin as the transfection agent and allowed to further propagate for 2 days. Cells were harvested, aliquotted (0.3 ml, approximately $3*10^5$ cells) and aliquots were treated with either polyclonal serum raised against H3 HA (Protein Sciences Corp, Meriden, Conn., USA) to probe expression or a HA-specific monoclonal antibody (5 microgram/ml) and a secondary antibody used for staining. The cells were then analyzed by fluorescence associated cell sorting (FACS) for expression of the membrane attached HA stem domain polypeptides of the disclosure using polyclonal serum raised against H3 HA or H1 HA to probe expression. A panel of monoclonal antibodies of known specificity that bind the full-length protein (CR8020, CR8043 and CR9114) were used to probe for the presence of conserved epitopes and, by inference, correct folding of the full-length HA and the mini-HA polypeptides of the disclosure. Monoclonal antibody CR6261 (known not to bind to H3 HAs) and CR8057 (binds to the head domain of HA from A/Wisconsin/67/2005) were also included in the experiment. Results are expressed as percentage positive cells and are shown in FIGS. 8A and 8B.

The results show that all constructs are expressed on the cell surface since the reaction with the H3 polyclonal serum results in 80-90% of all cells analyzed being positive for H3-based sequences and more than 50% for the full-length H1 sequence compared to below 4% for non-transfected cells. Using the anti-H1 polyclonal 60-70% of all cells are positive, except for the full-length H1 sequence that approaches 100%. Control experiments in the absence of IgG, using only the labeled anti-Human or anti-rabbit IgG are all negative. Both the A/Wisconsin/67/2005 and the A/Brisbane/59/2007 full-length HA proteins are recognized by monoclonal antibody CR9114, known to be capable of neutralizing both strains. A/Wisconsin/67/2005 full-length HA further binds CR8020, CR8043, and CR8057 (binds only to some H3 strains, described in WO 2010/130636), but not CR6261 (Throsby et al. (2008), WO 2008/028946). For full-length HA from A/Brisbane/59/2007 the reverse is true: it does bind to CR6261 but not CR8020, CR8043 and CR8057.

Figure 8A:
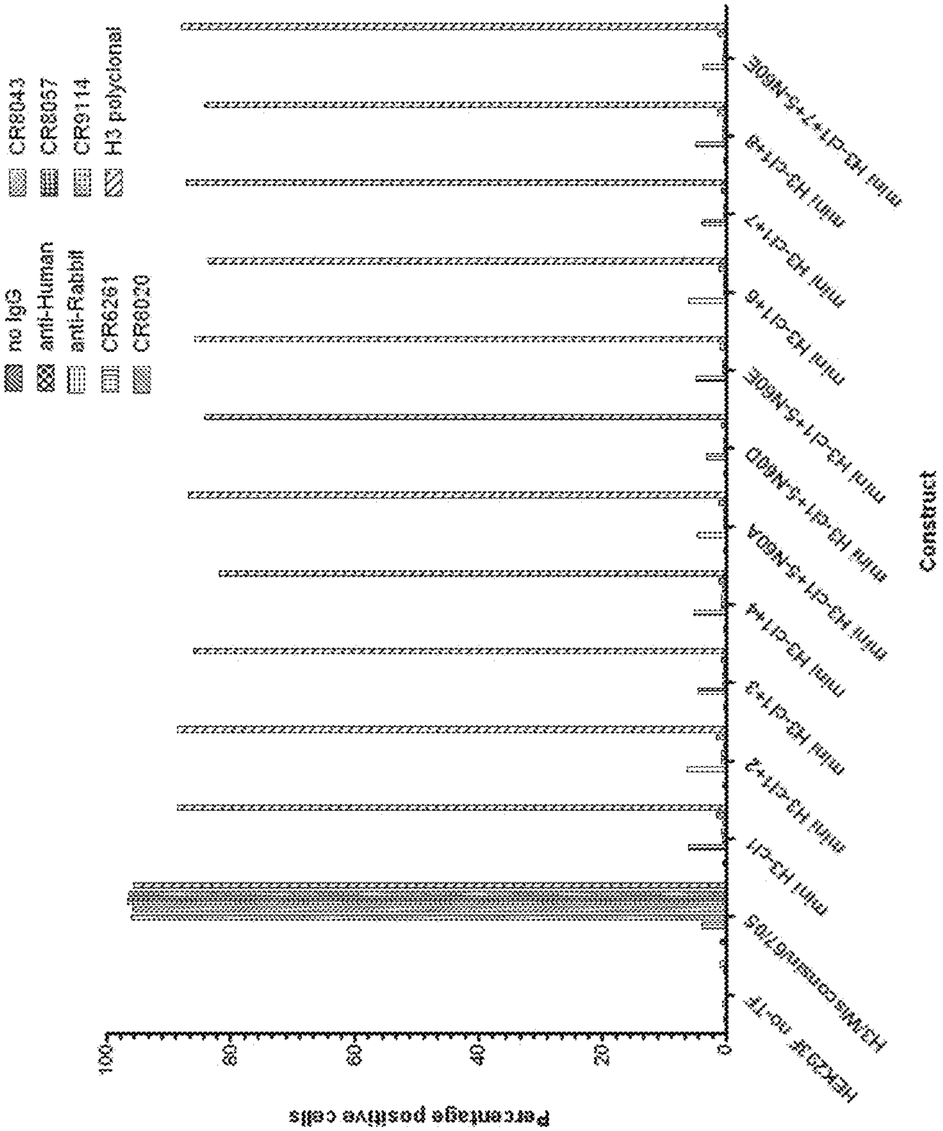
FIGS. 8A and 8B: Binding of monoclonal antibodies to full-length HA and HA stem domain polypeptides as analyzed by FACS.
Figure 8B:
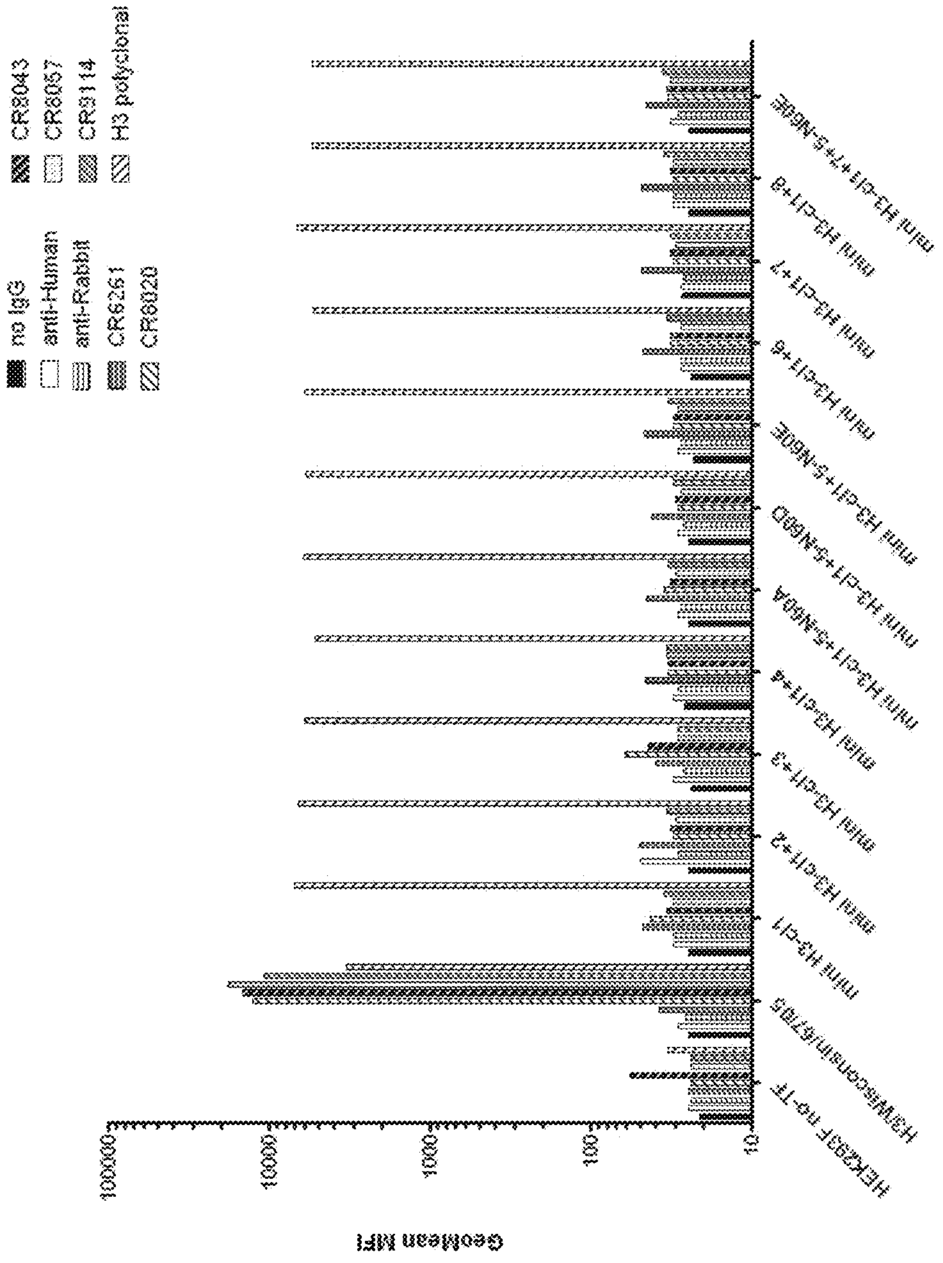

The polypeptides as described in SEQ ID NO: 91 to SEQ ID NO: 103 are not capable of binding to CR8020, CR8043 and CR9114 in any of the cases as evidenced by the lack of signals above background in FIGS. 8A and 8B. It was, therefore, concluded that these sequences do not present the epitopes of these antibodies and consequently that the proteins as present on the cell-membrane are not folded into their native 3-dimensional structure.

Example 12: Design of Further Stem Domain Polypeptides Comprising the Conserved Stem Domain Epitopes of CR8020, CR8043 and CR9114 Based on H3 HA In this example, the design of further polypeptides of the disclosure on the basis of serotype H3 is described. HA of the H3 influenza virus A/Wisconsin/67/2005 (SEQ ID NO: 89) and A/Hong Kong/1/1968 (SEQ ID NO: 121) were used as the parental sequence.

The first modification in the sequence is the removal of the cleavage site at position 345 (numbering refers to SEQ ID NO: 89 by mutating R to Q (R345Q) to prevent the formation of HA1 and HA2 from HA0. Optionally, residue 347 to 351 (IFGAI, part of the fusion peptide) can additionally be deleted to minimize the exposure of hydrophobic residues to the aqueous solvent. The positive charge at the cleavage is 100% conserved in H3 and this mutation can, therefore, be applied in all sequences.

The second modification is the removal of the head domain by deleting a large part of the HA1 sequence and reconnecting the N- and C-terminal sequences through a short linker. The deletion can vary in length, but it is preferred that the last residue of the N-terminal sequence of HA1 and the first residue of the C-terminal sequence are spatially close together to avoid introducing strain through the linking sequence. In H3 sequence deletions can be introduced at (the equivalent positions of) S62-P322 (mini2; SEQ ID NO: 105), S63-P305 (mini3; SEQ ID NO: 119) and T64-T317 (mini4; SEQ ID NO: 120. Equivalent positions can be easily determined by those skilled in the art by aligning the sequences using a suitable algorithm such as, e.g., Clustal or Muscle. The remaining parts of the sequence can be joined directly or alternatively a flexible linker can be introduced. Linker sequences can be 1 to 50, amino acids in length. Preferred are flexible linkers of limited length (smaller or equal to 10 amino acids), e.g., GGG, GGGG (SEQ ID NO: 194), GSA, GSAG (SEQ ID NO: 193), GSAGSA (SEQ ID NO: 189), GSAGSAG (SEQ ID NO: 188) or similar. The length of the deletion can also be varied, e.g., by decreasing the number of residues in the deletion by starting at (the equivalent of) position 63, 64, 65, 66, 67, or to increase the length of the deletion, by cutting at position 57, 58, 59, 60 or 61. Similarly, the last amino acid to be deleted can be at (the equivalent of) position 317, 318, 319, 320 or 321, or to increase the length of the deletion at (the equivalent of) position 323, 324, 325, 326, or 327. It is important to realize that changes in the length of the deletion can be in part compensated for by matching the length of the linker sequence, i.e., a larger deletion can be matched with a longer linker and vice versa. These polypeptides are also included in the disclosure.

The deletion of the head domain leaves the B-loop between residues 400 to 420 now exposed to the aqueous solvent. In H3 HAs this loop is highly conserved (see Table 9). The consensus sequence is: 401 I(E/G)KTNEKFHQ-IEKEFSEVEGR 421 (SEQ ID NO: 104; numbering refers to SEQ ID NO: 89). To increase the solubility of this loop for the polypeptides hereof in the pre-fusion conformation and destabilize the post-fusion conformation some hydrophobic residues have to be modified into polar (S, T, N, Q), charged amino acids (R, H, K, D, E), or flexibility has to be increased by mutation to G. Specifically mutations at positions 401, 408, 411, 415, 418, (numbering refers to SEQ ID NO: 89) will contribute to the stability of a polypeptide of the disclosure.

For positions F408 and F415 mutation to S is preferred but other polar (T, N, Q), charged (R, H, K, D, E) and highly flexible amino acids (G) will have the same effect. For position 411 (I), mutation to T is preferred. Other polar (S, N, Q), charged (R, H, K, D, E) and highly flexible amino acids (G) will have the same effect and are, therefore, also included in the disclosure. For position 418 (V), mutation to G is preferred. Other polar (S, T, N, Q), charged (R, H, K, D, E) will have the same effect and are, therefore, also included in the disclosure. For position 401 (I) mutation to R is preferred but other polar (S, T, N, Q), charged (H, K, D, E) or flexible (G) residues are also possible. So polypeptides of the disclosure contain at least one of the mutations described above. Combinations of more than one mutation are also possible, as shown, for example, in SEQ ID NOS: 123-127 and 129-131.

To stabilize the pre-fusion conformation of polypeptides of the disclosure, a covalent bond between two parts distant in the primary sequences but close in the folded pre-fusion conformation is introduced. To this end, a disulfide bridge is engineered in the polypeptides hereof, preferably between (the equivalent of) position 326 and 438 in H3 A/Wisconsin/67/2005 (SEQ ID NO: 89). Equivalent positions can be easily determined by those skilled in the art by aligning the sequences using a suitable algorithm such as Clustal, Muscle, etc. Engineered disulfide bridges are created by mutating at least one (if the other is already a cysteine), but usually two residues that are spatially close into cysteine, that will spontaneously or by active oxidation form a covalent bond between the sulfur atoms of these residues. An alternative cysteine bridge can be created between (the equivalent of) position 334 and 393 in H3 A/Wisconsin/67/2005 (SEQ ID NO: 89) by mutation of these residues into cysteine. In some cases the cysteine at (the equivalent of) position 321 is modified into a glycine to avoid formation of unwanted disulfide bridges.

The native HA exists as a trimer on the cell surface. Most of the interactions between the individual monomers that keep the trimer together are located in the head domain. After removal of the head the tertiary structure is thus destabilized and, therefore, reinforcing the interactions between the monomers in the truncated molecule will increase the stability. In the stem domain trimerization is mediated by the formation of a trimeric coiled coil motif. By strengthening this motif a more stable trimer can be created. A consensus sequence for the formation of a trimeric coiled coil, IEAIEKKIEAIEKKIEAIEKK (SEQ ID NO: 198), is introduced at (the equivalent of) position 421 to 441. To avoid interference with the formation of the disulfide bridge between positions 326 and 438 an alternative shorter sequence IEAIEKKIEAIEKKI (SEQ ID NO: 199) at (the equivalent of) positions 421 to 435 was also used. An alternative is to introduce the sequence RMKQIEDKIEE-IESKQKKIEN (SEQ ID NO: 200), derived from GCN4 and known to trimerize, at position 421-441 or the shorter sequence RMKQIEDKIEEIESK (SEQ ID NO: 201) at position 421 to 435.

The polypeptides hereof may contain the intracellular sequences of HA and the transmembrane domain so that the resulting polypeptides are presented on the cell surface when expressed in cells. In other embodiments, the cytoplasmic sequence and the transmembrane sequence from (the equivalent of) position 522 to the C-terminus is removed so that a secreted (soluble) polypeptide is produced following expression in cells. Optionally, some additional residues can be included in the soluble protein by deleting the sequence from (the equivalent of) 523, 524, 525, 526, 527, 528 or 529. The soluble polypeptide can be further stabilized by introducing a sequence known to form trimeric structures, i.e., AYVRKDGEWVLL (SEQ ID NO: 143) ("foldon" sequence), optionally connected through a linker. The linker may optionally contain a cleavage site for processing afterwards according to protocols well known to those skilled in the art. To facilitate purification of the soluble form a tag sequence may be added, e.g., a his-tag (HHHHHHEI (SEQ ID NO: 191)) connected via a short linker, e.g., EGR. In some embodiments, the linker and his-tag sequence are added without the foldon sequence being present.

An important residue of HA is position 345 (Arg) since this is the position where the protease cleavage occurs to render the protein fusion competent. Mutation of this Arg to a Gln (R345Q) prevents cleavage from occurring thereby locking the protein in the pre-fusion state.

The mutations described above were clustered as described below:

Cluster 9 F408S, I411T, F415S
Cluster 10 V418G
Cluster 11 I401R
Cluster 12 K326C, S438C
Cluster 13 T334C, I393C
Cluster 14 C321G
GCN4 RMKQIEDKIEEIESKQKKIEN (SEQ ID NO: 200) at position 421 to 441 or RMKQIEDKIEEIESK (SEQ ID NO: 201) at position 421 to 435
tri IEAIEKKIEAIEKKIEAIEKK (SEQ ID NO: 198) at position 421 to 441 or IEAIEKKIEAIEKKI (SEQ ID NO: 199) at positions 421 to 435

Using the sequence of full-length HA from H3N2 A/Wisconsin/67/2005 as starting point the clusters described above were combined with the S62-P322 deletion (mini2; SEQ ID NO: 105) to arrive at polypeptides of the disclosure:

SEQ ID NO: 105: H3-mini2
SEQ ID NO: 106: H3-mini2-cl9+10
SEQ ID NO: 107: H3-mini2-cl9+11
SEQ ID NO: 108: H3-mini2-cl9+10+11

SEQ ID NO: 109: H3-mini2-cl9+10+11-tri (tri sequence at position 421-441)
SEQ ID NO: 110: H3-mini2-cl9+10+11-GCN4 (GCN4 sequence at position 421-441)
SEQ ID NO: 111: H3-mini2-cl9+10+11+12
SEQ ID NO: 112: H3-mini2-cl9+10+12
SEQ ID NO: 113: H3-mini2-cl9+10+11+12-GCN4 (short GCN4 sequence at position 421-435)
SEQ ID NO: 114: H3-mini2-cl9+10+11+12-tri (short tri sequence at position 421-435)
SEQ ID NO: 115: H3-mini2-cl9+13
SEQ ID NO: 116: H3-mini2-cl9+10+11+13
SEQ ID NO: 117: H3-mini2-cl9+10+11+13-GCN4 (GCN4 sequence at position 421-441)
SEQ ID NO: 118: H3-mini2-cl9+10+11+13-tri (tri sequence at position 421-441)

In addition the deletions S63-P305 (mini3) and T64-T317 (mini4) were combined with clusters 9, 10, 11 and 14 to create the polypeptides hereof:

SEQ ID NO: 119: H3-mini3-cl9+10+11+12+14
SEQ ID NO: 120: H3-mini4-cl9+10+11+12+14

Using the sequence of full-length HA from H3N2 A/Hong Kong/1/1968 as starting point the clusters described above were combined with the S62-P322 deletion to arrive at polypeptides of the disclosure:

SEQ ID NO: 121: H3 Full-length A/Hong Kong/1/1968
SEQ ID NO: 122: HK68 H3m2-cl9
SEQ ID NO: 123: HK68 H3m2-cl9+10
SEQ ID NO: 124: HK68 H3m2-cl9+10+11
SEQ ID NO: 125: HK68 H3m2-cl9+10+12
SEQ ID NO: 126: HK68 H3m2-cl9+10+11+12
SEQ ID NO: 127: HK68 H3m2-cl9+10+11+13
SEQ ID NO: 128: HK68 H3m2-cl9+10+11+12-tri (short tri sequence at position 421-435)
SEQ ID NO: 129: HK68 H3m2-cl9+10+11+13-tri (tri sequence at position 421-441)
SEQ ID NO: 130: HK68 H3m2-cl9+10+11+12-GCN4 (short GCN4 sequence at position 421-435)
SEQ ID NO: 131: HK68 H3m2-cl9+10+11+13-GCN4 (GCN4 sequence at position 421-441).

The genes encoding the above protein sequences were synthesized and cloned into expression vector pcDNA2004 using methods generally known to those skilled in the art. For reasons of comparison the full-length HA sequence of H3 A/Wisconsin/67/2005 and/or H3 A/Hong Kong/1/1968 was included in the experiment.

Figure 9A:
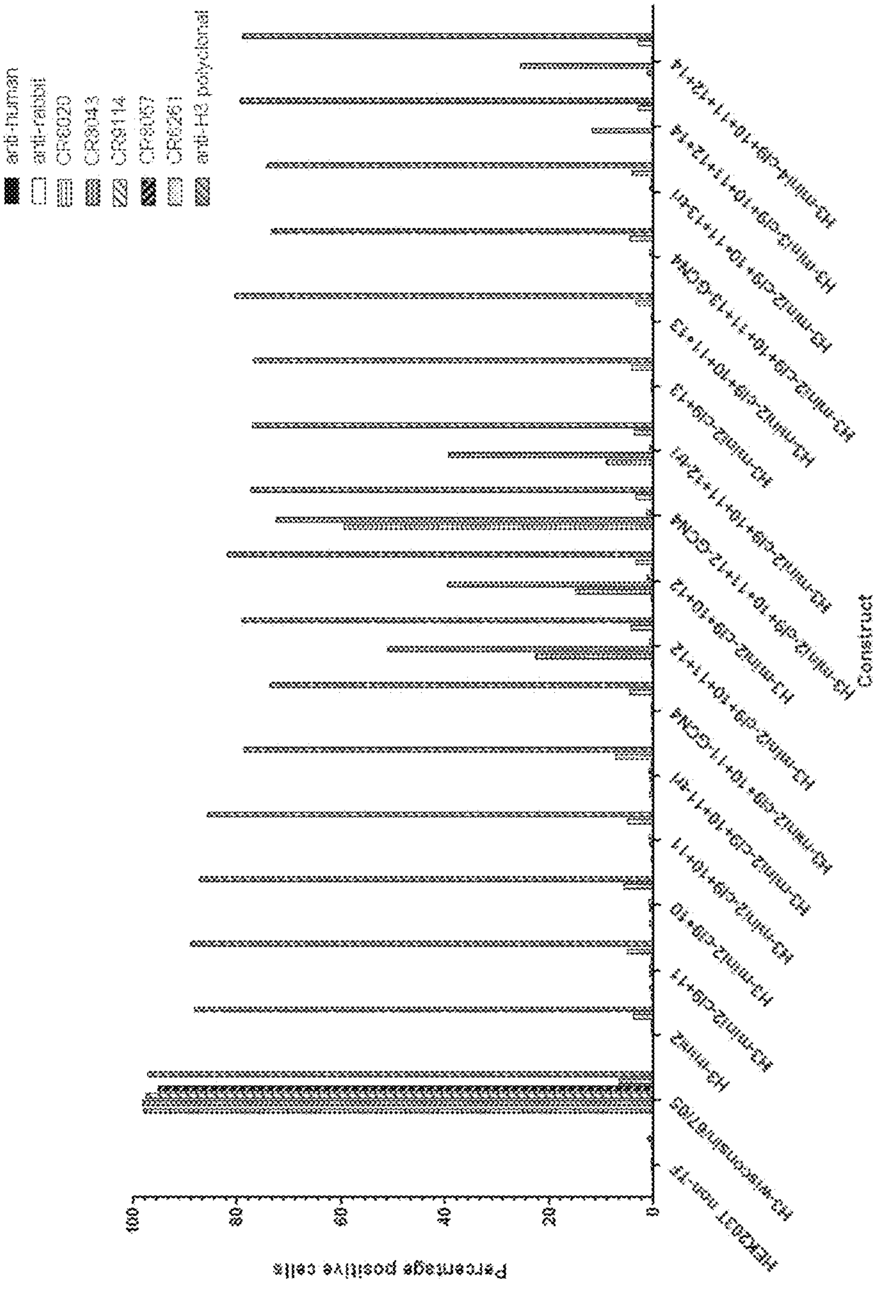
FIGS. 9A and 9B: Binding of monoclonal antibodies to full-length HA and HA stem domain polypeptides as analyzed by FACS.
Figure 9B:
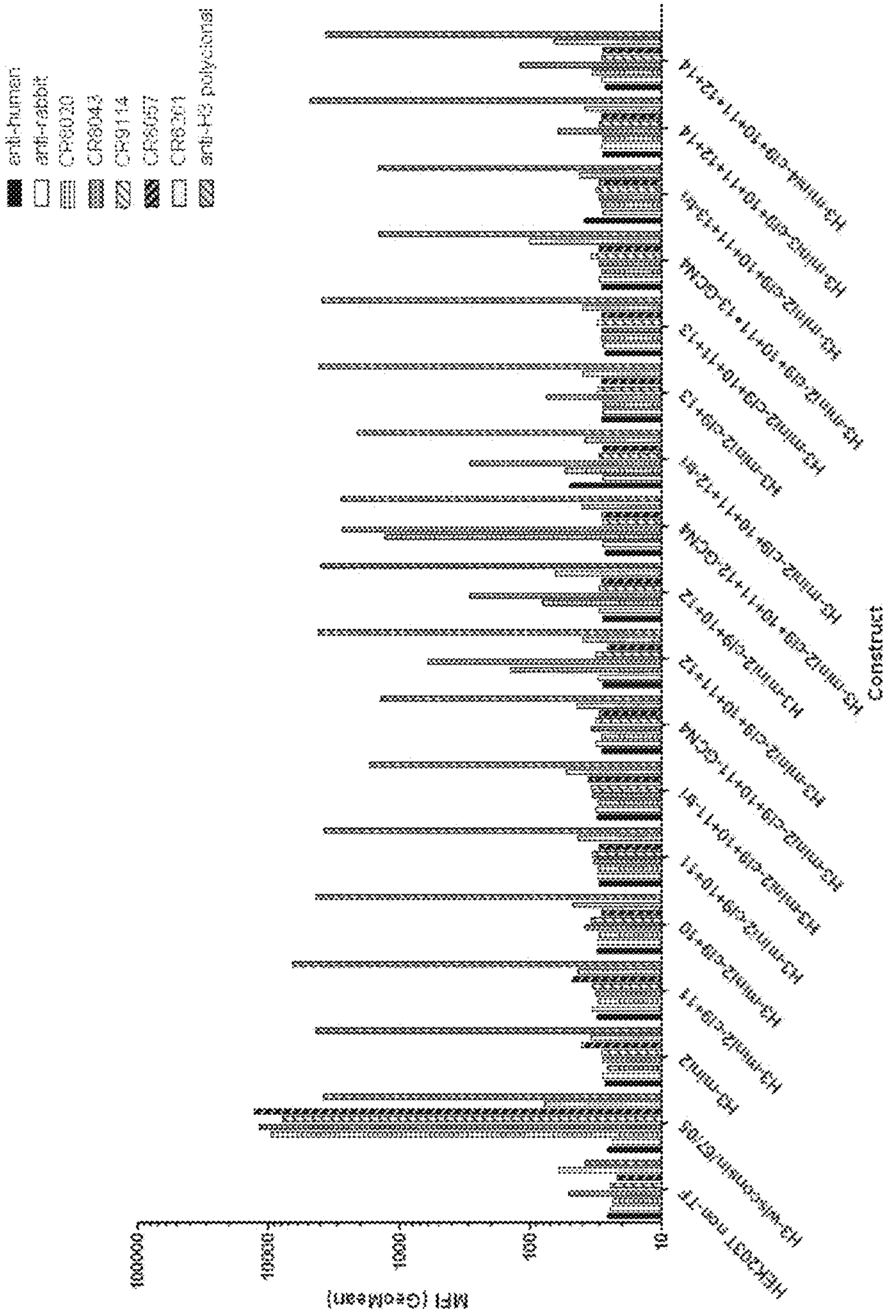

HEK293F (Invitrogen) suspension cells ($10^6$ cells/ml, 30 ml) were transfected with the expression vectors (1 μg/ml) using 40 μl 293 transfectin as the transfection agent and allowed to further propagate for 2 days. Cells were harvested, aliquotted (0.3 ml, approximately $3*10^5$ cells) and aliquots were treated with either polyclonal serum raised against H3 HA (Protein Sciences Corp, Meriden, Conn., USA) to probe expression or a HA-specific monoclonal antibody (5 microgram/ml) and a secondary antibody used for staining. The cells were then analyzed by fluorescence associated cell sorting (FACS) for expression of the membrane attached HA stem domain polypeptides of the disclosure using polyclonal serum raised against H3 HA or H1 HA to probe expression. A panel of monoclonal antibodies of known specificity that bind the full-length protein (CR8020, CR8043 and CR9114) were used to probe for the presence of conserved epitopes and, by inference, correct folding of the full-length HA and the mini-HA polypeptides of the disclosure. Monoclonal antibody CR6261 (known not to bind to H3 HAs) and CR8057 (binds to the head domain of HA from A/Wisconsin/67/2005) were also included in the experiments. Results are expressed as percentage positive cells and are shown in FIGS. 9A and 9B for H3 HA of A/Wisconsin/67/2005 based sequences and FIGS. 10A and 10B for H3 HA of A/Hong Kong/1/1968 based sequences.

The results show that all A/Wisconsin/67/2005 based constructs (FIGS. 9A and 9B) are expressed on the cell surface since the reaction with the H3 polyclonal serum results in ca 80% or more of all cells analyzed being positive compared to below 5% for non-transfected cells. Control experiments in the absence of IgG, using only the labeled anti-Human or anti-rabbit IgG are all negative. The A/Wisconsin/67/2005 full-length HA is recognized by monoclonal antibodies CR8020, CR8043, CR8057 (binds only to some H3 strains, described in WO 2010/130636) and CR9114 known to be capable of binding to this protein, but not by mAb CR6261. In contrast, most of the stem domain polypeptides are not recognized by CR8020, CR8043 or CR9114 with some notable exceptions. Polypeptides comprising the cluster 12 mutation were recognized by CR8020 and/or CR8043. H3-mini2-cl9+10+11+12 (SEQ ID NO: 111), H3-mini2-cl9+10+12 (SEQ ID NO: 112), H3-mini2-cl9+10+11+12-GCN4 (SEQ ID NO: 113) and H3-mini2-cl9+10+11+12-tri (SEQ ID NO: 114) exhibit recognition by CR8020 (% percentage positive cells ranging from ca 10 to 60) and CR8043 (40 to 70%) (indicated by arrows). Of the 4 positive constructs H3-mini2-cl9+10+11+12-GCN4 (SEQ ID NO: 113) exhibits the largest responses in this assay. The same results are obtained from the Mean fluorescence intensity that is shown in panel B (FIGS. 9A and 9B). H3-mini2-cl9+10+11+12 (SEQ ID NO: 111), H3-mini2-cl9+10+12 (SEQ ID NO: 112), H3-mini2-cl9+10+11+12-GCN4 (SEQ ID NO: 113) and H3-mini2-cl9+10+11+12-tri (SEQ ID NO: 114) exhibit mean fluorescence intensity well above background after exposure to CR8020 and CR8043 and staining, with the highest responses for H3-mini2-cl9+10+11+12-GCN4 (SEQ ID NO: 113). None of the polypeptides based on HA from A/Wisconsin/67/2005 is capable of recognizing CR9114.

Figure 10A:
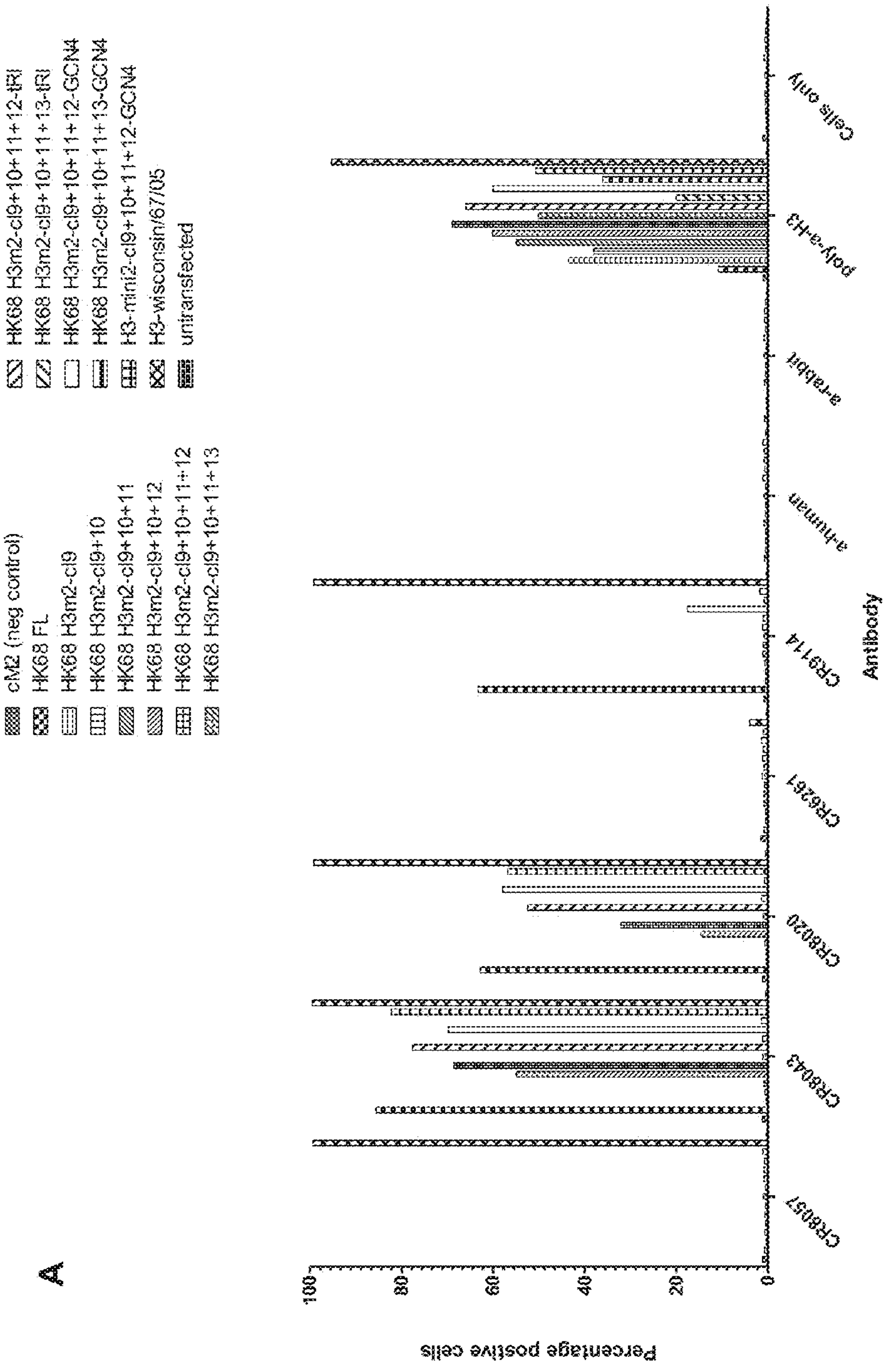
FIGS. 10A and 10B: Expression of Hong Kong/1/1968 based constructs on the cell surface.
Figure 10B:
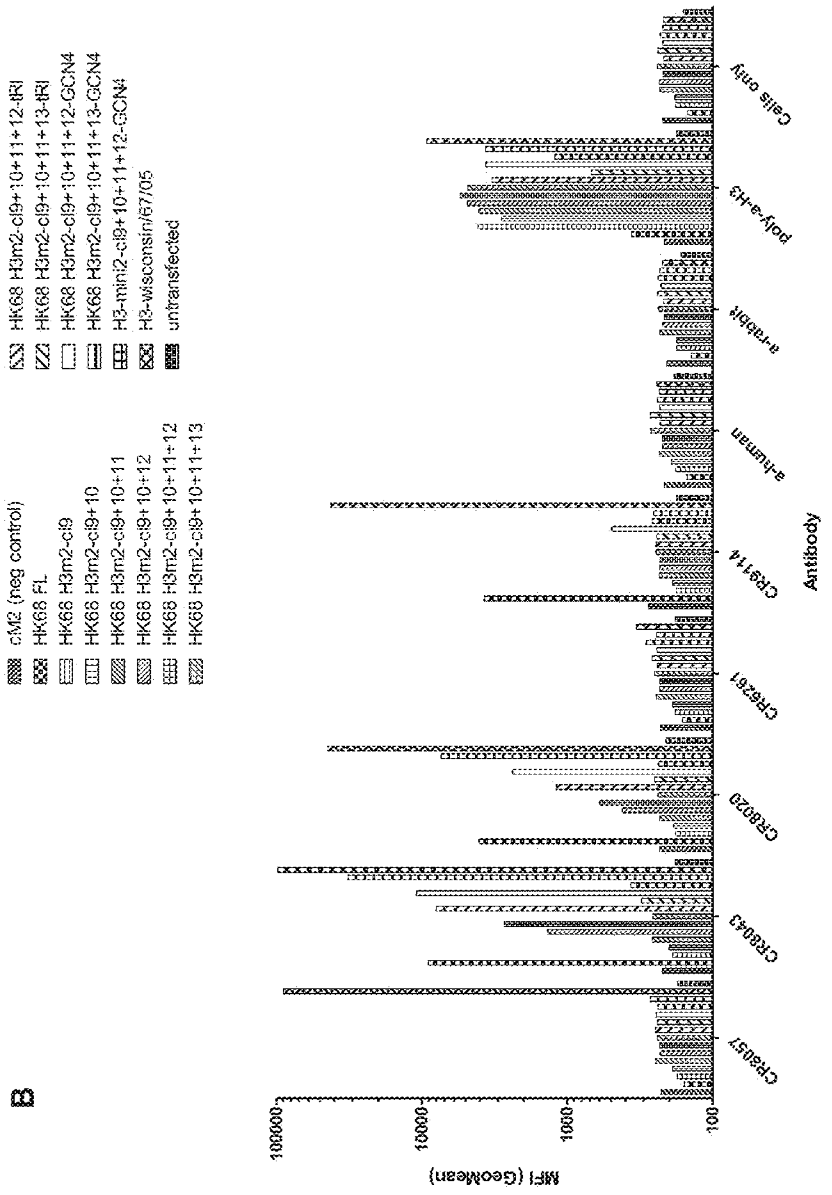
Figure 11A:
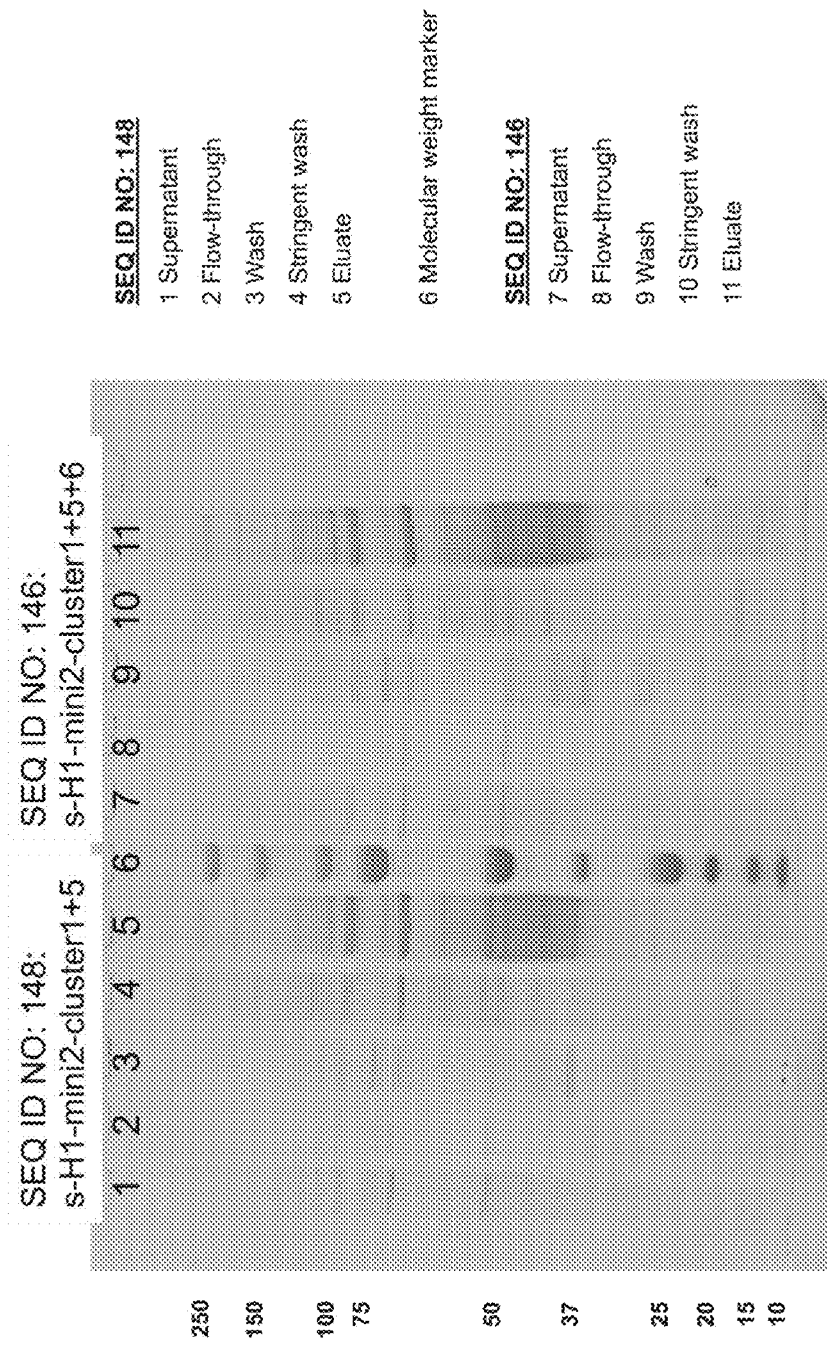
FIGS. 11A-11F: SDS-PAGE (FIGS. 11A-11D) and Western Blot (FIGS. 11E-11F) analysis of the purification of several polypeptides of the disclosure. For the Western Blot an antibody directed against the his-tag was used for detection.
Figure 11B:
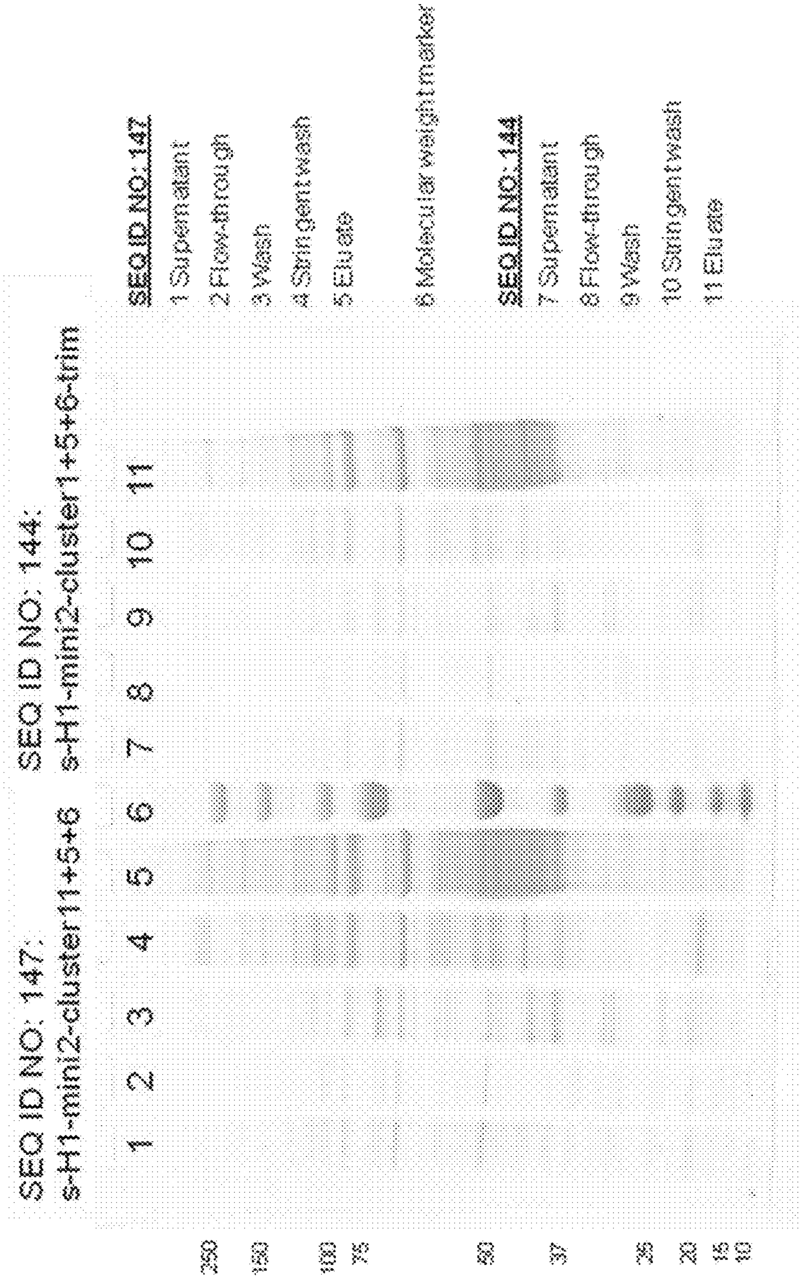
Figure 11C:
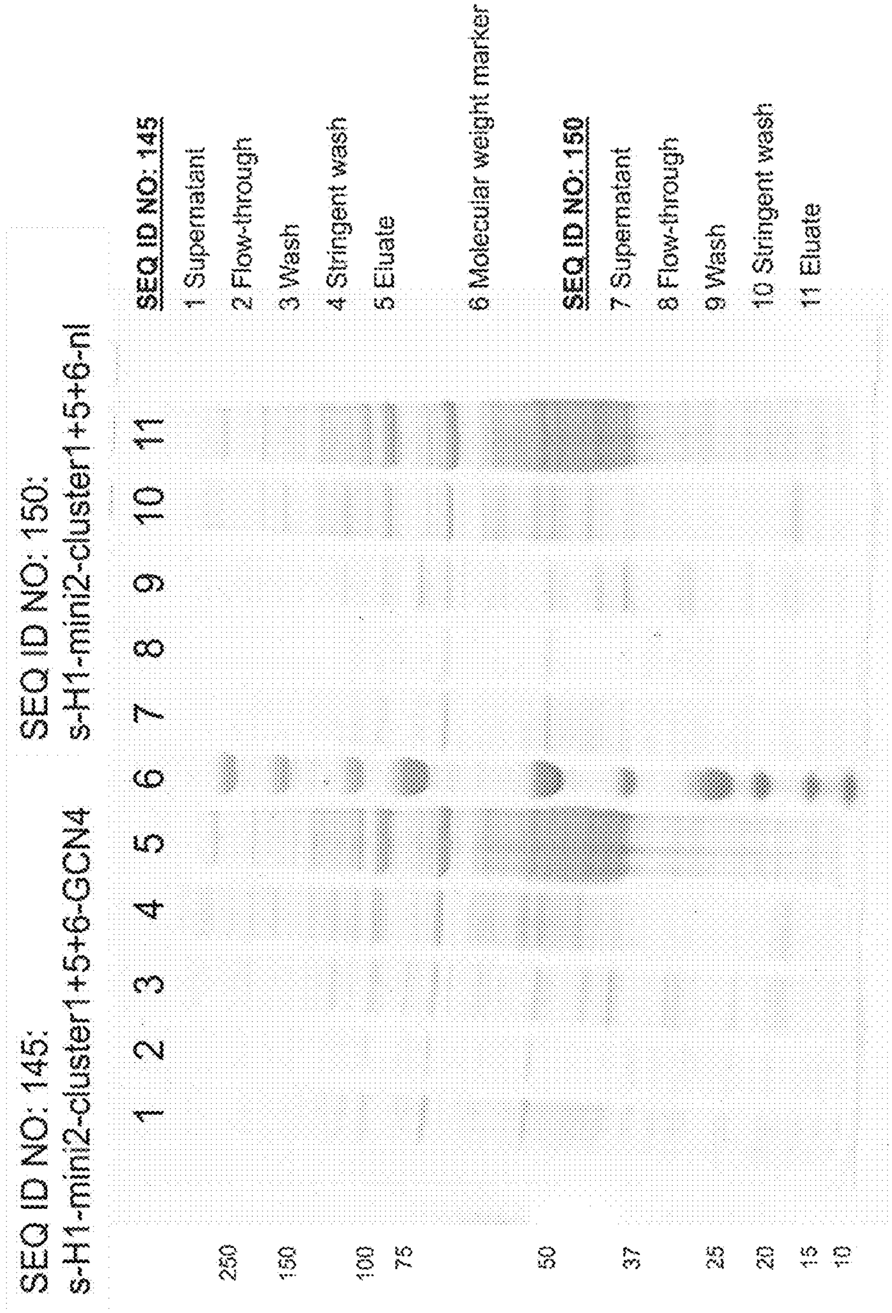
Figure 11D:
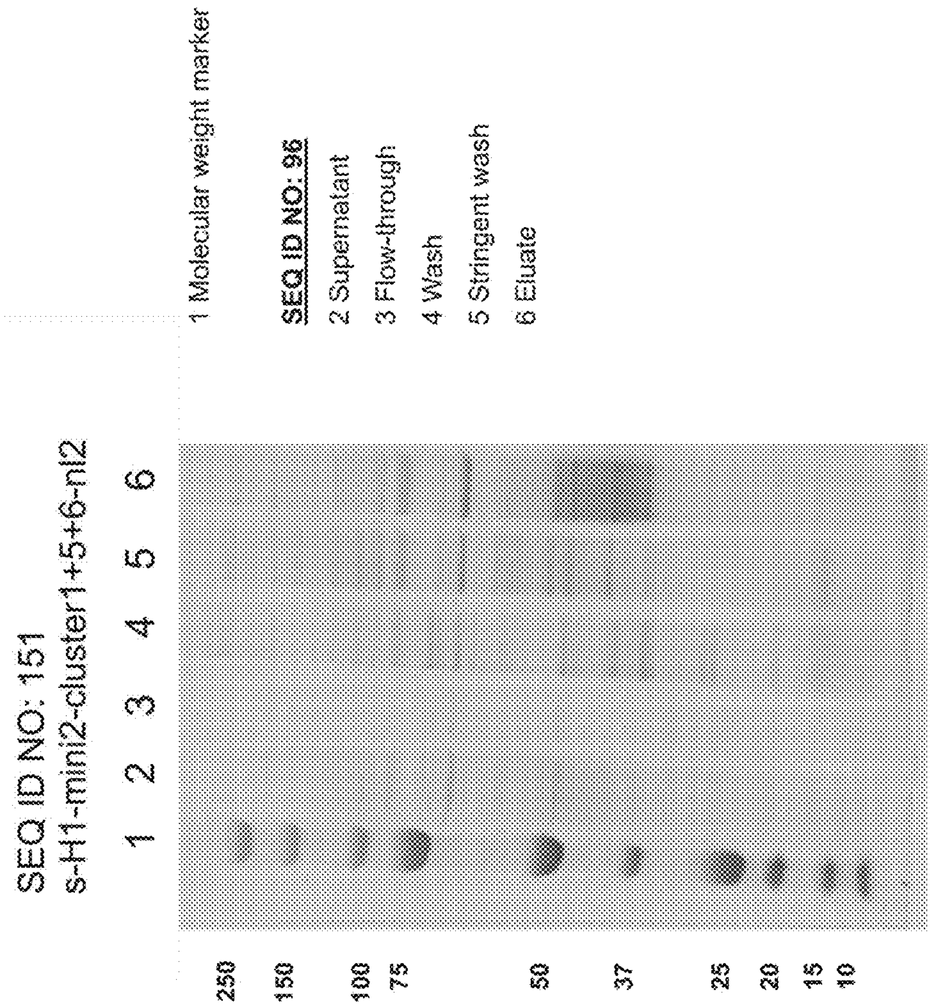
Figure 11E:
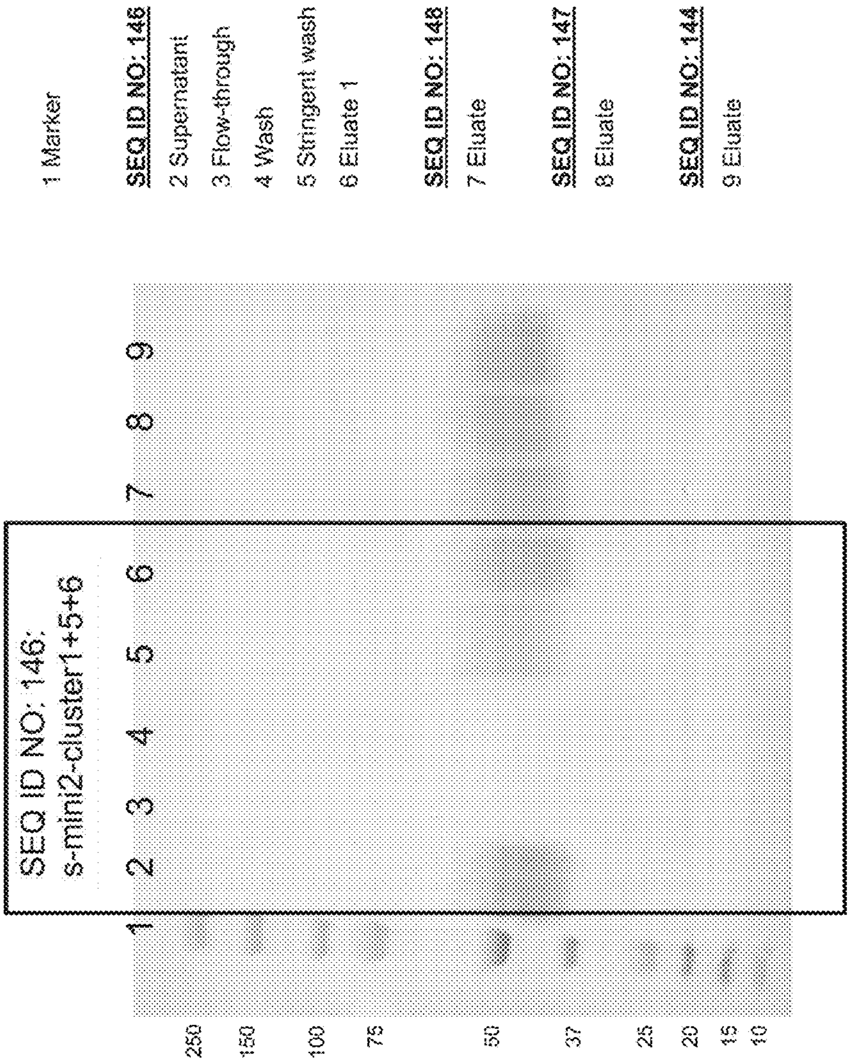
Figure 11F:
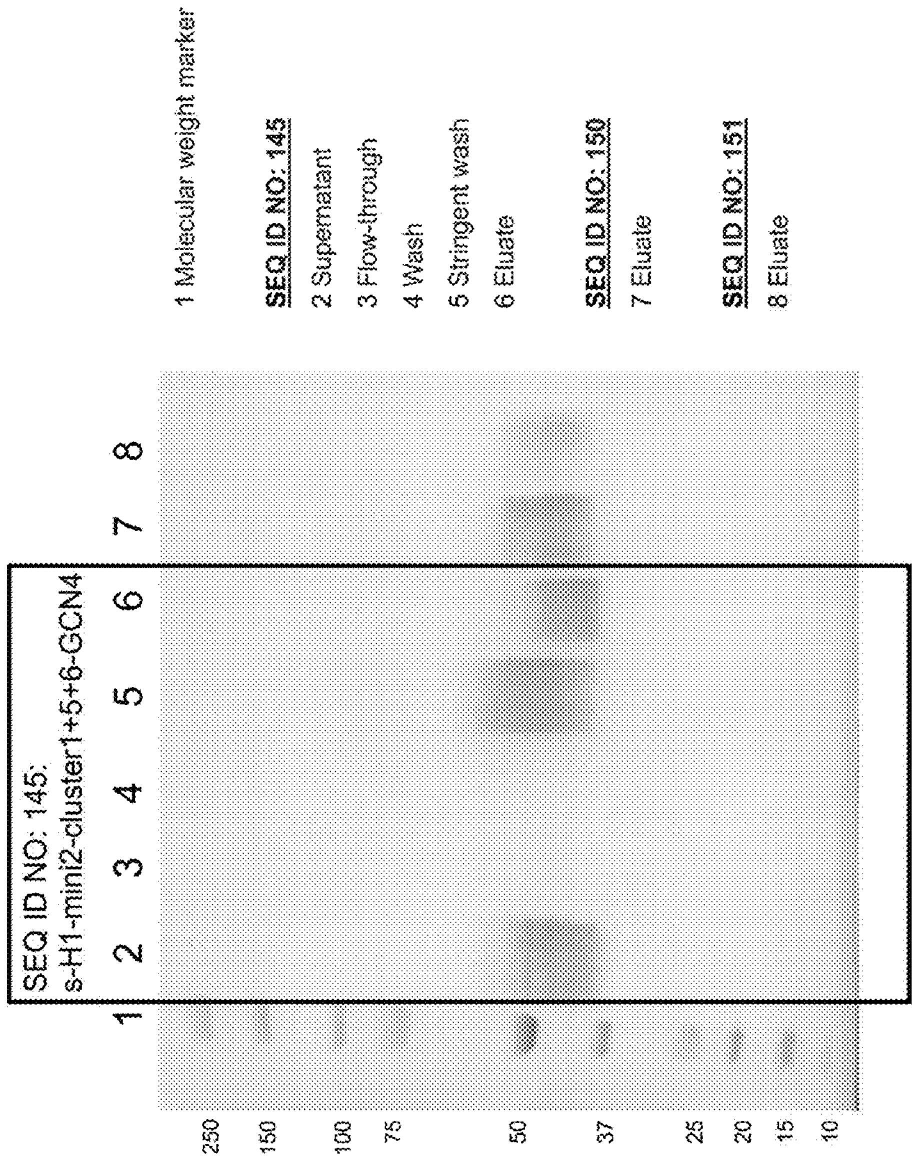

FIGS. 10A and 10B show that all A/Hong Kong/1/1968 based constructs are expressed on the cell surface since the reaction with the H3 polyclonal serum for most constructs results in ca 40-60% of all cells analyzed being positive compared to below 5% for non-transfected cells. Control experiments in the absence of IgG, using only the labeled anti-Human or anti-rabbit IgG are all negative. The percentage positive cells for the full-length protein from A/Hong Kong/1/1968 after treatment with the polyclonal serum is low (ca 10%), but strong signals obtained from the binding of CR8020, CR8043 and CR9114 indicate that the protein is present on the cell surface. CR8057 does not recognize A/Hong Kong/1/1968 based sequences, only the full-length protein from A/Wisconsin/67/2005. Four constructs (containing the cluster 12 mutation) are recognized by CR8020 and CR8043, i.e., HK68 H3m2-cl9+10+12 (SEQ ID NO: 125), HK68 H3m2-cl9+10+11+12 (SEQ ID NO: 126), HK68 H3m2-cl9+10+11+12-tri (SEQ ID NO: 128 containing the shortened tri sequence at position 421-435) and HK68 H3m2-cl9+10+11+12-GCN4 (SEQ ID NO: 130, containing the short GCN4 sequence at position 421-435), as indicated by the % positive cells (15% or higher) and MFI clearly above background. The strongest signals (MFI) are obtained for HK68 H3m2-cl9+10+11+12-GCN4 (SEQ ID NO: 130); this stem domain polypeptide construct also shows a detectable binding to CR9114.

In conclusion we have shown that following the method described above stem domain polypeptides of the disclosure can be obtained for serotypes of group 2, in particular influenza A viruses of the H3 subtype.

Example 13: Design, Expression and Partial Purification of Soluble Stem Domain Polypeptides Comprising the Conserved Stem Domain Epitopes In certain embodiments, the polypeptides hereof contain the intracellular sequences of HA and the transmembrane domain so that the resulting polypeptides are presented on the cell surface when expressed in cells. In other embodiments, the cytoplasmic sequence and the transmembrane sequence from position (or the equivalent of) 523, 524, 525, 526, 527, 528, 529 or 530 to the C-terminus of HA2 (numbering according to SEQ ID NO: 1) was removed so that expression in cells results in secreted (soluble) polypeptide which can be used, e.g., in a vaccine. The soluble polypeptide can further be stabilized by introducing a sequence known to form trimeric structures (also known as "foldon"), i.e., AYVRKDGEWVLL (SEQ ID NO: 143) optionally connected through a linker (e.g., GSGYIPEAPRDGQAYVRKDGEWVLLSTFL (SEQ ID NO: 202)). The linker may optionally contain a cleavage site for processing following purification according to protocols well known to those skilled in the art. To facilitate purification of the soluble form a tag sequence may be added, e.g., a histidine-tag (six or seven consecutive Histidines) connected via a short linker, e.g., EGR. In some embodiments, the linker and the histidine-tag are added without the foldon sequence being present.

According to the disclosure, the amino acid sequence from position 530 of the full-length HA from H1N1 A/Brisbane/59/2007 (numbering according to SEQ ID NO: 1) to the C-terminal amino acid of the HA2 domain was removed and replaced by the following sequences EGRHHHHHHH (SEQ ID NO: 81) comprising a short linker and a histidine tag. This exchange was applied to SEQ ID NO: 44: H1-mini2-cluster1+5+6-trim (resulting in SEQ ID NO: 144: s-H1-mini2-cluster1+5+6-trim), SEQ ID NO: 45: H1-mini2-cluster1+5+6-GCN4 (resulting in SEQ ID NO: 145: s-H1-mini2-cluster1+5+6-GCN4), SEQ ID NO: 46: mini2-cluster1+5+6 (A/Brisbane/59/2007) (resulting in SEQ ID NO: 146: s-H1-mini2-cluster1+5+6), SEQ ID NO: 47: mini2-cluster11+5+6 (A/Brisbane/59/2007) (resulting in SEQ ID NO: 147: s-H1-mini2-cluster11+5+6), SEQ ID NO: 48: mini2-cluster1+5 (A/Brisbane/59/2007) (resulting in SEQ ID NO: 148: s-H1-mini2-cluster1+5).

Similarly, for reasons of comparison the exchange was applied to the SEQ ID NO: 1: H1 Full-length (A/Brisbane/59/2007) and in addition the HA cleavage site was impaired by modifying Arginine 343 to a Glutamine (R343Q mutation) to yield SEQ ID NO: 149: s-H1 Full-length R343Q). Furthermore two polypeptides of the disclosure were created with a different linker between the N-terminal and C-terminal parts of HA1: s-H1-mini2-cluster1+5+6-n1 (SEQ ID NO: 150) and s-H1-mini2-cluster1+5+6-n12 (SEQ ID NO: 151).

The genes encoding the above protein sequences were synthesized and cloned into expression vector pcDNA2004neo using methods generally known to those skilled in the art. HEK293F (Invitrogen) suspension cells were transfected with the expression vectors using 293transfectin as the transfection agent following protocols well known in the art and allowed to further propagate for 7 days. Cells were separated from the culture medium by centrifugation and discarded, while the supernatant containing the soluble polypeptides of the disclosure was collected for further processing. The supernatant was purified by immobilized metal affinity chromatography on a Ni-NTA column to bind the His-tagged polypeptides of the disclosure to the resin and the flow-through was collected. The column was washed with 3-10 column volumes 20 mM sodium phosphate pH 7.4, 500 mM NaCl, 10 mM imidazole ("wash"), 5-15 column volumes 20 mM sodium phosphate pH 7.4, 500 mM NaCl, 100 mM imidazole ("stringent wash") and eluted with 20 mM sodium phosphate pH 7.4, 500 mM NaCl, 500 mM imidazole. In individual cases buffer compositions or used volumes were adapted to increase purity or yield, or a linear gradient was used instead of a step gradient. Fractions were collected throughout and analyzed on SDS-PAGE and Western blot, using a polyclonal anti-H1 HA serum for detection (see FIGS. 11A-11F). Results indicate a clear enrichment of the polypeptides hereof in the eluates compared to the starting materials.

In order to confirm proper folding and functionality of the purified polypeptides of the disclosure, the preparations were tested for binding of monoclonal antibody CR9114. To this end, a monoclonal antibody capable of binding a His-tag (6 or 7 consecutive histidines) at the C-terminus of a protein was coated on a standard 96-well plate by applying 100 microliter of a 1 μg/ml antibody solution to each well and incubating for overnight at 4° C. After removal of excess solution and washing, the plate was blocked with 150 microliter of a 2% skimmed milk solution for 1 hour at room temperature. After removal of the blocking agent and washing, 100 microliter of a 1 μg/ml solution of the polypeptides hereof, as well as the ectodomain of the corresponding full-length protein (SEQ ID NO: 149) was added and incubated for 2 hours at room temperature. After removal of excess polypeptides of the disclosure, mAb CR9114, mAb CR8020 (negative control) or polyclonal serum raised against H1 HA in rabbits (positive control) was added at concentrations varying between 2 and 20 μg/ml and incubated for 2 hours at room temperature. Binding was detected through HRP-conjugated anti-human antibody using protocols well known in the art.

Figure 12A:
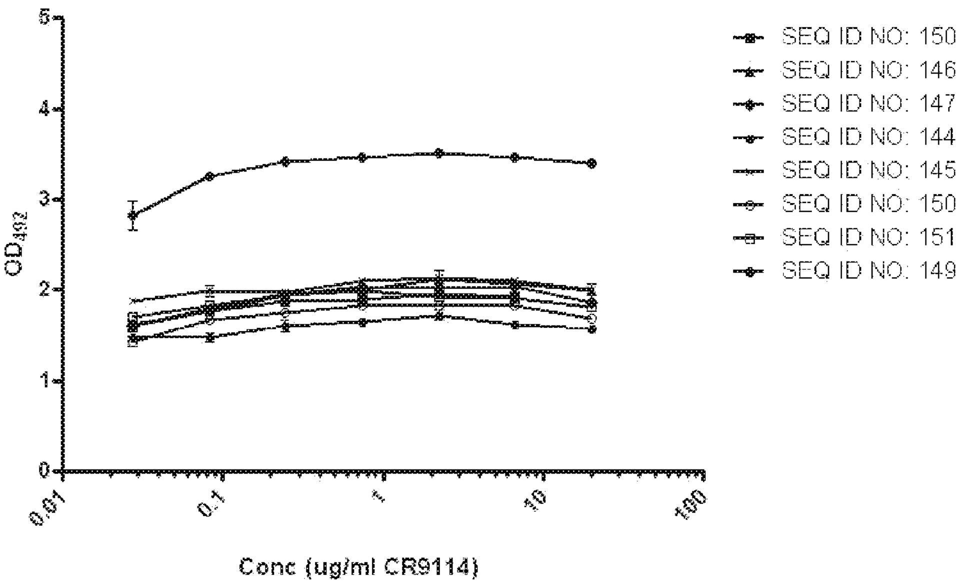
FIGS. 12A-12C: Binding of monoclonal antibody CR9114 (FIG. 12A), CR8020 (FIG. 12B) and polyclonal anti-H1 HA serum (FIG. 12C) to several polypeptides of the disclosure as detected by ELISA.
Figure 12B:
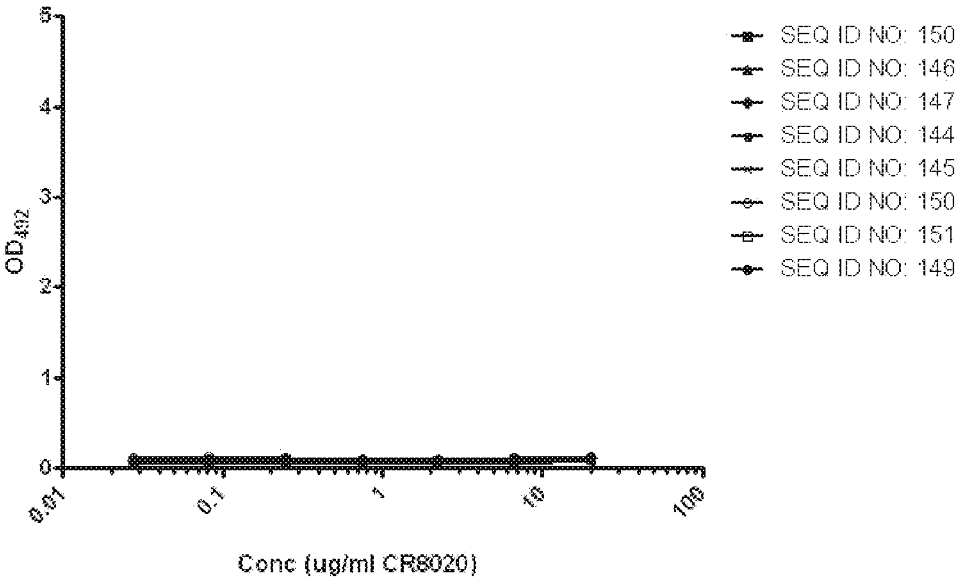
Figure 12C:
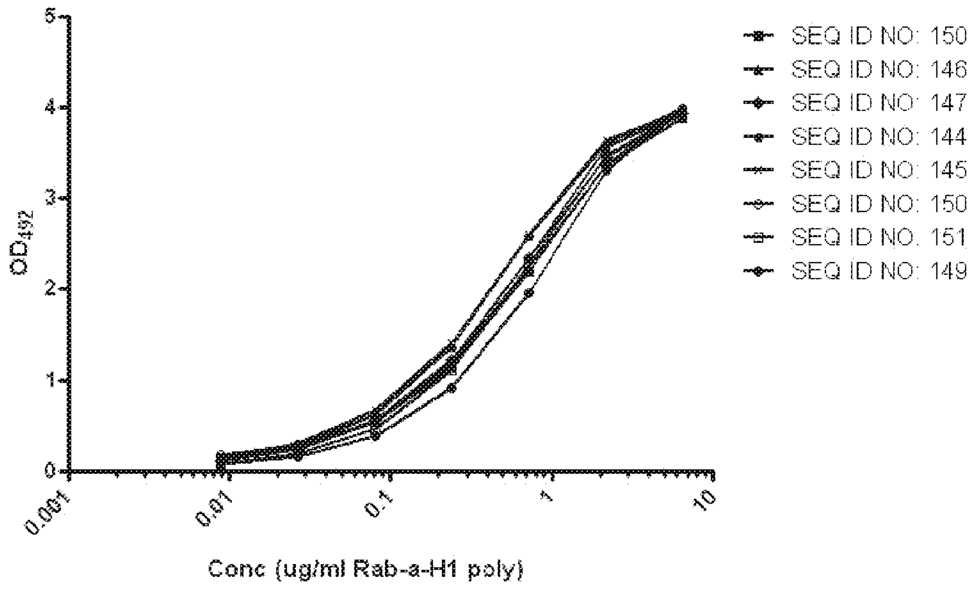

The results (FIGS. 12A-12C) show that monoclonal antibody CR9114 is binding to the purified soluble polypeptides of the disclosure, as well as to the full-length ectodomain (FIG. 12A), whereas monoclonal antibody CR8020 does not (FIG. 12B). Polyclonal anti-H1 serum also binds to the polypeptides hereof and the full-length ectodomain in a very similar manner (FIG. 12C). It is thus concluded that the broadly neutralizing epitope of CR9114 is preserved in the polypeptides hereof, and taking into account the discontinuous and conformational nature of this epitope, that the stem domain is properly folded and adopts a three-dimensional conformation equal or very similar to the conformation in the native full-length HA.

Figure 13A:
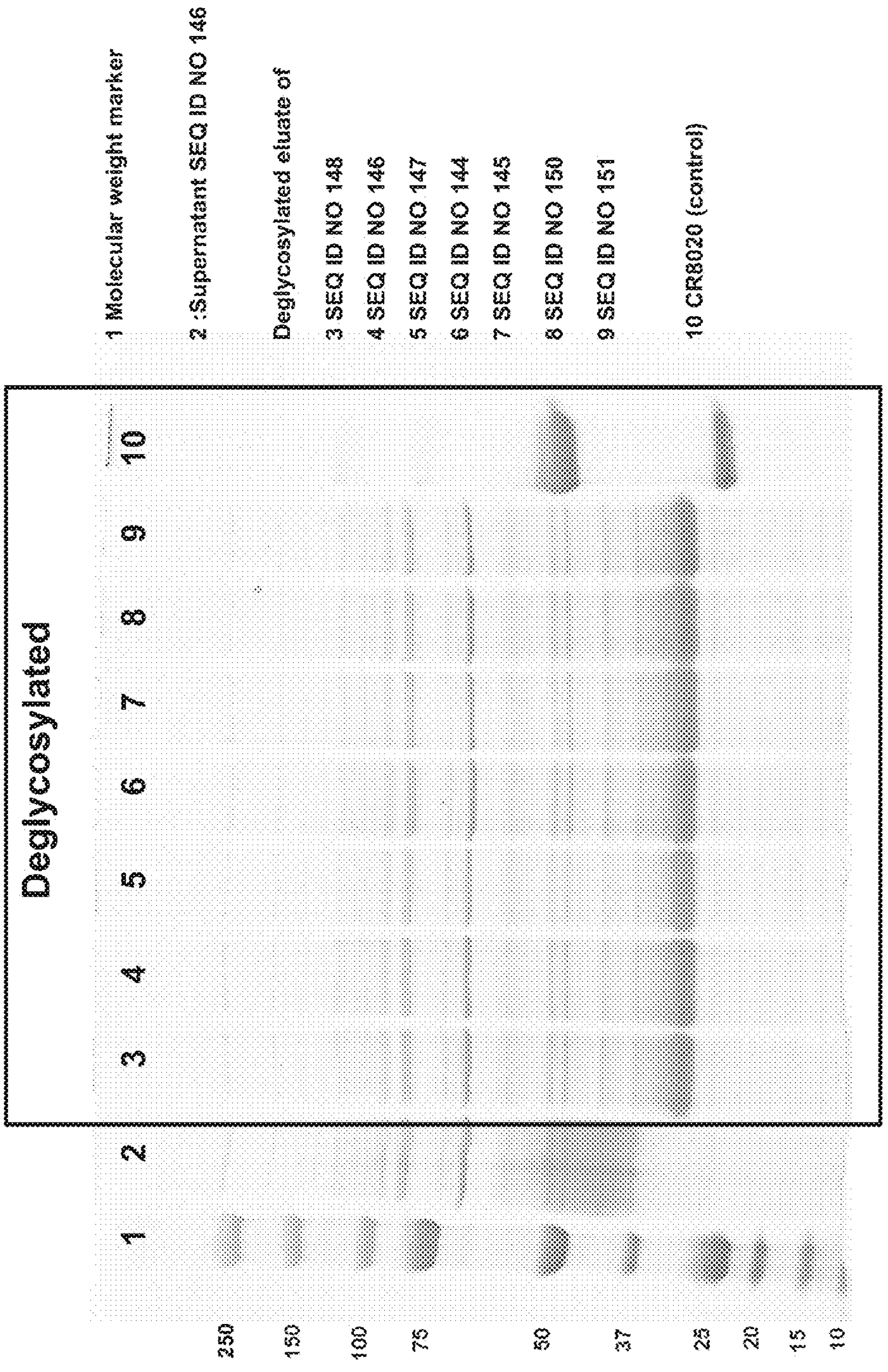
FIGS. 13A and 13B: SDS-PAGE (FIG. 13A) and Western Blot (FIG. 13B) analysis of the glycosylation of the polypeptides hereof. Upon deglycosylation, diffuse bands are focused at the expected molecular weight. For the Western Blot polyclonal serum directed against H1 HA was used for detection.
Figure 13B:
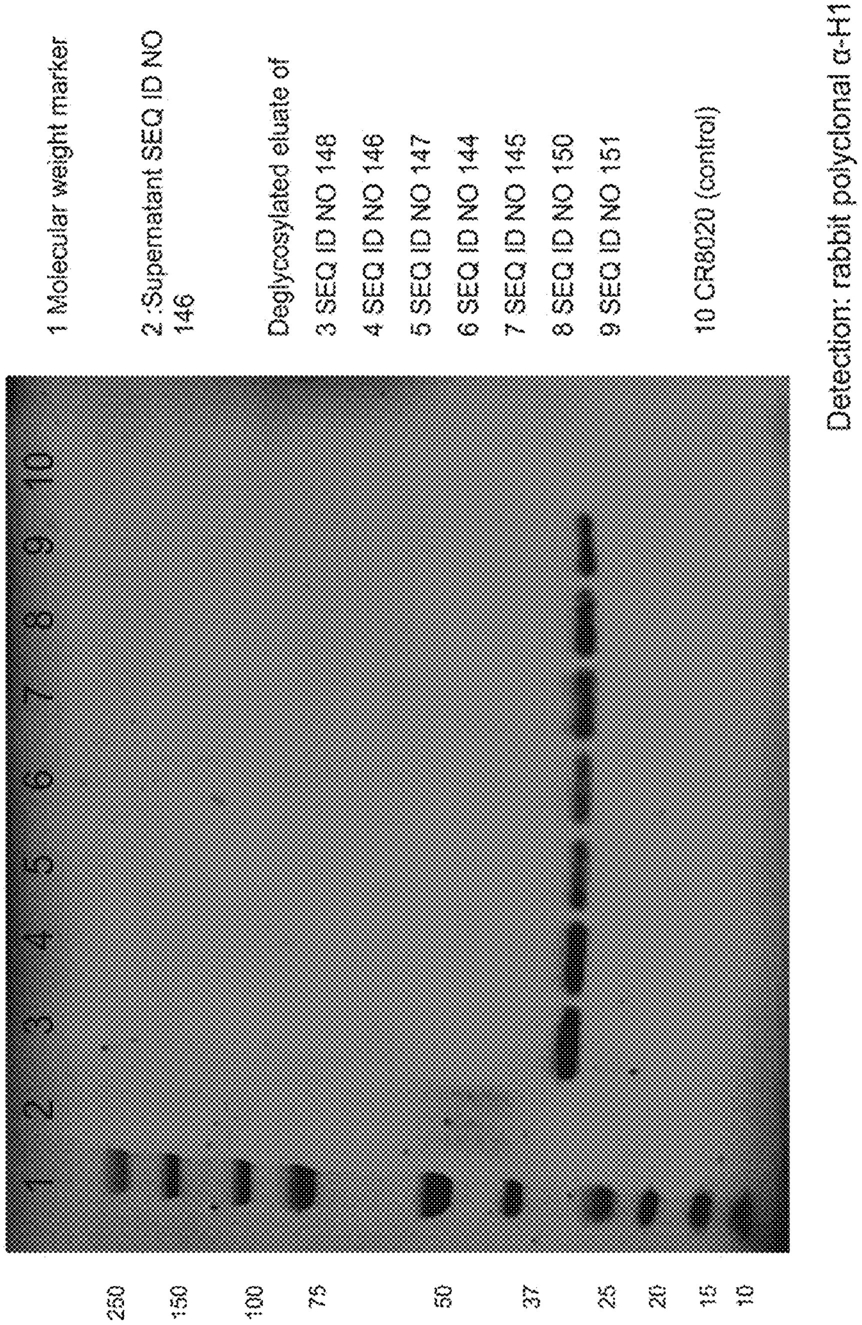

The preparations of the polypeptides hereof were inhomogeneous in size as determined from the SDS-PAGE and Western blot results. We hypothesized that the variation is due to variation in protein glycosylation patterns between individual protein molecules. To confirm this, small aliquots of the protein preparations were treated with 3 units of N-glycosidase F (an enzyme that removes N-linked carbohydrate moieties from Asparagine residues) for 18 hours at 37° C. and analyzed by SDS-PAGE and Western Blot. The results (FIGS. 13A and 13B) show that treatment with the N-glycosidase focuses the diffuse bands of the polypeptides hereof to a single band at the expected molecular weight calculated from the amino acid sequence. This is clear evidence that the observed size inhomogeneity indeed arises from variation in glycosylation patterns.

Figure 14:
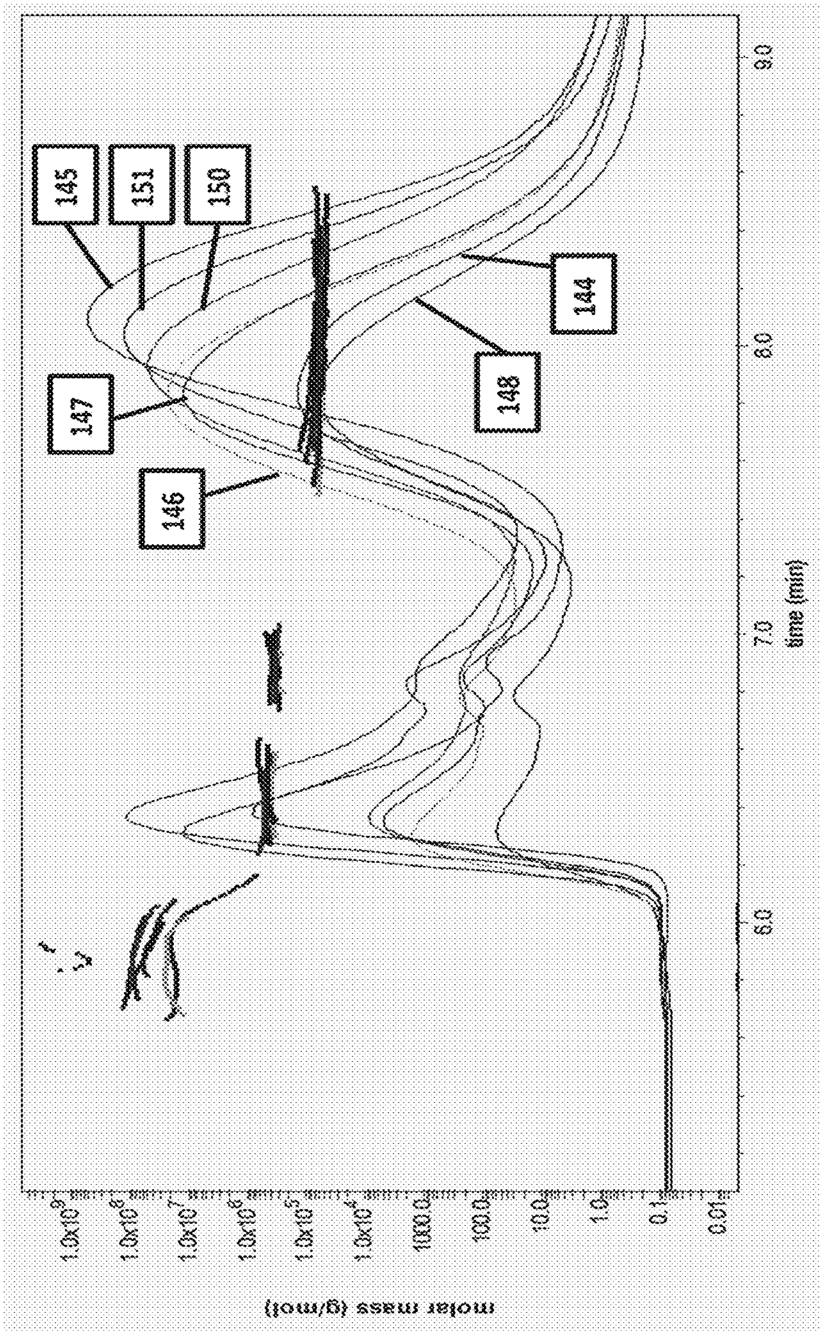
FIG. 14: SEC-MALS analysis of polypeptides of the disclosure. Traces are labeled with the SEQ ID NO.

The preparations of the polypeptides hereof were further characterized by HP-SEC. To this end, approximately 40 μg of the polypeptides hereof in a volume between 43 and 63 μl (concentration of polypeptide between 0.64 and 0.93 mg/ml) was applied to a Tosoh TSK-gel G2000 SW×1 column connected to a multi-angle light scattering detector. Results are shown in FIG. 14. The main peak (retention time ca 8 minutes) arises from the polypeptides hereof, and is well separated from the larger species, indicating that further purification can be achieved. Based on the data of the multi-angle light scattering detector the main peaks correspond to a molecular species with molecular weight between 50 and 80 kilo Dalton (see Table 9) depending on the polypeptide of the disclosure under study. In light of the size inhomogeneity and variety in polypeptide glycosylation described above, as well as the dependence of the results on the hydrodynamic shape of the molecules, these numbers should be taken as an indication only.

Example 14: Expression and Partial Purification of a Soluble Stem Domain Polypeptide Comprising the Conserved Stem Domain Epitope of Monoclonal Antibodies CR9114, CR6261 and FI6v3

In order to obtain a highly pure preparation of a polypeptide of the disclosure, HEK293F cells were transfected with expression vector pcDNA2004 containing the gene encoding s-H1-mini2-cluster1+5+6-GCN4 (SEQ ID NO: 145). It will be understood by the skilled person that the leader sequence (or signal sequence) that directs transport of a protein during production (corresponding to amino acids 1-17 of SEQ ID NO: 145) will not be present in the secreted final polypeptide. To this end, 1.0*$10^6$ vc/mL were seeded by spinning down HEK293F cells (Invitrogen) at 300 g for 5 minutes and resuspending in 300 mL pre-warmed FREESTYLE™ medium per SF1000. This culture was incubated for 1 hour at 37° C., 10% $CO_2$ at 110 rpm in a multitron incubator. After 1 hour the plasmid DNA was pipetted in 9.9 mL Opti-MEM® medium to a concentration of 1.0 μg/mL in the 300 mL culture volume. In parallel 440 μL 293Fectin® was pipetted in 9.9 mL Opti-MEM® medium and incubated for 5 minutes at room temperature. After 5 minutes the plasmid DNA/Opti-MEM® mix was added to the 293Fectin®/Opti-MEM® mix and incubated at room temperature for 20 minutes. After the incubation the plasmid DNA/293Fectin® mix was added drop wise to the cell suspension. The transfected cultured was incubated at 37° C., 10% $CO_2$ and 110 rpm in a multitron incubator. At day 7, cells were separated from the culture medium by centrifugation (30 minutes at 3000 g), while the supernatant containing the soluble polypeptides of the disclosure was filtrated over a 0.2 μm bottle top filter for further processing.

Figure 15A:
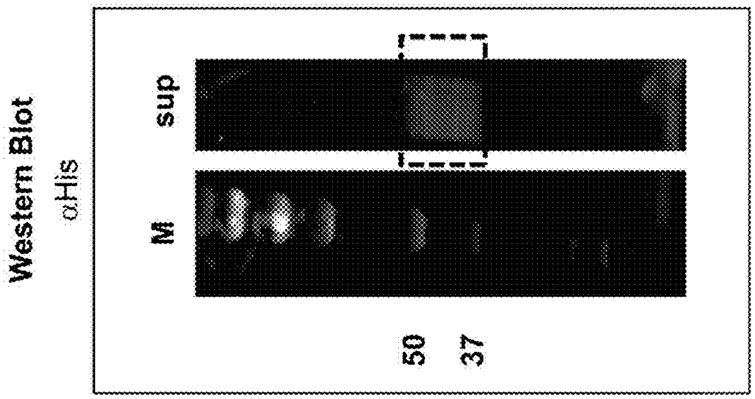
FIGS. 15A and 15B.

To verify the presence of the polypeptide of the disclosure, a small aliquot of the supernatant was analyzed by Western Blot, using a monoclonal antibody directed against the his-tag for detection (FIG. 15A). Several bands were observed at an apparent molecular weight between 37 and 50 kDa, which is close to or above the calculated molecular weight based on the amino acid composition of the protein. The size in homogeneity is caused by variation in glycosylation patterns, since earlier experiments have shown that treatment of this protein with N-glycosidase F to remove attached N-linked glycans from the protein results in focusing of the band at the expected molecular weight.

Figure 15B:
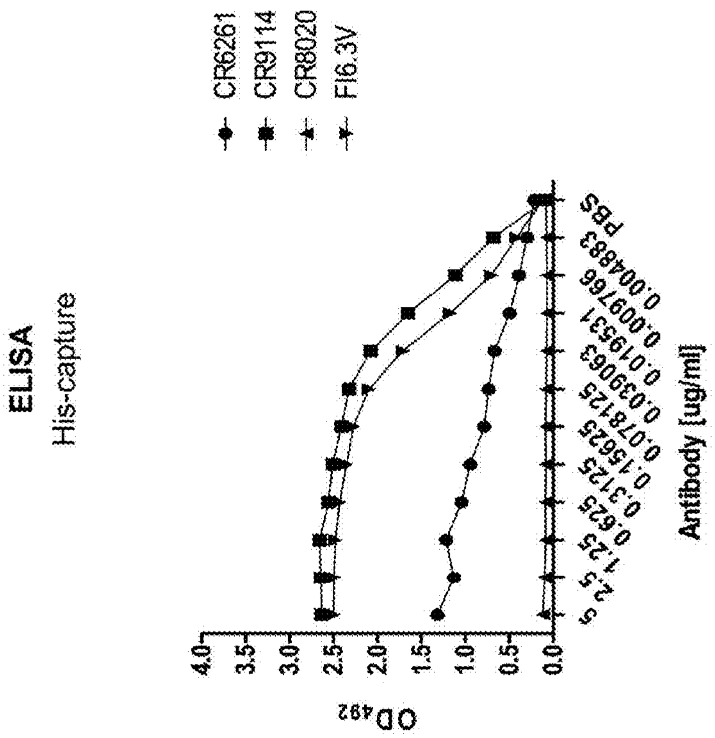

The presence of the broadly neutralizing epitopes on the polypeptide of the disclosure was confirmed by ELISA, using broadly neutralizing antibodies CR6261, CR9114 and FI6v3 as probes. For reasons of comparison monoclonal antibody CR8020 was also included as a negative control in the experiment; this antibody is capable of binding to HA molecules from group 2 viruses (e.g., H3 and H7 HA), but not from group 1 (e.g., H1 and H5 HA). To this end, a monoclonal antibody capable of binding a His-tag (6 or 7 consecutive histidines) at the C-terminus of a protein was coated on a standard 96-well plate by applying 100 microliter of a 1 μg/ml antibody solution to each well and incubation overnight at 4° C. After removal of excess solution and washing, the plate was blocked with 150 microliter of a 2% skimmed milk solution for 1 hour at room temperature. After removal of the blocking agent and washing, 100 microliter of the supernatant was added and incubated for 2 hours at room temperature. After removal of excess polypeptides of the disclosure, mAb CR9114 was added, in a 1:2 dilution series starting at a 5 μg/ml concentration, and incubated for 2 hours at room temperature. Binding was detected through HRP-conjugated anti-human antibodies using protocols well known in the art. Clear binding of CR9114, FI6v3 and to a lesser extent CR6261 to the polypeptide of the disclosure is observed, whereas no response is observed for CR8020 indicating that the observed binding is specific for the monoclonal antibodies tested (FIG. 15B).

Figure 16:
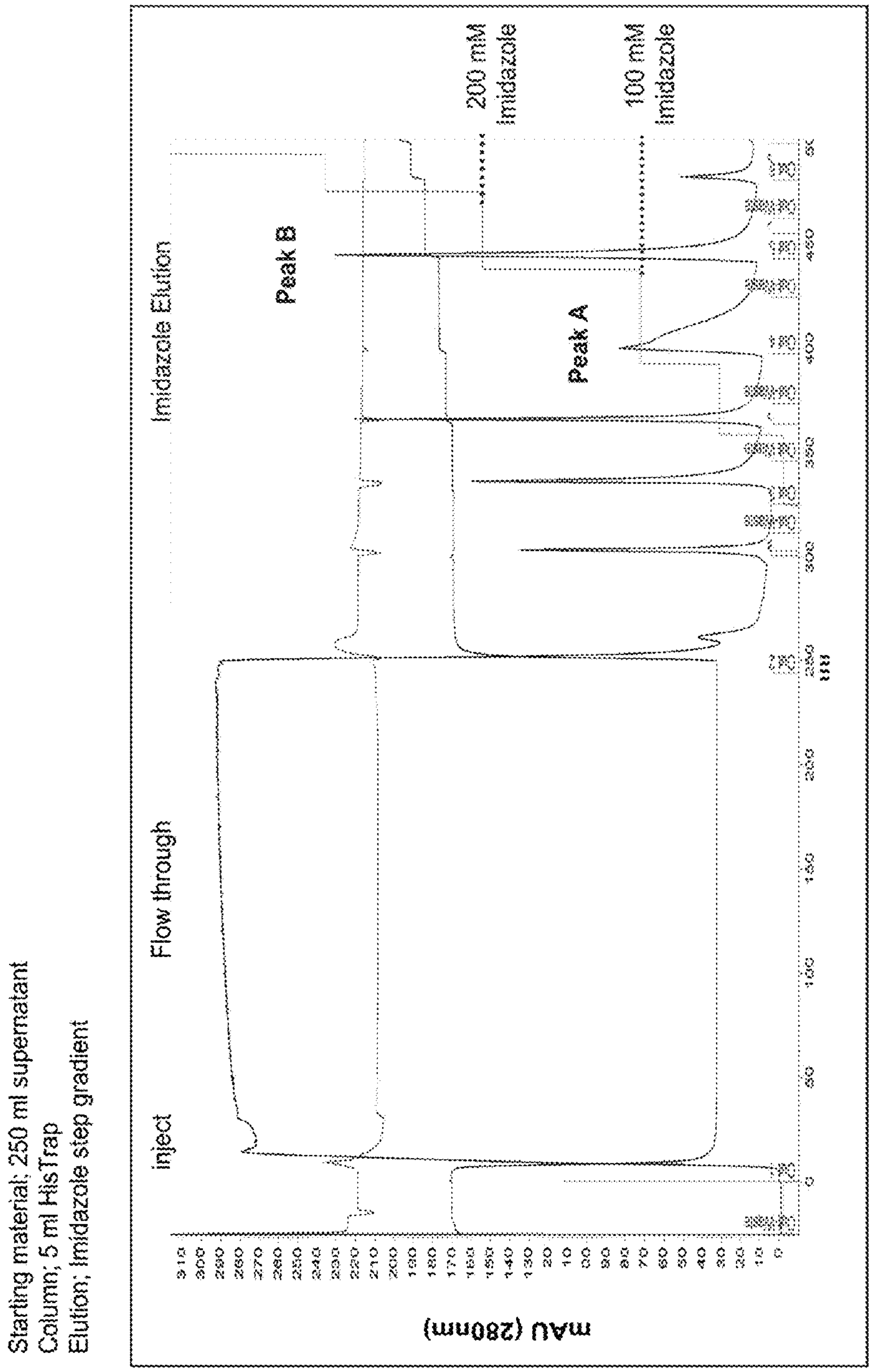
FIG. 16: Elution profile of the purification of SEQ ID NO: 145 from culture supernatant on a His trap column. The polypeptide of the disclosure elutes at 100 (peak A) and 200 mM (peak B) imidazole, respectively.
Figure 17:
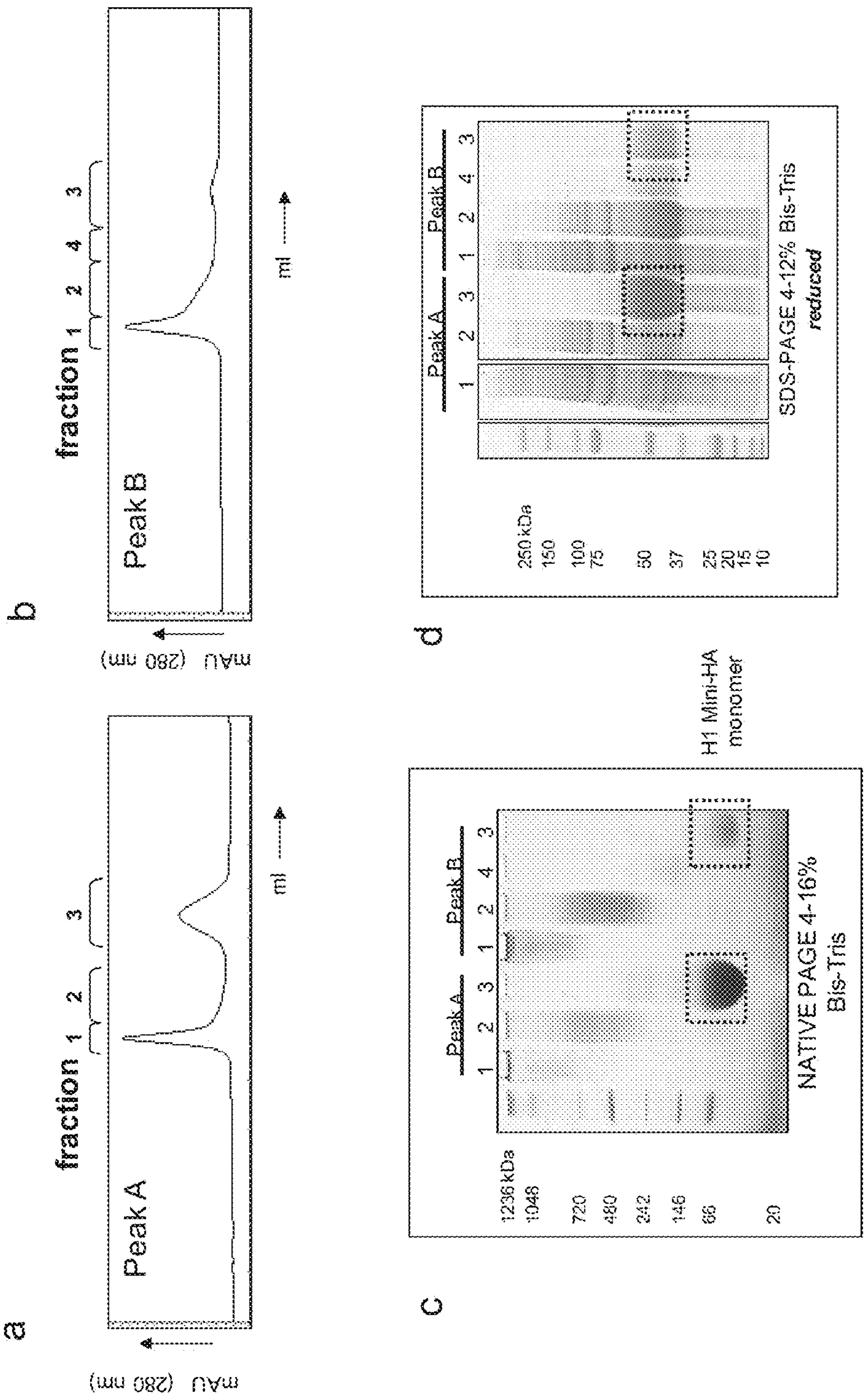
FIG. 17: Panels a and b: Elution profile of the purification of SEQ ID NO: 145 by size exclusion chromatography (Superdex 200). Both peaks A and B contain polypeptide of the disclosure. Panel c: Native PAGE analysis of fractions from the size exclusion chromatography. The majority of the purified protein runs at a molecular weight consistent with a monomeric form of the protein. Panel d: SDS PAGE analysis of fractions from the size exclusion chromatography.

For purification purposes, 250 ml of culture supernatant was applied to a 5 ml His-trap column, washed with 75 ml wash buffer (20 mM TRIS, 500 mM NaCl, pH 7.8), and eluted with a step-wise gradients of imidazole (10, 50, 100, 200, 300 and 500 mM in wash buffer). The chromatogram (FIG. 16) exhibits multiple peaks, with the polypeptides hereof eluting at 100 mM imidazole (peak A) and 200 mM imidazole (peak B). Both peaks were collected, concentrated, and applied to a size exclusion column for further purification (Superdex 200). Elution profiles are shown in FIG. 17, Panels a and b. Fractions were collected and analyzed on SDS-PAGE (FIG. 17, Panels c and d). Fraction 3 derived from both peak A and B contain highly pure polypeptide of the disclosure. The final yield was ca 10 μg/ml of culture supernatant. Purified batches are free of endotoxin (dosing at 5 mg/kg; <1 EU/mg); Chromogenic LAL) and bio burden is below 1 CFU/50 μg.

Example 15: Design of a Stem Domain Polypeptide Comprising the Conserved Stem Domain Epitope of CR9114 Based on Influenza B HA The procedure described above to design polypeptides of the disclosure was also applied to Influenza B. In this Example, polypeptides of the disclosure on the basis of HA sequences taken from virus strains of both known lineages, i.e., B/Florida/4/2006 (B/Yamagata lineage) and B/Malaysia/2506/2004 (B/Victoria lineage) are described. Those skilled in the art will understand that the use of other Influenza B HA sequences is also possible because the sequences are well conserved, in particular in the stem region. Therefore, polypeptides derived from other Influenza B HA sequences according to the description below are also encompassed by the disclosure.

The first modification in the HA sequence of B/Florida/4/2006 was the removal of the cleavage site at position 361 (numbering refers to SEQ ID NO: 132) by mutating R (or in a limited number of cases K) to Q (R361Q) to prevent the formation of HA1 and HA2 from HA0. Optionally, residue 363 to 367 (GFGAI, part of the fusion peptide) (numbering refers to SEQ ID NO: 132) can additionally be deleted to minimize the exposure of hydrophobic residues to the aqueous solvent. The positive charge at the cleavage is 100% conserved in HA from Influenza B and this mutation can, therefore, be applied in all sequences.

The second modification is the removal of the head domain by deleting a large part of the HA1 sequence and reconnecting the N- and C-terminal sequences through a short linker. The deletion can vary in length, but it is preferred that the last residue of the N-terminal sequence of HA1 and the first residue of the C-terminal sequence are spatially close together to avoid introducing strain through the linking sequence. In B sequences deletions can be introduced at (the equivalent positions of) P51-I336 (m2; SEQ ID NO: 133) in B/Florida/4/2006 (SEQ ID NO: 132). Equivalent positions can be easily determined by those skilled in the art by aligning the sequences using a suitable algorithm such as, e.g., Clustal or Muscle. The remaining parts of the sequence can be joined directly or alternatively a flexible linker can be introduced. Linker sequences can be 1 to 50 amino acids in length. Preferred are flexible linkers of limited length (smaller or equal to 10 amino acids), e.g., GGG, GGGG (SEQ ID NO: 194), GSA, GSAG (SEQ ID NO: 193), GSAGSA (SEQ ID NO: 189), GSAGSAG (SEQ ID NO: 188) or similar.

SEQ ID NO: 133 describes such a polypeptide of the disclosure containing deletion P51-I332 (m2; SEQ ID NO: 133). The deletions described above ensure that the unstructured regions formed by residues between P51 and N58 and between E306 and 1337 are also removed; this is beneficial to the overall stability of the polypeptides hereof. A similar effect was observed for polypeptides of the disclosure derived from a H1 sequence (see above).

The deletion of the head domain leaves the loop between residues 416 to 436 now exposed to the aqueous solvent. In B HAs, this loop is highly conserved (see Table 10). The consensus sequence is: LSELEVKNLQRLSGAMDELHN (SEQ ID NO: 203).

To increase the solubility of this loop in the pre-fusion conformation and destabilize the post-fusion conformation some hydrophobic residues were modified into polar (S, T, N, Q), charged amino acids (R, H, K, D, E), or flexibility has to be increased by mutation to G. Specifically mutations at positions 421, 424, 427, 434 (numbering refers to SEQ ID NO: 132) will contribute to the stability of a polypeptide of the disclosure.

For positions V421 and L427 mutation to T is preferred but other polar (S, N, Q), charged (R, H, K, D, E) and highly flexible amino acids (G) will have the same effect. For position 424, mutation to S is preferred. Other polar (N, T, Q), charged (R, H, K, D, E) and highly flexible amino acids (G) will have the same. For position L434 mutation to G is preferred. Other polar (S, T, N, Q), charged (R, H, K, D, E) will have the same effect. Polypeptides containing at least one of the mutations described above were made. Combinations of more than one mutation are also possible, as shown, for example, in SEQ ID NOs: 134-136.

To stabilize the pre-fusion conformation of polypeptides of the disclosure a covalent bond between two parts distant in the primary sequences but close in the folded pre-fusion conformation was introduced. To this end, a disulfide bridge is engineered in the polypeptides, preferably between (the equivalent of) position K340 and S454 in HA from B/Florida/4/2006 (SEQ ID NOS: 134-136). Equivalent positions can be easily determined by those skilled in the art by aligning the sequences using a suitable algorithm such as Clustal, Muscle, etc. Engineered disulfide bridges are created by mutating at least one (if the other is already a cysteine), but usually two residues that are spatially close into cysteine, that will spontaneously or by active oxidation form a covalent bond between the sulfur atoms of these residues.

In the stem domain trimerization is mediated by the formation of a trimeric coiled coil motif. By strengthening this motif a more stable trimer can be created. Sequences supporting the formation of a trimeric coiled coil derived from GCN4 are introduced at (the equivalent of) position 436 to 452 RRMKQIEDKIEEILSKI (SEQ ID NO: 135), or alternatively RMKQIEDKIEEILSKI at position 436 to 451 (SEQ ID NO: 136).

The same procedure was followed for HA from B/Malaysia/2506/2004 (SEQ ID NO: 137) to provide polypeptides. Compared to HA from B/Florida/4/2006 this HA has an additional asparagine residue inserted at position 178 as can be readily seen in an alignment of the two sequences. Consequently the cleavage site is at position 362, and the corresponding mutation to prevent cleavage is R362Q. The deletion to remove the head region of in this case is, for example, P51 to 1337 (m2; SEQ ID NO: 138). Again the remaining parts of the sequence can be joined directly or alternatively a flexible linker can be introduced. Linker sequences can be 1 to 50 amino acids in length. Preferred are flexible linkers of limited length (smaller or equal to 10 amino acids), e.g., GGG, GGGG (SEQ ID NO: 194), GSA, GSAG (SEQ ID NO: 193), GSAGSA (SEQ ID NO: 189), GSAGSAG (SEQ ID NO: 188) or similar.

SEQ ID NO: 138 describes such a polypeptide-containing deletion P51-I332 (m2; SEQ ID NO: 138). The deletions described above ensure that the unstructured regions formed by residues between P51 and N58 and between E307 and I338 are also removed; this is beneficial to the overall stability of the polypeptides hereof. A similar effect was observed for polypeptides of the disclosure derived from a H1 sequence (see above).

The deletion of the head domain leaves the loop between residues L420 to H436 now exposed to the aqueous solvent. In B HAs, this loop is highly conserved (see Table 10). The consensus sequence is: LSELEVKNLQRLSGAMDELHN (SEQ ID NO: 203).

To increase the solubility of this loop in the pre-fusion conformation and destabilize the post-fusion conformation some hydrophobic residues were modified into polar (S, T, N, Q), charged amino acids (R, H, K, D, E), or flexibility has to be increased by mutation to G. Specifically mutations at positions 422, 425, 428, 435 (numbering refers to SEQ ID NO: 137) were tested.

For positions V422 and L428 mutation to T is preferred but other polar (S, N, Q), charged (R, H, K, D, E) and highly flexible amino acids (G) will have the same effect. For position 425, mutation to S is preferred. Other polar (N, T, Q), charged (R, H, K, D, E) and highly flexible amino acids (G) will have the same. For position L435 mutation to G is preferred. Other polar (S, T, N, Q), charged (R, H, K, D, E) will have the same. Polypeptides containing at least one of the mutations described above were made. Combinations of more than one mutation are also possible, as shown, for example, in SEQ ID NOs: 139-141.

To stabilize the pre-fusion conformation of polypeptides of the disclosure a covalent bond between two parts distant in the primary sequences but close in the folded pre-fusion conformation is introduced. To this end, a disulfide bridge is engineered in the polypeptides hereof, preferably between (the equivalent of) position K341 and S455 in HA from B/Malaysia/2506/2004 (SEQ ID NOS: 139-141). Equivalent positions can be easily determined by those skilled in the art by aligning the sequences using a suitable algorithm such as Clustal, Muscle, etc. Engineered disulfide bridges are created by mutating at least one (if the other is already a cysteine), but usually two residues that are spatially close into cysteine, that will spontaneously or by active oxidation form a covalent bond between the sulfur atoms of these residues.

As described above, the native HA exists as a trimer on the cell surface. Most of the interactions between the individual monomers that keep the trimer together are located in the head domain. After removal of the head the tertiary structure is thus destabilized and, therefore, reinforcing the interactions between the monomers in the truncated molecule will increase the stability. In the stem domain trimerization is mediated by the formation of a trimeric coiled coil motif. By strengthening this motif a more stable trimer can be created. Sequences supporting the formation of a trimeric coiled coil derived from GCN4 are introduced at (the equivalent of) position 437 to 453 RRMKQIEDKIEEILSKI (SEQ ID NO: 135), or alternatively RMKQIEDKIEEILSKI at position 437 to 452 (SEQ ID NO: 136).

The polypeptides based on influenza B hemagglutinin, SEQ ID NOS: 133-136 and 138-141 were tested for the presence of the epitope of CR9114 by Fluorescence Associated C ell Sorting as described above. However, no binding of mAb CR9114 was observed for these constructs.

Example 16: Immunogenicity of Third Generation HA Stem Domain Polypeptides

In order to assess the immunogenicity of the stem domain polypeptides mice were immunized with the expression vectors encoding full-length H1 from A/Brisbane/59/2007 (SEQ ID NO: 1), Mini3-cluster11 (SEQ ID NO: 11), Mini2-cluster11+5 (SEQ ID NO: 14), mini2-cluster1+5 (SEQ ID NO: 48), mini2-cluster1+5+6 (SEQ ID NO: 46), mini2-cluster1+5+6-GCN4 (SEQ ID NO: 45) and mini2-cluster1+5+6-n1 (SEQ ID NO: 152). An expression vector encoding for cM2 was also included as a negative control.

Groups of 4 mice (BALB\c) were immunized with 50 μg construct+50 μg adjuvant (pUMCV1-GM-CSF) i.m. on day 1, 21 and 42. On day 49 a final bleed was performed and serum collected. The sera were analyzed by ELISA using the recombinant ectodomains of the full-length HA from the A/Brisbane/59/2007 and the A/California/07/2009 strains (obtained from Protein Sciences Corporation, Meriden, Conn., USA) as the antigen. In short, 96-well plates were coated with 50 ng HA overnight at 4° C., followed by incubation with block buffer (100 μl PBS, pH 7.4+2% skim milk) for 1 hour at room temperature. Plates were washed with PBS+0.05% TWEEN®-20, and 100 μl of a 2-fold dilution series in block buffer, starting from a 20-fold dilution of the serum is added. Bound antibody is detected using HRP-conjugated goat-anti-mouse IgG, using standard protocols well-established in the art. Titers are compared to a standard curve using mAb 3AH1 InA134 (Hytest, Turku, Finland) to derive ELISA units/ml (EU/ml).

Figure 18:
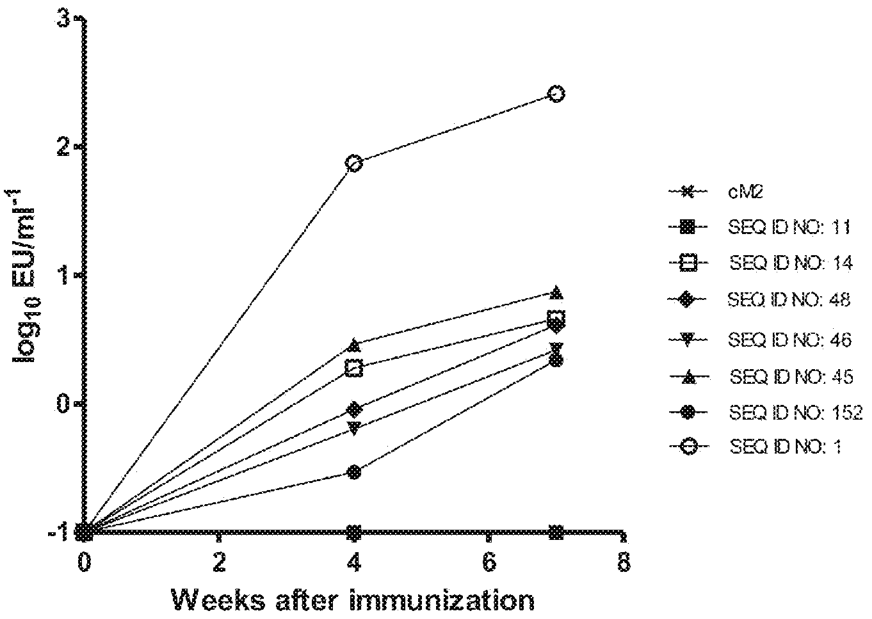
FIG. 18: Time course of the IgG response towards the ectodomain of the homologous full-length protein as a result of the DNA immunization schedule described in this application.

The time course of the IgG response towards the ectodomain of the homologous full-length protein induced by the immunization schedule described above are shown in FIG. 18. A high response can already be observed for the mice immunized with DNA (SEQ ID NO: 1) encoding the full-length protein after 4 weeks. The response is increased by a boost injection, as shown from the increased titer at 7 weeks. Immunization with DNA encoding polypeptides of the disclosure mini2-cluster11+5 (SEQ ID NO: 14), mini2-cluster1+5 (SEQ ID NO: 48), mini2-cluster1+5+6 (SEQ ID NO: 46), mini2-cluster1+5+6-GCN4 (SEQ ID NO: 45) and mini2-cluster1+5+6-n1 (SEQ ID NO: 152) leads to intermediate titers that are further increased upon a booster immunization as evidenced from titers at week 7. Immunization with DNA encoding Mini3-cluster11 (SEQ ID NO: 11) and negative control cM2 do not result in a detectable response in this assay.

Figure 19A:
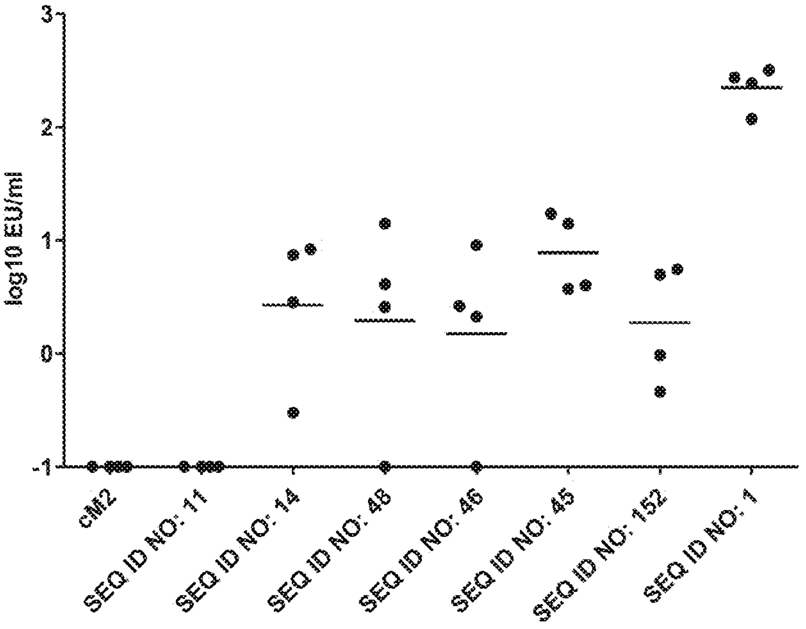
FIGS. 19A and 19B: IgG responses at week 7 after initial immunization for individual mice against the ectodomain of the full-length hemagglutinin from the homologous strain H1N1 A/Brisbane/59/2007 (FIG. 19A) and the heterologous strain H1N1 A/California/07/2009 (FIG. 19B). Open symbols correspond to values below the limit of detection of the assay.
Figure 19B:
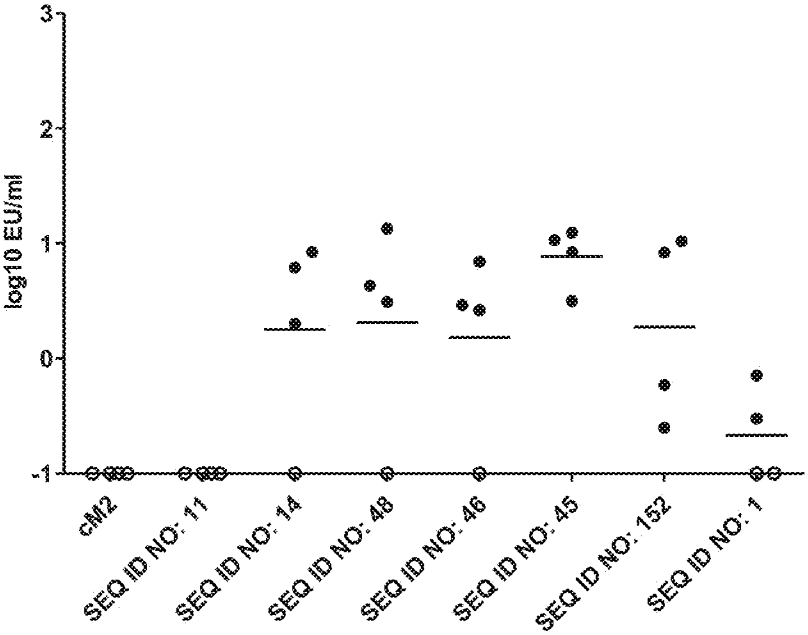

FIGS. 19A and 19B exhibit the IgG responses at week 7 after initial immunization for individual mice against the ectodomain of the full-length hemagglutinin from the homologous strain H1N1 A/Brisbane/59/2007 (FIG. 19A) and the heterologous strain H1N1 A/California/07/2009. Antibodies induced by DNA encoding polypeptides of the disclosure mini2-cluster11+5 (SEQ ID NO: 14), mini2-cluster1+5 (SEQ ID NO: 48), mini2-cluster1+5+6 (SEQ ID NO: 46), mini2-cluster1+5+6-GCN4 (SEQ ID NO: 45) and mini2-cluster1+5+6-n1 (SEQ ID NO: 152) bind equally well to the ectodomain of hemagglutinin derived from the homologous and heterologous strain. In contrast, immunization with DNA encoding the full-length protein (SEQ ID NO: 1) results in high titers against the homologous hemagglutinin (more than an order of magnitude higher than titers observed for immunization with DNA encoding the polypeptides hereof), but in low titers against the ectodomain of the heterologous hemagglutinin. Immunization with DNA encoding Mini3-cluster11 (SEQ ID NO: 11) and negative control cM2 do not result in a detectable response against either of the hemagglutinin ectodomains in this assay.

In conclusion, antibodies raised against the polypeptides hereof mini2-cluster11+5 (SEQ ID NO: 14), mini2-cluster1+5 (SEQ ID NO: 48), mini2-cluster1+5+6 (SEQ ID NO: 46), mini2-cluster1+5+6-GCN4 (SEQ ID NO: 45) and mini2-cluster1+5+6-n1 (SEQ ID NO: 152) are capable of recognizing full-length hemagglutinin. Their epitopes necessarily are located on the hemagglutinin stem domain and are conserved between the full-length hemagglutinins from H1N1 A/Brisbane/59/2007 and H1N1 A/California/07/2009.

Example 17: Immunogenicity of Third Generation HA Stem Domain Polypeptide Mini2-Cluster1+5+6-GCN4

In order to further assess the immunogenicity of the stem domain polypeptides of the disclosure, mice were immunized once with the expression vector encoding mini2-cluster1+5+6-GCN4 (SEQ ID NO: 45) (prime) and boosted twice with purified protein s-H1-mini2-cluster1+5+6-GCN4 (SEQ ID NO: 145) at three week intervals. For reasons of comparison, separate groups were immunized three times at three week intervals immunization with the expression vectors encoding mini2-cluster1+5+6-GCN4 (SEQ ID NO: 45) as well as full-length H1 from A/Brisbane/59/2007 (SEQ ID NO: 1). An expression vector encoding for cM2 was also included as a negative control.

Groups of 4 mice (BALB\c) were immunized intramuscularly (i.m.) with 1000 μg construct encoding mini2-cluster1+5+6-GCN4 (SEQ ID NO: 45)+100 μg adjuvant (pUMCV1-GM-CSF) on day 1 and with s-H1-mini2-cluster1+5+6-GCN4 (SEQ ID NO: 145; 100 μg purified protein) adjuvanted with 10 μg Matrix-M on day 21 and 42. One group received $2^{nd}$ and $3^{rd}$ immunization s.c., whereas another received $2^{nd}$ and $3^{rd}$ immunizations i.m. A third group was again primed with 100 μg construct encoding mini2-cluster1+5+6-GCN4 (SEQ ID NO: 45)+100 μg adjuvant (pUMCV1-GM-CSF) on day 1 as above and received booster immunizations on day 21 and 41 of s-H1-mini2-cluster1+5+6-GCN4 (SEQ ID NO: 145; 100 μg purified protein) adjuvanted with MONTANIDE® ISA-720 (1:1 v/v). For comparison, groups of 4 mice (BALB\c) were immunized i.m. on day 1, 21 and 42 with 100 μg construct encoding mini2-cluster1+5+6-GCN4 (SEQ ID NO: 45), full-length H1 from A/Brisbane/59/2007 (SEQ ID NO: 1) or cM2, adjuvanted with 100 μg adjuvant (pUMCV1-GM-CSF).

Figure 20A:
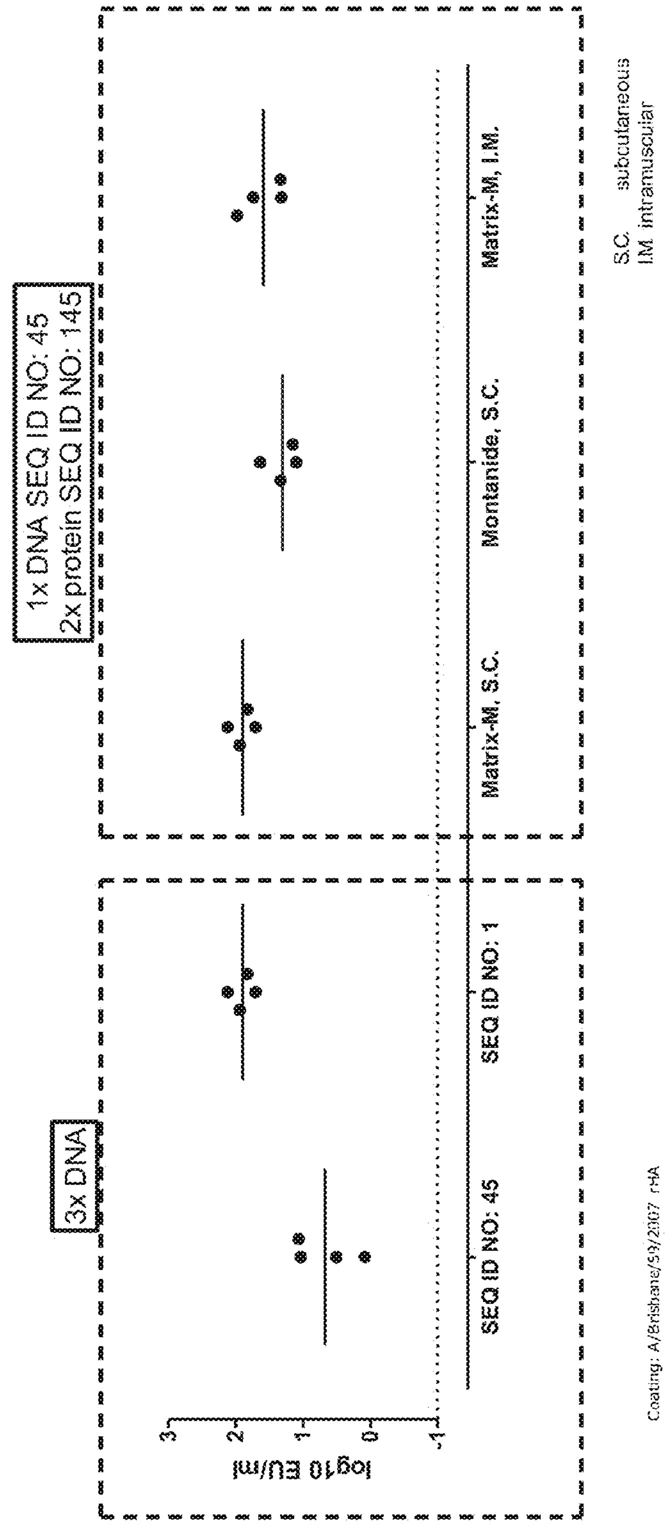
FIGS. 20A-20D: IgG responses at week 7 after initial immunization for individual mice against the ectodomain of the full-length hemagglutinin from the homologous strain H1N1 A/Brisbane/59/2007 (FIG. 20A), the heterologous strain H1N1 A/California/07/2009 (FIG. 20B) the heterosubtypic strain H5N1 A/Vietnam/1203/2004 (FIG. 20C) and the heterosubtypic strain H3N2 A/Hong Kong/1/1968 (FIG. 20D). Open symbols correspond to values below the limit of detection of the assay.
Figure 20B:
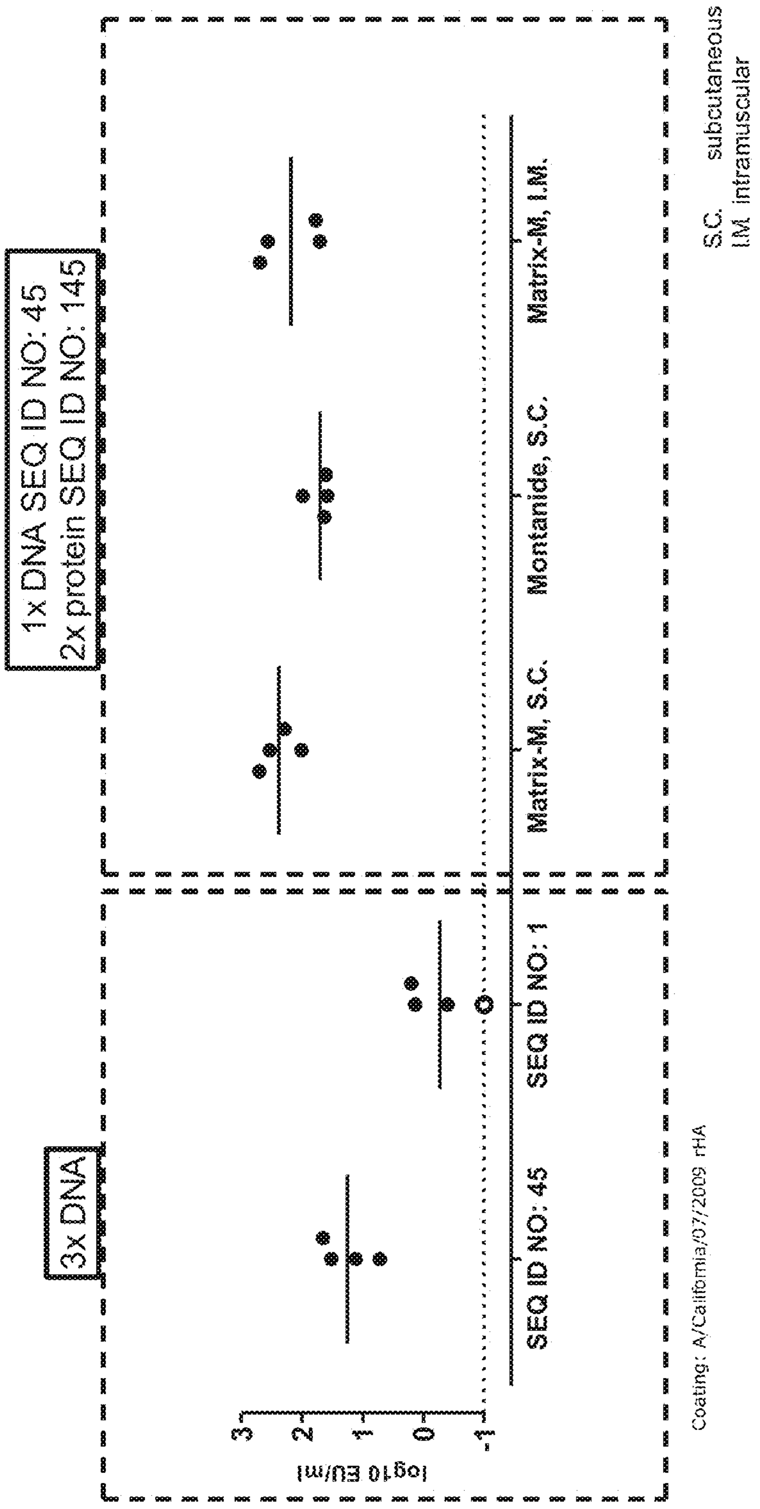
Figure 20C:
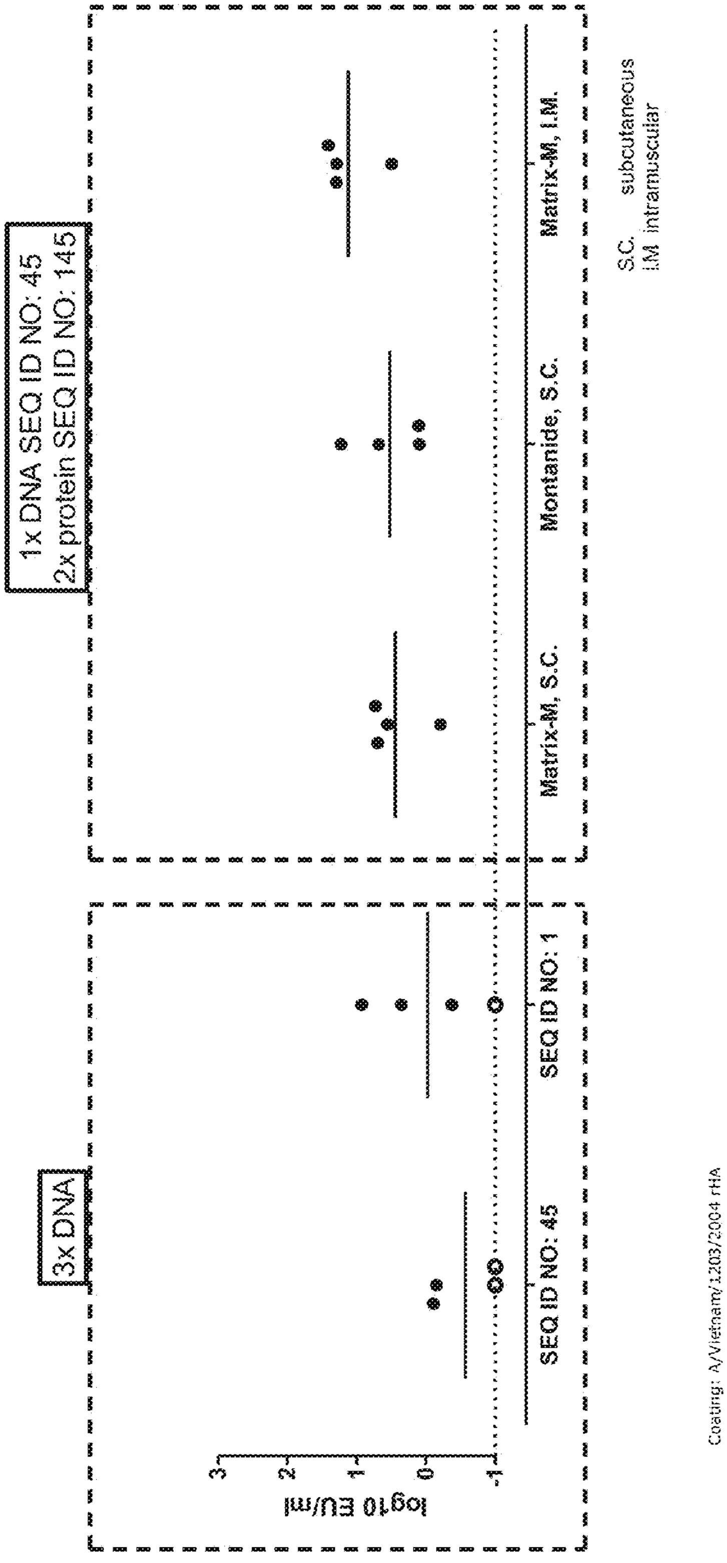
Figure 20D:
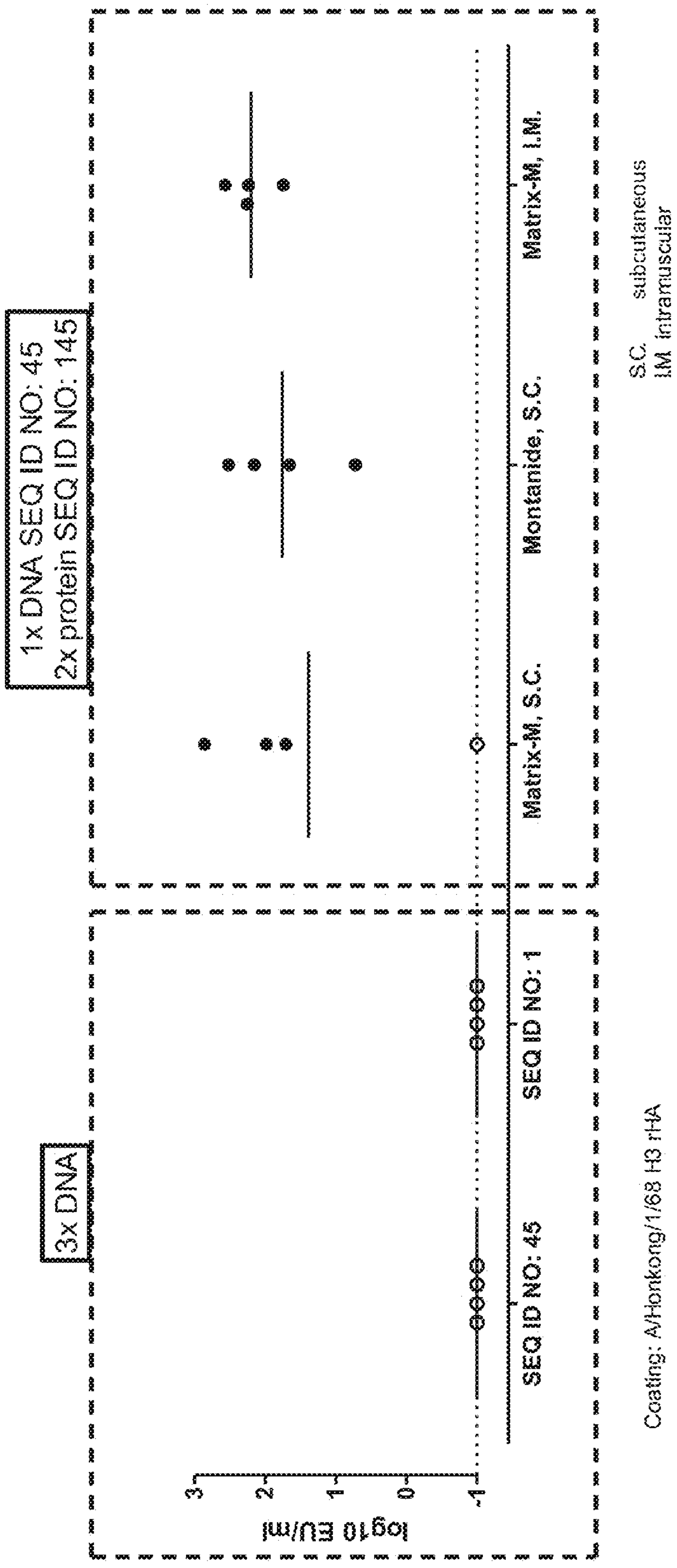

On day 49, a final bleed was performed and serum collected. The sera were analyzed by ELISA using the recombinant full-length HA from the H1N1 A/Brisbane/59/2007, H1N1 A/California/07/2009, H5N1 A/Vietnam/1203/2004 and H3N2 A/Hong Kong//1968 strains (obtained from Protein Sciences Corporation, Meriden, Conn., USA) as the antigen. In short, 96-well plates were coated with 50 ng HA overnight at 4° C., followed by incubation with block buffer (100 μl PBS, pH 7.4+2% skim milk) for 1 hour at room temperature. Plates were washed with PBS+0.05% TWEEN®-20, and 100 μl of a 2-fold dilution series in block buffer, starting from a 20-fold dilution of the serum is added. Bound antibody is detected using HRP-conjugated goat-anti-mouse IgG, using standard protocols well-established in the art. Titers are compared to a standard curve composed of a serial dilution of a mouse monoclonal antibody binding to the HA antigen and expressed as ELISA units per ml (EU/ml). FIGS. 20°-20D exhibit the IgG responses at week 7 after initial immunization for individual mice against the ectodomain of the full-length hemagglutinin from the homologous strain H1N1 A/Brisbane/59/2007 (FIG. 20A), the heterologous strain H1N1 A/California/07/2009 (FIG. 20B) the heterosubtypic strain H5N1 A/Vietnam/1203/2004 (FIG. 20C) and the heterosubtypic strain H3N2 A/Hong Kong/1/1968 (FIG. 20D). Antibodies induced by immunization with DNA encoding the polypeptide of the disclosure mini2-cluster1+5+6-GCN4 (SEQ ID NO: 45) are capable of recognizing the HA of H1N1 A/Brisbane/59/2007, H1N1 A/California/07/2009 and to a lesser extent H5N1 A/Vietnam/1203/2004. Antibodies elicited by immunization with DNA encoding the full-length H1 from A/Brisbane/59/2007 (SEQ ID NO: 1) recognize the homologous protein very well, but the heterologous HA from H1N1 A/California/07/2009, and heterosubtypic HA from H5N1 A/Vietnam/1203/2004 much less so, as is evidenced by the lower titers in FIG. 17, Panels b and c. The group of mice immunized with DNA encoding mini2-cluster1+5+6-GCN4 (SEQ ID NO: 45; prime) followed by booster immunizations with s-H1-mini2-cluster1+5+6-GCN4 (SEQ ID NO: 145) protein exhibit high titers against the ectodomains of HA derived from homologous H1N1 A/Brisbane/59/2007, heterologous H1N1 A/California/07/2009 and heterosubtypic H5N1 A/Vietnam/1203/2004.

FIG. 20D exhibits the IgG responses at week 7 against the ectodomain of HA from H3N2 A/Hong Kong/1/1968. Unlike mini2-cluster1+5+6-GCN4 (SEQ ID NO: 45) and s-H1-mini2-cluster1+5+6-GCN4 (SEQ ID NO: 145) that are derived from HA of H1N1 A/Brisbane/59/2007, a strain that belongs to Influenza group 1, H3N2 A/Hong Kong/1/1968 belongs to Influenza group 2 and is, therefore, phylogenetically distant from the parent sequence used to design the polypeptides hereof used in this experiment. Immunizing three times with DNA encoding mini2-cluster1+5+6-GCN4 (SEQ ID NO: 45) or full-length HA from H1N1 A/Brisbane/59/2007 (SEQ ID NO: 1) does not result in IgG levels detectable by ELISA against this antigen. In contrast, the immunization with DNA encoding mini2-cluster1+5+6-GCN4 (SEQ ID NO: 45) followed by two booster immunizations with purified protein s-H1-mini2-cluster1+5+6-GCN4 (SEQ ID NO: 145) results in high titers against HA from H3N2 A/Hong Kong/1/1968. This result is obtained independent from the immunization route used (i.e., intramuscular vs subcutaneous) or the adjuvant added to the protein boost immunizations (Matrix-M or MONTANIDE® ISA-720).

In conclusion, immunization with polypeptides of the disclosure can elicit IgGs that are capable of recognizing HA from a broad range of influenza strains, including homologous, heterologous, and heterosubtypic strains from influenza group 1 as well as a strain form influenza group 2. In contrast immunization with the full-length HA results in high titers against HA of the homologous strains, reduced titers against heterologous and heterosubtypic strains and IgG levels below the limit of detection for the strain from influenza group 2.

Example 18: Design of Further Stem Domain Polypeptides Comprising the Conserved Stem Domain Epitopes of CR6261 and CR9114

Polypeptides of the disclosure designed following the procedure described above can be further modified to increase the stability. Such modifications can be introduced to enhance the formation of trimeric forms of the polypeptides hereof over monomeric and/or dimeric species. As described, the native HA exists as a trimer on the cell surface. Many of the interactions between the individual monomers that keep the trimer together are located in the head domain. After removal of the head the tertiary structure is thus destabilized and, therefore, reinforcing the interactions between the monomers in the truncated molecule will increase the stability of the trimeric form. Trimerization is mediated by the formation of a trimeric. By strengthening the coiled coil motif in the stem domain a more stable trimer form can be achieved.

According to the disclosure, a consensus sequence for the formation of a trimeric coiled coil, IEAIEKKIEAIEKKIE (SEQ ID NO: 83), is introduced in a polypeptide of the disclosure at (the equivalent of) position 418 to 433 (SEQ ID NO: 44) in H1 A/Brisbane/59/2007 (numbering according to SEQ ID NO: 1). Alternatively, IEAIEKKIEAIEKKI (SEQ ID NO: 85) can be introduced at 419-433 (SEQ ID NO: 49) or IEAIEKKIEAIEKK (SEQ ID NO: 86) at 420-433 (SEQ ID NO: 50). An alternative is to introduce the sequence MKQIEDKIEEIESKQ (SEQ ID NO: 84), derived from GCN4 and known to trimerize, at position 419-433 (SEQ ID NO: 45). Alternatively MKQIEDKIEEIESK (SEQ ID NO: 87) can be introduced at position 420-433 (SEQ ID NO: 51) or RMKQIEDKIEEIESKQK (SEQ ID NO: 88) at position 417-433 (SEQ ID NO: 52). Similarly, the trimer interface might be strengthened by modifying M420, L423, V427, G430 into Isoleucine (SEQ ID NO: 53).

In certain embodiments, the polypeptides hereof contain the intracellular sequences of H1 HA and the transmembrane domain. In other embodiments, the cytoplasmic sequence and the transmembrane sequence from position (or the equivalent thereof) 523, 524, 525, 526, 527, 528, 529, or 530 of HA2 to the C-terminus of HA2 (numbering according to SEQ ID NO: 1) is removed so that a secreted (soluble) polypeptide is produced. The soluble polypeptide can be further stabilized as described above.

Description Linker Variants

Figure 21:
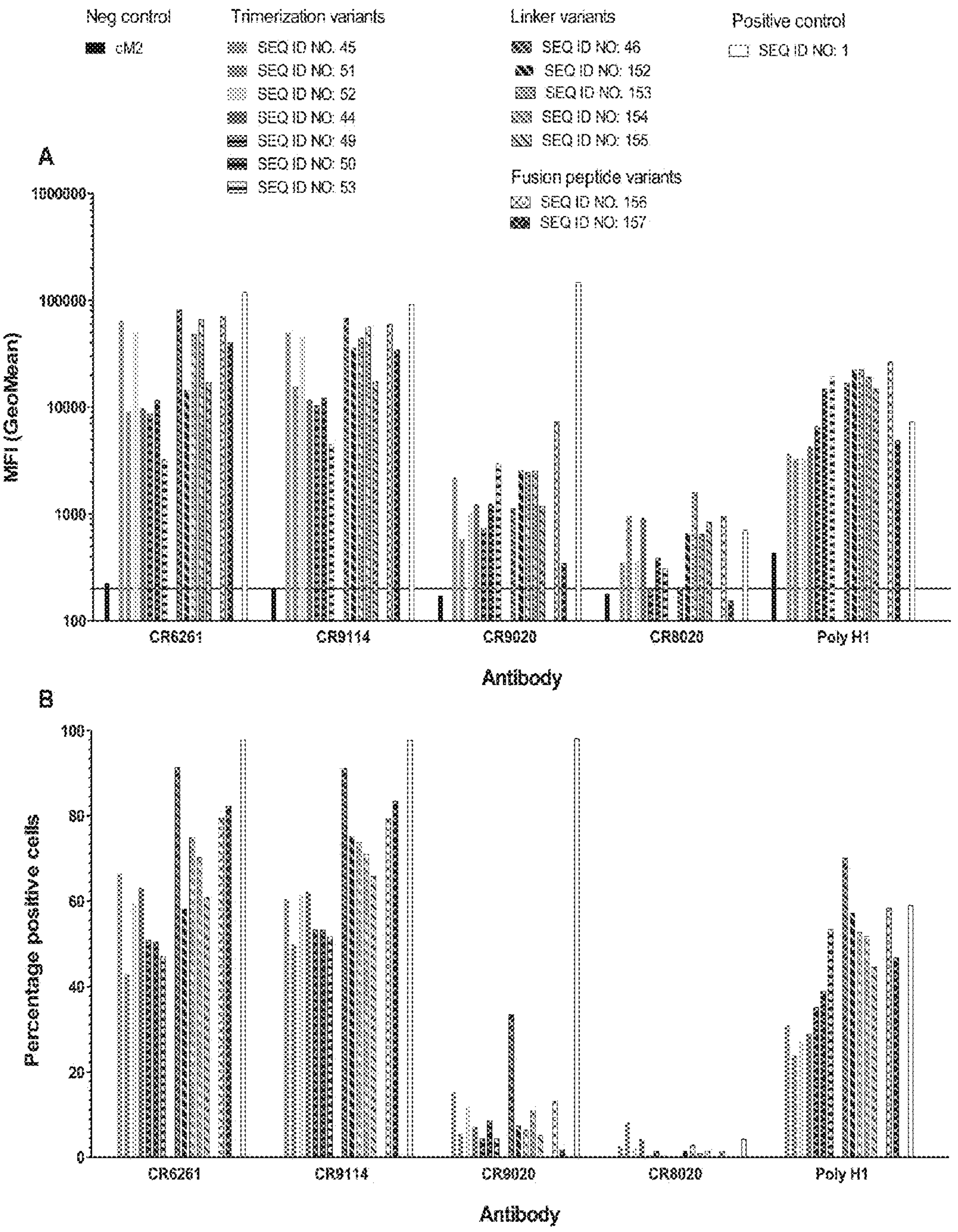
FIG. 21: FACS assay of stem domain polypeptides based on H3 HA. Mean fluorescence intensity (Panel A) and % positive cells (Panel B) are shown.

The genes encoding the above protein sequences (SEQ ID NOS: 44 to 46; SEQ ID NOS: 49 to 53 and SEQ ID NOS: 152-157 were synthesized and cloned into expression vector pcDNA2004 using methods generally known to those skilled in the art. For reasons of comparison an expression vector encoding the full-length sequence (SEQ ID NO: 1) as well as cM2 was included in the experiment HEK293F (Invitrogen) suspension cells ($10^6$ cells/ml, 30 ml) were transfected with the expression vectors (1 μg/ml) using 40 μl 293-transfectin as the transfection agent and allowed to further propagate for 2 days. Cells were harvested; aliquotted (0.3 ml, approximately $3*10^5$ cells) and aliquots were treated with either polyclonal serum raised against H1 HA to probe expression or a HA-specific monoclonal antibody (5 microgram/ml) and a secondary antibody used for staining. The cells were then analyzed by fluorescence associated cell sorting (FACS) for expression of the membrane attached HA stem domain polypeptides of the disclosure using polyclonal serum raised against H1 HA to probe expression. A panel of monoclonal antibodies of known specificity that bind the full-length protein (CR6261, CR9114, CR9020 and CR8020) were used to probe for the presence of conserved epitopes and, by inference, correct folding of the full-length HA and the mini-HA polypeptides of the disclosure. Results are expressed as percentage positive cells and mean fluorescence intensity and are shown in FIG. 21.

Results show that all tested variants are expressed on the cell surface as evidenced by the positive response from the polyclonal anti-H1 serum. H3 HA specific antibody CR8020 does not recognize any of the constructs included in the experiment, whereas CR9020, which binds to the head domain of H1, HAs only clearly recognizes the full-length protein. All polypeptides of the disclosure, as well as the full-length protein are recognized by CR6261 and CR9114, indicating that the correspondent epitopes are present in the polypeptides hereof in the same conformation as in the wild-type protein. Among the polypeptides hereof with an additional trimerization motif included in helix CD (see FIG. 1), SEQ ID NOS: 45, 51 and 52 containing the GCN4-derived sequences SEQ ID NOS: 84, 87 and 88, respectively result in an equal or higher responses (MFI) than SEQ ID NOS: 44, 49 and 50, containing the consensus trimerization sequences of SEQ ID NOS: 83, 85 and 86.

The variation in the composition of the linker connecting amino acids 52 and 321 (numbering refers to SEQ ID NO: 1) in the polypeptides hereof does not lead to major changes in the recognition of monoclonal antibodies CR6261 and CR9114. The largest change is observed when GGGG (SEQ ID NO: 194) in SEQ ID NO: 46 is replaced with HNGK (SEQ ID NO: 210), resulting in SEQ ID NO: 152, which leads to a somewhat lower response to CR6261, but does not affect the response to CR9114. Removing the linker and introducing amino acids 53-56 of SEQ ID NO: 1 (SHNG), i.e., creating a polypeptide of the disclosure without a linker in SEQ ID NO: 46 (resulting in SEQ ID NO: 153), SEQ ID NO: 45 (resulting in SEQ ID NO: 154) or SEQ ID NO: 50 (resulting in SEQ ID NO: 155) does not impact the response in the FACS assay, indicating that the linker sequence is not critical.

SEQ ID NO: 156 is derived from SEQ ID NO: 46 by introducing mutations 1337N, 1340N and F352Y, whereas SEQ ID NO: 157 contains an additional mutation at position 353, i.e., 1353N. These mutations do not lead to an improved response to CR6261 and CR9114 in the FACS assay shown in FIG. 21.

In certain embodiments, the polypeptides hereof contain the intracellular sequences of HA and the transmembrane domain. In other embodiments, the cytoplasmic sequence and the transmembrane sequence from position (or the equivalent thereof) 523, 524, 525, 526, 527, 528, 529, or 530 of HA2 to the C-terminus of HA2 (numbering according to SEQ ID NO: 1) is removed, and optionally replaced by introducing a sequence known to form trimeric structures, i.e., AYVRKDGEWVLL (SEQ ID NO: 143), optionally connected through a linker. The linker may optionally contain a cleavage site for processing afterwards according to protocols well known to those skilled in the art. To facilitate purification of the soluble form a tag sequence may be added, e.g., a His-tag HHHHHHH (SEQ ID NO: 191) connected via a short linker, e.g., EGR. According to the disclosure, the amino acid sequence from position 530 (numbering according to SEQ ID NO: 1) to the C-terminal amino acid of the HA2 domain was removed and replaced by SEQ ID NO: 81 or SEQ ID NO: 82.

Example 19: Immunogenicity of Third Generation HA Stem Domain Polypeptides

In order to assess the immunogenicity of the stem domain polypeptides mice were immunized with the expression vectors encoding full-length H1 from A/Brisbane/59/2007 (SEQ ID NO: 1), Mini3-cluster11 (SEQ ID NO: 11), Mini2-cluster11+5 (SEQ ID NO: 14), mini2-cluster1+5+6 (SEQ ID NO: 46), mini2-cluster1+5+6-GCN4 (SEQ ID NO: 45), mini2-cluster1+5+6-n1 (SEQ ID NO: 152), mini2-cluster1+5+6-nl2 (SEQ ID NO: 153), mini2-cluster1+5+6-nl2s-GCN4 (SEQ ID NO: 154), mini2-cluster1+5+6-GCN4t2 (SEQ ID NO: 51), mini2-cluster1+5+6-GCN4t3 (SEQ ID NO: 52), mini2-cluster1+5+6+12 (SEQ ID NO: 156) and mini2-cluster1+5+6+12+13 (SEQ ID NO: 157). An expression vector encoding for cM2 was also included as a negative control.

Groups of 4 mice (BALB\c) were immunized with 100 μg construct+100 μg adjuvant (pUMCV1-GM-CSF) i.m. on day 1, 21 and 42. On day 49 a final bleed was performed and serum collected. The sera were analyzed by ELISA using recombinant full-length HA from the H1N1 A/Brisbane/59/2007, H1N1 A/California/07/2009 and H5N1 A/Vietnam/1203/2004 strains (obtained from Protein Sciences Corporation, Meriden, Conn., USA) as the antigen. In short, 96-well plates were coated with 50 ng HA overnight at 4° C., followed by incubation with block buffer (100 μl PBS, pH 7.4+2% skim milk) for 1 hour at room temperature. Plates were washed with PBS+0.05% TWEEN®-20, and 100 μl of a 2-fold dilution series in block buffer, starting from a 50-fold dilution of the serum is added. Bound antibody is detected using HRP-conjugated goat-anti-mouse IgG, using standard protocols well-established in the art. Titers are compared to a standard curve composed of a serial dilution of a mouse monoclonal antibody binding to the HA antigen and expressed as ELISA units per ml (EU/ml).

Figure 22A:
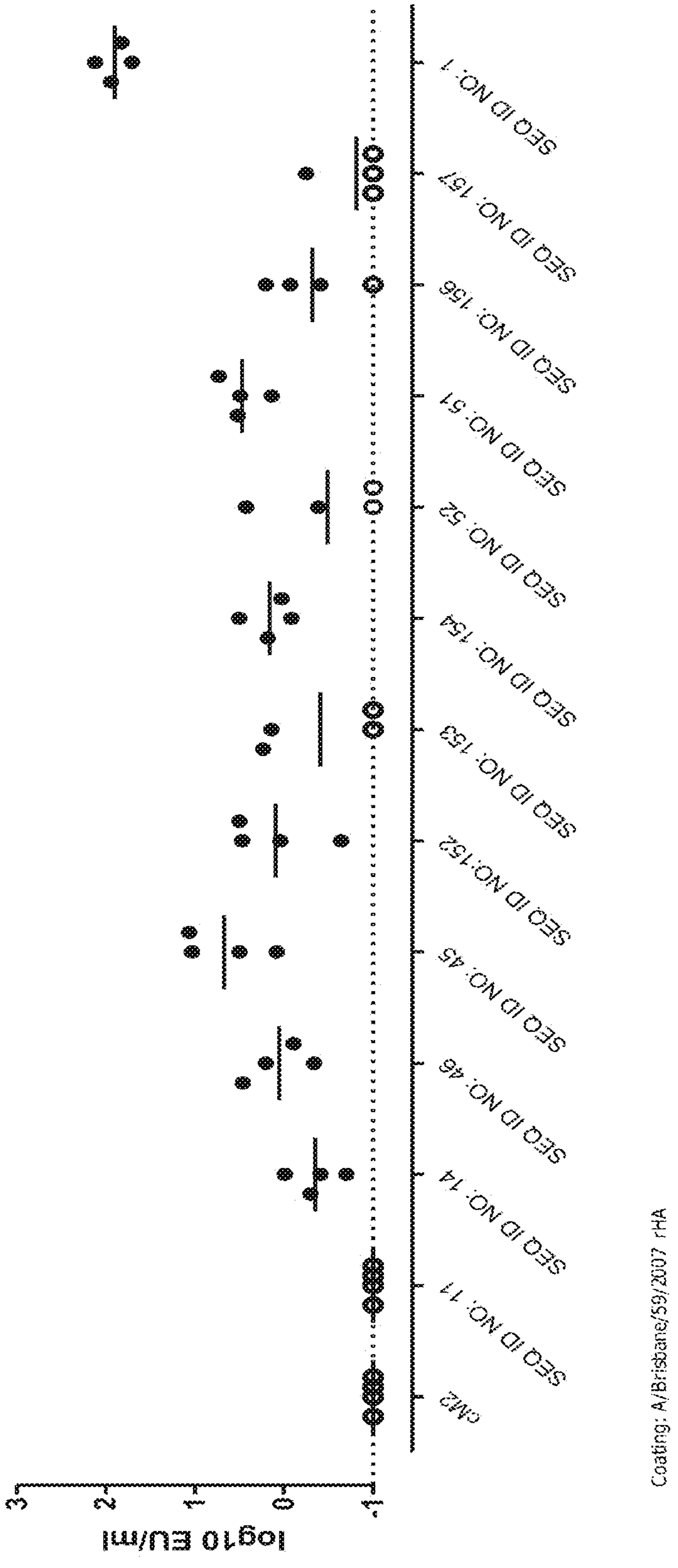
FIGS. 22A-22C: IgG responses at week 7 after initial immunization for individual mice against the full-length hemagglutinin from the homologous strain H1N1 A/Brisbane/59/2007 (FIG. 22A), the heterologous strain H1N1 A/California/07/2009 (FIG. 22B) and the heterosubtypic strain H5N1 A/Vietnam/1203/2004 (FIG. 22C). Open symbols correspond to values below the limit of detection of the assay.
Figure 22B:
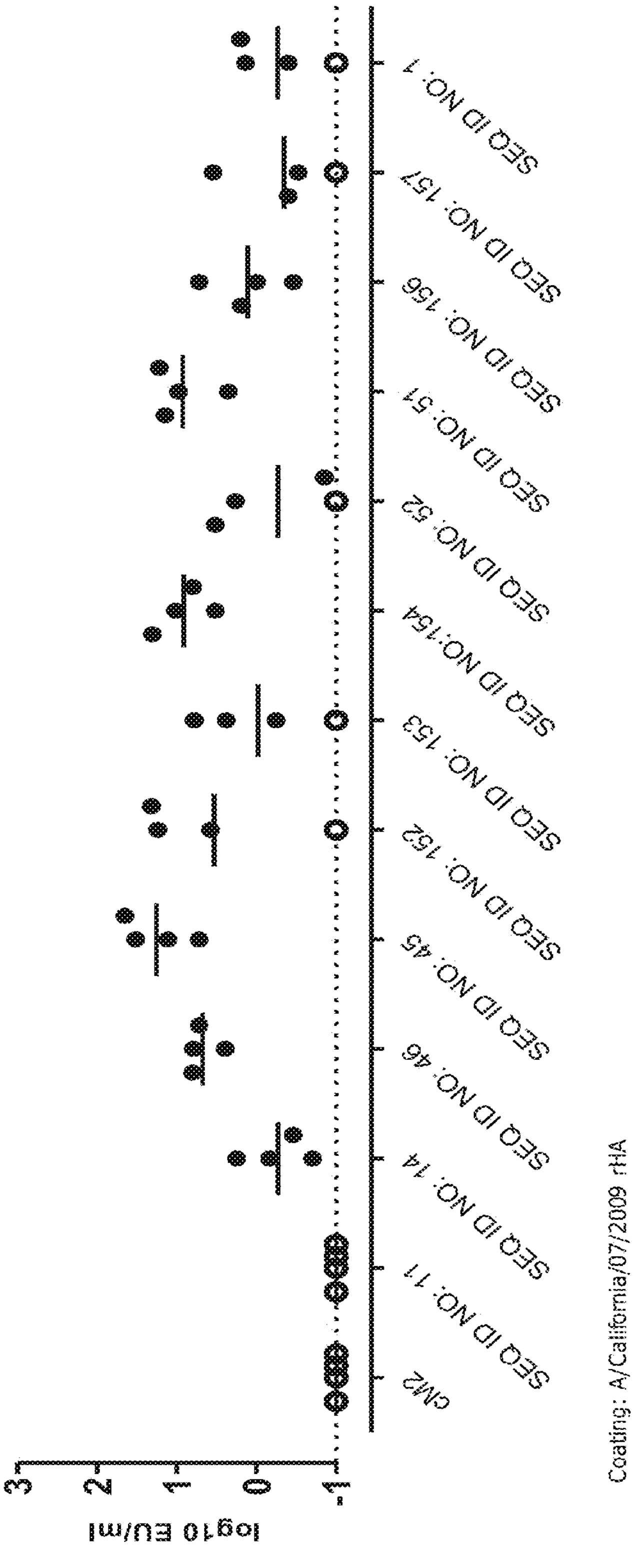
Figure 22C:
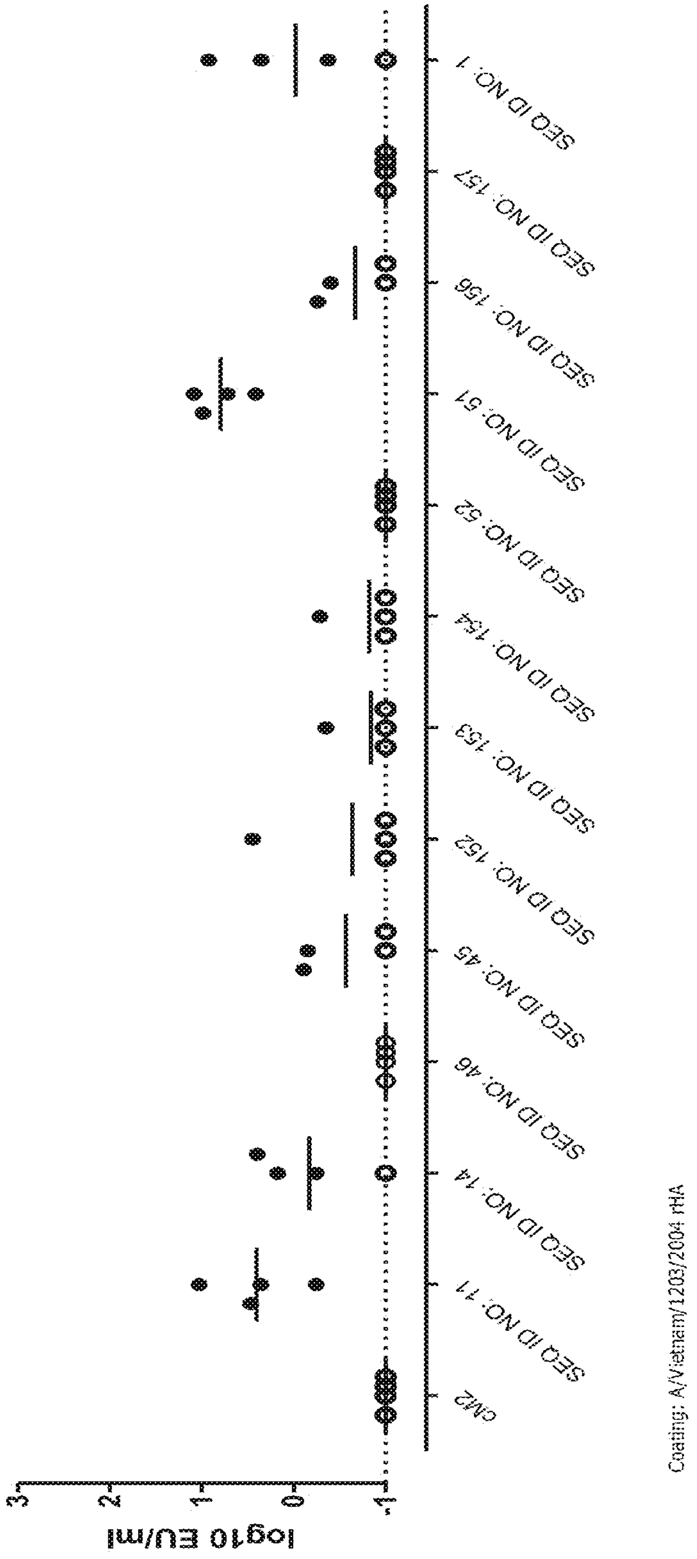

FIGS. 22A-22C exhibit the IgG responses at week 7 after initial immunization for individual mice against the full-length hemagglutinin from the homologous strain H1N1 A/Brisbane/59/2007 (FIG. 22A), the heterologous strain H1N1 A/California/07/2009 (FIG. 22B) and the heterosubtypic strain H5N1 A/Vietnam/1203/2004 (FIG. 22C). Antibodies induced by immunization with DNA encoding polypeptides of the disclosure Mini2-cluster11+5 (SEQ ID NO: 14), mini2-cluster1+5+6 (SEQ ID NO: 46), mini2-cluster1+5+6-GCN4 (SEQ ID NO: 45), mini2-cluster1+5+6-n1 (SEQ ID NO: 152), mini2-cluster1+5+6-nl2 (SEQ ID NO: 153), mini2-cluster1+5+6-nl2s-GCN4 (SEQ ID NO: 154), mini2-cluster1+5+6-GCN4t2 (SEQ ID NO: 51), mini2-cluster1+5+6-GCN4t3 (SEQ ID NO: 52), mini2-cluster1+5+6+12 (SEQ ID NO: 156) and mini2-cluster1+5+6+12+13 (SEQ ID NO: 157) bind equally well to the ectodomain of hemagglutinin derived from the homologous H1N1 A/Brisbane/

59/2007 and heterologous H1N1 A/California/07/2009 strain (FIGS. 22A and 22B). Highest titers are observed for mini2-cluster1+5+6-GCN4 (SEQ ID NO: 45), mini2-cluster1+5+6-GCN4t2 (SEQ ID NO: 51) and mini2-cluster1+5+6-nl2s-GCN4 (SEQ ID NO: 154). In contrast, immunization with DNA encoding the full-length protein (SEQ ID NO: 1) results in high titers against the homologous hemagglutinin (more than an order of magnitude higher than titers observed for immunization with DNA encoding the polypeptides of the disclosure), but in low titers against the ectodomain of the heterologous hemagglutinin (more than an order of magnitude). Immunization with DNA encoding Mini3-cluster11 (SEQ ID NO: 11) and negative control cM2 do not result in a detectable response against either of the hemagglutinin ectodomains in this assay.

The titers against the ectodomain of the heterosubtypic hemagglutinin from H5N1 A/Vietnam/1203/2004 (FIG. 22C) indicate a clear response for mini2-cluster1+5+6-GCN4t2 (SEQ ID NO: 51). Observable titers are also obtained for 2 out of 4 mice after immunization with DNA encoding mini2-cluster1+5+6-GCN4 (SEQ ID NO: 45) and for 1 out of 4 mice for mini2-cluster1+5+6-n1 (SEQ ID NO: 152), mini2-cluster1+5+6-nl2 (SEQ ID NO: 153), mini2-cluster1+5+6-nl2s-GCN4 (SEQ ID NO: 154). Surprisingly, we also find detectable titers after immunization with DNA encoding Mini3-cluster11 (SEQ ID NO 11) and Mini2-cluster11+5 (SEQ ID NO: 14). The former construct did not induce any detectable antibody titers against homologous and heterologous H1 HA, whereas the latter induced only moderate responses (FIGS. 22A and 22B). Comparison of the sequences of all constructs in this experiment and H5 HA point towards a putative linear epitope located at the membrane distal end of the long CD helix (see FIG. 1). The methionine to isoleucine mutation at position 175 in SEQ ID NO: 11 and position 156 in SEQ ID NO: 14 results in linear sequence ERRIENLNKK (position 172 to 181 in SEQ ID NO: 11; position 153 to 162 in SEQ ID NO: 14). This sequence is also present in HA from H5N1 A/Vietnam/1203/2004, but not in the HA from H1N1 A/Brisbane/59/2007 and H1N1 A/California/07/2009, where the corresponding sequences are ERRMENLNKK (SEQ ID NO: 211) and EKRIENLNKK (SEQ ID NO: 212), respectively.

In conclusion, antibodies raised against the polypeptides hereof mini2-cluster11+5 (SEQ ID NO: 14), mini2-cluster1+5+6 (SEQ ID NO: 46), mini2-cluster1+5+6-GCN4 (SEQ ID NO: 45), mini2-cluster1+5+6-n1 (SEQ ID NO: 152), mini2-cluster1+5+6-nl2 (SEQ ID NO: 153), mini2-cluster1+5+6-nl2s-GCN4 (SEQ ID NO: 154), mini2-cluster1+5+6-GCN4t3 (SEQ ID NO: 52), mini2-cluster1+5+6-GCN4t2 (SEQ ID NO: 51), mini2-cluster1+5+6+12 (SEQ ID NO: 156) and mini2-cluster1+5+6+12+13 (SEQ ID NO: 157) are capable of recognizing full-length hemagglutinin. The epitopes of these antibodies must be located on the hemagglutinin stem domain and are conserved between the full-length hemagglutinins from H1N1 A/Brisbane/59/2007 and H1N1 A/California/07/2009. Antibodies elicited through immunization with DNA encoding mini2-cluster1+5+6-GCN4t2 (SEQ ID NO: 51), and to a lesser extent mini2-cluster11+5 (SEQ ID NO: 14), mini2-cluster1+5+6-GCN4 (SEQ ID NO: 45), mini2-cluster1+5+6-n1 (SEQ ID NO: 152), mini2-cluster1+5+6-nl2 (SEQ ID NO: 153), mini2-cluster1+5+6-nl2s-GCN4 (SEQ ID NO: 154) and mini2-cluster1+5+6+12 (SEQ ID NO: 156) are also able to recognize the ectodomain of HA from H5N1 A/Vietnam/1203/2004. Polypeptide of the disclosure Mini3-cluster11 (SEQ ID NO: 11) is capable of inducing antibodies that recognize from H5N1 A/Vietnam/1203/2004.

Example 20: General Method to Design of Stem Domain Polypeptides Comprising the Conserved Stem Domain Epitopes of CR6261 and CR9114

On the basis of the results described above a general method is defined to create a polypeptide of the disclosure from an influenza virus HA0 sequence, in particular from an influenza HA0 sequence of serotype H1. The method comprises the steps:

1. Removal of the cleavage site between HA1 and HA2. This can be achieved by mutation of R (in a small number of cases K) to Q at the P1 position (see, e.g., Sun et al., 2010, for an explanation of the nomenclature of the cleavage site (position 343 in SEQ ID NO: 1). A mutation to Q is preferred but S, T, N, D or E are alternatives.

2. Removal of the head domain by deleting amino acids 53 to 320 from SEQ ID NO: 1, or at equivalent positions in HA from other influenza viruses. Equivalent positions can be easily determined by those skilled in the art by aligning the sequences using suitable algorithms such as, e.g., Clustal or Muscle. The remaining parts of the sequence can be joined directly or alternatively by introducing a flexible linker. Linker sequences can be 1 to 50 amino acids in length. Preferred are flexible linkers of limited length (smaller or equal to 10 amino acids), e.g., GGG, GGGG (SEQ ID NO: 194), GSA, GSAG (SEQ ID NO: 193), GSAGSA (SEQ ID NO: 189), GSAGSAG (SEQ ID NO: 188) or similar. The length of the deletion can also be varied, e.g. by starting the deletion at (the equivalent of) position 54, 55, 56, 57 or 58, or to increase the length of the deletion, by cutting at position 47, 48, 49, 50, 51, or 52. Similarly, the last amino acid to be deleted can be at (the equivalent of) position 315, 316, 317, 318 or 319, or to increase the length of the deletion at (the equivalent of) position 321, 322, 323, 324, or 325. It is important to realize that changes in the length of the deletion can be in part compensated for by matching the length of the linker sequence, i.e., a larger deletion can be matched with a longer linker and vice versa. These polypeptides are also encompassed by the disclosure.

3. Increasing the solubility of the loop (between the A-helix and the CD helix) formed by (the equivalent of) residues 402 to 418 in H1 A/Brisbane/59/2007 (SEQ ID NO: 1) to increase the stability of the pre-fusion conformation and destabilize the post-fusion conformation of the modified HA. This loop is highly conserved in H1 sequences, as can be seen in Table 6 below. This can, for example, be achieved by replacing I, L, F or V residues in the loop with hydrophilic counterparts. Equivalent positions can be easily determined by those skilled in the art by aligning the sequences using a suitable algorithm such as, e.g., Clustal or Muscle. Mutations to glycine destabilize the post-fusion conformation since the high flexibility of this amino acid leads to a decrease in stability of the post-fusion helix to be formed by this part of the HA sequence. The consensus sequence describing the loop between residue 402-418 of influenza HA of serotype H1 is (SEQ ID NO: 17) MNTQFTAVGKEFN(H/K)LE(K/R). In polypeptides of the disclosure, the amino acid at positions 406, 409, 413 and/or 416 (or their equivalent, as determined from a sequence alignment) is a polar (S, T, N, Q), charged (R, H, K, D, E) or flexible (G) amino acid. It should be noted that mutation of L416 to either S or T also introduces a consensus N-glycosylation site (consensus sequence is NX(S/T)). Glycosylation of the Asparagine this position will further increase the solubility of this region. Combinations of mutations at these sites are also possible, for example, F406S, V409T, L416S as in SEQ ID NO: 10 and SEQ ID NO: 14. In some cases a mutation to restore the consensus amino acid is preferred, e.g., where V or M is at position 404 (to T), Vat 408 (to A) or 410 (to G) or I at 414 (to N); the incidence of sequences with these particular amino acids is very low. An overview of the mutations described above that characterize polypeptides of the disclosure is given in Table 6.

4. Introducing a disulfide bridge in the polypeptides hereof, preferably between amino acids of (the equivalent of) position 324 and 436 in H1 A/Brisbane/59/2007; SEQ ID NO: 13-16. Equivalent positions can be easily determined by those skilled in the art by aligning the sequences using a suitable algorithm such as Clustal, Muscle, etc. Engineered disulfide bridges are created by mutating at least one (if the other is already a cysteine), but usually two residues that are spatially close into a cysteine, that will spontaneously or by active oxidation form a covalent bond between the sulfur atoms of these residues.

Using the general method according to the disclosure, described above, polypeptides of the disclosure were created based on the HA0 sequences of H1N1 A/California/04/2009 (SEQ ID NO: 159), H1N1 A/California/07/2009 (SEQ ID NO: 56), H1N1 A/Puerto Rico/8/1934 (SEQ ID NO: 78), and H1N1 A/Texas/36/1991 (SEQ ID NO: 64). In addition the method was applied to HA from another subtype that is part of Group 1, i.e., H5, using HA from H5N1 A/Vietnam/1203/2004 (SEQ ID NO: 158).

H1 mini-HA A/California/07/2009 (SEQ ID NO: 160) is created from H1 FL HA A/California/07/2009 (SEQ ID NO: 56) by:

1. Removing the cleavage site: mutation R344Q (numbering refers to SEQ ID NO: 56.

2. Deleting residues K53 to P321 and introducing a GGGG (SEQ ID NO: 194) linker between D52 and K322 (numbering refers to SEQ ID NO: 56)

3. Introducing a Serine residue at position 407, 417 (F407S, L417S; numbering refers to SEQ ID NO: 2), Threonine at position 410 (V410T; numbering refers to SEQ ID NO: 56) and a Glycine residue at position 414 (F414G; numbering refers to SEQ ID NO: 2) in the loop between the A-helix and the CD helix (residues 403-419 in SEQ ID NO: 56)

4. Introducing a disulfide bridge by mutating residues Lysine 325 and Threonine 437 into a cysteine (K325C, T437C; numbering refers to SEQ ID NO: 56)

5. An additional stabilizing element was introduced by replacing 419KRIENLNKKVDDGFLD434 (numbering refers to SEQ ID NO: 56) with the sequence RMKQIEDKIEEIESKQ (SEQ ID NO: 204).

The mini-HA sequence based on the full-length HA from A/California/04/2009 (SEQ ID NO: 159) can be created in the same manner and is identical to the sequence of H1 mini-HA A/California/07/2009 (SEQ ID NO: 160).

Similarly, H1 mini-HA A/Puerto Rico/8/1934 (SEQ ID NO: 161) is created from H1 FL HA A/Puerto Rico/8/1934 (SEQ ID NO: 78) by:

1. Removing the cleavage site: mutation R343Q (numbering refers to SEQ ID NO: 78)

2. Deleting residues S53 to P320 and introducing a GGGG (SEQ ID NO: 194) linker between D52 and K321 (numbering refers to SEQ ID NO: 78)

3. Introducing a Serine residue at position 406, 416 (F406S, L416S; numbering refers to SEQ ID NO: 78) Threonine at position 409 (V409T; numbering refers to SEQ ID NO: 78) and a Glycine residue at position 413 (F413G; numbering refers to SEQ ID NO: 78) in the loop between the A-helix and the CD helix (residues 402-418 in SEQ ID NO: 78)

4. Introducing a disulfide bridge by mutating residues Arginine 324 and Threonine 436 into a cysteine (R324C, T436C; numbering refers to SEQ ID NO: 78)

5. An additional stabilizing element was introduced by replacing 418KRMENLNNKVDDGFLD433 (numbering refers to SEQ ID NO: 78) with the sequence RMKQIEDKIEEIESKQ (SEQ ID NO: 204).

An additional difference between H1 mini-HA A/Puerto Rico/8/1934 (SEQ ID NO: 161) and H1 FL HA A/Puerto Rico/8/1934 (SEQ ID NO: 78) is at position 397, which is a Serine in the full-length protein (SEQ ID NO: 78) but a Threonine in the polypeptide of the disclosure of SEQ ID NO: 161 (S397T mutation). This is a naturally occurring variation in the A/Puerto Rico/8/1934 sequence, and sequences containing this mutation are, therefore, also included in the disclosure.

H1 mini-HA A/Texas/36/1991 (SEQ ID NO: 162) is created from H1 FL HA A/Texas/36/1991 (SEQ ID NO: 64) by:

1. Removing the cleavage site: mutation R344Q (numbering refers to SEQ ID NO: 64)

2. Deleting residues S53 to P321 and introducing a GGGG (SEQ ID NO: 194) linker between D52 and K322 (numbering refers to SEQ ID NO: 64)

3. Introducing a Serine residue at position 407, 417 (F407S, L417S; numbering refers to SEQ ID NO: 64), Threonine at position 410 (V410T; numbering refers to SEQ ID NO: 64) and a Glycine residue at position 414 (F414G; numbering refers to SEQ ID NO: 64) in the loop between the A-helix and the CD helix (residues 403-419 in SEQ ID NO: 64)

4. Introducing a disulfide bridge by mutating residues Arginine 325 and Threonine 437 into a cysteine (R325C, T437C; numbering refers to SEQ ID NO: 64)

5. An additional stabilizing element was introduced by replacing 419RRMENLNKKVDDGFLD434 (numbering refers to SEQ ID NO: 64) with the sequence RMKQIEDKIEEIESKQ (SEQ ID NO: 204).

H5 mini-HA A/Vietnam/1203/2004 (SEQ ID NO: 163) is created from H5 FL HA A/Vietnam/1203/2004 (SEQ ID NO: 158) by:

1. Removing the cleavage site. Since H5 FL HA A/Vietnam/1203/2004 (SEQ ID NO: 158) contains a polybasic cleavage site (341RRRKKR346 (residues 341-346 in SEQ ID NO: 158)) a single site mutation is not enough to prevent protein cleavage. Instead 341RRRKK345 (residues 341-345 in SEQ ID NO: 158) is deleted and a R346Q mutation is introduced.

2. Deleting residues K52 to P319 and introducing a GGGG (SEQ ID NO: 194) linker between K51 and K320 (numbering refers to SEQ ID NO: 158)

3. Introducing a Serine residue at position 409, 419 (F409S, L419S; numbering refers to SEQ ID NO: 158), Threonine at position 412 (V412T; numbering refers to SEQ ID NO: 158) and a Glycine residue at position 416 (F416G; numbering refers to SEQ ID NO: 158) in the loop between the A-helix and the CD helix (residues 405-421 in SEQ ID NO: 158)

4. Introducing a disulfide bridge by mutating residues Lysine 323 and Threonine 439 into a cysteine (K323C, T439C; numbering refers to SEQ ID NO: 158)

5. An additional stabilizing element was introduced by replacing 421RRIENLNKKMEDGFLDV437 (numbering refers to SEQ ID NO: 158) with the sequence RMKQIEDKIEEIESKQI (SEQ ID NO: 205).

The genes encoding the protein sequences of SEQ ID NOS: 56, 160, 78, 161, 162, 158 and 163 were synthesized and cloned into expression vector pcDNA2004 using methods generally known to those skilled in the art. For reasons of comparison the full-length HA sequence of H3 A/Hong Kong/1/1968 (SEQ ID NO: 121), as well as the full-length HA sequence of H1 A/Brisbane/59/2007 (SEQ ID NO: 1) with additional cleavage site mutation R343Q were included in the experiment.

Figure 23:
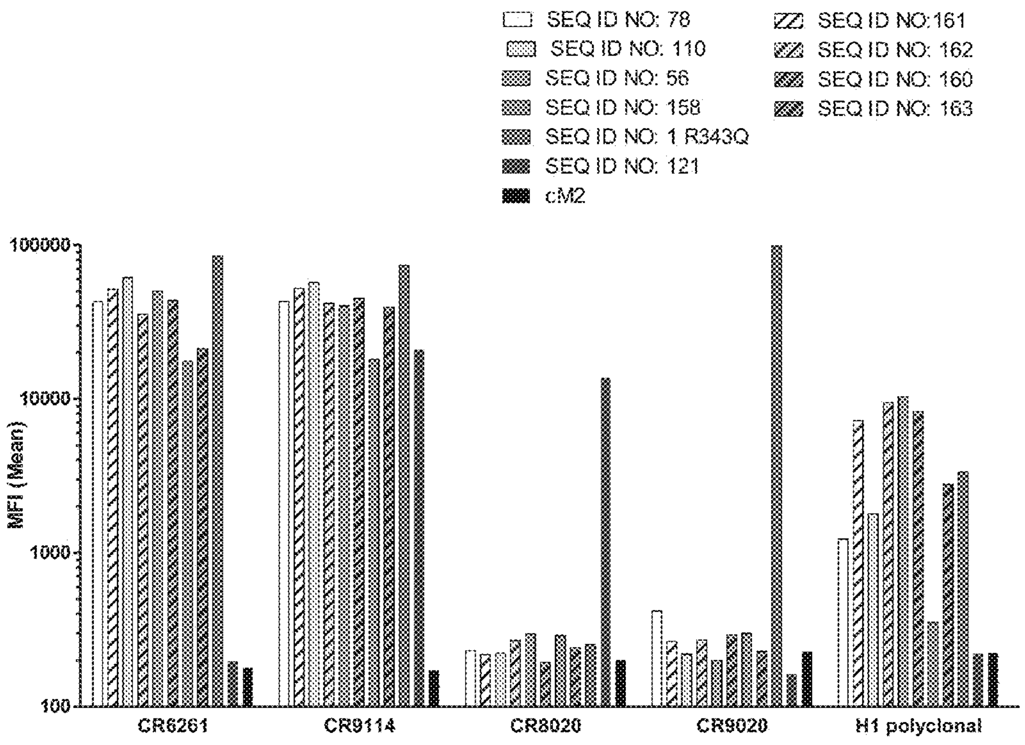
FIG. 23: FACS analysis of binding of mAbs CR6261, CR9114, CR8020 and CR9020, as well as polyclonal anti-H1 serum to full-length HA and corresponding polypeptides of the disclosure. Top: Mean Fluorescence Intensity. Bottom: percentage positive cells. Solid bars represent full-length proteins, striped bars represent polypeptides of the disclosure. Full-length HA and the corresponding polypeptide of the disclosure derived from that sequence have the same background color.

HEK293F (Invitrogen) suspension cells ($10^6$ cells/ml, 30 ml) were transfected with the expression vectors (1 μg/ml) using 40 μl 293 transfectin as the transfection agent and allowed to further propagate for 2 days. Cells were harvested, aliquotted (0.3 ml, approximately $3*10^5$ cells) and aliquots were treated with either polyclonal serum raised against H1 HA (Sino Biological Inc., Beijing, China) to probe expression or a HA-specific monoclonal antibody (5 microgram/ml) and a secondary antibody used for staining. The cells were then analyzed by Fluorescence Associated Cell Sorting (FACS) for expression of the membrane attached HA stem domain polypeptides of the disclosure on the cell surface. A panel of monoclonal antibodies of known specificity that bind the stem domain in the full-length protein (CR6261, CR9114) were used to probe for the presence of conserved epitopes and, by inference, correct folding of the full-length HA and the mini-HA polypeptides of the disclosure. Monoclonal antibody CR8020 (known not to bind to H1 and H5 HAs) and CR9020 (binds to the head domain of HA from H1 A/Brisbane/59/2007) were also included in the experiment. Results are expressed as percentage positive cells and Mean Fluorescence Intensity (MFI) and are shown in FIG. 23.

Treatment of the transfected cells with polyclonal anti-H1 serum results in 20 to 80% positive cells for the full-length HA (solid bars) and 40-50% positive cells for the mini-HAs. Negative controls FL H3 A/Hong Kong/1/1968 and cM2 only display very low numbers of positive cells. This is mirrored by mean fluorescence intensity (bottom panel) which shows a clearly detectable signal for all H1 full-length HA proteins. The signal for the full-length H5 HA remains low; however, this can be explained by a lower number of transfected cells in combination with a reduced recognition by the polyclonal H1 serum. Negative controls FL A/Hong Kong/1/1968 and cM2 show intensities at background level.

Both CR6261 and CR9114, known to be strong group 1 stem binders, recognize all Group 1 full-length HA and mini-HA proteins as indicated by high numbers of positive cells (ca. 50 to ca. 95%) and high MFI. This is strong evidence that the neutralizing epitopes of these antibodies are present in the mini-HA proteins, indicating a three-dimensional structure that strongly resembles the native structure of the HA stem domain in the full-length HA. As expected, negative control CR8020 (specific for group 2 HA) does not bind to H1 and H5 full-length HA or H1 and H5 mini-HA, indicating that the observed binding of the CR6261/CR9114 neutralizing antibodies to the mini-HA proteins does not arise from a-specific protein-protein interactions. Binding between full-length H3 HA from A/Hong Kong/1/1968 and CR9114 or CR8020 is clearly observed from both the percentage positive cells and the MFI, in line with earlier observations and proving the functionality of these monoclonal antibodies. Similarly, negative control antibody CR9020 (HA head binder for A/Brisbane/59/2007) does not recognize the mini-HAs or full-length HA proteins, with the exception of HA from A/Brisbane/59/2007, further underlining the specificity of the observed binding between CR6261 and CR9114.

In conclusion, four novel HA derived polypeptides of the disclosure have been created that have shown to contain the epitopes recognized by the neutralizing CR6261 and CR9114 antibodies in the absence of the HA head domain.

Example 21: Protection Against Lethal Influenza Challenge in Mice by Polypeptides of the Disclosure In order to determine whether polypeptides of the disclosure are capable of inducing an immune response that protects mice from death upon an exposure to influenza virus that would otherwise be lethal an influenza challenge experiment was performed. Mice were immunized i.m. with expression vectors encoding SEQ ID NOS: 78, 161, 45 and 6, as well as full-length HA from A/Brisbane/59/2007 (SEQ ID NO: 1) containing an additional R343Q mutation to remove the cleavage site. An expression vector encoding cM2 was included as a negative control. Immunization was performed using 50 μg expression construct+50 μg adjuvant (pUMCV1-GM-CSF) according to the study protocol below.

Study Protocol

| | |
|---|---|
| Day −1 | Bleed. |
| Day 0 | Administration of vaccine (i.m.). |
| Day 21 | Administration of vaccine (i.m.). |
| Day 28 | Bleed. |
| Day 42 | Administration of vaccine (i.m.). |
| Day 47 | Bleed. |
| Day 48 | Measurement of weight, temperature, clinical score and lethality. |
| Day 49 | Challenge with lethal dose of influenza viral infection (per nasal). |
| Day 49 | Remaining inoculum is utilized for back titration of virus. |
| Day 49-70 | Daily measurement of weight, temperature, clinical score and lethality. Animals with clinical score ≥3 are monitored two times per day. Animals with clinical score ≥4 or temperature >32° C., whichever comes first, are immediately removed from the study. |
| Day 70 | Sacrifice of all mice. |

Group 1-6: Challenge with PR8 (A/Puerto Rico8/34, H1N1)

| | |
|---|---|
| Group 1: | SEQ ID NO: 78 |
| Group 2: | SEQ ID NO: 161 |
| Group 3: | SEQ ID NO: 1 R343Q |
| Group 4: | SEQ ID NO: 45 |
| Group 5: | SEQ ID NO: 6 |
| Group 6: | empty vector |

10 mice per group. Total 60 mice. BALB/c.

Materials and Methods:

Virus Strain and Source:

Influenza virus strain PR8 (A/Puerto Rico8/34, H1N1) was sourced from Virapur (San Diego). Stock solution 1×10e8 pfu/ml Batch #E2004B.

Storage conditions. −75° C.±10° C. Freezer: −86° C. UCT freezer. Thermo Form. Fisher Scientific.

Animals:

Mouse, BALB/c (Specified Pathogen Free; SPF), female. 6 to 8 weeks old on Study Day 0 ~17-19 grams. Sourced from Charles River Laboratories and identified by “ear identification.” All animals were acclimatized and maintained for 11 days before the start of the experiment.

DNA Administration

Method of Inoculum Reconstitution

Appropriate DNA formulations, as listed above were prepared aliquotted and stored at −20° C. Per construct one aliquot was thawed to room temperature immediately before injection, drawn into a syringe and injected. The remainder of each aliquot was discarded after completion of all injections of each immunization round.

Dose Level and Method of Administration

Mice are anaesthetized by intraperitoneal injection with 9.75 mg Xylasol (Graeub E Dr. AG (on the World Wide Web at graeub.com); Cat: 763.02) and 48.75 mg Ketasol (Graeub E Dr. AG (on the World Wide Web at graeub.com); Cat: 668.51) per kg body weight. 50 μl DNA solution was injected using a 0.5 ml syringe with a G29 needle intramuscularly (i.m.) in the quadriceps muscle of each hind leg, yielding a total volume of 100 μl injected per mouse. The remainder of each aliquot was discarded after completion of all injections of each immunization round.

Virus Administration:

Method of Inoculum Reconstitution

The virus material was stored at −75° C.±10° C. and was defrosted prior to administration. Once defrosted, the material was diluted in cold PBS (4° C.) corresponding to 5 LD50/50 μl for the A/PR/8/34 challenges. The diluted virus was kept on ice until administration to the mice.

Dose Level and Method of Administration

The animals were anaesthetized by intraperitoneal injection with 9.75 mg Xylasol and 48.75 mg Ketasol per kg body weight and each animal received 50 μl virus solution by intranasal. Unused material was returned to the lab for back titration.

Blood Withdrawal and Serum Preparation

At days specified in the Study Protocol, above, blood samples were taken (intermediate bleedings: 100-150 μl via retro-orbital cannulation, terminal bleeding via cardiac puncture: approximately 300-500 μl). Serum was isolated from this blood by centrifugation for 5 minutes at 14000 g and stored at −20° C. until shipment on dry ice.

Clinical Scoring

Clinical signs after virus challenge were scored with a scoring system (1 point for a healthy mouse; 2 points for a mouse showing signs of malaise, including slight piloerection, slightly changed gait and increased ambulation; 3 points for a mouse showing signs of strong piloerection, constricted abdomen, changed gait, periods of inactivity, increased breathing rate and sometime rales (clicking/crackling noise); 4 points for a mouse with enhanced characteristics of the previous group, but showing little activity and becoming moribund; 5 points for a dead mouse). Animals were inspected twice a day as long as they received a score of 3. Scoring was performed by a single investigator and mice with symptoms partially represented by two scores were score+/−0.5.

Weighing

All animals were weighed daily, starting on day 48 (authorization number 2216). Animals were also weighed prior to the end of the study in case of death, i.e., at removal from study. Bodyweight was recorded in grams (s).

Virus Back Titration

The dose of the virus administered was determined by titrating 8 replicate samples from the inoculum remaining after inoculation of the animals was completed. For viral back titration TCID50 measurement was utilized following the protocol outlined in "Current Protocols in Immunology, Animal Models of Infectious Disease 19.11.7."

Results:

The study was performed without technical difficulties and in line with the defined study protocol. Back titration of the inoculums of Influenza virus strain PR8 (A/Puerto Rico8/34, H1N1) resulted in the following TCID50: PR8 (A/Puerto Rico8/34, H1N1): $3.2\times10^4$ TCID50/ml.

Figure 24A:
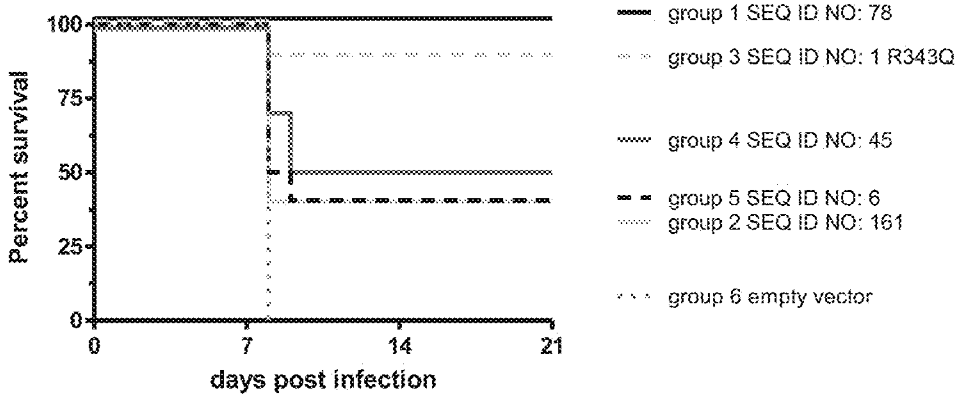
FIGS. 24A-24C: Kaplan-Meier survival curves (FIG. 24A), weight changes (FIG. 24B) and median clinical scores (FIG. 24C) for the influenza challenge experiment described in Example 21.

FIG. 24A shows the Kaplan-Meier survival curves for this experiment. Immunization with DNA encoding polypeptides of the disclosure SEQ ID NOS: 45, 6 and 161 results in survival of 50, 40 and 40% of mice infected with a lethal dose of influenza, respectively, indicating that immunization with the polypeptides hereof can indeed induce a protective immune response. In contrast animals immunized with the empty vector control all succumb to infection 8 days after the viral challenge. Immunization with DNA encoding the full-length HA homologous to the challenge strain (SEQ ID NO: 78) fully protects all animals (i.e., 100% survival) from the lethal challenge, whereas immunization with DNA encoding full-length HA derived from the heterologous strain A/Brisbane/59/2007 (SEQ ID NO: 1) containing an additional cleavage site mutation (R343Q; numbering refers to SEQ ID NO: 1) leads to survival of 90% of the animals infected.

Figure 24B:
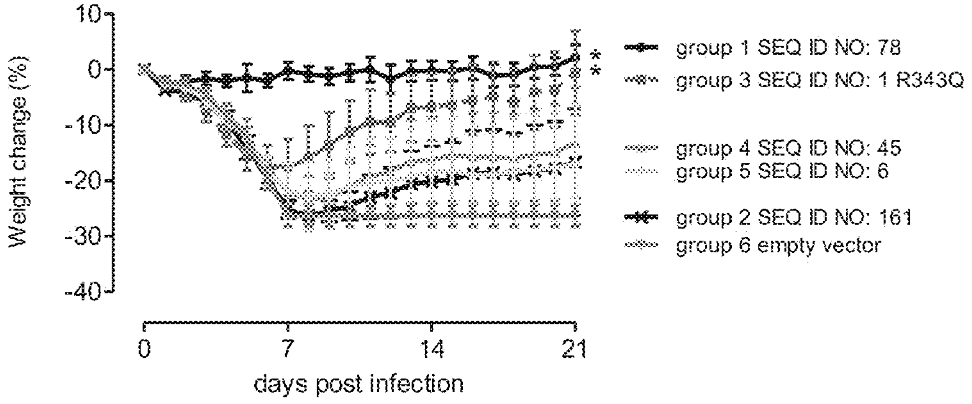
Figure 24:
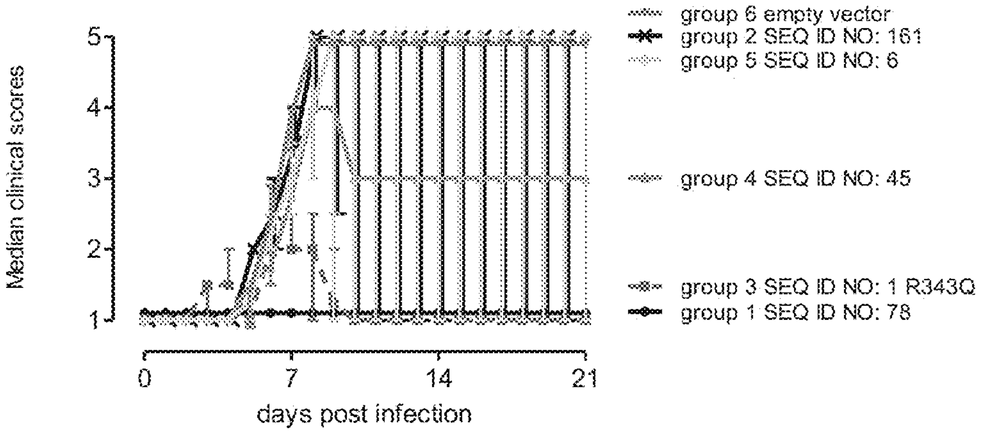

The results obtained from the survival curves are also reflected in the mean body weight change and median clinical scores for each group shown in FIGS. 24B and 24C. Animals immunized with polypeptides of the disclosure SEQ ID NOS: 45, 6 and 161 exhibit weight loss up to 25-30%, but animals surviving after day 9 post-infection show an increase in weight. For animals immunized with SEQ ID NO: 45 a drop in clinical score from 4 to 3 is also observed. Animals immunized with DNA encoding the full-length HA homologous to the challenge strain (SEQ ID NO: 78) do not show weight loss, whereas animals immunized with DNA encoding full-length HA derived from the heterologous strain A/Brisbane/59/2007 (SEQ ID NO: 1) containing an additional cleavage site mutation (R343Q; numbering refers to SEQ ID NO: 1) experience weight loss and clinical symptoms but survivors fully cover. The highest weight loss is and clinical symptoms are observed for the control group immunized with an empty vector, in line with the lack of survival of these animals.

In conclusion, polypeptides SEQ ID NOS: 6, 45 and 78 are capable of inducing a protective response against a lethal challenge with H1N1 A/Puerto Rico/8/1934 in mice. It is of note that polypeptides of the disclosure SEQ ID NOS: 6 and 45 are derived from an HA molecule heterologous to the challenge strain, whereas SEQ ID NO: 78 is derived from the homologous influenza strain. So polypeptides of the disclosure can induce protection against both homologous and heterologous influenza infection.

Example 22: Selection of a Panel of Representative HINT HA Sequences and Design of Polypeptides of the Disclosure Based on these Sequences In order to show the wide applicability of the design method described in Example 20, the method was applied to a panel of selected HA0 sequences that cover a large percentage of the natural sequence variation found in H1N1 viruses. The selection of a panel of representative HA sequences from the pool of known human H1N1 HA sequences in this example has the objective to select a minimum number of strains with a maximum representativeness. To achieve this, all differences between the HA sequences of human H1N1 influenza viruses present in the Influenza Virus Sequence Database have been quantified, the structure in these differences has been investigated and homogenous subgroups have been identified. From each of such groups the most representative sequence has been selected to contribute to the panel.

The primary step in the procedure is the quantification of the difference between each pair or sequences in the considered sequence database. The reverse PAM250 (rPAM250) matrix (Xu, 2004) is used to quantify the difference at each amino acid position. Euclidian addition is then used to quantify the total difference for that pair. All pair-wise differences are used to form a symmetric n×n matrix of differences, where n equals the number virus strains considered.

Principal Coordinates Analysis (PCA) is used to structure the matrix of differences (Higgins, 1992). PCA is based on dimension reduction. The input matrix is considered a distribution in n dimensional space (where n equals the number of strains considered). The variability is then analyzed and structured in such a way that a minimum dimensionality is required to cover most (or all) variability. The result is an m dimensional coordinate system (where m is the number dimension to cover most or all variability) with most variation on the first axis and then decreasing. All considered sequences are positioned within that coordinate system. In the case where only 2 or 3 dimensions are needed, the result can be plotted completely in a 2D or 3D graph, respectively, in which the difference between the strains can be visualized. In the case where more dimensions are needed, also a 3D plot can be constructed from the first 3 axes, but that graph does not cover all variability, since part of the variation is in the $4^{th}$ and higher dimensions.

The sequences in the m dimensional space are then clustered, using both hierarchical and k means clustering. Average linkage within groups is used to obtain groups with similar internal variability, and to avoid a large proportion of single strain clusters. Clustering is done at all levels, starting at 1 (all strains in one cluster) till n (each strain forming its own cluster). From each cluster the most central strain is selected as the most representative. The set of most central strains then form the panel of representative strains for that level clustering. For each level of clustering the coverage (or percentage of variation explained) is estimated by computing the sum of squared distances of each strain to its center strain as compared to the sum of squared distances of each strain to the center of the coordinate system. A minimum level of coverage to be achieved is then set to be the smallest required size of the representative panel.

Additionally to the Xu rPAM250 matrix, small values were assigned for the difference when one of the two sequences had a gap on a certain position (due to inserts or deletions). Also a weight factor was included in the procedure, to account for the large differences in numbers of isolates through the years. This variation was considered to be partially true variation in occurrence, partially driven by different levels of surveillance/awareness. Therefore, the weight factor was set at one divided by the square root of the numbers of observations in a particular year. This weight factor was taken into consideration when constructing the m dimensional space, during the cluster analysis and selection of center points, and at estimation of the level of covered variation.

In this example, constructed sequences are used, consisting of the parts of HA coding for the polypeptide of the disclosure. Two different sets of constructed sequences were created. In the first set the natural sequences with the exception of the signal sequence (e.g., amino acids 1-18), amino acids 53 to 320 (the HA head domain), the transmembrane sequence (amino acid 530 to the C-terminal amino acid) (numbering refers to SEQ ID NO: 1) or the equivalent of these positions in other sequences were taken into consideration. In the second set amino acids at position (or the equivalent position) 406, 409, 416, 324, 436, 413 were also not taken into consideration, since these are modified according to the general method described in Example 20. Furthermore, (the equivalent of) positions 419-433 were also not taken into account in the second set reflecting the addition of a GCN4-based stabilization sequence in polypeptides of the disclosure as described in Example 9.

Using the method described above 7 HA sequences were selected from constructed sequences set 1, selected, covering 75% of the sequence variation and 8 HA sequences from constructed sequences set 2 covering 74% of the sequence variation. The strains are listed in Table 10. Three of the selected sequences appear in both sets, so 13 unique HA sequences remain. These sequences were used to design polypeptides of the disclosure according to the method described in Example 20. In addition the stabilizing GCN4 sequence MKQIEDKIEEIESKQ (SEQ ID NO: 84) is introduced at the equivalent of position 419-433 (numbering refers to SEQ ID NO: 1), as described in Example 9. The polypeptides hereof designed on the basis of the HA sequences of H1N1 A/Memphis/20/1978 and H1N1 A/USSR/92/1977 are identical, as are the polypeptides hereof designed on the basis of the HA sequences of A/Wisconsin/629-D01415/2009 and H1N1 A/Sydney/DD3-55/2010. So in total 10 unique polypeptides of the disclosure were designed, and an alignment of these sequences is shown in FIG. 25.

Figure 26:
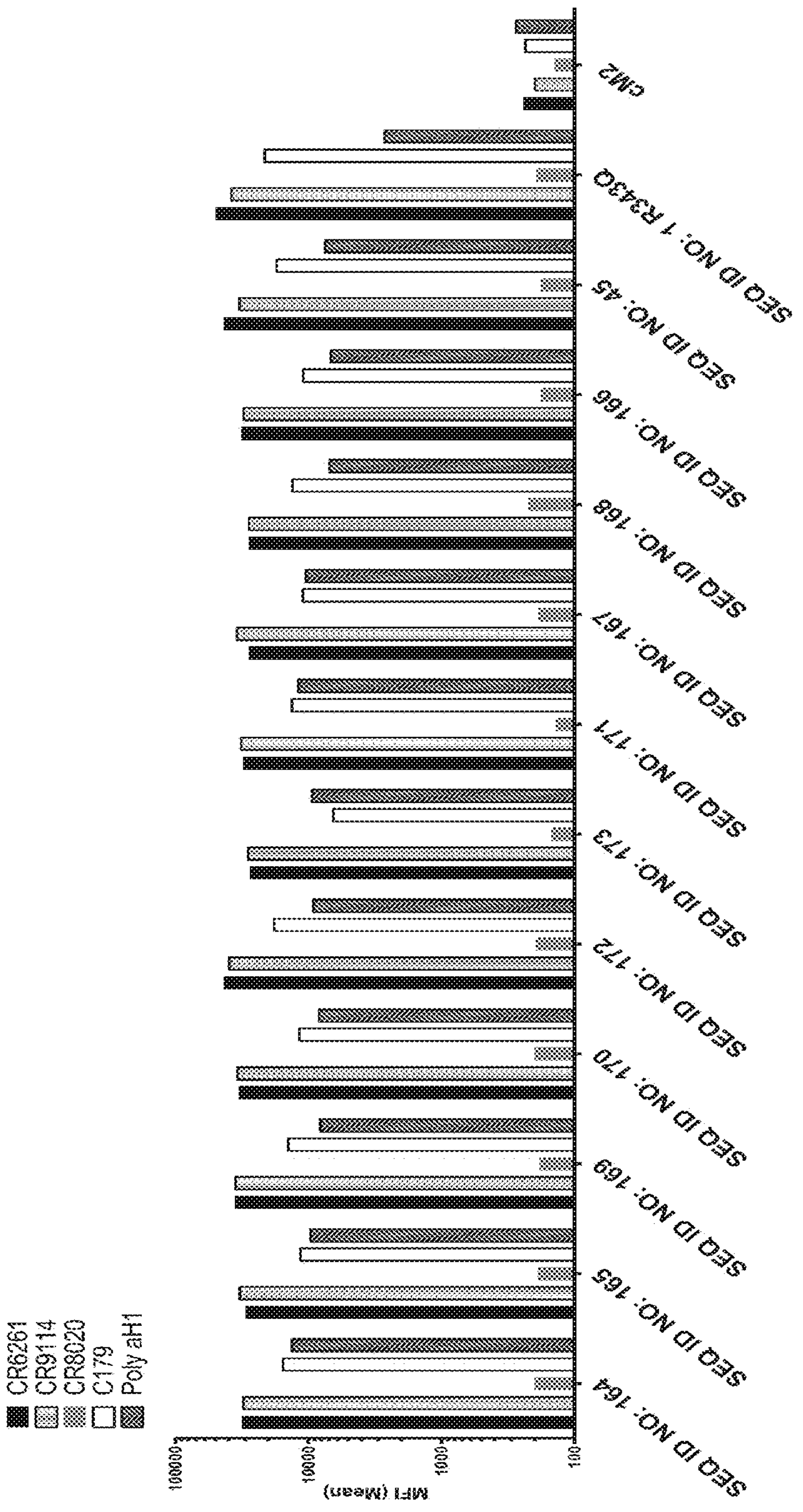
FIG. 26: FACS assay of stem domain polypeptides based on H1 HA selected according Example 22. Mean fluorescence intensity is shown.

Expression vectors containing the DNA encoding polypeptides of the disclosure SEQ ID NO: 164 to SEQ ID NO: 173, as well as polypeptide of the disclosure SEQ ID NO: 45 based on the HA sequences of A/Brisbane/59/2007 and the corresponding full-length HA SEQ ID NO: 1 with additional cleavage site mutation R343Q in expression vector pcDNA2004 were used for transfection of HEK293F cells and the cells were analyzed by FACS as before. In addition to human monoclonal antibodies CR6261, CR9114 and CR8020, also mouse monoclonal antibody C179 known to neutralize Influenza A H1 and H2 strains (Okuna et al., 1993) was included in the experiment. The results are shown in FIG. 26.

All polypeptides of the disclosure, as well as the full-length sequence of A/Brisbane/59/2007, are expressed on the cell surface and recognized by broadly neutralizing antibodies CR6261, CR9114 and C179, but not CR8020. The latter is known to bind only to HA from Influenza A group 2. The binding of the antibodies CR6261, CR9114 and C179 indicates that the broadly neutralizing epitopes are well preserved in the polypeptides hereof. Considering the sequence variation covered in these sequences this is clear evidence of the general applicability of our design method to generate polypeptides of the disclosure containing broadly neutralizing epitopes.

Example 23: Characterization of Polypeptide of the Disclosure s-H1-Mini2-Cluster1+5+6-GCN4 (SEQ ID NO: 145)

Purified polypeptide of the disclosure s-H1-mini2-cluster1+5+6-GCN4 (SEQ ID NO: 145) was obtained as described in Example 13. To confirm the presence of the conformational epitopes of CR6261 and CR9114 the binding of these antibodies with the purified protein was studied by biolayer interferometry (Octet $Red^{384}$, Forte Bio). To this end, biotinylated CR6261, CR9114 and CR8020 were immobilized on streptavidin coated sensors, the sensors were exposed first to a solution of the purified polypeptide (250 nM) of the disclosure to measure the rate of association and then to a wash solution to measure the rate of dissociation. For reasons of comparison the experiment was repeated with the full-length protein (SEQ ID NO 149) both in its trimeric and monomeric form. The results are shown in FIG. 27.

Figure 27:
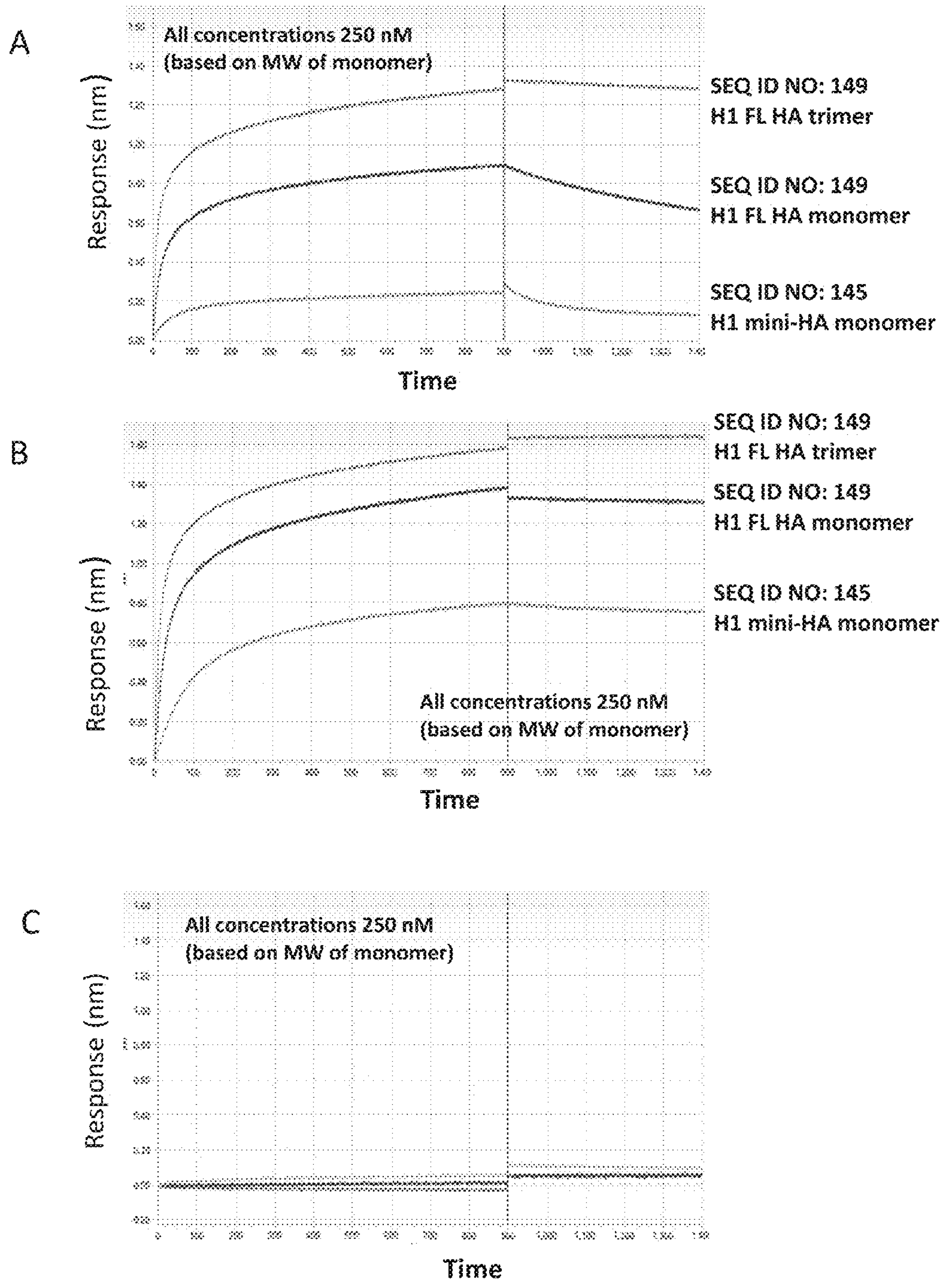
FIG. 27: Kinetics of binding of full-length H1 HA (SEQ ID NO 149) in its trimeric and monomeric form and s-H1-mini2-cluster1+5+6-GCN4 (SEQ ID NO: 145) to immobilized monoclonal antibody CR6261 (Panel A), CR9114 (Panel B) and CR8020 (Panel C) as determined by biolayer interferometry.

The immobilized CR6261 recognizes both the monomeric and trimeric forms of the ectodomain of full-length HA from H1N1 A/Brisbane/59/2007 as evidenced by the clear responses after exposure to these proteins in solution (FIG. 27, Panel A). The response observed for the trimeric protein is larger than observed for the monomer (ca. 1.3 nm vs 0.9) with the same sequence, an effect that is caused (at least in part) by the smaller size of the monomer compared to the trimer. Binding of CR6261 to s-H1-mini2-cluster1+5+6-GCN4 (SEQ ID NO: 145) results in a maximum response of approximately 0.25 nm. Upon exposure to the wash solution dissociation of the complex is observed for all three analytes with the fastest release observed for the polypeptide of the disclosure s-H1-mini2-cluster1+5+6-GCN4 (SEQ ID NO: 145), and the slowest for the trimeric form of the ectodomain of full-length HA from H1N1 A/Brisbane/59/2007 (SEQ ID NO 149).

Similar to CR6261 immobilized CR9114 also recognizes both trimeric and monomeric forms of the ectodomain of full-length HA from H1N1 A/Brisbane/59/2007, as well as the polypeptide of the disclosure s-H1-mini2-cluster1+5+6-GCN4 (SEQ ID NO: 145). Response are stronger for all three analytes compared to CR6261 (1.5, 1.4 and 0.8 nm for trimeric, monomeric full-length HA (SEQ ID NO: 149) and stem domain polypeptide s-H1-mini2-cluster1+5+6-GCN4 (SEQ ID NO: 145), respectively) and upon exposure of the complex to wash buffer release of the antigen is minimal or undetectable in all three cases. For CR8020 no responses were observed for any of the analytes, in line with the influenza group 2 stem domain specificity of this antibody.

Figure 28:
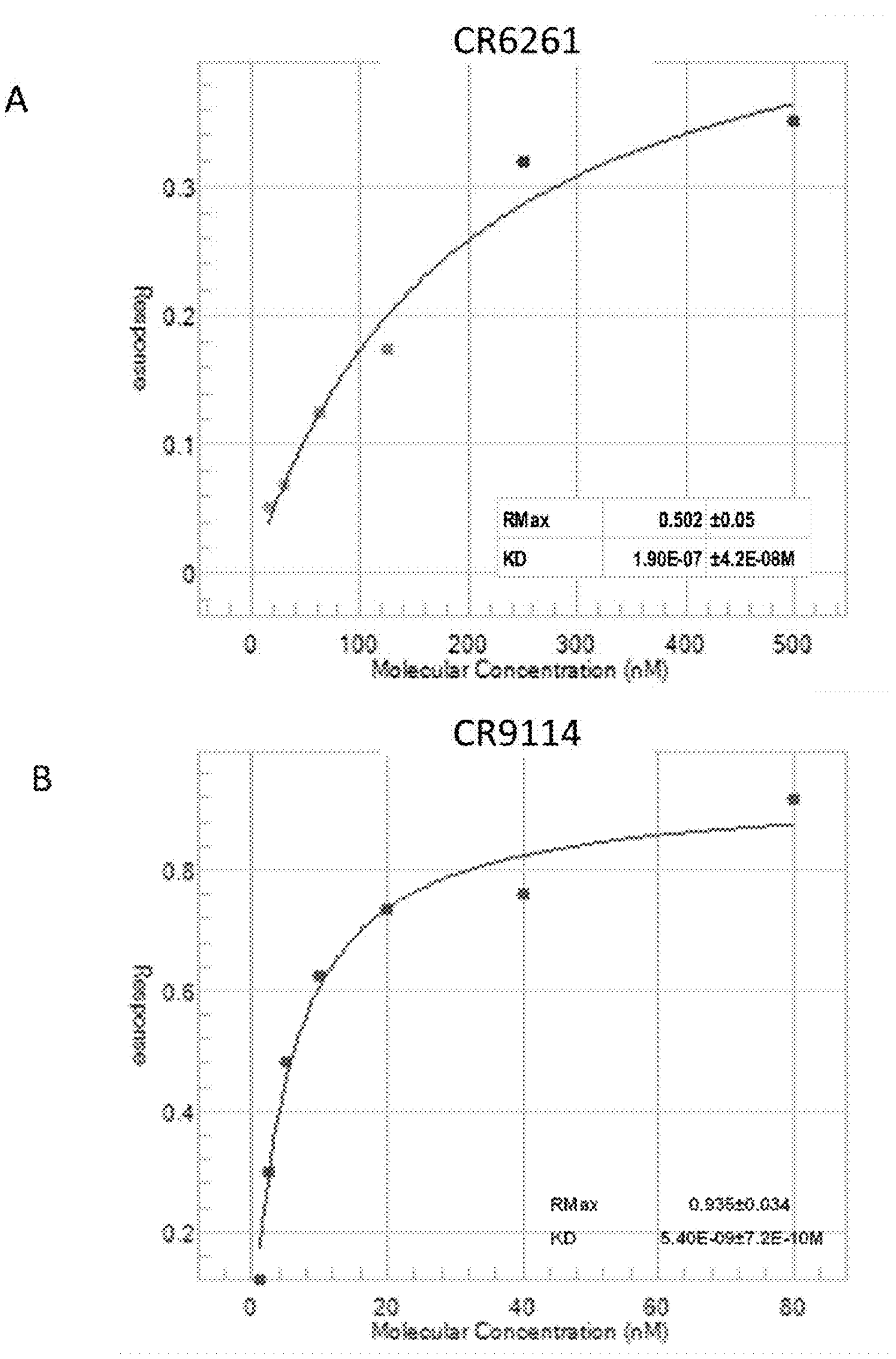
FIG. 28: Steady state titration of the binding of s-H1-mini2-cluster1+5+6-GCN4 (SEQ ID NO: 145) to immobilized CR6261 (Panel A) and CR9114 (Panel B) followed by biolayer interferometry.

To further characterize the binding of CR6261 and CR9114 to the purified stem domain polypeptide a titration was performed. To this end, immobilized CR6261 containing sensors were exposed to s-H1-mini2-cluster1+5+6-GCN4 (SEQ ID NO: 145) solutions at concentrations of 500, 250, 125, 63, 31, 16 and 8 nM, respectively, and the final response after 14000s recorded. The responses were plotted as a function of the stem domain polypeptide concentration, and a fit to a steady state 1:1 binding model was performed, yielding a dissociation constant $K_d$ of ca 190 nM for the CR6261/stem domain polypeptide complex (FIG. 28, Panel A). Similarly, sensors modified with immobilized CR9114 were exposed to s-H1-mini2-cluster1+5+6-GCN4 (SEQ ID NO: 145) at concentrations of 80, 40, 20, 10, 5, 2.5 and 1.3 nM, respectively, and the final response after 10800s recorded. Fitting of the final responses as a function of stem domain polypeptide concentration yields a $K_d$ value of 5.4 nM for the CR9114/stem domain polypeptide complex (FIG. 28, Panel B).

In conclusion, polypeptide of the disclosure s-H1-mini2-cluster1+5+6-GCN4 (SEQ ID NO: 145) is capable of binding broadly neutralizing monoclonal antibodies CR6261 and CR9114, confirming the presence of the corresponding neutralizing epitopes in this stem domain polypeptide.

Example 24: Protection Against Lethal Influenza Challenge in Mice by Polypeptides of the Disclosure In order to determine whether polypeptides of the disclosure are capable of inducing an immune response that protects mice from death upon an exposure to influenza virus that would otherwise be lethal an influenza challenge experiment was performed. Mice were immunized i.m. with expression vectors encoding H3 Full-length A/Hong Kong/1/1968 (SEQ ID NO: 121), HK68 H3m2-cl9+10+11 (SEQ ID NO: 124) and HK68 H3m2-cl9+10+11+12-GCN4 SEQ ID NO: 130. Immunization was performed using 50 μg expression construct+50 μg adjuvant (pUMCV1-GM-CSF) according to the study protocol below.

Study Protocol

| | |
|---|---|
| Day −1 | Bleed. |
| Day 0 | Administration of vaccine (i.m.). |
| Day 21 | Administration of vaccine (i.m.). |
| Day 28 | Bleed. |
| Day 42 | Administration of vaccine (i.m.). |
| Day 47 | Bleed. |
| Day 48 | Measurement of weight, temperature, clinical score and lethality. |
| Day 49 | Challenge with lethal dose of influenza viral infection (per nasal). |
| Day 49 | Remaining inoculum is utilized for back titration of virus. |
| Day 49-70 | Daily measurement of weight, temperature, clinical score and lethality.<br>Animals with clinical score ≥3 are monitored two times per day.<br>Animals with clinical score ≥4 or temperature >32° C., whichever comes first, are immediately removed from the study. |
| Day 70 | Sacrifice of all mice. |

Group 7-10: Challenge with HK68 (A/Hong Kong/1/68, H3N2)

| | |
|---|---|
| Group 7: | SEQ ID NO: 121 |
| Group 8: | SEQ ID NO: 130 |
| Group 9: | SEQ ID NO: 124 |
| Group 10: | empty vector |

10 mice per group. Total 40 mice. BALB/c.

Materials and Methods:

Virus Strain and Source:

Influenza virus strain HK68 (A/Hong Kong/1/68) was provided by Prof J. Katz (Center for Disease Control and Prevention, Atlanta, Ga., USA) followed by propagation by Virapur (San Diego). The virus has been passaged multiple times in mouse lungs to enhance virulence in mice. A suitable reference for this virus is: Frace et al., Vaccine 1999; 17:2237. Stock solution 3×10e8 pfu/ml. Batch #F1109A.

Storage conditions. −75° C.±10° C. Freezer: −86° C. UCT freezer. Thermo Form. Fisher Scientific.

Animals:

Mouse, BALB/c (Specified Pathogen Free; SPF), female. 6 to 8 weeks old on Study Day 0 ~17-19 grams. Sourced from Charles River Laboratories and identified by "ear identification." All animals were acclimatized and maintained for 11 days before the start of the experiment.

DNA Administration

Method of Inoculum Reconstitution

Appropriate DNA formulations, as listed above were prepared aliquoted and stored at −20° C. Per construct one aliquot was thawed to room temperature immediately before injection, drawn into a syringe and injected. The remainder of each aliquot was discarded after completion of all injections of each immunization round.

Dose Level and Method of Administration

Mice are anaesthetized by intraperitoneal injection with 9.75 mg Xylasol (Graeub E Dr. AG (on the World Wide Web at graeub.com); Cat: 763.02) and 48.75 mg Ketasol (Graeub E Dr. AG (on the World Wide Web at graeub.com); Cat: 668.51) per kg body weight. 50 μl DNA solution was injected using a 0.5 ml syringe with a G29 needle intramuscularly (i.m.) in the quadriceps muscle of each hind leg, yielding a total volume of 100 μl injected per mouse. The remainder of each aliquot was discarded after completion of all injections of each immunization round.

Virus Administration:

Method of Inoculum Reconstitution

The virus material was stored at −75° C.±10° C. and was defrosted prior to administration. Once defrosted, the material was diluted in cold PBS (4° C.) corresponding to 10 LD50/50 μl for the A/HK/1/68 challenges. The diluted virus was kept on ice until administration to the mice.

Dose Level and Method of Administration

The animals were anaesthetized by intraperitoneal injection with 9.75 mg Xylasol and 48.75 mg Ketasol per kg body weight and each animal received 50 μl virus solution by intranasal. Unused material was returned to the lab for back titration.

Blood Withdrawal and Serum Preparation

At days specified in the Study Protocol, above, blood samples were taken (intermediate bleedings: 100-150 μl via retro-orbital cannulation, terminal bleeding via cardiac puncture: approximately 300-500 μl). Serum was isolated from this blood by centrifugation for 5 minutes at 14000 g and stored at −20° C. until shipment on dry ice.

Clinical Scoring

Clinical signs after virus challenge were scored with a scoring system (1 point for a healthy mouse; 2 points for a mouse showing signs of malaise, including slight piloerection, slightly changed gait and increased ambulation; 3 points for a mouse showing signs of strong piloerection, constricted abdomen, changed gait, periods of inactivity, increased breathing rate and sometime rales (clicking/crackling noise); 4 points for a mouse with enhanced characteristics of the previous group, but showing little activity and becoming moribund; 5 points for a dead mouse). Animals were inspected twice a day as long as they received a score of 3. Scoring was performed by a single investigator and mice with symptoms partially represented by two scores were score+/−0.5.

Weighing

All animals were weighed daily, starting on day 48 (authorization number 2216). Animals were also weighed prior to the end of the study in case of death, i.e., at removal from study. Bodyweight was recorded in grams (g)

Virus Back Titration

The dose of the virus administered was determined by titrating 8 replicate samples from the inoculum remaining after inoculation of the animals was completed. For viral back titration TCID50 measurement was utilized following the protocol outlined in "Current Protocols in Immunology, Animal Models of Infectious Disease 19.11.7."

Results:

The study was performed without technical difficulties and in line with the defined study protocol. Back titration of the inoculums of Influenza virus strain HK68 (A/Hong Kong/1/68, H3N2) resulted in the following TCID50: HK68 (A/Hong Kong/1/68): $1\times10^3$ TCID50/ml.

Figure 29:
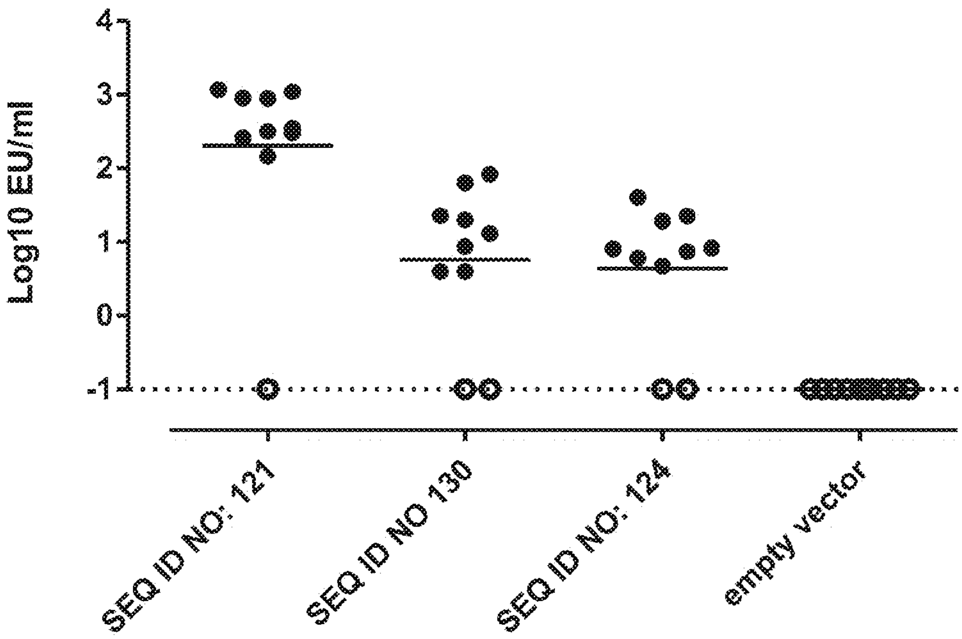
FIG. 29: IgG response against the ectodomain of HA from A/Hong Kong/1/1968 at day 49 as determined by ELISA. Details of the experiment are described in Example 24. Open symbols correspond to values below the limit of detection of the assay.

FIG. 29 shows the IgG response against the ectodomain of HA from A/Hong Kong/1/1968 at day 49 as determined by ELISA. Immunization with DNA encoding polypeptides of the disclosure SEQ ID NO: 124 and SEQ ID NO: 130 induces a clearly detectable response against the H3 HA HK68 ectodomain, whereas no response is detected for the empty vector negative control. As expected, the highest responses are observed for immunization with H3 Full-length A/Hong Kong/1/1968 (SEQ ID NO: 121).

Figure 30A:
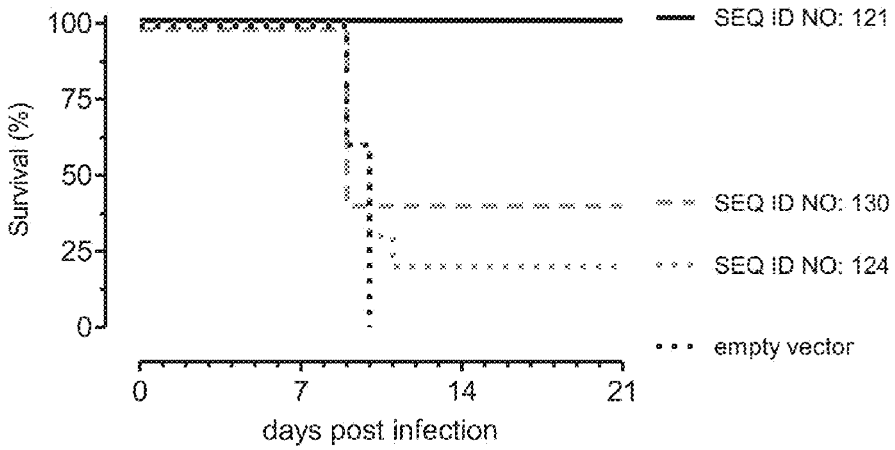
FIGS. 30A-30C: Kaplan-Meier survival curves (FIG. 30A), weight changes (FIG. 30B) and median clinical scores (FIG. 30C) for the influenza challenge experiment described in Example 24.

FIG. 30A shows the Kaplan-Meier survival curves for this experiment. Immunization with DNA encoding polypeptides of the disclosure SEQ ID NOS: 124 and 130 results in survival of 40 and 20% of mice infected with a lethal dose of influenza, respectively, indicating that immunization with the polypeptides hereof can indeed induce a protective immune response. In contrast animals immunized with the empty vector control all succumb to infection 10 days after the viral challenge. Immunization with DNA encoding the full-length HA (SEQ ID NO: 121) fully protects all animals (i.e., 100% survival) from the lethal challenge.

Figure 30B:
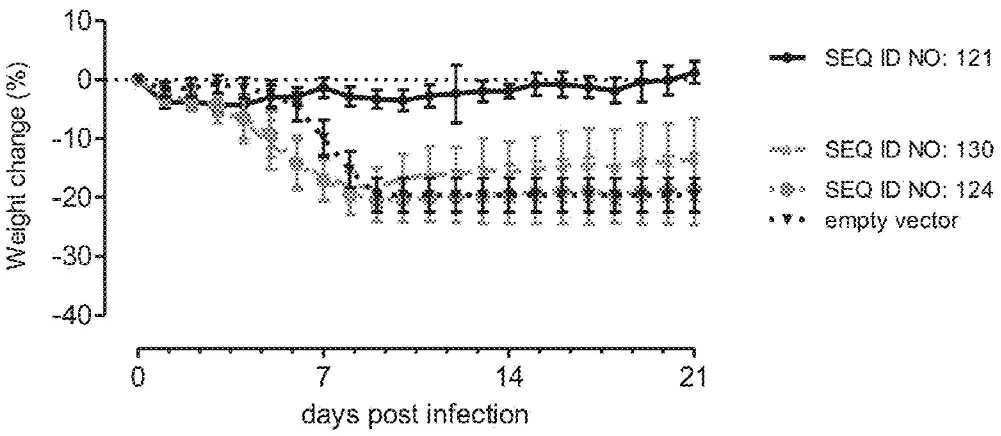
Figure 30C:
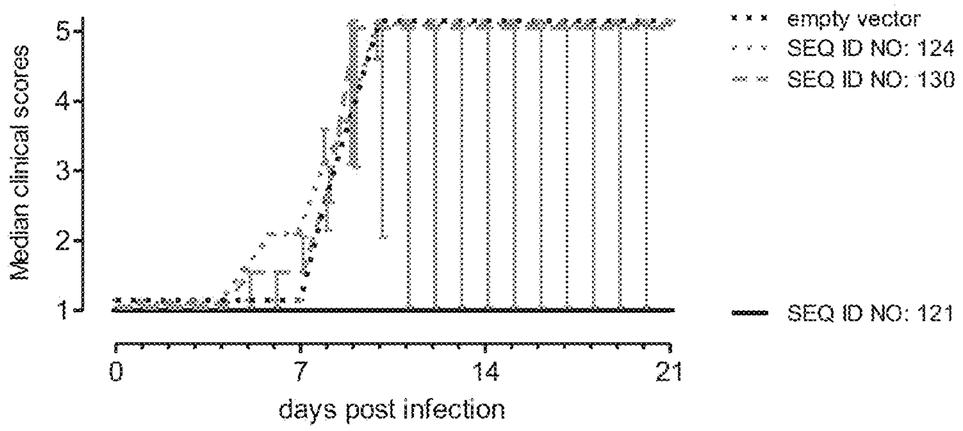

The results obtained from the survival curves are also reflected in the mean body weight change and median clinical scores for each group shown in FIGS. 30B and 30C. Animals immunized with DNA encoding polypeptides of the disclosure SEQ ID NOS: 124 and 130 exhibit weight loss up to 20%, but animals surviving after day 9 post-infection show an increase in weight. Animals immunized with DNA encoding the full-length HA (SEQ ID NO: 121) do not show weight loss. The highest weight loss and clinical symptoms are observed for the control group immunized with an empty vector, in line with the lack of survival of these animals.

In conclusion, polypeptides of the disclosure SEQ ID NOS: 124 and 130 are immunogenic and capable of inducing a protective response against a lethal challenge with H3N2 A/Hong Kong/1/1968 in mice.

Example 25: Design and Characterization of Stem Domain Polypeptides Based on H3 HA To further improve the stem domain polypeptides described in Example 12, an additional set of constructs was designed. Two additional sets of cysteine mutations were designed that will allow formation of stabilizing disulfide bridges at position 53 and 334 (T53C, G334C; cluster 16) and position 39 and 51 (G39C-E51C; cluster 17) (numbering refers to SEQ ID NO: 121). Furthermore, two sequences to be inserted between positions 420 and 421, i.e., at the N-terminal side of the long CD-helix (see FIG. 1). The insertion sequences have been designed such that they will facilitate the formation of inter-monomer disulfide bridges between individual monomers in the trimeric molecule. Two different sequences have been designed, i.e., NATGGCCGG (SEQ ID NO: 206) (Cluster 18) and GSGKCCGG (SEQ ID NO: 207) (Cluster 19). The sequence of cluster 18 also comprises a sequence introducing a glycosylation site (i.e., NAT) in the stem domain polypeptide. In some cases a glycosylation site is also introduced at position 417-419 by mutation into NAT.

Using the sequence of full-length HA from A/Hong Kong/1/1968 as a starting point the modifications described above were combined with the S62-P322 deletion to arrive at the following stem domain polypeptides:

SEQ ID NO: 174: H3 HK mini2a-linker+cl9+10+11+12+GCN4T-CG7-1

SEQ ID NO: 175: HK68 H3mini2a-linker+cl9_+10+12+18+GCN4T

SEQ ID NO: 176: HK68 H3mini2a-linker+cl9_+10+12+16+CG7-GCN4T

SEQ ID NO: 177: HK68 H3mini2a-linker+cl9_+10+12+19+GCN4T

SEQ ID NO: 178: HK68 H3mini2a-linker+cl9_+10+12+17+CG7-GCN4T

SEQ ID NO: 179: H3 HK68 mini2a-linker2+cl9_+10+12+GCN4T

The genes encoding the protein sequences described above were synthesized and cloned in expression vector pcDNA2004 using methods generally known in the art. Expression on the cell surface and binding of monoclonal antibodies was analyzed by fluorescence associated cell sorting as described above. For reasons of comparison also the full-length HA of H3N2 A/Hong Kong/1/1968 (SEQ ID NO: 121), additionally containing an R345Q mutation in the cleavage site, and SEQ ID NO: 130 (HK68 H3m2-cl9+10+11+12-GCN4) were also included in the experiment as well as negative control cM2.

Figure 31:
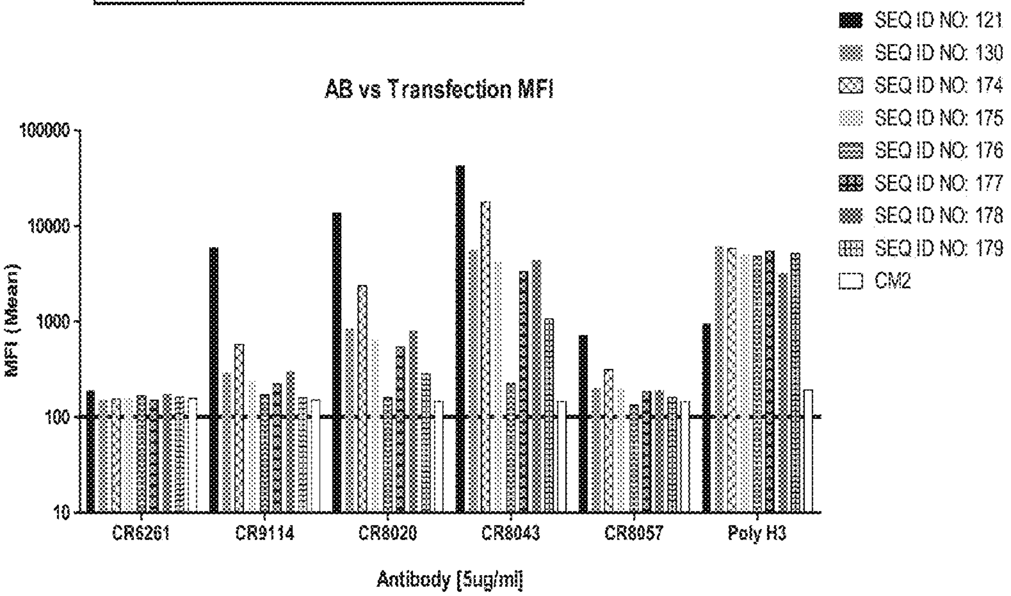
FIG. 31: FACS assay of stem domain polypeptides based on H1 HA selected according Example 25. Mean fluorescence intensity is shown.

FIG. 31 shows the results of this experiment. All constructs are expressed on the cell surface as evidenced by the responses (MFI, panel A; percentage positive cells, panel B) observed for the polyclonal anti-H3 serum. Binding of CR8043 and CR8020 is observed for SEQ ID NOS: 174, 175, 176, 177, 178, 179, 121 and 130, indicating that the mutations of cluster 16 do not contribute to stabilizing the conformational epitopes of these antibodies. For mAb CR9114 binding above background can only be observed for SEQ ID NO: 174: H3 HK mini2a-linker+cl9+10+11+12+GCN4T-CG7-1 and to a lesser extent SEQ ID NO: 177: HK68 H3mini2a-linker+cl9_+10+12+17+CG7-GCN4T. Both sequences contain an additional glycosylation site in the B-loop, indicating the stabilizing effect of this modification on the conformational neutralizing epitope of CR9114.

In conclusion, it is shown that following the method described above stem domain polypeptides of the disclosure can be obtained for serotypes of group 2, in particular H3 subtypes. Further stabilization of these stem domain polypeptides can be achieved by introducing a glycosylation site in the B-loop. These sequences are also encompassed by the disclosure.

Example 26: Immunogenicity HA Stem Domain Polypeptides Based on H3 HA

In order to assess the immunogenicity of the stem domain polypeptides mice were immunized with the expression vectors encoding full-length H3 from A/Wisconsin/67/2005 (SEQ ID NO: 89), SEQ ID NO: 105: H3-mini2, SEQ ID NO: 108: H3-mini2-cl9+10+11, SEQ ID NO: 112: H3-mini2-cl9+10+12, SEQ ID NO: 111: H3-mini2-cl9+10+11+12, SEQ ID NO: 114: H3-mini2-cl9+10+11+12-tri, SEQ ID NO: 113: H3-mini2-cl9+10+11+12-GCN4, SEQ ID NO: 119: H3-mini3-cl9+10+11+12+14, SEQ ID NO: 120: H3-mini4-cl9+10+11+12+14. An expression vector encoding for cM2 was also included as a negative control.

Figure 32A:
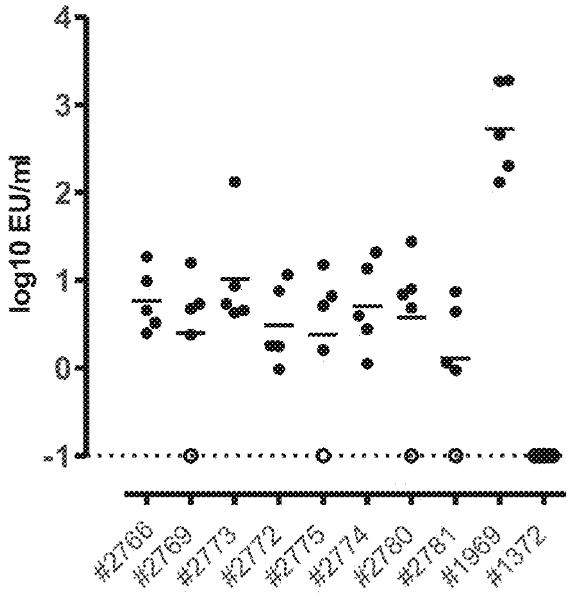
FIGS. 32A-32C: IgG response after 49 days against the ectodomain of HA as determined by HA from A/Wisconsin/67/2005 (FIG. 32A), A/Hong Kong/1/1968 (FIG. 32B) and A/Perth/16/2009 (FIG. 32C). Details of the experiment are described in Example 26. Open symbols correspond to values below the limit of detection of the assay.
Figure 32B:
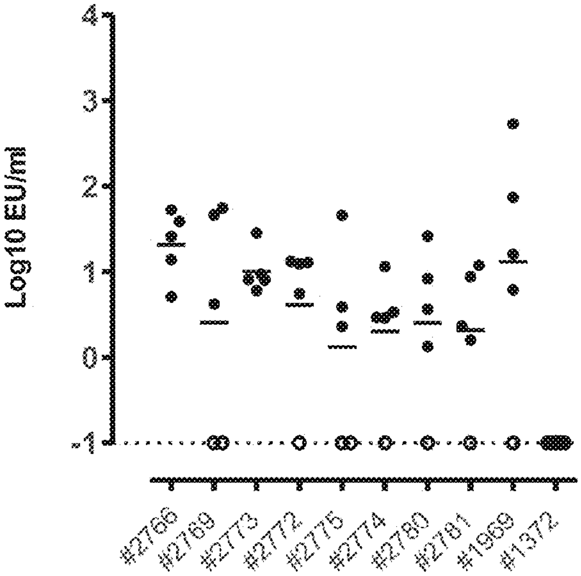
Figure 32C:
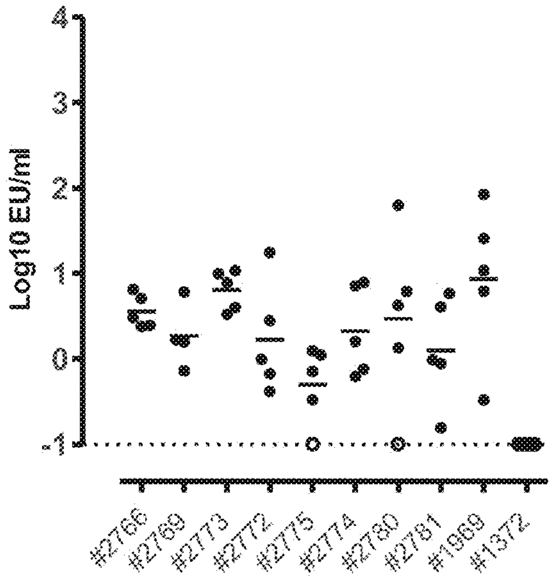

Groups of 4 mice (BALB\c) were immunized with 50 μg construct+50 μg adjuvant (pUMCV1-GM-CSF) i.m. on day 1, 21 and 42. On day 49 a final bleed was performed and serum collected. Negative control plasmid cM2 was administered by gene gun, using approximately 10 μg construct+approximately 2 μg adjuvant (pUMCV1-GM-CSF) and the same immunization scheme. The sera were analyzed by ELISA using recombinant full-length HA from A/Wisconsin/67/2005 and A/Hong Kong/1/1968 (obtained from Protein Sciences Corporation, Meriden, Conn., USA) as the antigen. In short, 96-well plates were coated with 50 ng HA overnight at 4° C., followed by incubation with block buffer (100 μl PBS, pH 7.4+2% skim milk) for 1 hour at room temperature. Plates were washed with PBS+0.05% TWEEN®-20, and 100 μl of a 2-fold dilution series in block buffer, starting from a 50-fold dilution of the serum is added. Bound antibody is detected using HRP-conjugated goat-anti-mouse IgG, using standard protocols well-established in the art. Titers are compared to a standard curve composed of a serial dilution of a mouse monoclonal antibody binding to the HA antigen and expressed as ELISA units per ml (EU/ml). Results of the ELISAs using HA from A/Wisconsin/67/2005, A/Hong Kong/1/1968 and A/Perth/16/2009 after 49 days are shown in FIGS. 32A, 32B and 32C, respectively. Sera obtained from mice immunized with DNA encoding the stem domain polypeptides included in this experiment are capable of recognizing the homologous full-length HA from A/Wisconsin/67/2005 and to a similar extent the heterologous full-length HA from A/Hong Kong/1/1968. In contrast, serum obtained from mice immunized with the full-length HA from A/Wisconsin/67/2005 (SEQ ID NO: 89) show a higher response towards the homologous HA than to the heterologous HA from A/Hong Kong/1/1968 and A/Perth/16/2009.

In conclusion, the data show that polypeptides of the disclosure derived from H3 HA are capable of inducing an immune response directed towards full-length HA.

Example 27: Immunogenicity HA Stem Domain Polypeptides Based on H3 HA of A/Hong Kong/1/1968

In order to assess the immunogenicity of the stem domain polypeptides mice were immunized with the expression vectors encoding full-length H3 from A/Hong Kong/1/1968 (SEQ ID NO: 121), SEQ ID NO: 124: HK68 H3m2-cl9+10+11, SEQ ID NO: 125: HK68 H3m2-cl9+10+12, SEQ ID NO: 126: HK68 H3m2-cl9+10+11+12, SEQ ID NO: 128: HK68 H3m2-cl9+10+11+12-tri, SEQ ID NO: 130: HK68 H3m2-cl9+10+11+12-GCN4. An expression vector encoding for cM2 was also included as a negative control.

Groups of 4 mice (BALB\c) were immunized with 100 μg construct+100 μg adjuvant (pUMCV1-GM-CSF) i.m. on day 1, 21 and 42. On day 49 a final bleed was performed and serum collected. Negative control plasmid cM2 was administered by gene gun, using approximately 10 μg construct+approximately 2 μg adjuvant (pUMCV1-GM-CSF) and the same immunization scheme. The sera were analyzed by ELISA using recombinant full-length HA from A/Hong Kong/1/1968 (obtained from Protein Sciences Corporation, Meriden, Conn., USA) as the antigen. In short, 96-well plates were coated with 50 ng HA overnight at 4° C., followed by incubation with block buffer (100 μl PBS, pH 7.4+2% skim milk) for 1 hour at room temperature. Plates were washed with PBS+0.05% TWEEN®-20, and 100 μl of a 2-fold dilution series in block buffer, starting from a 50-fold dilution of the serum is added. Bound antibody is detected using HRP-conjugated goat-anti-mouse IgG, using standard protocols well-established in the art. Titers are compared to a standard curve composed of a serial dilution of a mouse monoclonal antibody binding to the HA antigen and expressed as ELISA units per ml (EU/ml).

Figure 33:
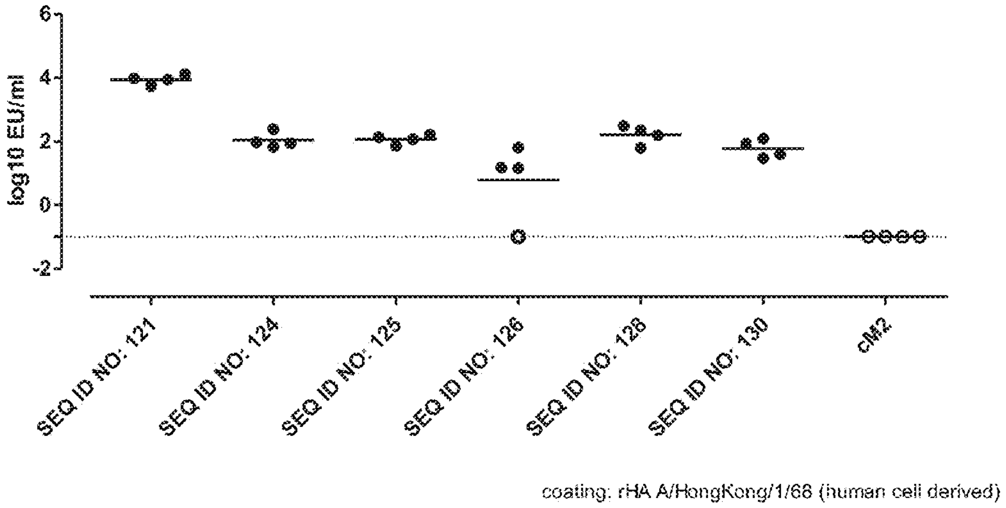
FIG. 33: IgG response after 49 days against the ectodomain of HA from A/Hong Kong/1/1968 as determined by ELISAs. Details of the experiment are described in Example 27. Open symbols correspond to values below the limit of detection of the assay.

Results of the ELISAs using HA from A/Hong Kong/1/1968 after 49 days are shown in FIG. 33. Sera obtained from mice immunized with DNA encoding the stem domain polypeptides included in this experiment are capable of recognizing the homologous full-length HA from A/Hong Kong/1/1968. As expected immunization with DNA encoding the full-length HA leads to high antibody titers to the homologous HA protein, whereas immunization with the negative control expression vector encoding cM2 does not induce antibodies that recognize the full-length HA of A/Hong Kong/1/1968.

In conclusion, the data show that polypeptides of the disclosure derived from H3 HA are capable of inducing an immune response directed towards the full-length H3 HA.

Example 28: Design of Another Stem-Domain Polypeptide Based on a H1 HA Capable of Eliciting Antibodies Neutralizing Group 1 and Group 2 Influenza Viruses Examples 4 and 6 disclose polypeptides based on H1 sequences that stably expose the epitope of the broadly neutralizing CR6261 antibody. Given the fact that CR6261 exclusively neutralizes influenza viruses from phylogenetic group 1, polypeptides designed to this epitope may not elicit a strong reaction to phylogenetic group 2 influenza viruses. Another way to design polypeptides according to the disclosure that induce such broadly cross-neutralizing antibodies is to use H1 HA sequence variants that more closely resemble H3 HA sequences in terms of structural and biochemical characteristics of the important amino acids in the epitope. Based on comparison between the structures of group-specific antibodies and molecules (CR6261, F10 and HB36) and the crystallized pan-influenza antibody FI6 (Corti et al., 2011), we found that the group 1-group 2 T49N (HA2) mutation can only be accommodated by FI6 without introduction of steric clashes. Asparagine at position 49 of HA2 exists in two group 1 viruses in the NCBI flu-database: A/swine/Hubei/S1/2009 (ACY06623) and A/swine/Haseluenne/IDT2617/2003 (ABV60697). Therefore, in one embodiment, the H1 sequences that constitute the basis of the disclosure as disclosed in Examples 4, 6 and 9 is one of these N-49-containing HA sequences. Alternatively, sequences according to the disclosure as described in Examples 4, 6 and 9 have an additional mutation at position 49 in HA2 to change the T into an N amino acid. Table 7 shows a sequence alignment of exemplary H1 HA sequences that can be used as starting sequences for the polypeptides hereof.

Figure 34:
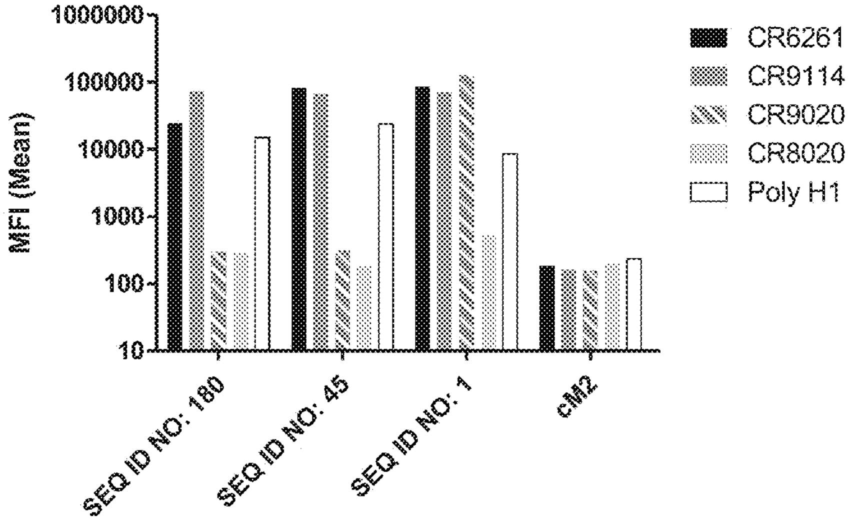
FIG. 34: FACS assay of stem domain polypeptide based on H1 HA selected according Example 28. Mean fluorescence intensity is shown.

SEQ ID NO: 180 is derived from SEQ ID NO: 45 by mutation T392N (numbering refers to SEQ ID NO: 1) T392 in SEQ ID NO: 1 corresponds to Threonine at position 49 in HA2 as described above. The gene encoding this polypeptide of the disclosure was synthesized and cloned into expression vector pcDNA2004 using methods well known to those skilled in the art. The presence of the neutralizing epitopes of CR9114 and CR6261 was confirmed by fluorescence associated cell sorting as described above. The results are shown in FIG. 34. MFI for SEQ ID NO: 180 is comparable to MFI observed for SEQ ID NO: 45 and SEQ ID NO: 1 for CR6261 and CR9114 binding, whereas CR9020 (known to bind to the head region of the full-length HA molecule) only recognizes SEQ ID NO: 1, and CR8020 (specific for HA of Influenza A group 2) does not recognize SEQ ID NO: 180, SEQ ID NO: 1 or SEQ ID NO: 45. Negative control cM2 is not recognized by any of the monoclonal antibodies used in this experiment.

In conclusion, SEQ ID NO: 180, containing mutation T392N comprises the neutralizing epitopes of CR6261 and CR9114.

Example 29: Design of Additional Polypeptides of the Disclosure Lacking the Transmembrane Sequence Influenza HA in its native form exists as a trimer on the cell or virus membrane. In certain embodiments, the intracellular and transmembrane sequence is removed so that a secreted (soluble) polypeptide is produced following expression in cells. Methods to express and purify secreted ectodomains of HA have been described (see, e.g., Dopheide et al., 2009; Ekiert et al., 2009, 2011; Stevens et al., 2004, 2006; Wilson et al., 1981). A person skilled in the art will understand that these methods can also be applied directly to stem domain polypeptides of the disclosure in order to achieve expression of secreted (soluble) polypeptide. Therefore, these polypeptides are also encompassed in the disclosure.

For example, in the case of a polypeptide of the disclosure derived from a HA sequence of group 1 influenza virus, a soluble polypeptide of the disclosure can be created from a by deletion of the polypeptide sequence from residue (the equivalent of) 514 to the C-terminus (numbering according to SEQ ID NO: 1), Alternatively, additional residues can be included in the polypeptide of the disclosure, e.g., by deleting the sequence from residue 515, 516, 517, 518, 519, 520, 521 or 522. Optionally, a his-tag sequence (HHHHHH (SEQ ID NO: 208) or HHHHHHH (SEQ ID NO: 191)) may be added, for purification purposes, optionally connected through a linker. Optionally, the linker may contain a proteolytic cleavage site to remove the his-tag after purification. The soluble polypeptide can be further stabilized by introducing a sequence known to form trimeric structures, such as the foldon sequence. Polypeptides obtained as described above are also encompassed in the disclosure.

SEQ ID NOS: 181 to 185 show sequences of soluble polypeptides derived from the HA sequence of H1N1 A/Brisbane/59/2007. Similarly, SEQ ID NOS: 186 to 187 show sequences of soluble polypeptides the HA sequence of H3N2 A/Hong Kong/1/1968. A person skilled in the art will understand that equivalent sequences for polypeptides derived from other HA sequences of other influenza A vaccine strains of, e.g., H1, H3, H5 subtypes can be designed. It will also be clear to that person that the C-terminal 6 histidines are attached for purification purposes. Since other purification methods that do not use this tag are in existence, the 6 histidine sequence is optional, and sequences lacking this purification tag are also encompassed in the disclosure.

TABLE 1

CDR regions of antibodies. The SEQ ID NO is given between brackets.

| Ab | HC CDR1 | HC CDR2 | HC CDR3 | LC CDR1 | LC CDR2 | LC CDR3 |
|---|---|---|---|---|---|---|
| 911 | GGTSNNY | ISPIFGST | ARHGNYYYYSGMD | DSNIGRRS | SND | AAWDDSLKGA |
| 4 | A (25) | (26) | V (27) | (28) | (29) | V (30) |

TABLE 2

Cross-binding reactivity of CR9114, as measured by ELISA and FACS.

| | IgG ELISA | | | | | | | IgG FACS | | | |
|---|---|---|---|---|---|---|---|---|---|---|---|
| | H1 | H3 | H5 | H7 | H9 | B | Rabies | PerC6 | mH1 | mH3 | mH7 |
| CR9114 | + | + | + | + | + | + | − | − | + | + | + |
| CR4098 | − | − | − | − | − | − | + | − | − | − | − |

H1 = soluble recombinant A/New Caledonia/20/1999 H1 HA;
H3 = soluble recombinant A/Wisconsin/67/2005 H3 HA;
H5 = soluble recombinant A/Vietnam/1203/04 H5 HA;
H7 = soluble recombinant A/Netherlands/219/2003 H7 HA;
H9 = soluble recombinant A/Hong Kong/1073/99 H9 HA;
B = soluble recombinant B/Ohio/01/05 influenza B HA;
Rabies = rabies glycoprotein;
PER.C6 ® = untransfected PER.C6 ® cells (control);
mH1 = PER.C6 ® expressed A/New Caledonia/20/1999 H1 HA;
mH3 = PER.C6 ® expressed A/Wisconsin/67/2005 H3 HA;
mH7 = PER.C6 ® expressed A/Netherlands/219/2003 H7 HA;
ND = not done.
+ = binding (>10x background);
+/− = low binding (2-10x background)
− = no detectable binding

TABLE 3

Cross-neutralizing activity of CR9114; Titers (indicated μg/ml) are geomean IC50 values as determined according to the Spearman-Karber method of at least duplicate experiments; >100 = not neutralizing at highest tested concentration (100 μg/ml).

| | Subtype | Strain | CR9114 |
|---|---|---|---|
| Group I | H1 | A/WSN/33 | 1.1 |
| | | A/New Caledonia/20/99 | 3.7 |
| | | A/Solomon Islands/3/2006 | 1.8 |

TABLE 3-continued

Cross-neutralizing activity of CR9114; Titers (indicated μg/ml) are geomean IC50 values as determined according to the Spearman-Karber method of at least duplicate experiments; >100 = not neutralizing at highest tested concentration (100 μg/ml).

| | Subtype | Strain | CR9114 |
|---|---|---|---|
| | | A/Brisbane/59/2007 | 2.6 |
| | | A/California/7/2009 | 0.3 |
| | H2 | A/Env/MPU3156/05 | 8.8 |
| | H5 | A/Hong Kong/156/97 | 0.4 |
| | | A/EW/MPF461/07 | 10.5 |
| | H6 | A/EW/MPD411/07 | 10.5 |
| | H8 | A/EW/MPH571/08 | 8.8 |
| | H9 | A/Hong Kong/1073/99 | 4.4 |
| | | A/Ck/HK/55P176/09 | 6.3 |
| Group II | H3 | A/Hong Kong/1/68 | 19 |
| | | A/Johannesburg/33/94 | 21.9 |
| | | A/Panama/2007/1999 | 39.9 |
| | | A/Hiroshima/52/2005 | 12.5 |
| | | A/Wisconsin/67/2005 | 32.4 |
| | | A/Brisbane/10/2007 | 5.6 |
| | H4 | A/WF/MPA 892/06 | 0.8 |
| | H7 | A/Mallard/Netherlands/12/2000 | 4.8 |
| | | A/New York/107/2003 | >100 |
| | H10 | A/Chick/Germany/N/49 | 15.7 |
| | H14 | A/Mallard/Astrakhan/263/1982 | >100 |

TABLE 4

Binding of serum obtained from mice immunized with either full-length HA or mini-HA constructs as analyzed by FACS. Data are the average values (n = 4) for percentage of cells positive after staining followed by the mean fluorescence intensity (in brackets). H1-FL (SEQ ID NO: 1), CL1 (SEQ ID NO: 3), CL1+2 (SEQ ID NO: 4) and CL1+4 (SEQ ID NO: 6). cM2 is a negative control.

| Immunization (serum) DNA transfected | cM2 | H1-FL | CL1 | CL1 + 2 | CL1 + 4 |
|---|---|---|---|---|---|
| cM2 | 47.5 (1817) | 4.8 (404) | 0.9 (272) | 0.7 (263) | 0.7 (269) |
| H1-FL | 2.1 (389) | 84.1 (7130) | 40.0 (1324) | 38.7 (1195) | 45.5 (1618) |
| CL1 | 2.1 (368) | 39.1 (1124) | 43.9 (1763) | ND | ND |
| CL1 + 2 | 1.7 (348) | 47.9 (1616) | ND | 51.4 (2472) | ND |
| CL1 + 4 | 1.7 (342) | 19.6 (787) | ND | ND | 30.0 (1047) |

% PE pos (Geometric MFI, n = 4)

TABLE 5

Standard amino acids, abbreviations and properties

| Amino Acid | 3-Letter | 1-Letter | Side chain polarity | Side chain charge (pH 7.4) |
|---|---|---|---|---|
| alanine | Ala | A | nonpolar | Neutral |
| arginine | Arg | R | polar | Positive |
| asparagine | Asn | N | polar | Neutral |
| aspartic acid | Asp | D | polar | Negative |
| cysteine | Cys | C | nonpolar | Neutral |

TABLE 5-continued

| Standard amino acids, abbreviations and properties | | | | |
|---|---|---|---|---|
| Amino Acid | 3-Letter | 1-Letter | Side chain polarity | Side chain charge (pH 7.4) |
| glutamic acid | Glu | E | polar | Negative |
| glutamine | Gln | Q | polar | Neutral |
| glycine | Gly | G | nonpolar | Neutral |
| histidine | His | H | polar | positive (10%) neutral (90%) |
| isoleucine | Ile | I | nonpolar | Neutral |
| leucine | Leu | L | nonpolar | Neutral |
| lysine | Lys | K | polar | Positive |
| methionine | Met | M | nonpolar | Neutral |
| phenylalanine | Phe | F | nonpolar | Neutral |
| proline | Pro | P | nonpolar | Neutral |
| serine | Ser | S | polar | Neutral |
| threonine | Thr | T | polar | Neutral |
| tryptophan | Trp | W | nonpolar | Neutral |
| tyrosine | Tyr | Y | polar | Neutral |
| valine | Val | V | nonpolar | Neutral |

TABLE 6

Consensus sequence for H1 402-418 (SEQ ID NO: 17), other natural variants and mutations that stabilize polypeptides of the disclosure. One or more mutations in the parental sequence are present in polypeptides of the disclosure.

| position | amino acid | conservation (%) | other naturally occurring a.a. | preferred mutation | Other polar mutations | Other charged mutations | Other flexible mutations |
|---|---|---|---|---|---|---|---|
| 402 | M | 99.88 | T, I | | | | |
| 403 | N | 99.88 | T, D | | | | |
| 404 | T | 96.24 | S, A, M, N, I, V | | | | |
| 405 | Q | 99.92 | H, K | | | | |
| 406 | F | 99.92 | L | S | T, N, Q | R, H, K, D, E | G |
| 407 | T | 99.73 | A, I, K | | | | |
| 408 | A | 96.71 | S, G, V | | | | |
| 409 | V | 99.45 | Q, M, I, G, L | T, Q, G | S, N | R, H, K, D, E | |
| 410 | G | 99.1 | S, N, D, C, V | | | | |
| 411 | K | 99.8 | T, N, R, E | | | | |
| 412 | E | 99.84 | A, G | | | | |
| 413 | F | 99.92 | S, L | S | T, N, Q | R, H, K, D, E | G |
| 414 | N | 96.52 | S, D, I | | | | |
| 415 | H/K | 56.20/32.76 | S, T, N, E, Q, R, D | | | | |
| 416 | L | 99.8 | F, S, I, P | S | T, N, Q | R, H, K, D, E | G |
| 417 | E | 99.84 | A, D, R | | | | |
| 418 | K/R | 63.95/35.69 | S, Q, T, N | | | | |

TABLE 7

Sequence alignment of H1 sequences according to particular embodiments of the disclosure.

| | | |
|---|---|---|
| 1. | A/Solomon Islands/6/2003 (H1N1) | (SEQ ID NO: 54) |
| 2. | A/Brisbane/59/2007 (H1N1) | (SEQ ID NO: 1) |
| 3. | A/New Caledonia/20/1999(H1N1) | (SEQ ID NO: 55) |
| 4. | A/California/07/2009 (H1N1) | (SEQ ID NO: 56) |
| 5. | A/swine/Hubei/S1/2009(H1N1) | (SEQ ID NO: 57) |
| 6. | A/swine/Haseluenne/IDT2617/2003(H1N1) | (SEQ ID NO: 58) |
| 7. | A/NewYork/8/2006(H1N1) | (SEQ ID NO: 59) |
| 8. | A/SolomonIslands/3/2006(H1N1) | (SEQ ID NO: 60) |
| 9. | A/NewYork/146/2000(H1N1) | (SEQ ID NO: 61) |
| 10. | A/NewYork/653/1996(H1N1) | (SEQ ID NO: 62) |
| 11. | A/Beijing/262/1995(H1N1) | (SEQ ID NO: 63) |
| 12. | A/Texas/36/1991(H1N1) | (SEQ ID NO: 64) |
| 13. | A/Singapore/6/1986(H1N1) | (SEQ ID NO: 65) |
| 14. | A/Chile/1/1983(H1N1) | (SEQ ID NO: 66) |
| 15. | A/Baylor/11515/1982(H1N1) | (SEQ ID NO: 67) |

TABLE 7-continued

Sequence alignment of H1 sequences according to particular embodiments of the disclosure.

| | | |
|---|---|---|
| 16. | A/Brazil/11/1978(H1N1) | (SEQ ID NO: 68) |
| 17. | A/USSR/90/1977(H1N1) | (SEQ ID NO: 69) |
| 18. | A/NewJersey/8/1976(H1N1) | (SEQ ID NO: 70) |
| 19. | A/Denver/1957(H1N1) | (SEQ ID NO: 71) |
| 20. | A/Albany/4835/1948(H1N1) | (SEQ ID NO: 72) |
| 21. | A/FortMonmouth/1/1947(H1N1) | (SEQ ID NO: 73) |
| 22. | A/Cameron/1946(H1N1) | (SEQ ID NO: 74) |
| 23. | A/Weiss/1943(H1N1) | (SEQ ID NO: 75) |
| 24. | A/Iowa/1943(H1N1) | (SEQ ID NO: 76) |
| 25. | A/Bellamy/1942(H1N1) | (SEQ ID NO: 77) |
| 26. | A/PuertoRico/8/1934(H1N1) | (SEQ ID NO: 78) |
| 27. | A/WSN/1933(H1N1) | (SEQ ID NO: 79) |
| 28. | A/SouthCarolina/1/1918(H1N1) | (SEQ ID NO: 80) |

TABLE 8

```
 1. MKVKLLVLLC TFTATYADTI CIGYHANNST DTVDTVLEKN VTVTHSVNLL EDSHNGKLCL  60
 2. MKVKLLVLLC TFTATYADTI CIGYHANNST DTVDTVLEKN VTVTHSVNLL ENSHNGKLCL  60
 3. MKAKLLVLLC TFTATYADTI CIGYHANNST DTVDTVLEKN VTVTHSVNLL EDSHNGKLCL  60
 4. MKAILVVLLY TFATANADTL CIGYHANNST DTVDTVLEKN VTVTHSVNLL EDKHNGKLCK  60
 5. MEAKLFVLFC AFTALKADTF CVGYHANYST HTVDTILEKN VTVTHSVNLL ENSHNGKLCS  60
 6. MEAKLFVLFC AFTALKADTI CVGYHANNST DTVDTILEKN VTVTHSINLL ENNHNGKLCS  60
 7. MKVKLLVLLC TFTATYADTI CIGYHANNST DTVDTVLEKN VTVTHSVNLL EDSHNGKLCL  60
 8. MKVKLLVLLC TFTATYADTI CIGYHANNST DTVDTVLEKN VTVTHSVNLL EDSHNGKLCL  60
 9. MKAKLLVLLC AFTATYADTI CIGYHANNST DTVDTVLEKN VTVTHSVNLL EDSHNGKLCR  60
10. MKAKLLVLLC AFTATYADTI CIGYHANNST DTVDTVLEKN VTVTHSVNLL EDSHNGKLCR  60
11. MKAKLLVLLC TFTATYADTI CIGYHANNST DTVDTVLEKN VTVTHSVNLL EDSHNGKLCL  60
12. MKAKLLVLLC AFTATYADTI CIGYHANNST DTVDTVLEKN VTVTHSVNLL EDSHNGKLCR  60
13. MKAKLLVLLC AFTATDADTI CIGYHANNST DTVDTVLEKN VTVTHSVNLL EDSHNGKLCR  60
14. MKAKLLVLLC ALSATDADTI CIGYHANNST DTVDTVLEKN VTVTHSVNLL EDNHNGKLCK  60
15. MKAKLLVLLC ALSATDADTI CIGYHANNST DTVDTVLEKN VTVTHSVNLL EDSHNGKLCR  60
16. MKAKLLVLLC ALSATDADTI CIGYHANNST DTVDTVLEKN VTVTHSVNLL EDSHNGKLCR  60
17. MKAKLLVLLC ALSATDADTI CIGYHANNST DTVDTVLEKN VTVTHSVNLL EDSHNGKLCR  60
18. MKAKLLVLLC AFTATDADTI CIGYHANNST DTVDTVLEKN VTVTHSVNLL EDSHNGKLCR  60
19. MKAKLLILLC ALSATDADTI CIGYHANNST DTVDTVLEKN VTVTHSVNLL EDSHNGKLCR  60
20. MKAKLLVLLC ALSATDADTI CIGYHANNST DTVDTVLEKN VTVTHSVNLL EDSHNGKLCR  60
21. MKAKLLILLC ALTATDADTI CIGYHANNST DTVDTVLEKN VTVTHSVNLL EDSHNGKLCR  60
22. MKAKLLILLC ALSATDADTI CIGYHANNST DTVDTVLEKN VTVTHSVNLL EDSHNGKLCR  60
23. MKARLLVLLC ALAATDADTI CIGYHANNST DTVDTILEKN VTVTHSVNLL EDSHNGKLCR  60
24. MKARLLVLLC ALAATDADTI CIGYHANNST DTVDTVLEKN VTVTHSVNLL EDSHNGKLCR  60
25. MKARLLVLLC AIAATDADTI CIGYHANNST DTVDTILEKN VTVTHSVNLL EDSHNGKLCR  60
26. MKANLLVLLC ALAAADADTI CIGYHANNST DTVDTVLEKN VTVTHSVNLL EDSHNGKLCR  60
27. MKAKLLVLLY AFVATDADTI CIGYHANNST DTVDTIFEKN VAVTHSVNLL EDRHNGKLCK  60
28. MEARLLVLLC AFAATNADTI CIGYHANNST DTVDTVLEKN VTVTHSVNLL EDSHNGKLCK  60
    *:. *::**  :: :: ***: ********** *****::*** *:******** *: ******

 1. LKGIAPLQLG NCSVAGWILG NPECELLISR ESWSYIVEKP NPENGTCYPG HFADYEELRE 120
 2. LKGIAPLQLG NCSVAGWILG NPECELLISK ESWSYIVEKP NPENGTCYPG HFADYEELRE 120
 3. LKGIAPLQLG NCSVAGWILG NPECELLISK ESWSYIVETP NPENGTCYPG YFADYEELRE 120
 4. LRGVAPLHLG KCNIAGWILG NPECESLSTA SSWSYIVETP SSDNGTCYPG DFIDYEELRE 120
 5. LNGKIPLQLG NCNVAGWILG NPKCDLLLTA NSSSYIIETS KSKNGACYPG EFADYEELKE 120
 6. LNGKAPLQLG NCNVAGWILG NPECDLLLTV DSWSYIIETS NSKNGACYPG EFADYEELRE 120
 7. LKGIAPLQLG NCSVAGWILG NPECELLISK ESWSYIVETP NPENGTCYPG YFADYEELRE 120
 8. LKGIAPLQLG NCSVAGWILG NPECELLISR ESWSYIVEKP NPENGTCYPG HFADYEELRE 120
 9. LKGTAPLQLG NCSIAGWILG NPECESLFSK ESWSYIAETP NPKNGTCYPG YFADYEELRE 120
10. LKGTAPLQLG NCSVAGWILG NPECESLFSK ESWSYIAETP NPENGTCYPG YFADYEELRE 120
11. LKGIAPLQLG NCSVAGWILG NPECESLISK ESWSYIVETP NPENGTCYPG YFADYEELRE 120
12. LKGIAPLQLG NCSVAGWILG NPKCESLFSK ESWSYIAETP NPENGTCYPG YFADYEELRE 120
13. LKGIAPLQLG NCSIAGWILG NPECESLFSK KSWSYIAETP NSENGTCYPG YFADYEELRE 120
14. LKGIAPLQLG KCSIAGWILG NPECESLFSK KSWSYIAETP NSENGTCYPG YFADYEELRE 120
15. LKGIAPLQLG KCSIAGWILG NPECESLFSK KSWSYIAETP NSENGTCYPG YFADYEELRE 120
16. LKGIAPLQLG KCSIAGWILG NPECESLFSK KSWSYIAETP NSENGTCYPG YFADYEELRE 120
17. LKGIAPLQLG KCNIAGWILG NPECESLFSK KSWSYIAETP NSENGTCYPG YFADYEELRE 120
18. LKGIAPLQLG NCSIAGWILG NPECESLFSK KSWSYIAETP NSENGTCYPG YFADYEELRE 120
19. LKGKAPLQLG NCNIAGWVLG NPECESLLSN RSWSYIAETP NSENGTCYPG DFADYEELRE 120
20. LKGIAPLQLG KCNIAGWILG NPECESLFSK KSWSYIAETP NSENGTCYPG YFADYEELRE 120
21. LKGIAPLQLG KCNIAGWILG NPECESLLSK RSWSYIAETP NSENGACYPG DFADYEELRE 120
22. LKGIAPLQLG KCNIAGWILG NPECESLLSK RSWSYIAETP NSENGACYPG DFADYEELRE 120
23. LKGIAPLQLG KCNIAGWILG NPECESLLSE RSWSYIVEIP NSENGTCYPG DFTDYEELRE 120
24. LKGIAPLQLG KCNIAGWILG NPECESLLSE RSWSYIVETP NSENGTCYPG DFIDYEELRE 120
25. LKGIAPLQLG KCNIAGWILG NPECESLLSE RSWSYIVETP NSENGTCYPG DFIDYEELRE 120
26. LKGIAPLQLG KCNIAGWLLG NPECDPLLPV RSWSYIVETP NSENGICYPG DFIDYEELRE 120
27. LKGIAPLQLG KCNITGWLLG NPECDSLLPA RSWSYIVETP NSENGACYPG DFIDYEELRE 120
28. LKGIAPLQLG KCNIAGWLLG NPECDLLLTA SSWSYIVETS NSENGTCYPG DFIDYEELRE 120
    *:* ***:** :*.::**:** **:*: * . ***** .* . ... ** ****  * *******

 1. QLSSVSSFER FEIFPKESSW PNHTTT-GVS ASCSHNGESS FYKNLLWLTG KNGLYPNLSK 179
 2. QLSSVSSFER FEIFPKESSW PNHTVT-GVS ASCSHNGESS FYRNLLWLTG KNGLYPNLSK 179
 3. QLSSVSSFER FEIFPKESSW PNHTVT-GVS ASCSHNGKSS FYRNLLWLTG KNGLYPNLSK 179
 4. QLSSVSSFER FEIFPKTSSW PNHDSNKGVT AACPHAGAKS FYKNLIWLVK KGNSYPKLSK 180
 5. QLSTVSSFER FEIFPKAISW PDHDATRGTT VACSHSGVNS FYRNLLSTVK KGNSYPKLSK 180
 6. QLSTVSSFER FEIFPKATSW PNHDTTRGTT ISCSHSGANS FYRNLLWIVK KGNSYPKLSK 180
 7. QLSSVSSFER FEIFPKESSW PNHTVT-GVS ASCSHNGKSS FYRNLLWLTG KNGLYPNLSK 179
 8. QLSSVSSFER FEIFPKESSW PNHTTT-GVS ASCSHNGESS FYKNLLWLTG KNGLYPNLSK 179
 9. QLSSVSSFER FEIFPKDSSW PNHTVTKGVT ASCSHNGKSS FYKNLLWLTE KNGLYPNLSK 180
10. QLSSVSSFER FEIFPKESSW PNHTVTKGVT ASCSHNGKSS FYKNLLWLTE KNGLYPNLSK 180
11. QLSSVSSFER FEIFPKESSW PNHTVT-GVT ASCSHNGKSS FYRNLLWLTE KNGLYPNLSN 179
12. QLSSVSSFER FEIFPKESSW PNHTVTKGVT TSCSHNGKSS FYRNLLWLTK KNGLYPNVSK 180
13. QLSSVSSFER FEIFPKESSW PNHTVTKGVT ASCSHKGRSS FYRNLLWLTK KNGSYPNLSK 180
14. QLSSVSSFER FEIFPKESSW PKHNVTKGVT AACSHKGKSS FYRNLLWLTE KNGSYPNLSK 180
15. QLSSVSSFER FEIFPKESSW PKHSVTRGVT ASCSHKGKSS FYRNLLWLTE KNGSYPNLSK 180
16. QLSSVSSFER FEIFPKERSW PKHNITRGVT ASCSHKGKSS FYRNLLWLTE KNGSYPNLSK 180
17. QLSSVSSFER FEIFPKERSW PKHNVTRGVT ASCSHKGKSS FYRNLLWLTE KNGSYPNLSK 180
18. QLSSVSSFER FEIFPKESSW PNHTVTKGVT ASCSHKGRSS FYRNLLWLTK KNGSYPNLSK 180
19. QLSSVSSFER FEIFPKERSW PNHTTR-GVT AACPHARKSS FYKNLVWLTE ANGSYPNLSR 179
20. QLSSVSSFER FEIFPKERSW PKHNITRGVT AACSHKGKSS FYRNLLWLTE KNGSYPNLNK 180
```

TABLE 8-continued

```
21. QLSSVSSFER FEIFPKERSW PKHNITRGVT AACSHAGKSS FYKNLLWLTE TDGSYPKLSK 180
22. QLSSVSSFER FEIFPKGRSW PEHNIDIGVT AACSHAGKSS FYKNLLWLTE KDGSYPNLNK 180
23. QLSSVSSFER FEIFPKESSW PKHNTARGVT AACSHAGKSS FYRNLLWLTE KDGSYPNLKN 180
24. QLSSVSSFER FEIFSKESSW PKHTTG-GVT AACSHAGKSS FYRNLLWLTE KDGSYPNLNN 179
25. QLSSVTSFER FEIFPKETSW PKHNTTKGVT AACSHAGKCS FYRNLLWLTE KDGSYPNLNN 180
26. QLSSVSSFER FEIFPKESSW PNHNTN-GVT AACSHEGKSS FYRNLLWLTE KEGSYPKLKN 179
27. QLSSVSSLER FEIFPKESSW PNHTFN-GVT VSCSHRGKSS FYRNLLWLTK KGDSYPKLTN 179
28. QLSSVSSFEK FEIFPKTSSW PNHETTKGVT AACSYAGASS FYRNLLWLTK KGSSYPKLSK 180
    *****:*:*: ****.*  ** *:*    **: .:*.:    * **:**:**.    . **::..

 1. SYANNKEKEV LVLWGVHHPP NIGDQRALYH KENAYVSVVS SHYSRKFTPE IAKRPKVRDQ 239
 2. SYANNKEKEV LVLWGVHHPP NIGNQKALYH TENAYVSVVS SHYSRKFTPE IAKRPKVRDQ 239
 3. SYVNNKEKEV LVLWGVHHPP NIGNQRALYH TENAYVSVVS SHYSRRFTPE IAKRPKVRDQ 239
 4. SYINDKGKEV LVLWGIHHPS TSADQQSLYQ NADAYVFVGS SRYSKKFKPE IAIRPKVRXX 240
 5. SYTNNKGKEV LVIWGVHHPP TDSVQQTLYQ NKHTYVSVGS SKYYKRFTPE IVARPKVRGQ 240
 6. SYTNNKGKEV LVIWGVHHPP TDSDQQTLYQ NNHTYVSVGS SKYYQRFTPE IVTRPKVRGQ 240
 7. SYANNKEKEV LVLWGVHHPP NIGDQRALYH TENAYVSVVS SHYSRRFTPE IAKRPKVRDQ 239
 8. SYANNKEKEV LVLWGVHHPP NIGDQRALYH KENAYVSVVS SHYSRKFTPE IAKRPKVRDQ 239
 9. SYVNKKGKEV LVLWGVHHPS NMGDQRAIYH KENAYVSVLS SHYSRRFTPE IAKRPKVRDQ 240
10. SYVNNKEKEV LVLWGVHHPS NIGDQRAIYH TENAYVSVVS SHYSRRFTPE ITKRPKVRDQ 240
11. SYVNNKEKEV LVLWGVHHPS NIRDQRAIYH TENAYVSVVS SHYSRRFTPE IAKRPKVRGQ 239
12. SYVNNKEKEV LVLWGVHHPS NIGDQRAIYH TENAYVSVVS SHYSRRFTPE IAKRPKVRDQ 240
13. SYVNNKEKEV LVLWGVHHPS NIGDQRAIYH TENAYVSVVS SHYNRRFTPE IAKRPKVRDQ 240
14. SYVNNKEKEV LVLWGVHHPS NIEDQKTIYR KENAYVSVVS SHYNRRFTPE IAKRPKVRNQ 240
15. SYVNDKEKEV LVLWGVHHPS NIEDQKTIYR KENAYVSVVS SHYNRRFTPE IAKRPKVRDQ 240
16. SYVNNKEKEV LVLWGVHHPS NIEDQKTIYR KENAYVSVVS SNYNRRFTPE IAKRPKVRGQ 240
17. SYVNNKEKEV LVLWGVHHPS NIEDQKTIYR KENAYVSVVS SNYNRRFTPE IAERPKVRGQ 240
18. SYVNNKEKEV LVLWGVHHPS NIGDQRAIYH TENAYVSVVS SHYNRRFTPE IAKRPKVRDQ 240
19. SYVNNQEKEV LVLWGVHHPS NIEEQRALYR KDNAYVSVVS SNYNRRFTPE IAKRPKVRDQ 239
20. SYVNNKEKEV LVLWGVHHPS NIEDQKTLYR KENAYVSVVS SNYNRRFTPE IAERPKVRGQ 240
21. SYVNNKEKEV LVLWGVHHPS NIEDQKTLYR KENAYVSVVS SNYNRRFTPE IAERPKVRGQ 240
22. SYVNKKEKEV LILWGVHHPP NIENQKTLYR KENAYVSVVS SNYNRRFTPE IAERPKVRGQ 240
23. SYVNKKGKEV LVLWGVHHPS SIKEQQTLYQ KENAYVSVVS SNYNRRFTPE IAERPKVRDQ 240
24. SYVNKKGKEV LVLWGVHHPS NIKDQQTLYQ KENAYVSVVS SNYNRRFTPE IAERPKVRGQ 239
25. SYVNKKGKEV LVLWGVHHPS NIKDQQTLYQ KENAYVSVVS SNYNRRFTPE IAERPKVRGQ 240
26. SYVNKKGKEV LVLWGIHHPP NSKEQQNLYQ NENAYVSVVT SNYNRRFTPE IAERPKVRDQ 239
27. SYVNNKGKEV LVLWGVHHPS SSDEQQSLYS NGNAYVSVAS SNYNRRFTPE IAARPKVKDQ 239
28. SYVNNKGKEV LVLWGVHHPP TGTDQQSLYQ NADAYVSVGS SKYNRRFTPE IAARPKVRDQ 240
    ** *.: *** *:***:***. .  :*: :*  . :*** * : *.*.::*.** *: ****:

 1. EGRINYYWTL LEPGDTIIFE ANGNLIAPRY AFALSRGFGS GIINSNAPMD ECDAKCQTPQ 299
 2. EGRINYYWTL LEPGDTIIFE ANGNLIAPRY AFALSRGFGS GIINSNAPMD KCDAKCQTPQ 299
 3. EGRINYYWTL LEPGDTIIFE ANGNLIAPWY AFALSRGFGS GIITSNAPMD ECDAKCQTPQ 299
 4. EGRMNYYWTL VEPGDKITFE ATGNLVVPRY AFAMERNAGS GIIISDTPVH DCNTTCQTPK 300
 5. AGRMNYYWTL FDQGDTITFE ATGNLIAPWH AFALKKGSSS GIMLSDAQVH NCTTKCQTPH 300
 6. AGRMNYYWTL LDQGDTITFE ATGNLIAPWH AFALNKGPSS GIMISDAHVH NCTTKCQTPH 300
 7. EGRINYYWTL LEPGDTIIFE ANGNLIAPRF AFALSRGFGS GIITSNAPMD ECDAKCQTPQ 299
 8. EGRINYYWTL LEPGDTIIFE ANGNLIAPRY AFALSRGFGS GIINSNAPMD ECDAKCQTPQ 299
 9. EGRINYYWTL LEPGDTIIFE ANGNLIAPWY AFALSRGFGS GIIISNASMG ECDAKCQTPQ 300
10. EGRINYYWTL LEPGDTIIFE ANGNLIAPWY AFALSRGFGS GIITSNASMG ECDAKCQTPQ 300
11. EGRINYYWTL LEPGDTIIFE ANGNLIAPWY AFALSRGFGS GIITSNAPMN ECDAKCQTPQ 299
12. EGRINYYWTL LEPGDTIIFE ANGNLIAPWY AFALSRGFGS GIITSNASMD ECDAKCQTPQ 300
13. EGRINYYWTL LEPGDTIIFE ANGNLIAPWY AFALSRGFGS GIITSNASMD ECDAKCQTPQ 300
14. EGRINYYWTL LEPGDTIIFE ANGNLIAPWY AFALSRGFGS GIITSNASMD ECDAKCQTPQ 300
15. EGRINYYWTL LEPGDTIIFE ANGNLIAPWY AFALSRGFGS GIITSNVSMD ECDAKCQTPQ 300
16. EGRINYYWTL LEPGDTIIFE ANGNLIAPWY AFALSRGFGS GIITSNASMD ECDTKCQTPQ 300
17. AGRINYYWTL LEPGDTIIFE ANGNLIAPWH AFALNRGFGS GIITSNASMD ECDTKCQTPQ 300
18. EGRINYYWTL LEPGDTIIFE ANGNLIAPWY AFALSRGFGS GIITSNASMD ECDAKCQTPQ 300
19. SGRMNYYWTL LEPGDTIIFE ATGNLIAPWY AFALSRGPGS GIITSNAPLD ECDTKCQTPQ 299
20. AGRINYYWTL LEPGDTIIFE ANGNLIAPWH AFALSRGFGS GIITSNASMD ECDTKCQTPQ 300
21. AGRINYYWTL LEPGDTIIFE ANGNLIAPWY AFALSRDFGS GIITSNASMD ECDTKCQTPQ 300
22. AGRINYYWTL LEPGDTIIFE ANGNLIAPWY AFALNRGIGS GIITSNASMD ECDTKCQTPQ 300
23. AGRMNYYWTL LEPGDTIIFE ANGNLIAPWY AFALSRGFGS GIITSNASMH ECDTKCQTPQ 300
24. AGRINYYWTL LKPGDTIMFE ANGNLIAPWY AFALSRGFGS GIITSNASMH ECDTKCQTPQ 299
25. AGRMNYYWTL LEPGDTIIFE ANGNLIAPWY AFALSRGFGS GIITSNASMH ECNTKCQTPQ 300
26. AGRMNYYWTL LKPGDTIIFE ANGNLIAPMY AFALRRGFGS GIITSNASMH ECNTKCQTPL 299
27. HGRMNYYWTL LEPGDTIIFE ATGNLIAPWY AFALSRGFES GIITSNASMH ECNTKCQTPQ 299
28. AGRMNYYWTL LEPGDTITFE ATGNLIAPWY AFALNRGSGS GIITSDAPVH DCNTKCQTPH 300
     **:****** ::***.* ** *.***:.* . ***: *.  * *** *:..:  .*::.****

 1. GAINSSLPFQ NVHPVTIGEC PKYVRSAKLR MVTGLRNIPS IQSRGLFGAI AGFIEGGWTG 359
 2. GAINSSLPFQ NVHPVTIGEC PKYVRSAKLR MVTGLRNIPS IQSRGLFGAI AGFIEGGWTG 359
 3. GAINSSLPFQ NVHPVTIGEC PKYVRSAKLR MVTGLRNIPS IQSRGLFGAI AGFIEGGWTG 359
 4. GAINTSLPFQ NIHPITIGKC PKYVKSTKLR LATGLRNIPS IQSRGLFGAI AGFIEGGWTG 360
 5. GALKNNLPLQ NVHLFTIGEC PKYVKSTQLR MATGLRNIPS IQSRGLFGAI AGFIEGGRTG 360
 6. GALKSNLPFQ NVHPSTIGEC PKYVKSTQLR MATGLRNIPS IQSRGLFGAI AGFIEGGWTG 360
 7. GAINSSLPFQ NVHPVTIGEC PKYVRSAKLR MVTGLRNIPS IQSRGLFGAI AGFIEGGWTG 359
 8. GAINSSLPFQ NVHPVTIGEC PKYVRSAKLR MVTGLRNIPS IQSRGLFGAI AGFIEGGWTG 359
 9. GAINSSLPFQ NVHPVTIGEC PKYVRSTKLR MVTGLRNVPS IQSRGLFGAI AGFIEGGWTG 360
10. GAINSSLPFQ NVHPVTIGEC PKYVRSTKLR MVTGLRNIPS IQSRGLFGAI AGFIEGGWTG 360
```

TABLE 8-continued

| | | | | | | | |
|---|---|---|---|---|---|---|---|
| 11. | GAINSSLPFQ | NVHPVTIGEC | PKYVRSTKLR | MVTGLRNIPS | IQSRGLFGAI | AGFIEGGWTG | 359 |
| 12. | GAINSSLPFQ | NVHPVTIGEC | PKYVRSTKLR | MVTGLRNIPS | IQSRGLFGAI | AGFIEGGWTG | 360 |
| 13. | GAINSSLPFQ | NVHPVTIGEC | PKYVRSTKLR | MVTGLRNIPS | IQSRGLFGAI | AGFIEGGWTG | 360 |
| 14. | GAINSSLPFQ | NVHPVTIGEC | PKYVRSTKLR | MVTGLRNIPS | IQSRGLFGAI | AGFIEGGWTG | 360 |
| 15. | GAINSSLPFQ | NVHPVTIGEC | PKYVRSTKLR | MVTGLRNIPS | IQSRGLFGAI | AGFIEGGWTG | 360 |
| 16. | GAINSSLPFQ | NVHPVTIGEC | PKYVRSTKLR | MVTGLRNIPS | IQSRGLFGAI | AGFIEGGWTG | 360 |
| 17. | GAINSSLPFQ | NIHPVTIGEC | PKYVRSTKLR | MVTGLRNIPS | IQSRGLFGAI | AGFIEGGWTG | 360 |
| 18. | GAINSSLPFQ | NVHPVTIGEC | PKYVRSTKLR | MVTGLRNIPS | IQSRGLFGAI | AGFIEGGWTG | 360 |
| 19. | GAINSSLPFQ | NIHPVTIGEC | PKYVRSTKLR | MVTGLRNIPS | VQSRGLFGAI | AGFIEGGWTG | 359 |
| 20. | GAINSSLPFQ | NIHPVTIGEC | PKYVRSTKLR | MVTGLRNIPS | IQSRGLFGAI | AGFIEGGWTG | 360 |
| 21. | GAINSSLPFQ | NIHPVTIGEC | PKYVKSTKLR | MVTGLRNIPS | IQSRGLFGAI | AGFIEGGWTG | 360 |
| 22. | GAINSSLPFQ | NIHPFTIGEC | PKYVRSTKLR | MVTGLRNIPS | IQSRGLFGAI | AGFIEGGWDG | 360 |
| 23. | GAINSSLPFQ | NIHPVTIGEC | PKYVRSTKLR | MVTGLRNIPS | IQSRGLFGAI | AGFIEGGWTG | 360 |
| 24. | GAINSSLPFQ | NIHPVTIGEC | PKYVRSTKLR | MVTGLRNIPS | IQSRGLFGAI | AGFIEGGWTG | 359 |
| 25. | GAINSSLPFQ | NIHPVTIGEC | PKYVRSTKLR | MVTGLRNIPS | IQSRGLFGAI | AGFIEGGWTG | 360 |
| 26. | GAINSSLPYQ | NIHPVTIGEC | PKYVRSAKLR | MVTGLRNIPS | IQSRGLFGAI | AGFIEGGWTG | 359 |
| 27. | GSINSNLPFQ | NIHPVTIGEC | PKYVRSTKLR | MVTGLRNIPS | IQYRGLFGAI | AGFIEGGWTG | 359 |
| 28. | GAINSSLPFQ | NIHPVTIGEC | PKYVRSTKLR | MATGLRNIPS | IQSRGLFGAI | AGFIEGGWTG | 360 |
| | *:**:.**:* | *:**.***:* | ****:*:*** | :.*****:** | :* ******* | ******** * | |
| 1. | MVDGWYGYHH | QNEQGSGYAA | DQKSTQNAIN | GITNKVNSVI | EKMNTQFTAV | GKEFNKLERR | 419 |
| 2. | MVDGWYGYHH | QNEQGSGYAA | DQKSTQNAIN | GITNKVNSVI | EKMNTQFTAV | GKEFNKLERR | 419 |
| 3. | MVDGWYGYHH | QNEQGSGYAA | DQKSTQNAIN | GITNKVNSVI | EKMNTQFTAV | GKEFNKLERR | 419 |
| 4. | MVDGWYGYHH | QNEQGSGYAA | DLKSTQNAID | EITNKVNSVI | EKMNTQFTAV | GKEFNHLEKR | 420 |
| 5. | MIDGWYGYHH | QNEQGSGYAA | DQKSTQIAID | GINNKANSVI | GKMNIQLTSV | GKEFNSLEKR | 420 |
| 6. | MIDGWYGYHH | QNEQGSGYAA | DQKSTQIAID | GINNKVNSII | EKMNTQFTSV | GKEFNDLEKR | 420 |
| 7. | MVDGWYGYHH | QNEQGSGYAA | DQKSTQNAIN | GITNKVNSVI | EKMNTQFTAV | GKEFNKLERR | 419 |
| 8. | MVDGWYGYHH | QNEQGSGYAA | DQKSTQNAIN | GITNKVNSVI | EKMNTQFTAV | GKEFNKLERR | 419 |
| 9. | MIDGWYGYHH | QNEQGSGYAA | DQKSTQNAIN | GITNKVNSII | EKMNTQFTAV | GKEFNKLEKR | 420 |
| 10. | MIDGWYGYHH | QNEQGSGYAA | DQKSTQNAID | GITNKVNSVI | EKMNTQFTAV | GKEFNKLERR | 420 |
| 11. | MMDGWYGYHH | QNEQGSGYAA | DQKSTQNAIN | GITNKVNSVI | EKMNTQFTAV | GKEFNKLERR | 419 |
| 12. | MIDGWYGYHH | QNEQGSGYAA | DQKSTQNAIN | GITNKVNSVI | EKMNTQFTAV | GKEFNKLERR | 420 |
| 13. | MIDGWYGYHH | QNEQGSGYAA | DQKSTQNAIN | GITNKVNSVI | EKMNTQFTAV | GKEFNKLERR | 420 |
| 14. | MIDGWYGYHH | QNEQGSGYAA | DQKSTQNAIN | GITNKVNSII | EKMNTQFTAV | GKEFNKLEKR | 420 |
| 15. | MIDGWYGYHH | QNEQGSGYAA | DQKSTQNAIN | GITNKVNSVI | EKMNTQFTAV | GKEFNKLEKR | 420 |
| 16. | MIDGWYGYHH | QNEQGSGYAA | DQKSTQNAIN | GITNKVNSVI | EKMNTQFTAV | GKEFNKLEKR | 420 |
| 17. | MIDGWYGYHH | QNEQGSGYAA | DQKSTQNAIN | GITNKVNSVI | EKMNTQFTAV | GKEFNKLEKR | 420 |
| 18. | MIDGWYGYHH | QNEQGSGYAA | DQKSTQNAIN | GITNKVNSVI | EKMNTQFTAV | GKEFNKLERR | 420 |
| 19. | MMDGWYGYHH | QNEQGSGYAA | DQKSTQNAIN | GITNKVNSVI | EKMNTQFTAV | GKEFNKLEKR | 419 |
| 20. | MIDGWYGYHH | QNEQGSGYAA | DQKSTQNAIN | GITNKVNSVI | EKMNTQFTAV | GKEFNKLEKR | 420 |
| 21. | MIDGWYGYHH | QNEQGSGYAA | DQKSTQNAIN | WITNKVNSVI | EKMNTQFTAV | GKEFNKLEKR | 420 |
| 22. | MIDGWYGYHH | QNEQGSGYAA | DQKSTQNAIN | GITNKVNSVI | EKMNTQFTAV | GKEFNKLEKR | 420 |
| 23. | MIDGWYGYHH | QNEQGSGYAA | DQKSTQNAIN | GITNKVNSVI | EKMNTQFTAV | GKEFNNLEKR | 420 |
| 24. | MIDGWYGYHH | QNEQGSGYAA | DQKSTQNAIN | GITNKVNSVI | EKMNTQFTAV | GKEFNNLEKR | 419 |
| 25. | MIDGWYGYHH | QNEQGSGYAA | DQKSTQNAIN | GITNKVNSVI | EKMNTQFTAV | GKEFNNLEKR | 420 |
| 26. | MIDGWYGYHH | QNEQGSGYAA | DQKSTQNAIN | GITNKVNSVI | EKMNIQFTAV | GKEFNKLEKR | 419 |
| 27. | MIDGWYGYHH | QNEQGSGYAA | DQKSTQNAIN | GITNKVNSVI | EKMNTQFTAV | GKEFNNLEKR | 419 |
| 28. | MIDGWYGYHH | QNEQGSGYAA | DQKSTQNAID | GITNKVNSVI | EKMNTQFTAV | GKEFNNLERR | 420 |
| | *:******** | ********** | * *******: | *******:* | **** ***** | *****:**:* | |
| 1. | MENLNKKVDD | GFIDIWTYNA | ELLVLLENER | TLDFHDSNVK | NLYEKVKSQL | KNNAKEIGNG | 479 |
| 2. | MENLNKKVDD | GFIDIWTYNA | ELLVLLENER | TLDFHDSNVK | NLYEKVKSQL | KNNAKEIGNG | 479 |
| 3. | MENLNKKVDD | GFLDIWTYNA | ELLVLLENER | TLDFHDSNVK | NLYEKVKSQL | KNNAKEIGNG | 479 |
| 4. | IENLNKKVDD | GFLDIWTYNA | ELLVLLENER | TLDYHDSNVK | NLYEKVRSQL | KNNAKEIGNG | 480 |
| 5. | KENLNKTVDD | RFLDVWTFNA | ELLVLLENQR | TLEFHDLNIK | SLYEKVKSHL | RNNDKEIGNG | 480 |
| 6. | IENLNKKVDD | GFLDVWTYNA | ELLILLENER | TLDFHDFNVK | NLYEKVKSQL | RNNAKEIGNG | 480 |
| 7. | MENLNKKVDD | GFLDIWTYNA | ELLVLLENER | TLDFHDSNVK | NLYEKVKSQL | KNNAKEIGNG | 479 |
| 8. | MENLNKKVDD | GFIDIWTYNA | ELLVLLENER | TLDFHDSNVK | NLYEKVKSQL | KNNAKEIGNG | 479 |
| 9. | MENLNKKVDD | GFLDIWTYNA | ELLVLLENER | TLDFHDLNVK | NLYEKVKNQL | KNNAKEIGNG | 480 |
| 10. | MENLNKKVDD | GFLDIWTYNA | ELLVLLENER | TLDFHDSNVK | NLYEKVKTQL | KNNAKEIGNG | 480 |
| 11. | MENLNKKVDD | GFLDIWTYNA | ELLVLLENER | TLDFHDSNVK | NLYEKVKSQL | KNNAKEIGNG | 479 |
| 12. | MENLNKKVDD | GFLDIWTYNA | ELLVLLENGR | TLDFHDSNVK | NLYEKVKSQL | KNNAKEIGNG | 480 |
| 13. | MENLNKKVDD | GFLDIWTYNA | ELLVLLENER | TLDFHDSNVK | NLYEKVKSQL | KNNAKEIGNG | 480 |
| 14. | MENLNKKVDD | GFLDIWTYNA | ELLVLLENER | TLDFHDSNVK | NLYEKVKSQL | KNNAKEIGNG | 480 |
| 15. | MENLNKKVDD | GFLDIWTYNA | ELLVLLENER | TLDFHDSNVK | NLYEKVKSQL | KNNAKEIGNG | 480 |
| 16. | MENLNKKVDD | GFLDIWTYNA | ELLVLLENER | TLDFHDSNVK | NLYEKVKSQL | KNNAKEIGNG | 480 |
| 17. | MENLNKKVDD | GFLDIWTYNA | ELLVLLENER | TLDFHDSNVK | NLYEKVKSQL | KNNAKEIGNG | 480 |
| 18. | MENLNKKVDD | GFLDIWTYNA | ELLVLLENER | TLDFHDSNVK | NLYEKVKSQL | KNNAKEIGNG | 480 |
| 19. | MENLNKKVDD | GFMDIWTYNA | ELLVLLENER | TLDFHDSNVK | NLYEKVKNQL | RNNAKELGNG | 479 |
| 20. | MENLNKKVDD | GFLDIWTYNA | ELLVLLENER | TLDFHDSNVK | NLYEKVKSQL | KNNAKEIGNG | 480 |
| 21. | MENLNKKVDD | GFLDIWTYNA | ELLVLLENER | TLDFHDSNVK | NLYEKVKNQL | RNNAKEIGNG | 480 |
| 22. | MENLNKKVDD | GFLDIWTYNA | ELLVLLENER | TLDFHDSNVK | NLYEKVKNQL | RNNAKEIGNG | 480 |
| 23. | MENLNKKVDD | GFLDIWTYNA | ELLILLENER | TLDFHDSNVK | NLYEKVKSQL | RNNAKEIGNG | 480 |
| 24. | MENLNKKVDD | GFLDIWTYNA | ELLVLLENER | TLDFHDSNVK | NLYEKVKNQL | RNNAKEIGNG | 479 |
| 25. | MENLNKKVDD | GFLDIWTYNA | ELLVLLENER | TLDFHDSNVK | NLYEKVKSQL | RNNAKEIGNG | 480 |
| 26. | MENLNNKVDD | GFLDIWTYNA | ELLVLLENER | TLDFHDSNVK | NLYEKVKSQL | KNNAKEIGNG | 479 |

TABLE 8-continued

```
27. MENLNKKVDD GFLDIWTYNA ELLVLLENER TLDFHDLNVK NLYEKVKSQL KNNAKEIGNG 479
28. IENLNKKVDD GFLDIWTYNA ELLVLLENER TLDFHDSNVR NLYEKVKSQL KNNAKEIGNG 480
    :****:**** **:******* ***:**** * ***:** **: ******:.** :*****:***

 1. CFEFYHKCND ECMESVKNGT YDYPKYSEES KLNREKIDGV KLESMGVYQI LAIYSTVASS 539
 2. CFEFYHKCND ECMESVKNGT YDYPKYSEES KLNREKIDGV KLESMGVYQI LAIYSTVASS 539
 3. CFEFYHKCNN ECMESVKNGT YDYPKYSEES KLNREKIDGV KLESMGVYQI LAIYSTVASS 539
 4. CFEFYHKCDN TCMESVKNGT YDYPKYSEEA KLNREEIDGV KLESTRIYQI LAIYSTVASS 540
 5. CFEFYHKRDN ECLECVKNGT YNYPKYSEES KFNREEIVGV KLESMGIHQI LAIYSTVASS 540
 6. CFEFYHKCDN ECMESVKNGT YNYPKYSEES KLNREKIDGV KLESMGVHQI LAIYSTVASS 540
 7. CFEFYHKCND ECMESVKNGT YDYPKYSEES KLNRERIDGV KLESMGVYQI LAIYSTVASS 539
 8. CFEFYHKCND ECMESVKNGT YDYPKYSEES KLNREKIDGV KLESMGVYQI LAIYSTVASS 539
 9. CFEFYHKCNN ECMESVKNGT YDYPKYSKES KLNREKIDGV KLESMGVYQI LAIYSTVASS 540
10. CFEFYHKCNN ECMESVKNGT YDYPKYSEES KLNREKIDGV KLESMGVYQI LAIYSTVASS 540
11. CFEFYHKCNN ECMESVKNGT YDYPKYSEES KLNREKIDGV KLESMGVYQI LAIYSTVASS 539
12. CFEFYHKCNN ECMESVKNGT YDYPKYSEES KLNRGKIDGV KLESMGVYQI LAIYSTVASS 540
13. CFEFYHKCNN ECMESVKNGT YDYPKYSEES KLNREKIDGV KLESMGVYQI LAIYSTVASS 540
14. CFEFYHKCNN ECMESVKNGT YDYPKYSEES KLNREKIDGV KLESMGVYQI LAIYSTVASS 540
15. CFEFYHKCNN ECMESVKNGT YDYPKYSEES KLNREKIDGV KLESMGVYQI LAIYSTVASS 540
16. CFEFYHKCNN ECMESVKNGT YDYPKYSEES KLNREKIDGV KLESMGVYQI LAIYSTVASS 540
17. CFEFYHKCNN ECMESVKNGT YDYPKYSEES KLNREKIDGV KLESMGVYQI LAIYSTVASS 540
18. CFEFYHKCNN ECMESVKNGT YDYPKYSEES KLNREKIDGV KLESMGVYQI LAIYSTVASS 540
19. CFEFYHKCDN ECMESVKNGT YDYPKYSEES KLNREKIDGV KLESMGVYRI LAIYSTVASS 539
20. CFEFYHKCNN ECMESVKNGT YDYPKYSEES KLNREKIDGV KLESMGVYQI LAIYSTVASS 540
21. CFEFYHKCNN ECMESVKNGT YDYPKYSEES KLNREKIDGV KLESMGVYQI LAIYSTVASS 540
22. CFEFYHKCNN ECMESVKNGT YDYPKFSEES KLNREKIDGV KLESMGVYQI LAIYSTVASS 540
23. CFEFYHKCNN ECMESVKNGT YDYPKYSEES KLNREKIDGV KLESMGVYQI LAIYSTVASS 540
24. CFEFYHKCNN ECMESVKNGT YDYPKYSEES KLNREKIDGV KLESMGVYQI LAIYSTAASS 539
25. CFEFYHKCNN ECMESVKNGT YDYPKYSEES KLNREKIDGV KLESMGVYQI LAIYSTVASS 540
26. CFEFYHKCDN ECMESVRNGT YDYPKYSEES KLNREKVDGV KLESMGIYQI LAIYSTVASS 539
27. CFEFYHKCDN ECMESVRNGT YDYPKYSEES KLNREKIDGV KLESMGVYQI LAIYSTVASS 539
28. CFEFYHKCDD ACMESVRNGT YDYPKYSEES KLNREEIDGV KLESMGVYQI LAIYSTVASS 540
    ********:: *****:*** *****:*:*: **** .:*** ****   :*:* ******.***

 1. LVLLVSLGAI SFWMCSNGSL QCRICI                                    565
 2. LVLLVSLGAI SFWMCSNGSL QCRICI                                    565
 3. LVLLVSLGAI SFWMCSNGSL QCRICI                                    565
 4. LVLVVSLGAI SFWMCSNGSL QCRICI                                    566
 5. LVLLVSLGAI SFWMCSNGSL QCRVCI                                    566
 6. LVLLVSLGAI SFWMCSNGSL QCRICI                                    566
 7. LVLLVSLGAI SFWMCSNGSL QCRICI                                    565
 8. LVLLVSLGAI SFWMCSNGSL QCRICI                                    565
 9. LVLLVSLGAI SFWMCSNGSL QCRICI                                    566
10. LVLLVSLGAI SFWMCSNGSL QCRICI                                    566
11. LVLLVSLGAI SFWMCSNGSL QCRICI                                    565
12. LVLLVSLGAI SFWMCSNGSL QCRICI                                    566
13. LVLLVSLGAI SFWMCSNGSL QCRICI                                    566
14. LVLLVSLGAI SFWMCSNGSL QCRICI                                    566
15. LVLLVSLGAI SFWMCSNGSL QCRICI                                    566
16. LVLLVSLGAI SFWMCSNGSL QCRICI                                    566
17. LVLLVSLGAI SFWMCSNGSL QCRICI                                    566
18. LVLLVSLGAI SFWMCSNGSL QCRICI                                    566
19. LVLLVSLGAI SFWMCSNGSL QCRICI                                    565
20. LVLLVSLGAI SFWMCSNGSL QCRICI                                    566
21. LVLLVSLGAI SFWMCSNGSL QCRICI                                    566
22. LVLLVSLGAI SFWMCSNGSL QCRICI                                    566
23. LVLLVSLGAI SFWMCSNGSL QCRICI                                    566
24. LVLLVSLGAI SFWMCSNGSL QCRICI                                    565
25. LVLLVSLGAI SFWMCSNGSL QCRICI                                    566
26. LVLLVSLGAI SFWMCSNGSL QCRICI                                    565
27. LVLLVSLGAI SFWMCSNGSL QCRICI                                    565
28. LVLLVSLGAI SFWMCSNGSL QCRICI                                    566
    ***:****** ********** ******
```

TABLE 9

Consensus sequence for H3 401-421 (SEQ ID NO: 104), other natural variants and mutations that stabilize polypeptides hereof. One or more mutations in the parental sequence are present in the polypeptides.

| Position | amino acid | conservation (%) | other natural | preferred mutation | polar | charged | flexible |
|---|---|---|---|---|---|---|---|
| 401 | I | 99.26 | V | R | | K | |
| 402 | E/G | 56.2/40.3 | K | | | | |
| 403 | K | 94.85 | R | | | | |
| 404 | T | 99.88 | A | | | | |
| 405 | N | 99.88 | S | | | | |
| 406 | E | 100 | | | | | |
| 407 | K | 100 | | | | | |
| 408 | F | 100 | | S | T, N, Q | R, H, K, D, E | G |
| 409 | H | 100 | | | | | |
| 410 | Q | 100 | | | | | |
| 411 | I | 100 | | T | S, N, Q | R, H, K, D, E | G |
| 412 | E | 100 | | | | | |
| 413 | K | 100 | | | | | |
| 414 | E | 100 | | | | | |
| 415 | F | 100 | | S | T, N, Q | R, H, K, D, E | G |
| 416 | S | 99.46 | T, L | | | | |
| 417 | E | 99.71 | G, D | | | | |
| 418 | V | 98.64 | I | G | S, T, N, Q | R, H, K, D, E | |
| 419 | E | 100 | | | | | |
| 420 | G | 99.84 | E | | | | |
| 421 | R | 100 | | | | | |

TABLE 10

Calculated and experimental molecular weight as determined from SEC-MALS. The calculated molecular weight is based on the amino acid composition of the processed polypeptide of the disclosure, i.e., after the leader peptide has been cleaved of. Addtional mass arising from glycosylation ahs nopt been taken into account.

| SEQ ID NO | Calculated molecular weight (Da) | Experimental molecular weight (kDa) |
|---|---|---|
| 144 | 29137 | 75 |
| 145 | 29257 | 50 |
| 146 | 29203 | 56 |
| 147 | 29119 | 60 |
| 148 | 29293 | 66 |
| 150 | 29411 | 64 |
| 151 | 29283 | 79 |

TABLE 11

Selected strains

| Set 1 | Set 2 |
|---|---|
| H1N1 A/Maryland/12/1991 | H1N1 A/Maryland/12/1991 |
| H1N1 A/Henry/1936/ | H1N1 A/Henry/1936/ |
| H1N1 A/AA/Marton/1943 | H1N1 A/AA/Marton/1943 |
| H1N1 A/Memphis/20/1978 | H1N1 A/USSR/92/1977 |
| H1N1 A/New York/607/1995 | H1N1 A/New York/629/1995 |
| H1N1 A/New Jersey/11/2007 | H1N1 A/Virginia/UR06-0549/2007 |
| H1N1 A/Wisconsin/629-D01415/2009 | H1N1 A/Texas/UR06-0526/2007 |
| | H1N1 A/Sydney/DD3-55/2010 |

REFERENCES

Bommakanti et al. (2010), PNAS 107(31):13701-13706.
Chen et al. (1995), PNAS 92, 12205-12209.
Coffman et al. (2010), Immunity 33:492.
Corti et al. (2011), Science 333(6044):850-856.
Delhaise, et al. (1984), J. Mol. Graph. 2:103-106.
Devereux et al. (1984), Nucl. Acids Res. 12:387.
Dopheide, Ward (1981), J. Gen. Virol. 367-370.
Edgar R. C. (2004), Nucleic Acids Res. 32, 1792-1797.
Ekiert et al. (2009), Science 324:246.
Ekiert et al. (2011), Science 333:844.
Ferguson et al. (2003), Nature 422:428-443.
Higgins (1992), Comput. Appl. Biosci. 8:15-22.
Lorieau et al. (2010), Proc. Natl. Acad. Sci. USA, 107: 11341.
Okuno et al. (1993), J. Virol. 67:2552-2558.
Russel et al. (2004), Virology 325:287.
Samantha et al. (2002), Prot. Eng. 15, 659-667.
Steel et al. (2010), mBio. 1(1):1-9.
Steven et al. (2004), Science 303:1866.
Steven et al. (2006), Science 312:404.
Sun et al. (2010), J. Virol. 84:8683
Suzuki et al. (2005), Prot. Eng. 11, 1051.
Throsby et al. (2008), Plos One 12(3):1-15.
Wilson et al. (1981), Nature 289:366.
Woolfson (2005), Adv Protein Chem 70:79-112.
Xu & Miranker (2004), Bioinformatics 8:1214-1221.

SEQUENCES

SEQ ID NO: 1: H1 Full-length (A/Brisbane/59/2007)

```
MKVKLLVLLC TFTATYADTI CIGYHANNST DTVDTVLEKN VTVTHSVNLL    50
ENSHNGKLCL LKGIAPLQLG NCSVAGWILG NPECELLISK ESWSYIVEKP   100
NPENGTCYPG HFADYEELRE QLSSVSSFER FEIFPKESSW PNHTVTGVSA   150
SCSHNGESSF YRNLLWLTGK NGLYPNLSKS YANNKEKEVL VLWGVHHPPN   200
```

-continued

SEQUENCES

IGDQKALYHT ENAYVSVVSS HYSRKFTPEI AKRPKVRDQE GRINYYWTLL 250
EPGDTIIFEA NGNLIAPRYA FALSRGFGSG IINSNAPMDK CDAKCQTPQG 300
AINSSLPFQN VHPVTIGECP KYVRSAKLRM VTGLRNIPSI QSRGLFGAIA 350
GFIEGGWTGM VDGWYGYHHQ NEQGSGYAAD QKSTQNAING ITNKVNSVIE 400
KMNTQFTAVG KEFNKLERRM ENLNKKVDDG FIDIWTYNAE LLVLLENERT 450
LDFHDSNVKN LYEKVKSQLK NNAKEIGNGC FEFYHKCNDE CMESVKNGTY 500
DYPKYSEESK LNREKIDGVK LESMGVYQIL AIYSTVASSL VLLVSLGAIS 550
FWMCSNGSLQ CRICI 565

SEQ ID NO: 2: miniHA (A/Brisbane/59/2007)
MKVKLLVLLC TFTATYADTI CIGYHANNST DTVDTVLEKN VTVTHSVNLL 50
ENSHNGKLCG GGGCDAKCQT PQGAINSSLP FQNVHPVTIG ECPKYVRSAK 100
LRMVTGLRNI PSIQSQGLFG AIAGFIEGGW TGMVDGWYGY HHQNEQGSGY 150
AADQKSTQNA INGITNKVNS VIEKMNTQFT AVGKEFNKLE RRMENLNKKV 200
DDGFIDIWTY NAELLVLLEN ERTLDFHDSN VKNLYEKVKS QLKNNAKEIG 250
NGCFEFYHKC NDECMESVKN GTYDYPKYSE ESKLNREKID GVKLESMGVY 300
QILAIYSTVA SSLVLLVSLG AISFWMCSNG SLQCRICI 338

SEQ ID NO: 3: miniHA cluster1 (A/Brisbane/59/2007)
MKVKLLVLLC TFTATYADTI CIGYHANNST DTVDTVLEKN VTVTHSVNLL 50
ENSHNGKTCG GGGCDAKCQT PQGAINSSLP FQNVHPTTTG ECPKYVRSAK 100
LRMVTGLRNI PSIQSQGLFG AIAGFIEGGW TGMVDGWYGY HHQNEQGSGY 150
AADQKSTQNA INGITNKVNS VIEKMNTQST ATGKEFNKSE RRMENLNKKV 200
DDGFIDIWTY NAELLVLLEN ERTLDFHDSN VKNLYEKVKS QLKNNAKEIG 250
NGCFEFYHKC NDECMESVKN GTYDYPKYSE ESKLNREKID GVKLESMGVY 300
QILAIYSTVA SSLVLLVSLG AISFWMCSNG SLQCRICI 338

SEQ ID NO: 4: miniHA cluster1 + 2 (A/Brisbane/59/2007)
MKVKLLVLLC TFTATYADTI CIGYHANNST DTVDTVLEKN VTVTHSVNLL 50
ENSHNGKTCG GGGCDAKCQT PQGAINSSLP FQNVHPTTTG ECPCYVRSAK 100
LRMVTGLRNI PSIQSQGLFG AIAGFIEGGW TGMVDGWYGY HHQNEQGSGY 150
AADQKSTQNA INGITNKVNS VIEKMNTCST ATGKEFNKSE RRMENLNKKV 200
DDGFIDIWTY NAELLVLLEN ERTLDFHDSN VKNLYEKVKS QLKNNAKEIG 250
NGCFEFYHKC NDECMESVKN GTYDYPKYSE ESKLNREKID GVKLESMGVY 300
QILAIYSTVA SSLVLLVSLG AISFWMCSNG SLQCRICI 338

SEQ ID NO: 5: miniHA cluster1 + 3 (A/Brisbane/59/2007)
MKVKLLVLLC TFTATYADTI CIGYHANNST DTVDTVLEKN VTVTHSVNLL 50
ENSHNGKTCG GGGCDAKCQT PQGAINSSLP FQNVHPTTTG ECPKYVRSAK 100
LRMVTGLRNI PSIQSQGLFG AIAGFIEGGW TGMVDGWYGY HHQNEQGSGY 150
AADQKSTQNA INGITNKVNS VIEKMNTQST ATGKECNKSE RRMCNLNKKV 200
DDGFIDIWTY NAELLVLLEN ERTLDFHDSN VKNLYEKVKS QLKNNAKEIG 250
NGCFEFYHKC NDECMESVKN GTYDYPKYSE ESKLNREKID GVKLESMGVY 300
QILAIYSTVA SSLVLLVSLG AISFWMCSNG SLQCRICI 338

SEQ ID NO: 6: miniHA cluster1 + 4 (A/Brisbane/59/2007)
MKVKLLVLLC TFTATYADTI CIGYHANNST DTVDTVLEKN VTVTHSVNLL 50
ENSHNGKTCG GGGCDAKCQT PQGAINSSLP FQNVHPTTTG ECPKYVRSAK 100
LRMVTGLRNI PSIQSQGLFG AIAGFIEGGW TGMVDGWYGY HHQNEQGSGY 150
AADQKSTQNA INGITNKVNS VIEKMNTQST ATGKEFNKSE RRMENLNKKV 200
DDGFIDIWTY NAELLVLLEN ERTLDFHDSN VKNLYEKVKS QLKNNAKEIG 250
NGCFEFYHKC NDECMESVKN GTYDYPKYSE ESKLNREKID GVKLESMGVY 300
QILAIYSTVA SSLVLLVSLG AISFWMCSNG SLQCRICI 338

SEQ ID NO: 7: miniHA cluster1 + 2 + 3 (A/Brisbane/59/2007)
MKVKLLVLLC TFTATYADTI CIGYHANNST DTVDTVLEKN VTVTHSVNLL 50
ENSHNGKTCG GGGCDAKCQT PQGAINSSLP FQNVHPTTTG ECPCYVRSAK 100
LRMVTGLRNI PSIQSQGLFG AIAGFIEGGW TGMVDGWYGY HHQNEQGSGY 150
AADQKSTQNA INGITNKVNS VIEKMNTCST ATGKECNKSE RRMCNLNKKV 200
DDGFIDIWTY NAELLVLLEN ERTLDFHDSN VKNLYEKVKS QLKNNAKEIG 250
NGCFEFYHKC NDECMESVKN GTYDYPKYSE ESKLNREKID GVKLESMGVY 300
QILAIYSTVA SSLVLLVSLG AISFWMCSNG SLQCRICI 338

SEQ ID NO: 8: miniHA cluster1 + 2 + 3 + 4 (A/Brisbane/59/2007)
MKVKLLVLLC TFTATYADTI CIGYHANNST DTVDTVLEKN VTVTHSVNLL 50
ENSHNGKTCG GGGCDAKCQT PQGAINSSLP FQNVHPTTTG ECPCYVRSAK 100
LRMVTGLRNI PSIQSQGLFG AIAGFIEGGW TGMVDGWYGY HHQNEQGSGY 150
AADQKSTQNA INGITNKVNS VIEKMNTCST ATGKECNKSE RRMCNLNKKV 200
DDGFIDIWTY NAELLVLLEN ERTLDFHDSN VKNLYEKVKS QLKNNAKEIG 250
NGCFEFYHKC NDECMESVKN GTYDSPKYSE ESKLNREKID GVKLESMGVY 300
QILAIYSTVA SSLVLLVSLG AISFWMCSNG SLQCRICI 338

SEQ ID NO: 9: mini1 cluster11 (A/Brisbane/59/2007)
MKVKLLVLLC TFTATYADTI CIGYHANNST DTVDTVLEKN VTVTHSVNLL 50
ENSHNGKTCG GGGCDAKCQT PQGAINSSLP FQNVHPTTTG ECPKYVRSAK 100
LRMVTGLRNI PSIQSQGLFG AIAGFIEGGW TGMVDGWYGY HHQNEQGSGY 150
AADQKSTQNA INGITNKVNS VIEKMNTQST ATGKEFNKSE RRIENLNKKI 200

-continued

SEQUENCES

DDGFIDIWTY NAELLVLLEN ERTLDFHDSN VKNLYEKVKS QLKNNAKEIG 250
NGCFEFYHKC NDECMESVKN GTYDYPKYSE ESKLNREKID GVKLESMGVY 300
QILAIYSTVA SSLVLLVSLG AISFWMCSNG SLQCRICI 338

SEQ ID NO: 10: mini2 cluster11 (A/Brisbane/59/2007)
MKVKLLVLLC TFTATYADTI CIGYHANNST DTVDTVLEKN VTVTHSVNLL 50
ENGGGGKYVR SAKLRMVTGL RNIPSIQSQG LFGAIAGFIE GGWTGMVDGW 100
YGYHHQNEQG SGYAADQKST QNAINGITNK VNSVIEKMNT QSTATGKEFN 150
KSERRIENLN KKIDDGFIDI WTYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 11: mini3 cluster11 (A/Brisbane/59/2007)
MKVKLLVLLC TFTATYADTI CIGYHANNST DTVDTVLEKN VTVTHSVNLL 50
ENSGGGGNSS LPFQNVHPTT TGECPKYVRS AKLRMVTGLR NIPSIQSQGL 100
FGAIAGFIEG GWTGMVDGWY GYHHQNEQGS GYAADQKSTQ NAINGITNKV 150
NSVIEKMNTQ STATGKEFNK SERRIENLNK KIDDGFIDIW TYNAELLVLL 200
ENERTLDFHD SNVKNLYEKV KSQLKNNAKE IGNGCFEFYH KCNDECMESV 250
KNGTYDYPKY SEESKLNREK IDGVKLESMG VYQILAIYST VASSLVLLVS 300
LGAISFWMCS NGSLQCRICI 320

SEQ ID NO: 12: mini4 cluster11 (A/Brisbane/59/2007)
MKVKLLVLLC TFTATYADTI CIGYHANNST DTVDTVLEKN VTVTHSVNLL 50
ENSHNGGGGE CPKYVRSAKL RMVTGLRNIP SIQSQGLFGA IAGFIEGGWT 100
GMVDGWYGYH HQNEQGSGYA ADQKSTQNAI NGITNKVNSV IEKMNTQSTA 150
TGKEFNKSER RIENLNKKID DGFIDIWTYN AELLVLLENE RTLDFHDSNV 200
KNLYEKVKSQ LKNNAKEIGN GCFEFYHKCN DECMESVKNG TYDYPKYSEE 250
SKLNREKIDG VKLESMGVYQ ILAIYSTVAS SLVLLVSLGA ISFWMCSNGS 300
LQCRICI 307

SEQ ID NO: 13: mini1 cluster1 1 + 5 (A/Brisbane/59/2007)
MKVKLLVLLC TFTATYADTI CIGYHANNST DTVDTVLEKN VTVTHSVNLL 50
ENSHNGKTCG GGGCDAKCQT PQGAINSSLP FQNVHPTTTG ECPKYVCSAK 100
LRMVTGLRNI PSIQSQGLFG AIAGFIEGGW TGMVDGWYGY HHQNEQGSGY 150
AADQKSTQNA INGITNKVNS VIEKMNTQST ATGKEFNKSE RRIENLNKKI 200
DDGFIDIWCY NAELLVLLEN ERTLDFHDSN VKNLYEKVKS QLKNNAKEIG 250
NGCFEFYHKC NDECMESVKN GTYDYPKYSE ESKLNREKID GVKLESMGVY 300
QILAIYSTVA SSLVLLVSLG AISFWMCSNG SLQCRICI 338

SEQ ID NO: 14: mini2 cluster1 1 + 5 (A/Brisbane/59/2007)
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEFN 150
KSERRIENLN KKIDDGFIDI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 15: mini3 cluster1 1 + 5 (A/Brisbane/59/2007)
MKVKLLVLLC TFTATYADTI CIGYHANNST DTVDTVLEKN VTVTHSVNLL 50
ENSGGGGNSS LPFQNVHPTT TGECPKYVCS AKLRMVTGLR NIPSIQSQGL 100
FGAIAGFIEG GWTGMVDGWY GYHHQNEQGS GYAADQKSTQ NAINGITNKV 150
NSVIEKMNTQ STATGKEFNK SERRIENLNK KIDDGFIDIW CYNAELLVLL 200
ENERTLDFHD SNVKNLYEKV KSQLKNNAKE IGNGCFEFYH KCNDECMESV 250
KNGTYDYPKY SEESKLNREK IDGVKLESMG VYQILAIYST VASSLVLLVS 300
LGAISFWMCS NGSLQCRICI 320

SEQ ID NO: 16: mini4 cluster1 1 + 5 (A/Brisbane/59/2007)
MKVKLLVLLC TFTATYADTI CIGYHANNST DTVDTVLEKN VTVTHSVNLL 50
ENSHNGGGGE CPKYVCSAKL RMVTGLRNIP SIQSQGLFGA IAGFIEGGWT 100
GMVDGWYGYH HQNEQGSGYA ADQKSTQNAI NGITNKVNSV IEKMNTQSTA 150
TGKEFNKSER RIENLNKKID DGFIDIWCYN AELLVLLENE RTLDFHDSNV 200
KNLYEKVKSQ LKNNAKEIGN GCFEFYHKCN DECMESVKNG TYDYPKYSEE 250
SKLNREKIDG VKLESMGVYQ ILAIYSTVAS SLVLLVSLGA ISFWMCSNGS 300
LQCRICI 307

SEQ ID NO: 17: H1 consensus sequence residue 402-418 (numbering according to SEQ ID NO: 1)
402 MNTQFTAVG KEFN (H/K)LE(K/R) 418

>SC09-114 VH PROTEIN (SEQ ID NO: 18):
QVQLVQSGAEVKKPGSSVKVSCKSSGGTSNNYAISWVRQAPGQGLDWMGGISPIFGSTAYAQKFQGRVTISAD
IFSNTAYMELNSLTSEDTAVYFCARHGNYYYYSGMDVWGQGTTVTVSS

-continued

| SEQUENCES |
| --- |

>SC09-114 VL PROTEIN (SEQ ID NO: 19):
SYVLTQPPAVSGTPGQRVTISCSGSDSNIGRRSVNWYQQFPGTAPKLLIYSNDQRPSVVPDRFSGSKSGTSAS
LAISGLQSEDEAEYYCAAWDDSLKGAVFGGGTQLTVL

>CR6261 VH PROTEIN (SEQ ID NO: 20):
E V Q L V E S G A E V K K P G S S V K V S C K A S G G P F R S Y A I S W V
R Q A P G Q G P E W M G G I I P I F G T T K Y A P K F Q G R V T I T A D D
F A G T V Y M E L S S L R S E D T A M Y Y C A K H M G Y Q V R E T M D V W
G K G T T V T V S S

>CR6261 VL PROTEIN (SEQ ID NO: 21):
Q S V L T Q P P S V S A A P G Q K V T I S C S G S S S N I G N D Y V S W Y
Q Q L P G T A P K L L I Y D N N K R P S G I P D R F S G S K S G T S A T L
G I T G L Q T G D E A N Y Y C A T W D R R P T A Y V V F G G G T K L T V L
G

>SC08-057 VH PROTEIN (SEQ ID NO: 22):
EVQLVESGGGLVQPGGSLRLSCAASGFTDSVIFMSWVRQAPGKGLECVSIIYIDDSTYYADSVKGRFTISRHN
SMGTVFLEMNSLRPDDTAVYYCATESGDFGDQTGPYHYYAMDV

>SC08-057 VL PROTEIN (SEQ ID NO: 23):
QSALTQPASVSGSPGQSITISCTGSSGDIGGYNAVSWYQHHPGKAPKLMIYEVTSRPSGVSDRFSASRSGDTA
SLTVSGLQAEDEAHYYCCSFADSNILI

SEQ ID NO: 24 (STEEL):
MKANLLVLLC ALAAADADTI CIGYHANNST DTVDTVLEKN VTVTHSVNLL 50
EDSHNGKLCG GGGCNTKCQT PLGAINSSLP YQNIHPVTIG ECPKYVRSAK 100
LRMVTGLRNI PSIQSR*GLFG AIAGFIEGGW TGMIDGWYGY HHQNEQGSGY* 150
*AADQKSTQNA INGITNKVNS VIEKMNIQFT AVGKEFNKLE KRMENLNNKV* 200
*DDGFLDIWTY NAELLVLLEN ERTLDFHDSN VKNLYEKVKS QLKNNAKEIG* 250
*NGCFEFYHKC DNECMESVRN GTYDYPKYSE ESKLNREKVD GVKLESMGIY* 300
*QILAIYSTVA SSLVLLVSLG AISFWMCSNG SLQCRICI* 338

SEQ ID NO: 31: H7 Full-length (A/Mallard/Netherlands/12/2000)
MNTQILVFAL MAIIPTNADK ICLGHHAVSN GTKVNTLTER GVEVVNATET 50
VERTNVPRIC SKGKRTVDLG QCGLLGTITG PPQCDQFLEF SADLIIERRE 100
GSDVCYPGKF VNEEALRQIL RESGGIDKET MGFTYSGIRT NGATSACRRS 150
GSSFYAEMKW LLSNTDNAAF PQMTKSYKNT RKDPALIIWG IHHSGSTTEQ 200
TKLYGSGNKL ITVGSSNYQQ SFVPSPGARP QVNGQSGRID FHWLILNPND 250
TVTFSFNGAF IAPDRASFLR GKSMGIQSGV QVDANCEGDC YHSGGTIISN 300
LPFQNINSRA VGKCPRYVKQ ESLLLATGMK NVPEIPKGR*G LFGAIAGFIE* 350
*NGWEGLIDGW YGFRHQNAQG EGTAADYKST QSAIDQITGK LNRLIEKTNQ* 400
*QFELIDNEFT EVEKQIGNVI NWTRDSMTEV WSYNAELLVA MENQHTIDLA* 450
*DSEMNKLYER VKRQLRENAE EDGTGCFEIF HKCDDDCMAS IRNNTYDHSK* 500
*YREEAMQNRI QIDPVKLSSG YKDVILWFSF GASCFILLAI AMGLVFICVK* 550
*NGNMRCTICI* 560

SEQ ID NO: 32: H7 consensus sequence residue 394-414 (numbering according to SEQ ID NO: 31)
394 LI(E/D/G)KTNQQFELIDNEF (N/T/S) E (I/V) E (Q/K) 414

SEQ ID NO: 33: H7-mini2 (A/Mallard/Netherlands/12/2000)
MNTQILVFAL MAIIPTNADK ICLGHHAVSN GTKVNTLTER GVEVVNATET 50
VEGGGGRYVK QESLLLATGM KNVPEIPKGQ *GLFGAIAGFI ENGWEGLIDG* 100
*WYGFRHQNAQ GEGTAADYKS TQSAIDQITG KLNRLIEKTN QQFELIDNEF* 150
*TEVEKQIGNV INWTRDSMTE VWSYNAELLV AMENQHTIDL ADSEMNKLYE* 200
*RVKRQLRENA EEDGTGCFEI FHKCDDDCMA SIRNNTYDHS KYREEAMQNR* 250
*IQIDPVKLSS GYKDVILWFS FGASCFILLA IAMGLVFICV KNGNMRCTIC* 300
*I* 301

SEQ ID NO: 34: H7-mini2-cluster15
MNTQILVFAL MAIIPTNADK ICLGHHAVSN GTKVNTLTER GVEVVNATET 50
VEGGGGRYVK QESLLLATGM KNVPEIPKGQ *GLFGAIAGFI ENGWEGLIDG* 100
*WYGFRHQNAQ GEGTAADYKS TQSAIDQITG KLNRLIEKTN QQSELTDNES* 150
*TEVEKQIGNV INWTRDSMTE VWSYNAELLV AMENQHTIDL ADSEMNKLYE* 200
*RVKRQLRENA EEDGTGCFEI FHKCDDDCMA SIRNNTYDHS KYREEAMQNR* 250
*IQIDPVKLSS GYKDVILWFS FGASCFILLA IAMGLVFICV KNGNMRCTIC* 300
*I* 301

SEQ ID NO: 35: H7-mini2-cluster15 + 16
MNTQILVFAL MAIIPTNADK ICLGHHAVSN GTKVNTLTER GVEVVNATET 50
VEGGGGRYVK QESLLLATGM KNVPEIPKGQ *GLFGAIAGFI ENGWEGLIDG* 100
*WYGFRHQNAQ GEGTAADYKS TQSAIDQITG KLNRLIEKTN QQSENTDNES* 150
*TENEKQIGNV INWTRDSMTE VWSYNAELLV AMENQHTIDL ADSEMNKLYE* 200

-continued

SEQUENCES

RVKRQLRENA EEDGTGCFEI FHKCDDDCMA SIRNNTYDHS KYREEAMQNR 250
IQIDPVKLSS GYKDVILWFS FGASCFILLA IAMGLVFICV KNGNMRCTIC 300
I 301

SEQ ID NO: 36: H7-mini2-cluster17
MNTQILVFAL MAIIPTNADK ICLGHHAVSN GTKVNTLTER GVEVVNATET 50
VEGGGGRYVC QESLLLATGM KNVPEIPKGQ GLFGAIAGFI ENGWEGLIDG 100
WYGFRHQNAQ GEGTAADYKS TQSAIDQITG KLNRLIEKTN QQFELIDNEF 150
TEVEKQIGNV INWTRDSMTE VWCYNAELLV AMENQHTIDL ADSEMNKLYE 200
RVKRQLRENA EEDGTGCFEI FHKCDDDCMA SIRNNTYDHS KYREEAMQNR 250
IQIDPVKLSS GYKDVILWFS FGASCFILLA IAMGLVFICV KNGNMRCTIC 300
I 301

SEQ ID NO: 37: H7-mini2-cluster15 + 16 + 17
MNTQILVFAL MAIIPTNADK ICLGHHAVSN GTKVNTLTER GVEVVNATET 50
VEGGGGRYVC QESLLLATGM KNVPEIPKGQ GLFGAIAGFI ENGWEGLIDG 100
WYGFRHQNAQ GEGTAADYKS TQSAIDQITG KLNRLIEKTN QQSENTDNES 150
TENEKQIGNV INWTRDSMTE VWCYNAELLV AMENQHTIDL ADSEMNKLYE 200
RVKRQLRENA EEDGTGCFEI FHKCDDDCMA SIRNNTYDHS KYREEAMQNR 250
IQIDPVKLSS GYKDVILWFS FGASCFILLA IAMGLVFICV KNGNMRCTIC 300
I 301

SEQ ID NO: 38: H7-mini2-cluster15 + 16 + 17 + 18
MNTQILVFAL MAIIPTNADK ICLGHHAVSN GTKVNTLTER GVEVVNATET 50
VEGGGGRYVC QESLLLATGM KNVPEIPKGQ GLFGAIAGFI ENGWEGLIDG 100
WYGFRHQNAQ GEGTAADYKS TQSAIDQITG KLNRLIEKTN QQSENTDNES 150
TENEKQIGNI INWIRDIMTE IWCYNAELLV AMENQHTIDL ADSEMNKLYE 200
RVKRQLRENA EEDGTGCFEI FHKCDDDCMA SIRNNTYDHS KYREEAMQNR 250
IQIDPVKLSS GYKDVILWFS FGASCFILLA IAMGLVFICV KNGNMRCTIC 300
I 301

SEQ ID NO: 39: H7-mini2-cluster15 + 16 + 17 + tri
MNTQILVFAL MAIIPTNADK ICLGHHAVSN GTKVNTLTER GVEVVNATET 50
VEGGGGRYVC QESLLLATGM KNVPEIPKGQ GLFGAIAGFI ENGWEGLIDG 100
WYGFRHQNAQ GEGTAADYKS TQSAIDQITG KLNRLIEKTN QQSENTDNES 150
TENEKQIEAI EKKIEAIMTE IWCYNAELLV AMENQHTIDL ADSEMNKLYE 200
RVKRQLRENA EEDGTGCFEI FHKCDDDCMA SIRNNTYDHS KYREEAMQNR 250
IQIDPVKLSS GYKDVILWFS FGASCFILLA IAMGLVFICV KNGNMRCTIC 300
I 301

SEQ ID NO: 40: H7-mini5
MNTQILVFAL MAIIPTNADK ICLGHHAVSN GTKVNTLTER GVEVVNATET 50
VERGGGGPRY VKQESLLLAT GMKNVPEIPK GQGLFGAIAG FIENGWEGLI 100
DGWYGFRHQN AQGEGTAADY KSTQSAIDQI TGKLNRLIEK TNQQFELIDN 150
EFTEVEKQIG NVINWTRDSM TEVWSYNAEL LVAMENQHTI DLADSEMNKL 200
YERVKRQLRE NAEEDGTGCF EIFHKCDDDC MASIRNNTYD HSKYREEAMQ 250
NRIQIDPVKL SSGYKDVILW FSFGASCFIL LAIAMGLVFI CVKNGNMRCT 300
ICI 303

SEQ ID NO: 41: H7-mini5-cluster15 + 16
MNTQILVFAL MAIIPTNADK ICLGHHAVSN GTKVNTLTER GVEVVNATET 50
VERGGGGPRY VKQESLLLAT GMKNVPEIPK GQGLFGAIAG FIENGWEGLI 100
DGWYGFRHQN AQGEGTAADY KSTQSAIDQI TGKLNRLIEK TNQQSENTDN 150
ESTENEKQIG NVINWTRDSM TEVWSYNAEL LVAMENQHTI DLADSEMNKL 200
YERVKRQLRE NAEEDGTGCF EIFHKCDDDC MASIRNNTYD HSKYREEAMQ 250
NRIQIDPVKL SSGYKDVILW FSFGASCFIL LAIAMGLVFI CVKNGNMRCT 300
ICI 303

SEQ ID NO: 42: H7-mini5-cluster17
MNTQILVFAL MAIIPTNADK ICLGHHAVSN GTKVNTLTER GVEVVNATET 50
VERGGGGPRY CKQESLLLAT GMKNVPEIPK GQGLFGAIAG FIENGWEGLI 100
DGWYGFRHQN AQGEGTAADY KSTQSAIDQI TGKLNRLIEK TNQQFELIDN 150
EFTEVEKQIG NVINWTRDSM TEVWCYNAEL LVAMENQRTI DLADSEMNKL 200
YERVKRQLRE NAEEDGTGCF EIFHKCDDDC MASIRNNTYD HSKYREEAMQ 250
NRIQIDPVKL SSGYKDVILW FSFGASCFIL LAIAMGLVFI CVKNGNMRCT 300
ICI 303

SEQ ID NO: 43: H7-mini5-cluster15 + 16 + 17 + 18
MNTQILVFAL MAIIPTNADK ICLGHHAVSN GTKVNTLTER GVEVVNATET 50
VERGGGGPRY VCQESLLLAT GMKNVPEIPK GQGLFGAIAG FIENGWEGLI 100
DGWYGFRHQN AQGEGTAADY KSTQSAIDQI TGKLNRLIEK TNQQSENTDN 150
ESTENEKQIG NIINWIRDIM TEIWCYNAEL LVAMENQRTI DLADSEMNKL 200

| SEQUENCES |
| --- |

YERVKRQLRE NAEEDGTGCF EIFHKCDDDC MASIRNNTYD HSKYREEAMQ 250
NRIQIDPVKL SSGYKDVILW FSFGASCFIL LAIAMGLVFI CVKNGNMRCT 300
ICI 303

SEQ ID NO: 44: H1-mini2-cluster1 + 5 + 6-trim
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSEIEAIEKK IEAIEKKIEI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 45: H1-mini2-cluster1 + 5 + 6-GCN4
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSERMKQIED KIEEIESKQI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 46: mini2-cluster1 + 5 + 6 (A/Brisbane/59/2007)
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSERRMENLN KKVDDGFIDI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 47: mini2-cluster11 + 5 + 6 (A/Brisbane/59/2007)
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSERRIENLN KKIDDGFIDI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 48: mini2-cluster1 + 5 (A/Brisbane/59/2007)
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEFN 150
KSERRMENLN KKVDDGFIDI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 49: H1-mini2-cluster1 + 5 + 6-trim2
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSERIEAIEK KIEAIEKKII WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 50: H1-mini2-cluster1 + 5 + 6-trim3
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSERRIEAIE KKIEAIEKKI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 51: H1-mini2-cluster1 + 5 + 6-GCN4t2
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150

-continued

SEQUENCES

KSERRMKQIE DKIEEIESKI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 52: H1-mini2-cluster1 + 5 + 6-GCN4t3
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSRMKQIEDK IEEIESKQKI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 53: H1-mini2-cluster1 + 5 + 6-IleTri
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSERRIENIN KKIDDIFIDI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQILAIYS TVASSLVLLV SLGAISFWMC SNGSLQCRIC 300
I 301

SEQ ID NO: 89: H3 Full-length A/Wisconsin/67/2005
MKTIIALSYI LCLVFAQKLP GNDNSTATLC LGHHAVPNGT IVKTITNDQI 50
EVTNATELVQ SSSTGGICDS PHQILDGENC TLIDALLGDP QCDGFQNKKW 100
DLFVERSKAY SNCYPYDVPD YASLRSLVAS SGTLEFNDES FNWTGVTQNG 150
TSSSCKRRSN NSFFSRLNWL THLKFKYPAL NVTMPNNEKF DKLYIWGVHH 200
PVTDNDQIFL YAQASGRITV STKRSQQTVI PNIGSRPRIR NIPSRISIYW 250
TIVKPGDILL INSTGNLIAP RGYFKIRSGK SSIMRSDAPI GKCNSECITP 300
NGSIPNDKPF QNVNRITYGA CPRYVKQNTL KLATGMRNVP EKQTRGIFGA 350
IAGFIENGWE GMVDGWYGFR HQNSEGIGQA ADLKSTQAAI NQINGKLNRL 400
IGKTNEKFHQ IEKEFSEVEG RIQDLEKYVE DTKIDLWSYN AELLVALENQ 450
HTIDLTDSEM NKLFERTKKQ LRENAEDMGN GCFKIYHKCD NACIGSIRNG 500
TYRHDVYRDE ALNNRFQIKG VELKSGYKDW ILWISFAISC FLLCVVLLGF 550
IMWACQKGN1 RCNICI 566

SEQ ID NO: 90: mini-H3
MKTIIALSYI LCLVFAQKLP GNDNSTATLC LGHHAVPNGT IVKTITNDQI 50
EVTNATELVQ SSSTGGICGG GGCNSECITP NGSIPNDKPF QNVNRITYGA 100
CPRYVKQNTL KLATGMRNVP EKQTQGIFGA IAGFIENGWE GMVDGWYGFR 150
HQNSEGIGQA ADLKSTQAAI NQINGKLNRL IGKTNEKFHQ IEKEFSEVEG 200
RIQDLEKYVE DTKIDLWSYN AELLVALENQ HTIDLTDSEM NKLFERTKKQ 250
LRENAEDMGN GCFKIYHKCD NACIGSIRNG TYDHDVYRDE ALNNRFQIKG 300
VELKSGYKDW ILWISFAISC FLLCVVLLGF IMWACQKGNI RCNICI 346

SEQ ID NO: 91: mini-H3 cluster1
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGA 100
CPRYVKQNTL KLATGMRNVP EKQTQGIFGA IAGFIENGWE GMVDGWYGFR 150
HQNSEGIGQA ADLKSTQAAI NQINGKLNRL IGKTNEKTSQ IEKEFSESEG 200
RIQDLEKYVE DTKIDLWSYN AELLVALENQ HTIDLTDSEM NKLFERTKKQ 250
LRENAEDMGN GCFKIYHKCD NACIGSIRNG TYDHDVYRDE ALNNRFQIKG 300
VELKSGYKDW ILWISFAISC FLLCVVLLGF IMWACQKGNI RCNICI 346

SEQ ID NO: 92: mini-H3 cluster1 + 2
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGC 100
CPRYVKQNTL KLATGMRNVP EKQTQGIFGA IAGFIENGWE GMVDGWYGFR 150
HQNSEGIGQA ADLKSTQAAI NQINGKLNRL IGKTNCKTSQ IEKEFSESEG 200
RIQDLEKYVE DTKIDLWSYN AELLVALENQ HTIDLTDSEM NKLFERTKKQ 250
LRENAEDMGN GCFKIYHKCD NACIGSIRNG TYDHDVYRDE ALNNRFQIKG 300
VELKSGYKDW ILWISFAISC FLLCVVLLGF IMWACQKGNI RCNICI 346

SEQ ID NO: 93: mini-H3 cluster1 + 3
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGA 100
CPRYVCQNTL KLATGMRNVP EKQTQGIFGA IAGFIENGWE GMVDGWYGFR 150
HQNSEGIGQA ADLKSTQAAI NQINGKLNRL IGKTNEKTSQ IEKEFSESEG 200
RIQDLEKYVE DTKIALWCYN AELLVALENQ HTIDLTDSEM NKLFERTKKQ 250
LRENAEDMGN GCFKIYHKCD NACIGSIRNG TYDHDVYRDE ALNNRFQIKG 300
VELKSGYKDW ILWISFAISC FLLCVVLLGF IMWACQKGNI RCNICI 346

SEQ ID NO: 94: mini-H3 cluster1 + 4
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGA 100
CPRYVKQNTL KLATGMRNVP EKQTQGIFGA IAGFIENGWE GMVDGWYGFR 150

-continued

SEQUENCES

HQNSEGIGQA ADLKSTQAAI NQINGKKNRL TGKTNEKTSQ IEKEFSESEG 200
RIQDLEKYVE DTKIDLWSYN AELLVALENQ HTIDLTDSEM NKLFERTKKQ 250
LRENAEDMGN GCFKIYHKCD NACIGSIRNG TYDHDVYRDE ALNNRFQIKG 300
VELKSGYKDW ILWISFAISC FLLCVVLLGF IMWACQKGNI RCNICI 346

SEQ ID NO: 95: mini-H3 cluster1 + 5 N60A
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGA 100
CPRYVKQNTL KLATGMRNVP EKQTQGIFGA IAGFIENGWE GMVDGWYGFR 150
HQNSEGIGQA ADLKSTQAAI NQINGKLNRL IGKTAEKTSQ IEKEFSESEG 200
RIQDLEKYVE DTKIDLWSYN AELLVALENQ HTIDLTDSEM NKLFERTKKQ 250
LRENAEDMGN GCFKIYHKCD NACIGSIRNG TYDHDVYRDE ALNNRFQIKG 300
VELKSGYKDW ILWISFAISC FLLCVVLLGF IMWACQKGNI RCNICI 346

SEQ ID NO: 96: mini-H3 cluster1 + 5 N60D
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGA 100
CPRYVKQNTL KLATGMRNVP EKQTQGIFGA IAGFIENGWE GMVDGWYGFR 150
HQNSEGIGQA ADLKSTQAAI NQINGKLNRL IGKTDEKTSQ IEKEFSESEG 200
RIQDLEKYVE DTKIDLWSYN AELLVALENQ HTIDLTDSEM NKLFERTKKQ 250
LRENAEDMGN GCFKIYHKCD NACIGSIRNG TYDHDVYRDE ALNNRFQIKG 300
VELKSGYKDW ILWISFAISC FLLCVVLLGF IMWACQKGNI RCNICI 346

SEQ ID NO: 97: mini-H3 cluster1 + 5 N60E
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGA 100
CPRYVKQNTL KLATGMRNVP EKQTQGIFGA IAGFIENGWE GMVDGWYGFR 150
HQNSEGIGQA ADLKSTQAAI NQINGKLNRL IGKTEEKTSQ IEKEFSESEG 200
RIQDLEKYVE DTKIDLWSYN AELLVALENQ HTIDLTDSEM NKLFERTKKQ 250
LRENAEDMGN GCFKIYHKCD NACIGSIRNG TYDHDVYRDE ALNNRFQIKG 300
VELKSGYKDW ILWISFAISC FLLCVVLLGF IMWACQKGNI RCNICI 346

SEQ ID NO: 98: mini-H3 cluster1 + 6
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGA 100
CPRYVKQNTL KLATGMRNVP EKQTQGIFGA IAGFIENGWE GMVDGWYGFR 150
HQNSEGIGQA ADLKSTQAAI NQINGKLNRL IGKTNEKTSQ IEKECSESEG 200
RICDLEKYVE DTKIDLWSYN AELLVALENQ HTIDLTDSEM NKLFERTKKQ 250
LRENAEDMGN GCFKIYHKCD NACIGSIRNG TYDHDVYRDE ALNNRFQIKG 300
VELKSGYKDW ILWISFAISC FLLCVVLLGF IMWACQKGNI RCNICI 346

SEQ ID NO: 99: mini-H3 cluster1 + 7
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGA 100
CPRYVKQNTL KLATGMRNVP EKQTQGIFGA IAGFIENGWE GMVDGWYGFR 150
HQNSEGIGQA ADLKSTQAAI NQINGKLNRL IGKTNEKTSQ IEKEFSESEG 200
RIQDLEKYVE DTKIDLWSYN AELLVALENQ HTIDLTDSEM NKLFERTKKQ 250
LRENAEDMGN GCFKIYHKCD NACIESIRNG TYDHDVYRDE ALNNRFQIKG 300
VELKSGYKDW ILWISFAISC FLLCVVLLGF IMWACQKGNI RCNICI 346

SEQ ID NO: 100: mini-H3 cluster1 + 2 + 3 + 4 + 5 + 6 + 7-N405E
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGC 100
CPRYVCQNTL KLATGMRNVP EKQTQGIFGA IAGFIENGWE GMVDGWYGFR 150
HQNSEGIGQA ADLKSTQAAI NQINGKKNRL TGKTECKTSQ IEKECSESEG 200
RICDLEKYVE DTKIALWCYN AELLVALENQ HTIDLTDSEM NKLFERTKKQ 250
LRENAEDMGN GCFKIYHKCD NACIESIRNG TYDHDVYRDE ALNNRFQIKG 300
VELKSGYKDW ILWISFAISC FLLCVVLLGF IMWACQKGNI RCNICI 346

SEQ ID NO: 101: mini-H3 cluster1 + 2 + 3 + 4 + 5 + 6 + 7-N405A
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGC 100
CPRYVCQNTL KLATGMRNVP EKQTQGIFGA IAGFIENGWE GMVDGWYGFR 150
HQNSEGIGQA ADLKSTQAAI NQINGKKNRL TGKTACKTSQ IEKECSESEG 200
RICDLEKYVE DTKIALWCYN AELLVALENQ HTIDLTDSEM NKLFERTKKQ 250
LRENAEDMGN GCFKIYHKCD NACIESIRNG TYDHDVYRDE ALNNRFQIKG 300
VELKSGYKDW ILWISFAISC FLLCVVLLGF IMWACQKGNI RCNICI 346

SEQ ID NO: 102: mini-H3 cluster1 + 2 + 3 + 4 + 5 + 6 + 7-N405D
MKTIIALSYI LCLVFAQKLP GNDNSTATLC LGHHAVPNGT IVKTITNDQI 50
EVTNATELVQ SSSTGGTCGG GGCNSECTTP NGSIPNDKPF QNVNRQTYGC 100
CPRYVCQNTL KLATGMRNVP EKQTQGIFGA IAGFIENGWE GMVDGWYGFR 150
HQNSEGIGQA ADLKSTQAAI NQINGKKNRL TGKTDCKTSQ IEKECSESEG 200
RICDLEKYVE DTKIALWCYN AELLVALENQ HTIDLTDSEM NKLFERTKKQ 250
LRENAEDMGN GCFKIYHKCD NACIESIRNG TYDHDVYRDE ALNNRFQIKG 300
VELKSGYKDW ILWISFAISC FLLCVVLLGF IMWACQKGNI RCNICI 346

-continued

| SEQUENCES |
|---|
| SEQ ID NO: 103: mini-H3 cluster1 + 8<br>MKTIIALSYI LCLVFAQKLP GNDNSTATLC LGHHAVPNGT IVKTITNDQI 50<br>EVTNATELVQ SSSTGGTCGG GGCNSECTTP NGSIPNDKPF QNVNRQTYGA 100<br>CPRYVKQNTL KLATGMRNVP EKQTQGICGA IAGFIENGWE GMVDGWYGFR 150<br>HQNSEGIGQA ADLKCTQAAI NQINGKLNRL IGKTNEKTSQ IEKEFSESEG 200<br>RIQDLEKYVE DTKIDLWSYN AELLVALENQ HTIDLTDSEM CKCFERTKKQ 250<br>LRENAEDMGN GCFKIYHKCD NACIGSIRNG TYDHDVYRDE ALNNRFQIKG 300<br>VELKSGYKDW ILWISFAISC FLLCVVLLGF IMWACQKGNI RCNICI 346 |
| SEQ ID NO: 104: H3 consensus sequence residue 401-421 (numbering according to SEQ ID No: 1)<br>401 I(E/G)KTNEKFHQIEKEFSEVEGR 421 |
| SEQ ID NO: 105: H3-mini2<br>MKTIIALSYI LCLVFAQKLP GNDNSTATLC LGHHAVPNGT IVKTITNDQI 50<br>EVTNATELVQ SGGGGRYVKQ NTLKLATGMR NVPEKQTQGI FGAIAGFIEN 100<br>GWEGMVDGWY GFRHQNSEGI GQAADLKSTQ AAINQINGKL NRLIGKTNEK 150<br>FHQIEKEFSE VEGRIQDLEK YVEDTKIDLW SYNAELLVAL ENQHTIDLTD 200<br>SEMNKLFERT KKQLRENAED MGNGCFKIYH KCDNACIGSI RNGTYDHDVY 250<br>RDEALNNRFQ IKGVELKSGY KDWILWISFA ISCFLLCVVL LGFIMWACQK 300<br>GNIRCNICI 309 |
| SEQ ID NO: 106: H3-mini2-cl9 + 10<br>MKTIIALSYI LCLVFAQKLP GNDNSTATLC LGHHAVPNGT IVKTITNDQI 50<br>EVTNATELVQ SGGGGRYVKQ NTLKLATGMR NVPEKQTQGI FGAIAGFIEN 100<br>GWEGMVDGWY GFRHQNSEGI GQAADLKSTQ AAINQINGKL NRLIGKTNEK 150<br>SHQTEKESSE GEGRIQDLEK YVEDTKIDLW SYNAELLVAL ENQHTIDLTD 200<br>SEMNKLFERT KKQLRENAED MGNGCFKIYH KCDNACIGSI RNGTYDHDVY 250<br>RDEALNNRFQ IKGVELKSGY KDWILWISFA ISCFLLCVVL LGFIMWACQK 300<br>GNIRCNICI 309 |
| SEQ ID NO: 107: H3-mini2-cl9 + 11<br>MKTIIALSYI LCLVFAQKLP GNDNSTATLC LGHHAVPNGT IVKTITNDQI 50<br>EVTNATELVQ SGGGGRYVKQ NTLKLATGMR NVPEKQTQGI FGAIAGFIEN 100<br>GWEGMVDGWY GFRHQNSEGI GQAADLKSTQ AAINQINGKL NRIRGKTNEK 150<br>SHQTEKESSE VEGRIQDLEK YVEDTKIDLW SYNAELLVAL ENQHTIDLTD 200<br>SEMNKLFERT KKQLRENAED MGNGCFKIYH KCDNACIGSI RNGTYDHDVY 250<br>RDEALNNRFQ IKGVELKSGY KDWILWISFA ISCFLLCVVL LGFIMWACQK 300<br>GNIRCNICI 309 |
| SEQ ID NO: 108: H3-mini2-cl9 + 10 + 11<br>MKTIIALSYI LCLVFAQKLP GNDNSTATLC LGHHAVPNGT IVKTITNDQI 50<br>EVTNATELVQ SGGGGRYVKQ NTLKLATGMR NVPEKQTQGI FGAIAGFIEN 100<br>GWEGMVDGWY GFRHQNSEGI GQAADLKSTQ AAINQINGKL NRIRGKTNEK 150<br>SHQTEKESSE GEGRIQDLEK YVEDTKIDLW SYNAELLVAL ENQHTIDLTD 200<br>SEMNKLFERT KKQLRENAED MGNGCFKIYH KCDNACIGSI RNGTYDHDVY 250<br>RDEALNNRFQ IKGVELKSGY KDWILWISFA ISCFLLCVVL LGFIMWACQK 300<br>GNIRCNICI 309 |
| SEQ ID NO: 109: H3-mini2-cl9 + 10 + 11-tri<br>MKTIIALSYI LCLVFAQKLP GNDNSTATLC LGHHAVPNGT IVKTITNDQI 50<br>EVTNATELVQ SGGGGRYVKQ NTLKLATGMR NVPEKQTQGI FGAIAGFIEN 100<br>GWEGMVDGWY GFRHQNSEGI GQAADLKSTQ AAINQINGKL NRIRGKTNEK 150<br>SHQTEKESSE GEGIEAIEKK IEAIEKKIEA IEKKELLVAL ENQHTIDLTD 200<br>SEMNKLFERT KKQLRENAED MGNGCFKIYH KCDNACIGSI RNGTYDHDVY 250<br>RDEALNNRFQ IKGVELKSGY KDWILWISFA ISCFLLCVVL LGFIMWACQK 300<br>GNIRCNICI 309 |
| SEQ ID NO: 110: H3-mini2-cl9 + 10 + 11-GCN4<br>MKTIIALSYI LCLVFAQKLP GNDNSTATLC LGHHAVPNGT IVKTITNDQI 50<br>EVTNATELVQ SGGGGRYVKQ NTLKLATGMR NVPEKQTQGI FGAIAGFIEN 100<br>GWEGMVDGWY GFRHQNSEGI GQAADLKSTQ AAINQINGKL NRIRGKTNEK 150<br>SHQTEKESSE GEGRMKQIED KIEEIESKQK KIENELLVAL ENQHTIDLTD 200<br>SEMNKLFERT KKQLRENAED MGNGCFKIYH KCDNACIGSI RNGTYDHDVY 250<br>RDEALNNRFQ IKGVELKSGY KDWILWISFA ISCFLLCVVL LGFIMWACQK 300<br>GNIRCNICI 309 |
| SEQ ID NO: 111: H3-mini2-cl9 + 10 + 11 + 12<br>MKTIIALSYI LCLVFAQKLP GNDNSTATLC LGHHAVPNGT IVKTITNDQI 50<br>EVTNATELVQ SGGGGRYVCQ NTLKLATGMR NVPEKQTQGI FGAIAGFIEN 100<br>GWEGMVDGWY GFRHQNSEGI GQAADLKSTQ AAINQINGKL NRIRGKTNEK 150<br>SHQTEKESSE GEGRIQDLEK YVEDTKIDLW CYNAELLVAL ENQHTIDLTD 200<br>SEMNKLFERT KKQLRENAED MGNGCFKIYH KCDNACIGSI RNGTYDHDVY 250 |

-continued

SEQUENCES

RDEALNNRFQ IKGVELKSGY KDWILWISFA ISCFLLCVVL LGFIMWACQK 300
GNIRCNICI 309

SEQ ID NO: 112 H3-mini2-cl9 + 10 + 12
MKTIIALSYI LCLVFAQKLP GNDNSTATLC LGHHAVPNGT IVKTITNDQI 50
EVTNATELVQ SGGGGRYVCQ NTLKLATGMR NVPEKQTQGI FGAIAGFIEN 100
GWEGMVDGWY GFRHQNSEGI GQAADLKSTQ AAINQINGKL NRLIGKTNEK 150
CHQTEKECSE GEGRIQDLEK YVEDTKIDLW CYNAELLVAL ENQHTIDLTD 200
SEMNKLFERT KKQLRENAED MGNGCFKIYH KCDNACIGSI RNGTYDHDVY 250
RDEALNNRFQ IKGVELKSGY KDWILWISFA ISCFLLCVVL LGFIMWACQK 300
GNIRCNICI 309

SEQ ID NO: 113: H3-mini2-cl9+10+11+12-GCN4
MKTIIALSYI LCLVFAQKLP GNDNSTATLC LGHHAVPNGT IVKTITNDQI 50
EVTNATELVQ SGGGGRYVCQ NTLKLATGMR NVPEKQTQGI FGAIAGFIEN 100
GWEGMVDGWY GFRHQNSEGI GQAADLKSTQ AAINQINGKL NRIRGKTNEK 150
SHQTEKESSE GEGRMKQIED KIEEIESKLW CYNAELLVAL ENQHTIDLTD 200
SEMNKLFERT KKQLRENAED MGNGCFKIYH KCDNACIGSI RNGTYDHDVY 250
RDEALNNRFQ IKGVELKSGY KDWILWISFA ISCFLLCVVL LGFIMWACQK 300
GNIRCNICI 309

SEQ ID NO: 114: H3-mini2-cl9 + 10 + 11 + 12-tri
MKTIIALSYI LCLVFAQKLP GNDNSTATLC LGHHAVPNGT IVKTITNDQI 50
EVTNATELVQ SGGGGRYVCQ NTLKLATGMR NVPEKQTQGI FGAIAGFIEN 100
GWEGMVDGWY GFRHQNSEGI GQAADLKSTQ AAINQINGKL NRIRGKTNEK 150
SHQTEKESSE GEGIEAIEKK IEAIEKKILW CYNAELLVAL ENQHTIDLTD 200
SEMNKLFERT KKQLRENAED MGNGCFKIYH KCDNACIGSI RNGTYDHDVY 250
RDEALNNRFQ IKGVELKSGY KDWILWISFA ISCFLLCVVL LGFIMWACQK 300
GNIRCNICI 309

SEQ ID NO: 115: H3-mini2-cl9 + 13
MKTIIALSYI LCLVFAQKLP GNDNSTATLC LGHHAVPNGT IVKTITNDQI 50
EVTNATELVQ SGGGGRYVKQ NTLKLACGMR NVPEKQTQGI FGAIAGFIEN 100
GWEGMVDGWY GFRHQNSEGI GQAADLKSTQ AAINQCNGKL NRLIGKTNEK 150
SHQTEKESSE VEGRIQDLEK YVEDTKIDLW SYNAELLVAL ENQHTIDLTD 200
SEMNKLFERT KKQLRENAED MGNGCFKIYH KCDNACIGSI RNGTYDHDVY 250
RDEALNNRFQ IKGVELKSGY KDWILWISFA ISCFLLCVVL LGFIMWACQK 300
GNIRCNICI 309

SEQ ID NO: 116: H3-mini2-cl9 + 10 + 11 + 13
MKTIIALSYI LCLVFAQKLP GNDNSTATLC LGHHAVPNGT IVKTITNDQI 50
EVTNATELVQ SGGGGRYVKQ NTLKLACGMR NVPEKQTQGI FGAIAGFIEN 100
GWEGMVDGWY GFRHQNSEGI GQAADLKSTQ AAINQCNGKL NRIRGKTNEK 150
SHQTEKECSE GEGRIQDLEK YVEDTKIDLW SYNAELLVAL ENQHTIDLTD 200
SEMNKLFERT KKQLRENAED MGNGCFKIYH KCDNACIGSI RNGTYDHDVY 250
RDEALNNRFQ IKGVELKSGY KDWILWISFA ISCFLLCVVL LGFIMWACQK 300
GNIRCNICI 309

SEQ ID NO: 117: H3-mini2-cl9 + 10 + 11 + 13-GCN4
MKTIIALSYI LCLVFAQKLP GNDNSTATLC LGHHAVPNGT IVKTITNDQI 50
EVTNATELVQ SGGGGRYVKQ NTLKLACGMR NVPEKQTQGI FGAIAGFIEN 100
GWEGMVDGWY GFRHQNSEGI GQAADLKSTQ AAINQCNGKL NRIRGKTNEK 150
SHQTEKESSE GEGRMKQIED KIEEIESKQK KIENELLVAL ENQHTIDLTD 200
SEMNKLFERT KKQLRENAED MGNGCFKIYH KCDNACIGSI RNGTYDHDVY 250
RDEALNNRFQ IKGVELKSGY KDWILWISFA ISCFLLCVVL LGFIMWACQK 300
GNIRCNICI 309

SEQ ID NO: 118: H3-mini2-cl9 + 10 + 11 + 13-tri
MKTIIALSYI LCLVFAQKLP GNDNSTATLC LGHHAVPNGT IVKTITNDQI 50
EVTNATELVQ SGGGGRYVKQ NTLKLACGMR NVPEKQTQGI FGAIAGFIEN 100
GWEGMVDGWY GFRHQNSEGI GQAADLKSTQ AAINQCNGKL NRIRGKTNEK 150
SHQTEKESSE GEGIEAIEKK IEAIEKKIEA IEKKELLVAL ENQHTIDLTD 200
SEMNKLFERT KKQLRENAED MGNGCFKIYH KCDNACIGSI RNGTYDHDVY 250
RDEALNNRFQ IKGVELKSGY KDWILWISFA ISCFLLCVVL LGFIMWACQK 300
GNIRCNICI 309

SEQ ID NO: 119: H3-mini3-cl9 + 10 + 11 + 12 + 14
MKTIIALSYI LCLVFAQKLP GNDNSTATLC LGHHAVPNGT IVKTITNDQI 50
EVTNATELVQ SSGGGGNDKP FQNVNRITYG AGPRYVCQNT LKLATGMRNV 100
PEKQTQGIFG AIAGFIENGW EGMVDGWYGF RHQNSEGIGQ AADLKSTQAA 150
INQINGKLNR IRGKTNEKSH QTEKESSEGE GRIQDLEKYV EDTKIDLWCY 200
NAELLVALEN QHTIDLTDSE MNKLFERTKK QLRENAEDMG NGCFKIYHKC 250
DNACIGSIRN GTYRHDVYRD EALNNRFQIK GVELKSGYKD WILWISFAIS 300
CFLLCVVLLG FIMWACQKGN IRCNICI 327

SEQ ID NO: 120: H3-mini4-cl9 + 10 + 11 + 12 + 14
MKTIIALSYI LCLVFAQKLP GNDNSTATLC LGHHAVPNGT IVKTITNDQI 50

-continued

SEQUENCES

```
EVTNATELVQ SSSTGGGGYG AGPRYVCQNT LKLATGMRNV PEKQTQGIFG        100
AIAGFIENGW EGMVDGWYGF RHQNSEGIGQ AADLKSTQAA INQINGKLNR        150
LRGKTNEKSH QTEKESSEGE GRIQDLEKYV EDTKIDLWCY NAELLVALEN        200
QHTIDLTDSE MNKLFERTKK QLRENAEDMG NGCFKIYHKC DNACIGSIRN        250
GTYDHDVYRD EALNNRFQIK GVELKSGYKD WILWISFAIS CFLLCVVLLG        300
FIMWACQKGN IRCNICI                                            317

SEQ ID NO: 121: H3 Full-length A/Hong Kong/1/1968
MKTIIALSYI FCLALGQDLP GNDNSTATLC LGHHAVPNGT LVKTITDDQI         50
EVTNATELVQ SSSTGKICNN PHRILDGIDC TLIDALLGDP HCDVFQNETW        100
DLFVERSKAF SNCYPYDVPD YASLRSLVAS SGTLEFITEG FTWTGVTQNG        150
GSNACKRGPG SGFFSRLNWL TKSGSTYPVL NVTMPNNDNF DKLYIWGVHH        200
PSTNQEQTSL YVQASGRVTV STRRSQQTII PNIGSRPWVR GLSSRISIYW        250
TIVKPGDVLV INSNGNLIAP RGYFKMRTGK SSIMRSDAPI DTCISECITP        300
NGSIPNDKPF QNVNKITYGA CPKYVKQNTL KLATGMRNVP EKQTRGLFGA        350
IAGFIENGWE GMIDGWYGFR HQNSEGTGQA ADLKSTQAAI DQINGKLNRV        400
IEKTNEKFHQ IEKEFSEVEG RIQDLEKYVE DTKIDLWSYN AELLVALENQ        450
HTIDLTDSEM NKLFEKTRRQ LRENAEDMGN GCFKIYHKCD NACIESIRNG        500
TYRHDVYRDE ALNNRFQIKG VELKSGYKDW ILWISFAISC FLLCVVLLGF        550
IMWACQRGN1 RCNICI                                             566

SEQ ID NO: 122: HK68 H3m2-cl9
MKTIIALSYI FCLALGQDLP GNDNSTATLC LGHHAVPNGT LVKTITDDQI         50
EVTNATELVQ SGGGGKYVKQ NTLKLATGMR NVPEKQTQGL FGAIAGFIEN        100
GWEGMIDGWY GFRHQNSEGT GQAADLKSTQ AAIDQINGKL NRVIEKTNEK        150
SHQTEKESSE VEGRIQDLEK YVEDTKIDLW SYNAELLVAL ENQHTIDLTD        200
SEMNKLFEKT RRQLRENAED MGNGCFKIYH KCDNACIESI RNGTYDHDVY        250
RDEALNNRFQ IKGVELKSGY KDWILWISFA ISCFLLCVVL LGFIMWACQR        300
GNIRCNICI                                                     309

SEQ ID NO: 123: HK68 H3m2-cl9 + 10
MKTIIALSYI FCLALGQDLP GNDNSTATLC LGHHAVPNGT LVKTITDDQI         50
EVTNATELVQ SGGGGKYVKQ NTLKLATGMR NVPEKQTQGL FGAIAGFIEN        100
GWEGMIDGWY GFRHQNSEGT GQAADLKSTQ AAIDQINGKL NRVIEKTNEK        150
SHQTEKESSE GEGRIQDLEK YVEDTKIDLW SYNAELLVAL ENQHTIDLTD        200
SEMNKLFEKT RRQLRENAED MGNGCFKIYH KCDNACIESI RNGTYDHDVY        250
RDEALNNRFQ IKGVELKSGY KDWILWISFA ISCFLLCVVL LGFIMWACQR        300
GNIRCNICI                                                     309

SEQ ID NO: 124: HK68 H3m2-cl9 + 10 + 11
MKTIIALSYI FCLALGQDLP GNDNSTATLC LGHHAVPNGT LVKTITDDQI         50
EVTNATELVQ SGGGGKYVKQ NTLKLATGMR NVPEKQTQGL FGAIAGFIEN        100
GWEGMIDGWY GFRHQNSEGT GQAADLKSTQ AAIDQINGKL NRVREKTNEK        150
SHQTEKESSE GEGRIQDLEK YVEDTKIDLW SYNAELLVAL ENQHTIDLTD        200
SEMNKLFEKT RRQLRENAED MGNGCFKIYH KCDNACIESI RNGTYDHDVY        250
RDEALNNRFQ IKGVELKSGY KDWILWISFA ISCFLLCVVL LGFIMWACQR        300
GNIRCNICI                                                     309

SEQ ID NO: 125: HK68 H3m2-cl9 + 10 + 12
MKTIIALSYI FCLALGQDLP GNDNSTATLC LGHHAVPNGT LVKTITDDQI         50
EVTNATELVQ SGGGGKYVCQ NTLKLATGMR NVPEKQTQGL FGAIAGFIEN        100
GWEGMIDGWY GFRHQNSEGT GQAADLKSTQ AAIDQINGKL NRVIEKTNEK        150
SHQTEKESSE GEGRIQDLEK YVEDTKIDLW CYNAELLVAL ENQHTIDLTD        200
SEMNKLFEKT RRQLRENAED MGNGCFKIYH KCDNACIESI RNGTYDHDVY        250
RDEALNNRFQ IKGVELKSGY KDWILWISFA ISCFLLCVVL LGFIMWACQR        300
GNIRCNICI                                                     309

SEQ ID NO: 126: HK68 H3m2-cl9 + 10 + 11 + 12
MKTIIALSYI FCLALGQDLP GNDNSTATLC LGHHAVPNGT LVKTITDDQI         50
EVTNATELVQ SGGGGKYVCQ NTLKLATGMR NVPEKQTQGL FGAIAGFIEN        100
GWEGMIDGWY GFRHQNSEGT GQAADLKSTQ AAIDQINGKL NRVREKTNEK        150
SHQTEKESSE GEGRIQDLEK YVEDTKIDLW CYNAELLVAL ENQHTIDLTD        200
SEMNKLFEKT RRQLRENAED MGNGCFKIYH KCDNACIESI RNGTYDHDVY        250
RDEALNNRFQ IKGVELKSGY KDWILWISFA ISCFLLCVVL LGFIMWACQR        300
GNIRCNICI                                                     309

SEQ ID NO: 127: HK68 H3m2-cl9 + 10 + 11 + 13
MKTIIALSYI FCLALGQDLP GNDNSTATLC LGHHAVPNGT LVKTITDDQI         50
EVTNATELVQ SGGGGKYVKQ NTLKLACGMR NVPEKQTQGL FGAIAGFIEN        100
GWEGMIDGWY GFRHQNSEGT GQAADLKSTQ AAIDQCNGKL NRVREKTNEK        150
SHQTEKESSE GEGRIQDLEK YVEDTKIDLW SYNAELLVAL ENQHTIDLTD        200
SEMNKLFEKT RRQLRENAED MGNGCFKIYH KCDNACIESI RNGTYDHDVY        250
RDEALNNRFQ IKGVELKSGY KDWILWISFA ISCFLLCVVL LGFIMWACQR        300
GNIRCNICI                                                     309

SEQ ID NO: 128: HK68 H3m2-cl9 + 10 + 11 + 12-tri
MKTIIALSYI FCLALGQDLP GNDNSTATLC LGHHAVPNGT LVKTITDDQI         50
```

-continued

SEQUENCES

```
EVTNATELVQ SGGGGKYVCQ NTLKLATGMR NVPEKQTQGL FGAIAGFIEN   100
GWEGMIDGWY GFRHQNSEGT GQAADLKSTQ AAIDQINGKL NRVREKTNEK   150
SHQTEKESSE GEGIEAIEKK IEAIEKKILW CYNAELLVAL ENQHTIDLTD   200
SEMNKLFEKT RRQLRENAED MGNGCFKIYH KCDNACIESI RNGTYDHDVY   250
RDEALNNRFQ IKGVELKSGY KDWILWISFA ISCFLLCVVL LGFIMWACQR   300
GNIRCNICI                                                309

SEQ ID NO: 129: HK68 H3m2-cl9 + 10 + 11 + 13-tri
MKTIIALSYI FCLALGQDLP GNDNSTATLC LGHHAVPNGT LVKTITDDQI    50
EVTNATELVQ SGGGGKYVKQ NTLKLACGMR NVPEKQTQGL FGAIAGFIEN   100
GWEGMIDGWY GFRHQNSEGT GQAADLKSTQ AAIDQCNGKL NRVREKTNEK   150
SHQTEKESSE GEGIEAIEKK IEAIEKKILW SYNAELLVAL ENQHTIDLTD   200
SEMNKLFEKT RRQLRENAED MGNGCFKIYH KCDNACIESI RNGTYDHDVY   250
RDEALNNRFQ IKGVELKSGY KDWILWISFA ISCFLLCVVL LGFIMWACQR   300
GNIRCNICI                                                309

SEQ ID NO: 130: HK68 H3m2-cl9 + 10 + 11 + 12-GCN4
MKTIIALSYI FCLALGQDLP GNDNSTATLC LGHHAVPNGT LVKTITDDQI    50
EVTNATELVQ SGGGGKYVCQ NTLKLATGMR NVPEKQTQGL FGAIAGFIEN   100
GWEGMIDGWY GFREQNSEGT GQAADLKSTQ AAIDQINGKL NRVREKTNEK   150
SHQTEKESSE GEGRMKQIED KIEEIESKLW CYNAELLVAL ENQHTIDLTD   200
SEMNKLFEKT RRQLRENAED MGNGCFKIYH KCDNACIESI RNGTYDHDVY   250
RDEALNNRFQ IKGVELKSGY KDWILWISFA ISCFLLCVVL LGFIMWACQR   300
GNIRCNICI                                                309

SEQ ID NO: 131: HK68 H3m2-cl9 + 10 + 11 + 13-GCN4
MKTIIALSYI FCLALGQDLP GNDNSTATLC LGHHAVPNGT LVKTITDDQI    50
EVTNATELVQ SGGGGKYVKQ NTLKLACGMR NVPEKQTQGL FGAIAGFIEN   100
GWEGMIDGWY GFRHQNSEGT GQAADLKSTQ AAIDQCNGKL NRVREKTNEK   150
SHQTEKESSE GEGRMKQIED KIEEIESKLW SYNAELLVAL ENQHTIDLTD   200
SEMNKLFEKT RRQLRENAED MGNGCFKIYH KCDNACIESI RNGTYDHDVY   250
RDEALNNRFQ IKGVELKSGY KDWILWISFA ISCFLLCVVL LGFIMWACQR   300
GNIRCNICI                                                309

SEQ ID NO: 13/ B/Florida/4/2006 Full-length HA
MKAIIVLLMV VTSNADRICT GITSSNSPHV VKTATQGEVN VTGVIPLTTT    50
PTKSYFANLK GTRTRGKLCP DCLNCTDLDV ALGRPMCVGT TPSAKASILH   100
EVKPVTSGCF PIMHDRTKIR QLPNLLRGYE NIRLSTQNVI DAEKAPGGPY   150
RLGTSGSCPN ATSKSGFFAT MAWAVPKDNN KNATNPLTVE VPYICTEGED   200
QITVWGFHSD DKTQMKNLYG DSNPQKFTSS ANGVTTHYVS QIGSFPDQTE   250
DGGLPQSGRI VVDYMMQKPG KTGTIVYQRG VLLPQKVWCA SGRSKVIKGS   300
LPLIGEADCL HEKYGGLNKS KPYYTGEHAK AIGNCPIWVK TPLKLANGTK   350
YRPPAKLLKE RGFFGAIAGF LEGGWEGMIA GWHGYTSHGA HGVAVAADLK   400
STQEAINKIT KNLNSLSELE VKNLQRLSGA MDELHNEILE LDEKVDDLRA   450
DTISSQIELA VLLSNEGIIN SEDEHLLALE RKLKKMLGPS AVEIGNGCFE   500
TKHKCNQTCL DRIAAGTFNA GEFSLPTFDS LNITAASLND DGLDNHTILL   550
YYSTAASSLA VTLMLAIFIV YMVSRDNVSC SICL                    584

SEQ ID NO: 133: FL4-06 B-m2
MKAIIVLLMV VTSNADRICT GITSSNSPHV VKTATQGEVN VTGVIPLTTT    50
GGGGIWVKTP LKLANGTKYR PPAKLLKEQG FFGAIAGFLE GGWEGMIAGW   100
HGYTSHGAHG VAVAADLKST QEAINKITKN LNSLSELEVK NLQRLSGAMD   150
ELHNEILELD EKVDDLRADT ISSQIELAVL LSNEGIINSE DEHLLALERK   200
LKKMLGPSAV EIGNGCFETK HKCNQTCLDR IAAGTENAGE FSLPTFDSLN   250
ITAASLNDDG LDNHTILLYY STAASSLAVT LMLAIFIVYM VSRDNVSCSI   300
CL                                                       302

SEQ ID NO: 134: FL4-06 B-m2-CL1 + 5
MKAIIVLLMV VTSNADRICT GITSSNSPHV VKTATQGEVN VTGVIPLTTT    50
GGGGIWVCTP LKLANGTKYR PPAKLLKEQG FFGAIAGFLE GGWEGMIAGW   100
HGYTSHGAHG VAVAADLKST QEAINKITKN LNSLSELETK NSQRTSGAMD   150
EGENEILELD EKVDDLRADT ICSQIELAVL LSNEGIINSE DEHLLALERK   200
LKKMLGPSAV EIGNGCFETK HKCNQTCLDR IAAGTENAGE FSLPTFDSLN   250
ITAASLNDDG LDNHTILLYY STAASSLAVT LMLAIFIVYM VSRDNVSCSI   300
CL                                                       302

SEQ ID NO: 135: FL4-06 B-m2-CL1 + 5-GCN4a
MKAIIVLLMV VTSNADRICT GITSSNSPHV VKTATQGEVN VTGVIPLTTT    50
GGGGIWVCTP LKLANGTKYR PPAKLLKEQG FFGAIAGFLE GGWEGMIAGW   100
HGYTSHGAHG VAVAADLKST QEAINKITKN LNSLSELETK NSQRTSGAMD   150
EGHRRMKQIE DKIEEILSKI ICSQIELAVL LSNEGIINSE DEHLLALERK   200
LKKMLGPSAV EIGNGCFETK HKCNQTCLDR IAAGTENAGE FSLPTFDSLN   250
ITAASLNDDG LDNHTILLYY STAASSLAVT LMLAIFIVYM VSRDNVSCSI   300
CL                                                       302

SEQ ID NO: 136: FL4-06 B-m2-CL1 + 5-GCN4b
MKAIIVLLMV VTSNADRICT GITSSNSPHV VKTATQGEVN VTGVIPLTTT    50
```

-continued

SEQUENCES

GGGGIWVCTP LKLANGTKYR PPAKLLKEQG FFGAIAGFLE GGWEGMIAGW 100
HGYTSHGAHG VAVAADLKST QEAINKITKN LNSLSELETK NSQRTSGAMD 150
EGHRMKQIED KIEEILSKIT ICSQIELAVL LSNEGIINSE DEHLLALERK 200
LKKMLGPSAV EIGNGCFETK HKCNQTCLDR IAAGTENAGE FSLPTFDSLN 250
ITAASLNDDG LDNHTILLYY STAASSLAVT LMLAIFIVYM VSRDNVSCSI 300
CL 302

SEQ ID NO: 137: B/Malaysia/2506/2004 Full-length HA
MKAIIVLLMV VTSNADRICT GITSSNSPHV VKTATQGEVN VTGVIPLTTT 50
PTKSHFANLK GTETRGKLCP KCLNCTDLDV ALGRPKCTGN IPSARVSILH 100
EVRPVTSGCF PIMHDRTKIR QLPNLLRGYE HIRLSTHNVI NAENAPGGPY 150
KIGTSGSCPN VTNGNGFFAT MAWAVPKNDN NKTATNSLTI EVPYICTEGE 200
DQITVWGFHS DNEAQMAKLY GDSKPQKFTS SANGVTTHYV SQIGGFPNQT 250
EDGGLPQSGR IVVDYMVQKS GKTGTITYQR GILLPQKVWC ASGRSKVIKG 300
SLPLIGEADC LHEKYGGLNK SKPYYTGEHA KAIGNCPIWV KTPLKLANGT 350
KYRPPAKLLK ERGFFGAIAG FLEGGWEGMI AGWHGYTSHG AHGVAVAADL 400
KSTQEAINKI TKNLNSLSEL EVKNLQRLSG AMDELHNEIL ELDEKVDDLR 450
ADTISSQIEL AVLLSNEGII NSEDEHLLAL ERKLKKMLGP SAVEIGNGCF 500
ETKHKCNQTC LDRIAAGTFD AGEFSLPTFD SLNITAASLN DDGLDNHTIL 550
LYYSTAASSL AVTLMIAIFV VYMVSRDNVS CSICL 585

SEQ ID NO: 138: Mal2506-04 B-m2
MKAIIVLLMV VTSNADRICT GITSSNSPHV VKTATQGEVN VTGVIPLTTT 50
GGGGIWVKTP LKLANGTKYR PPAKLLKEQG FFGAIAGFLE GGWEGMIAGW 100
HGYTSHGAHG VAVAADLKST QEAINKITKN LNSLSELEVK NLQRLSGAMD 150
ELHNEILELD EKVDDLRADT ISSQIELAVL LSNEGIINSE DEHLLALERK 200
LKKMLGPSAV EIGNGCFETK HKCNQTCLDR IAAGTFDAGE FSLPTFDSLN 250
ITAASLNDDG LDNHTILLYY STAASSLAVT LMIAIFVVYM VSRDNVSCSI 300
CL 302

SEQ ID NO: 139: Mal2506-04 B-m2-CL1 + 5
MKAIIVLLMV VTSNADRICT GITSSNSPHV VKTATQGEVN VTGVIPLTTT 50
GGGGIWVCTP LKLANGTKYR PPAKLLKEQG FFGAIAGFLE GGWEGMIAGW 100
HGYTSHGAHG VAVAADLKST QEAINKITKN LNSLSELETK NSQRTSGAMD 150
EGHNEILELD EKVDDLRADT ICSQIELAVL LSNEGIINSE DEHLLALERK 200
LKKMLGPSAV EIGNGCFETK HKCNQTCLDR IAAGTFDAGE FSLPTFDSLN 250
ITAASLNDDG LDNHTILLYY STAASSLAVT LMIAIFVVYM VSRDNVSCSI 300
CL 302

SEQ ID NO: 140: Mal2506-04 B-m2-CL1 + 5-GCN4a
MKAIIVLLMV VTSNADRICT GITSSNSPHV VKTATQGEVN VTGVIPLTTT 50
GGGGIWVCTP LKLANGTKYR PPAKLLKEQG FFGAIAGFLE GGWEGMIAGW 100
HGYTSHGAHG VAVAADLKST QEAINKITKN LNSLSELETK NSQRTSGAMD 150
EGHRRMKQIE DKIEEILSKI ICSQIELAVL LSNEGIINSE DEHLLALERK 200
LKKMLGPSAV EIGNGCFETK HKCNQTCLDR IAAGTFDAGE FSLPTFDSLN 250
ITAASLNDDG LDNHTILLYY STAASSLAVT LMIAIFVVYM VSRDNVSCSI 300
CL 302

SEQ ID NO: 141: Mal2506-04 B-m2-CL1 + 5-GCN4b
MKAIIVLLMV VTSNADRICT GITSSNSPHV VKTATQGEVN VTGVIPLTTT 50
GGGGIWVCTP LKLANGTKYR PPAKLLKEQG FFGAIAGFLE GGWEGMIAGW 100
HGYTSHGAHG VAVAADLKST QEAINKITKN LNSLSELETK NSQRTSGAMD 150
EGHRMKQIED KIEEILSKIT ICSQIELAVL LSNEGIINSE DEHLLALERK 200
LKKMLGPSAV EIGNGCFETK HKCNQTCLDR IAAGTFDAGE FSLPTFDSLN 250
ITAASLNDDG LDNHTILLYY STAASSLAVT LMIAIFVVYM VSRDNVSCSI 300
CL 302

SEQ ID NO: 142: Influenza B HA consensus sequence residue 416-436
416 LSELEVKNLQRLSGAMDELHN 436

SEQ ID NO: 144: s-H1-mini2-cluster1 + 5 + 6-trim (A/Brisbane/59/2007)
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSEIEAIEKK IEAIEKKIEI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQIEGRHH HHHHH 275

SEQ ID NO: 145: s-H1-mini2-cluster1 + 5 + 6-GCN4 (A/Brisbane/59/2007)
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSERMKQIED KIEEIESKQI WCYNAELLVL LENERTLDFH DSNVKNLYEK 200

-continued

SEQUENCES

VKSQLKNNAK EIGNGCFEFY HKCNDECMES VKNGTYDYPK YSEESKLNRE 250
KIDGVKLESM GVYQIEGRHH HHHHH 275

SEQ ID NO: 146: s-H1-mini2-cluster1 + 5 + 6 (A/Brisbane/59/2007)
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSERRMENLN KKVDDGFIDI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQIEGRHH HHHHH 275

SEQ ID NO: 147: s-H1-mini2-cluster11 + 5 + 6 (A/Brisbane/59/2007)
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSERRIENLN KKIDDGFIDI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQIEGRHH HHHHH 275

SEQ ID NO: 148: s-H1-mini2-cluster1 + 5 (A/Brisbane/59/2007)
MKVKLLVLLC TFTATYADTI CIGYHANNST DTVDTVLEKN VTVTHSVNLL 50
ENGGGGKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEFN 150
KSERRMENLN KKVDDGFIDI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQIEGRHH HHHHH 275

SEQ ID NO 149: s-H1 Full-length R343Q (A/Brisbane/59/2007)
MKVKLLVLLC TFTATYADTI CIGYHANNST DTVDTVLEKN VTVTHSVNLL 50
ENSHNGKLCL LKGIAPLQLG NCSVAGWILG NPECELLISK ESWSYIVEKP 100
NPENGTCYPG HFADYEELRE QLSSVSSFER FEIFPKESSW PNHTVTGVSA 150
SCSHNGESSF YRNLLWLTGK NGLYPNLSKS YANNKEKEVL VLWGVHHPPN 200
IGDQKALYHT ENAYVSVVSS HYSRKFTPEI AKRPKVRDQE GRINYYWTLL 250
EPGDTIIFEA NGNLIAPRYA FALSRGFGSG IINSNAPMDK CDAKCQTPQG 300
AINSSLPFQN VHPVTIGECP KYVRSAKLRM VTGLRNIPSI QSQGLFGAIA 350
GFIEGGWTGM VDGWYGYHHQ NEQGSGYAAD QKSTQNAING ITNKVNSVIE 400
KMNTQFTAVG KEFNKLERRM ENLNKKVDDG FIDIWTYNAE LLVLLENERT 450
LDFHDSNVKN LYEKVKSQLK NNAKEIGNGC FEFYHKCNDE CMESVKNGTY 500
DYPKYSEESK LNREKIDGVK LESMGVYQIE GRHHEREHH 539

SEQ ID NO:: s-H1-mini2-cluster1 + 5 + 6-n1 (A/Brisbane/59/2007
MKVKLLVLLC TFTATYADTI CIGYHANNST DTVDTVLEKN VTVTHSVNLL 50
ENHNGKKYVC SAKLRMVTGL RNIPSIQSQG LFGAIAGFIE GGWTGMVDGW 100
YGYHHQNEQG SGYAADQKST QNAINGITNK VNSVIEKMNT QSTATGKEGN 150
KSERRMENLN KKVDDGFIDI WCYNAELLVL LENERTLDFH DSNVKNLYEK 200
VKSQLKNNAK EIGNGCFEFY HKCNDECMES VKNGTYDYPK YSEESKLNRE 250
KIDGVKLESM GVYQIEGRHH HHHHH 275

SEQ ID NO: 151: s-H1-mini2-cluster1 + 5 + 6-n12 (A/Brisbane/59/2007)
MKVKLLVLLC TFTATYADTI CIGYHANNST DTVDTVLEKN VTVTHSVNLL 50
ENHNGKYVCS AKLRMVTGLR NIPSIQSQGL FGAIAGFIEG GWTGMVDGWY 100
GYHHQNEQGS GYAADQKSTQ NAINGITNKV NSVIEKMNTQ STATGKEGNK 150
SERRMENLNK KVDDGFIDIW CYNAELLVLL ENERTLDFED SNVKNLYEKV 200
KSQLKNNAKE IGNGCFEFYH KCNDECMESV KNGTYDYPKY SEESKLNREK 250
IDGVKLESMG VYQIEGRHHH HHHH 274

SEQ ID NO: 152: H1mini2a-cl1 + 5 + 6_no_linker(HNGK)
MKVKLLVLLCTFTATYADTICIGYHANNSTDTVDTVLEKNVTVTHSVNLL 50
ENHNGKKYVCSAKLRMVTGLRNIPSIQSQGLFGAIAGFIEGGWTGMVDGW 100
YGYHHQNEQGSGYAADQKSTQNAINGITNKVNSVIEKMNTQSTATGKEGN 150
KSERRMENLNKKVDDGFIDIWCYNAELLVLLENERTLDFHDSNVKNLYEK 200
VKSQLKNNAKEIGNGCFEFYHKCNDECMESVKNGTYDYPKYSEESKLNRE 250
KIDGVKLESMGVYQILAIYSTVASSLVLLVSLGAISFWMCSNGSLQCRIC 300
I 301

SEQ ID NO: 153: H1mini2a-cl1 + 5 + 6_no_linker2s
MKVKLLVLLCTFTATYADTICIGYHANNSTDTVDTVLEKNVTVTHSVNLL 50
ENHNGKYVCSAKLRMVTGLRNIPSIQSQGLFGAIAGFIEGGWTGMVDGWY 100
GYHHQNEQGSGYAADQKSTQNAINGITNKVNSVIEKMNTQSTATGKEGNK 150
SERRMENLNKKVDDGFIDIWCYNAELLVLLENERTLDFHDSNVKNLYEKV 200
KSQLKNNAKEIGNGCFEFYHKCNDECMESVKNGTYDYPKYSEESKLNREK 250
IDGVKLESMGVYQILAIYSTVASSLVLLVSLGAISFWMCSNGSLQCRICI 300

SEQ ID NO: 154: H1-mini2-cl1 + 5 + 6-no_linker2s-GCN4
MKVKLLVLLCTFTATYADTICIGYHANNSTDTVDTVLEKNVTVTHSVNLL 50
ENSHNGKYVCSAKLRMVTGLRNIPSIQSQGLFGAIAGFIEGGWTGMVDGW 100
YGYHHQNEQGSGYAADQKSTQNAINGITNKVNSVIEKMNTQSTATGKEGN 150

-continued

SEQUENCES

KSERMKQIEDKIEEIESKQIWCYNAELLVLLENERTLDFHDSNVKNLYEK 200
VKSQLKNNAKEIGNGCFEFYHKCNDECMESVKNGTYDYPKYSEESKLNRE 250
KIDGVKLESMGVYQILAIYSTVASSLVLLVSLGAISFWMCSNGSLQCRIC 300
I 301

SEQ ID NO: 155: H1mini2a-cl1 + 5 + 6_no_linker2s-trim3
MKVKLLVLLCTFTATYADTICIGYHANNSTDTVDTVLEKNVTVTHSVNLL 50
ENSHNGKYVCSAKLRMVTGLRNIPSIQSQGLFGAIAGFIEGGWTGMVDGW 100
YGYHHQNEQGSGYAADQKSTQNAINGITNKVNSVIEKMNTQSTATGKEGN 150
KSERRIEAIEKKIEAIEKKIWCYNAELLVLLENERTLDFHDSNVKNLYEK 200
VKSQLKNNAKEIGNGCFEFYHKCNDECMESVKNGTYDYPKYSEESKLNRE 250
KIDGVKLESMGVYQILAIYSTVASSLVLLVSLGAISFWMCSNGSLQCRIC 300
I 301

SEQ ID NO: 156: H1mini2a-cl1 + 5 + 6-12
MKVKLLVLLCTFTATYADTICIGYHANNSTDTVDTVLEKNVTVTHSVNLL 50
ENGGGGKYVCSAKLRMVTGLRNNPSNQSQGLFGAIAGYIEGGWTGMVDGW 100
YGYHHQNEQGSGYAADQKSTQNAINGITNKVNSVIEKMNTQSTATGKEGN 150
KSERRMENLNKKVDDGFIDIWCYNAELLVLLENERTLDFHDSNVKNLYEK 200
VKSQLKNNAKEIGNGCFEFYHKCNDECMESVKNGTYDYPKYSEESKLNRE 250
KIDGVKLESMGVYQILAIYSTVASSLVLLVSLGAISFWMCSNGSLQCRIC 300
I 301

SEQ ID NO: 157: H1mini2a-cl1 +5 + 6 − 12 + 13
MKVKLLVLLCTFTATYADTICIGYHANNSTDTVDTVLEKNVTVTHSVNLLENGGGGKYVCSAKLRMVTGLRNN
PSNQSQGLFGAIAGYNEGGWTGMVDGWYGYHHQNEQGSGYAADQKSTQNAINGITNKVNSVIEKMNTQSTATG
KEGNKSERRMENLNKKVDDGFIDIWCYNAELLVLLENERTLDFHDSNVKNLYEKVKSQLKNNAKEIGNGCFEF
YHKCNDECMESVKNGTYDYPKYSEESKLNREKIDGVKLESMGVYQILAIYSTVASSLVLLVSLGAISFWMCSN
GSLQCRICI SEQ ID NO: 158: H5 FL HA ANietnam/1203/2004
(341 RRRKK 345 is deleted and a R346Q mutation is introduced)
MEKIVLLFAIVSLVKSDQICIGYHANNSTEQVDTIMEKNVTVTHAQDILE 50
KKHNGKLCDLDGVKPLILRDCSVAGWLLGNPMCDEFINVPEWSYIVEKAN 100
PVNDLCYPGDFNDYEELKHLLSRINHFEKIQIIPKSSWSSHEASLGVSSA 150
CPYQGKSSFFRNVVWLIKKNSTYPTIKRSYNNTNQEDLLVLWGIHHPNDA 200
AEQTKLYQNPTTYISVGTSTLNQRLVPRIATRSKVNGQSGRMEFFWTILK 250
PNDAINFESNGNFIAPEYAYKIVKKGDSTIMKSELEYGNCNTKCQTPMGA 300
INSSMPFHNIHPLTIGECPKYVKSNRLVLATGLRNSPQRERRRKKR*GLFG* 350
AIAGFIEGGWQGMVDGWYGYHHSNEQGSGYAADKESTQKAIDGVTNKVNS 400
*IIDKMNTQFEAVGREFNNLERRIENLNKKMEDGFLDVWTYNAELLVLMEN* 450
*ERTLDFRDSNVKNLYDKVRLQLRDNAKELGNGCFEFYHKCDNECMESVRN* 500
*GTYDYPQYSEEARLKREEISGVKLESIGIITILSIYSTVASSLALAIMVA* 550
*GLSLWMCSNGSLQCRICI* 568

SEQ ID NO: 159: H1 FL HA A/California/04/2009 R343Q
MKAILVVLLYTFATANADTLCIGYHANNSTDTVDTVLEKNVTVTHSVNLL 50
EDKHNGKLCKLRGVAPLHLGKCNIAGWILGNPECESLSTASSWSYIVETP 100
SSDNGTCYPGDFIDYEELREQLSSVSSFERFEIFPKTSSWPNHDSNKGVT 150
AACPHAGAKSFYKNLIWLVKKGNSYPKLSKSYINDKGKEVLVLWGIHHPS 200
TSADQQSLYQNADTYVFVGSSRYSKKFKPEIAIRPKVRDQEGRMNYYWTL 250
VEPGDKITFEATGNLVVPRYAFAMERNAGSGIIISDTPVHDCNTTCQTPK 300
GAINTSLPFQNIHPITIGKCPKYVKSTKLRLATGLRNIPSIQSRGLFGAI 350
AGFIEGGWTGMVDGWYGYHHQNEQGSGYAADLKSTQNAIDEITNKVNSVI 400
EKMNTQFTAVGKEFNHLEKRIENLNKKVDDGFLDIWTYNAELLVLLENER 450
TLDYHDSNVKNLYEKVRSQLKNNAKEIGNGCFEFYHKCDNTCMESVKNGT 500
YDYPKYSEEAKLNREEIDGVKLESTRIYQILAIYSTVASSLVLVVSLGAI 550
SFWMCSNGSLQCRICI 566

SEQ ID NO: 160: H1mini-HAA/California/07/2009
MKAILVVLLYTFATANADTLCIGYHANNSTDTVDTVLEKNVTVTHSVNLL 50
EDGGGGKYVCSTKLRLATGLRNIPSIQSQGLFGAIAGFIEGGWTGMVDGW 100
YGYHHQNEQGSGYAADLKSTQNAIDEITNKVNSVIEKMNTQSTATGKEGN 150
HSERMKQIEDKIEEIESKQIWCYNAELLVLLENERTLDYHDSNVKNLYEK 200
VRSQLKNNAKEIGNGCFEFYHKCDNTCMESVKNGTYDYPKYSEEAKLNRE 250
EIDGVKLESTRIYQILAIYSTVASSLVLVVSLGAISFWMCSNGSLQCRIC 300
I 301

SEQ ID NO: 161: H1mini-HAA/PuertoRico/8/1934
MKANLLVLLCALAAADADTICIGYHANNSTDTVDTVLEKNVTVTHSVNLL 50
EDGGGGKYVCSAKLRMVTGLRNIPSIQSQGLFGAIAGFIEGGWTGMIDGW 100
YGYHHQNEQGSGYAADQKSTQNAINGITNKVNTVIEKMNTQSTATGKEGN 150
KSERMKQIEDKIEEIESKQIWCYNAELLVLLENERTLDFHDSNVKNLYEK 200

-continued

SEQUENCES

```
VKSQLKNNAKEIGNGCFEFYHKCDNECMESVRNGTYDYPKYSEESKLNRE         250
KVDGVKLESMGIYQILAIYSTVASSLVLLVSLGAISFWMCSNGSLQCRIC         300
I                                                          301

SEQ ID NO: 162: H1mini-HAA/Texas/36/1991
MKAKLLVLLCAFTATYADTICIGYHANNSTDTVDTVLEKNVTVTHSVNLL          50
EDGGGGKYVCSTKLRMVTGLRNIPSIQSQGLFGAIAGFIEGGWTGMIDGW         100
YGYHHQNEQGSGYAADQKSTQNAINGITNKVNSVIEKMNTQSTATGKEGN         150
KSERMKQIEDKIEEIESKQIWCYNAELLVLLENGRTLDFHDSNVKNLYEK         200
VKSQLKIVNAKIGNGCFEFYHKCNNECMESVKNGTYDYPKYSEESKLNRG         250
KIDGVKLESMGVYQILAIYSTVASSLVLLVSLGAISFWMCSNGSLQCRIC         300
I                                                          301

SEQ ID NO: 163: H5mini-HAANietnam/1203/2004
MEKIVLLFAIVSLVKSDQICIGYHANNSTEQVDTIMEKNVTVTHAQDILE          50
KGGGGKYVCSNRLVLATGLRNSPQRESQGLFGAIAGFIEGGWQGMVDGWY         100
GYHHSNEQGSGYAADKESTQKAIDGVTNKVNSIDKMNTQSEATGREGNN          150
SERMKQIEDKIEEIESKQIWCYNAELLVLMENERTLDFHDSNVKNLYDKV         200
RLQLRDNAKELGNGCFEFYHKCDNECMESVRNGTYDYPQYSEEARLKREE         250
ISGVKLESIGIYQILSIYSTVASSLALAIMVAGLSLWMCSNGSLQCRICI         300

SEQ ID NO: 164: mHA_H1N1_A_Maryland_12_1991
MKAILLVLLYTFTAANADTLCIGYHANNSTDTVDTVLEKNVTVTHSVNLLEDGGGGKYVC
STKLRMATGLRNIPSIQSQGLFGAIAGFIEGGWTGMIDGWYGYHHQNEQGSGYAADQKST
QNAIDGITNKVNSVIEKMNTQSTATGKEGNHSERMKQIEDKIEEIESKQVWCYNAELLVL
LENERTLDYHDSNVKNLYEKVRSQLKNNAKEIGNGCFEFYHKCDDTCMESVKNGTYDYPK
YSEESKLNREEIDGVKLESTRIYQILAIYSTVASSLVLLVSLGAISFWMCSNGSLQCRIC
I*

SEQ ID NO: 165: mHA_H1N1_A_Henry_1936
MKARLLVLLCALAATDADTICIGYHANNSTDTVDTVLEKNVTVTHSVNLLEDGGGGKYVC
SAKLRMVTGLRNIPSIQSQGLFGAIAGFIEGGWTGMIDGWYGYHHQNEQGSGYAADQKST
QNAINGITNKVNSVIEKMNTQSTATGKEGNNSERMKQIEDKIEEIESKQIWCYNAELLVL
LENERTLDFHDSNVKNLYEKVKSQLKNNAKEIGNGCFEFYHKCDNECMESVRNGTYDYPK
YSEESKLNREKIDGVKLESMGVYQILAIYSTVASSLVLLVSLGAISFWMCSNGSLQCRIC
I*

SEQ ID NO: 166: mHA_H1N1 A/AA/Marton/1943
MKARLLVLLCALAATDADTICIGYHANNSTDTVDTVLEKNVTVTHSVNLLEDGGGGKYVC
STKLRMVTGLRNIPSIQSQGLFGAIAGFIEGGWTGMIDGWYGYHHQNEQGSGYAADQKST
QNAINGITNKVNSVIEKMNTQSTATGKEGNNSERMKQIEDKIEEIESKDIWCYNAELLVL
LENERTLDFHDSNVKNLYEKVKNQLRNNAKEIGNGCFEFYHKCNNECMESVKNGTYDYPK
YSEESKLNREKIDGVKLESMGVYQILAIYSTVASSLVLLVSLGAISFWMCSNGSLQCRIC
I

SEQ ID NO: 167: _mHA_H1N1_A_New_York_607_1995
MKAKLLVLLCAFTATYADTICIGYHANNSTDTVDTVLEKNVTVTHSVNLLEDGGGGKYVC
STKLRMVTGLRNIPSIQSQGLFGAIAGFIEGGWTGMIDGWYGYHHQNEQGSGYAADQKST
QNAIDGITNKVNSVIEKMNTQSTATGKEGNKSERMKQIEDKIEEIESKQIWCYNAELLVL
LENERTLDFHDSNVKNLYEKVKTQLKNNAKEIGNGCFEFYHKCNNECMESVKNGTYDYPK
YSEESKLNREKIDGVKLESMGVYQILAIYSTVASSLVLLVSLGAISFWMCSNGSLQCRIC
I*

SEQ ID NO: 168: mHA_H1N1_A_Newiersey_11_2007
  1 MKARLLVLLCALAATDADTICIGYHANNSTDTVDTVLEKNVTVTHSVNLLEDGGGGKYVC
 61 SAKLRMVTGLRNIPSIQSQGLFGAIAGFIEGGWTGMVDGWYGYHHQNEQGSGYAADQKST
121 QNAINGITNKVNSVIEKMNTQSTATGKEGNKSERMKQIEDKIEEIESKQIWCYNAELLVL
181 LENERTLDFHDSNVKNLYEKVKSQLKNNAKEIGNGCFEFYHKCNDECMESVKNGTYDYPK
241 YSEESKLNREKIDGVKLESMGVYQILAIYSTVASSLVLLVSLGAISFWMCSNGSLQCRIC
301 I*

SEQ ID NO: 169: mHA_H1N1_A_USSR_92_1977
  1 MKAKLLVLLCALSATDADTICIGYHANNSTDTVDTVLEKNVTVTHSVNLLEDGGGGKYVC
 61 STKLRMVTGLRNIPSIQSQGLFGAIAGFIEGGWTGMIDGWYGYHHQNEQGSGYAADQKST
121 QNAINGITNKVNSVIEKMNTQSTATGKEGNKSERMKQIEDKIEEIESKQIWCYNAELLVL
181 LENERTLDFHDSNVKNLYEKVKSQLKNNAKEIGNGCFEFYHKCNNECMESVKNGTYDYPK
241 YSEESKLNREKIDGVKLESMGVYQILAIYSTVASSLVLLVSLGAISFWMCSNGSLQCRIC
301 I*

SEQ ID NO: 170: mHA_H1N1_A_New_York_629_1995
  1 MKVKLLVLLCAFTATYADTICIGYHANNSTDTVDTVLEKNVTVTHSVNLLEDGGGGKYVC
 61 STKLRMVTGLRNIPSIQSQGLFGAIAGFIEGGWTGMIDGWYGYHHQNEQGSGYAADQKST
121 QNAIDGITNKVNSVIEKMNTQSTATGKEGNKSERMKQIEDKIEEIESKQIWCYNAELLVL
181 LENERTLDFHDSNVKNLYEKVKNQLKNNAKEIGNGCFEFYHKCNNECMESVKNGTYDYPK
241 YSEESKLNREKIDGVKLESMGVYQILAIYSTVASSLVLLVSLGAISFWMCSNGSLQCRIC
301 I*
```

-continued

| SEQUENCES |
|---|

SEQ ID NO: 171: mHA_H1N1_A_Virginia_UR06-05492007
  1 MKVKLLVLLCTFTATYADTICIGYHANNSTDTVDTVLEKNVTVTHSVNLLEDGGGGKYVC
 61 SAKLRMVTGLRNIPSIQSQGLFGAIAGFIEGGWTGMVDGWYGYHHQNEQGSGYAADQKST
121 QNAINGITNKVNSVIEKMNTQSTATGKEGNKSERMKQIEDKIEEIESKQIWCYNAELLVL
181 LENERTLDFHDSNVKNLYEKVKSQLKNNAKEIGNGCFEFYHKCNDECMESVKNGTYDYPK
241 YSEESKLNREKIDGVKLESMGVYQILAIYSTVASSLVLLVSLGAISFWMCSNGSLQCRIC
301 I*

SEQ ID NO: 172: mHA_H1N1_A_Texas_URO-05262007
  1 MKVKLLVLLCTFTATYADTICIGYHANNSTDTVDTVLEKNVTVTHSVNLLEDGGGGKYVC
 61 SAKLRMVTGLRNIPSIQSQGLFGAIAGFIEGGWTGMVDGWYGYHHQNEQGSGYAADQKST
121 QNAINGITNKVNSVIEKMNTQSTATGKEGNKSERMKQIEDKIEEIESKQIWCYNAELLVL
181 LENERTLDFHDSNVKNLYEKVKNQLKNNAKEIGNGCFEFYHKCNDECMESVKNGTYDYPK
241 YSEESKLNREKIDGVKLESMGVYQILAIYSTVASSLVLLISLGAISFWMCSNGSLQCRIC
301 I*

SEQ ID NO: 173: mHA_H1N1_A_Sydney_DD3-55_2010
  1 MKAILVVLLYTFATANADTLCIGYHANNSTDTVDTVLEKNVTVTHSVNLLEDGGGGKYVC
 61 STKLRLATGLRNVPSIQSQGLFGAIAGFIEGGWTGMVDGWYGYHHQNEQGSGYAADLKST
121 QNAIDEITNKVNSVIEKMNTQSTATGKEGNHSERMKQIEDKIEEIESKQIWCYNAELLVL
181 LENERTLDYHDSNVKNLYEKVRSQLKNNAKEIGNGCFEFYHKCDNTCMESVKNGTYDYPK
241 YSEEAKLNREEIDGVKLESTRIYQILAIYSTVASSLVLVVSLGAISFWMCSNGSLQCRIC
301 I*

SEQ ID NO: 174: H3mini2a-linker + cl9_ + 10 + 11 + 12 + GCN4T_CG7-1
(A/HongKong/1/1968(H3N2)
  1 MKTIIALSYIFCLALGQDLPGNDNSTATLCLGHHAVPNGTLVKTITDDQIEVTNATELVQ
 61 SGGGGKYVCQNTLKLATGMRNVPEKQTQGLFGAIAGFIENGWEGMIDGWYGFRHQNSEGT
121 GQAADLKSTQAAIDQINGKLNRVREKTNEKSHQTEKESSNATGRMKQIEDKIEEIESKLW
181 CYNAELLVALENQHTIDLTDSEMNKLFEKTRRQLRENAEDMGNGCFKIYHKCDNACIESI
241 RNGTYDHDVYRDEALNNRFQIKGVELKSGYKDWILWISFAISCFLLCVVLLGFIMWACQR
301 GNIRCNICI SEQ ID NO: 175: H3mini2a-linker + cl9_ + 10 + 12 + 18 + GCN4T
(A/HongKong/1/1968(H3N2))
  1 MKTIIALSYIFCLALGQDLPGNDNSTATLCLGHHAVPNGTLVKTITDDQIEVTNATELVQ
 61 SGGGGKYVCQNTLKLATGMRNVPEKQTQGLFGAIAGFIENGWEGMIDGWYGFRHQNSEGT
121 GQAADLKSTQAAIDQINGKLNRVIEKTNEKSHQTEKESSEGEGNATGGCCGGRMKQIEDK
181 IEEIESKLWCYNAELLVALENQHTIDLTDSEMNKLFEKTRRQLRENAEDMGNGCFKIYHK
241 CDNACIESIRNGTYDHDVYRDEALNNRFQIKGVELKSGYKDWILWISFAISCFLLCVVLL
301 GFIMWACQRGNIRCNICI SEQ ID NO: 176: H3mini2a-linker+cl9_ + 10 + 12 + 16 + CG7-GCN4T
(A/HongKong/1/1968(H3N2))]
  1 MKTIIALSYIFCLALGQDLPGNDNSTATLCLGHHAVPNGTLVKTITDDQIEVCNATELVQ
 61 SGGGGKYVCQNTLKLATCMRNVPEKQTQGLFGAIAGFIENGWEGMIDGWYGFRHQNSEGT
121 GQAADLKSTQAAIDQINGKLNRVIEKTNEKSHQTEKESSNATGRMKQIEDKIEEIESKLW
181 CYNAELLVALENQHTIDLTDSEMNKLFEKTRRQLRENAEDMGNGCFKIYHKCDNACIESI
241 RNGTYDHDVYRDEALNNRFQIKGVELKSGYKDWILWISFAISCFLLCVVLLGFIMWACQR
301 GNIRCNIC I SEQ ID NO: 177: H3mini2a-linker + cl9_ + 10 + 12 + 19 + GCN4T
(A/HongKong/1/1968(H3N2))]
  1 MKTIIALSYIFCLALGQDLPGNDNSTATLCLGHHAVPNGTLVKTITDDQIEVTNATELVQ
 61 SGGGGKYVCQNTLKLATGMRNVPEKQTQGLFGAIAGFIENGWEGMIDGWYGFRHQNSEGT
121 GQAADLKSTQAAIDQINGKLNRVIEKTNEKSHQTEKESSEGEGSGSGGCCGGRMKQIEDK
181 IEEIESKLWCYNAELLVALENQHTIDLTDSEMNKLFEKTRRQLRENAEDMGNGCFKIYHK
241 CDNACIESIRNGTYDHDVYRDEALNNRFQIKGVELKSGYKDWILWISFAISCFLLCVVLL
301 GFIMWACQRGNIRCNICI SEQ ID NO: 178: H3mini2a-linker+cl9_ + 10 + 12 + 17 + CG7-GCN4T
(A/HongKong/1/1968(H3N2))]
  1 MKTIIALSYIFCLALGQDLPGNDNSTATLCLGHHAVPNCTLVKTITDDQICVTNATELVQ
 61 SGGGGKYVCQNTLKLATGMRNVPEKQTQGLFGAIAGFIENGWEGMIDGWYGFRHQNSEGT
121 GQAADLKSTQAAIDQINGKLNRVIEKTNEKSHQTEKESSNATGRMKQIEDKIEEIESKLW
181 CYNAELLVALENQHTIDLTDSEMNKLFEKTRRQLRENAEDMGNGCFKIYHKCDNACIESI
241 RNGTYDHDVYRDEALNNRFQIKGVELKSGYKDWILWISFAISCFLLCVVLLGFIMWACQR
301 GNIRCNICI SEQ ID NO: 179: H3_HK68_mini2a-linker2 + cl9_ + 10 + 12 + GCN4T
  1 LATMKTIIALSYIFCLALGQDLPGNDNSTATLCLGHHAVPNGTLVKTITDDQIEVTNATE
 61 LVQSGSGSGGKYVCQNTLKLATGMRNVPEKQTQGLFGAIAGFIENGWEGMIDGWYGFRHQ
121 NSEGTGQAADLKSTQAAIDQINGKLNRVIEKTNEKSHQTEKESSEGEGRMKQIEDKIEEI
181 ESKLWCYNAELLVALENQHTIDLTDSEMNKLFEKTRRQLRENAEDMGNGCFKIYHKCDNA
241 CIESIRNGTYDHDVYRDEALNNRFQIKGVELKSGYKDWILWISFAISCFLLCVVLLGFIM
301 WACQRGNIRCNICI**

| SEQUENCES |
|---|
| SEQ ID NO: 180: H1-mini2-cluster1 + 5 + 6 + GCN4-T49N<br>MKVKLLVLLCTFTATYADTICIGYHANNSTDTVDTVLEKNVTVTHSVNLLENGGGGKYVCSAKLRMVTGLRNI<br>PSIQSQGLFGAIAGFIEGGWTGMVDGWYGYHHQNEQGSGYAADQKSTQNAINGINNKVNSVIEKMNTQSTATG<br>KEGNKSERMKQIEDKIEEIESKQIWCYNAELLVLLENERTLDFHDSNVKNLYEKVKSQLKNNAKEIGNGCFEF<br>YHKCNDECMESVKNGTYDYPKYSEESKLNREKIDGVKLESMGVYQILAIYSTVASSLVLLVSLGAISFWMCSN<br>GSLQCRICI<br><br>SEQ ID NO: 181: sH1-mini2-cl1 + 5 + 6-GCN4-Bromelain<br>**MEWKLLVLLCTFTATYA**DTICIGYHANNSTDTVDTVLEKNVTVTHSVNLLENGGGGKYVCSAKLRMVTGLRNI<br>PSIQSQGLFGAIAGFIEGGWTGMVDGWYGYHHQNEQGSGYAADQKSTQNAINGITNKVNSVIEKMNTQSTATG<br>KEGNKSERMKQIEDKIEEIESKQIWCYNAELLVLLENERTLDFHDSNVKNLYEKVKSQLKNNAKEIGNGCFEF<br>YHKCNDECMESVKNGTYDYPKYSEESKLNREK*IDGRSLVPRGS*PGHHHHHH<br><br>SEQ ID NO: 182: sH1-mini2-cl1 + 5 + 6-GCN4-Bromelain-Foldon<br>**MEWKLLVLLCTFTATYA**DTICIGYHANNSTDTVDTVLEKNVTVTHSVNLLENGGGGKYVCSAKLRMVTGLRNI<br>PSIQSQGLFGAIAGFIEGGWTGMVDGWYGYHHQNEQGSGYAADQKSTQNAINGITNKVNSVIEKMNTQSTATG<br>KEGNKSERMKQIEDKIEEIESKQIWCYNAELLVLLENERTLDFHDSNVKNLYEKVKSQLKNNAKEIGNGCFEF<br>YHKCNDECMESVKNGTYDYPKYSEESKLNREK*IDGRSLVPRGS*<u>PGSGYIPEAPRDGQAYVRKDGEWVLLSTFL<br>G</u>HHHHHH<br><br>SEQ ID NO: 183: sH1-mini2-cl1 + 5 + 6-GCN4t2<br>**MEWKLLVLLCTFTATYA**DTICIGYHANNSTDTVDTVLEKNVTVTHSVNLLENGGGGKYVCSAKLRMVTGLRNI<br>PSIQSQGLFGAIAGFIEGGWTGMVDGWYGYHHQNEQGSGYAADQKSTQNAINGITNKVNSVIEKMNTQSTATG<br>KEGNKSERRMKQIEDKIEEIESKIWCYNAELLVLLENERTLDFHDSNVKNLYEKVKSQLKNNAKEIGNGCFEF<br>YHKCNDECMESVKNGTYDYPKYSEESKLNREKIDGVKLESMGVYQ*IEGR*HHHHHH<br><br>SEQ ID NO: 184: sH1-mini2-cl1 + 5 + 6-GCN4t2-Bromelain<br>**MKVKLLVLLCTFTATYA**DTICIGYHANNSTDTVDTVLEKNVTVTHSVNLLENGGGGKYVCSAKLRMVTGLRNI<br>PSIQSQGLFGAIAGFIEGGWTGMVDGWYGYHHQNEQGSGYAADQKSTQNAINGITNKVNSVIEKMNTQSTATG<br>KEGNKSERRMKQIEDKIEEIESKIWCYNAELLVLLENERTLDFHDSNVKNLYEKVKSQLKNNAKEIGNGCFEF<br>YHKCNDECMESVKNGTYDYPKYSEESKLNREK*IDGRSLVPRGS*PGHHHHHH<br><br>SEQ ID NO: 185: sH1-mini2-cl1 + 5 + 6-GCN4t2-Bromelain-Foldon<br>**MKVKLLVLLCTFTATYA**DTICIGYHANNSTDTVDTVLEKNVTVTHSVNLLENGGGGKYVCSAKLRMVTGLRNI<br>PSIQSQGLFGAIAGFIEGGWTGMVDGWYGYHHQNEQGSGYAADQKSTQNAINGITNKVNSVIEKMNTQSTATG<br>KEGNKSERRMKQIEDKIEEIESKIWCYNAELLVLLENERTLDFHDSNVKNLYEKVKSQLKNNAKEIGNGCFEF<br>YHKCNDECMESVKNGTYDYPKYSEESKLNREK*IDGRSLVPRGS*<u>PGSGYIPEAPRDGQAYVRKDGEWVLLSTFL<br>G</u>HHHHHH<br><br>SEQ ID NO: 186: sH3 HK mini2a-linker + c19 + 10 + 11 + 12 + GCN4T-CG7-His<br>**MKTIIALSYIFCLALG**QDLPGNDNSTATLCLGHHAVPNGTLVKTITDDQIEVTNATELVQSGGGGKYVCQNTL<br>KLATGMRNVPEKQTQGLFGAIAGFIENGWEGMIDGWYGFRHQNSEGTGQAADLKSTQAAIDQINGKLNRVREK<br>TNEKSHQTEKESSNATGRMKQIEDKIEEIESKLWCYNAELLVALENQHTIDLTDSEMNKLFEKTRRQLRENAE<br>DMGNGCFKIYHKCDNACIESIRNGTYDHDVYRDEALNNRFQIKGR*SLVPRGS*PGHHHHHH<br><br>SEQ ID NO: 187: sH3 HK mini2a-linker + c19 + 10 + 11 + 12 + GCN4T-CG7-Foldon-His<br>**MKTIIALSYIFCLALG**QDLPGNDNSTATLCLGHHAVPNGTLVKTITDDQIEVTNATELVQSGGGGKYVCQNTL<br>KLATGMRNVPEKQTQGLFGAIAGFIENGWEGMIDGWYGFRHQNSEGTGQAADLKSTQAAIDQINGKLNRVREK<br>TNEKSHQTEKESSNATGRMKQIEDKIEEIESKLWCYNAELLVALENQHTIDLTDSEMNKLFEKTRRQLRENAE<br>DMGNGCFKIYHKCDNACIESIRNGTYDHDVYRDEALNNRFQIKGR*SLVPRGS*<u>PGSGYIPEAPRDGQAYVRKDG<br>EWVLLSTFLG</u>HHHHHH |

What is claimed is:

1. A method for producing an influenza hemagglutinin stem domain polypeptide, the method comprising:

removing the cleavage site between HA1 and HA2 of an influenza HA0 peptide from an influenza virus comprising HA of the H1 subtype by mutating the C-terminal amino acid of HA1 into an amino acid other that arginine (R) or lysine (K);

removing the peptide of the globular head domain comprising at least amino acids 53 to 320 from the HA0 sequence;

introducing one or more mutations in the peptide connecting the C-terminal residue of helix A to the N-terminal residue of helix CD comprising the amino acid sequence $MNTQX_1TAX_7GKEX_3N(H/K)X_4E(K/R)$ (SEQ ID NO: 190), wherein one or more of the amino acids $X_1$, $X_2$, $X_3$ and $X_4$ has been changed into an amino acid selected from the group consisting of serine (S), threonine (T), asparagine (N), glutamine (Q), R, histidine (H), K, aspartic acid (D), glutamic acid (E), and glycine (G); and introducing a disulfide bridge in the HA stem domain polypeptide between the amino acids at position 324 and 436, so as to produce the influenza hemagglutinin stem domain polypeptide, wherein the numbering is based on the numbering of amino acids of the H1N1 influenza strain A/Brisbane/59/2007 (SEQ ID NO: 1).

2. The method according to claim 1, wherein the C-terminal amino acid residue of the HA1 C-terminal stem segment is mutated into Q, S, T, N, D or E.

3. The method according to claim 1, wherein the C-terminal amino acid residue of the HA1 C-terminal stem segment is mutated into Q.

4. The method according to claim 1, wherein $X_1$ has been changed into S, $X_2$ has been changed into T, Q, or G, $X_3$ has been changed into S, and $X_4$ has been changed into S.

* * * * *

UNITED STATES PATENT AND TRADEMARK OFFICE

CERTIFICATE OF CORRECTION

PATENT NO. : 9,969,778 B2
APPLICATION NO. : 15/253535
DATED : May 15, 2018
INVENTOR(S) : Jan Willem Meijberg et al.

It is certified that error appears in the above-identified patent and that said Letters Patent is hereby corrected as shown below:

In the Specification

| | | |
|---|---|---|
| Column 17, | Line 15, | change “325 of H1 HAL” to --325 of H1 HA1-- |
| Column 19, | Line 34, | change “HA1, In a specific” to --HA1. In a specific-- |
| Column 23, | Line 19, | change “a his-tag (HHHHHHHH” to --a his-tag (HHHHHHH-- |
| Column 24, | Line 46, | change “of H3 HAL preferably” to --of H3 HA1 preferably-- |
| Column 24, | Line 51, | change “of H3 HAL” to --of H3 HA1-- |
| Column 51, | Line 3, | change “the surrounding Nature” to --the surrounding. Nature-- |
| Column 54, | Line 38, | change “(HHHHHHEI (SEQ” to --(HHHHHHH (SEQ-- |
| Column 57, | Line 55, | change “5+6-n1 (SEQ” to --5+6-nl (SEQ-- |
| Column 61, | Line 29, | change “E306 to 1337” to --E306 to I337-- |
| Column 62, | Line 21, | change “P51 to 1337” to --P51 to I337-- |
| Column 63, | Line 38, | change “5+6-n1 (SEQ” to --5+6-nl (SEQ-- |
| Column 64, | Line 2, | change “5+6-n1 (SEQ” to --5+6-nl (SEQ-- |
| Column 64, | Line 17, | change “5+6-n1 (SEQ” to --5+6-nl (SEQ-- |
| Column 64, | Line 33, | change “5+6-n1 (SEQ” to --5+6-nl (SEQ-- |
| Column 67, | Line 57, | change “1337N, 1340N and” to --I337N, I340N and-- |
| Column 67, | Line 59, | change “i.e., 1353N.” to --i.e., I353N.-- |
| Column 68, | Line 24, | change “5+6-n1 (SEQ” to --5+6-nl (SEQ-- |
| Column 68, | Line 60, | change “5+6-n1 (SEQ” to --5+6-nl (SEQ-- |
| Column 69, | Line 22, | change “5+6-n1 (SEQ” to --5+6-nl (SEQ-- |
| Column 69, | Line 44, | change “5+6-n1 (SEQ” to --5+6-nl (SEQ-- |
| Column 69, | Line 60, | change “5+6-n1 (SEQ” to --5+6-nl (SEQ-- |
| Column 71, | Line 2, | change “Vat 408 (to A)” to --V at 408 (to A)-- |

Signed and Sealed this
Twenty-first Day of August, 2018

Andrei Iancu
*Director of the United States Patent and Trademark Office*

In the Claims

Claim 1, Column 483, Line 39, change "MNTQ$X_1$TA$X_7$GKE$X_3$N" to --MNTQ$X_1$TA$X_2$GKE$X_3$N--